(12) United States Patent
Jo

(10) Patent No.: US 10,961,292 B2
(45) Date of Patent: *Mar. 30, 2021

(54) CELL-PERMEABLE (ICP)-SOCS3 RECOMBINANT PROTEIN AND USES THEREOF

(71) Applicant: CELLIVERY THERAPEUTICS, INC., Seoul (KR)

(72) Inventor: Daewoong Jo, Brentwood, TN (US)

(73) Assignee: CELLIVERY THERAPEUTICS, INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/426,751

(22) Filed: May 30, 2019

(65) Prior Publication Data
US 2019/0359669 A1 Nov. 28, 2019

Related U.S. Application Data

(60) Division of application No. 15/361,701, filed on Nov. 28, 2016, now abandoned, which is a continuation of application No. 14/838,304, filed on Aug. 27, 2015, now abandoned.

(60) Provisional application No. 62/042,493, filed on Aug. 27, 2014.

(51) Int. Cl.
| | | |
|---|---|---|
| *A61K 38/10* | (2006.01) | |
| *C07K 14/51* | (2006.01) | |
| *C07K 7/08* | (2006.01) | |
| *C07K 14/47* | (2006.01) | |
| *A61K 38/17* | (2006.01) | |
| *A61K 38/00* | (2006.01) | |
| *C07K 7/06* | (2006.01) | |
| *A61K 38/08* | (2019.01) | |

(52) U.S. Cl.
CPC .......... *C07K 14/51* (2013.01); *A61K 38/1761* (2013.01); *C07K 7/08* (2013.01); *C07K 14/47* (2013.01); *C07K 14/4703* (2013.01); *A61K 38/00* (2013.01); *A61K 38/08* (2013.01); *A61K 38/10* (2013.01); *A61K 38/1709* (2013.01); *C07K 7/06* (2013.01); *C07K 14/4702* (2013.01); *C07K 2319/00* (2013.01); *C07K 2319/01* (2013.01); *C07K 2319/10* (2013.01); *C07K 2319/21* (2013.01); *C07K 2319/40* (2013.01)

(58) Field of Classification Search
None
See application file for complete search history.

(56) References Cited

U.S. PATENT DOCUMENTS

| | | | |
|---|---|---|---|
| 7,897,394 B2 | 3/2011 | Reed | |
| 8,420,096 B2 | 4/2013 | Hawiger et al. | |
| 10,385,103 B2* | 8/2019 | Jo ............................ | C07K 7/08 |
| 10,662,419 B2* | 5/2020 | Jo ............................ | C12N 9/93 |
| 10,669,531 B2* | 6/2020 | Jo ............................ | C12Y 207/07 |
| 2003/0104622 A1 | 6/2003 | Robbins et al. | |
| 2009/0209458 A1 | 8/2009 | Hawiger et al. | |
| 2010/0209447 A1 | 8/2010 | Kumar-Singh et al. | |
| 2014/0141452 A1 | 5/2014 | Watt et al. | |
| 2014/0186379 A1 | 7/2014 | Jo et al. | |
| 2014/0329737 A1 | 11/2014 | Shin et al. | |
| 2016/0060310 A1 | 3/2016 | Jo et al. | |
| 2016/0060311 A1 | 3/2016 | Jo et al. | |
| 2016/0060312 A1 | 3/2016 | Jo et al. | |
| 2016/0060313 A1 | 3/2016 | Jo et al. | |
| 2016/0060314 A1 | 3/2016 | Jo et al. | |
| 2016/0122793 A1 | 5/2016 | Shaw | |
| 2017/0137482 A1 | 5/2017 | Jo et al. | |
| 2017/0190754 A1* | 7/2017 | Jo ....................... | A61K 38/1761 |
| 2017/0198019 A1 | 7/2017 | Jo | |
| 2017/0226168 A1 | 8/2017 | Jo et al. | |
| 2017/0240598 A1 | 8/2017 | Jo | |
| 2018/0051060 A1* | 2/2018 | Jo ............................ | C07K 7/08 |
| 2019/0338000 A1* | 11/2019 | Jo ............................ | C07K 7/08 |

FOREIGN PATENT DOCUMENTS

| | | |
|---|---|---|
| EP | 1 362 917 A3 | 11/2003 |
| JP | 2010-516758 A | 5/2010 |
| KR | 10-1258279 B1 | 4/2013 |
| WO | 99/23220 A1 | 5/1999 |
| WO | 01/27154 A3 | 4/2001 |
| WO | 03/097671 A1 | 11/2003 |
| WO | 2005/086800 A2 | 9/2005 |
| WO | 2008/093982 A1 | 8/2008 |
| WO | 2009/139599 A2 | 11/2009 |
| WO | 2011/113048 A2 | 9/2011 |

(Continued)

OTHER PUBLICATIONS

International Searching Authority, International Search Report dated Nov. 1, 2016 in Application No. PCT/KR2016/009414.

(Continued)

*Primary Examiner* — Fred H Reynolds
(74) *Attorney, Agent, or Firm* — Sughrue Mion, PLLC

(57) ABSTRACT

Provided are an improved cell-permeable (iCP)-SOCS3 recombinant protein and uses thereof. Suppressor of cytokine signaling-3 (SOCS3) is an endogenous protein inhibitor of JAK/STAT pathway, and an aberrant expression of SOCS3 protein was observed in human solid tumors including gastric, colorectal and breast cancer, and glioblastoma. Thus, the iCP-SOCS3 recombinant protein may be used as protein-based anti-solid tumor agent by utilizing the platform technology for macromolecule intracellular transduction.

8 Claims, 113 Drawing Sheets

Specification includes a Sequence Listing.

(56) References Cited

FOREIGN PATENT DOCUMENTS

| WO | 2012/050402 | | 4/2012 |
|---|---|---|---|
| WO | 2012/072088 | A1 | 6/2012 |
| WO | 2014/093872 | A1 | 6/2014 |
| WO | 2015/075557 | A2 | 5/2015 |
| WO | 2015/112904 | A1 | 7/2015 |
| WO | 2017/030323 | A1 | 2/2017 |
| WO | 2017/034344 | A1 | 3/2017 |
| WO | 2017/034347 | A1 | 3/2017 |

OTHER PUBLICATIONS

Ying et al., "Loss of SOCS3 expression is associated with an increased risk of recurrent disease in breast carcinoma", J Cancer Res Clin Oncol, 2010, 136, pp. 1617-1626.
European Patent Office; Communication dated Aug. 13, 2018 in European application No. 16839621.6.
Garg et al., "MFPPI—Multi FASTA ProtParam Interface", Bioinformation, Open Access, vol. 12 No. 2, 4 pages 2016.
International Searching Authority, Communication dated Nov. 16, 2015 in PCT/KR2015/008544.
Australian Patent Office, Communication dated Oct. 13, 2017 by the Australian Patent Office in Application No. 2015304194.
European Patent Office, communication dated Nov. 27, 2017 by the European Patent Office in Application No. 15 833 496.1.
Japanese Patent Office; Communication dated Feb. 20, 2018 in Japanese application No. 2017-510405.
European Patent Office; Communication dated Feb. 9, 2018 in European application No. 15833496.1.
ChemPages. Hydrophobic Amino Acids. Datasheet [online], ChemPages Netorials. [retrieved on Jun. 15, 2018], Retrieved from the internet: URL:https://www.chem.wisc.edu/deptfiles/genchem/neotorial/modules/biomolecules/modules/protein1/prot13.htm.
Medical Physiology/Basic Biochemistry/Amino Acids. Classification of Amino Acids, [retrieved on Jun. 15, 2018], Retrieved from the internet: URL:https://en.wikibooks.org/w/index.php?title=MedicaLPhysiology/Basic_Biochemistry/Amino_Acids_and_Proteins & oldid=3436225. Last edited on Jun. 15, 2018. 4 pages.
ExPASy. ProtParam.Gasteiger, E et al. Protein identification and analysis tools on the ExPASy server. In: The Proteomics Protocols Handbook; Ed.: John M. Walker. Copyright 2005 Humana Press, [retrieved on Jun. 15, 2018],Retrieved from the internet <https://web.expasy.org/cgi-bin/protparam/protparam, 6 pages.
International Searching Authority, Communication dated Nov. 25, 2016 in PCT/KR2016/009446.
International Searching Authority, Communication dated Nov. 1, 2016 in PCT/KR2016/009416.
International Searching Authority, Communication dated Nov. 25, 2016 in PCT/KR2016/009441.
International Searching Authority, Communication dated Nov. 25, 2016 in PCT/KR2016/009456.
European Patent Office, Communication dated Jul. 11, 2018, issued in corresponding European Patent Application No. 16839623.2.
Jo et al., "Intracellular Protein Therapy with SOCS3 Inhibits Inflammation and Apoptosis", Nature Medicine, vol. 11, No. 8, Aug. 2005, pp. 892-898, 7 pages.
Ogata et al., "Deletion of the SOCS3 Gene in Liver Parenchymal Cells Promotes Hepatitis-Induced Hepaocarcinogenesis", Gastroenterology, 131, 2006, pp. 179-193, 15 pages.
Artimo et al.,"ExPASy: SIB bioinformatics resource portal", Nucleic Acids Res 40 (W1):W597-W603, 2012;; https://web.expasy.org/cgi-bin/protparam/protparam;; accessed Jul. 20, 2018; 3 total pages.
Chugh et al., "Cell-penetrating peptides: Nanocarrier for macromolecule delivery in living cells", IUBMB Life, 62(3): 183-193, 2010, 11 pages.
Chung et al., "Recent advances in cell-penetrating, non-peptide molecular carriers", Int J Pharmaceutics 354: 16-22, 2008, 7 pages.
Colagrande et al., "Challenges of advanced hepatocellular carcinoma", World J Gastroenterol 22(34): 7645-7659, 2016, 16 pages.
Cui et al., "Transfer of suppressor of cytokine signaling 3 by an oncolytic adenovirus induces potential antitumor activities in hepatocellular carcinoma", Hepatology 47: 105-112, 2008, 8 pages.
Fletcher et al., "Extended anti-inflammatory action of a degradation-resistant mutant of cell-penetrating suppressor of cytokine signaling 3", J Biol Chem 285(24): 18727-18736, 2010, 11 pages.
Hawiger et al., "Noninvasive intracellular delivery of functional peptides and proteins", Curr Opin Chem Biol 3: 89-94, 1999, 6 pages.
Mae et al., "Cell-penetrating peptides as vectors for peptide, protein and oligonucleotide delivery", Curr Opin Pharmacol 6: 509-514, 2006, 6 pages.
Wu et al., "Loss of suppressors of cytokine signaling 3 promotes aggressiveness of hepatocellular carcinoma", J Invest Surgery 27: 197-204, 2014, 9 pages.
He et al., "Activity of the Suppressor of Cytokine Signaling-3 Promoter in Human Non-Small-Cell Lung Cancer", translational medicine, Clinical Lung Cancer, vol. 5, No. 6, 366-370, 2004, 6 pages.
Catherine L Watkins et al., "Cellular uptake, distribution and cytotoxicity of the hydrophobic cell penetrating peptide sequence PFVYLI linked to the proapoptotic domain peptide PAD", journal of Controlled Release 140 (2009), pp. 237--244, 8 pages.
Yampolsky et al., "The Exchangeability of Amino Acids in Proteins", Genetics 170: pp. 1459-1472 (Aug. 2005), 14 pages.
Bechara et al., "Cell-penetrating peptides: 20 years later, where do we stand?", FEBS Letters 587 (2013) pp. 1693-1702, 10 pages total.
Stahl et al., "SOCS3 is an endogenous inhibitor of pathologic angiogenesis", Vascular Biology, Blood, vol. 120, No. 14, Oct. 2012, pp. 2925-2929, 7 pages.
He et al., "SOCS-3 is frequently silenced by hypermethylation and suppresses cell growth in human lung cancer", PNAS, vol. 100, No. 24, Nov. 25, 2003, pp. 14133-14138, 7 pages.
United States Patent and Trademark Office; communication dated Mar. 27, 2018 in U.S. Appl. No. 15/408,123.
United States Patent and Trademark Office; communication dated Mar. 27, 2018 in U.S. Appl. No. 15/361,230.
United States Patent and Trademark Office; communication dated Jul. 27, 2018 in U.S. Appl. No. 15/432,662.
United States Patent and Trademark Office; communication dated Sep. 25, 2018 in U.S. Appl. No. 15/631,982.
European Patent Office, communication dated Oct. 24, 2018 issued in European Application No. 16839637.2.
GenBank entry BC060858 for human SOCS3, dated 2006.
The webpage for Croda health care's arlasolveTM, http://www.crodahealthcare.com/home.aspx?view=dtl&d=content&s=149&r=346&p=2204&productname=Arlasolve&chemicaldescription=&chemicalgroup=&f%E2%80%A6, downloaded Aug. 2016.
The web page Wine Turtle, http://www.wineturtle.com/fining-wine-clarification-agents/, downloaded Aug. 2016.
Forli, Stefano, "Charting a path to success in virtula screening." Molecules (2015) 20(10) p. 18732-18758.
Kato, Atsushi et al, "Mutational analysis of protein solubility enhancement using short peptide tags." Biopolymers (2006) 85(1) p. 12-18.
Surapaneni, Madhu S. et al, "Designing paclitaxel drug delivery systems aimed at improved patient outcomes: current status and challenges." ISRN Pharmacol. (2012) article ID 623139.

\* cited by examiner

[Figure 1]
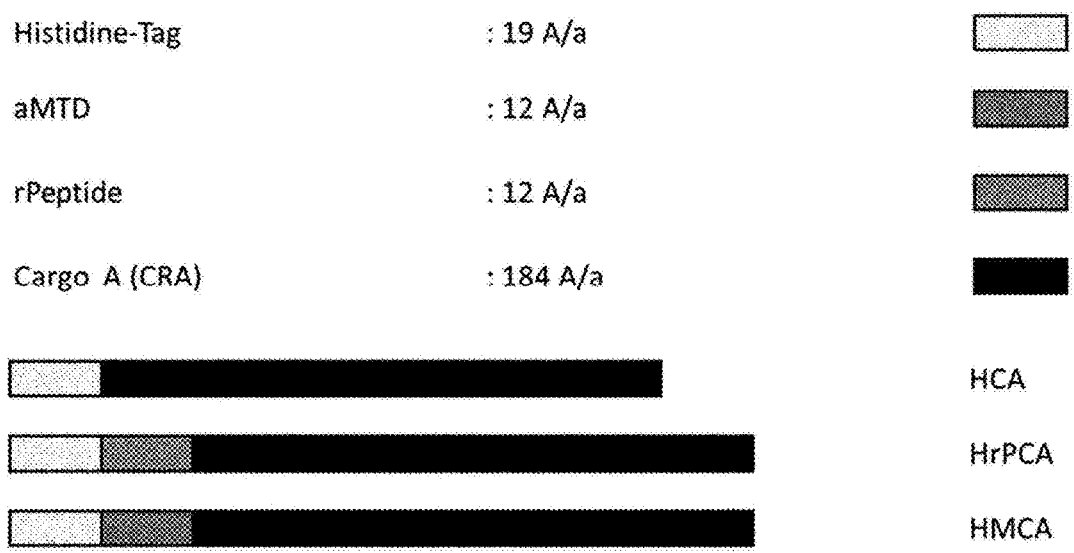
[Figure 2a]
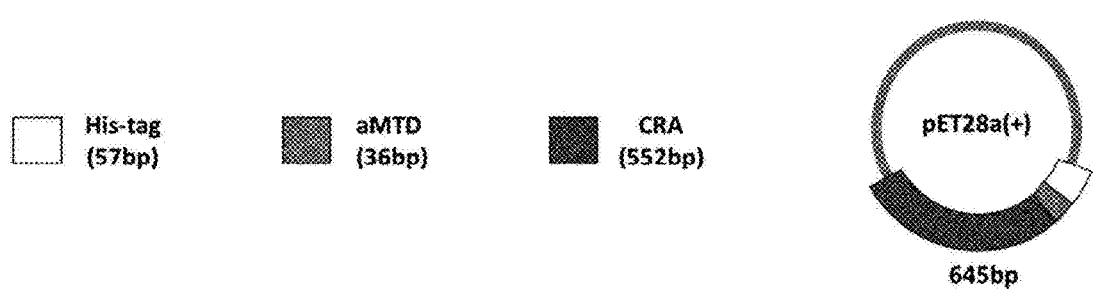

【Figure 2b】
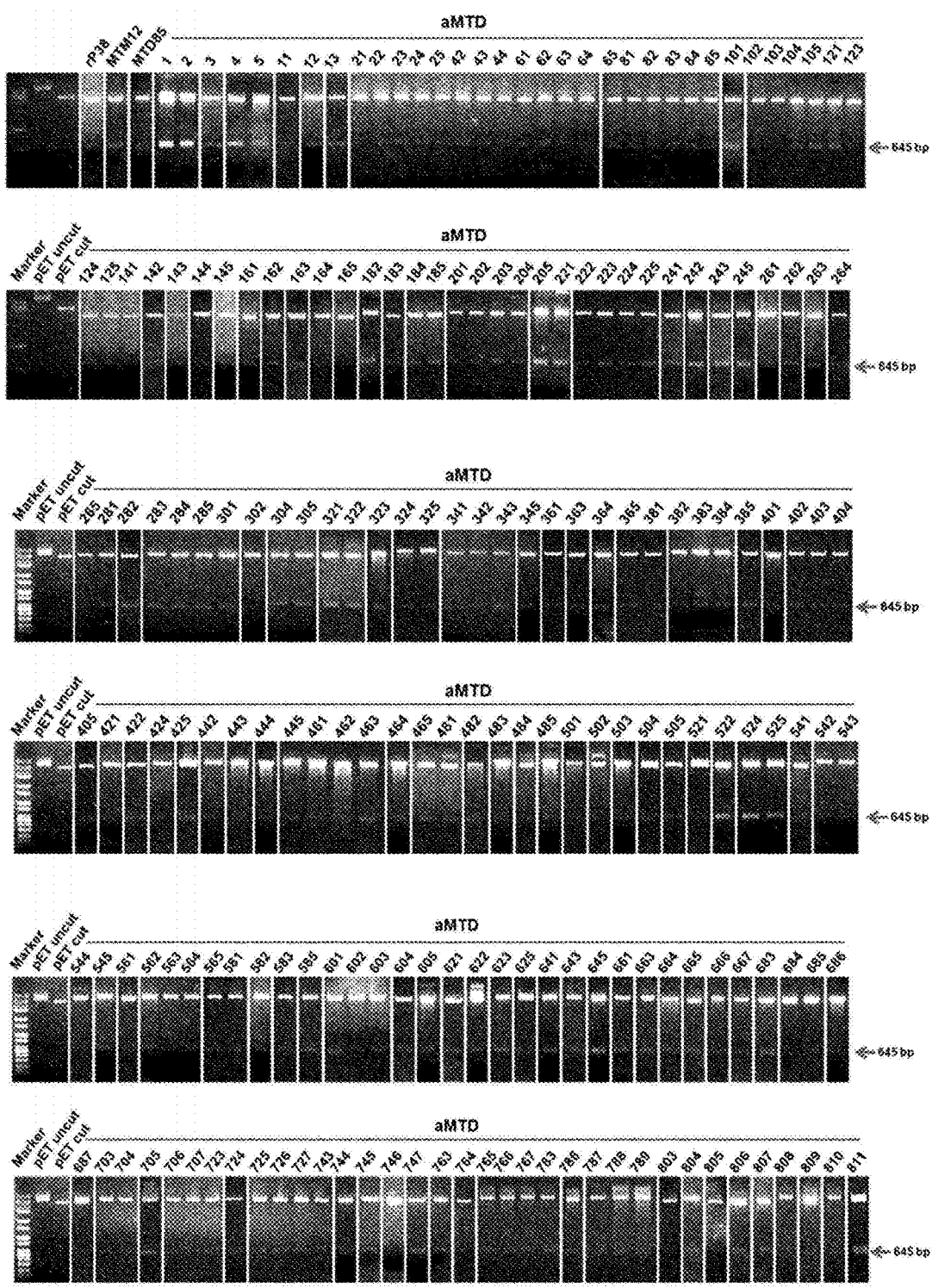

【Figure 2c】
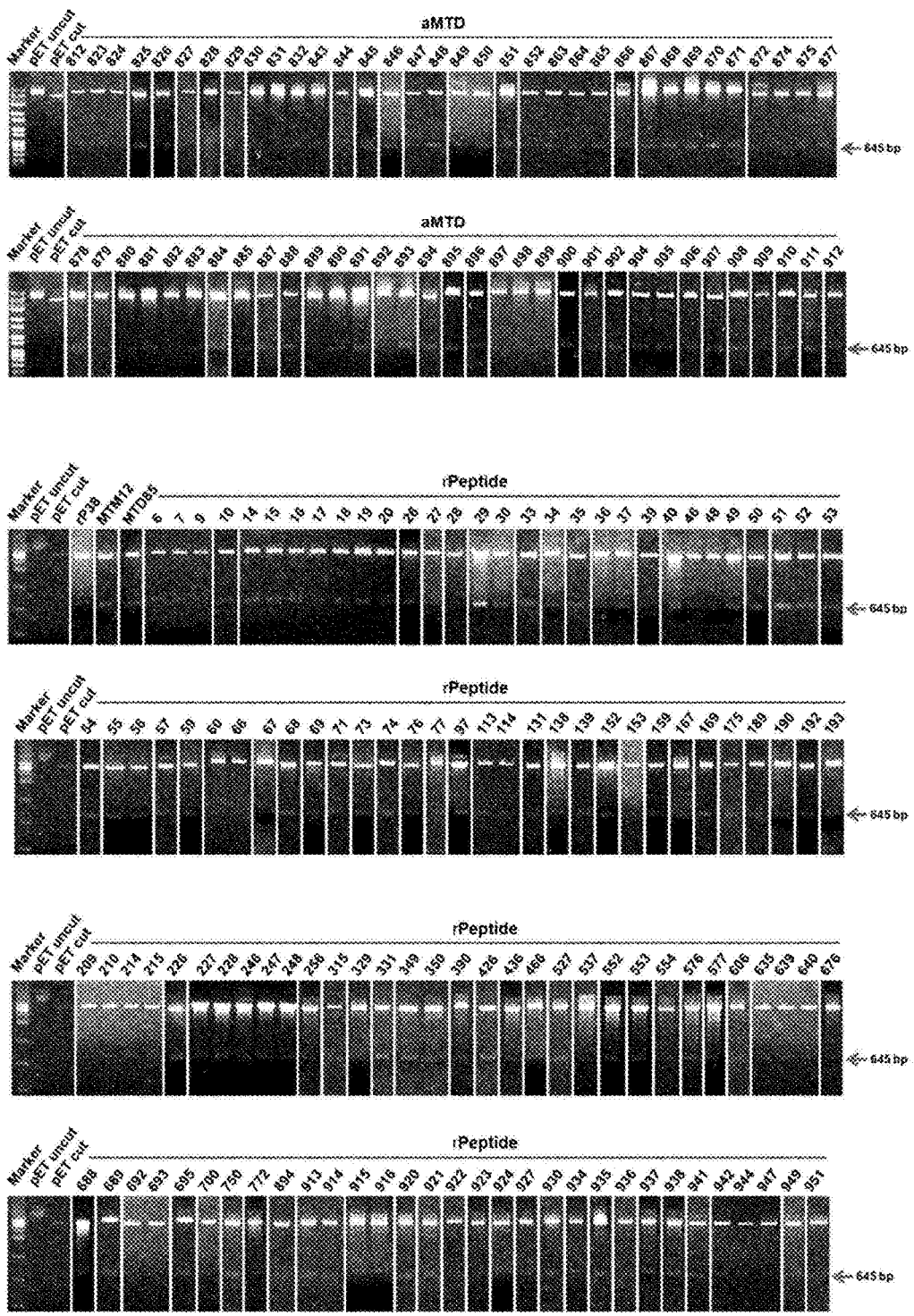

[Figure 3a]
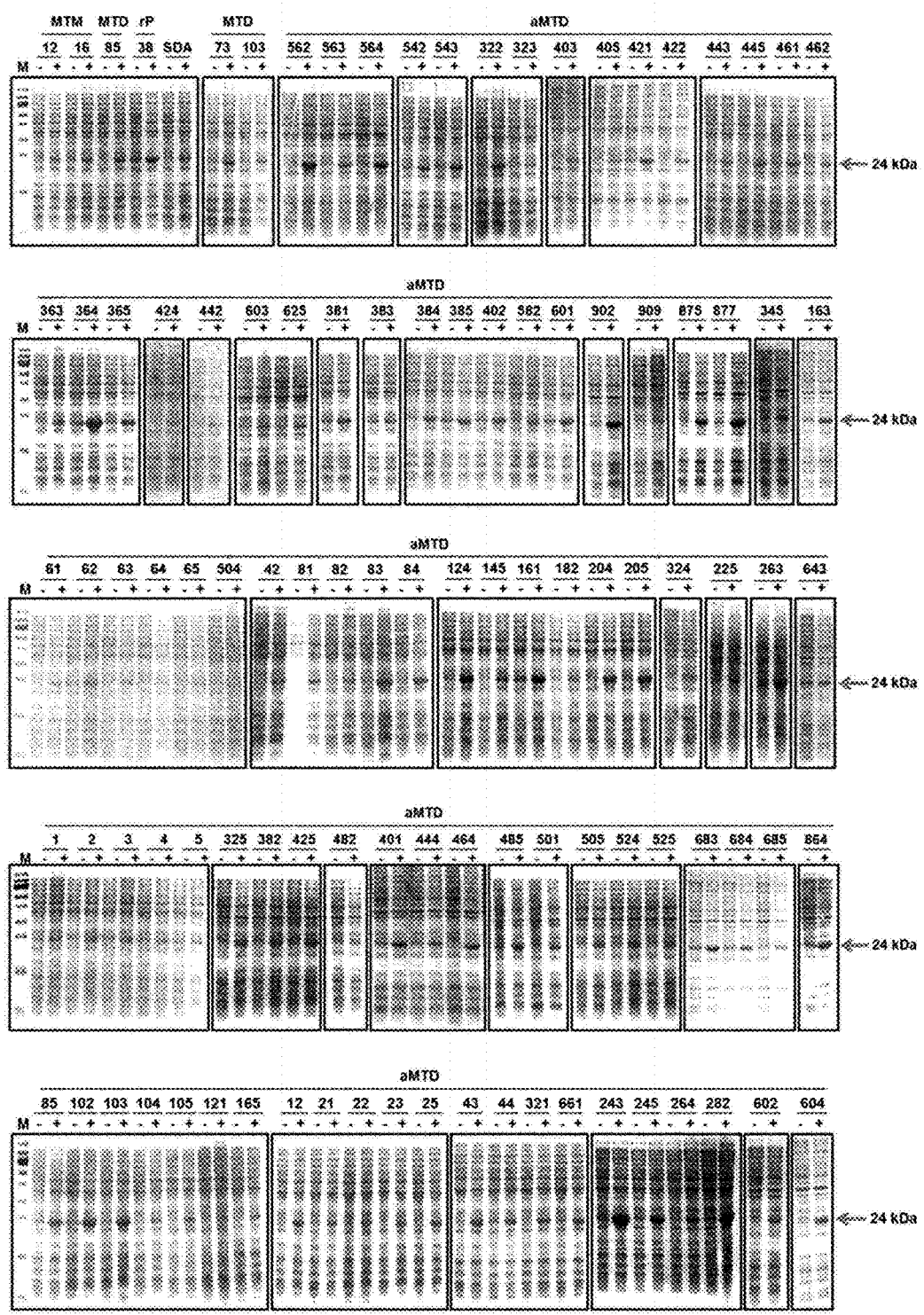

【Figure 3b】
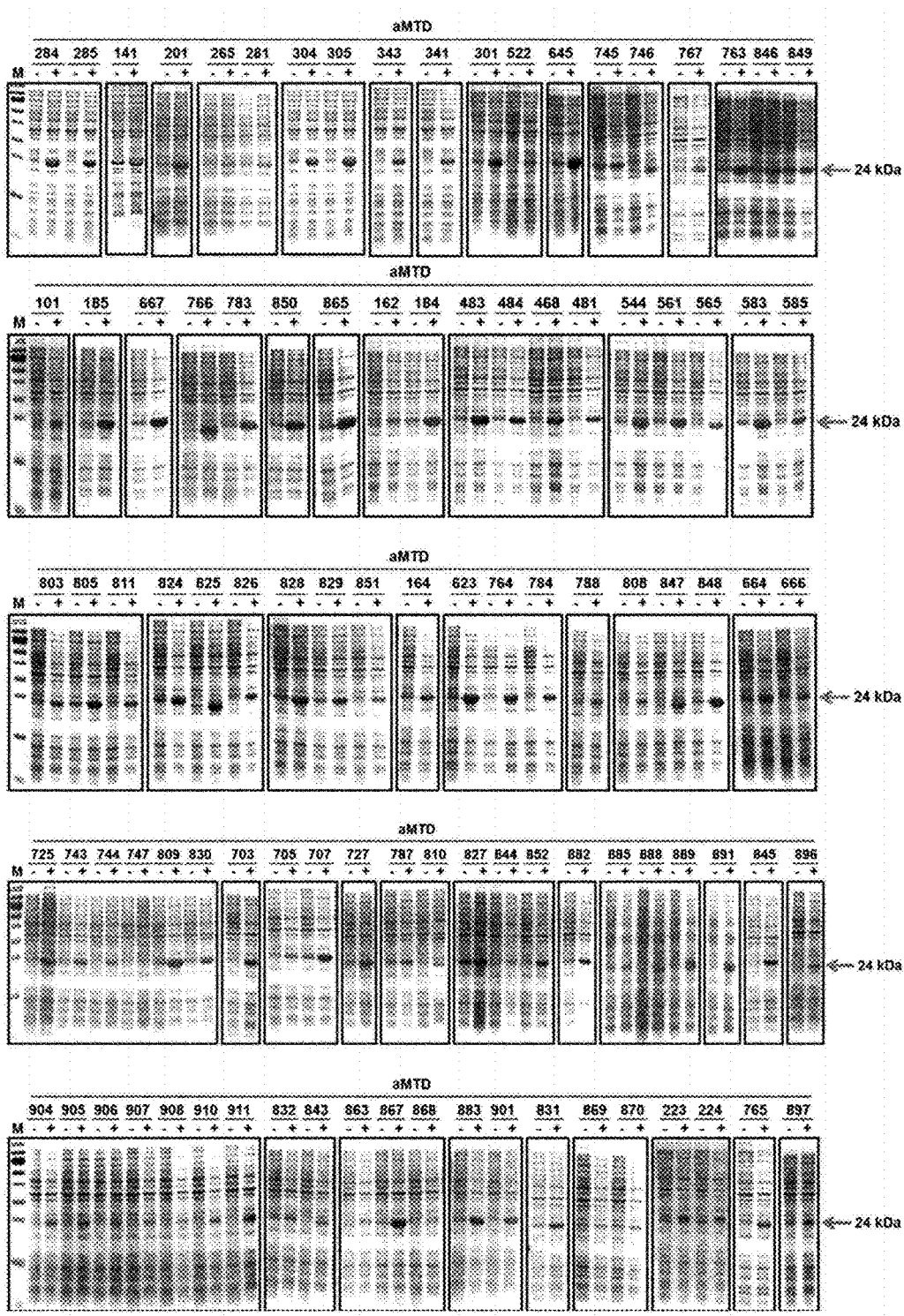

[Figure 3c]
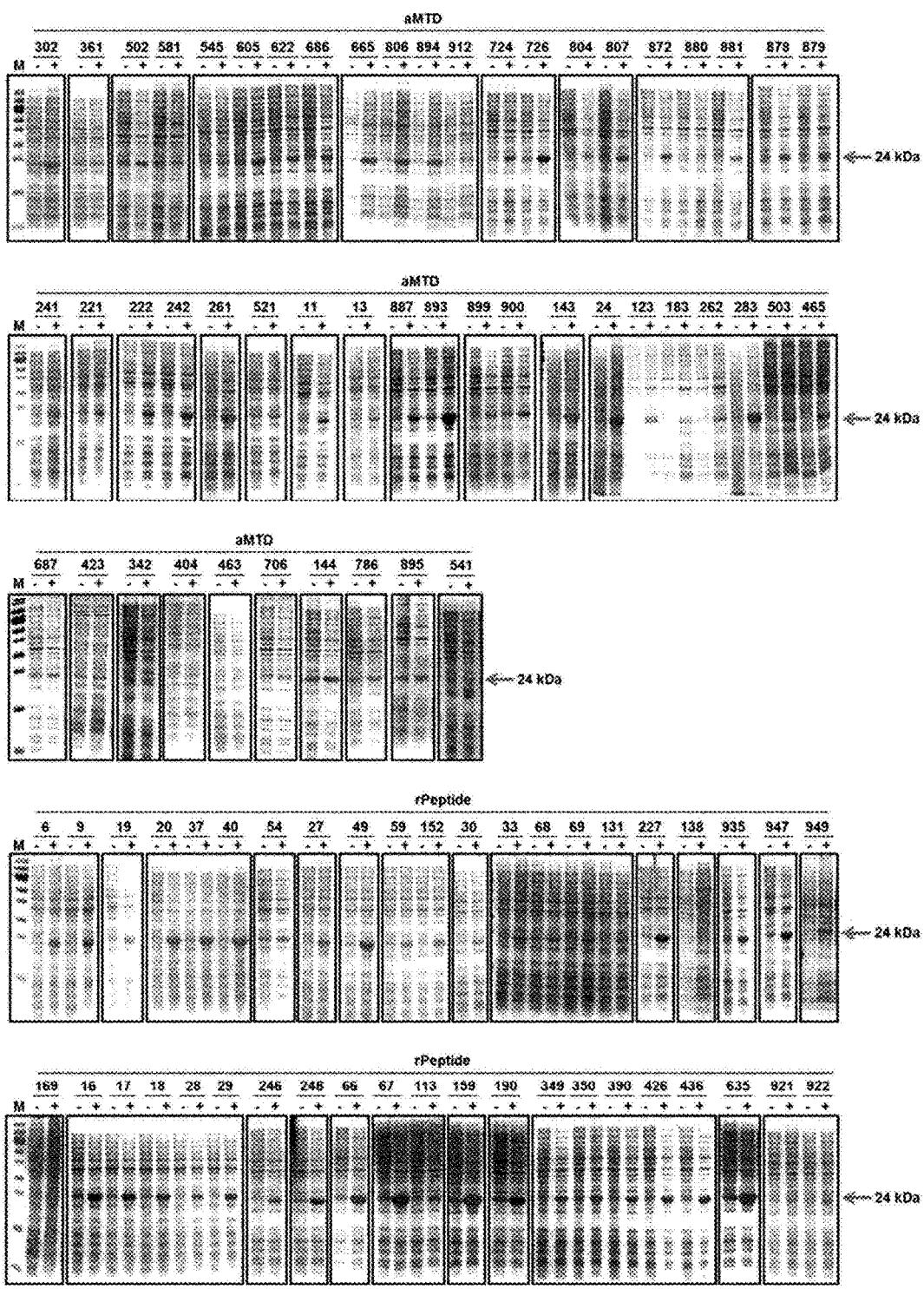

【Figure 3d】
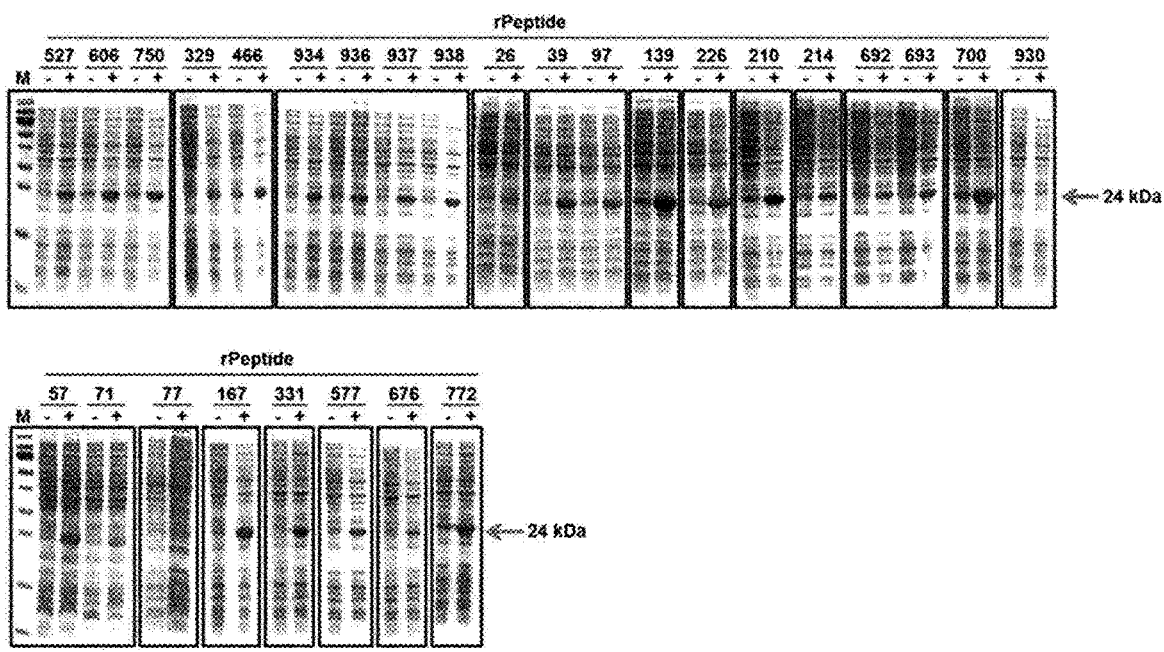

[Figure 4a]
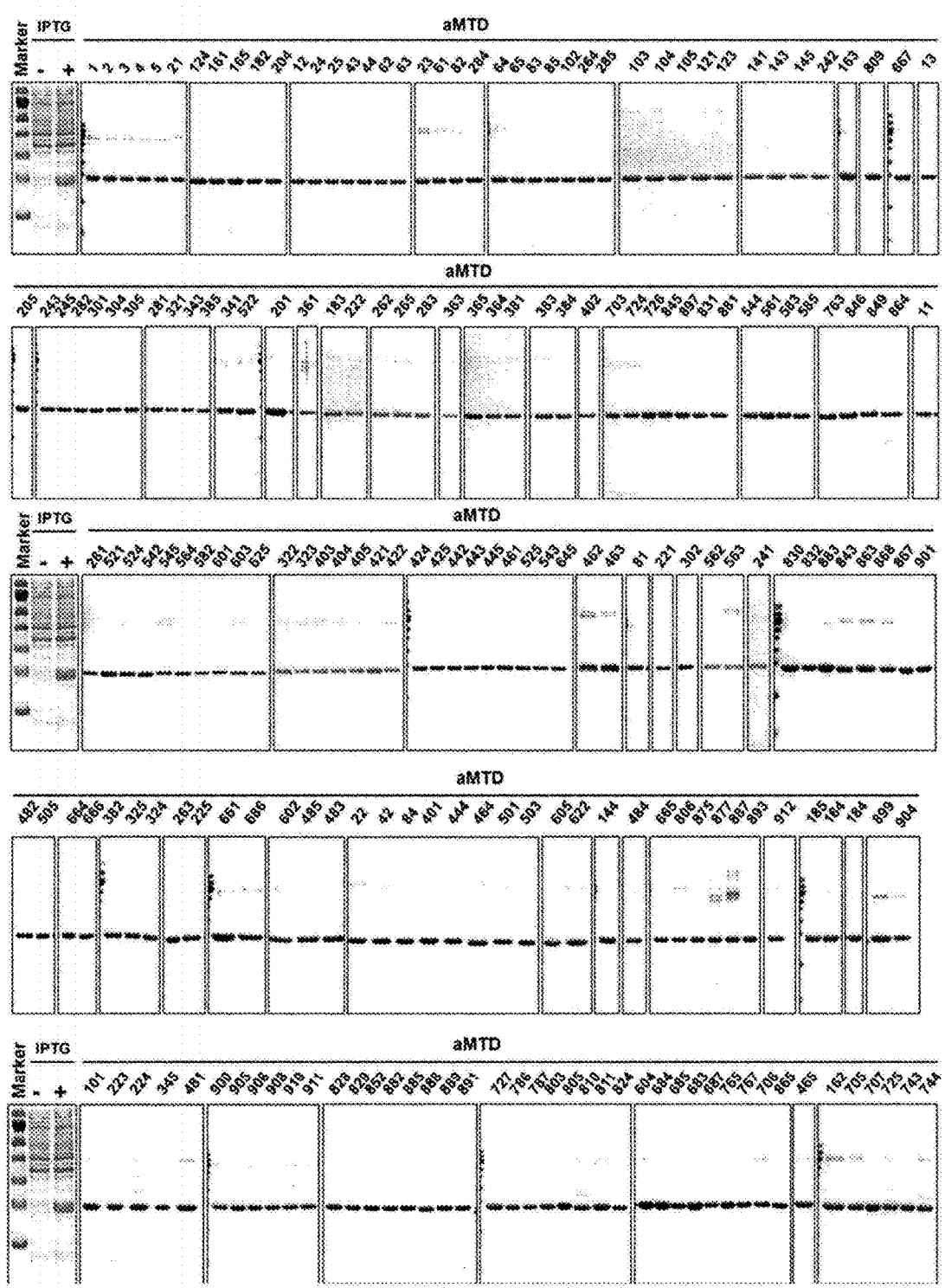

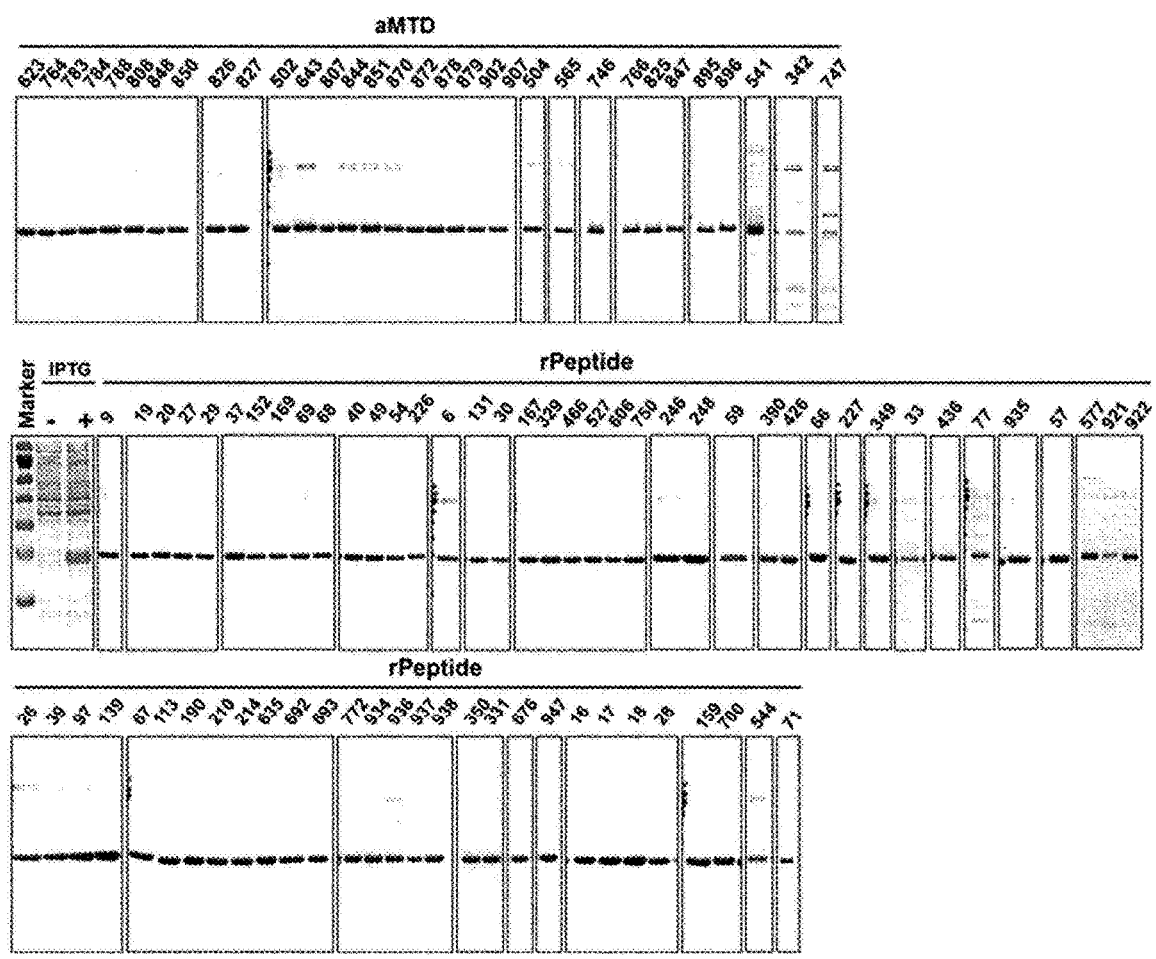
[Figure 4b]

【Figure 5a】
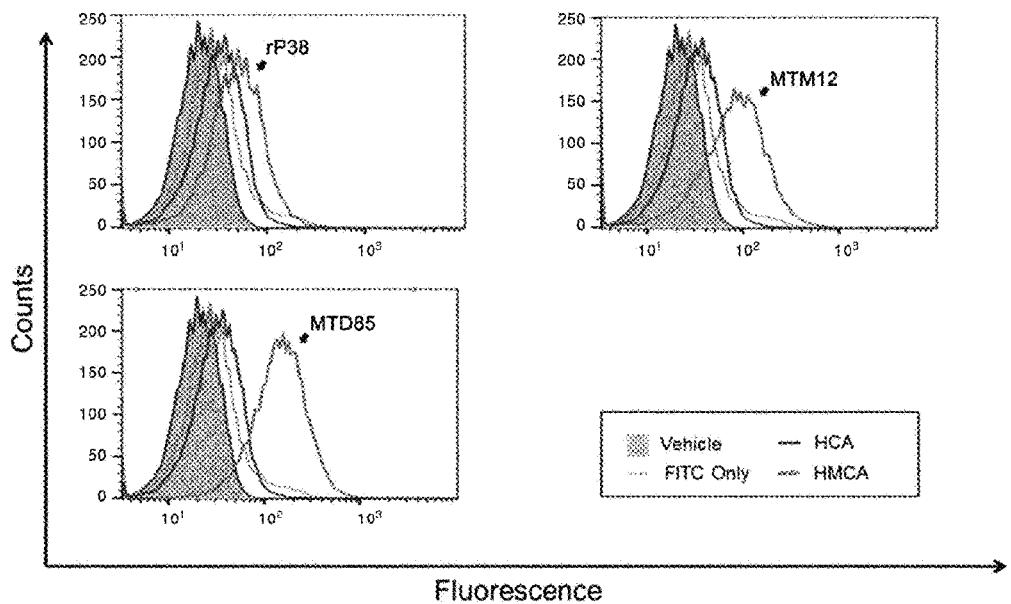
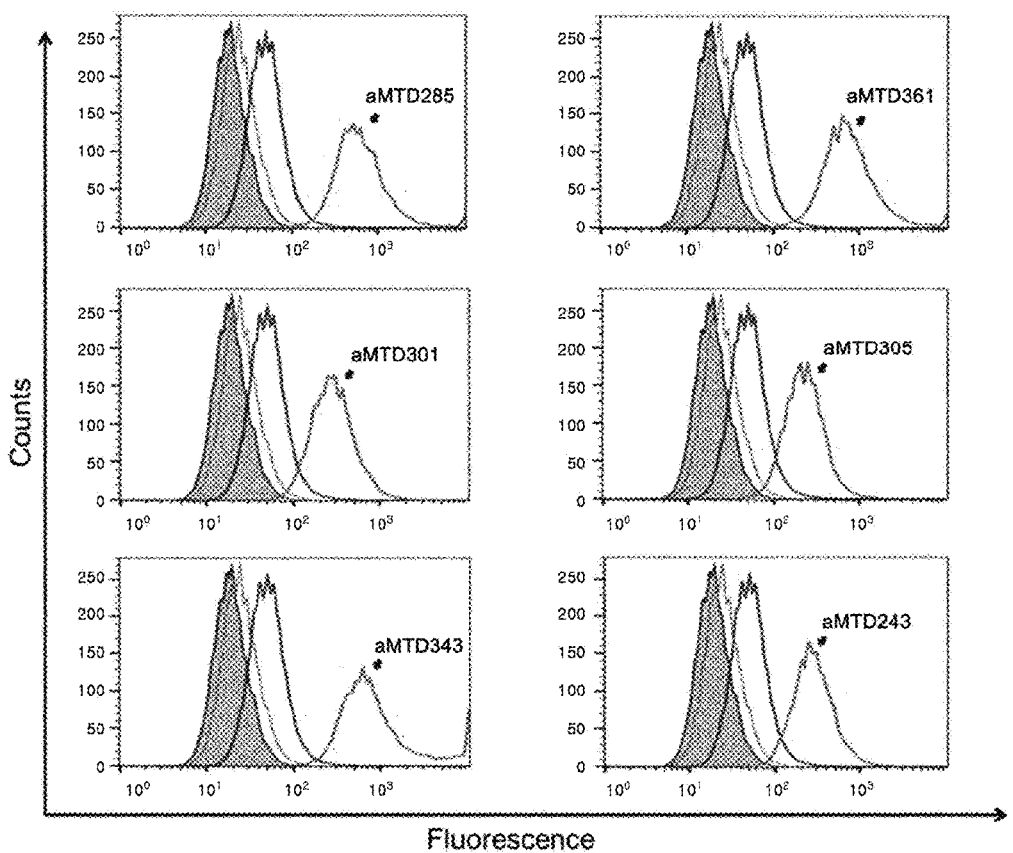

[Figure 5b]
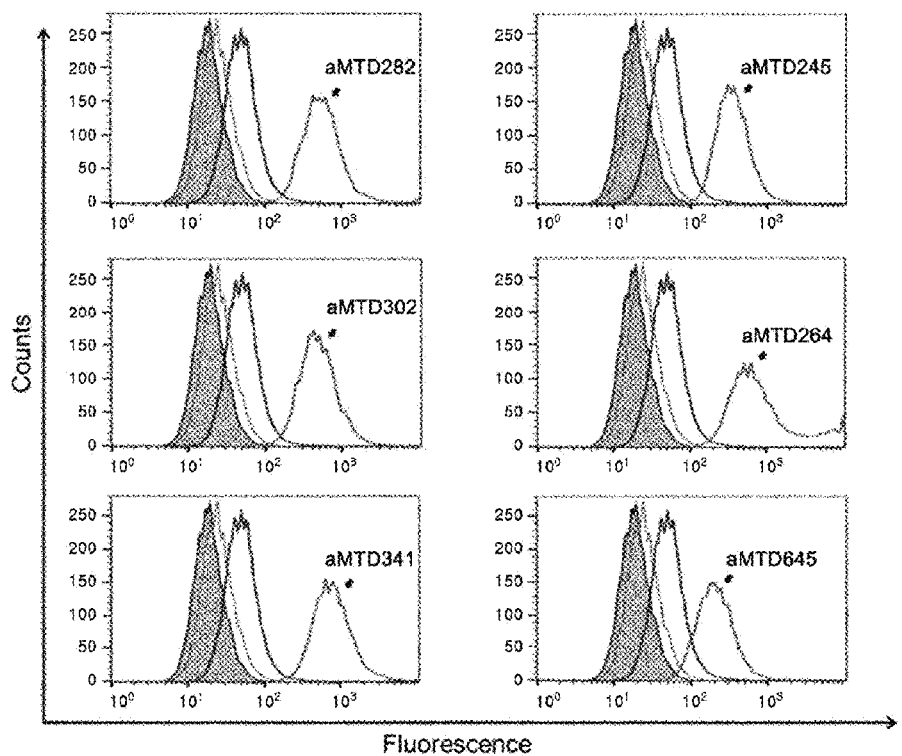
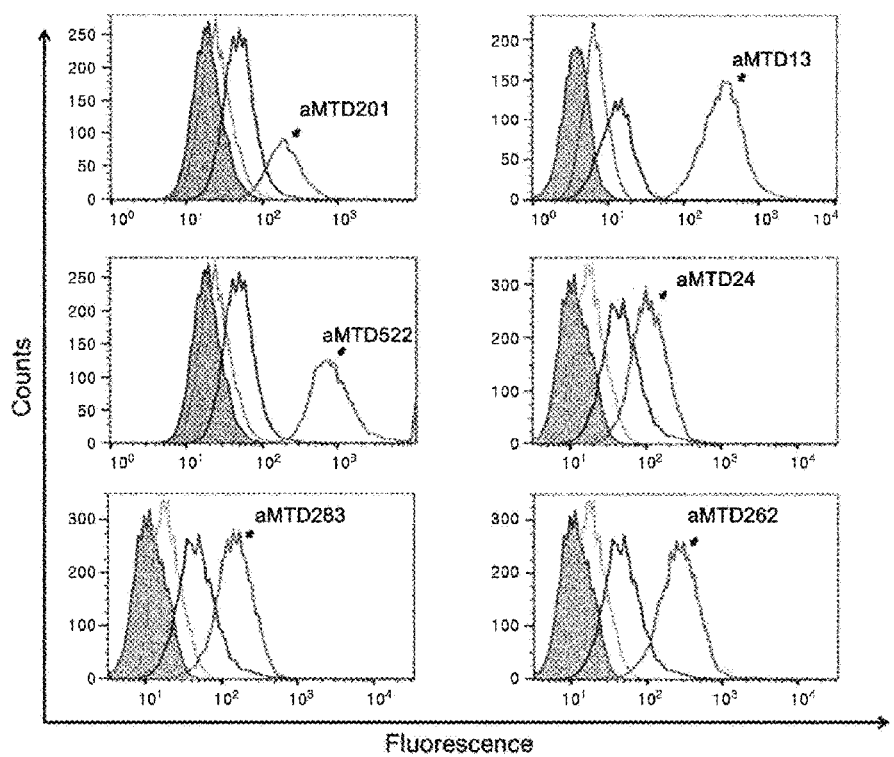

[Figure 5c]
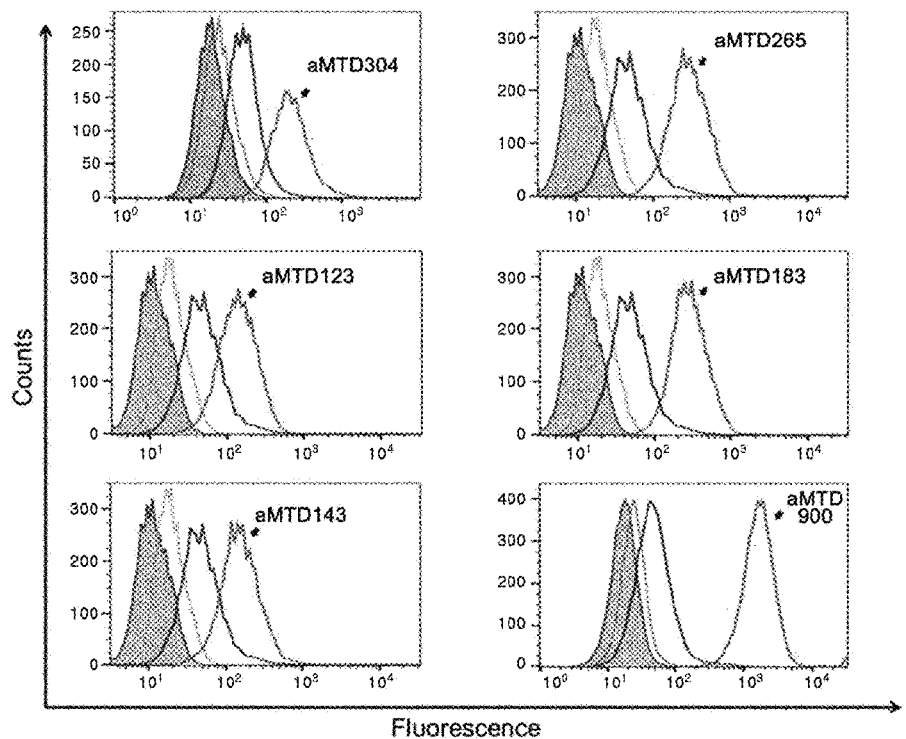
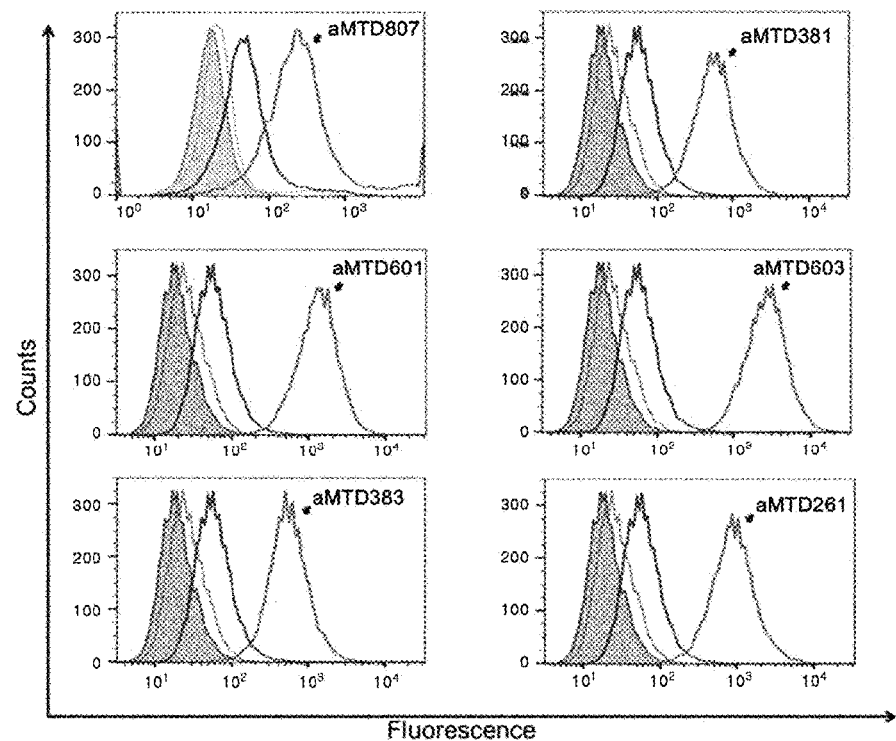

[Figure 5d]
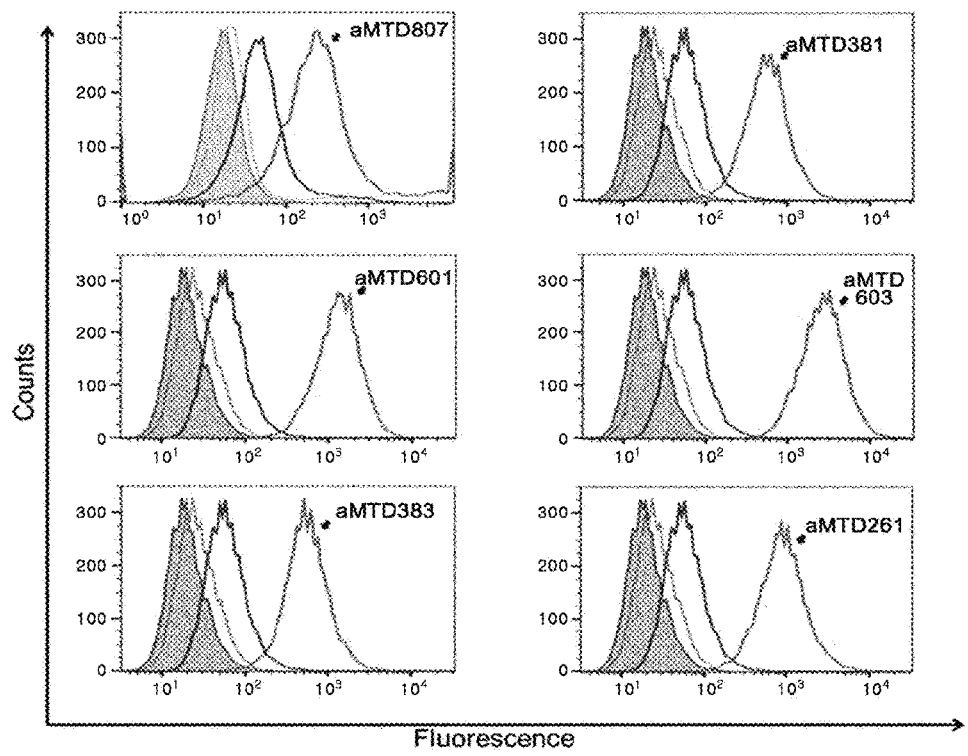
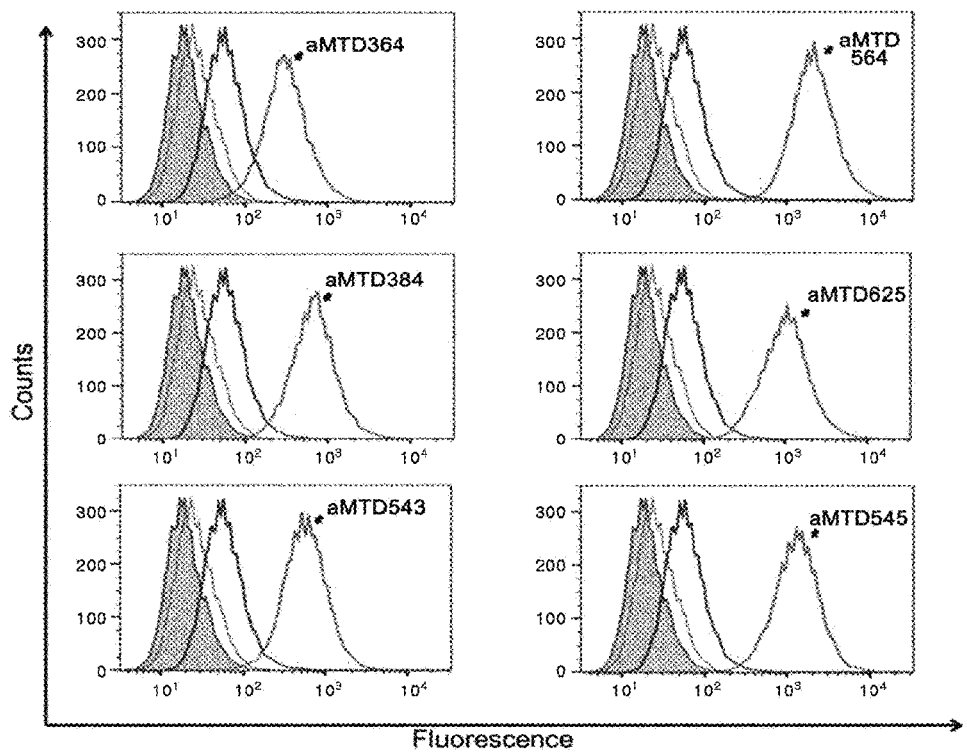

【Figure 5e】
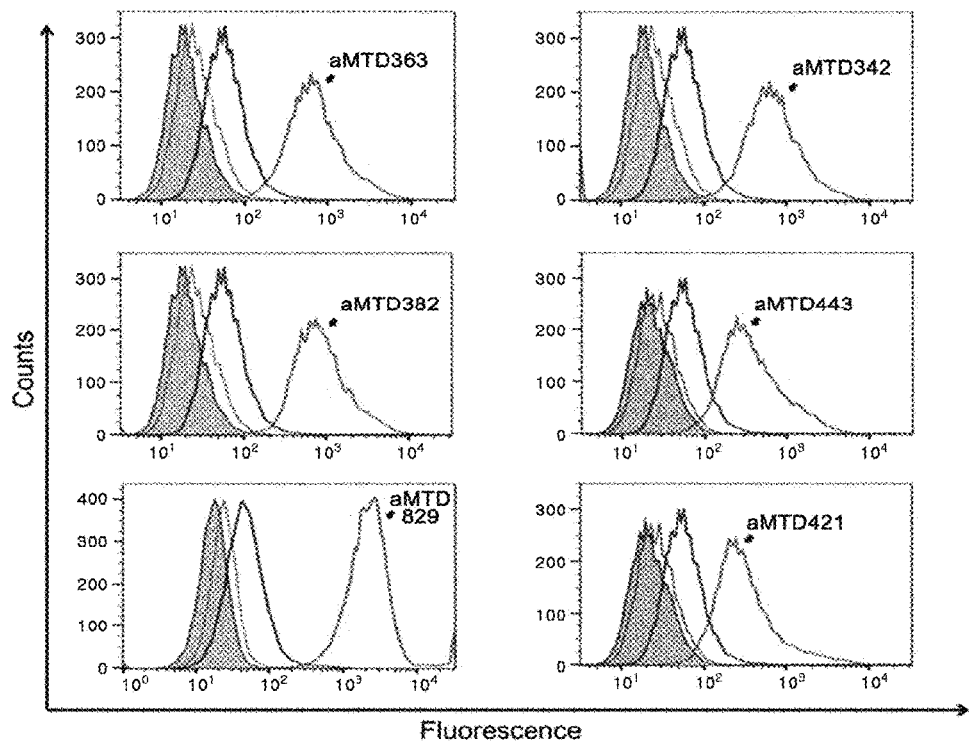
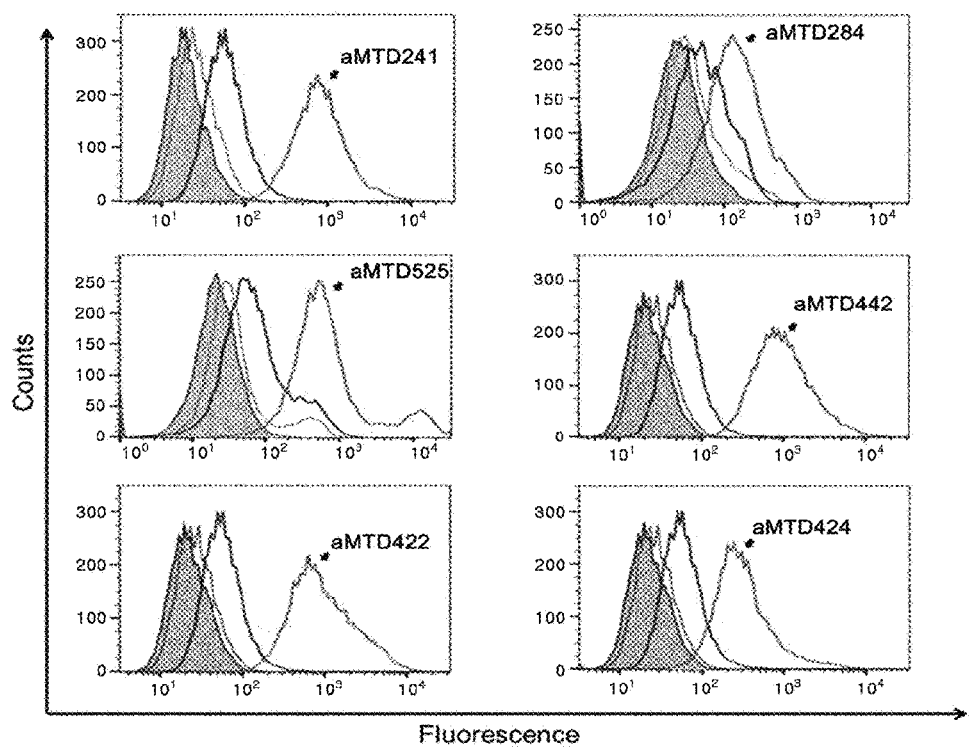

【Figure 5f】
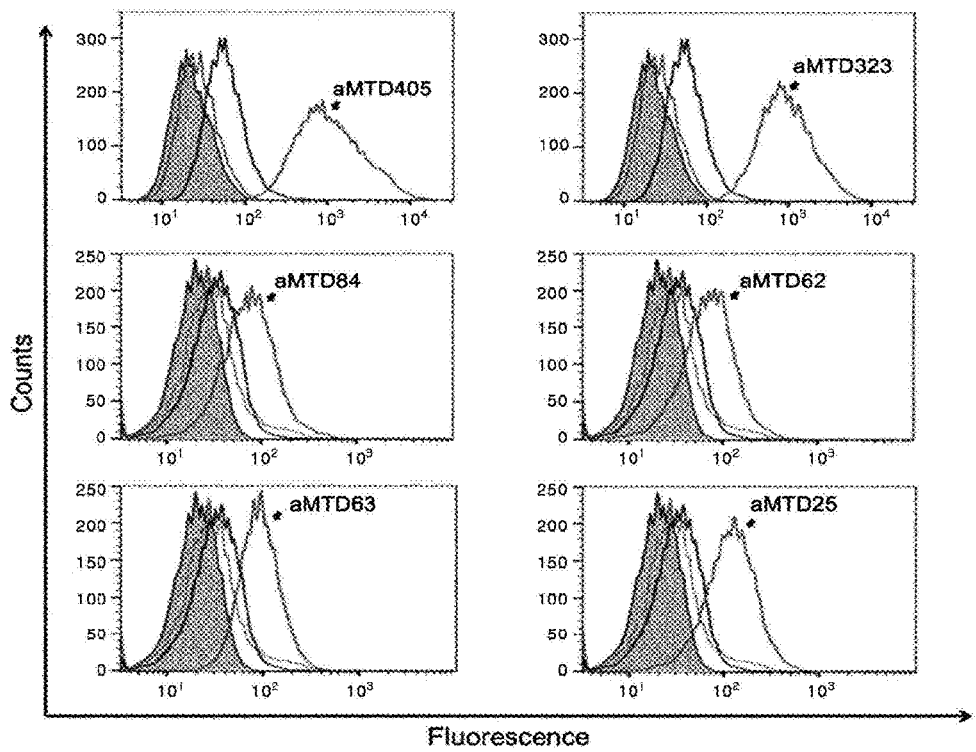
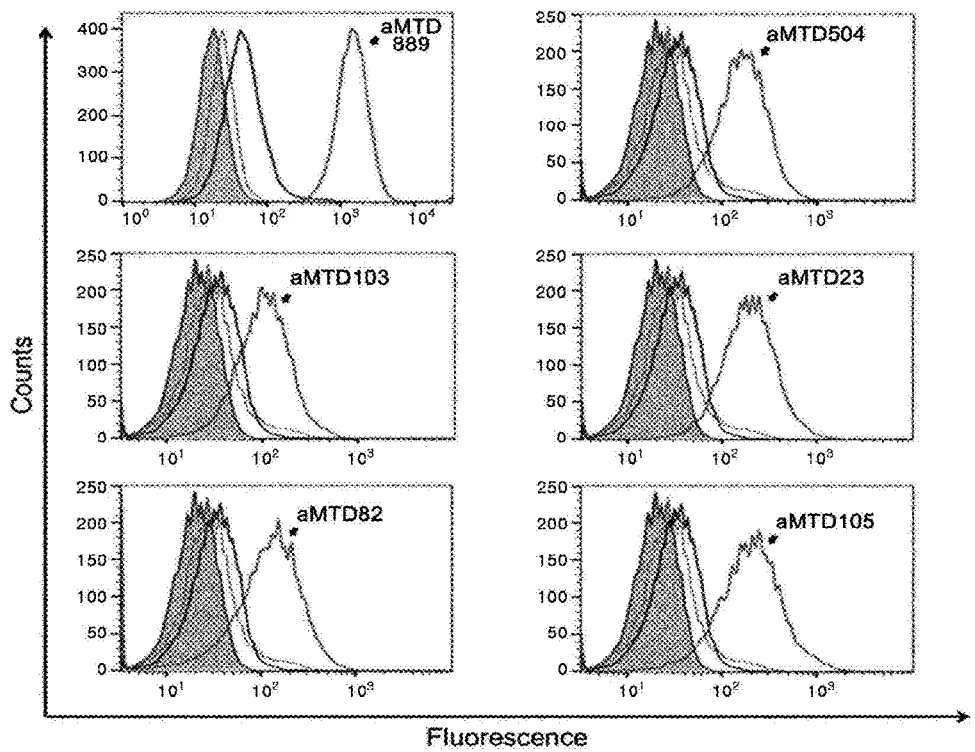

[Figure 5g]
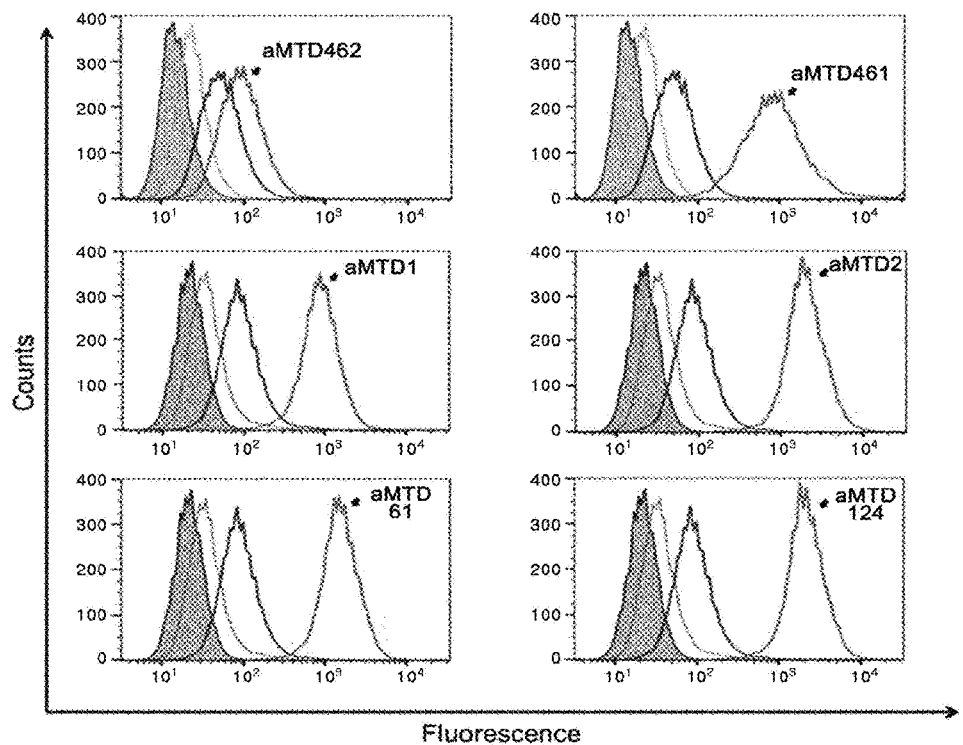
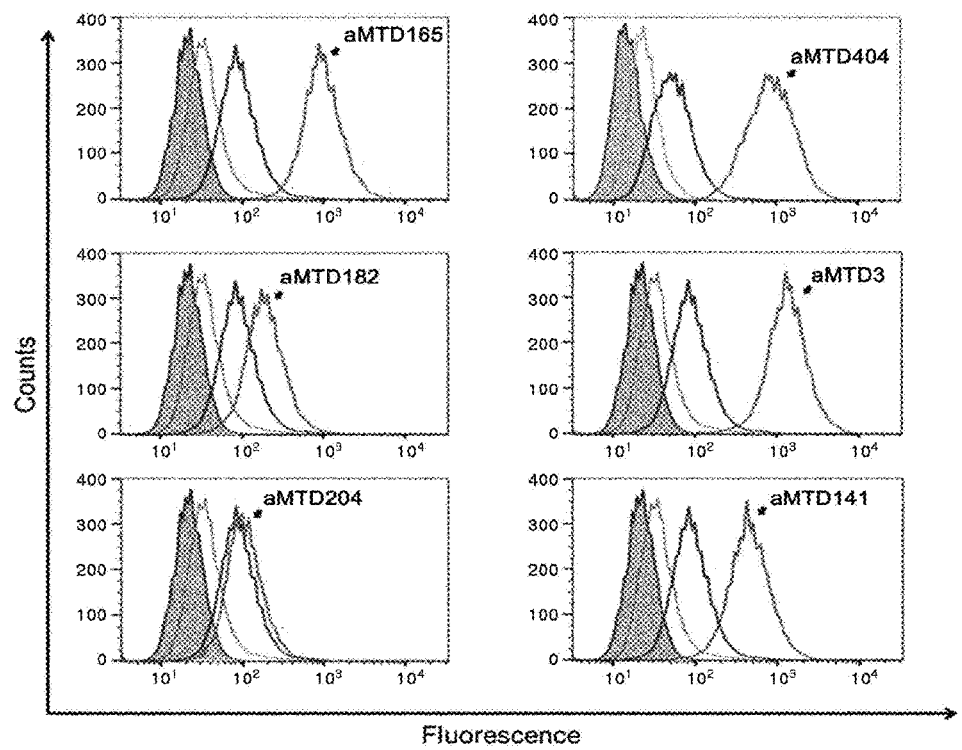

【Figure 5h】
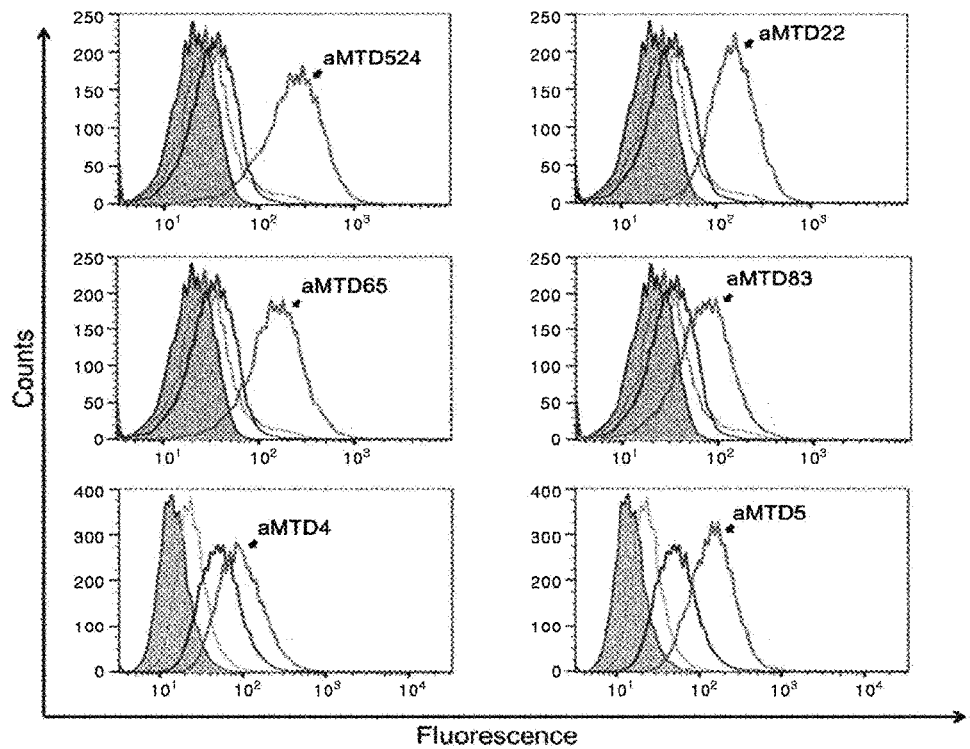
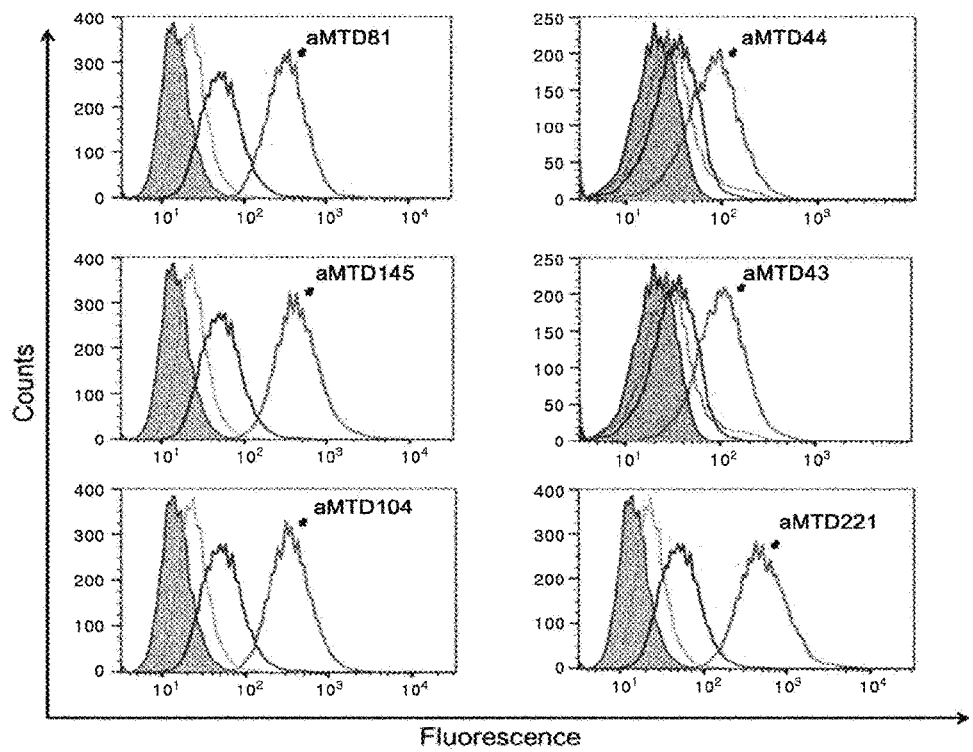

【Figure 5i】
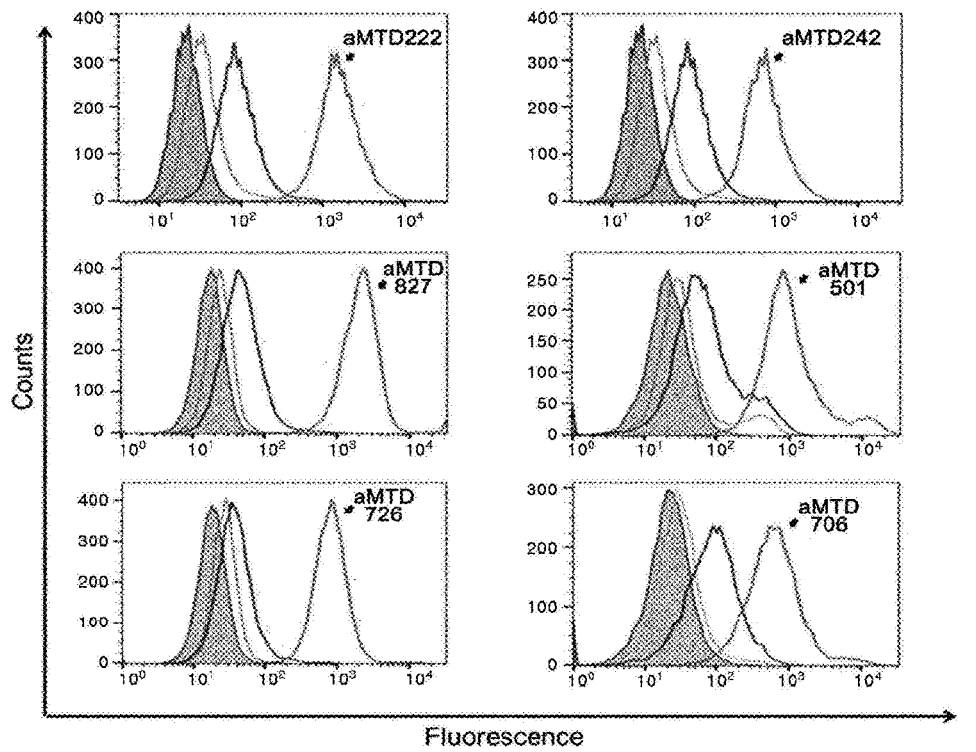
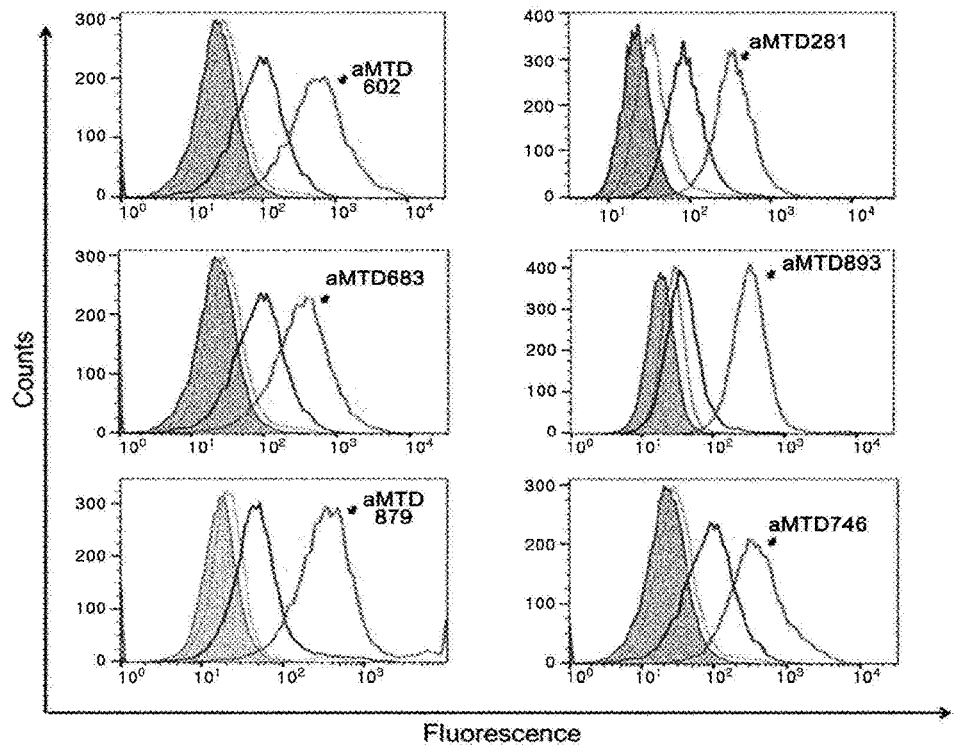

【Figure 5j】
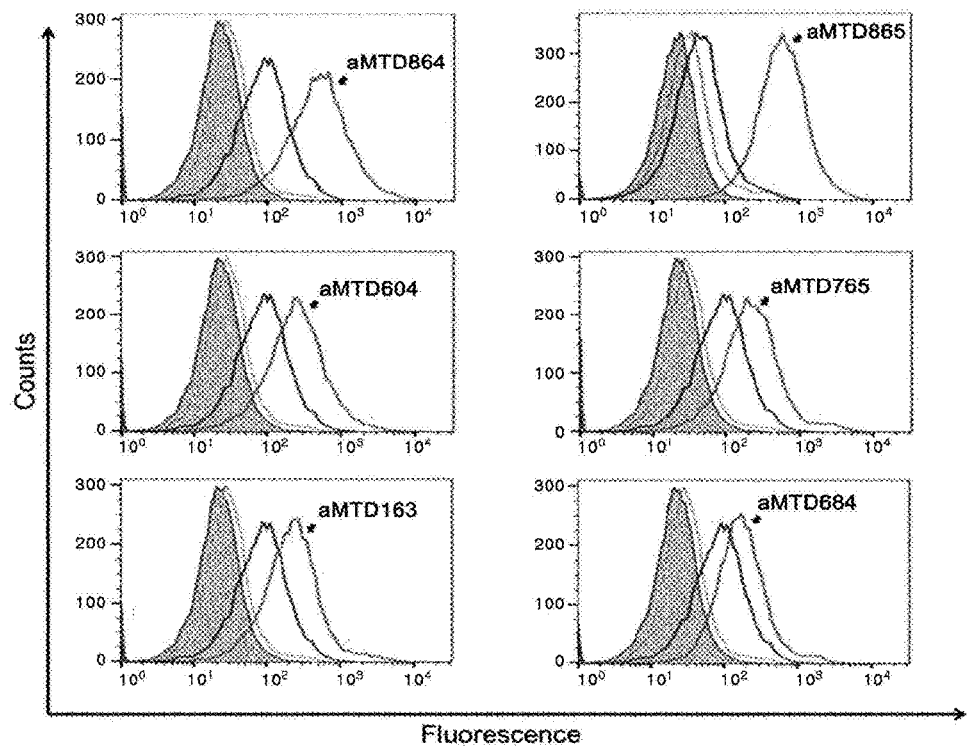
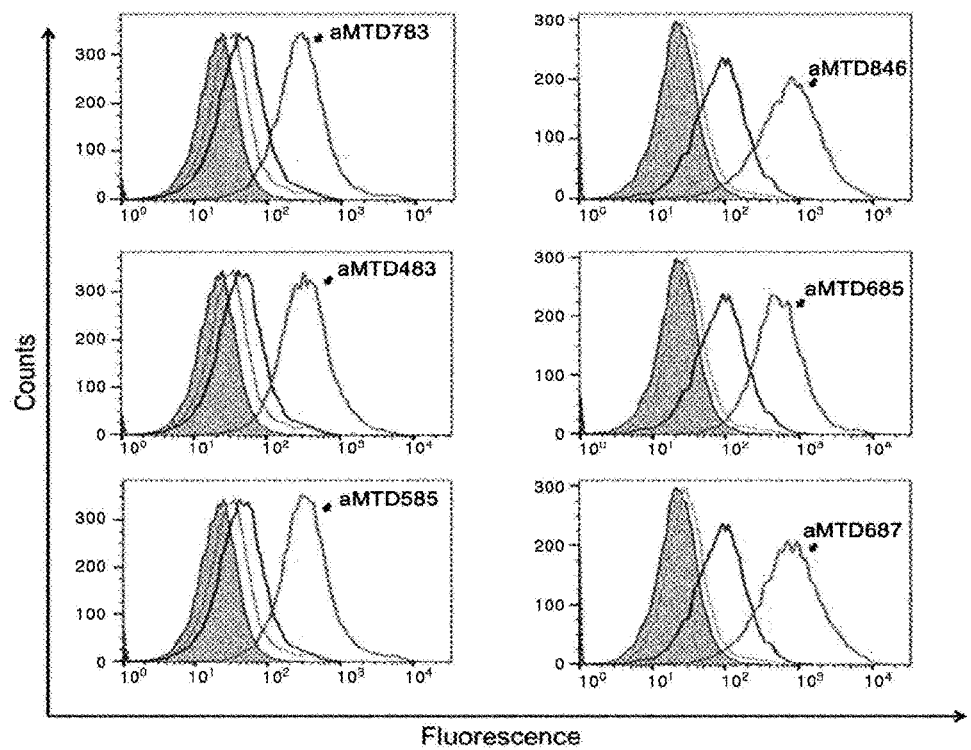

【Figure 5k】
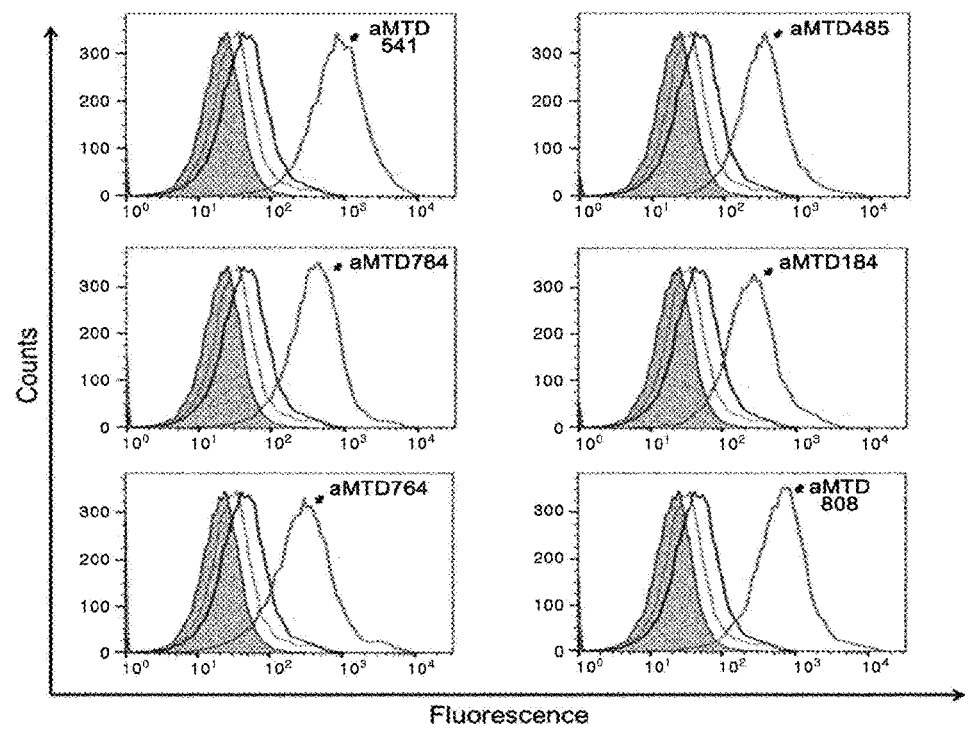
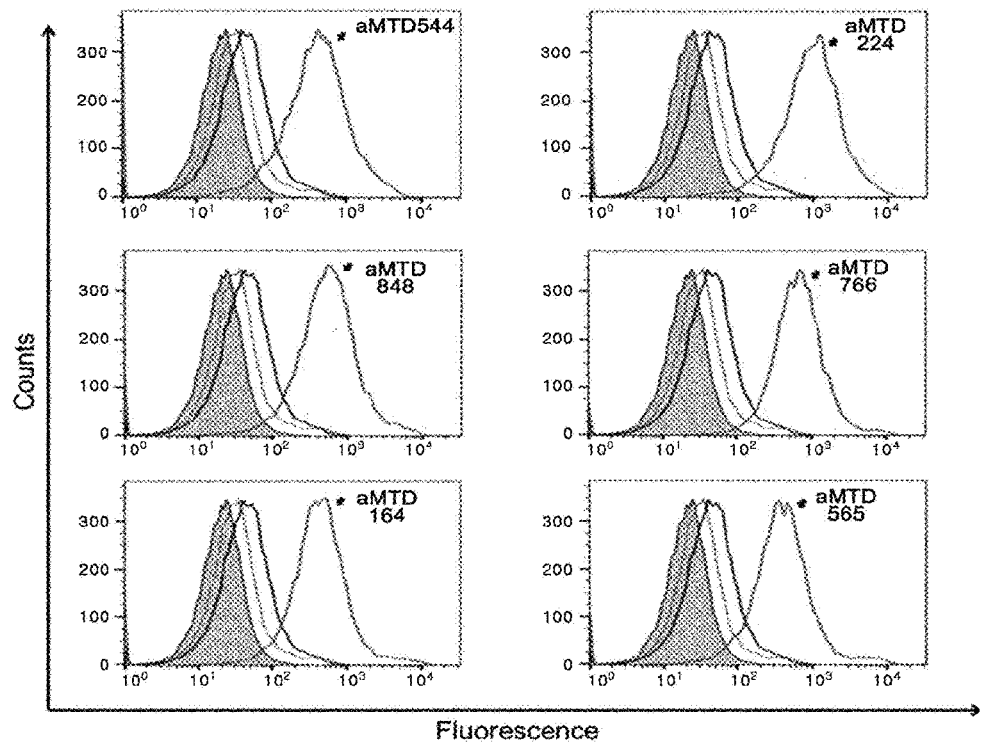

[Figure 51]
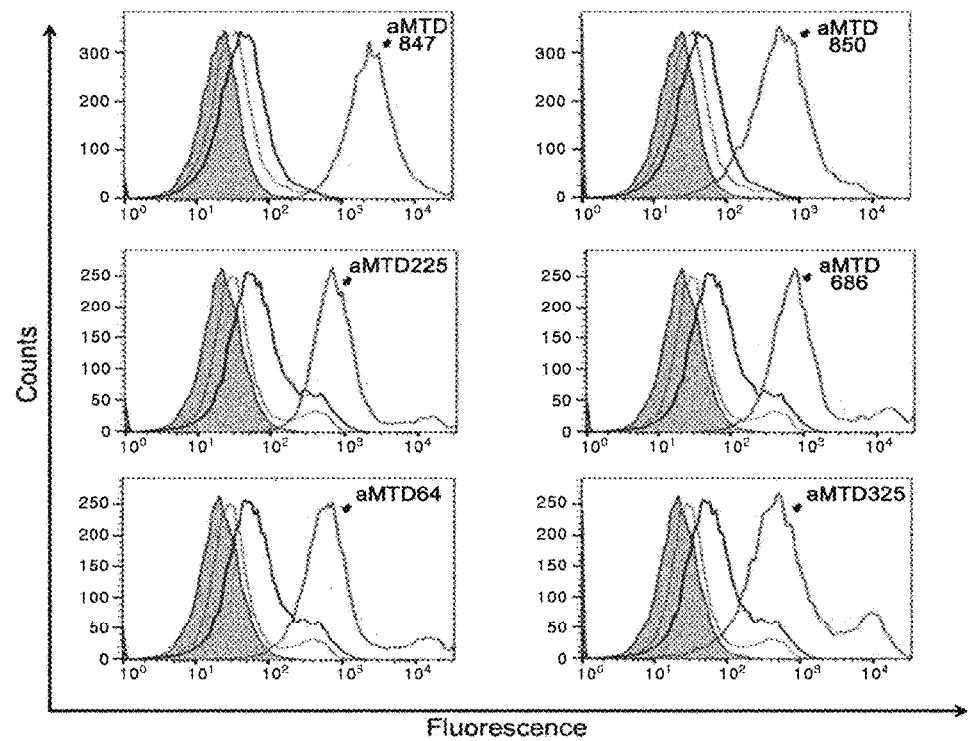
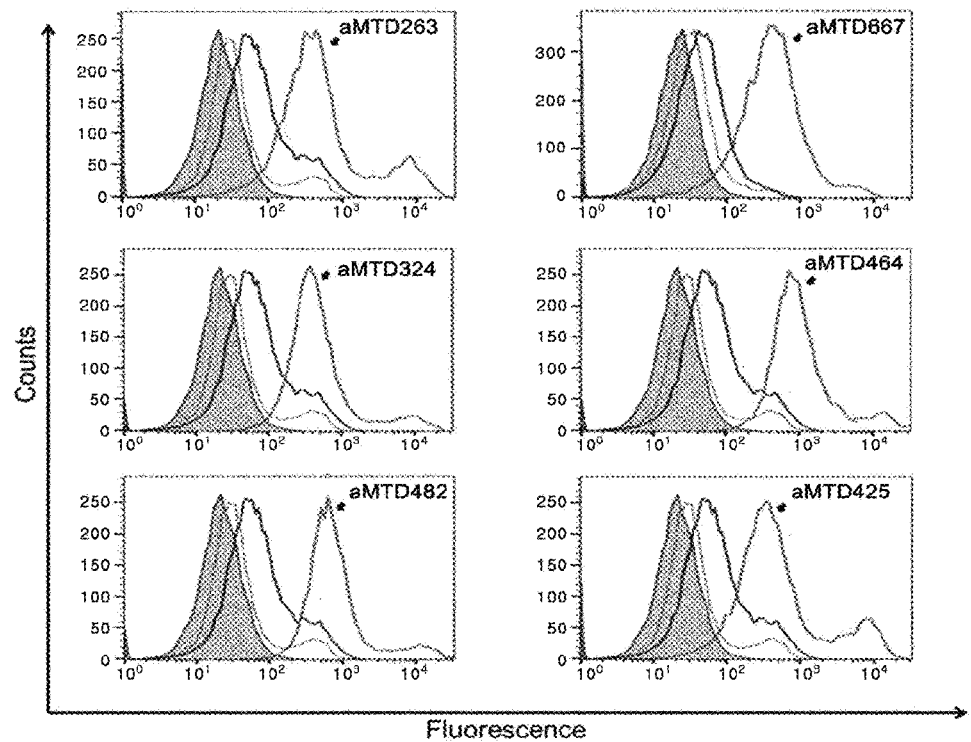

[Figure 5m]
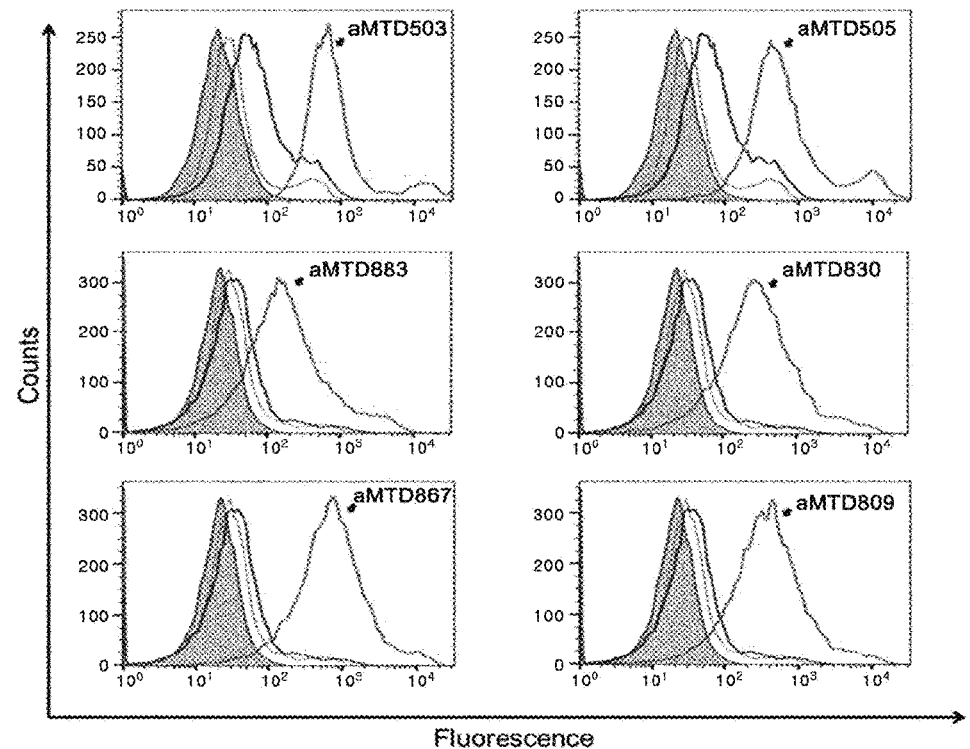
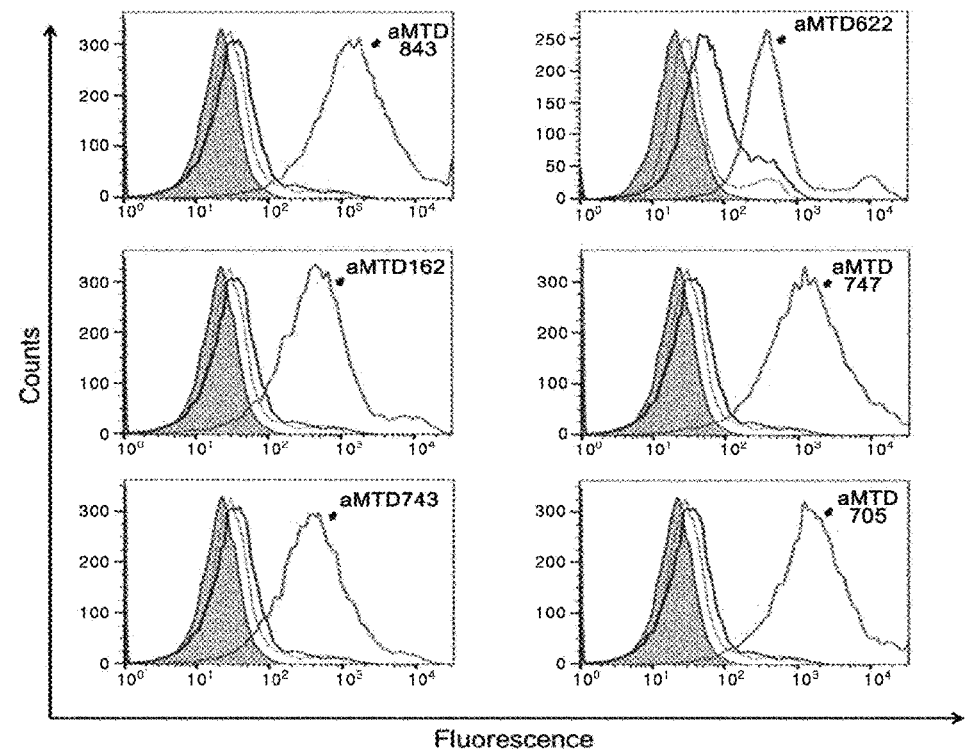

[Figure 5n]
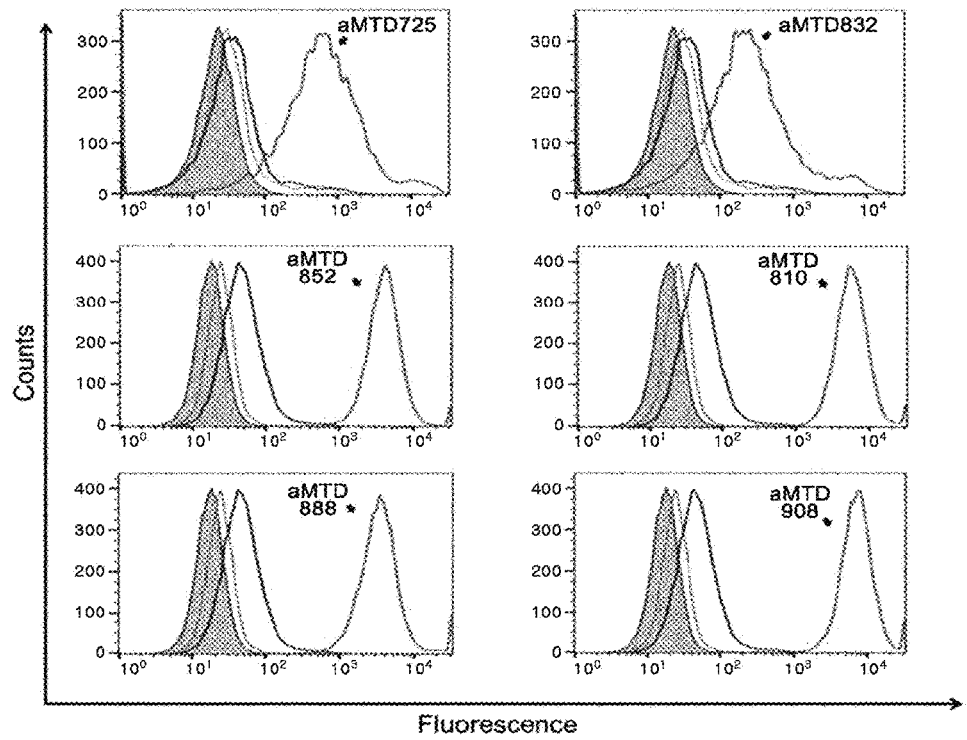
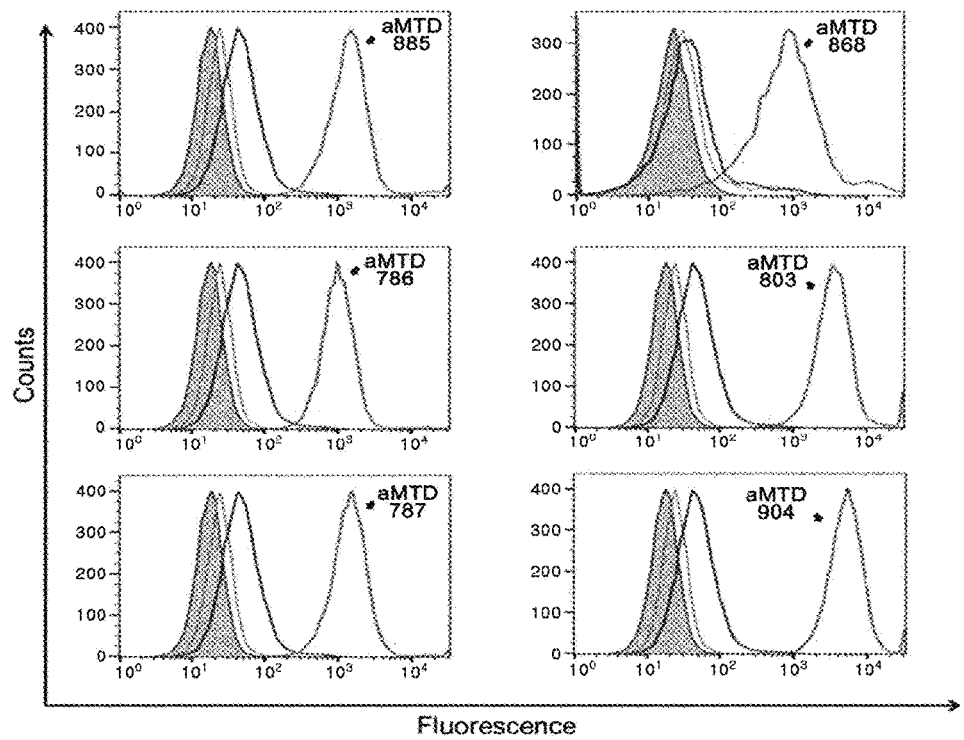

[Figure 5o]
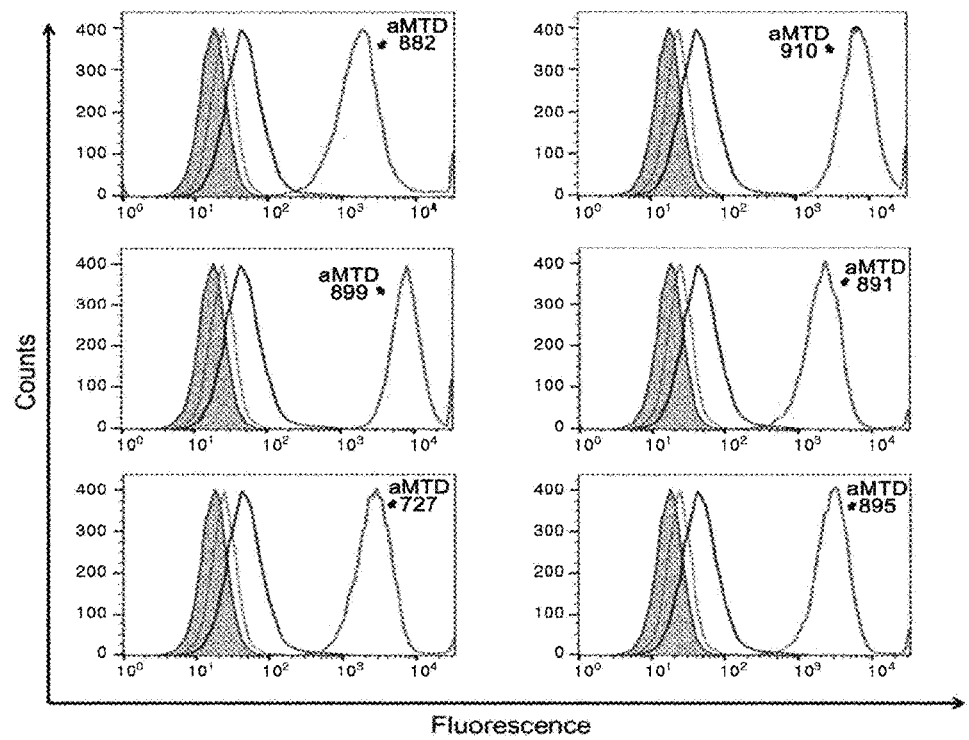
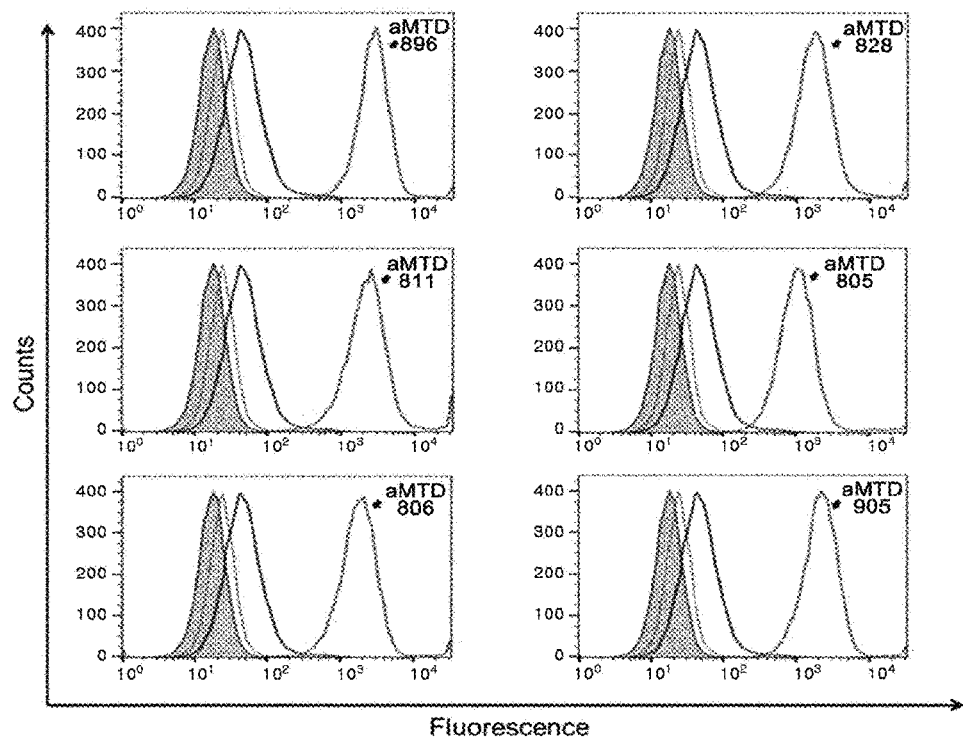

【Figure 5p】
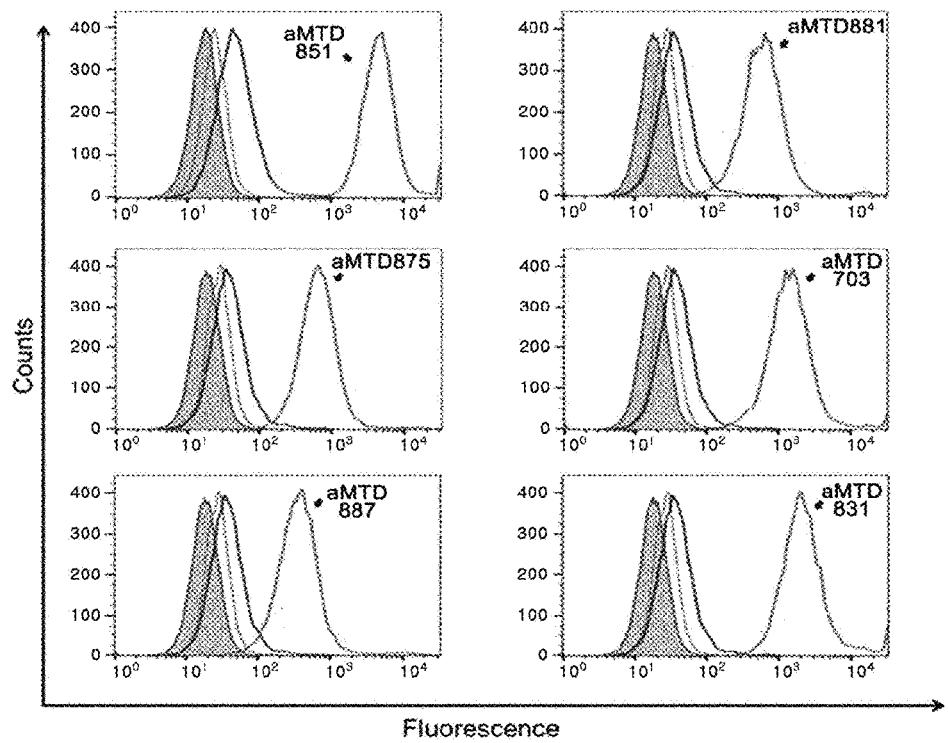
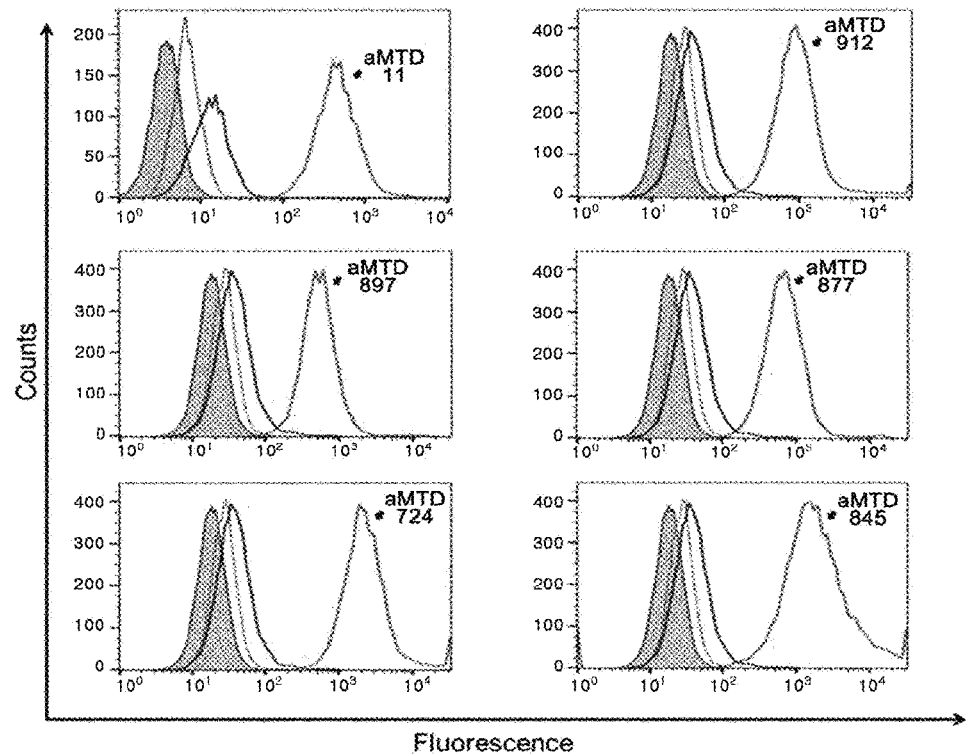

[Figure 5q]
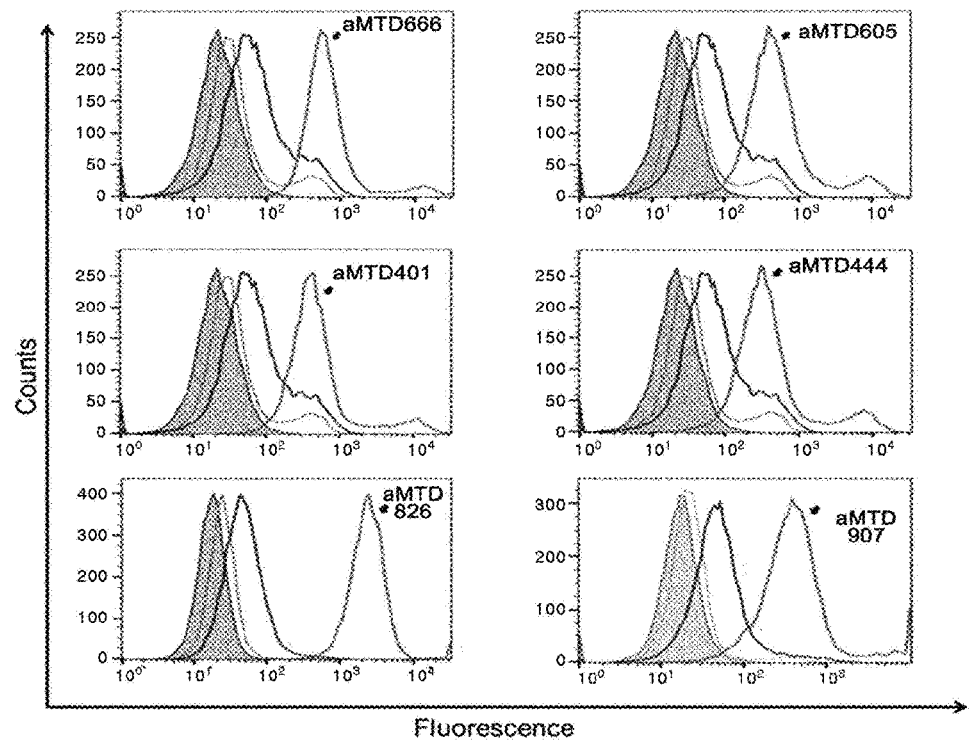
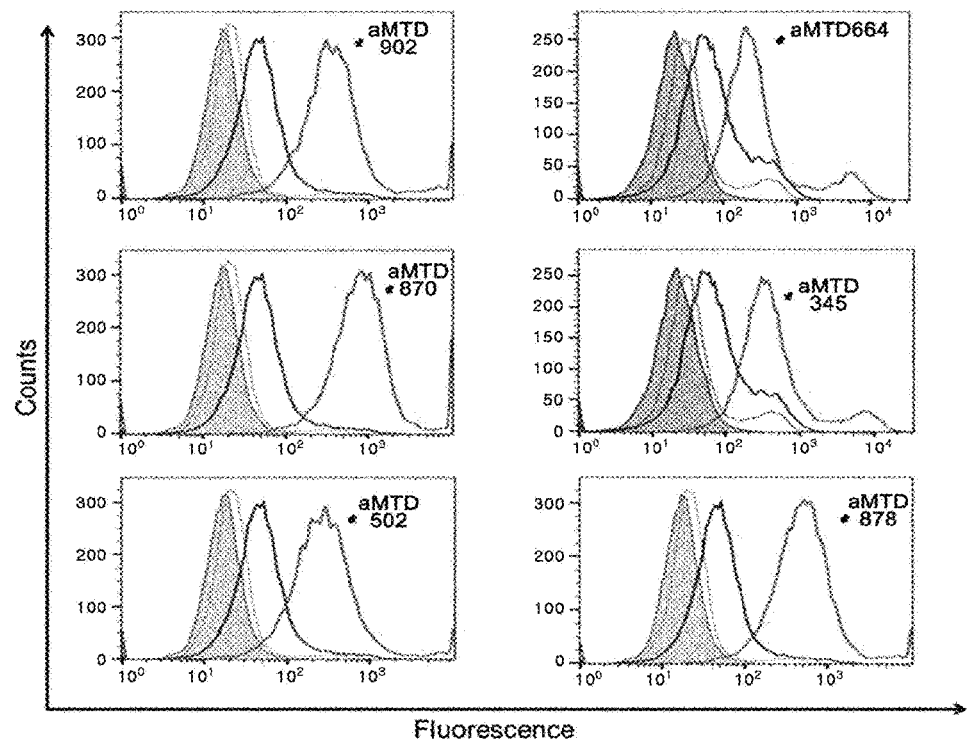

[Figure 5r]
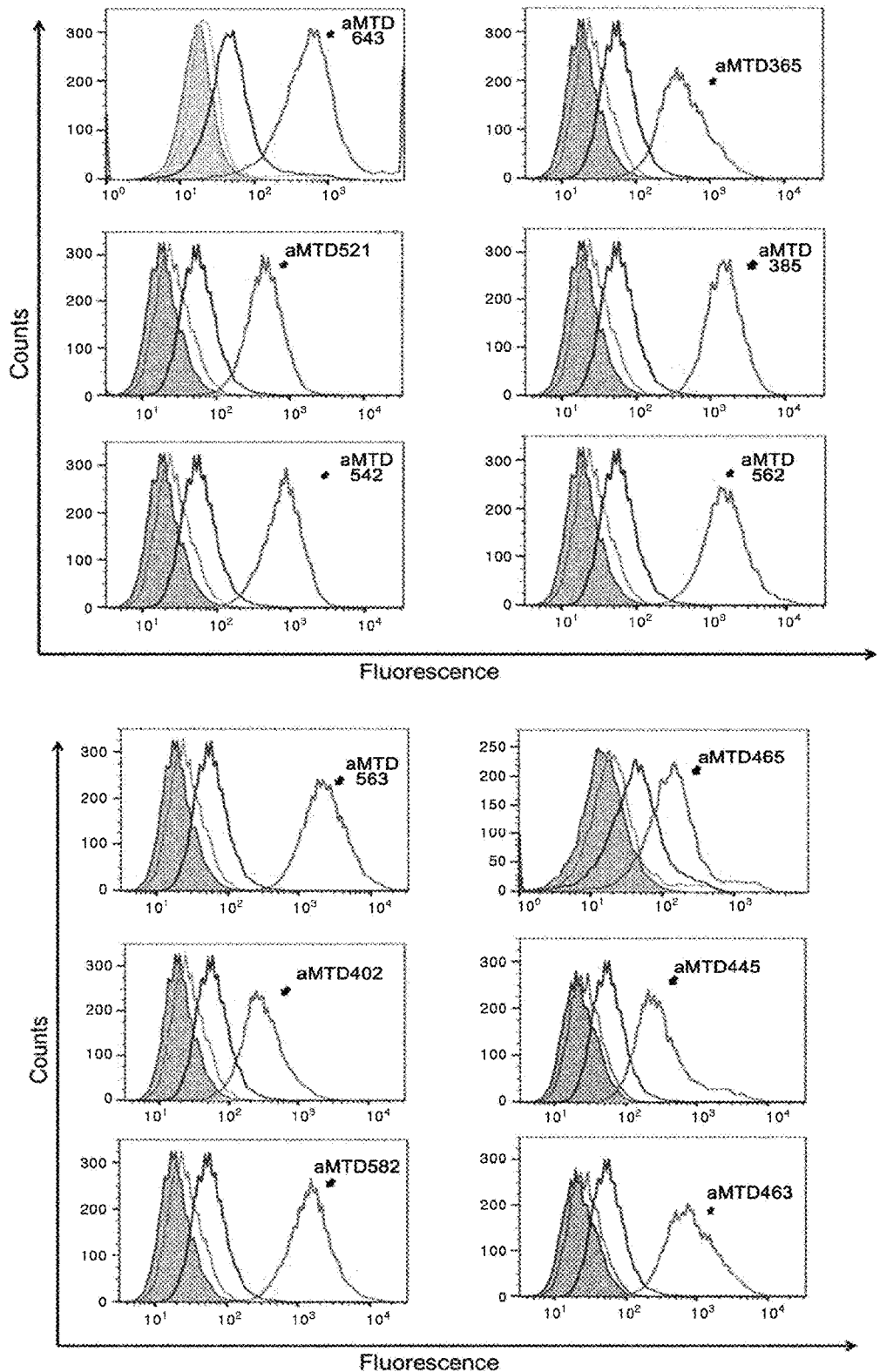

[Figure 5s]
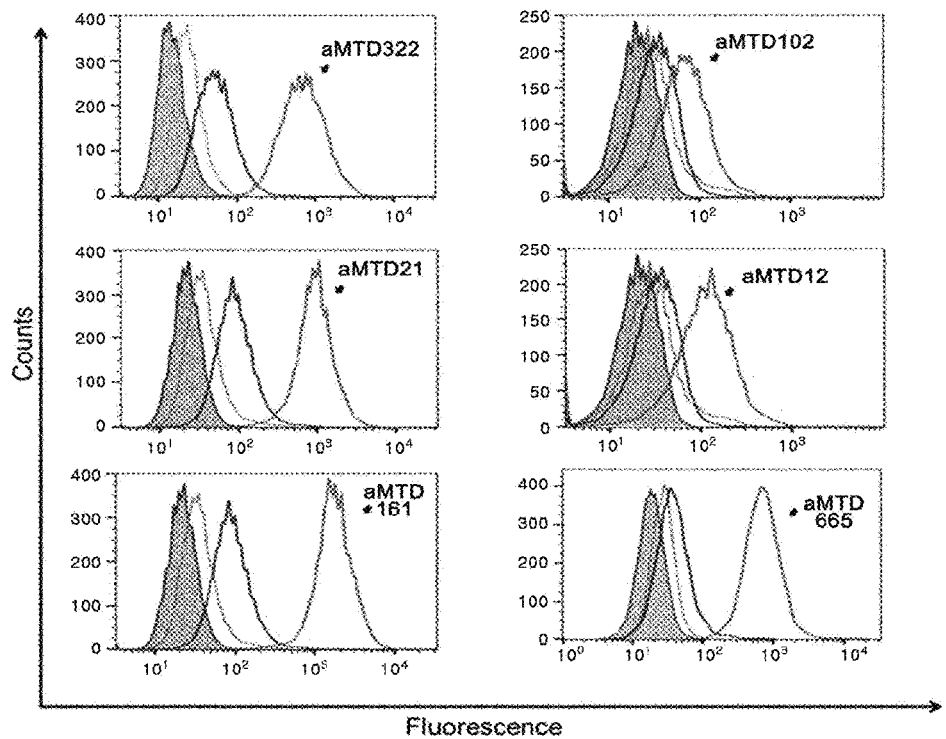
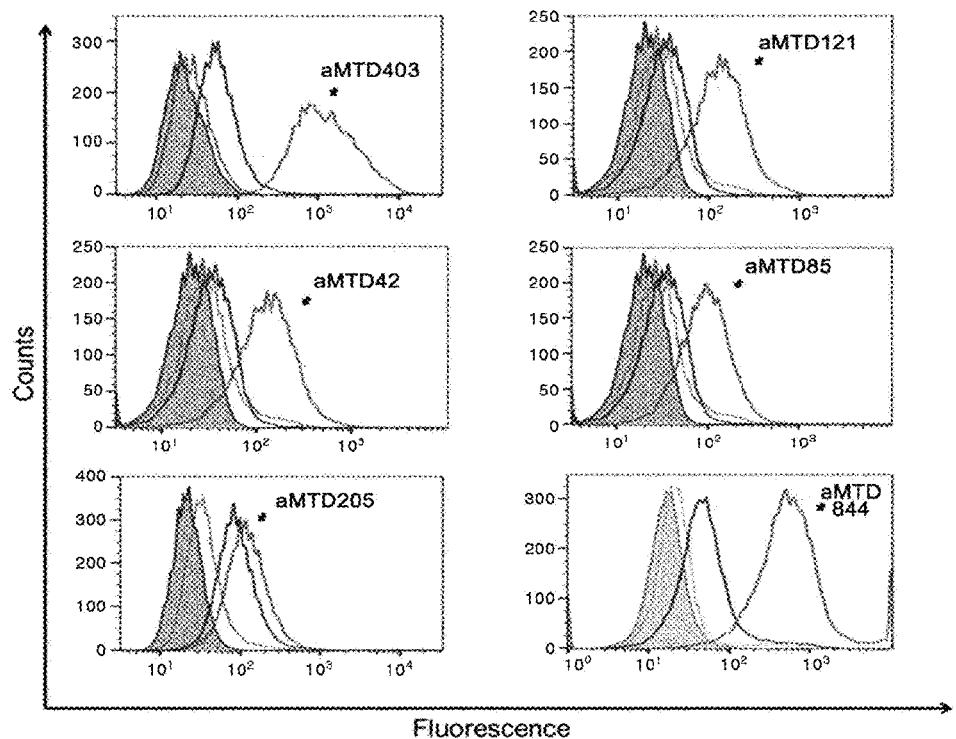

[Figure 5t]
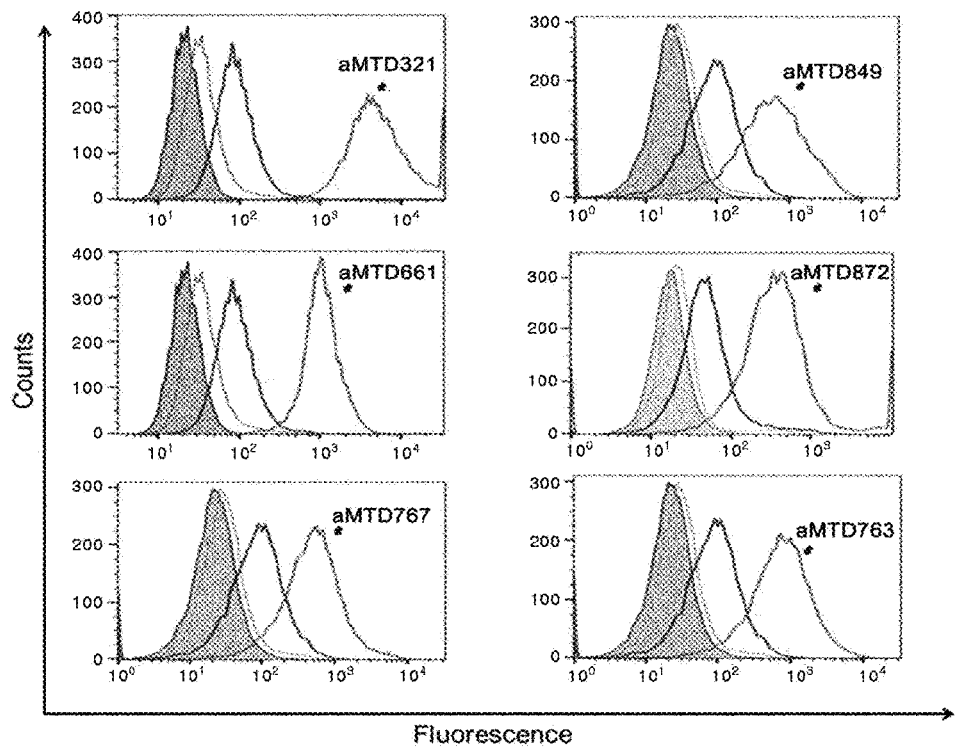
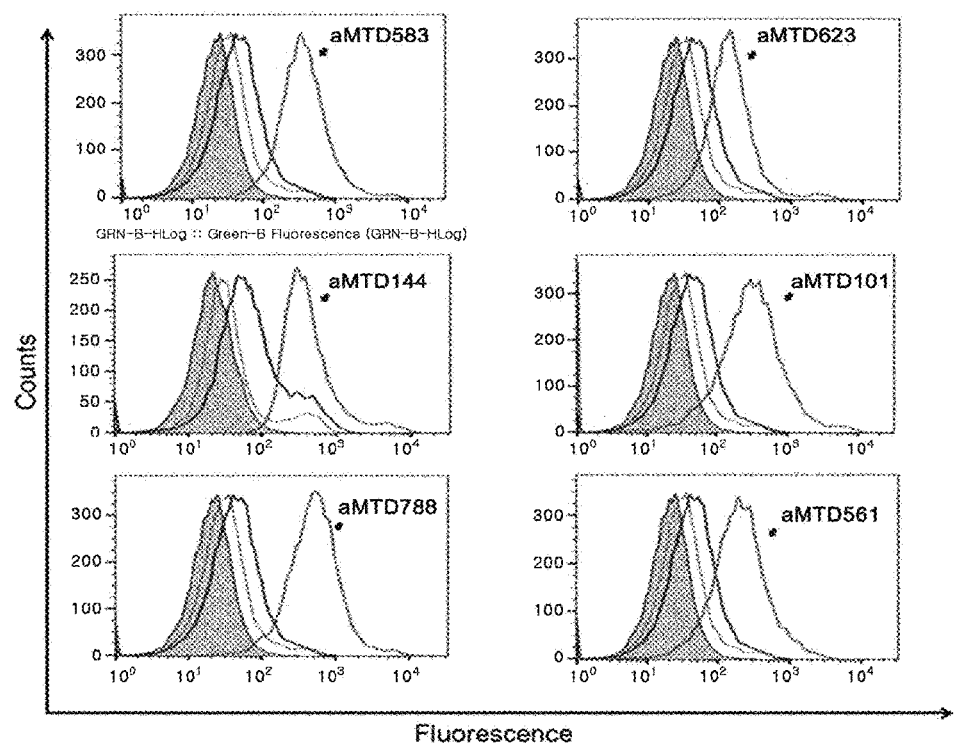

[Figure 5u]
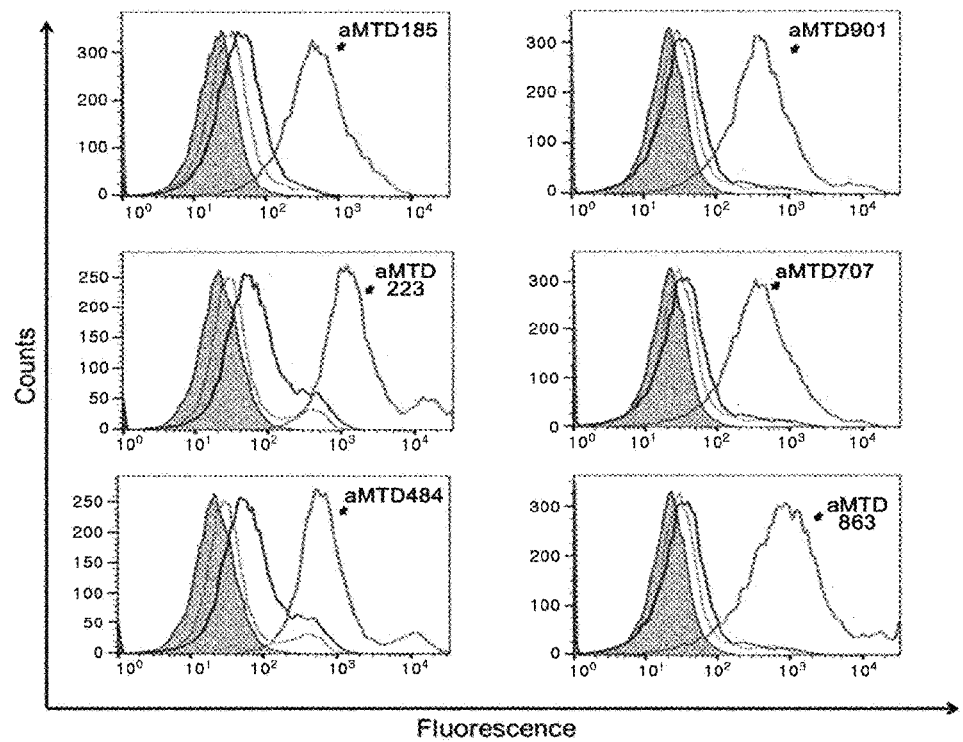
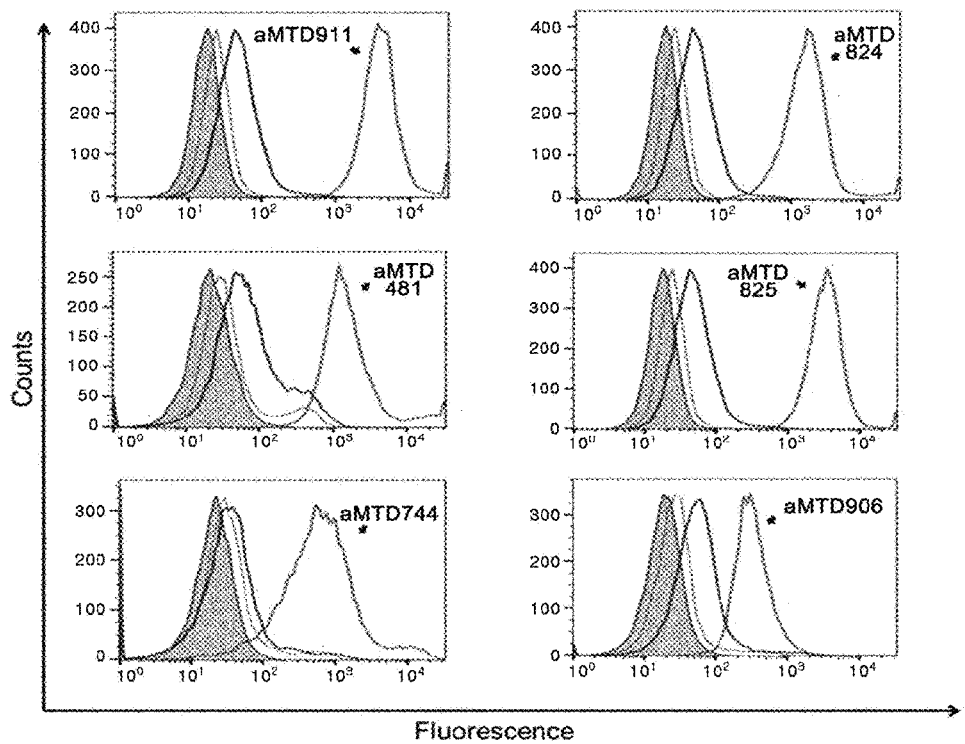

[Figure 6a]
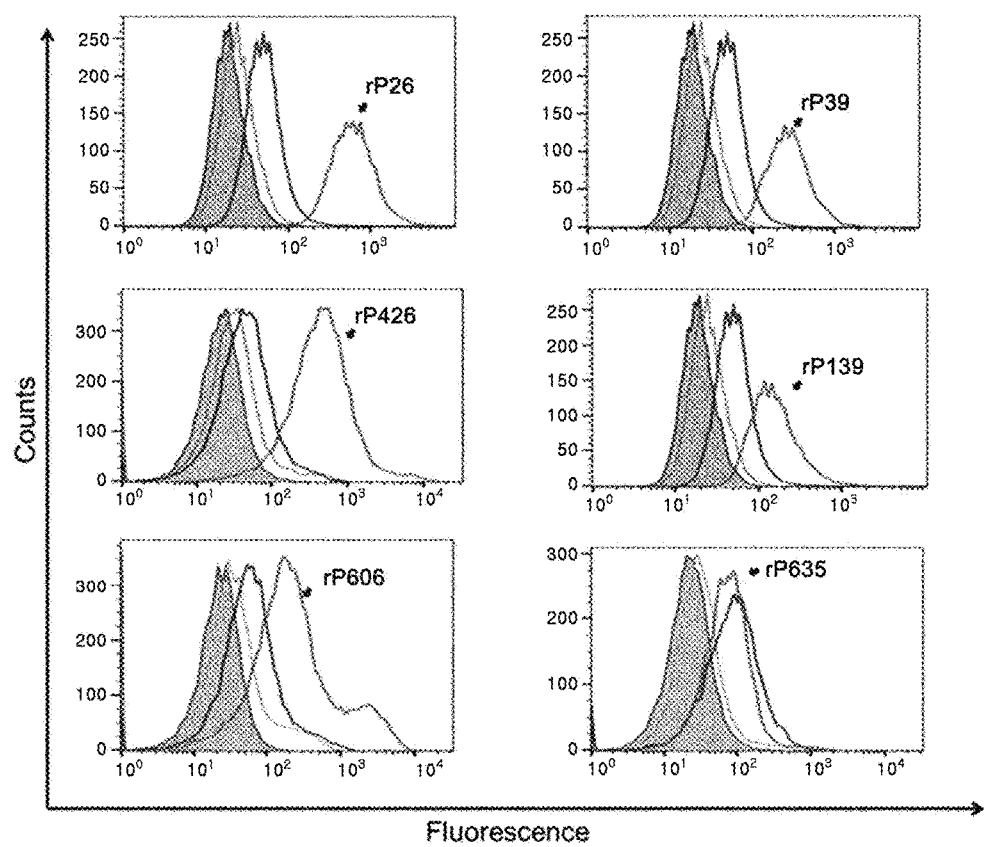

[Figure 6b]
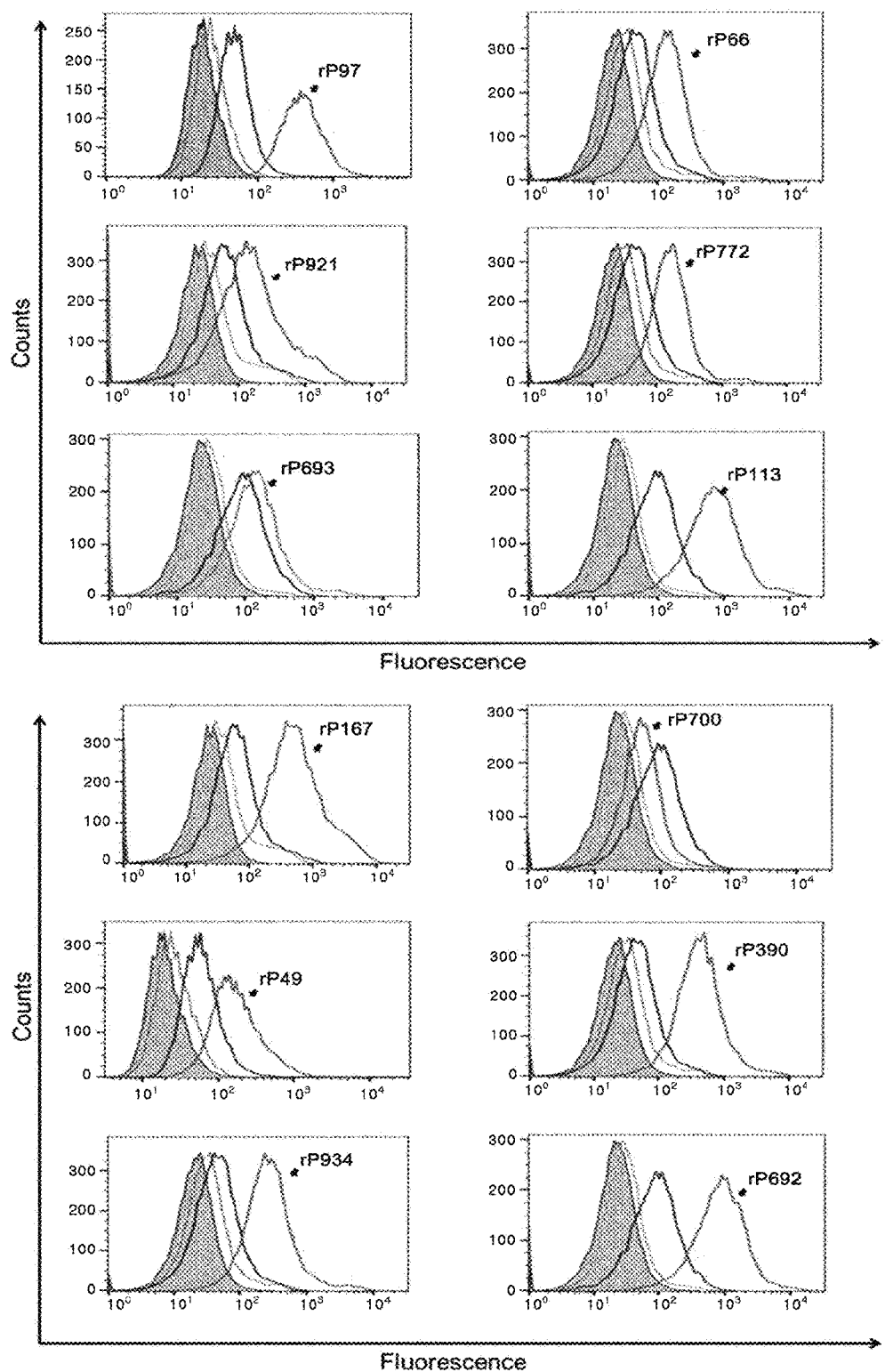

[Figure 6c]
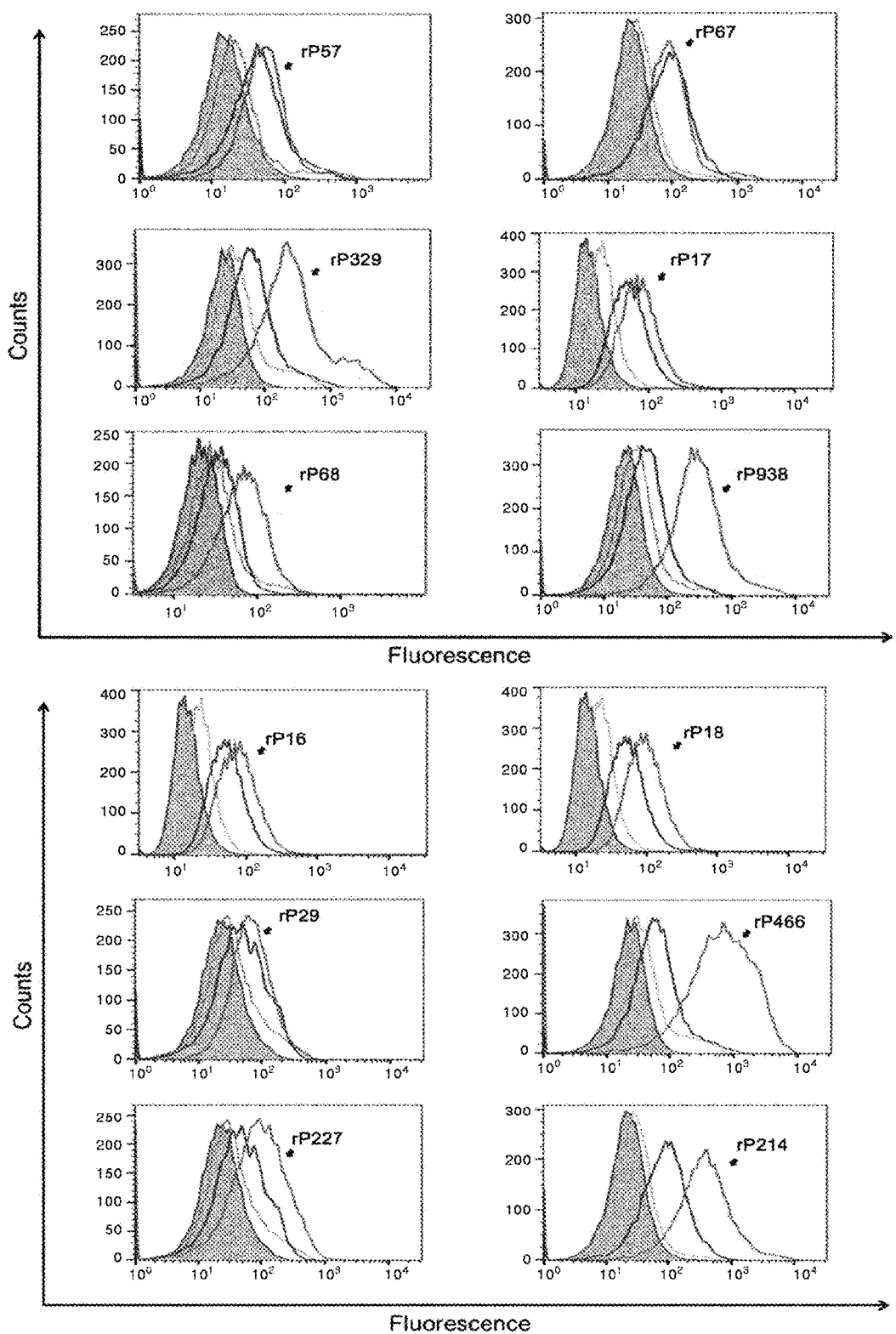

[Figure 7a]
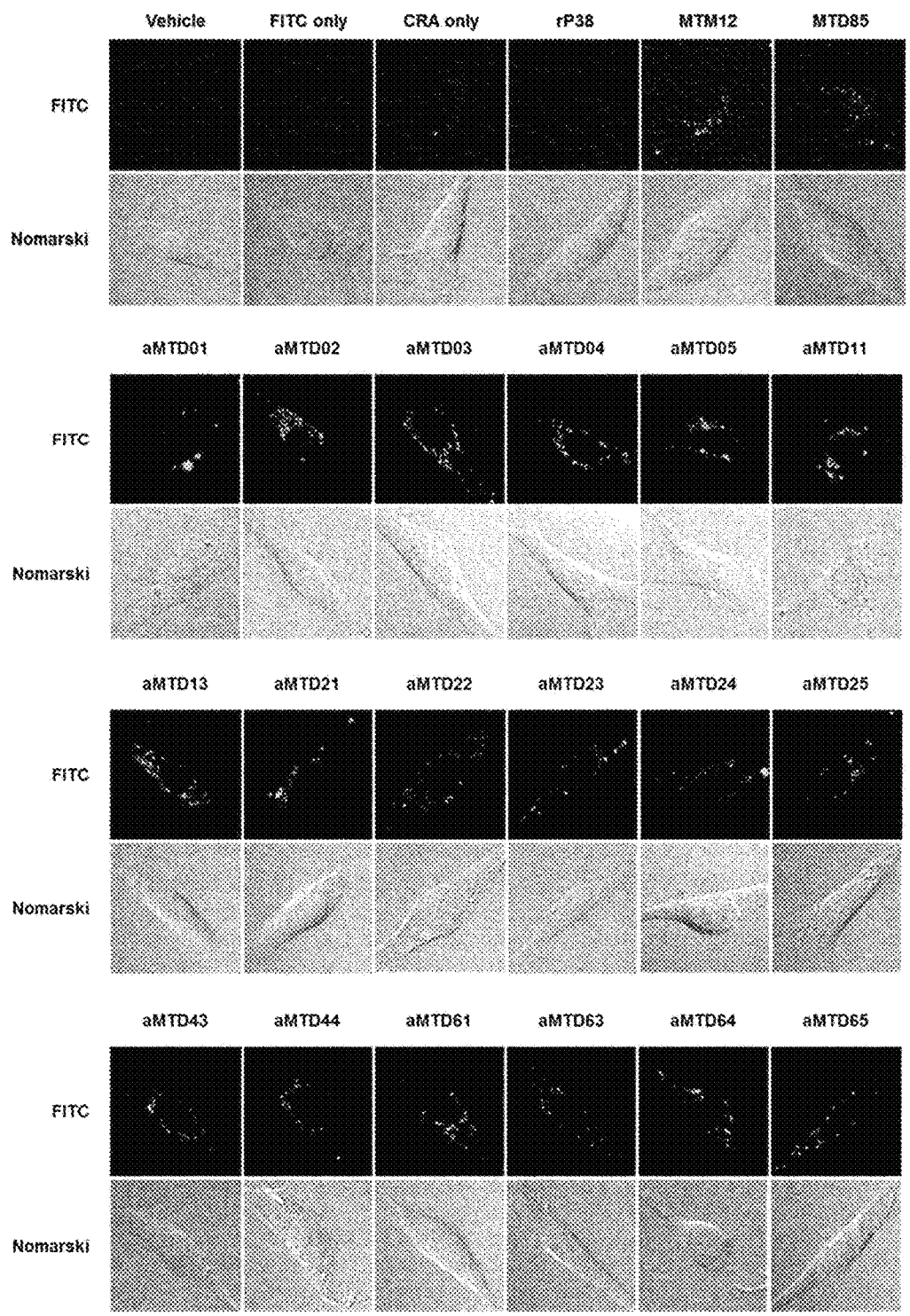

[Figure 7b]
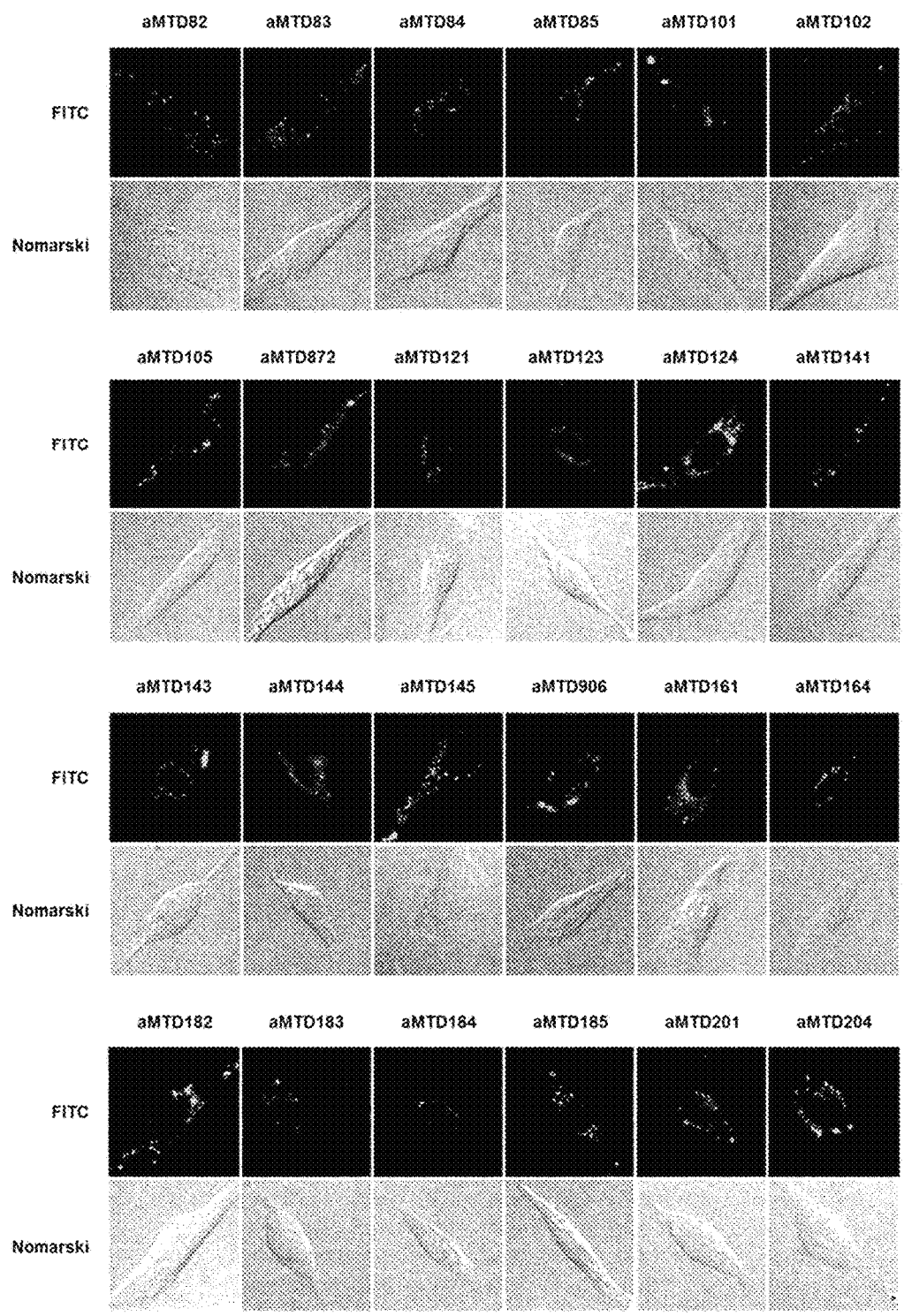

[Figure 7c]
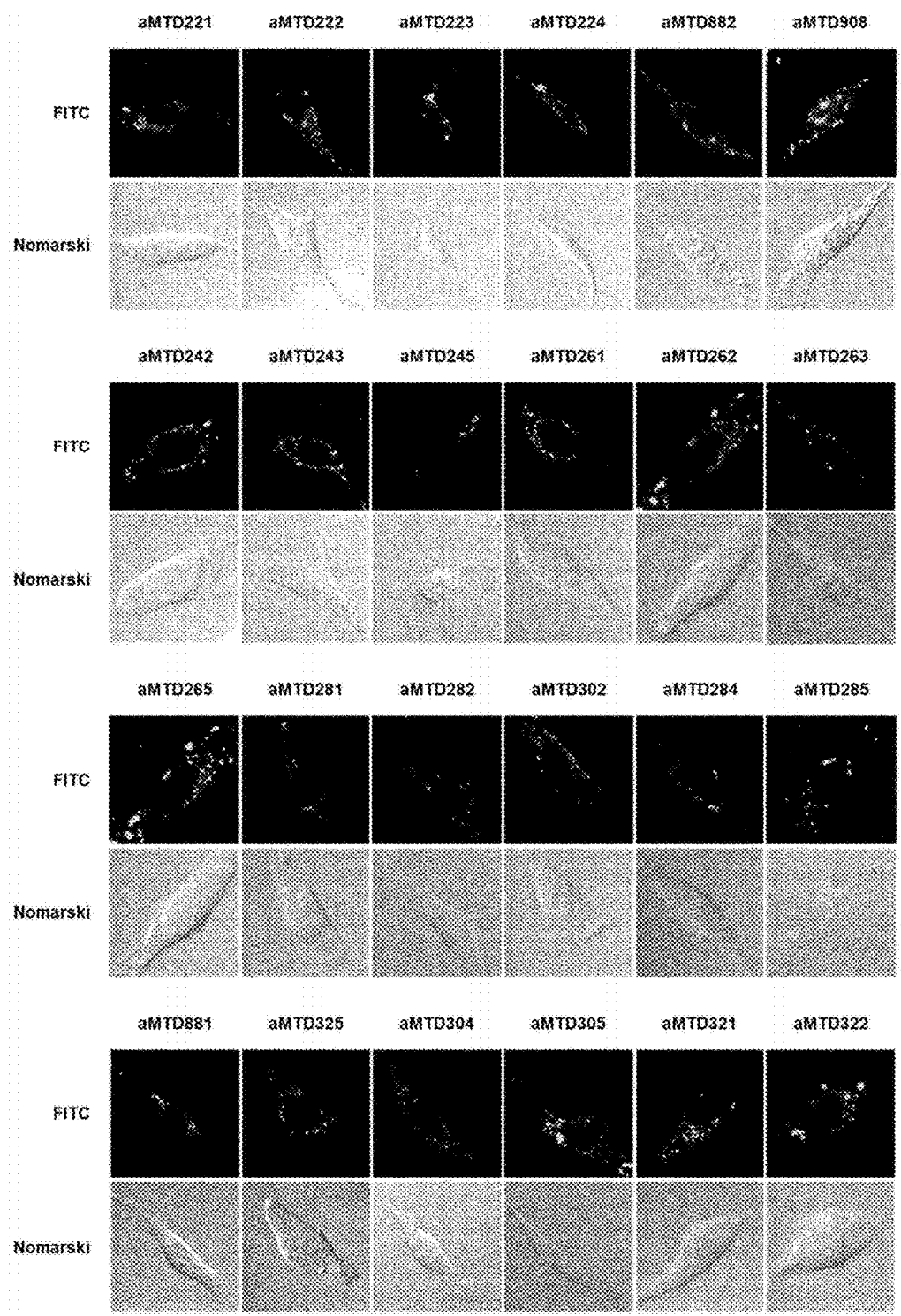

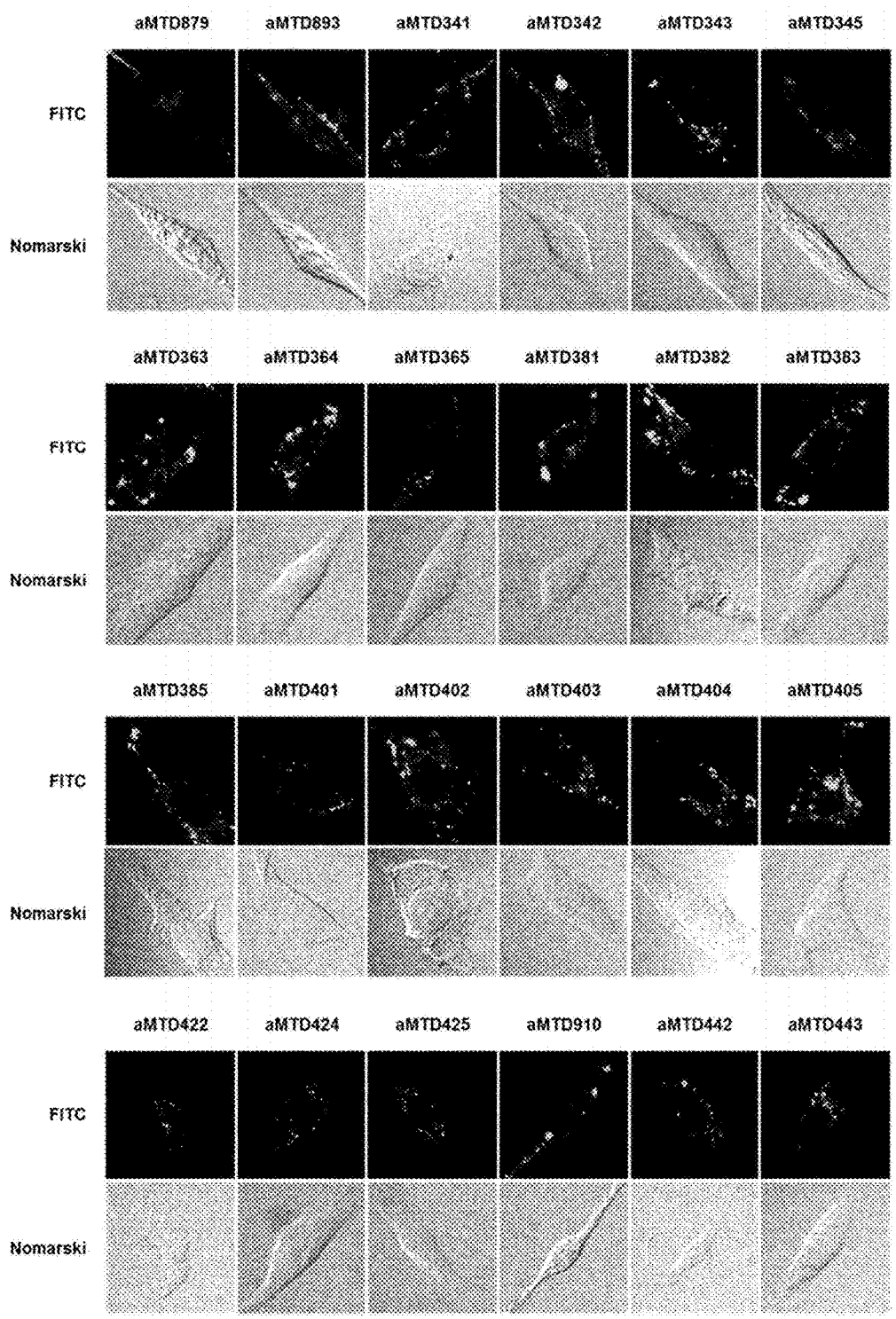
[Figure 7d]

[Figure 7e]
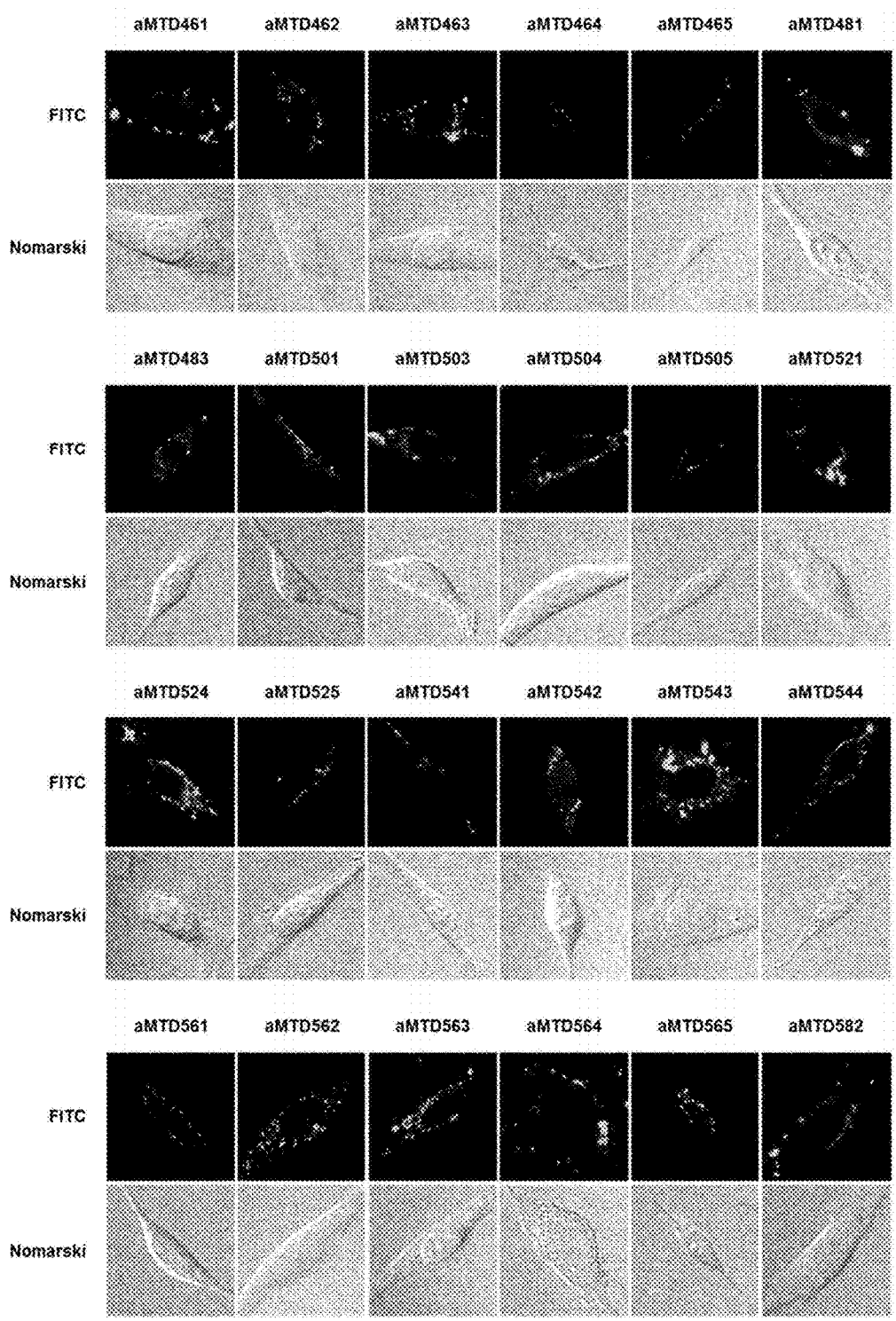

[Figure 7f]
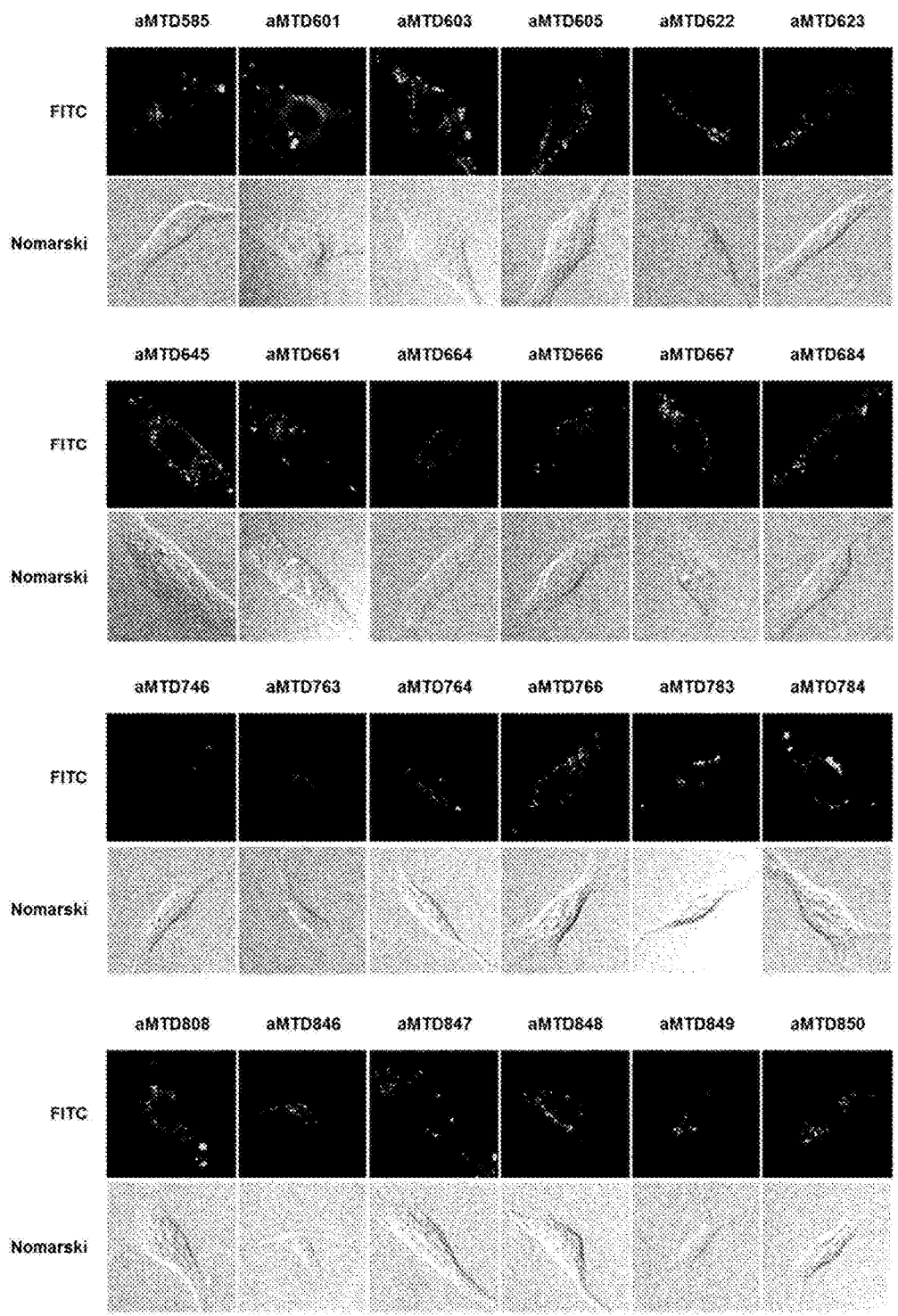

[Figure 7g]
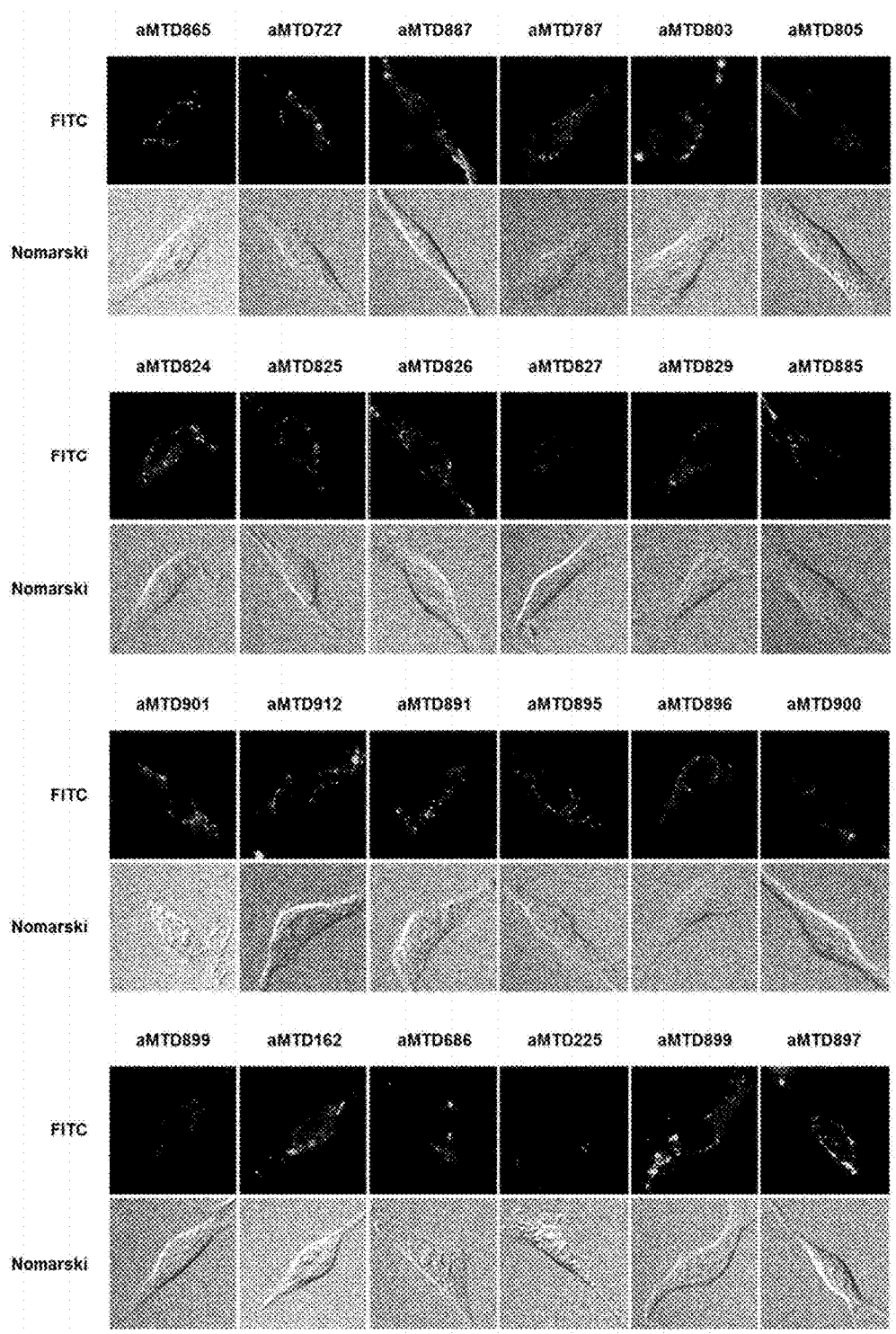

[Figure 7h]
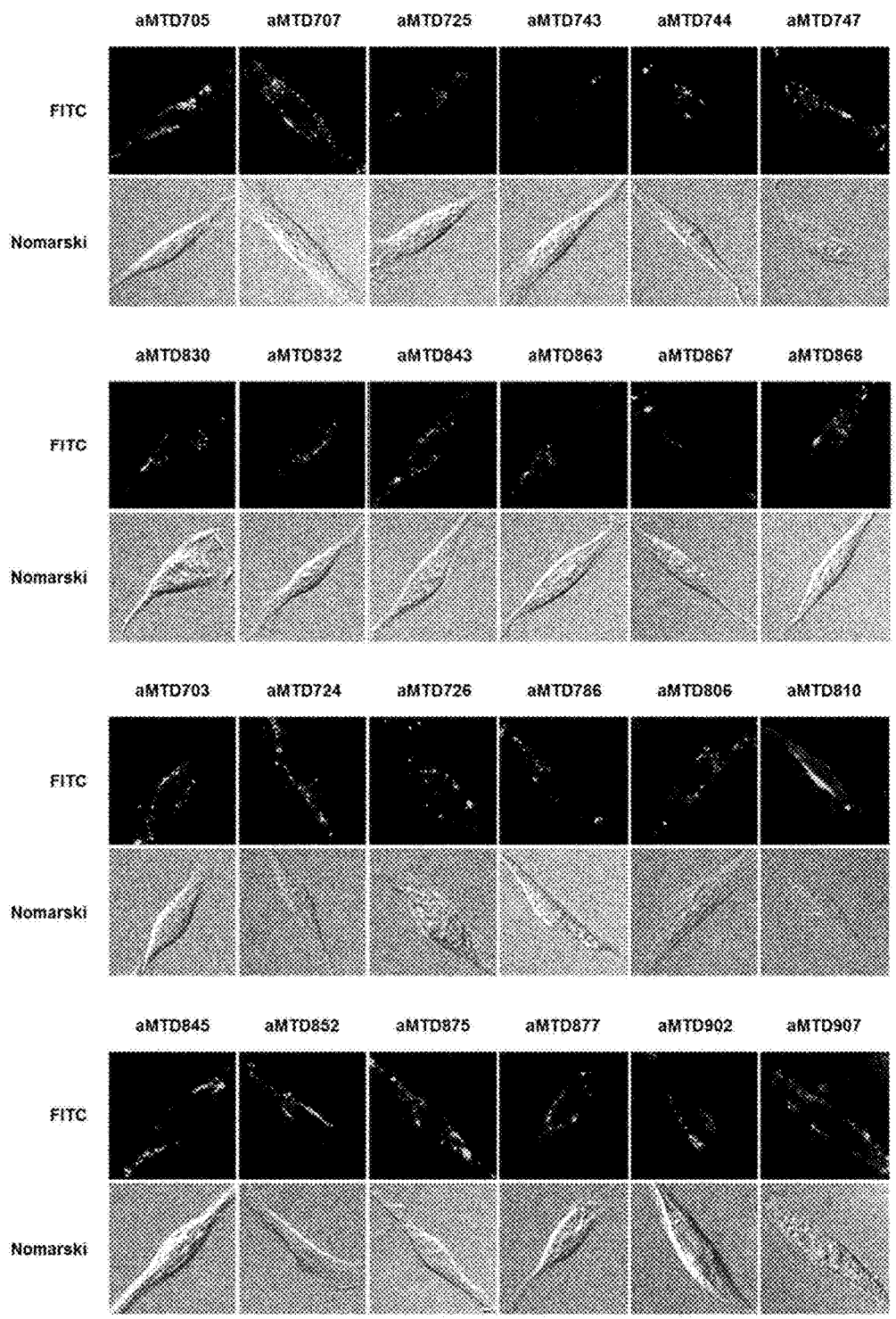

[Figure 7i]
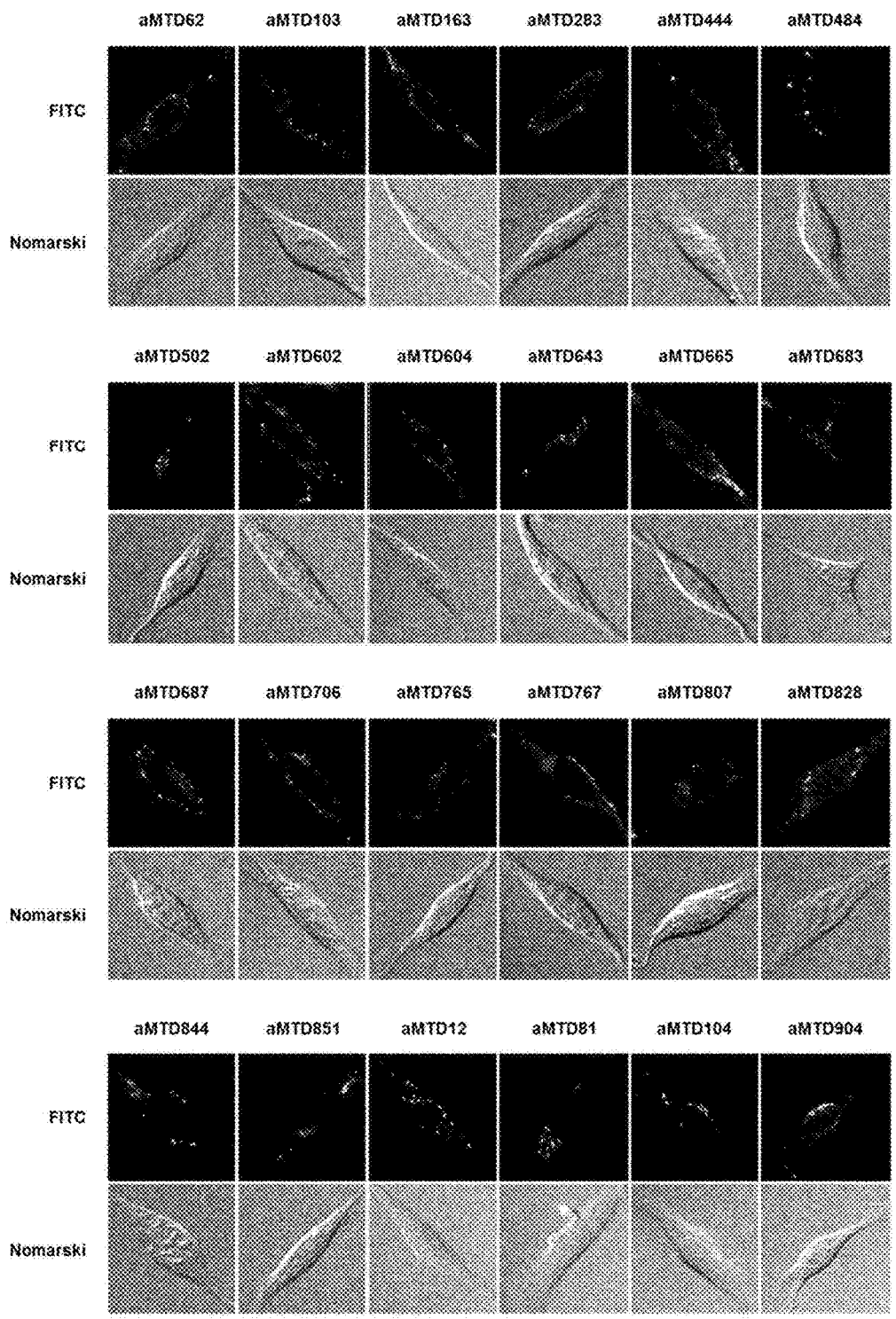

【Figure 7j】
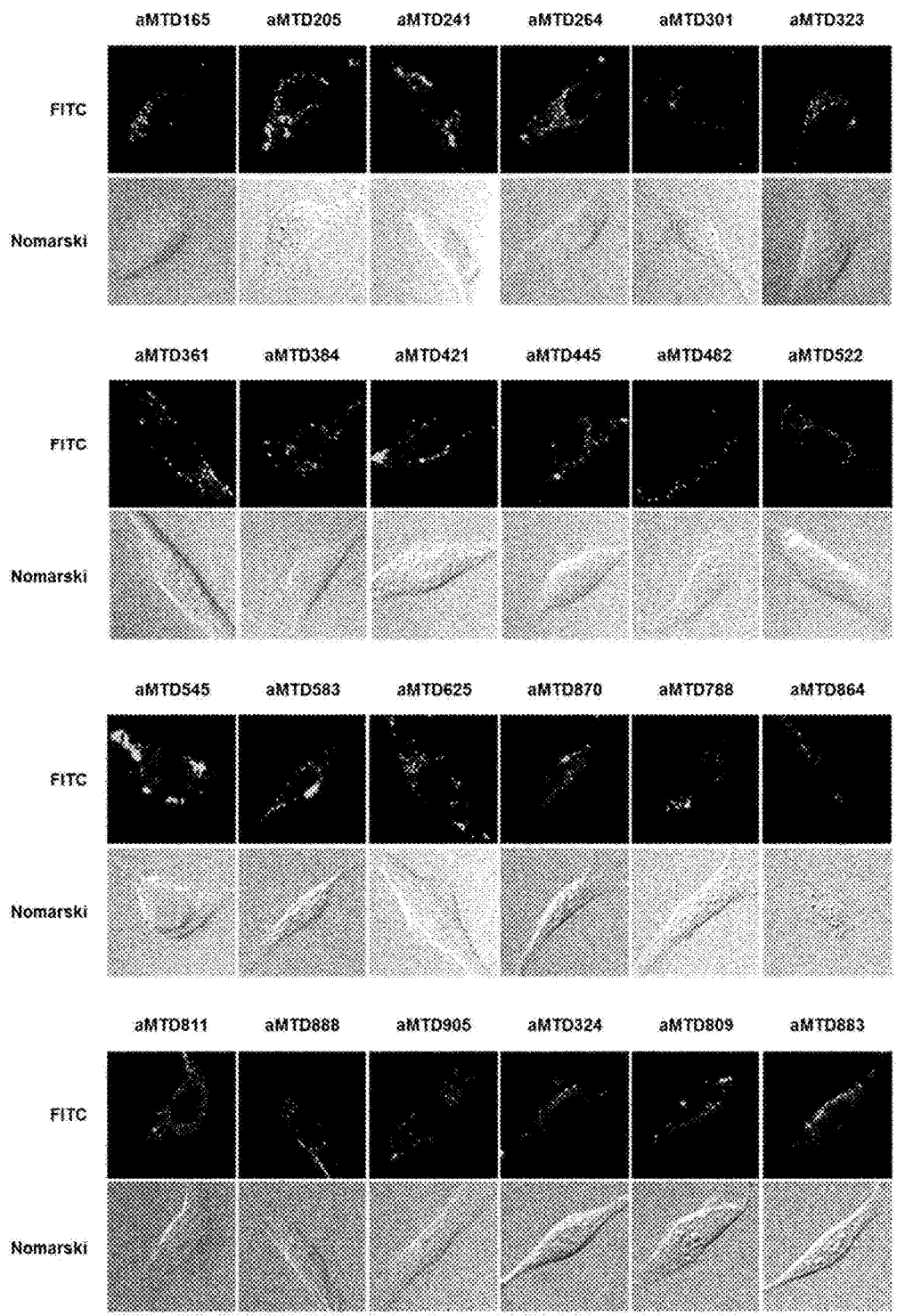

[Figure 7k]
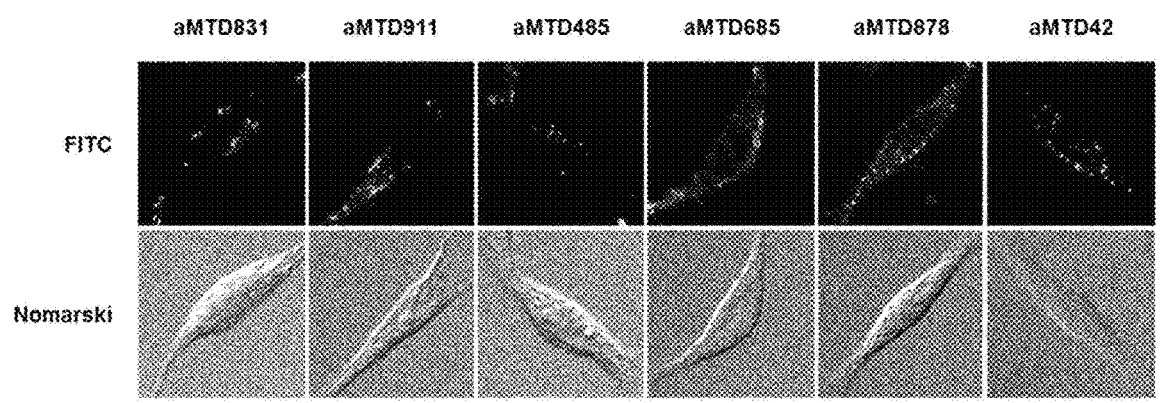

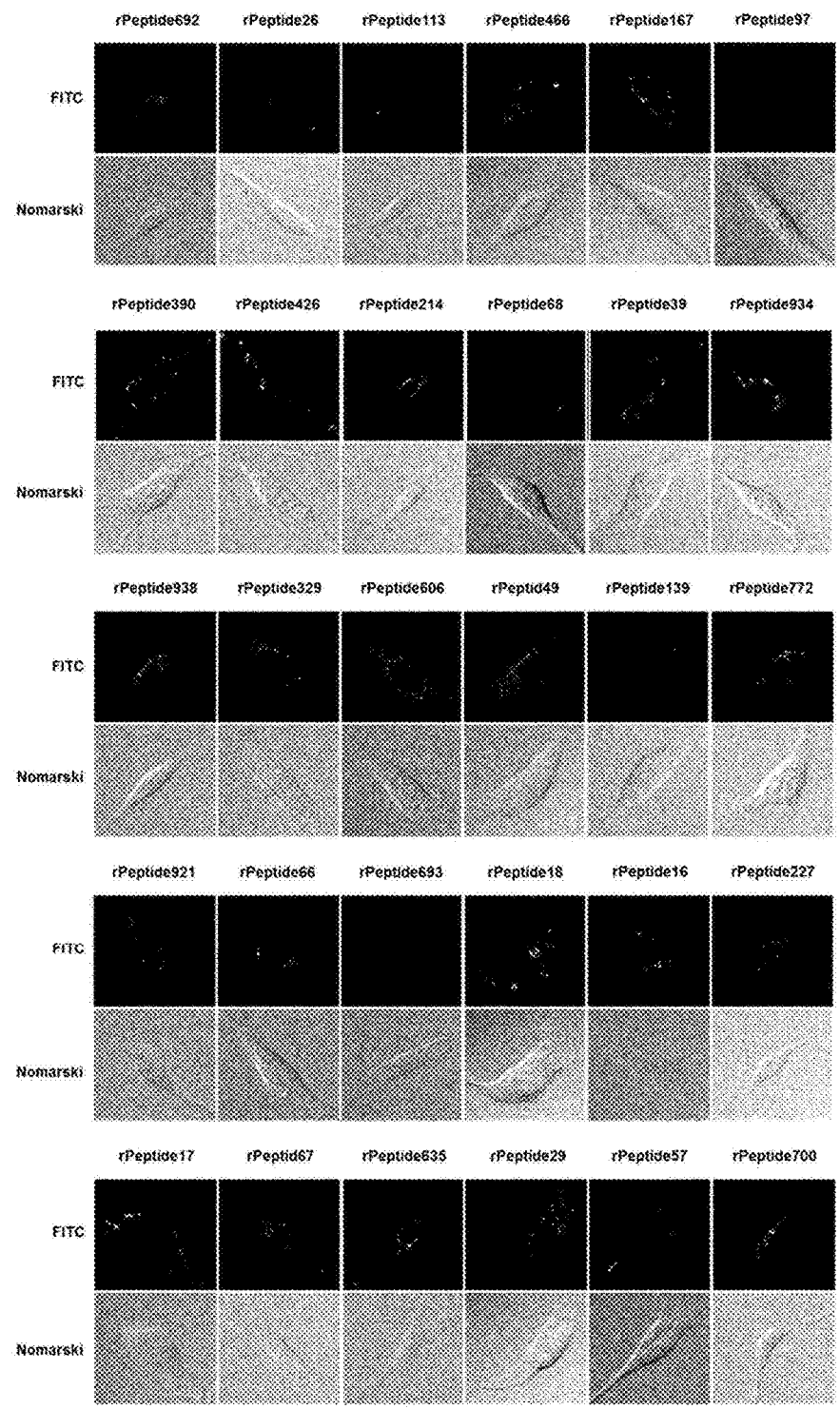
[Figure 8]

[Figure 9a]
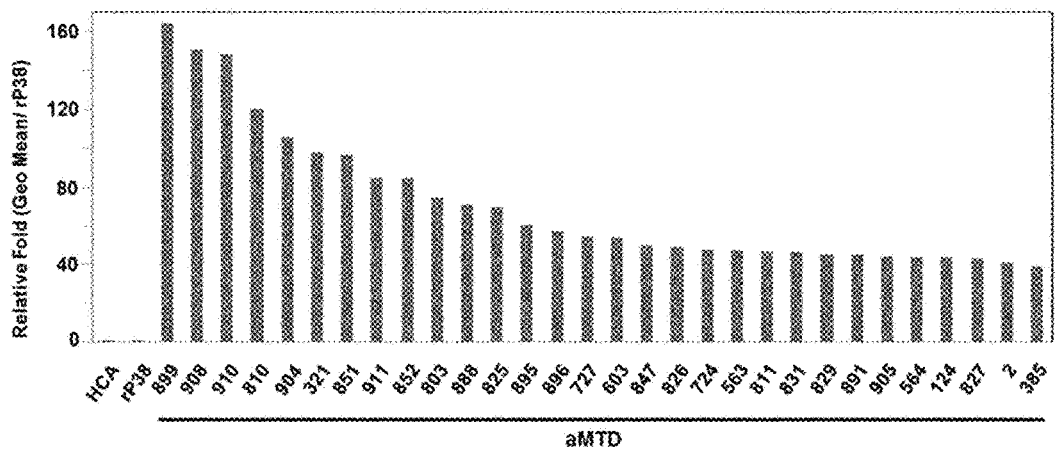
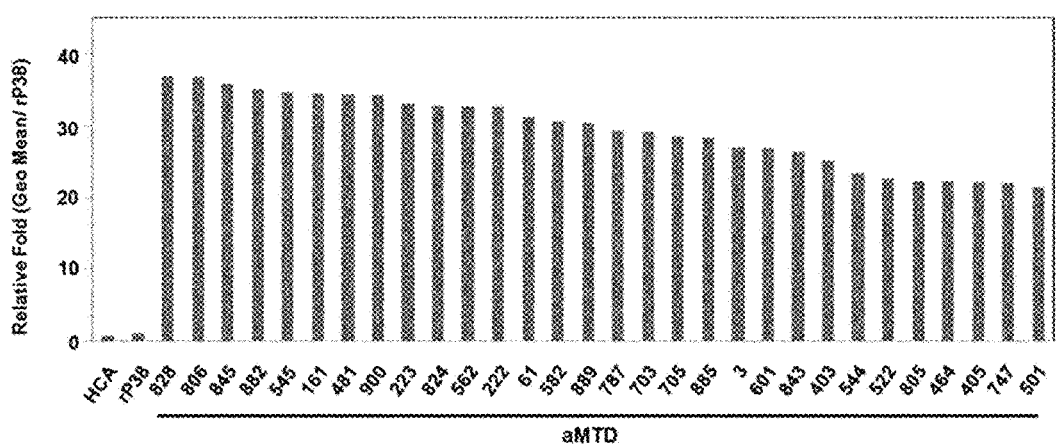
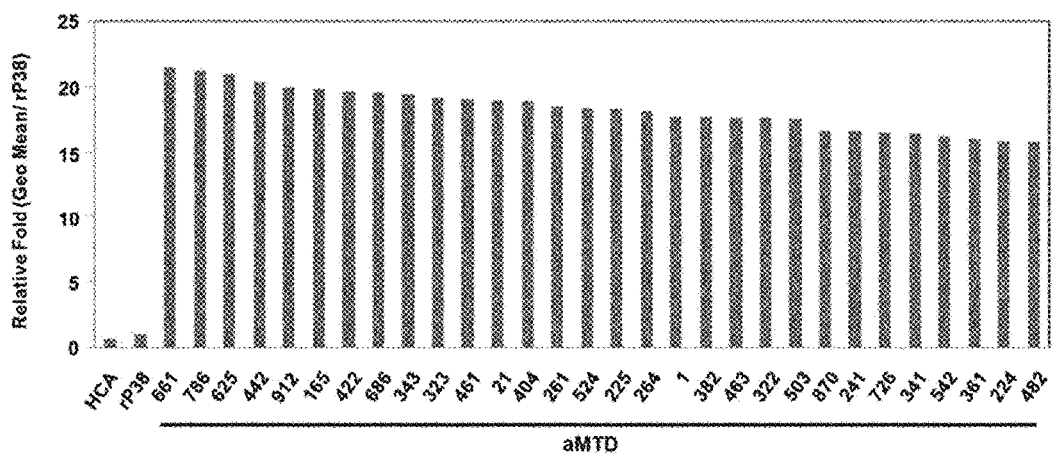

[Figure 9b]
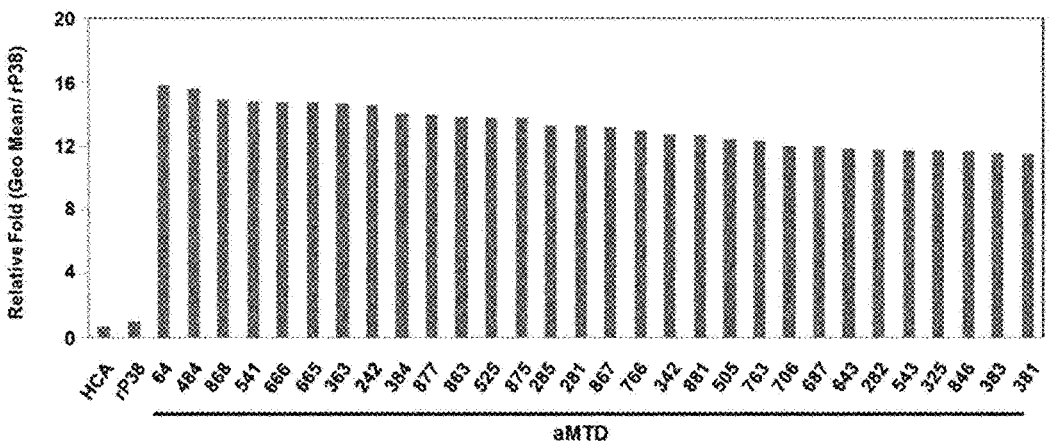
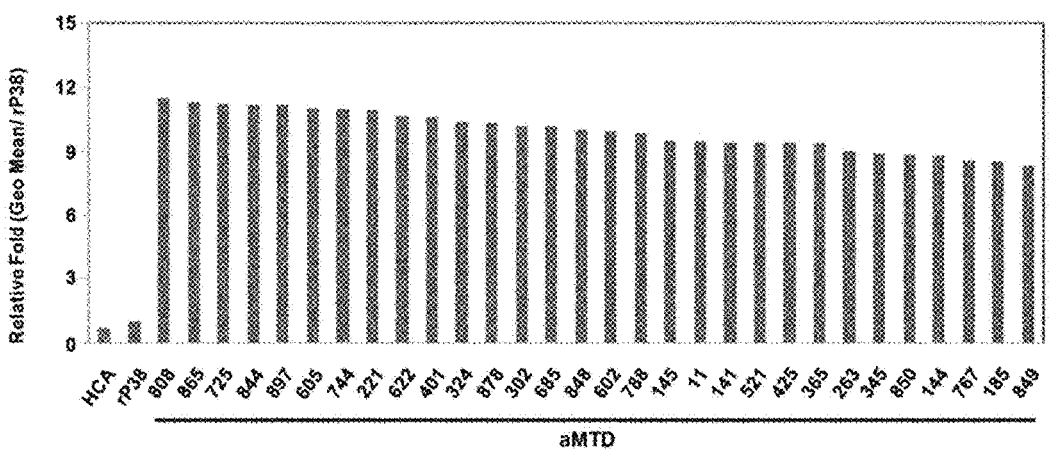
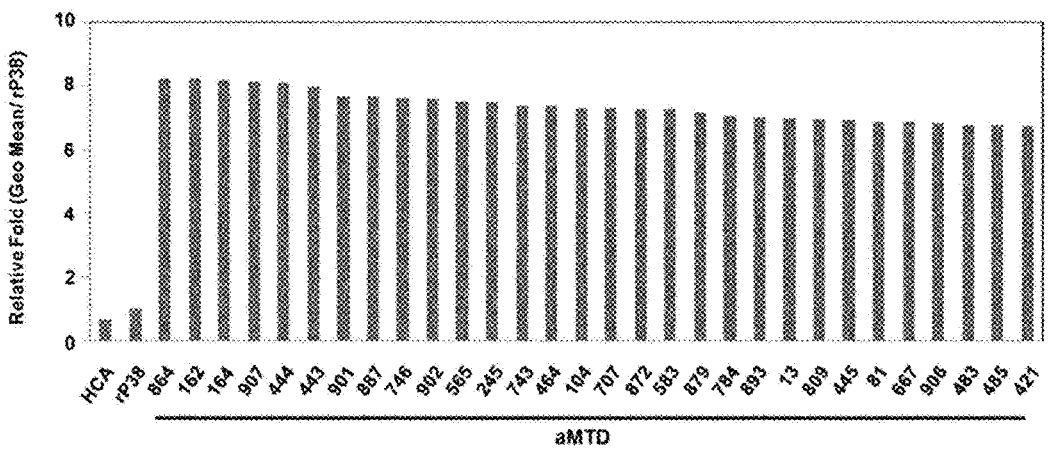

[Figure 9c]
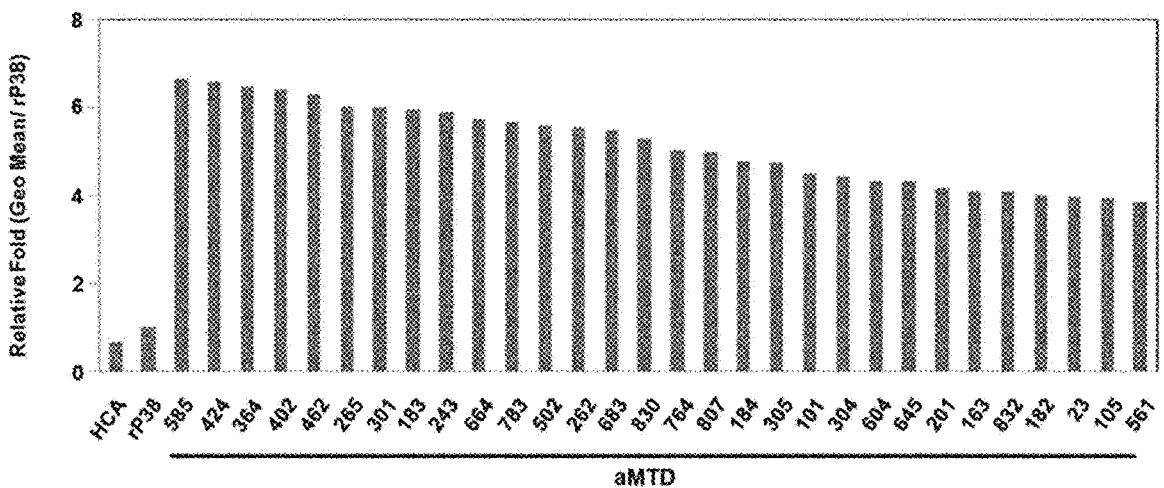
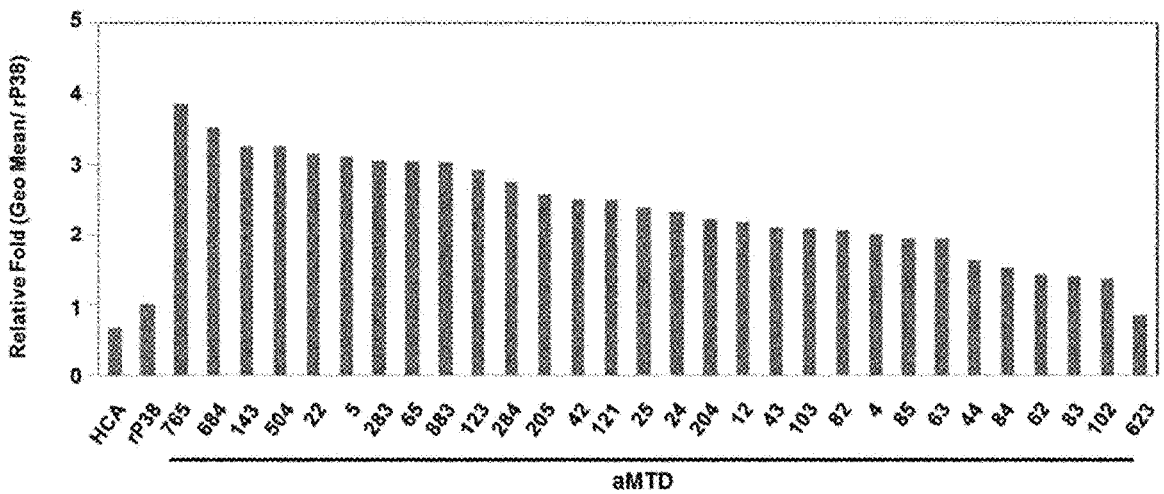

【Figure 10a】
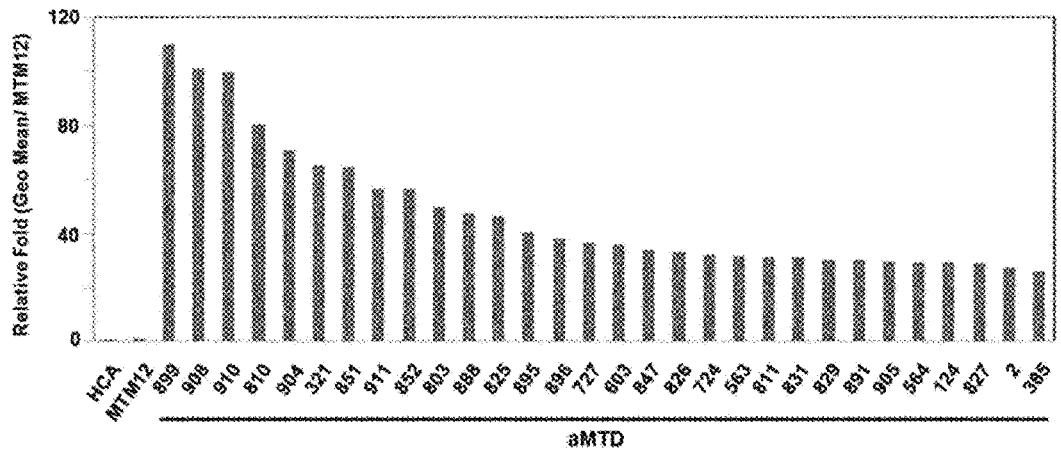
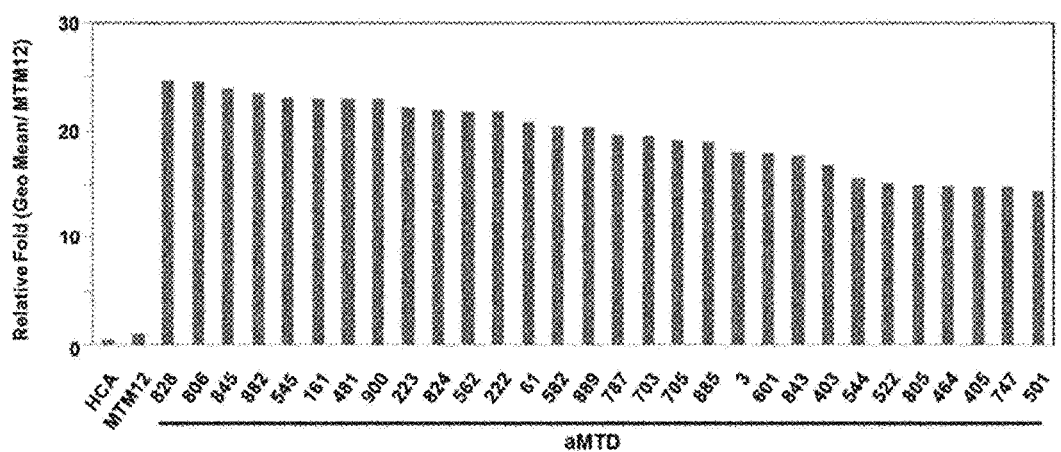
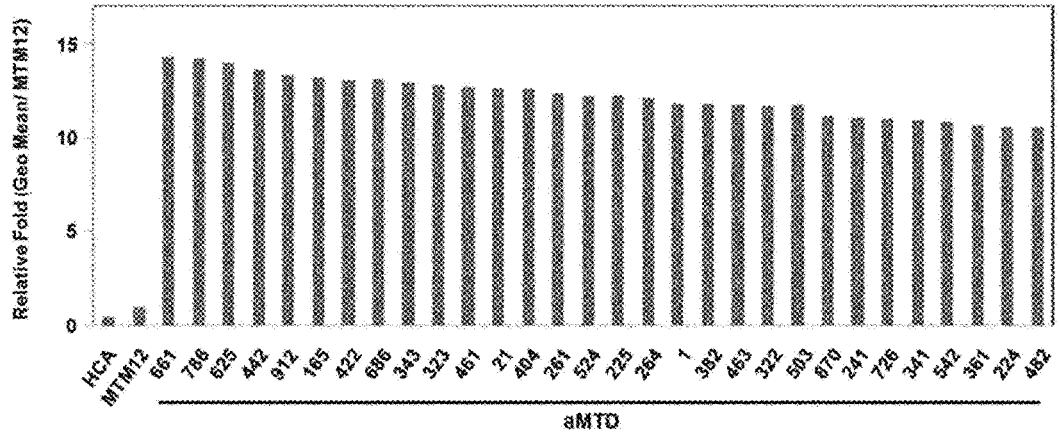

[Figure 10b]
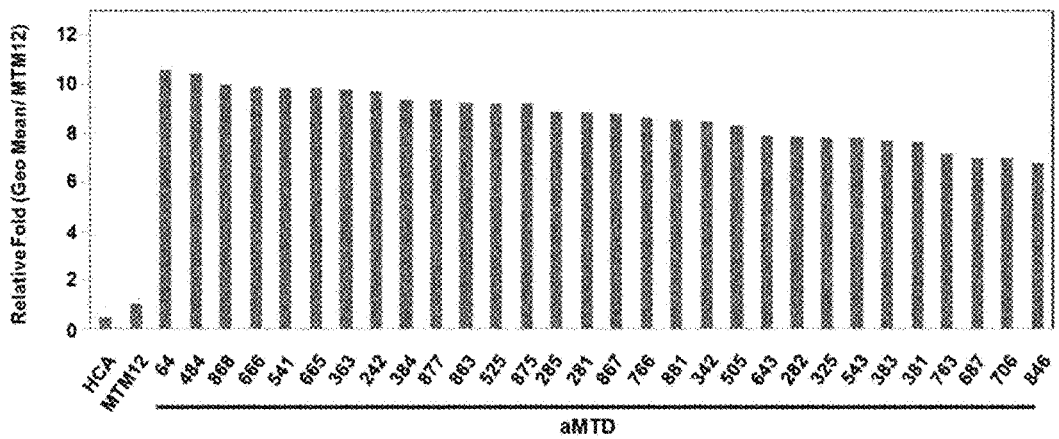
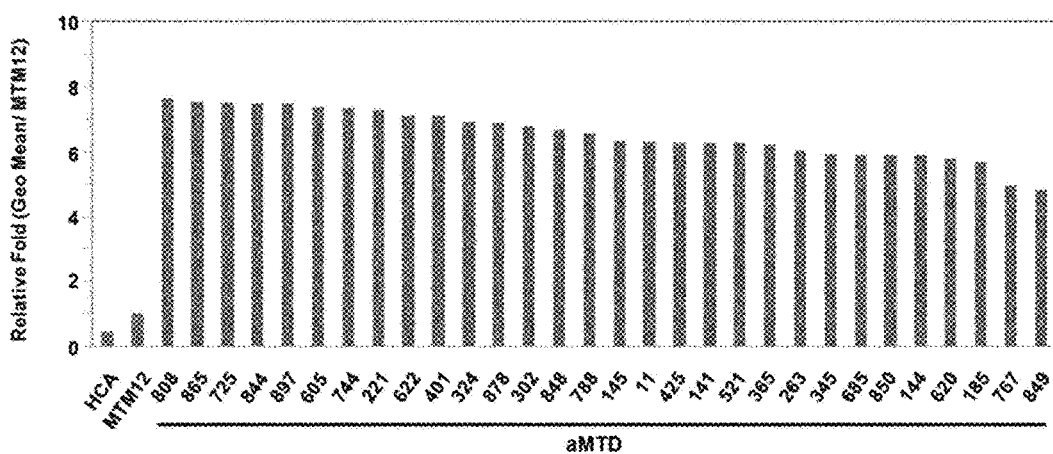
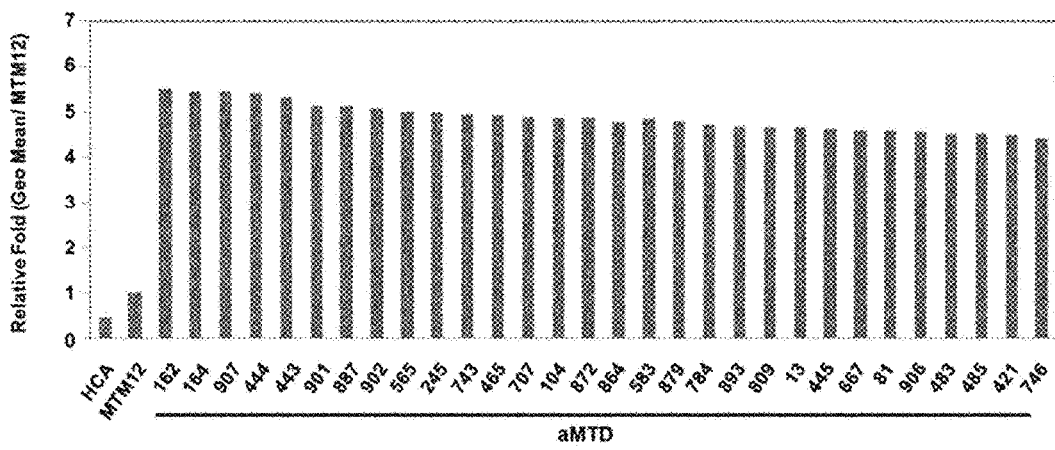

[Figure 10c]
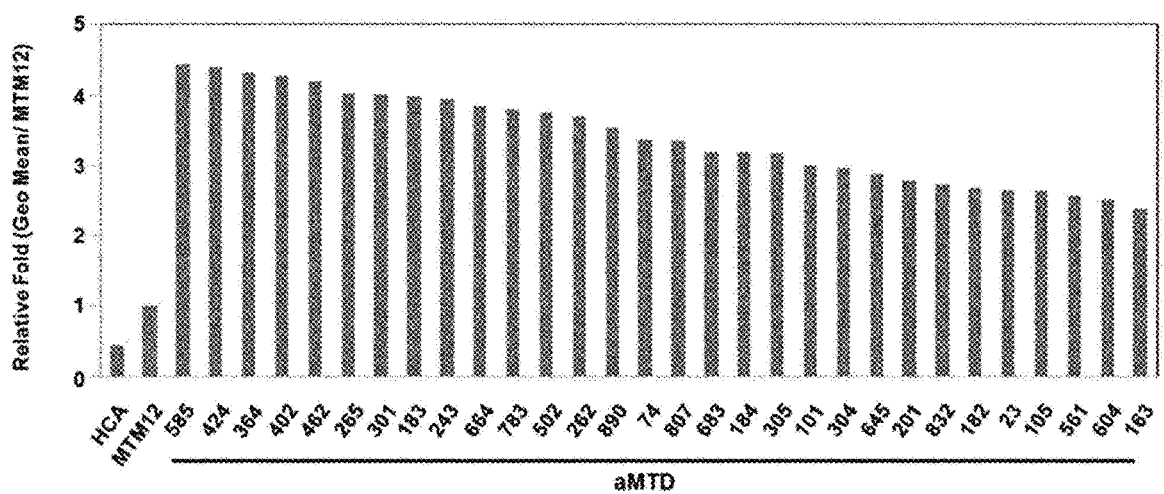
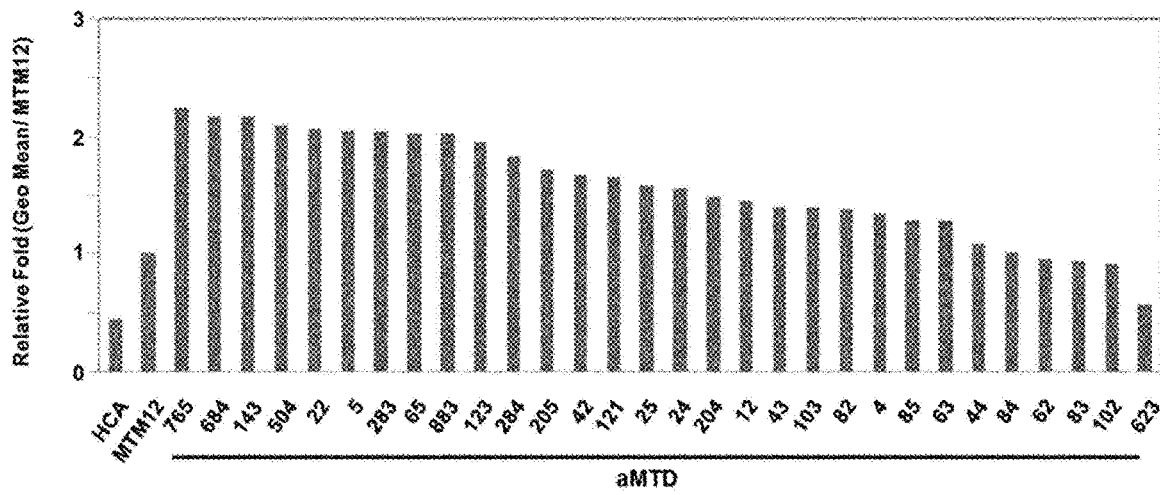

[Figure 11a]
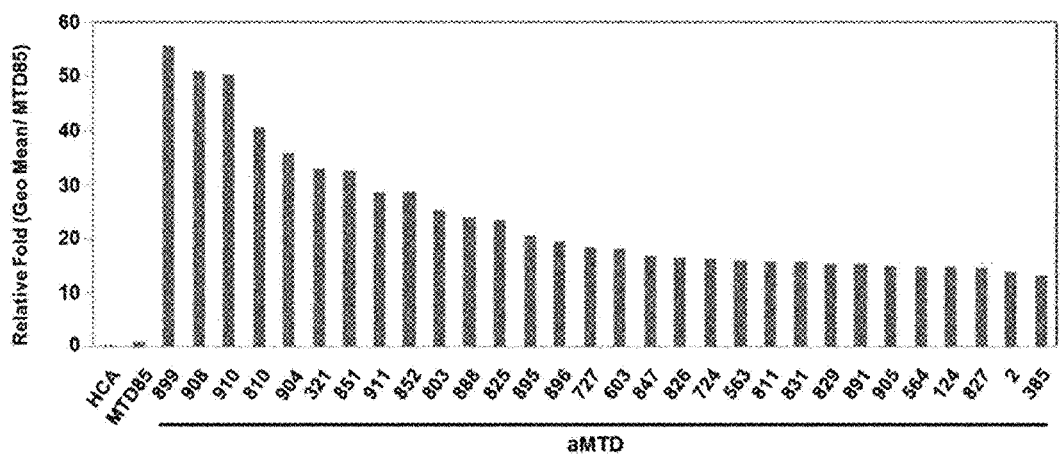
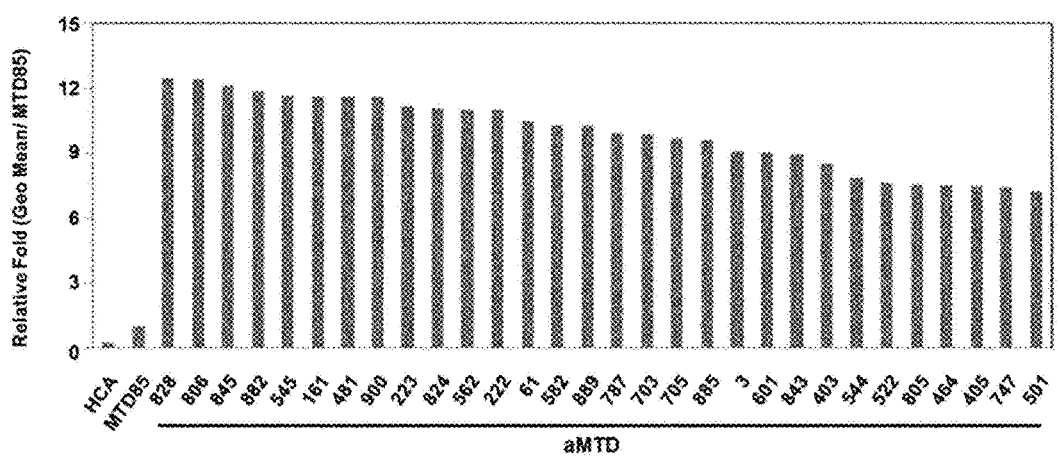
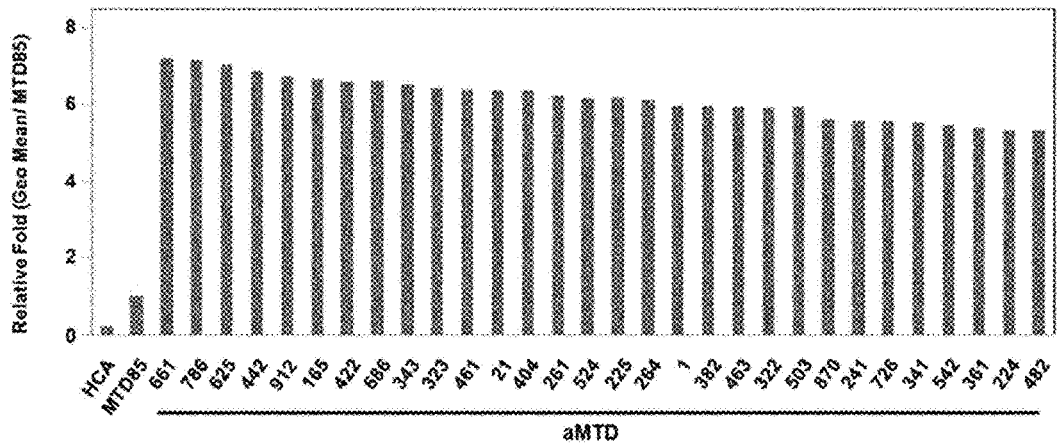

[Figure 11b]
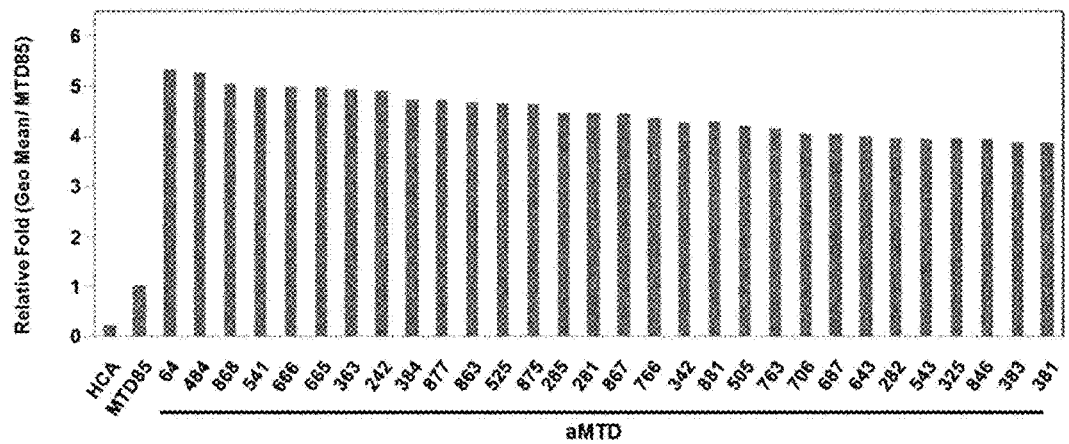
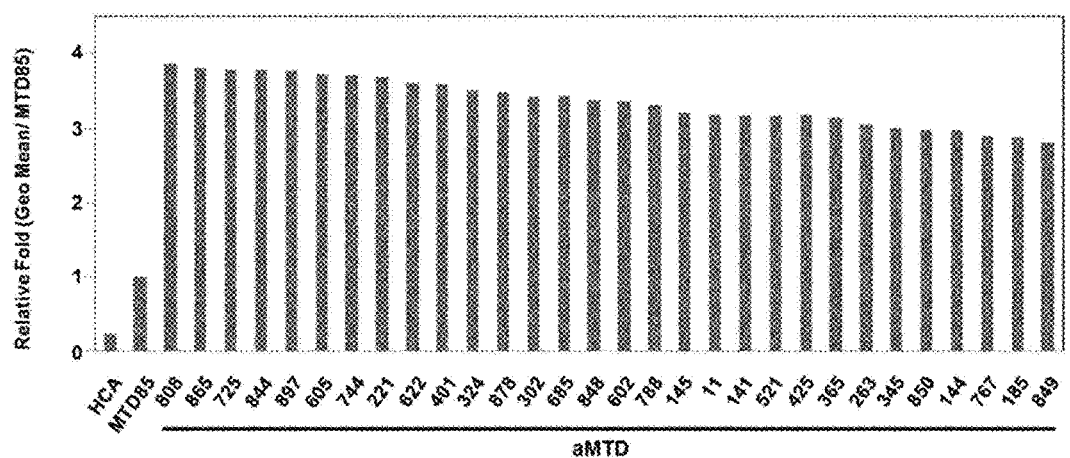
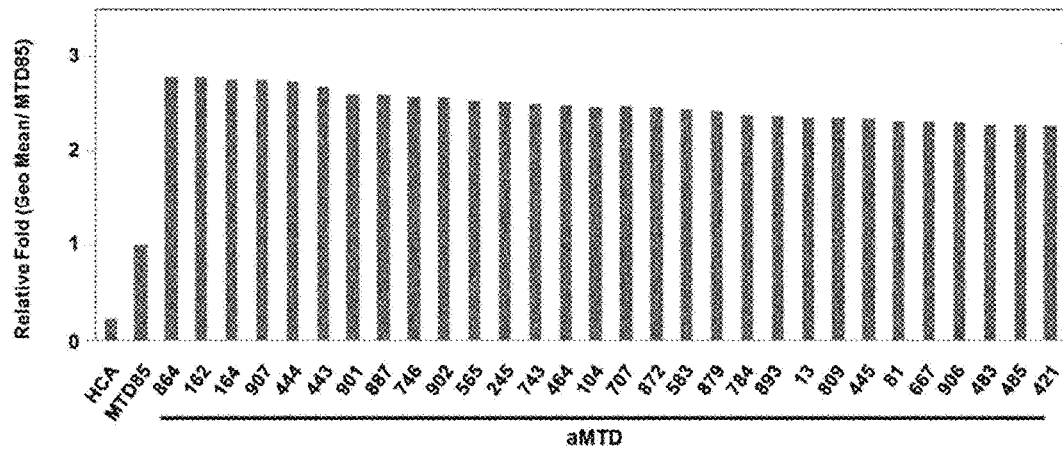

[Figure 11c]
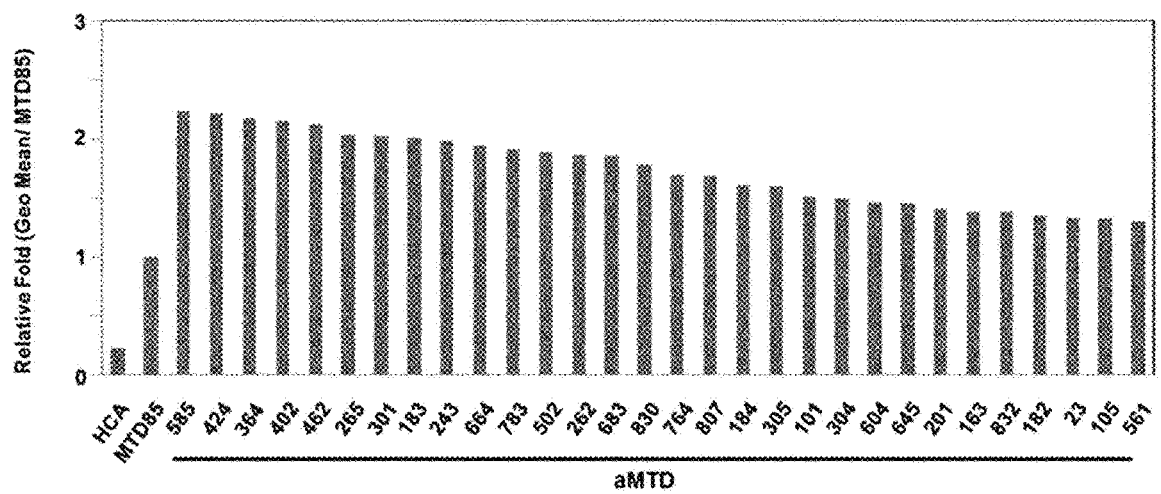
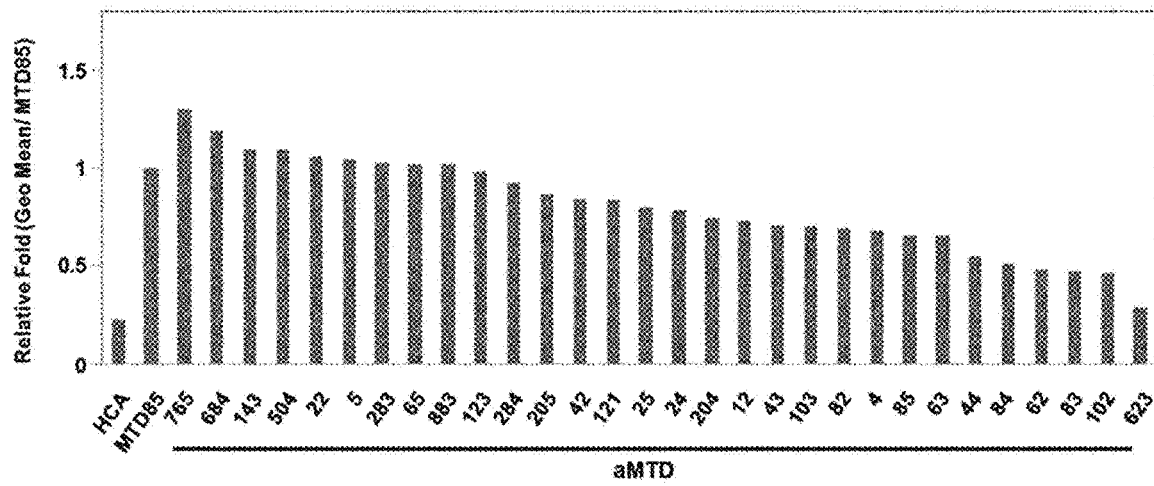

[Figure 12]
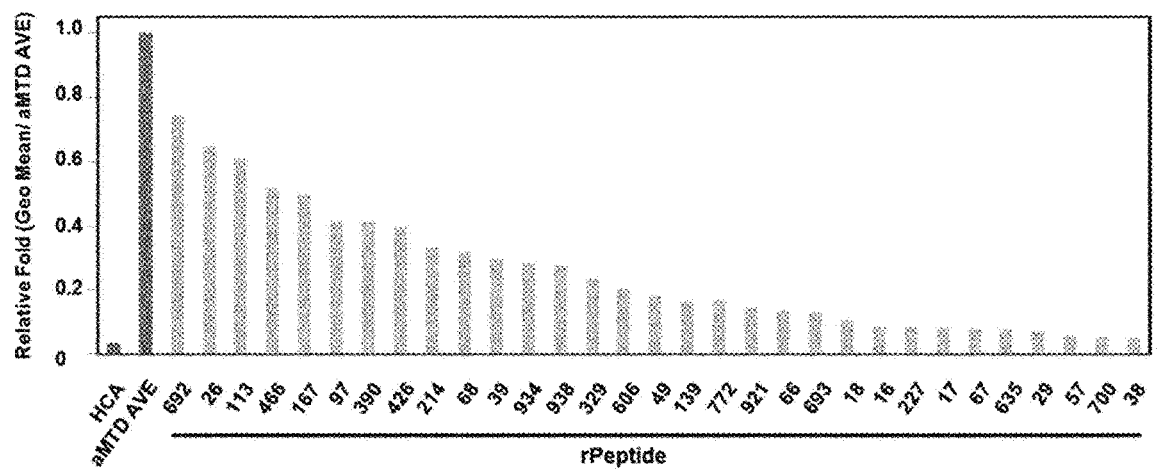

【Figure 13a】
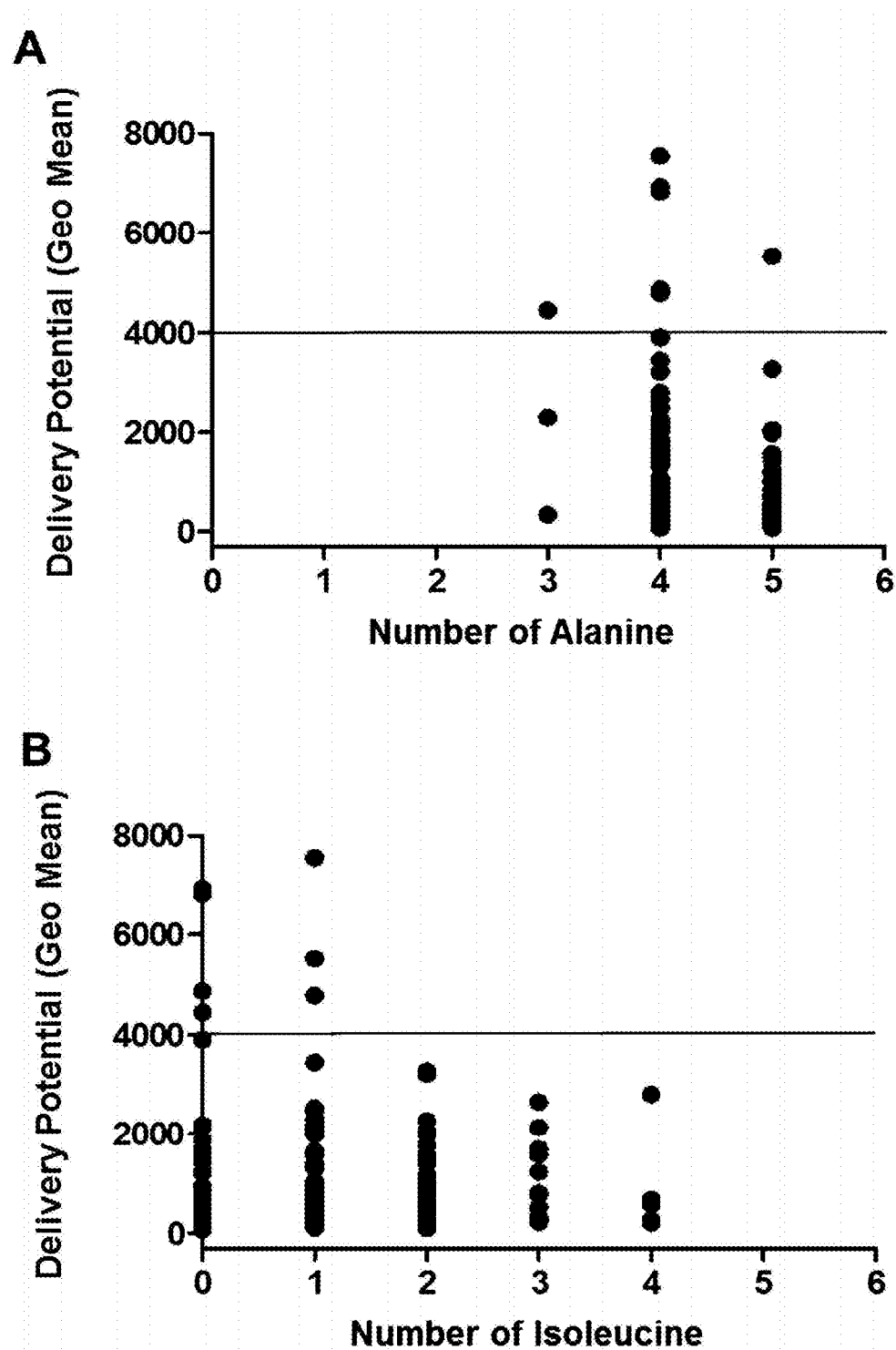

【Figure 13b】
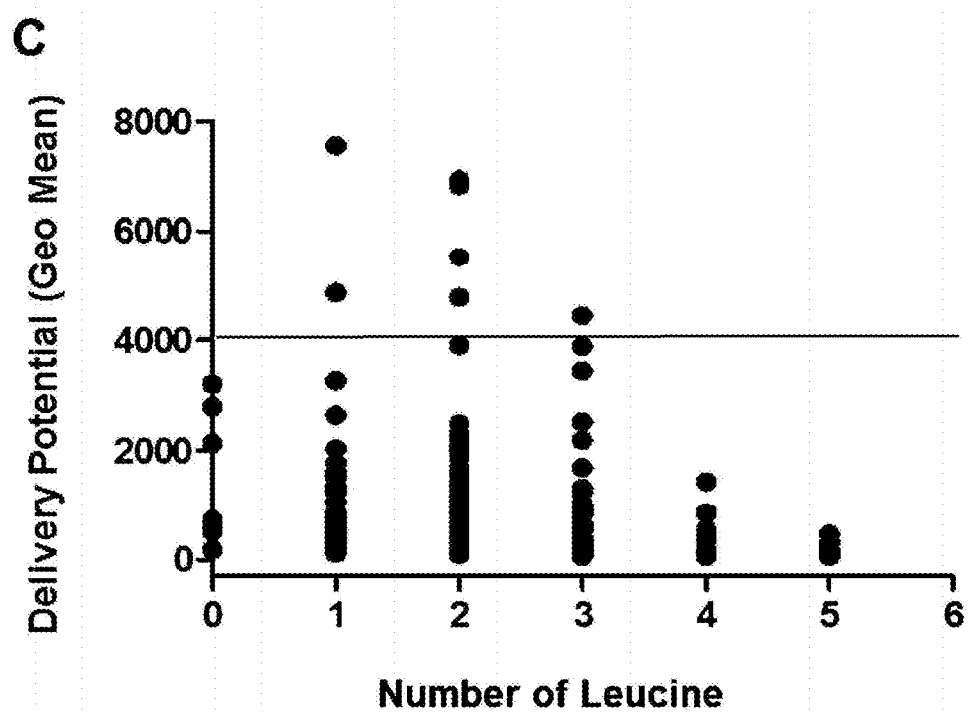
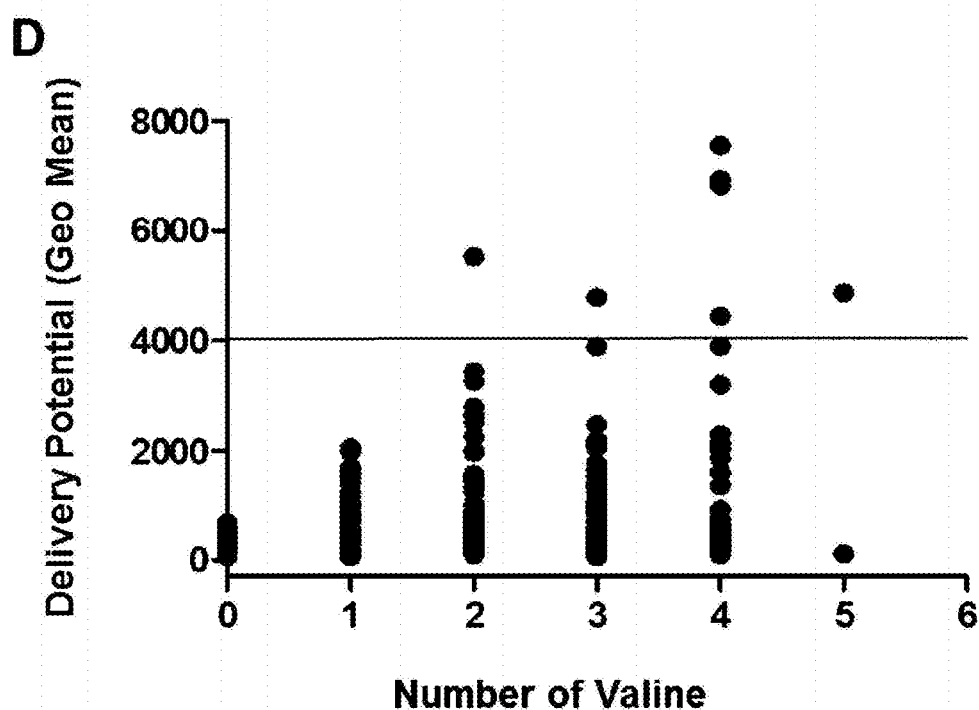

【Figure 14a】
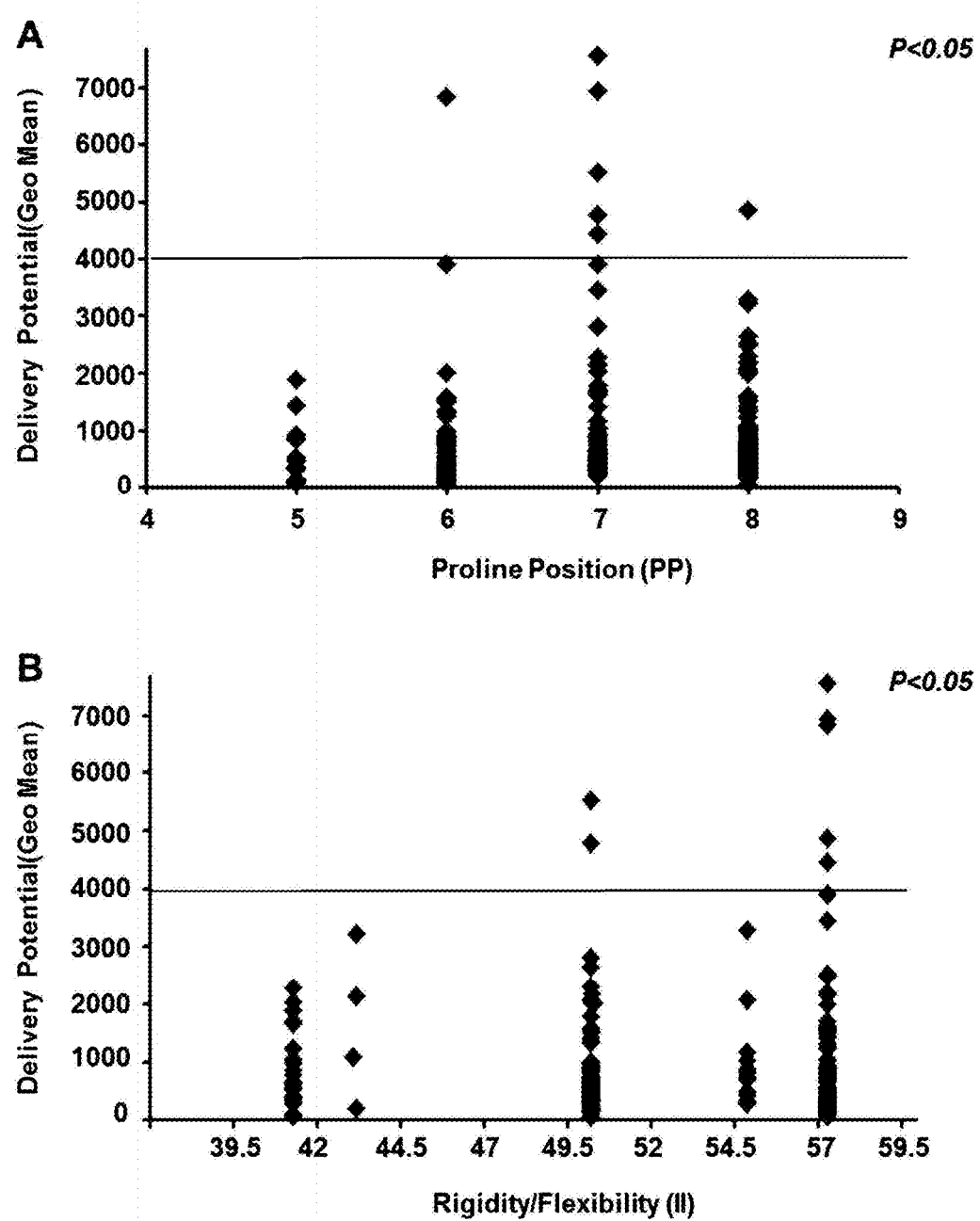

【Figure 14b】
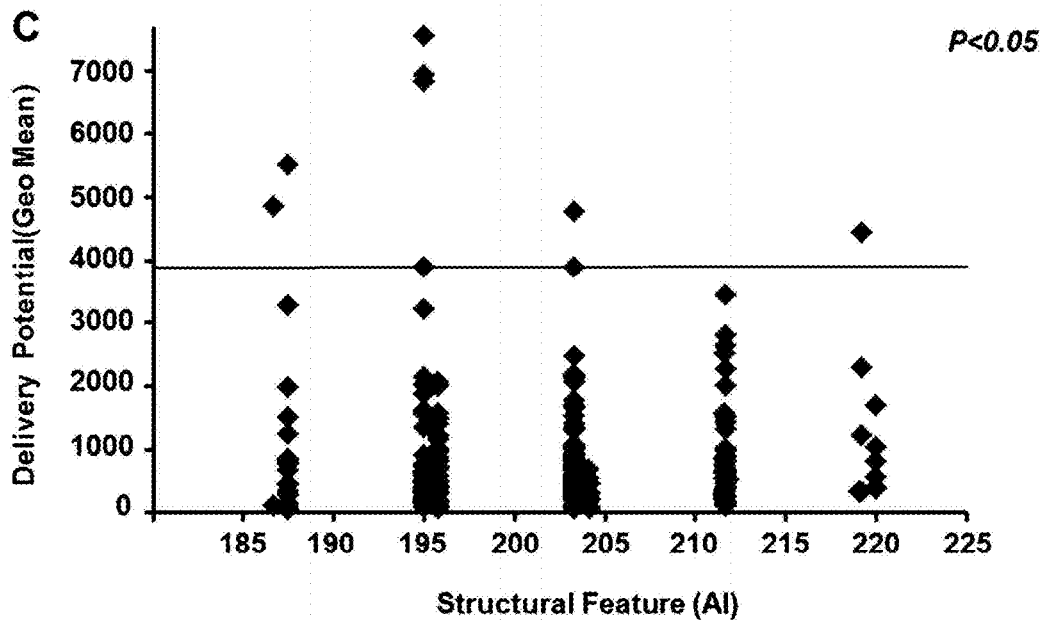
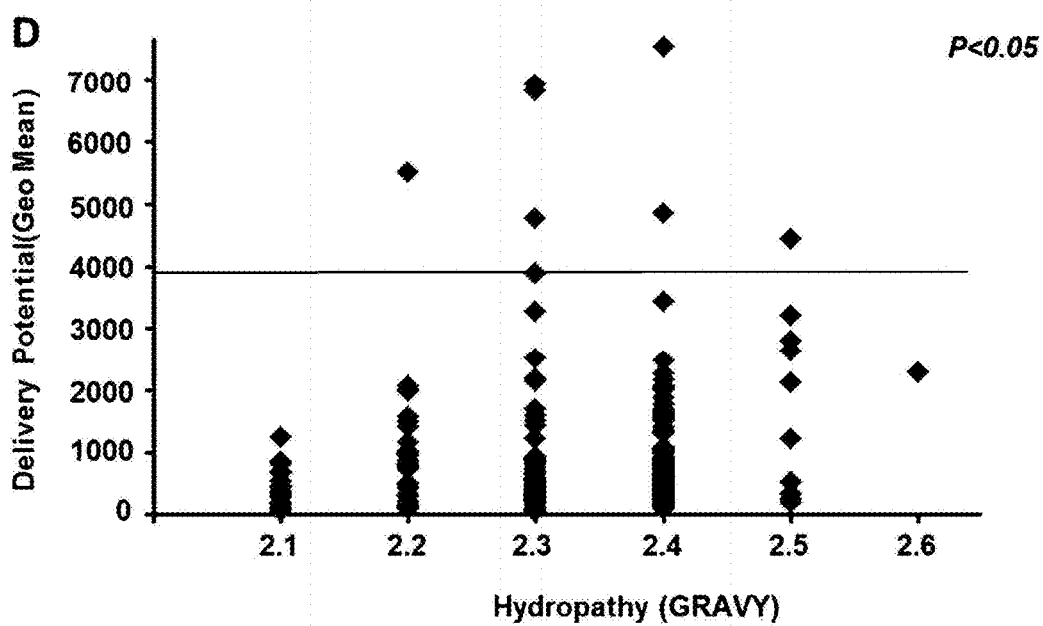

[Figure 15a]
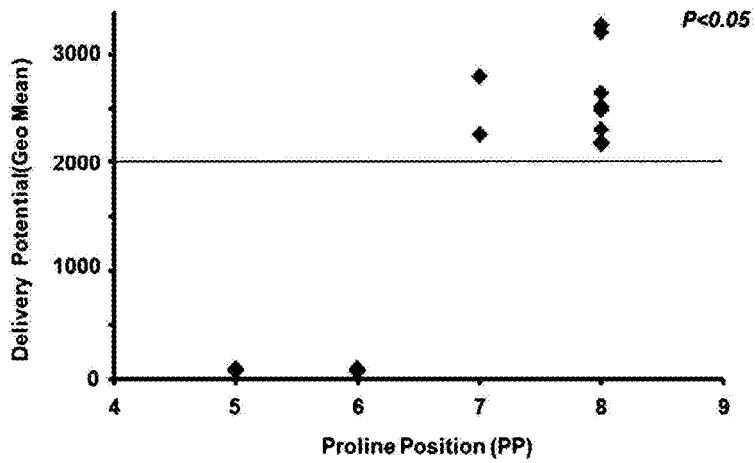
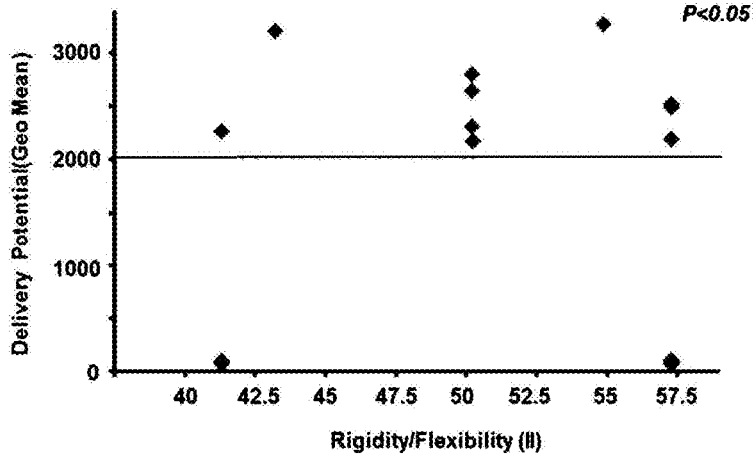

[Figure 15b]
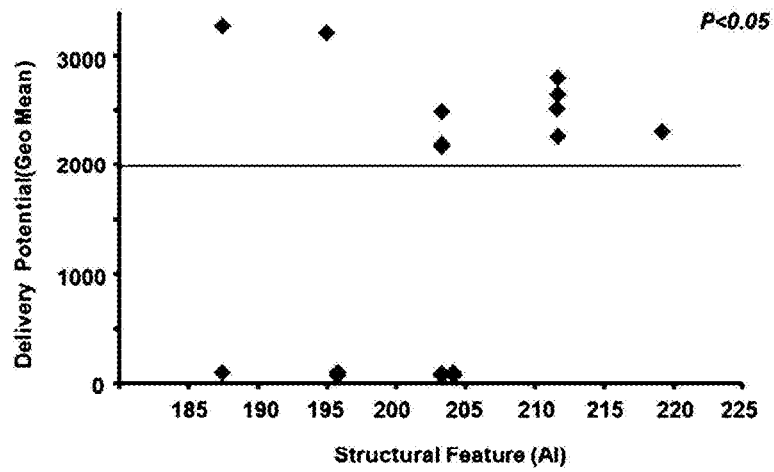
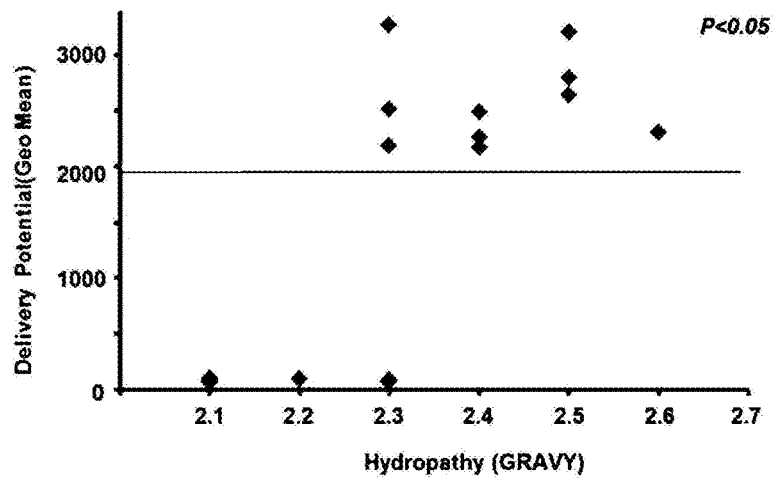

【Figure 16】
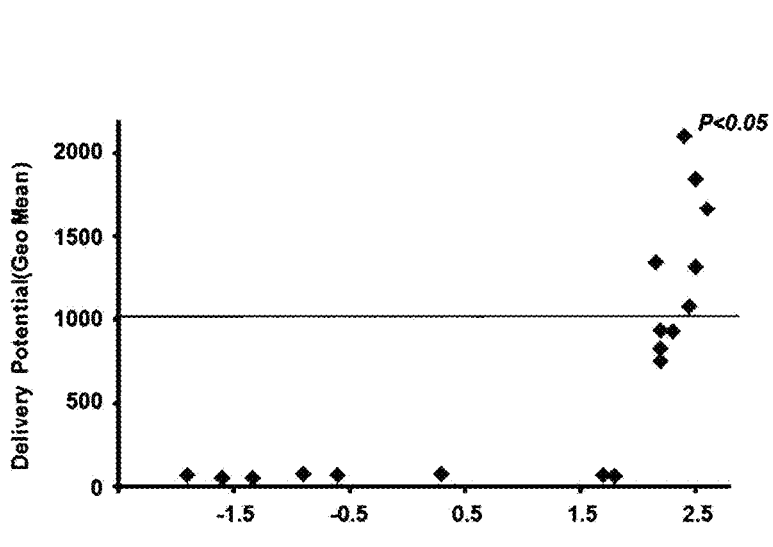
【Figure 17】
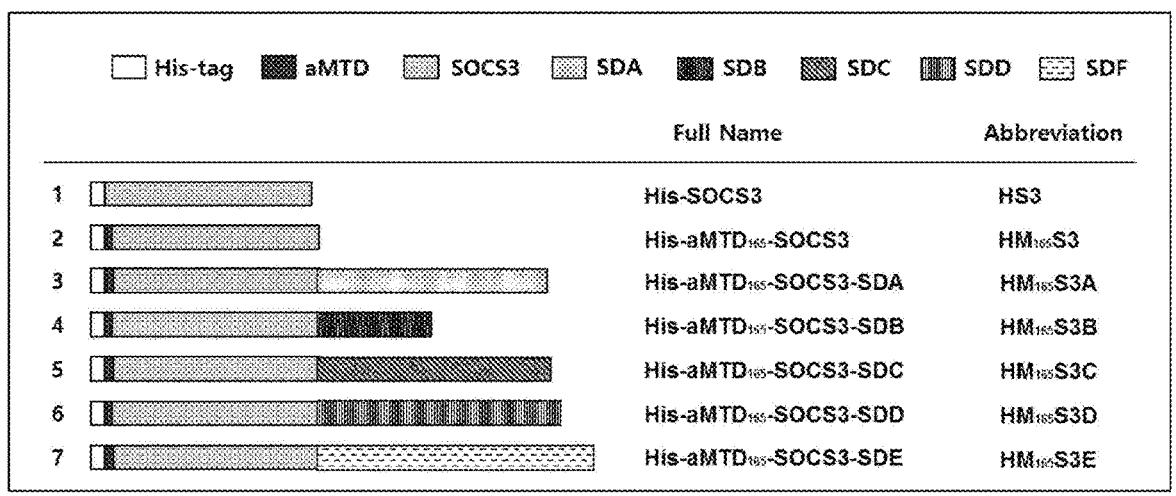

【Figure 18】
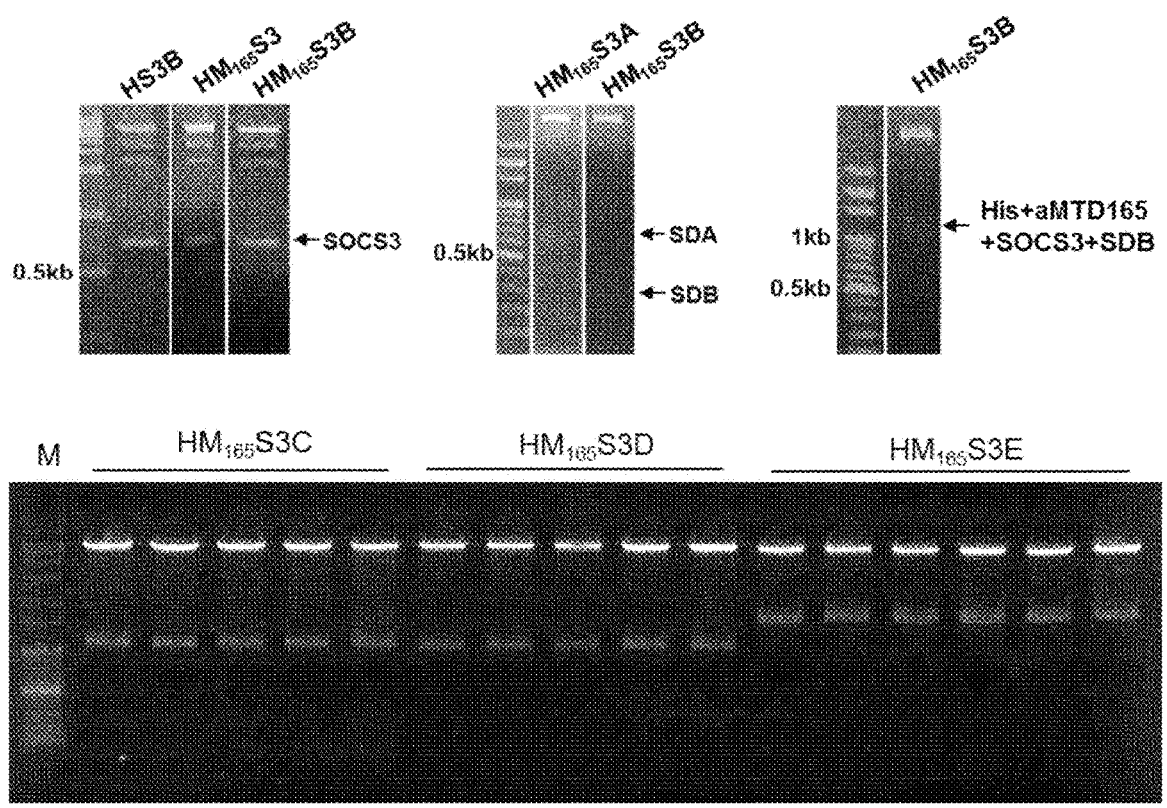
【Figure 19】
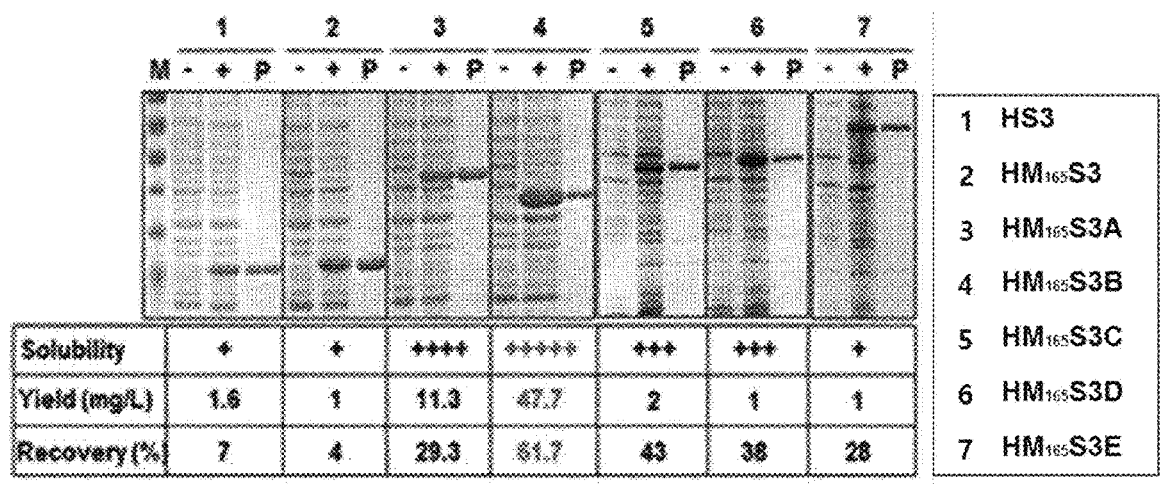

[Figure 20]
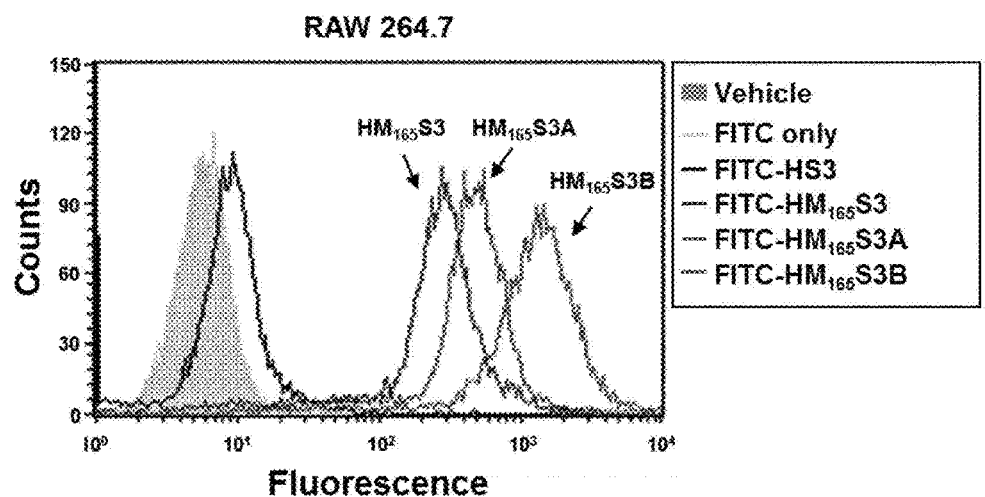
[Figure 21]
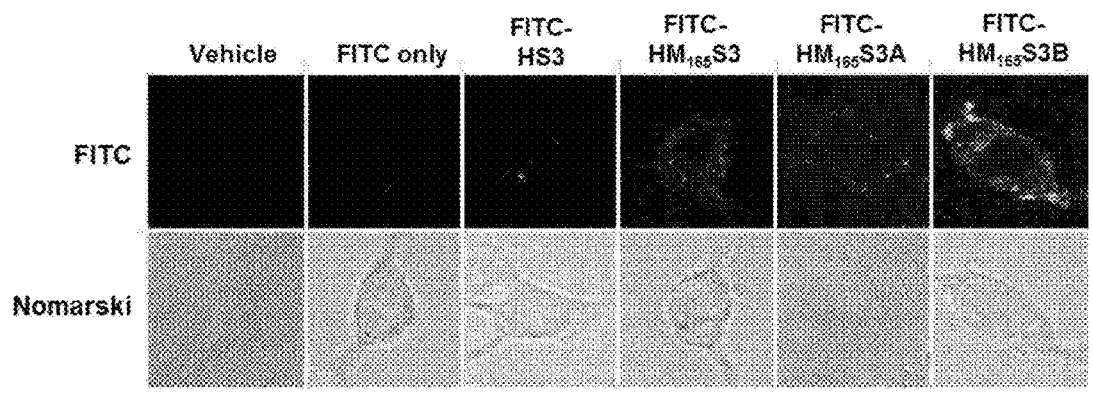

[Figure 22]
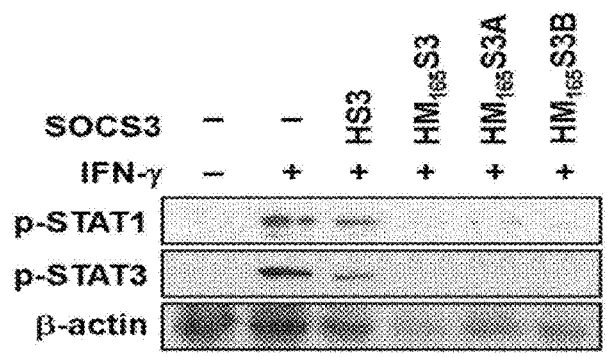
[Figure 23]

【Figure 24】
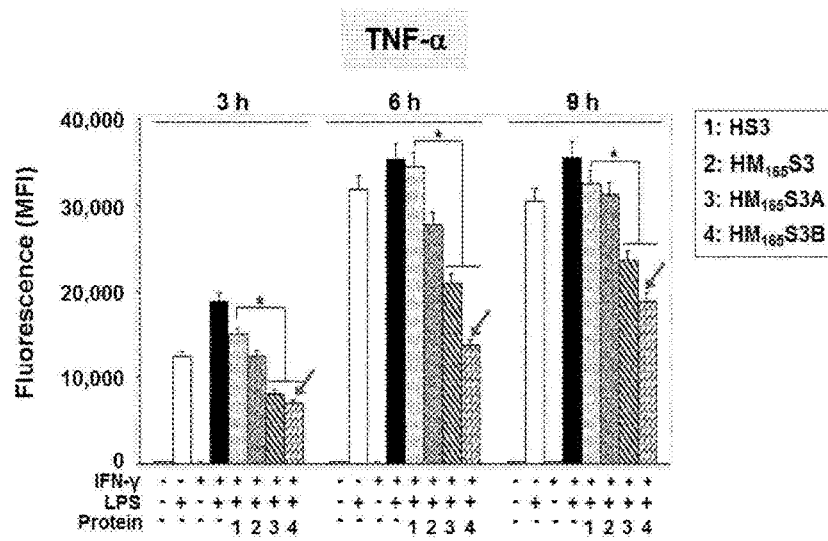
【Figure 25】
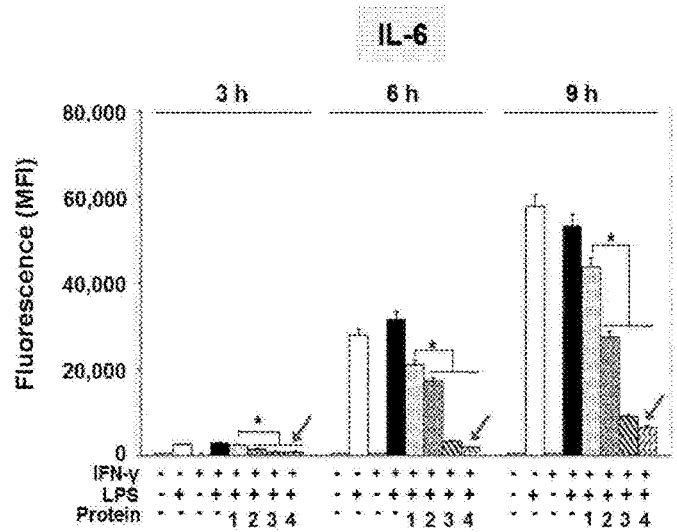
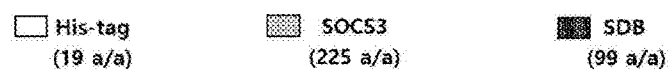

[Figure 26]
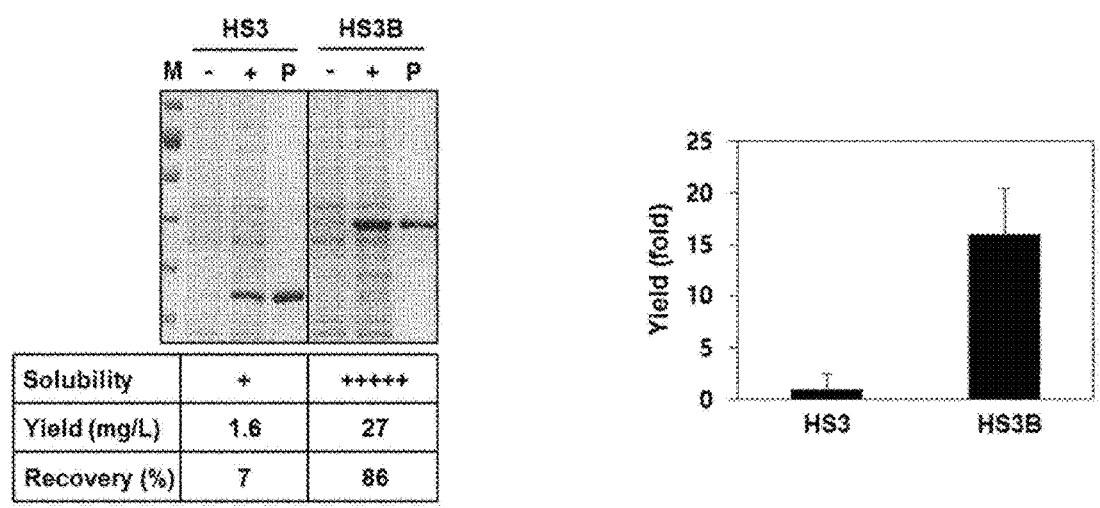
[Figure 27]
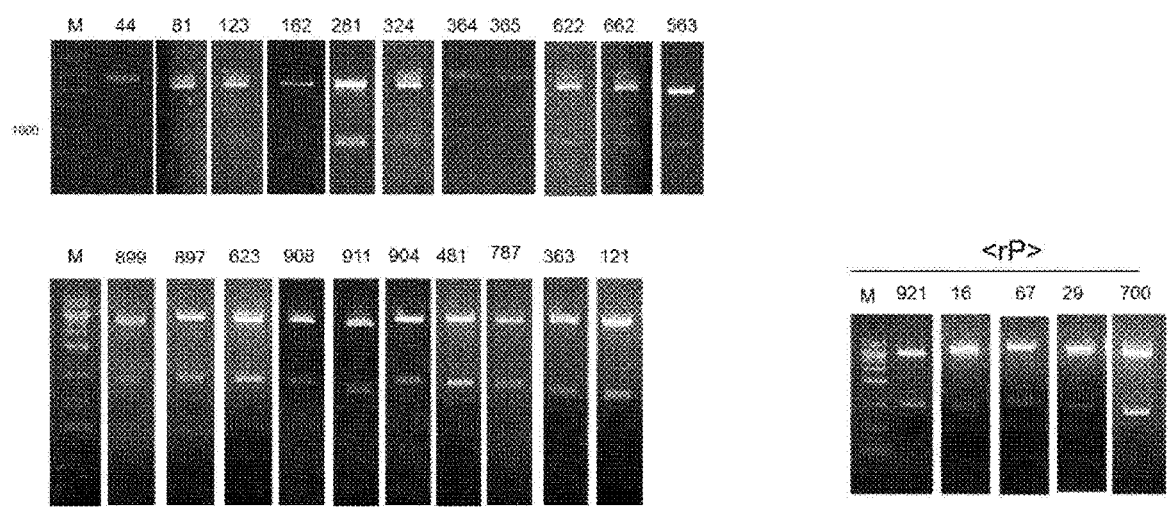

[Figure 28a]
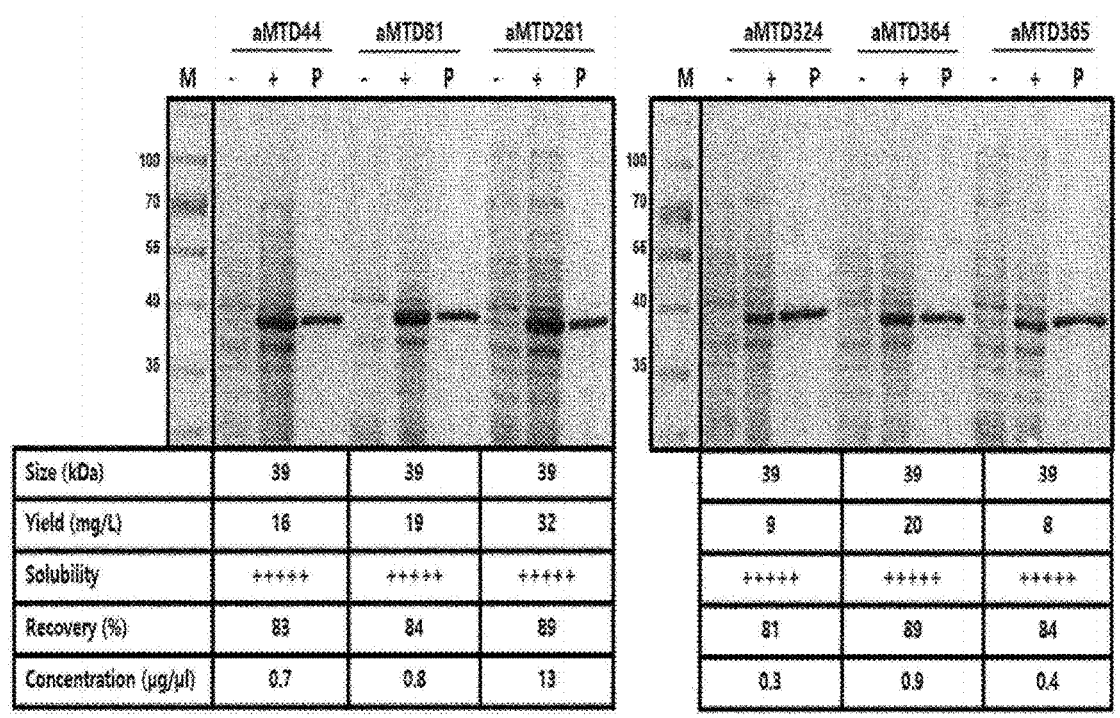

[Figure 28b]
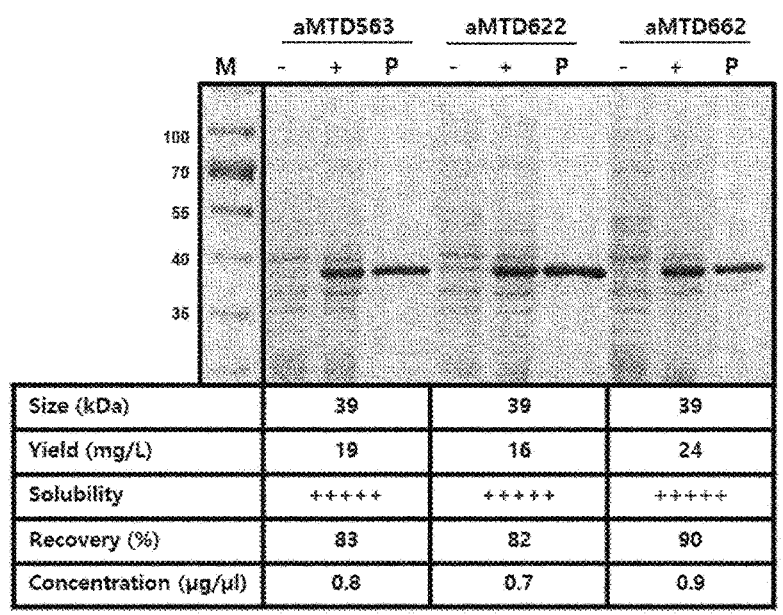
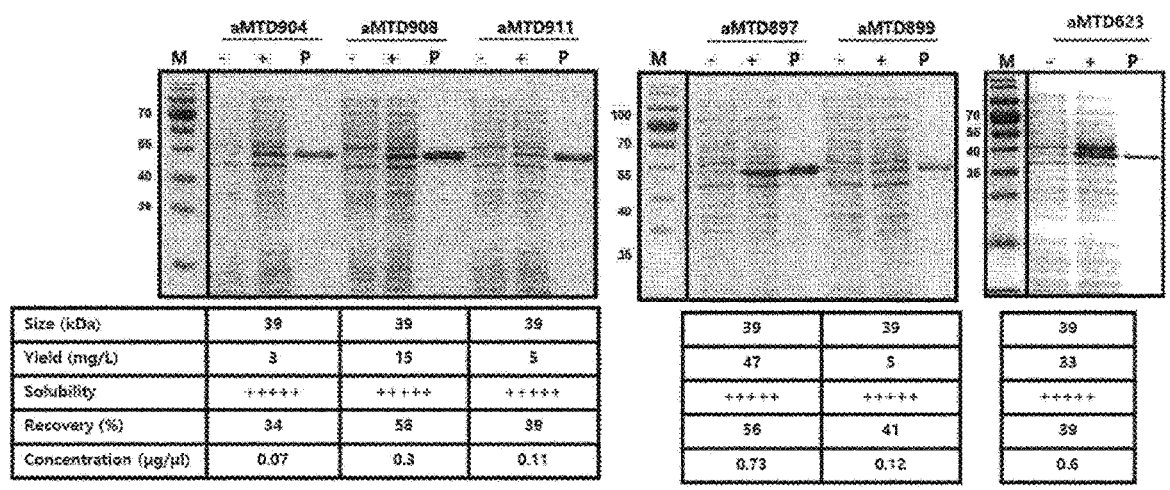

[Figure 29]
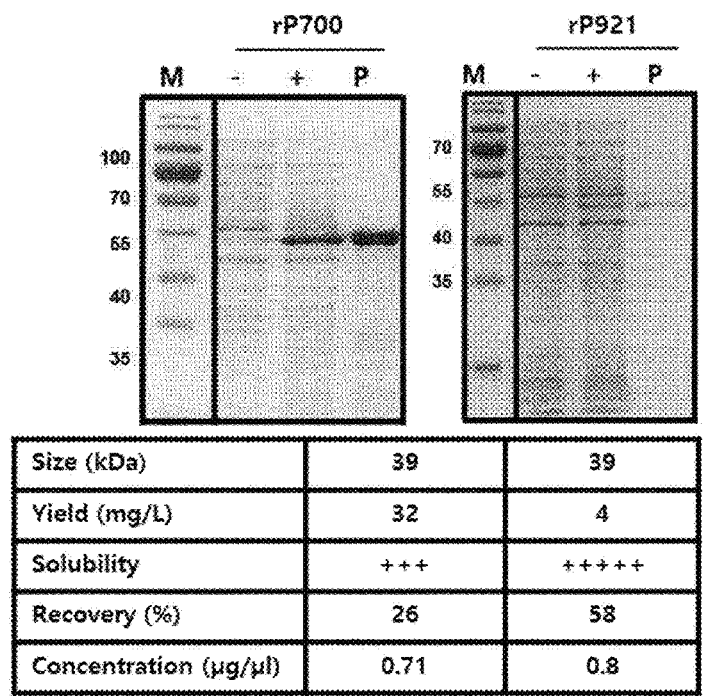

[Figure 30]

Solubility & Yield

| | 121 | 623 | 165 | 81 | 182 | 385 | 491 | 2 | 281 | 324 | 808 |
|---|---|---|---|---|---|---|---|---|---|---|---|
| Solubility | +++ | +++++ | +++++ | +++++ | +++++ | +++++ | +++++ | +++++ | +++++ | +++++ | +++++ |
| Yield (mg/L) | 37 | 33 | 60 | 43 | 9 | 36 | 77 | 54 | 55 | 58 | 15 |

| | 363 | 911 | 264 | 662 | 583 | 622 | 897 | 44 | 899 | 364 | 904 |
|---|---|---|---|---|---|---|---|---|---|---|---|
| Solubility | +++++ | +++++ | +++++ | +++++ | +++++ | +++++ | +++++ | +++++ | +++++ | ++++ | +++++ |
| Yield (mg/L) | 57 | 3 | 33 | 56 | 53 | 46 | 47 | 48 | 5 | 58 | 3 |

[Figure 31]
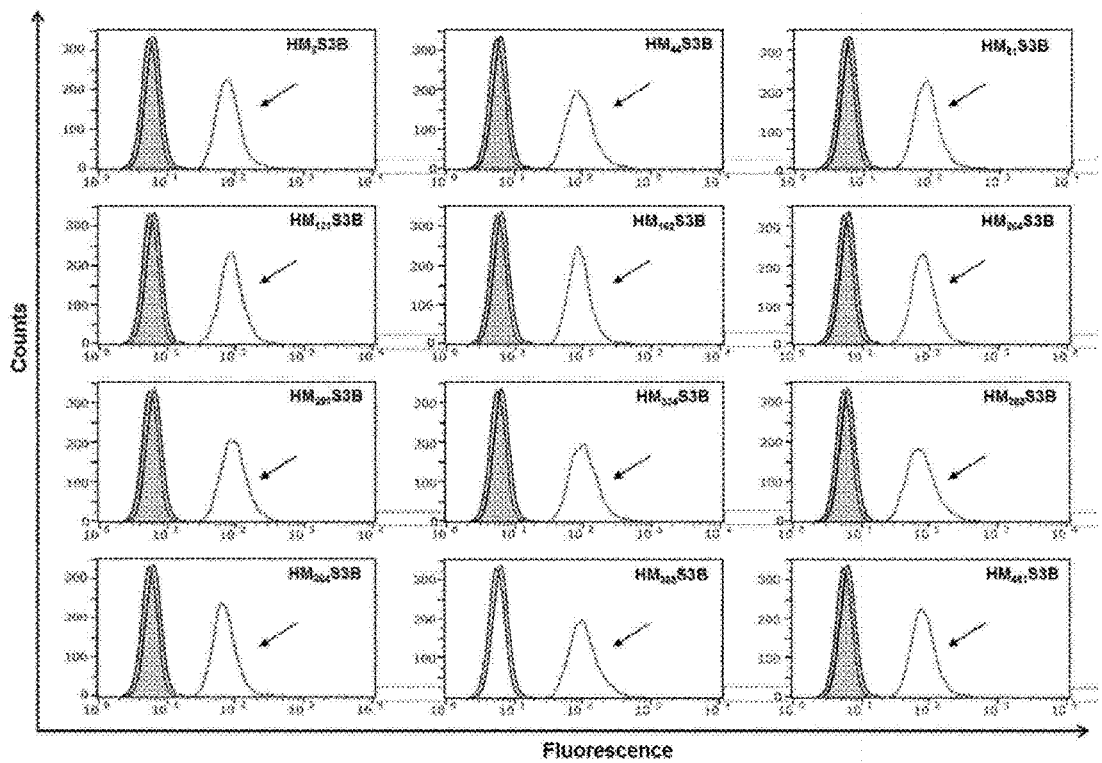
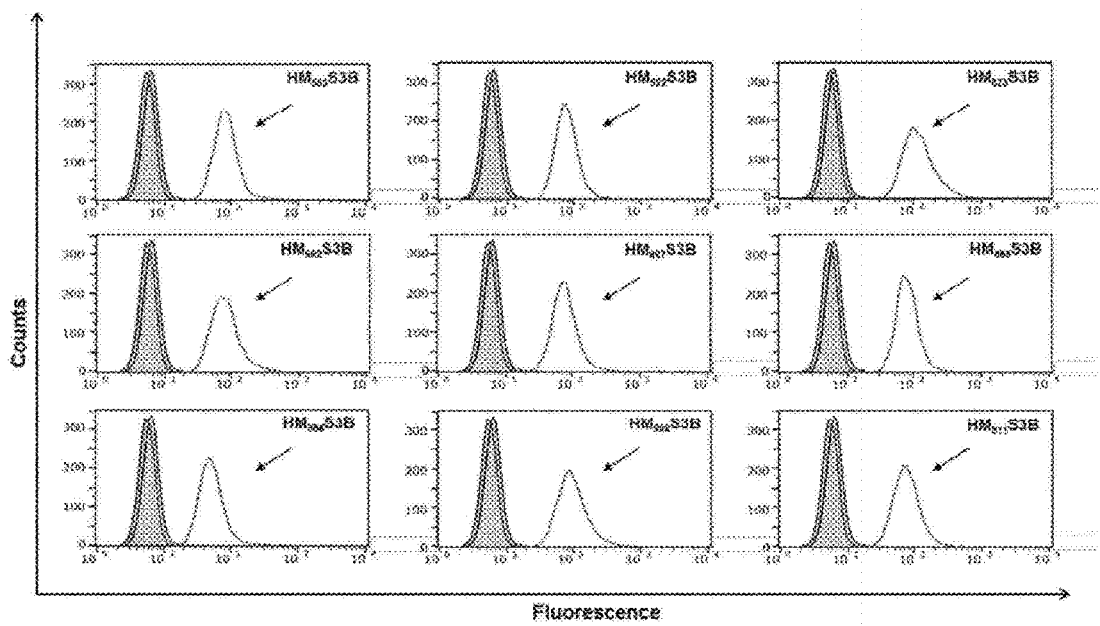

【Figure 32】
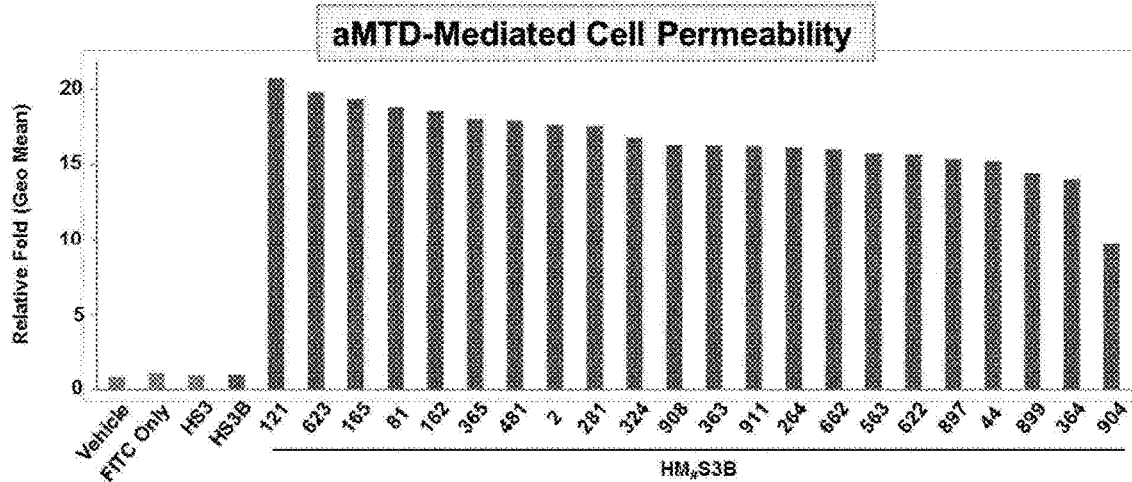
【Figure 33】
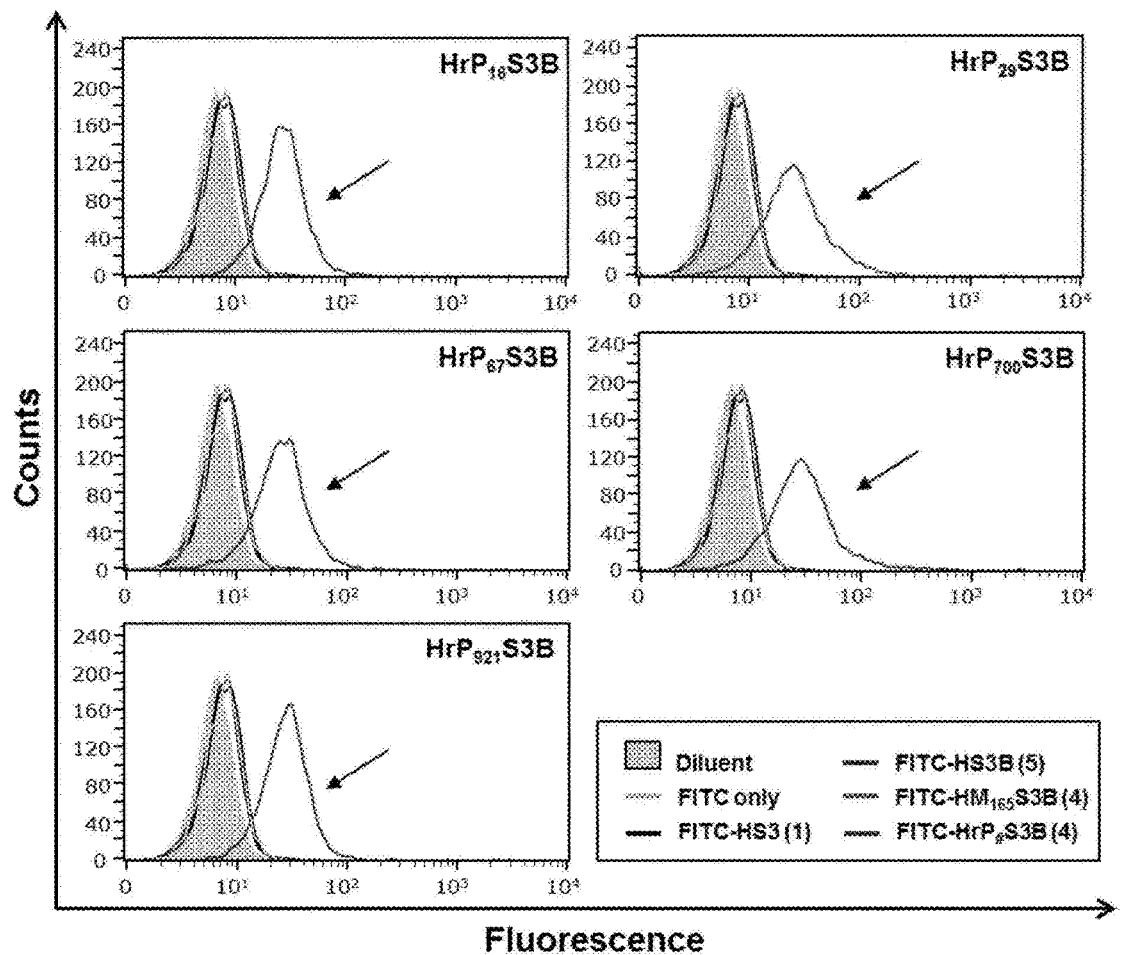

[Figure 34]
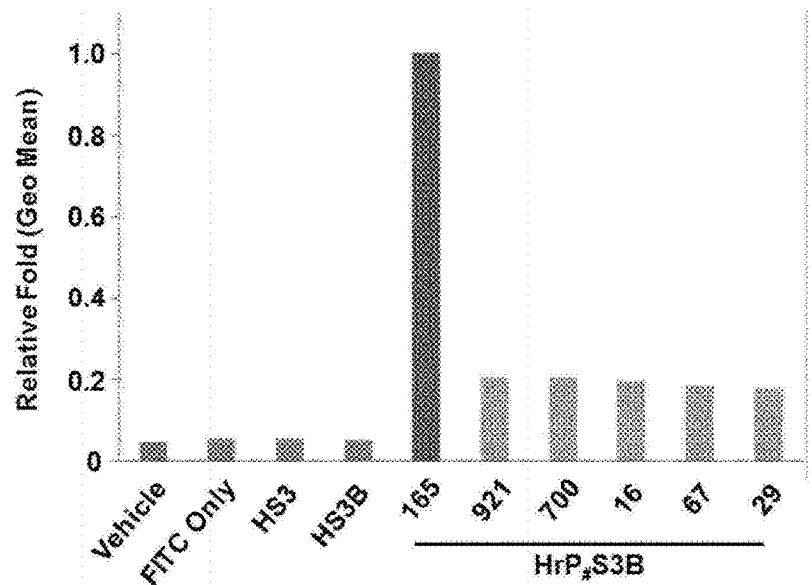
[Figure 35]
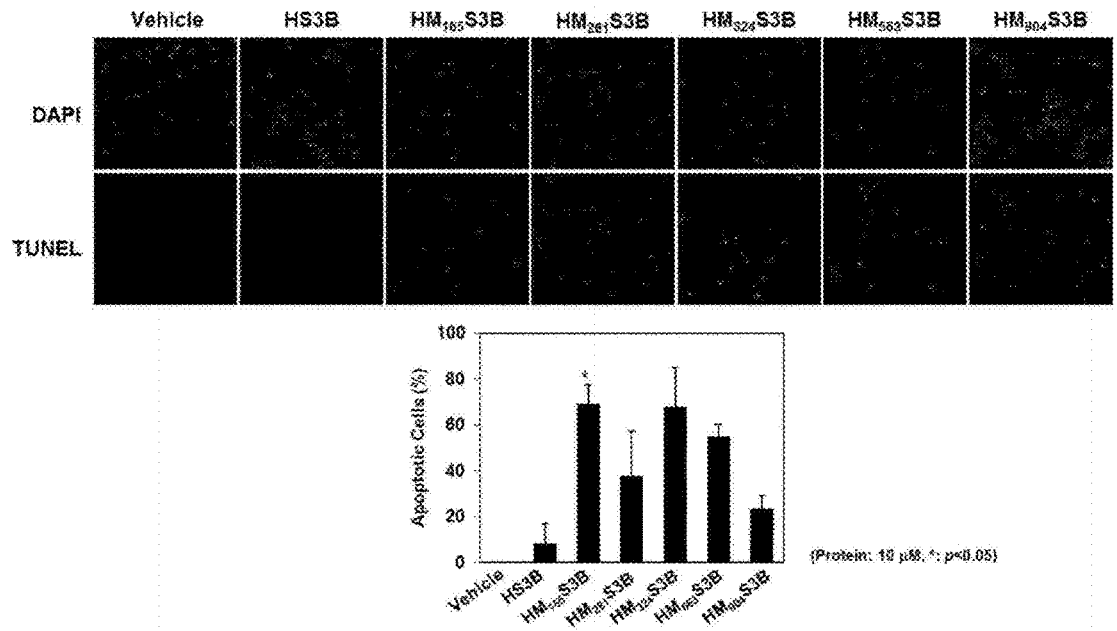

[Figure 36]
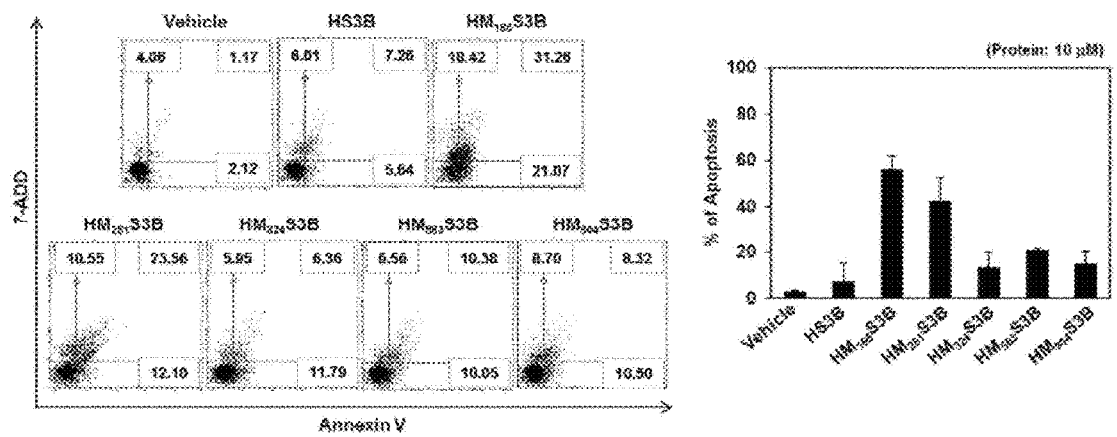
[Figure 37]
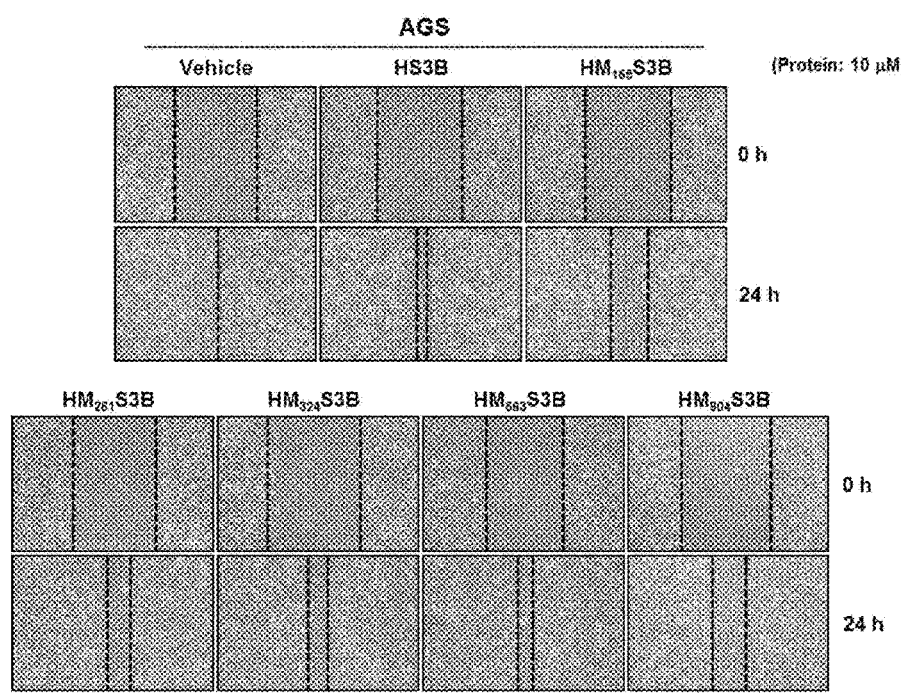

[Figure 38]

Solubility

| Rank | aMTD | Yield (mg/L) |
|---|---|---|
| 1 | 481 | 77 |
| 2 | 364 | 58 |
| 3 | 363 | 57 |
| 4 | 324/862 | 56 |
| 5 | 281 | 55 |
| 6 | 2 | 54 |
| 7 | 583 | 53 |
| 8 | 165 | 50 |
| 9 | 897 | 47 |
| 10 | 622/44 | 46 |

Permeability

| Rank | aMTD |
|---|---|
| 1 | 121 |
| 2 | 623 |
| 3 | 165 |
| 4 | 81 |
| 5 | 162 |
| 6 | 365 |
| 7 | 481 |
| 8 | 2 |
| 9 | 281 |
| 10 | 324 |

Biological Activity

Apoptosis (TUNEL Assay)

| Rank | 1 | 2 | 3 | 4 | 5 |
|---|---|---|---|---|---|
| aMTD | 165 | 324 | 583 | 281 | 904 |

Apoptosis (Annexin V)

| Rank | 1 | 2 | 3 | 4 | 5 |
|---|---|---|---|---|---|
| aMTD | 165 | 281 | 583 | 904 | 324 |

Wound Healing

| Rank | 1 | 2 | 3 | 4 | 5 |
|---|---|---|---|---|---|
| aMTD | 165 | 904 | 281 | 324 | 583 |

【Figure 39】
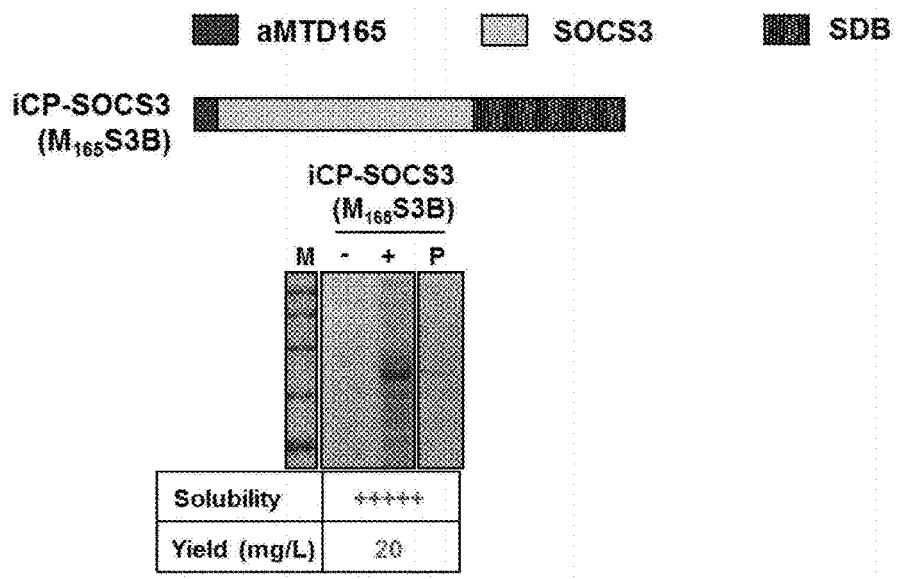
【Figure 40】
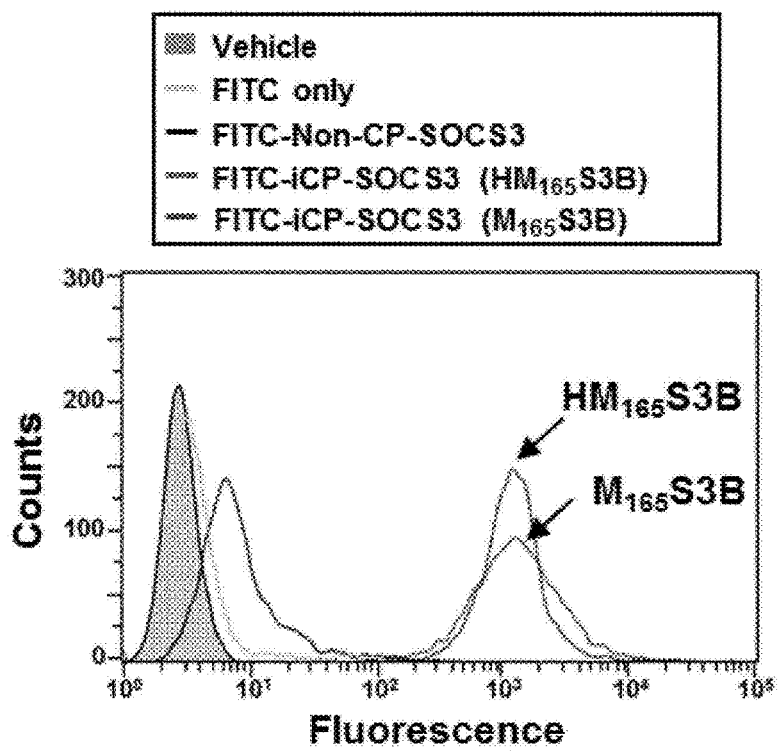

【Figure 41】
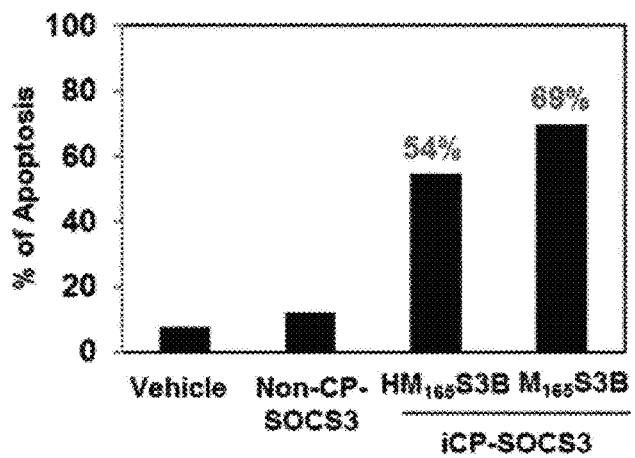
【Figure 42】
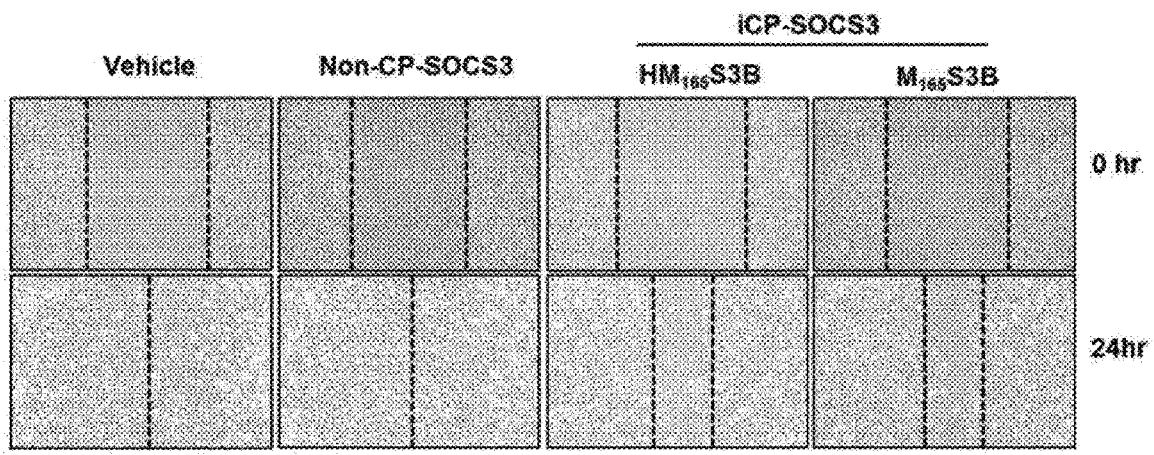
【Figure 43】
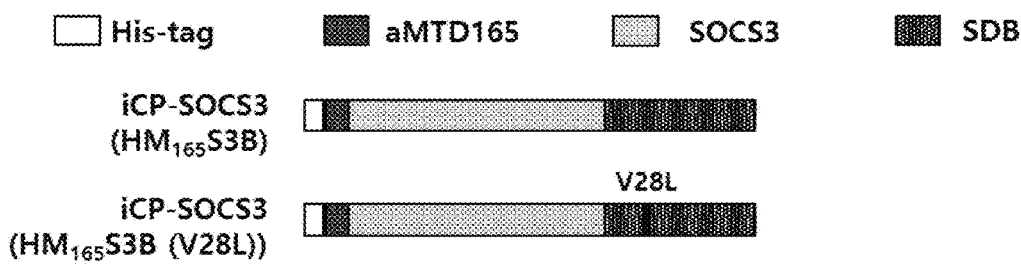

【Figure 44】
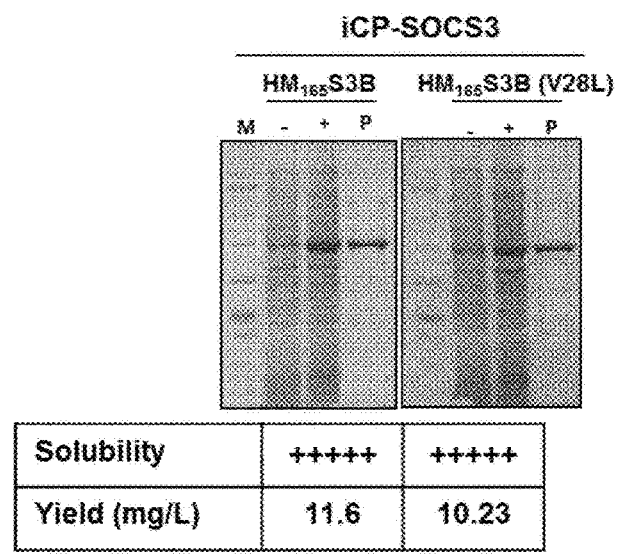
【Figure 45】
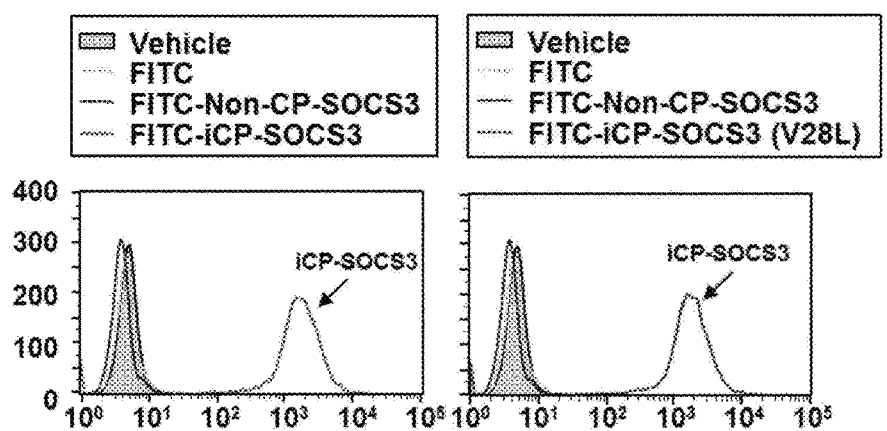

[Figure 46]
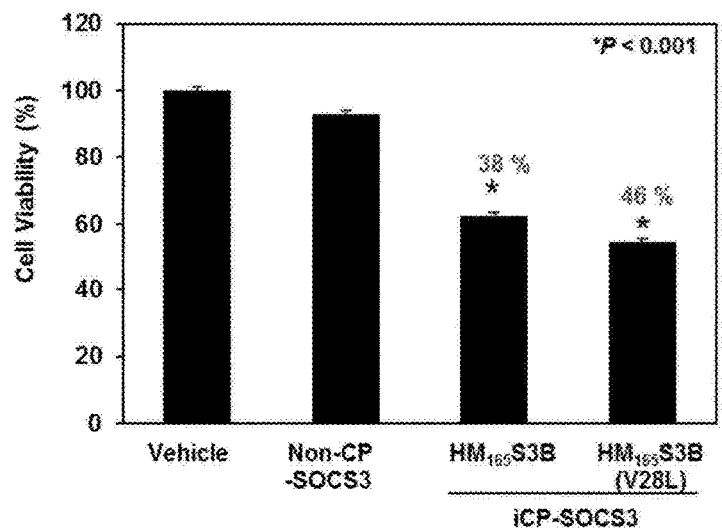
[Figure 47]
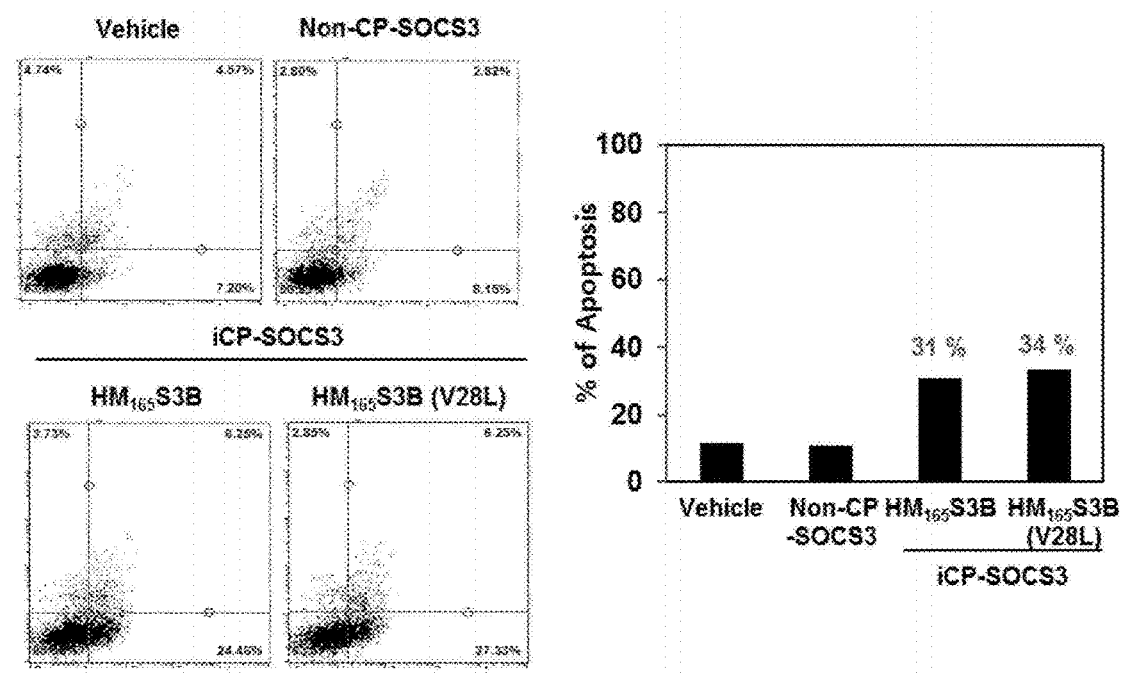

[Figure 48]
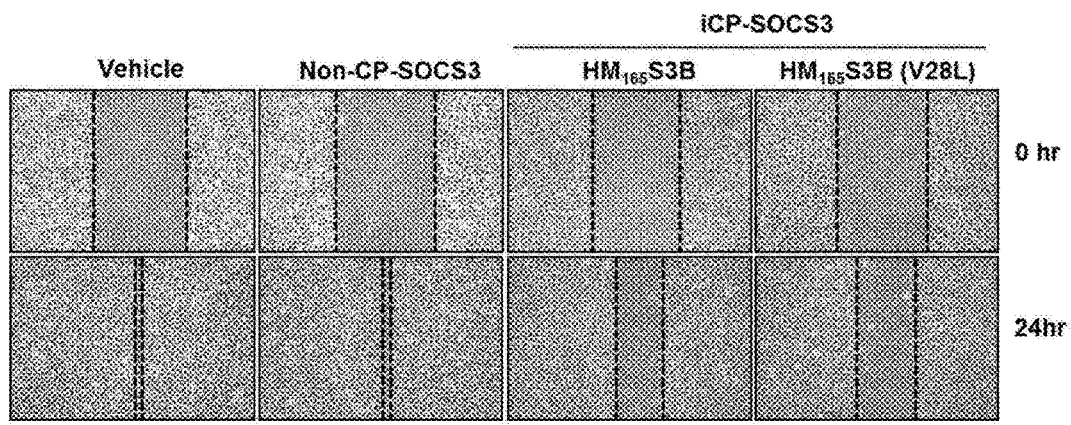
[Figure 49a]
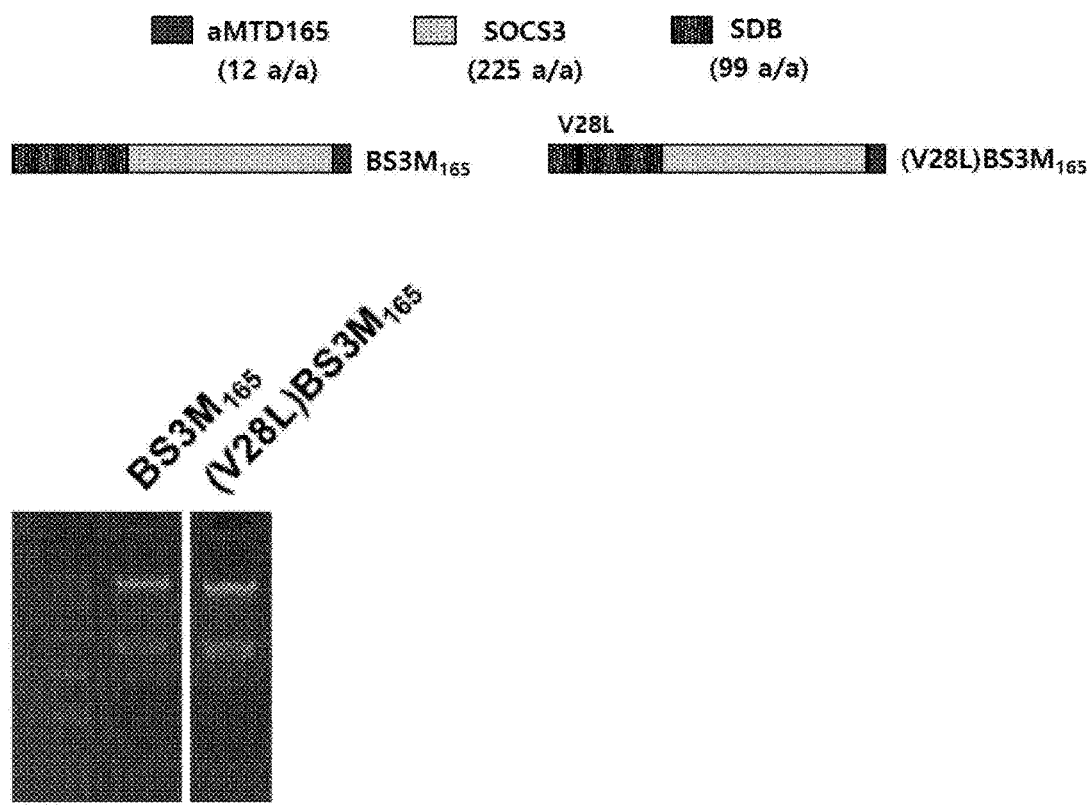

【Figure 49b】
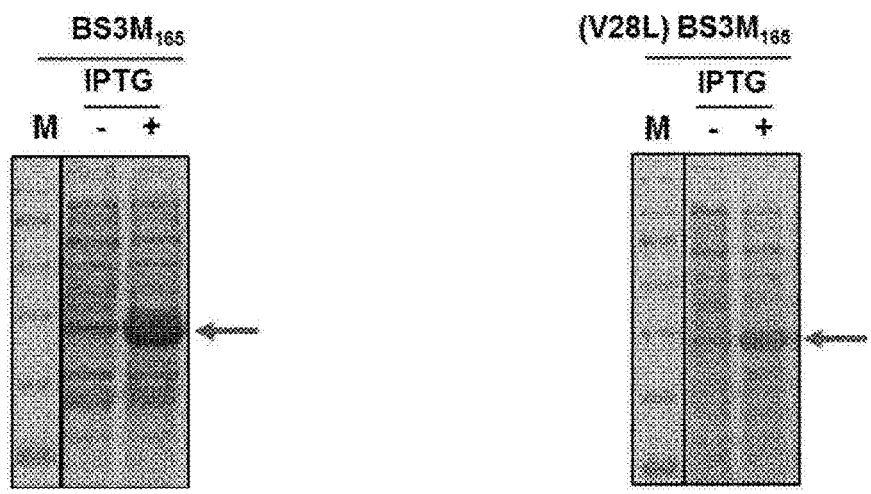
【Figure 50】
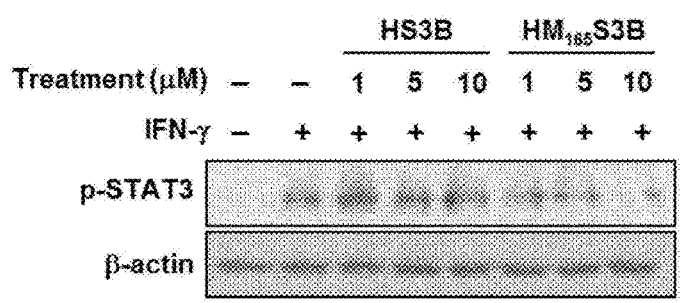

[Figure 51]
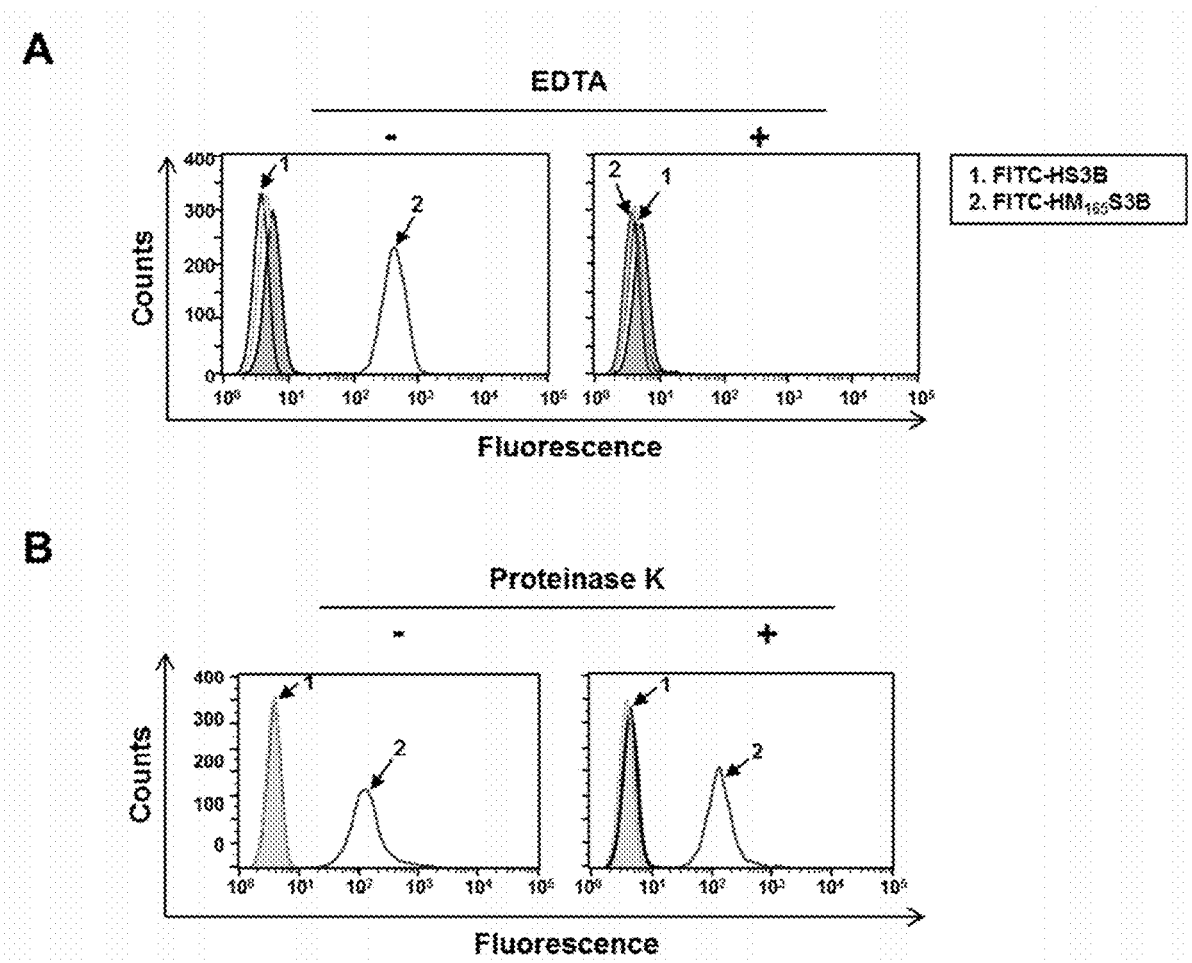

[Figure 52]
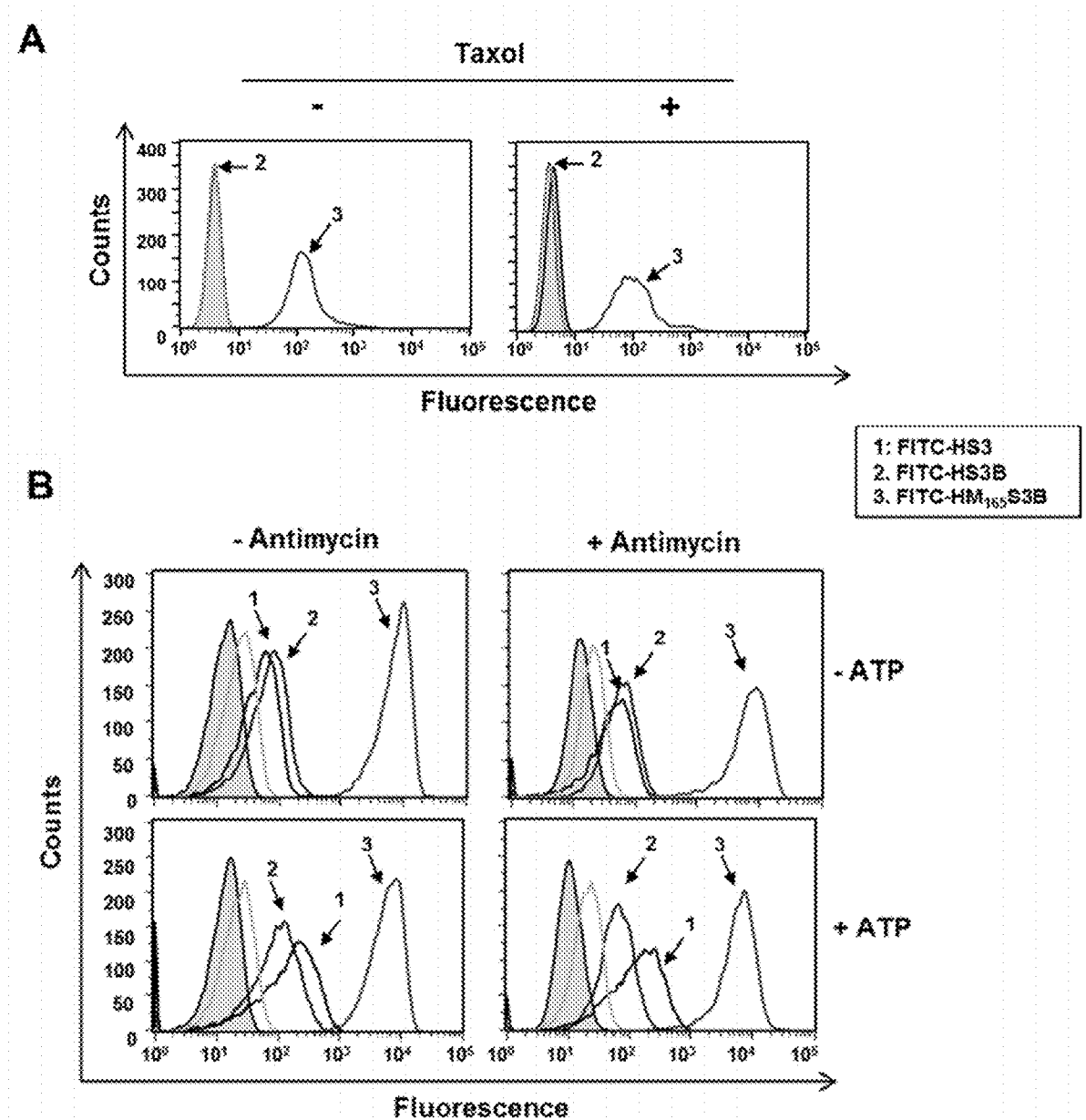

【Figure 53】
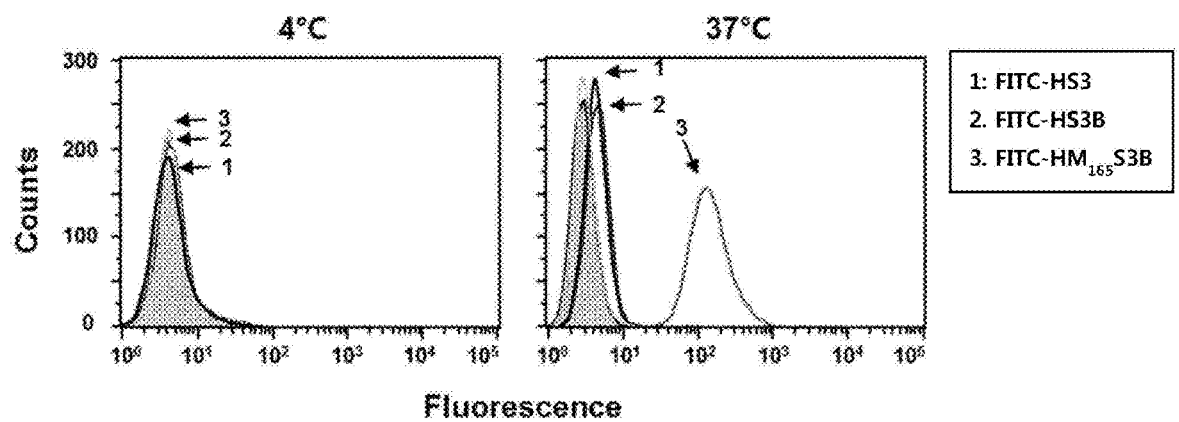
【Figure 54】
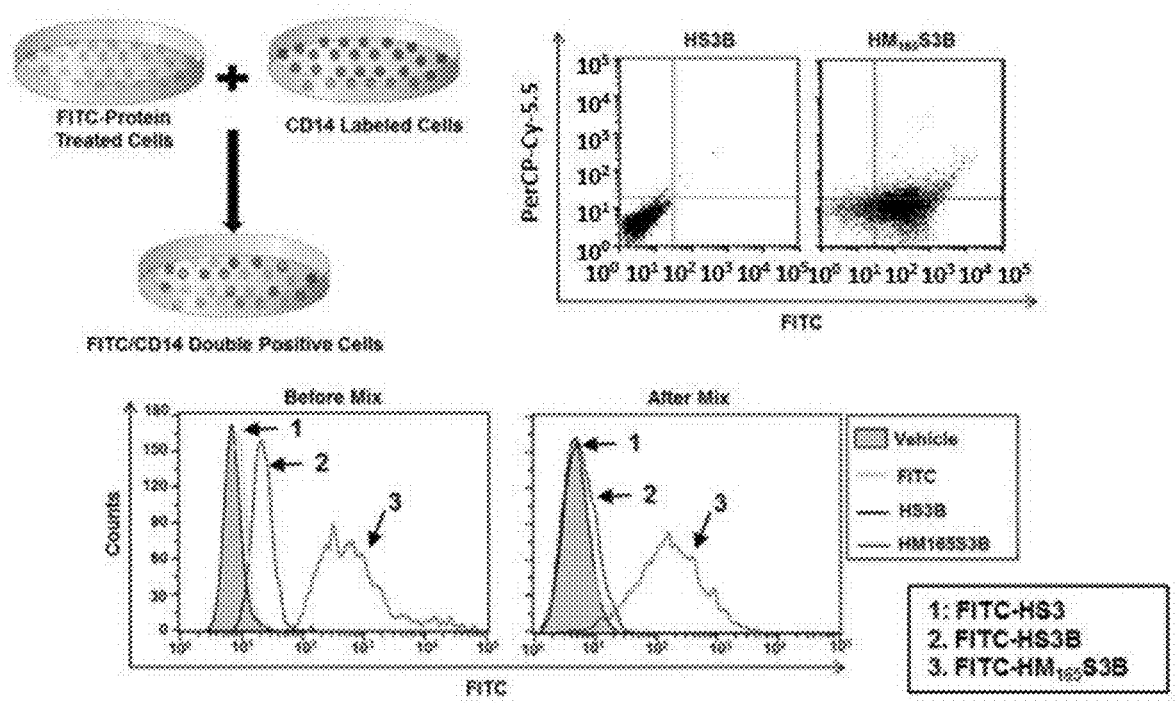

【Figure 55】
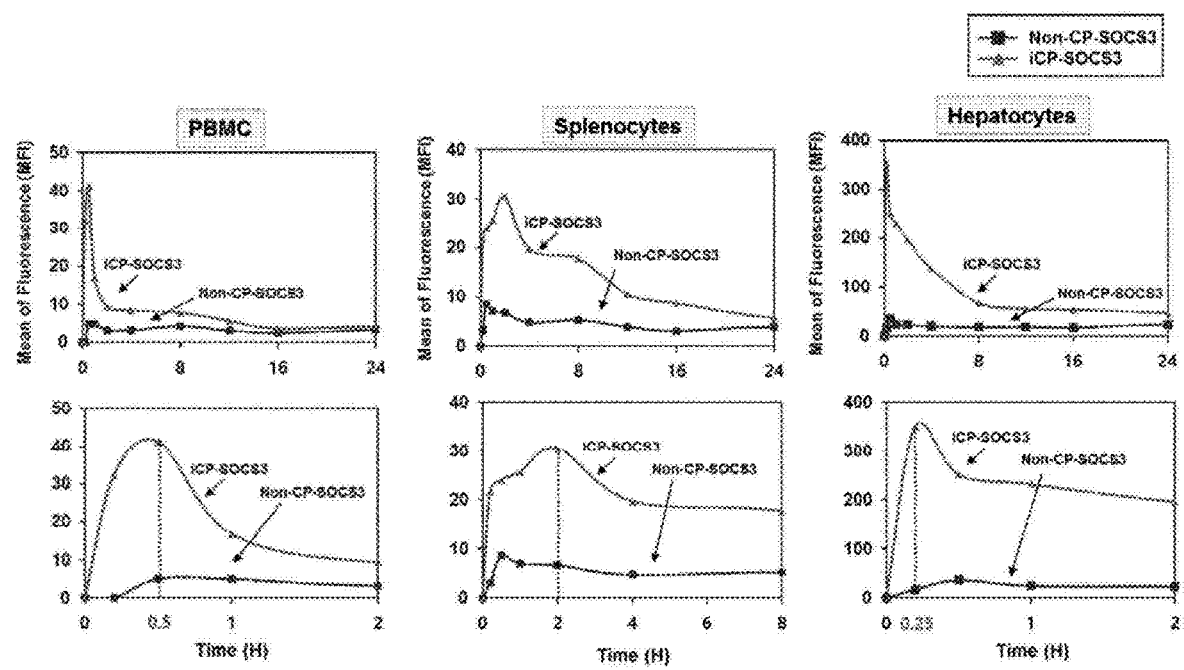
【Figure 56】
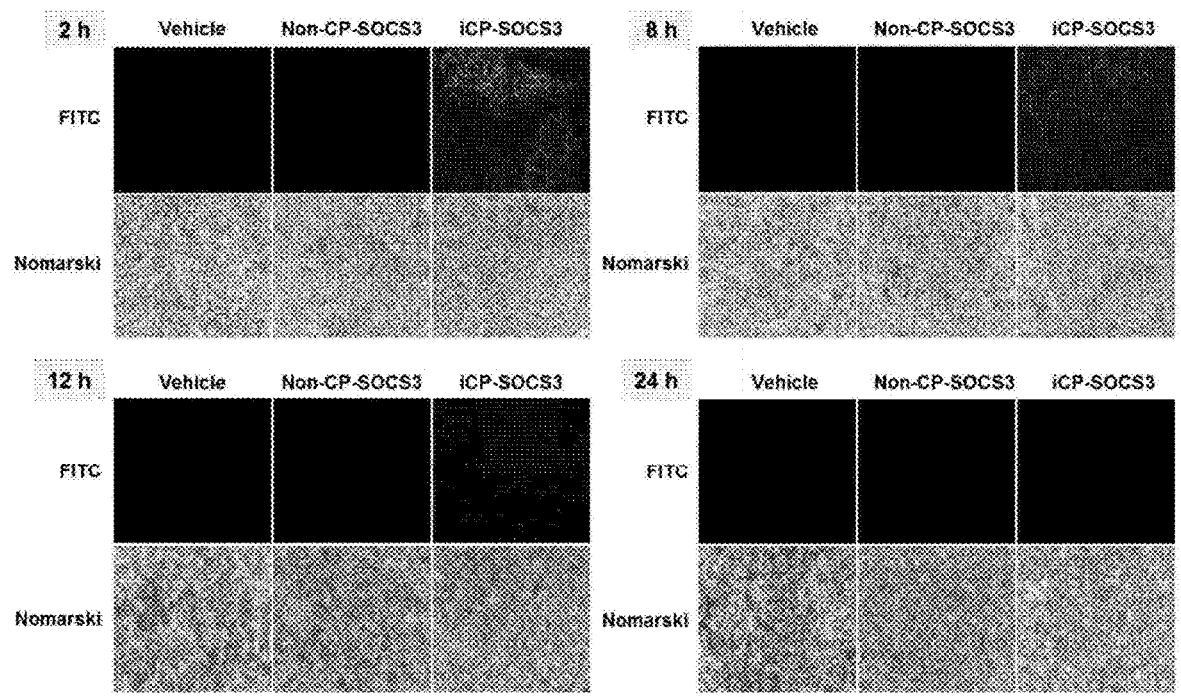

[Figure 57]
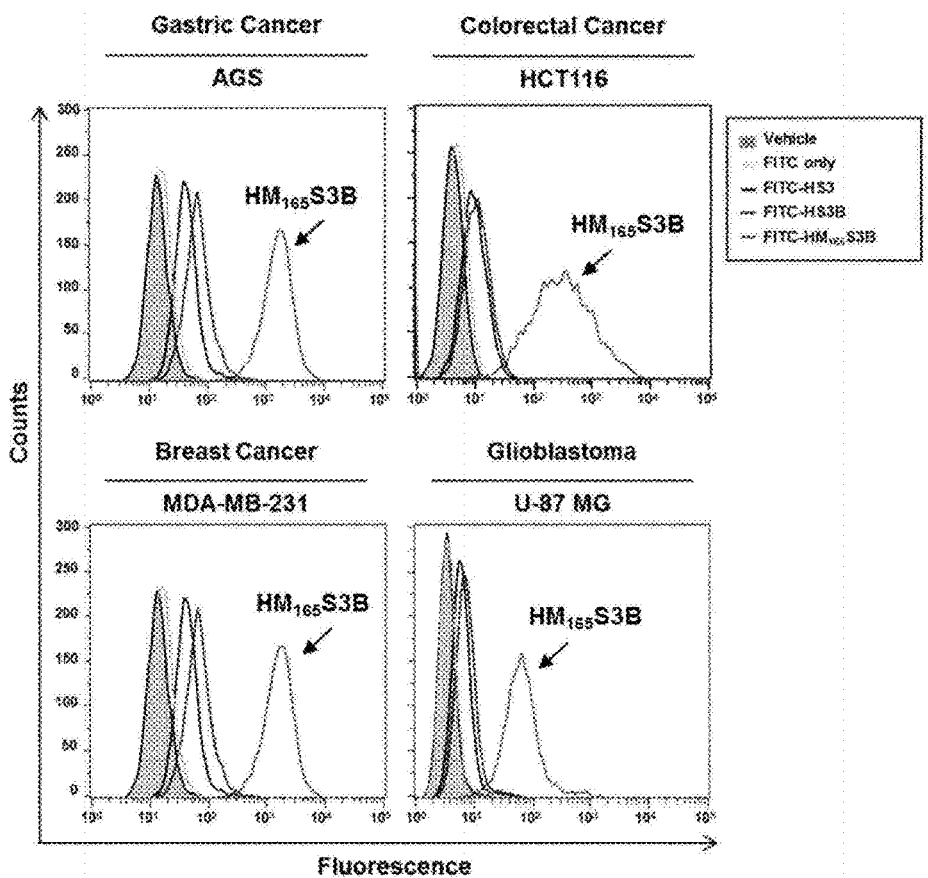
[Figure 58]
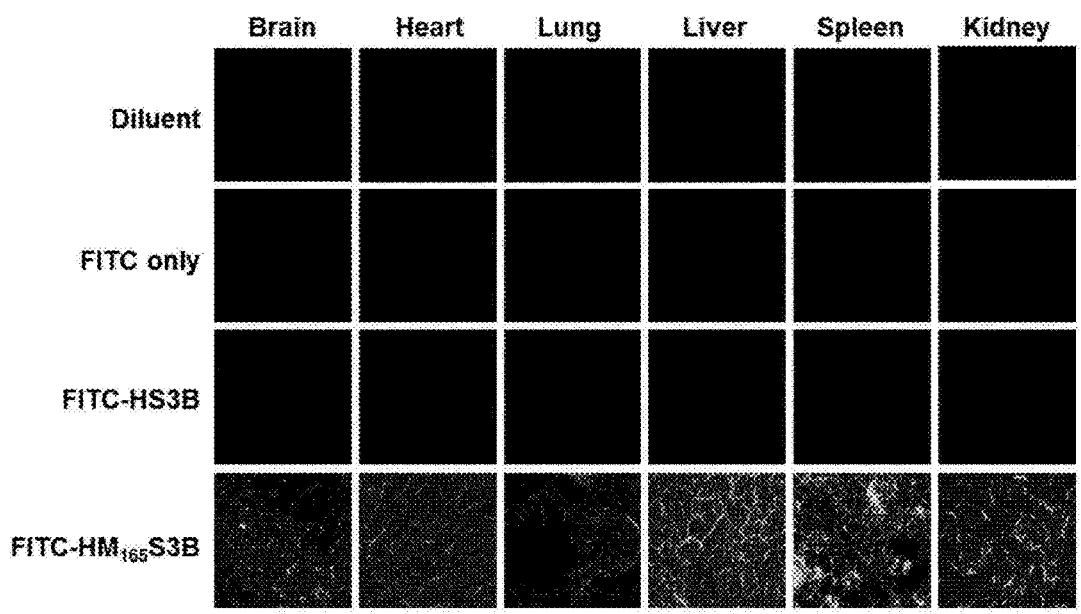

[Figure 59]
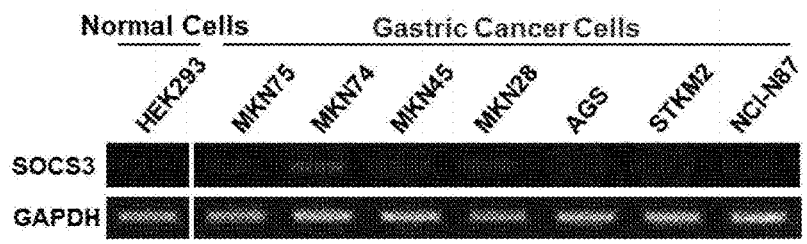
[Figure 60]
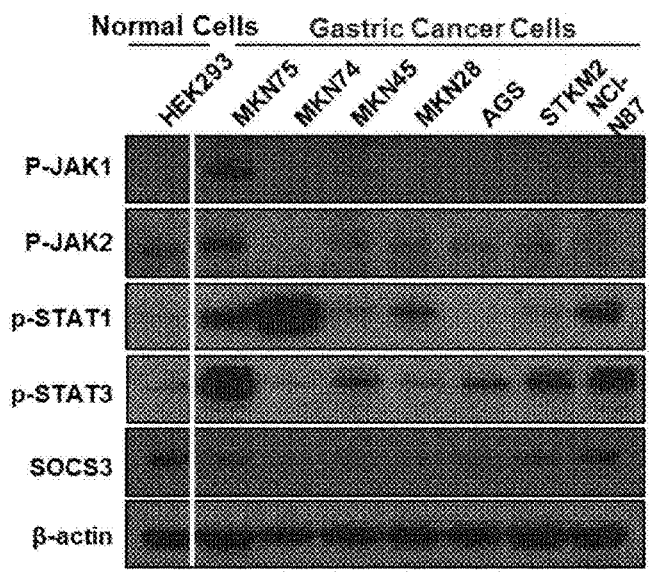
[Figure 61]
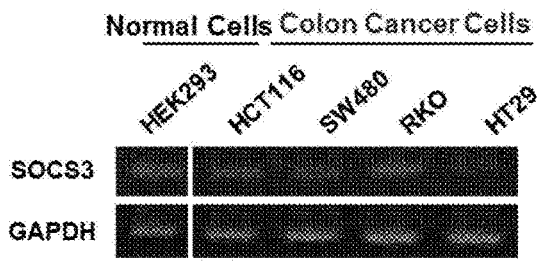

[Figure 62]
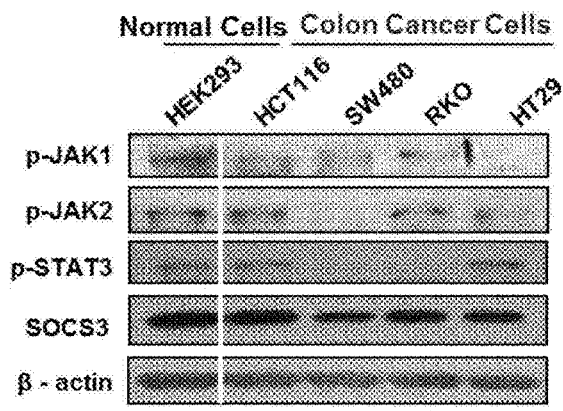
[Figure 63]
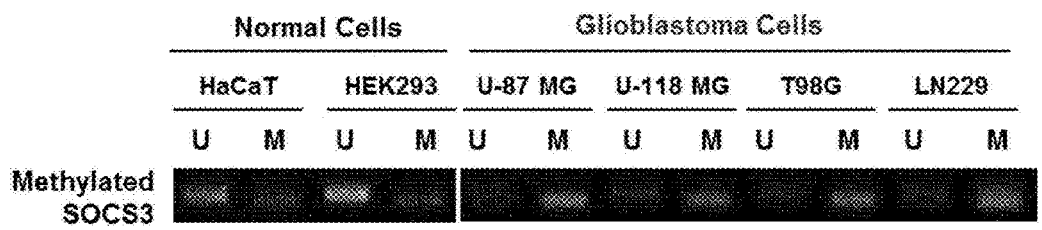
[Figure 64]
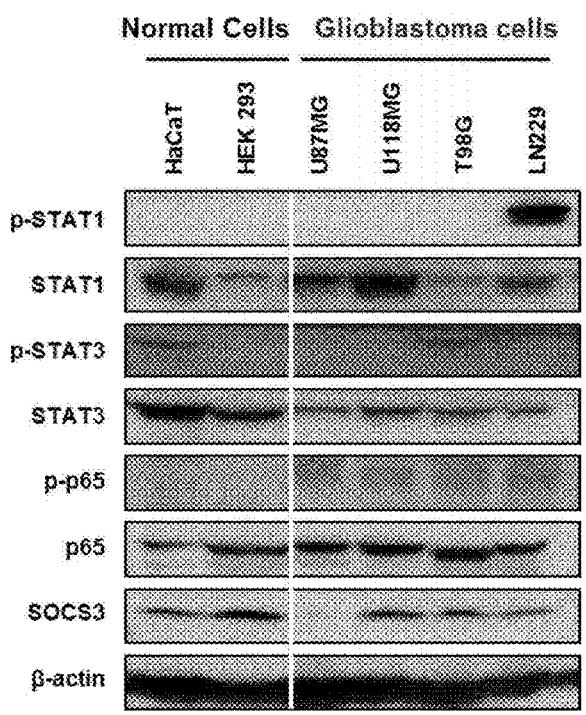

[Figure 65]
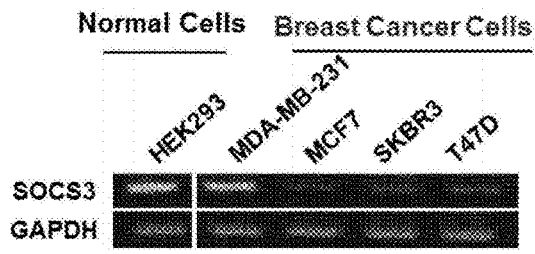
[Figure 66]
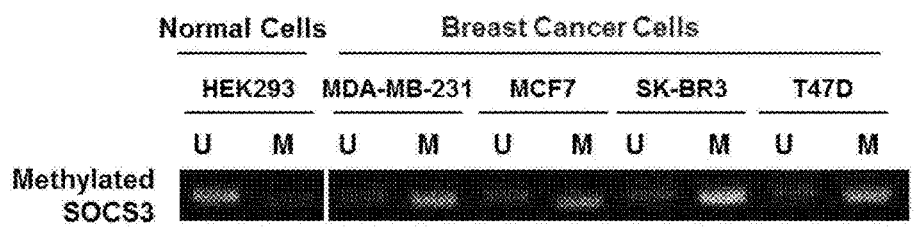
[Figure 67]
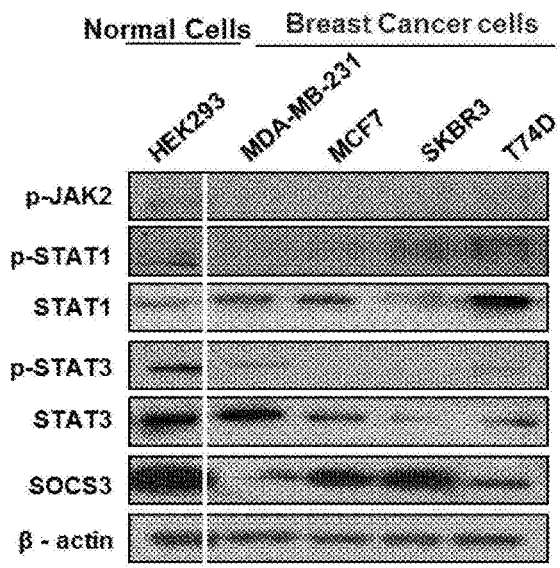

【Figure 68】
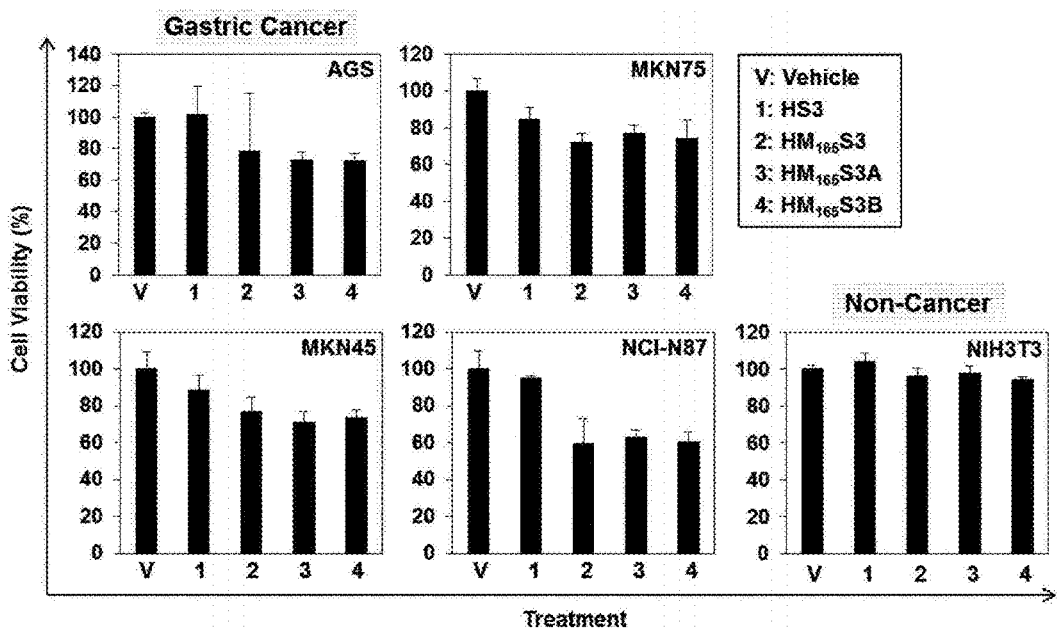
【Figure 69】
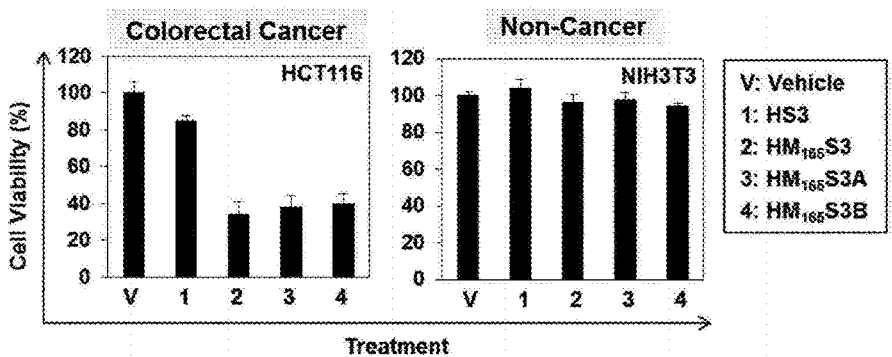
【Figure 70】
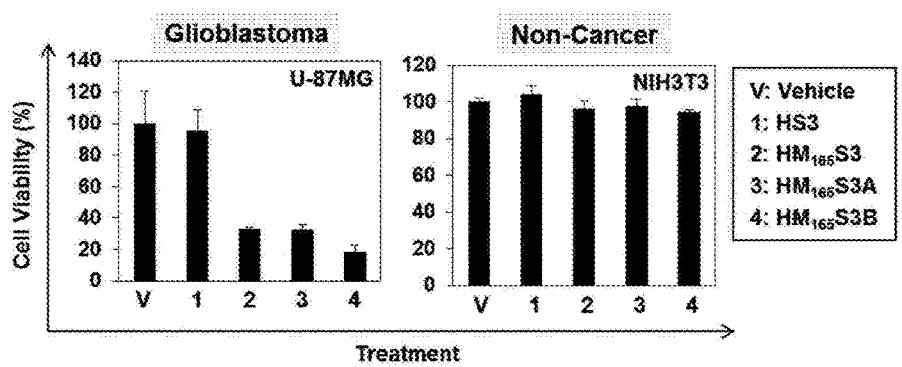

[Figure 71]
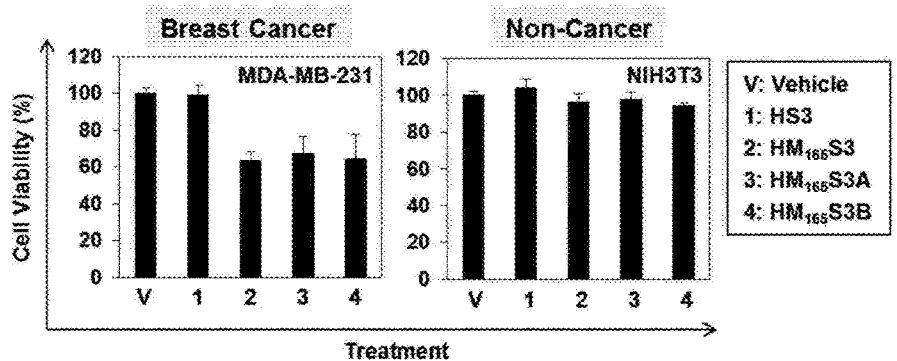
[Figure 72]
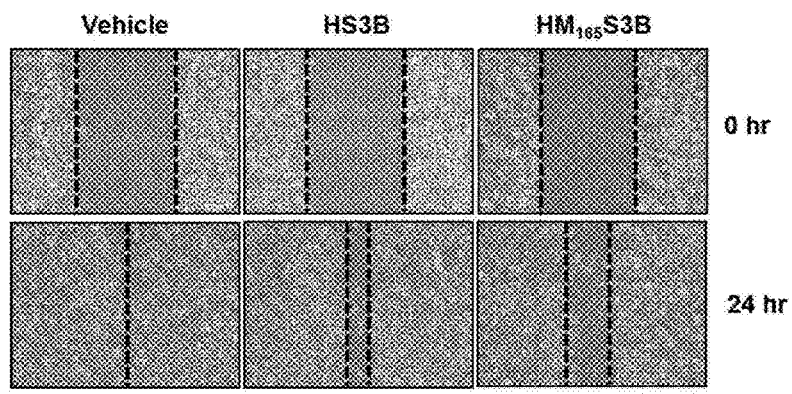
[Figure 73]
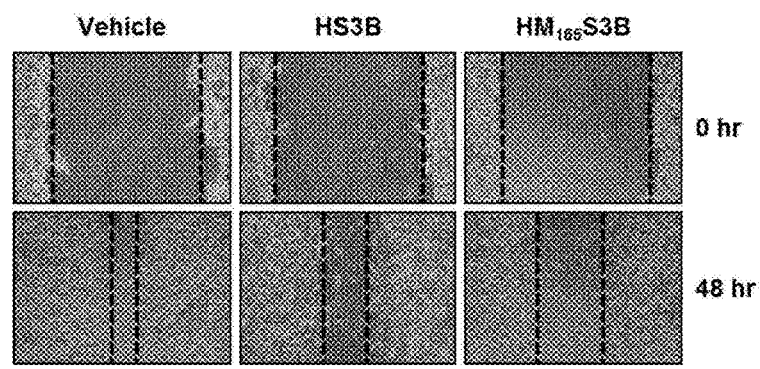

[Figure 74]
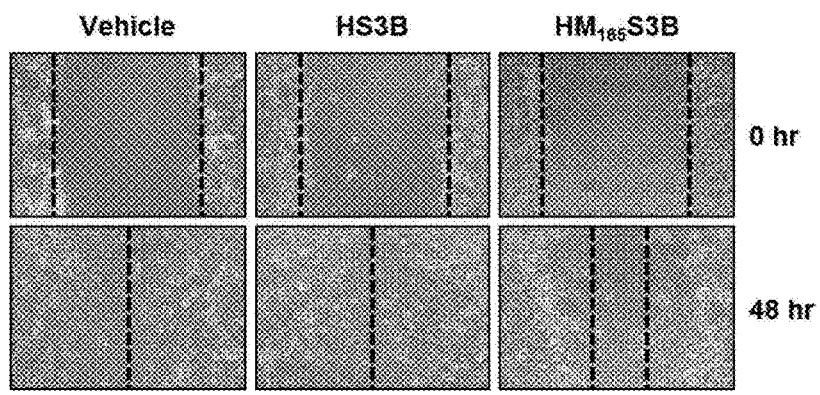
[Figure 75]
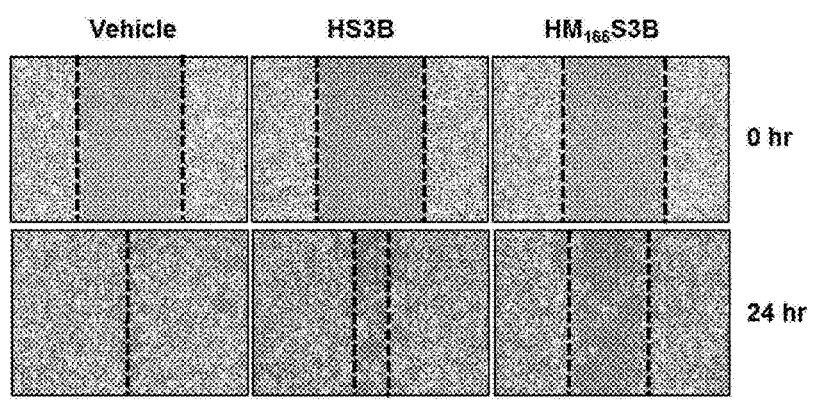
[Figure 76]
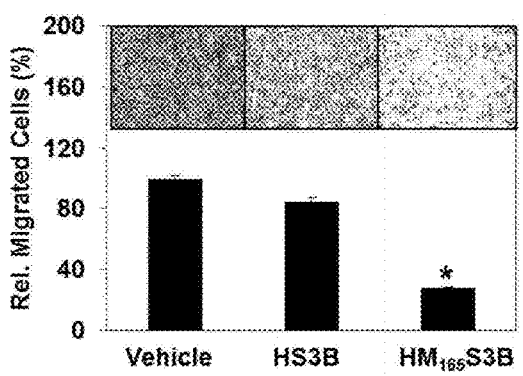 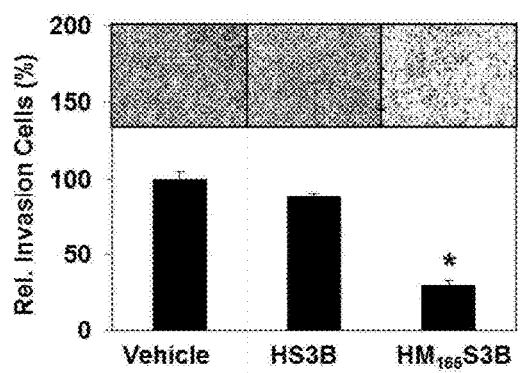

【Figure 77】
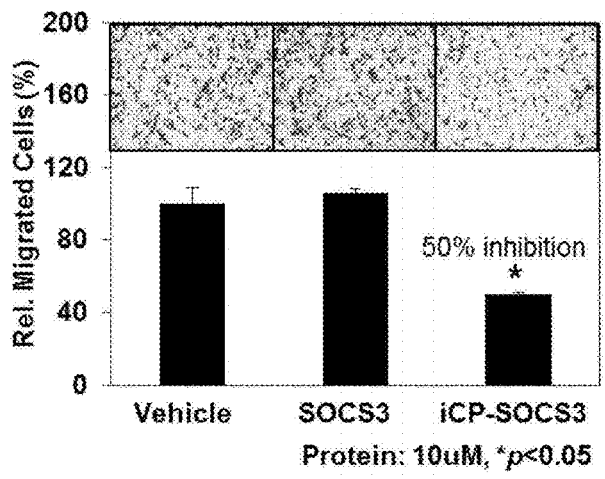
【Figure 78】
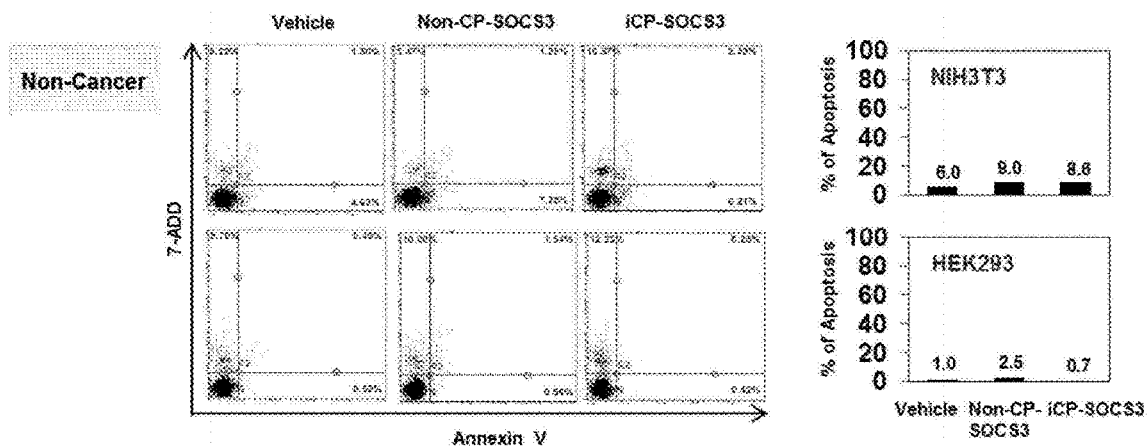
【Figure 79】
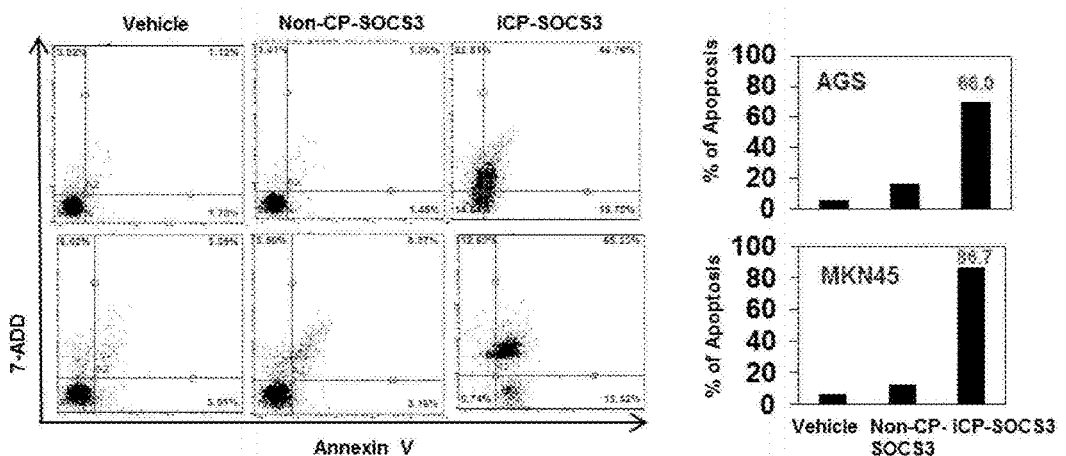

[Figure 80]
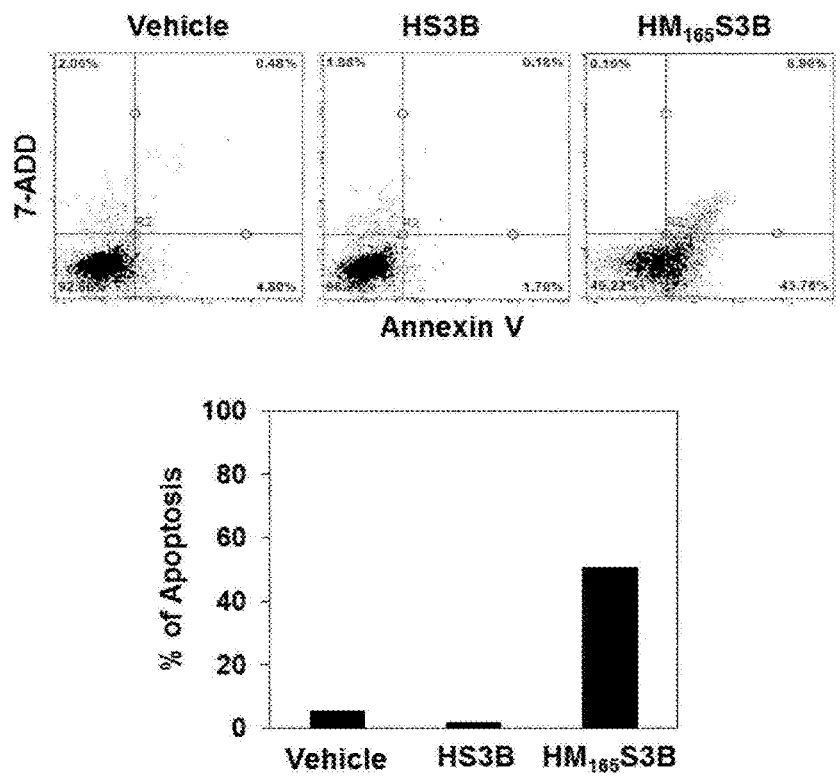
[Figure 81]
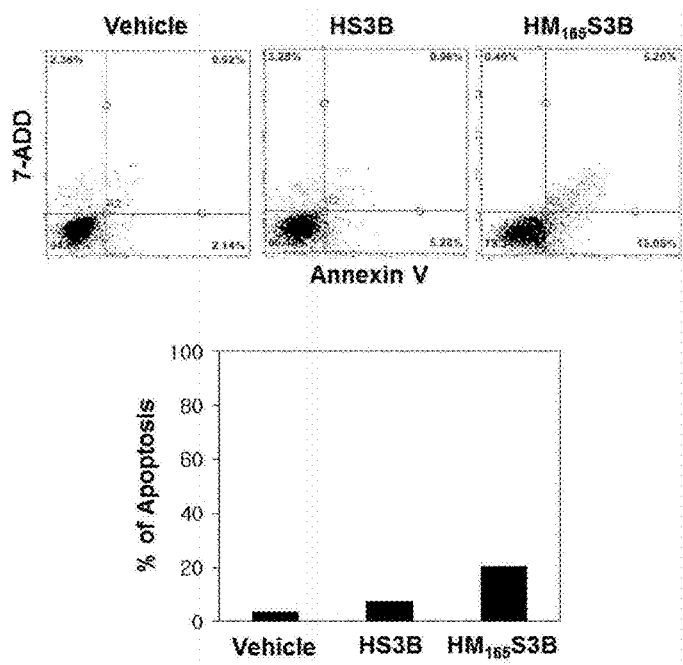

【Figure 82】
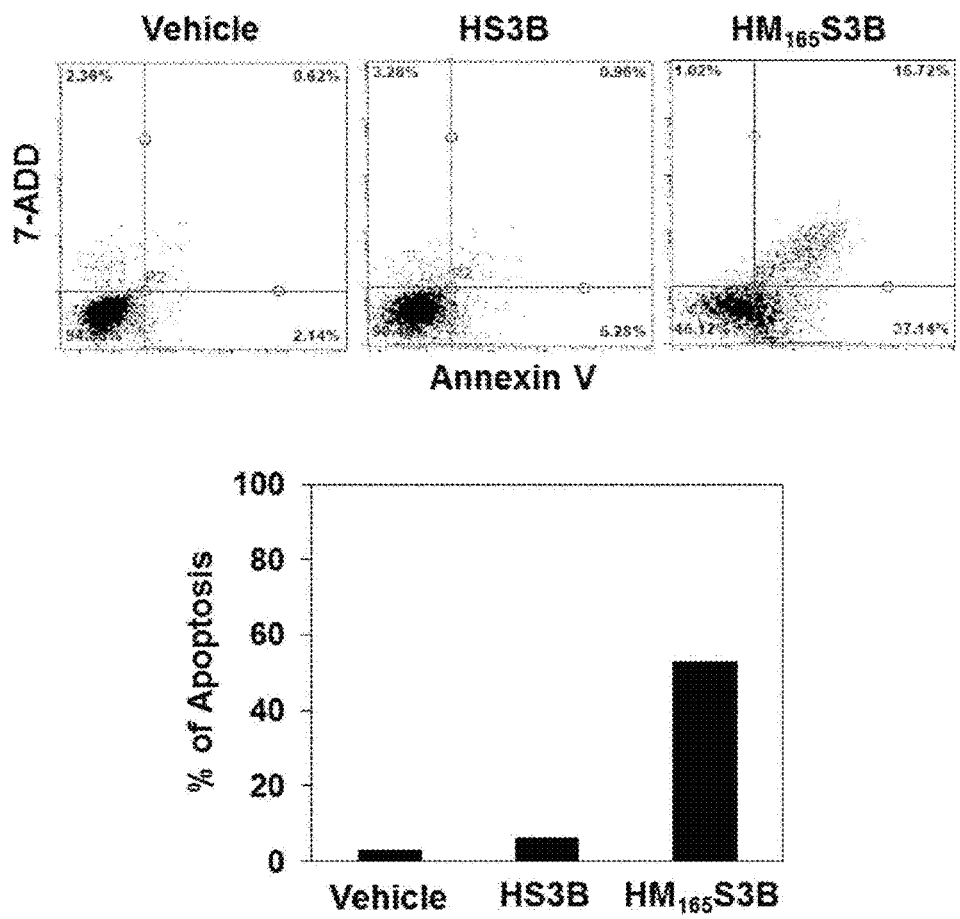
【Figure 83】
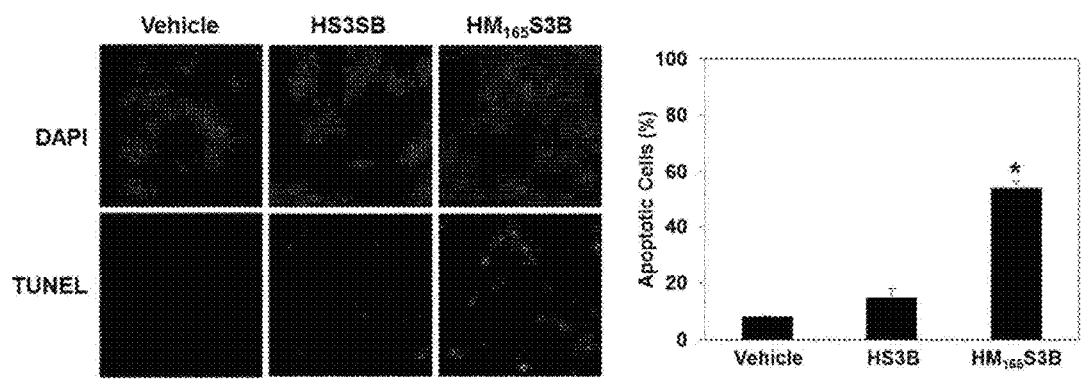

[Figure 84]
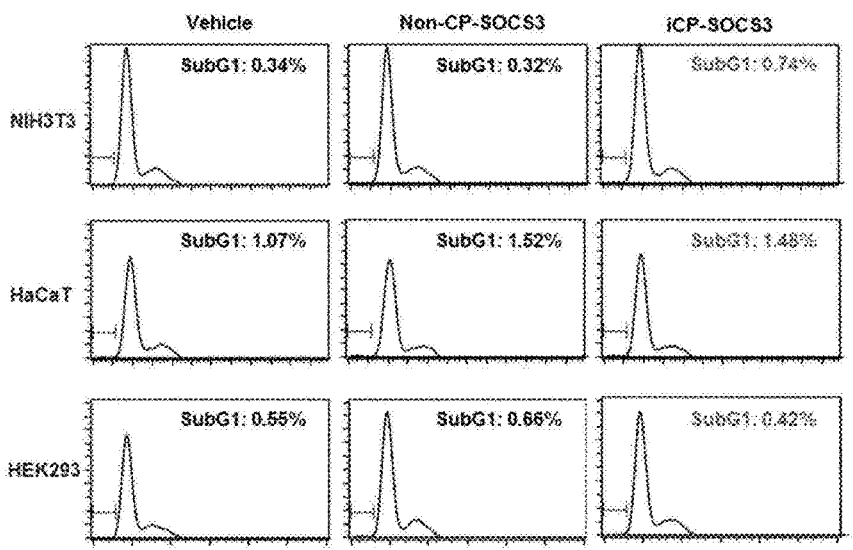
[Figure 85]
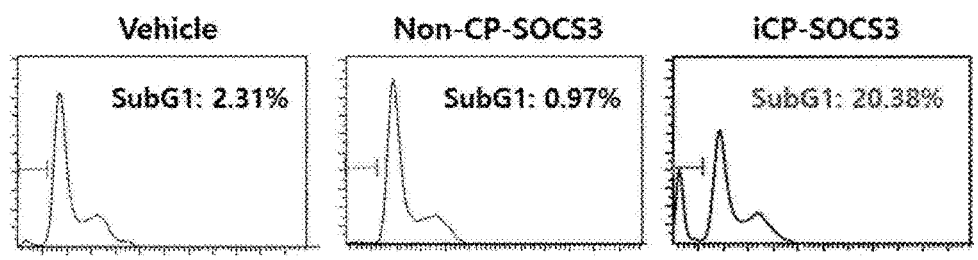
[Figure 86]
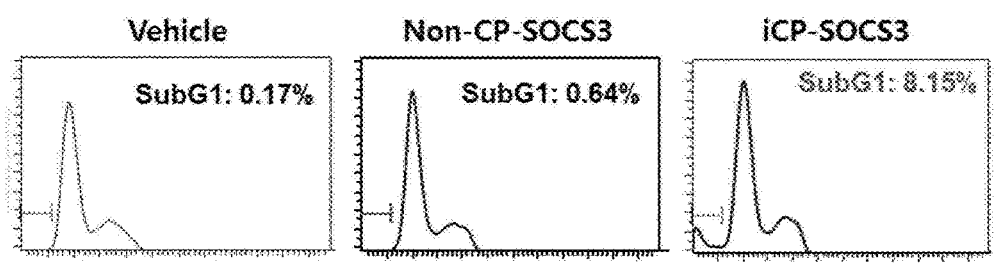
[Figure 87]
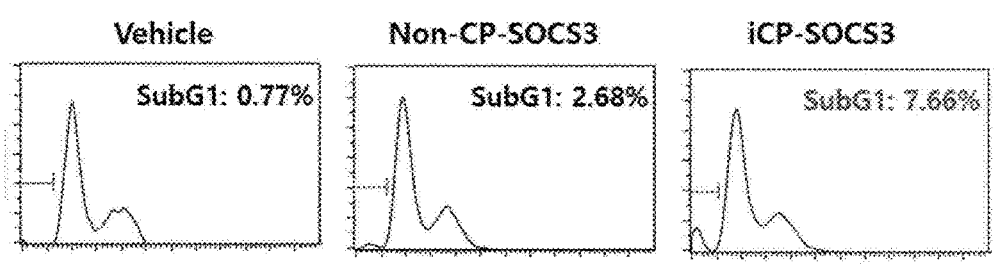

【Figure 88】
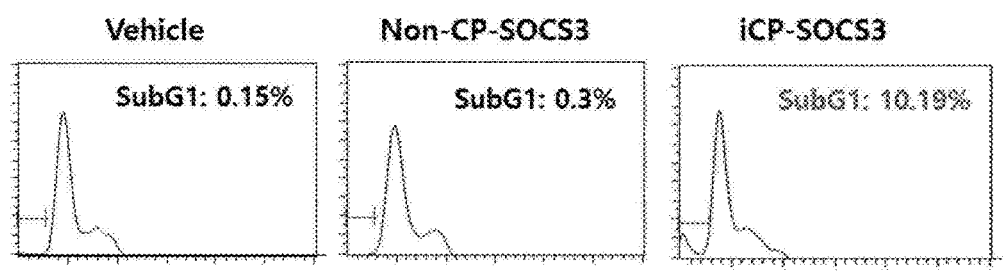
【Figure 89】
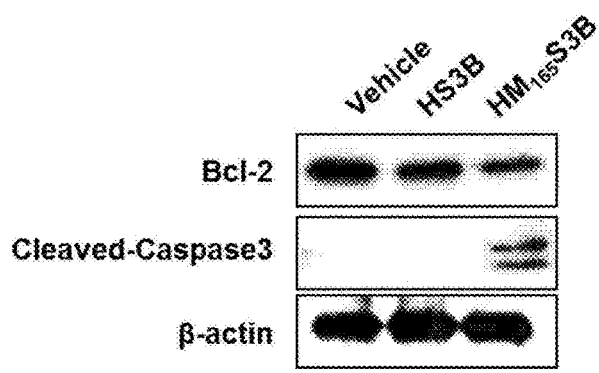

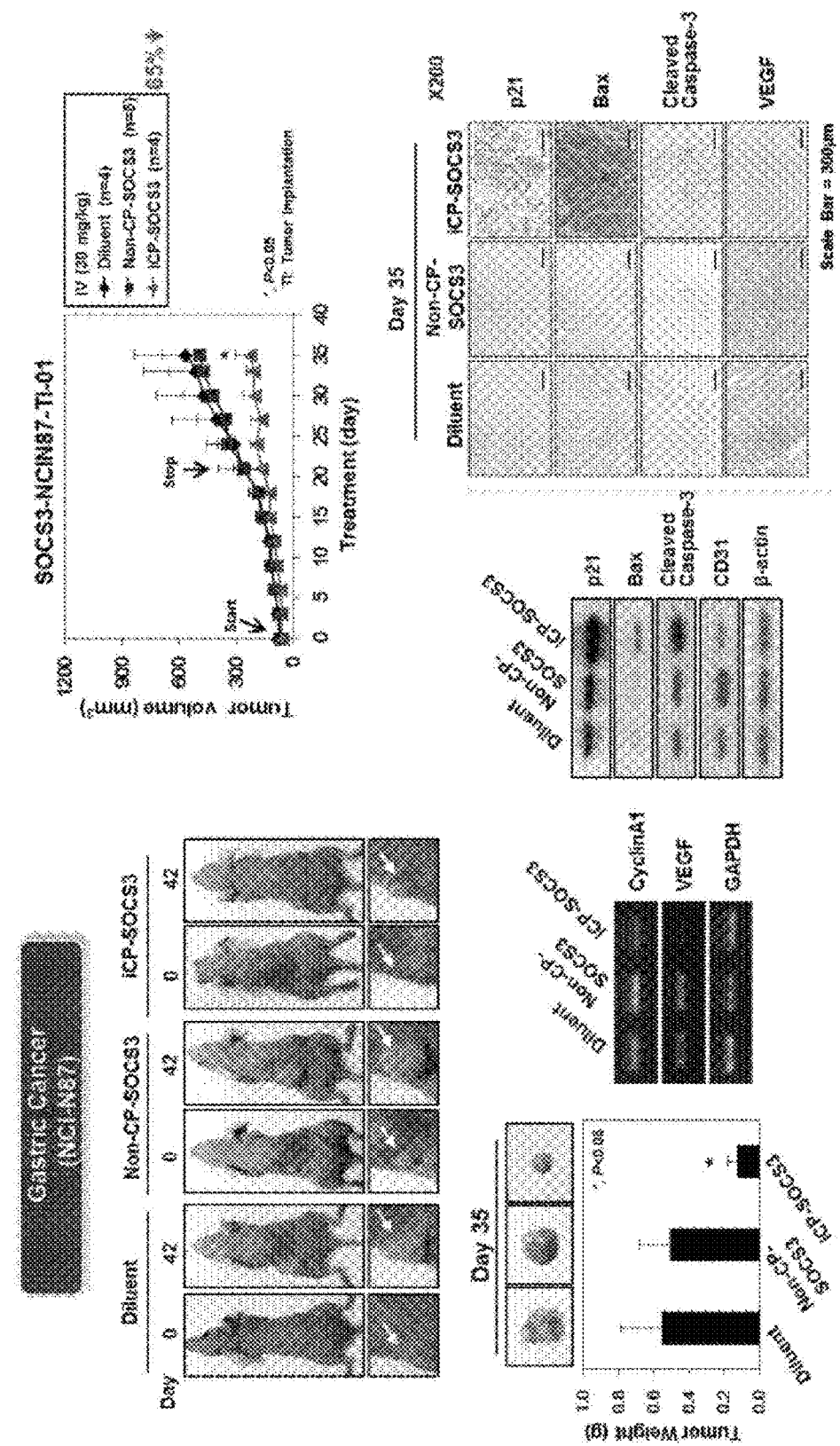
[Figure 90]

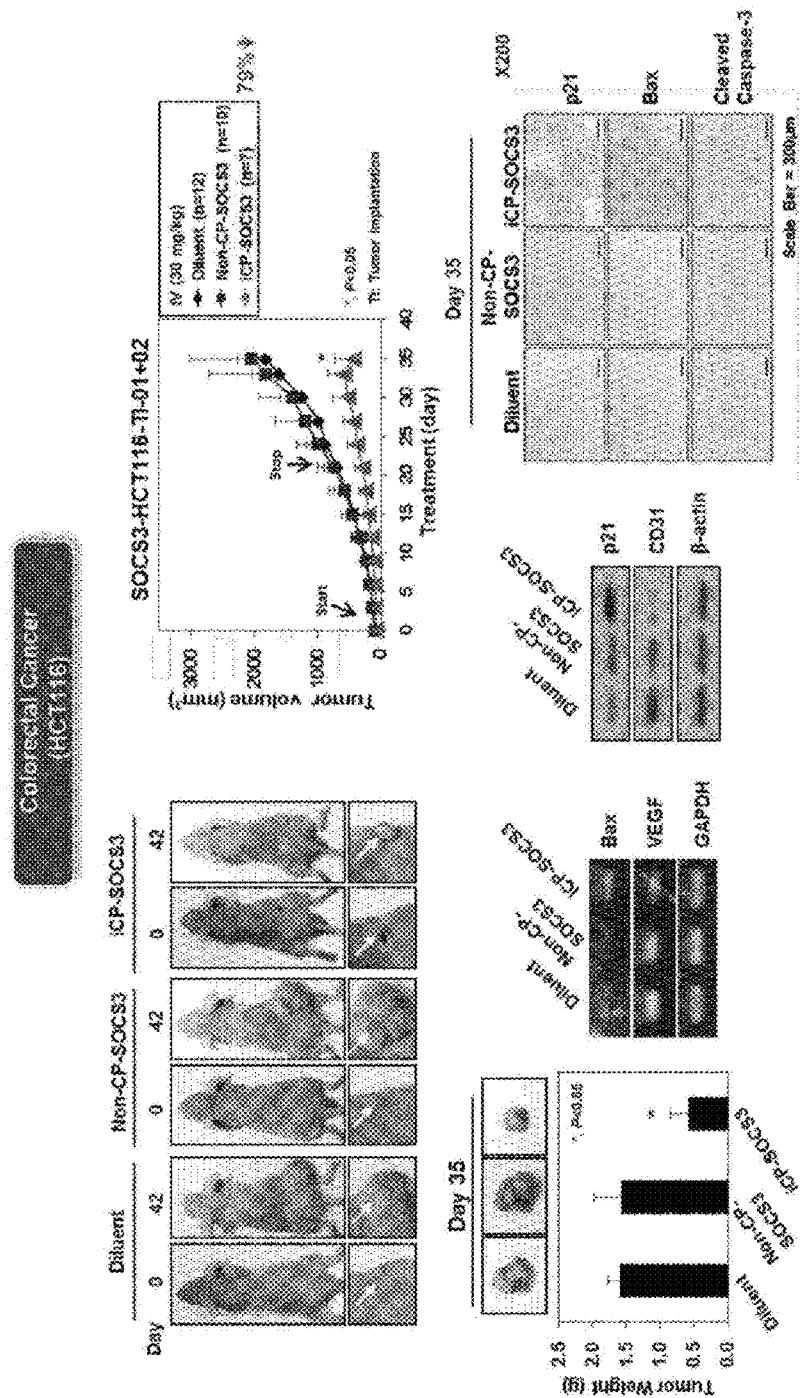
[Figure 91]

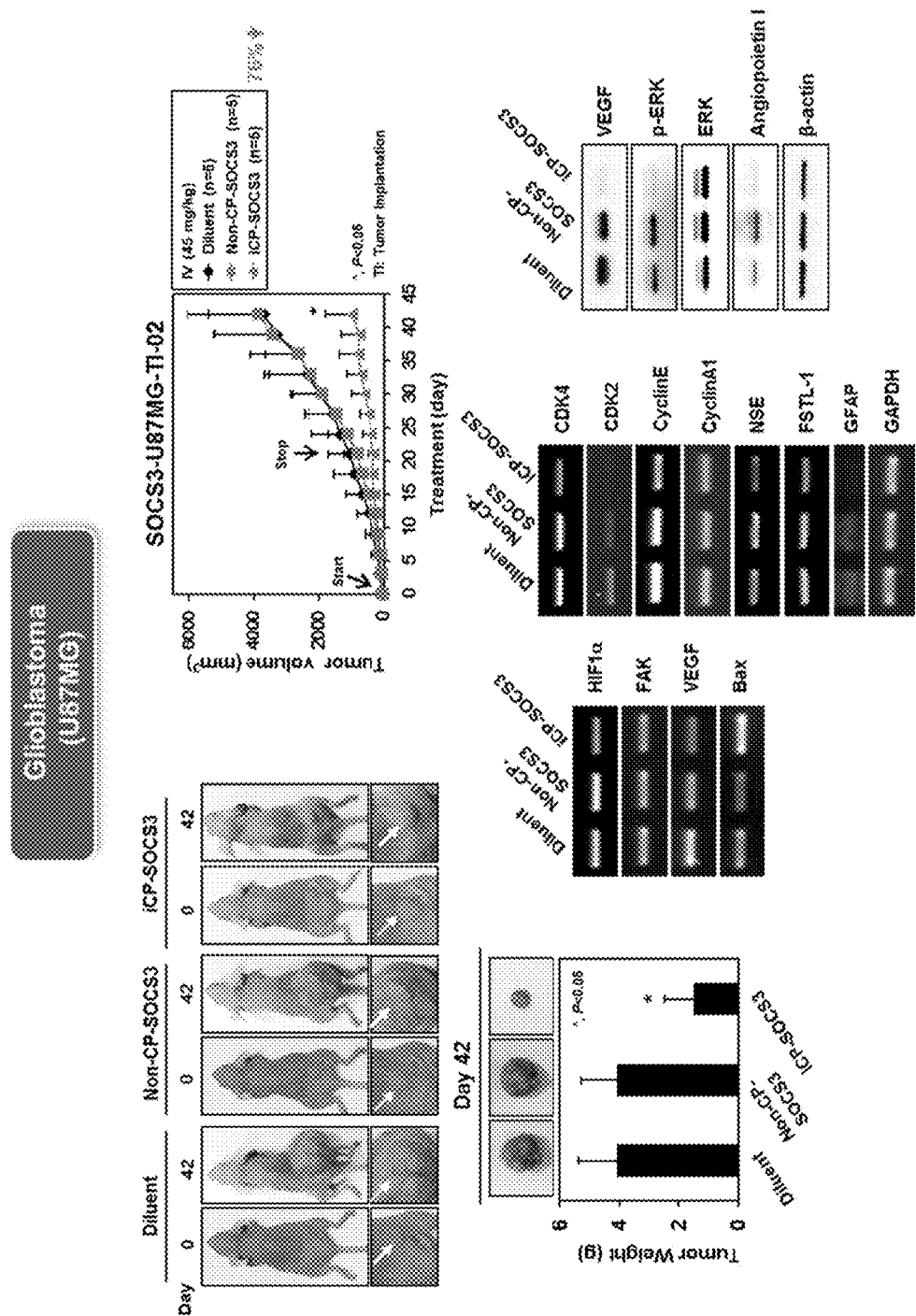
[Figure 92]

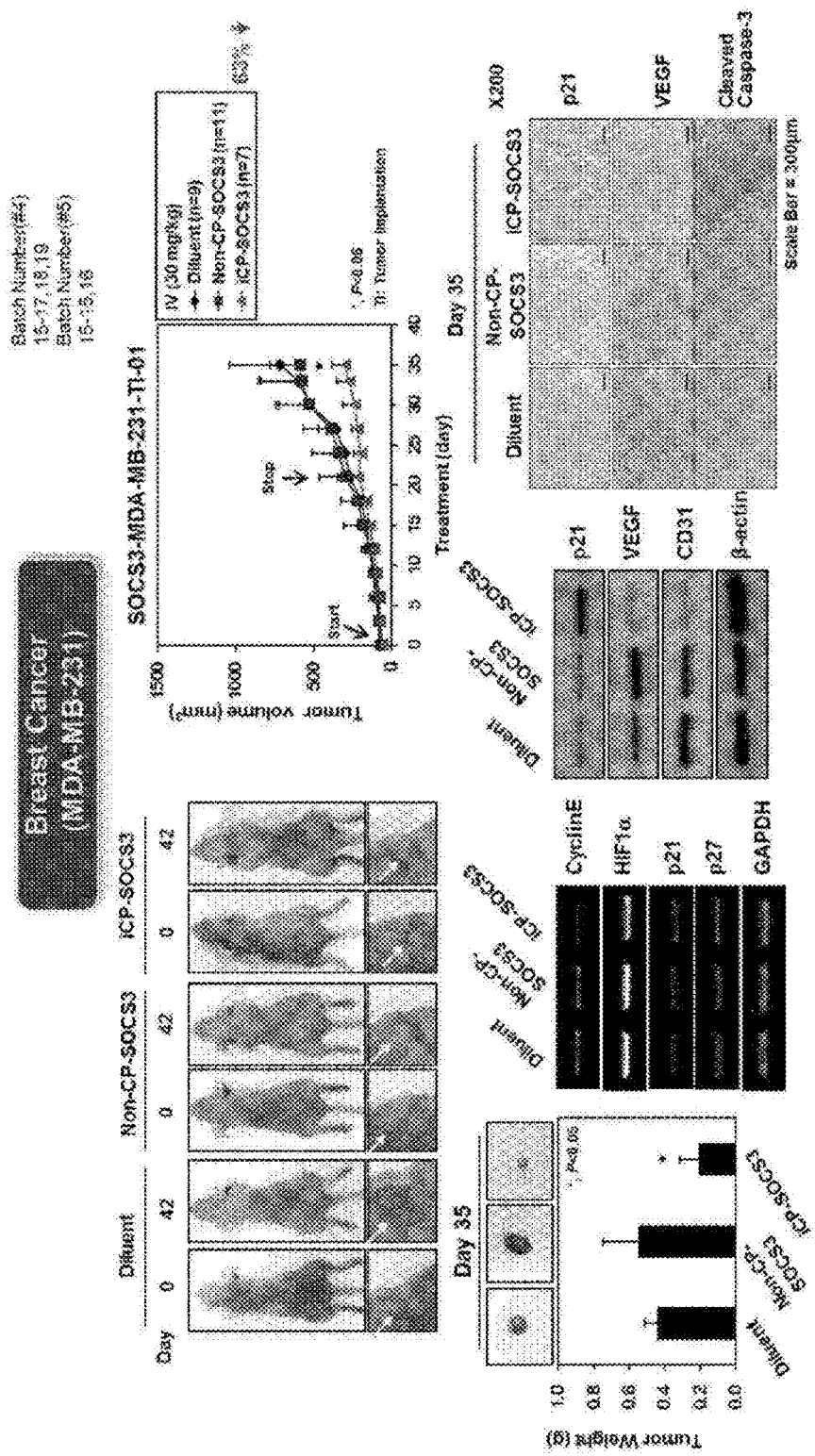
[Figure 93]

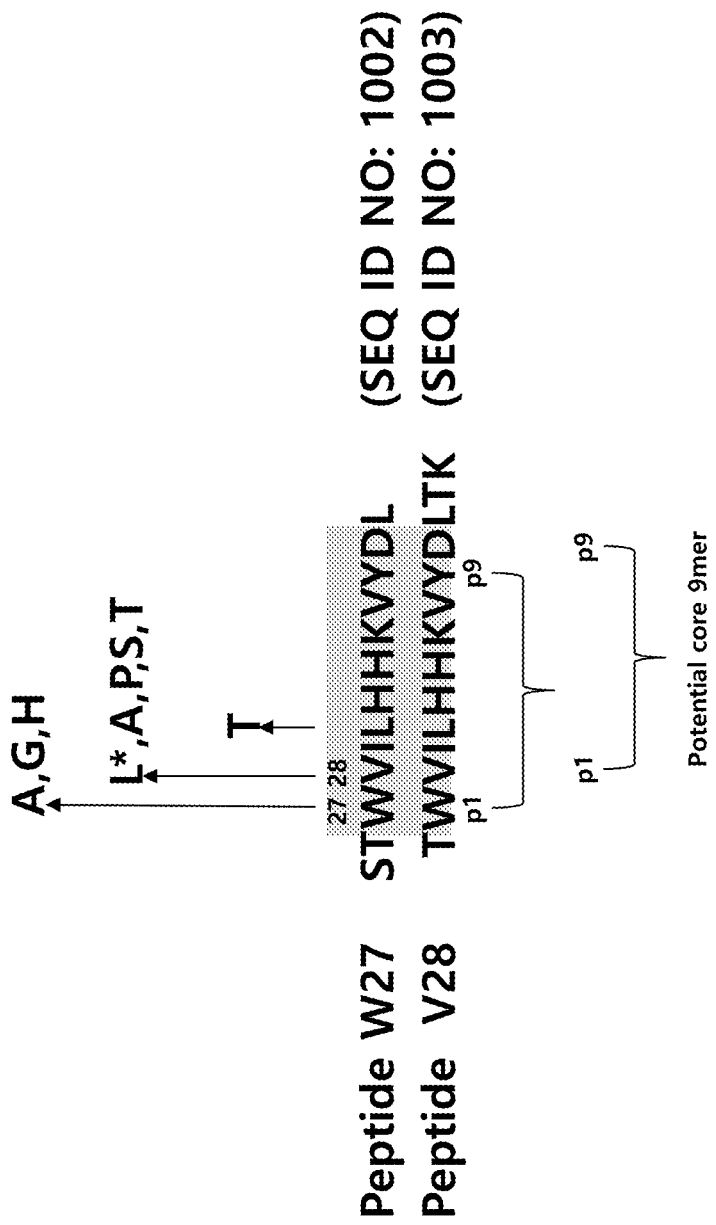
[Figure 94]

【Figure 95】

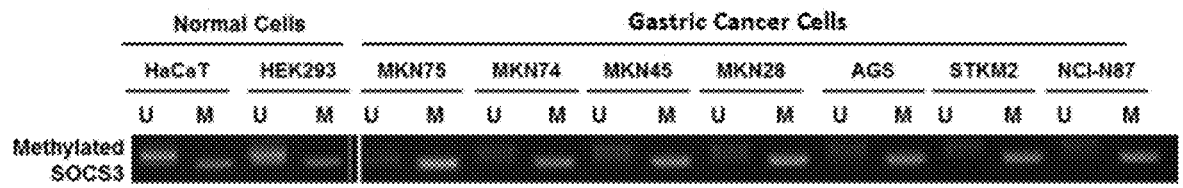

【Figure 96】

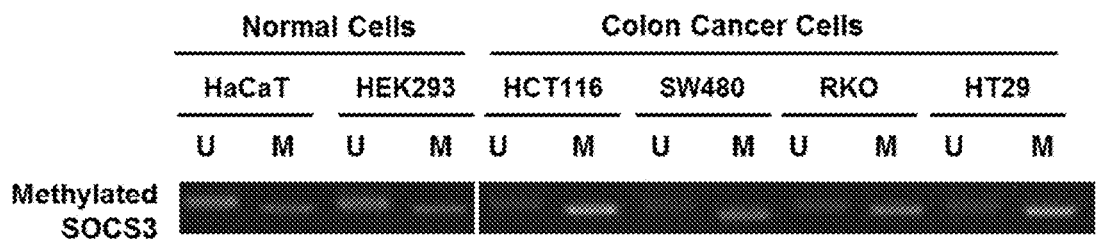

【Figure 97】

| Cargo | Basic CPP | Amino Acid Sequence | Nucleotide Sequence | 5'-Primers | 3' Primers |
|---|---|---|---|---|---|
| SOCS3 | TAT | YGRKKRRQRRR (SEQ ID NO: 832) | TATGGCCGCAAAAAACGCCGCCAGCGCCGCCGC (SEQ ID NO: 833) | GGAATTCCATATGTATGGCCGCAAAAAACGCCGCCAGCGCCGCCGCGTCACCCACAGCAAGTTTCCCGCCGCC (SEQ ID NO: 836) | CGCGTCGGACTTAAAGGGTTTCGAAGGCTTGGCTATCT (SEQ ID NO: 838) |
| | PolyR | RRRRRRRRR (SEQ ID NO: 834) | CGTCGTCGTCGTCGTCGTCGTCGTCGT (SEQ ID NO: 835) | GGAATTCCATATGCGTCGTCGTCGTCGTCGTCGTCGTCGTCACCCACAGCAA GTTTCCCGCCGCC (SEQ ID NO: 837) | |

【Figure 98】
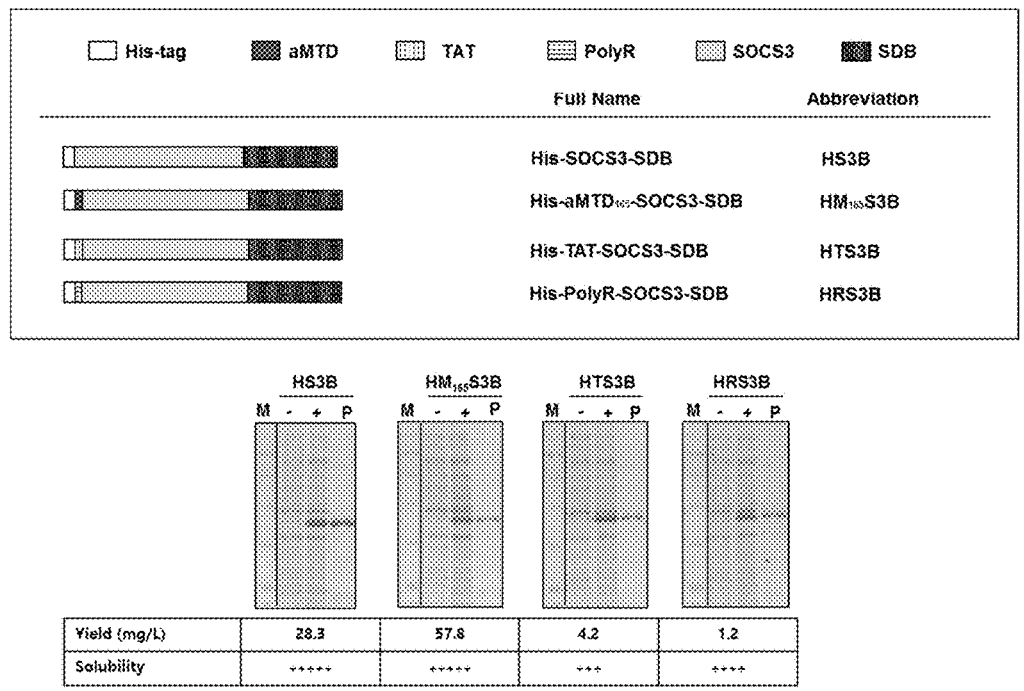
【Figure 99】
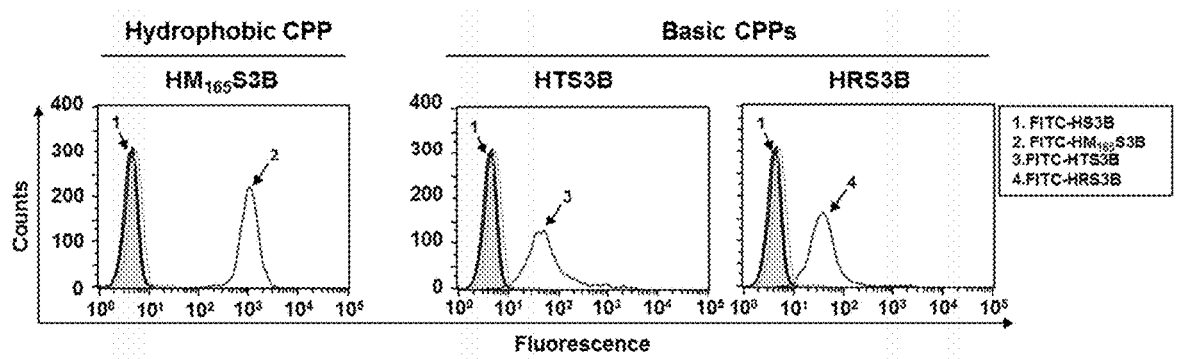

【Figure 100】
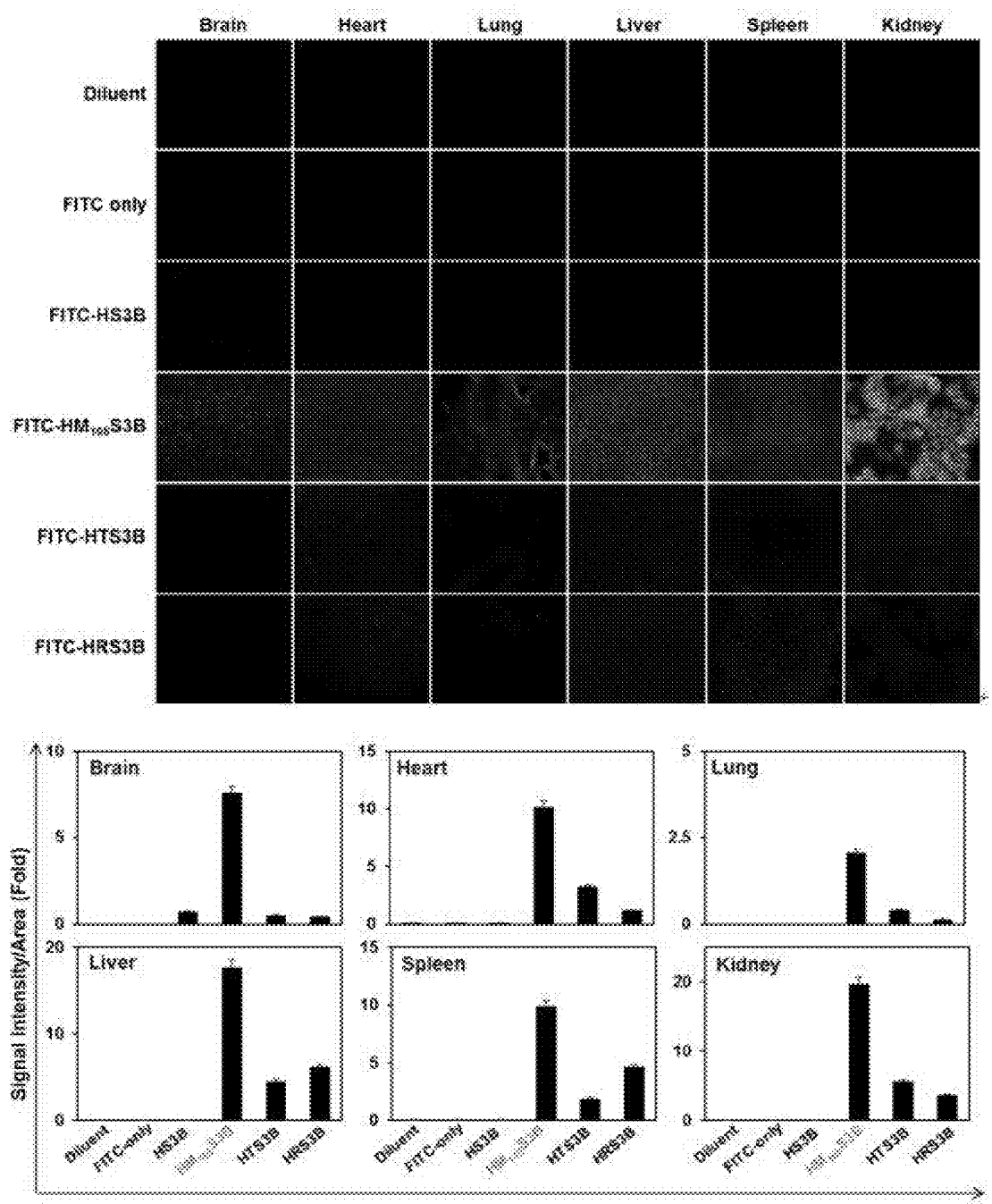

[Figure 101]
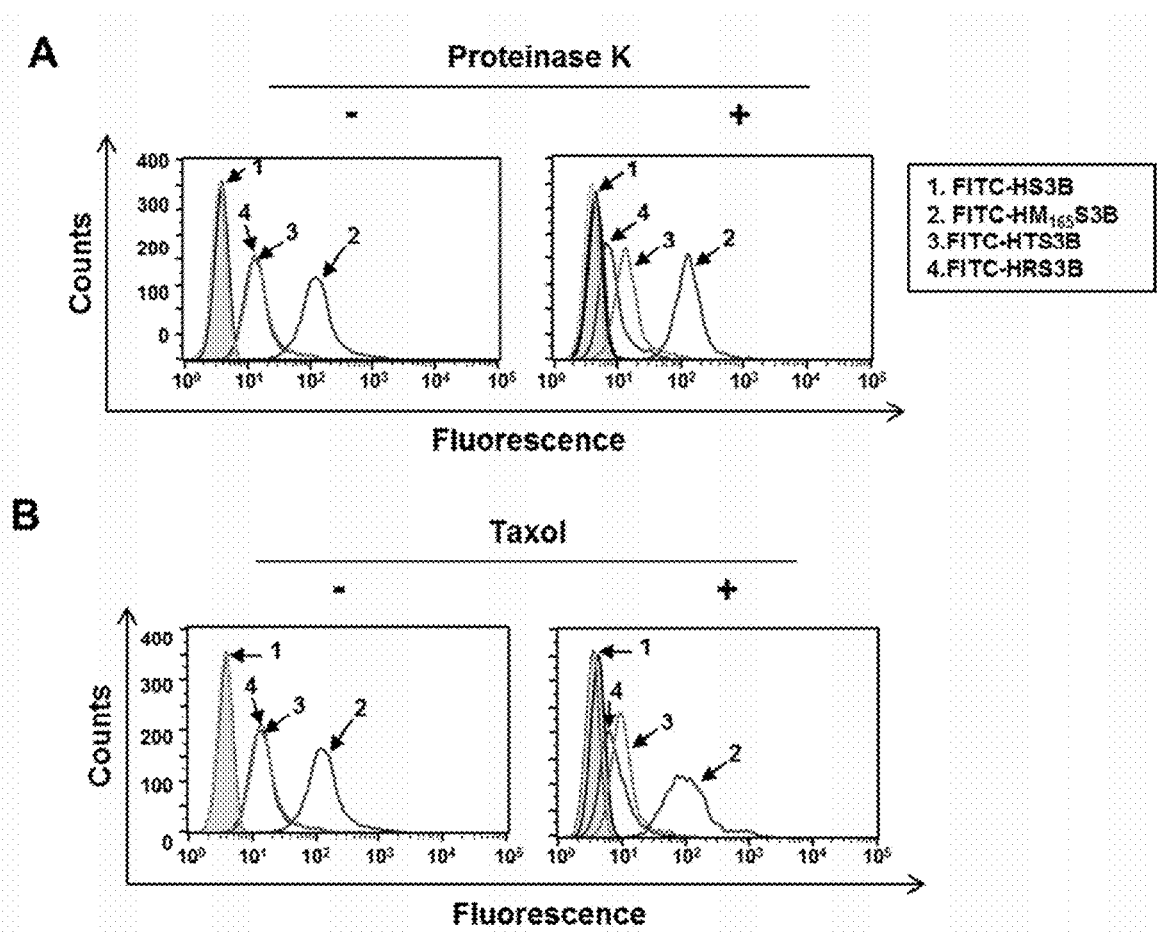

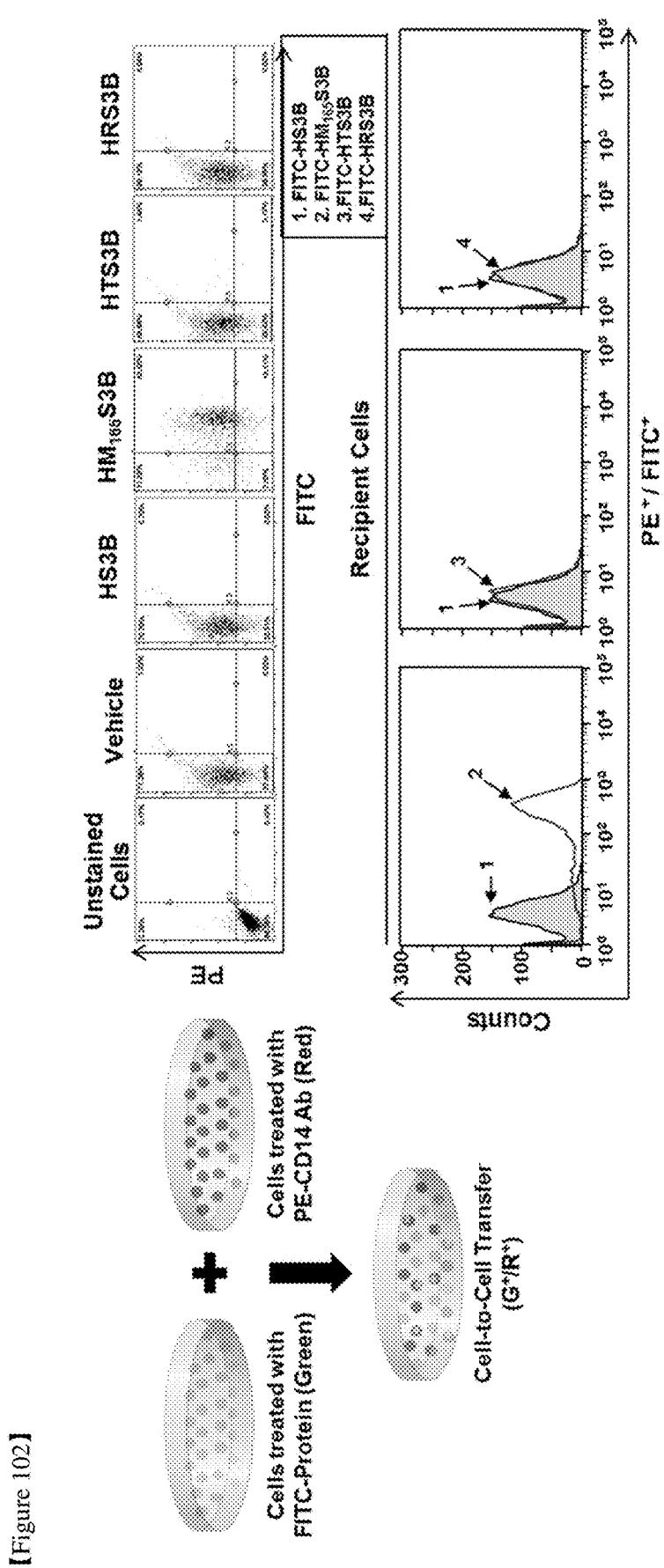
[Figure 102]

[Figure 103]
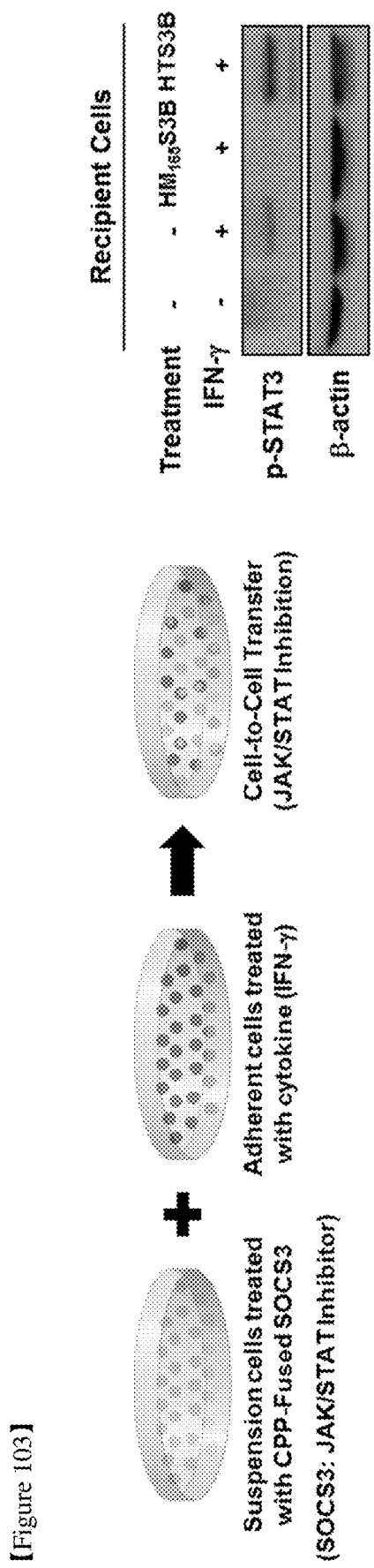

【Figure 104】
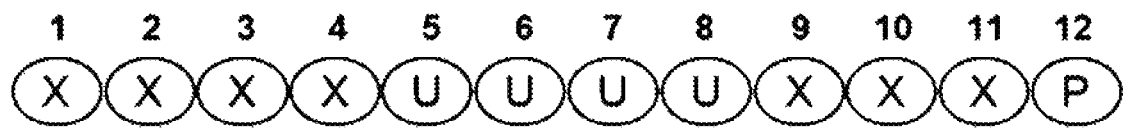

[Figure 105]

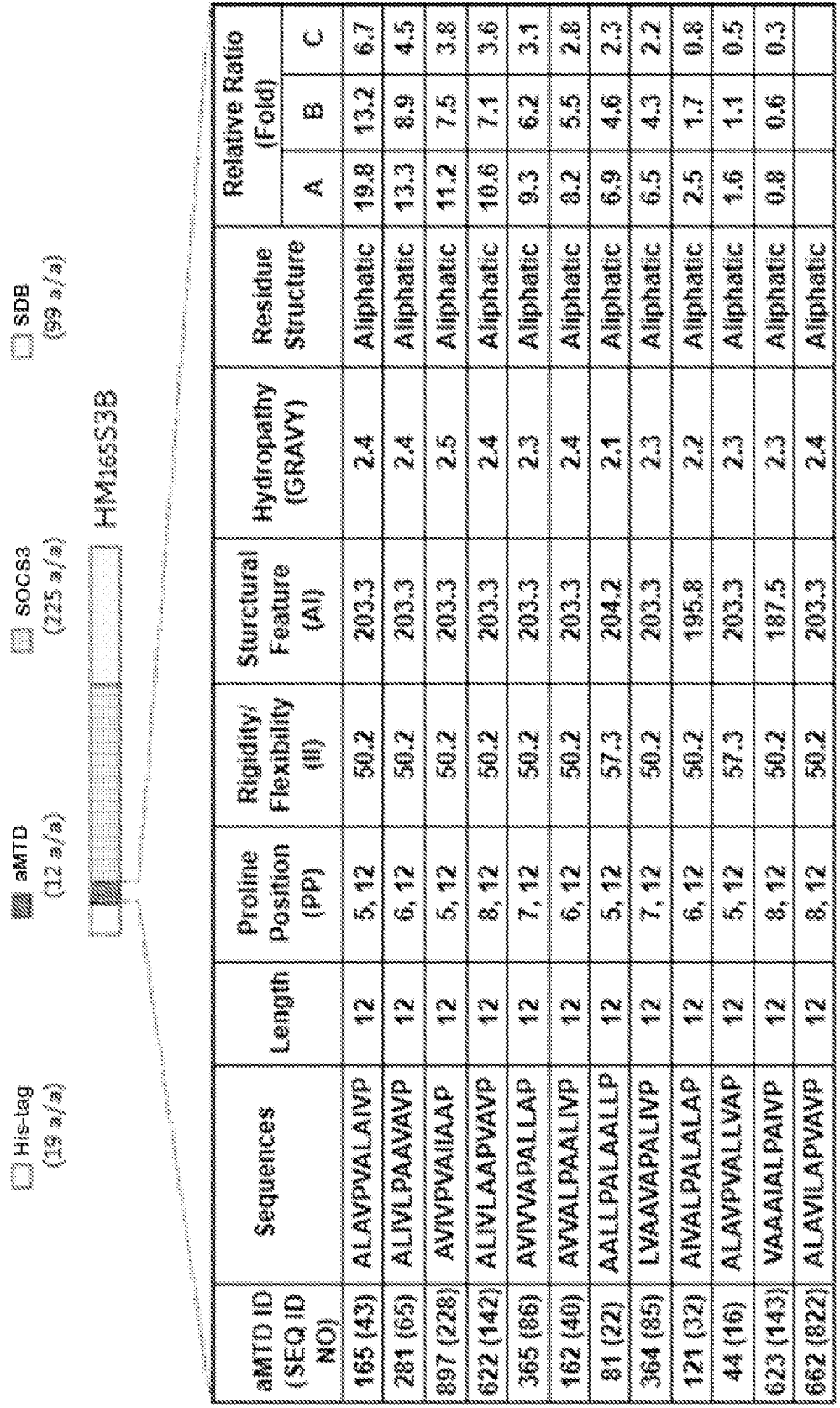

| aMTD ID (SEQ ID NO) | Sequences | Length | Proline Position (PP) | Rigidity/ Flexibility (II) | Structural Feature (AI) | Hydropathy (GRAVY) | Residue Structure | Relative Ratio (Fold) | | |
|---|---|---|---|---|---|---|---|---|---|---|
| | | | | | | | | A | B | C |
| 165 (43) | ALAVPVALAIVP | 12 | 5, 12 | 50.2 | 203.3 | 2.4 | Aliphatic | 19.8 | 13.2 | 6.7 |
| 281 (65) | ALIVLPAAVAVP | 12 | 6, 12 | 50.2 | 203.3 | 2.4 | Aliphatic | 13.3 | 8.9 | 4.5 |
| 897 (228) | AVIVPVAIIAAP | 12 | 5, 12 | 50.2 | 203.3 | 2.5 | Aliphatic | 11.2 | 7.5 | 3.8 |
| 622 (142) | ALIVLAAPVAVP | 12 | 8, 12 | 50.2 | 203.3 | 2.4 | Aliphatic | 10.6 | 7.1 | 3.6 |
| 365 (86) | AVIVVAPALLAP | 12 | 7, 12 | 50.2 | 203.3 | 2.3 | Aliphatic | 9.3 | 6.2 | 3.1 |
| 162 (40) | AVVALPAALIVP | 12 | 6, 12 | 50.2 | 203.3 | 2.4 | Aliphatic | 8.2 | 5.5 | 2.8 |
| 81 (22) | AALLPALAALLP | 12 | 5, 12 | 57.3 | 204.2 | 2.1 | Aliphatic | 6.9 | 4.6 | 2.3 |
| 364 (85) | LVAAVAPALIVP | 12 | 7, 12 | 50.2 | 203.3 | 2.3 | Aliphatic | 6.5 | 4.3 | 2.2 |
| 121 (32) | AIVALPALALAP | 12 | 6, 12 | 50.2 | 195.8 | 2.2 | Aliphatic | 2.5 | 1.7 | 0.8 |
| 44 (16) | ALAVPVALLVAP | 12 | 5, 12 | 57.3 | 203.3 | 2.3 | Aliphatic | 1.6 | 1.1 | 0.5 |
| 623 (143) | VAAAIALPAIVP | 12 | 8, 12 | 50.2 | 187.5 | 2.3 | Aliphatic | 0.8 | 0.6 | 0.3 |
| 662 (822) | ALAVILAPVAVP | 12 | 8, 12 | 50.2 | 203.3 | 2.4 | Aliphatic | | | |

[Figure 106]

| aMTD ID (SEQ ID NO) | Sequences | Length | Proline Position (PP) | Rigidity/ Flexibility (I) | Structural Feature (A) | Hydropathy (GRAVY) | Residue Structure | Relative Ratio (Fold) A | B | C |
|---|---|---|---|---|---|---|---|---|---|---|
| 165 (43) | ALAVPVALAIVP | 12 | 5, 12 | 50.2 | 203.3 | 2.4 | Aliphatic | 19.8 | 13.2 | 6.7 |
| 890 (229) | AVVIALPAVVAP | 12 | 7, 12 | 57.3 | 195.0 | 2.4 | Aliphatic | 164.2 | 109.9 | 55.5 |
| 908 (237) | VALALAPVVVAP | 12 | 7, 12 | 57.3 | 195.0 | 2.3 | Aliphatic | 150.6 | 100.9 | 50.9 |
| 904 (233) | AVLAVVAPVVAP | 12 | 8, 12 | 57.3 | 186.7 | 2.4 | Aliphatic | 105.7 | 70.8 | 35.8 |
| 911 (239) | VALALPAVVVAP | 12 | 6, 12 | 57.3 | 195.0 | 2.3 | Aliphatic | 84.8 | 56.8 | 28.7 |
| 563 (371) | ALAVVVPALAP | 12 | 8, 12 | 50.2 | 203.3 | 2.4 | Aliphatic | 47.1 | 31.4 | 15.9 |
| 2 (2) | AAAVPLLAVVP | 12 | 5, 12 | 41.3 | 195.0 | 2.4 | Aliphatic | 40.9 | 27.2 | 13.8 |
| 481 (350) | AIAAVPVALP | 12 | 8, 12 | 50.2 | 211.6 | 2.4 | Aliphatic | 34.3 | 23.0 | 11.6 |
| 787 (417) | AVALVPVVAAP | 12 | 6, 12 | 50.2 | 195.0 | 2.4 | Aliphatic | 29.3 | 19.6 | 9.9 |
| 264 (303) | LAAPVVVIAP | 12 | 5, 12 | 50.2 | 203.3 | 2.4 | Aliphatic | 18.2 | 12.1 | 6.1 |
| 563 (324) | AVILAVAPALIVP | 12 | 7, 12 | 50.2 | 203.3 | 2.3 | Aliphatic | 14.7 | 9.8 | 4.9 |
| 324 (317) | IVAVALPAALVP | 12 | 7, 12 | 50.2 | 203.3 | 2.3 | Aliphatic | 10.3 | 6.9 | 3.5 |

His-tag (19 a/a) | aMTD (12 a/a) | SOCS3 (225 a/a) | SDB (99 a/a)

HM165S3B

[Figure 107]
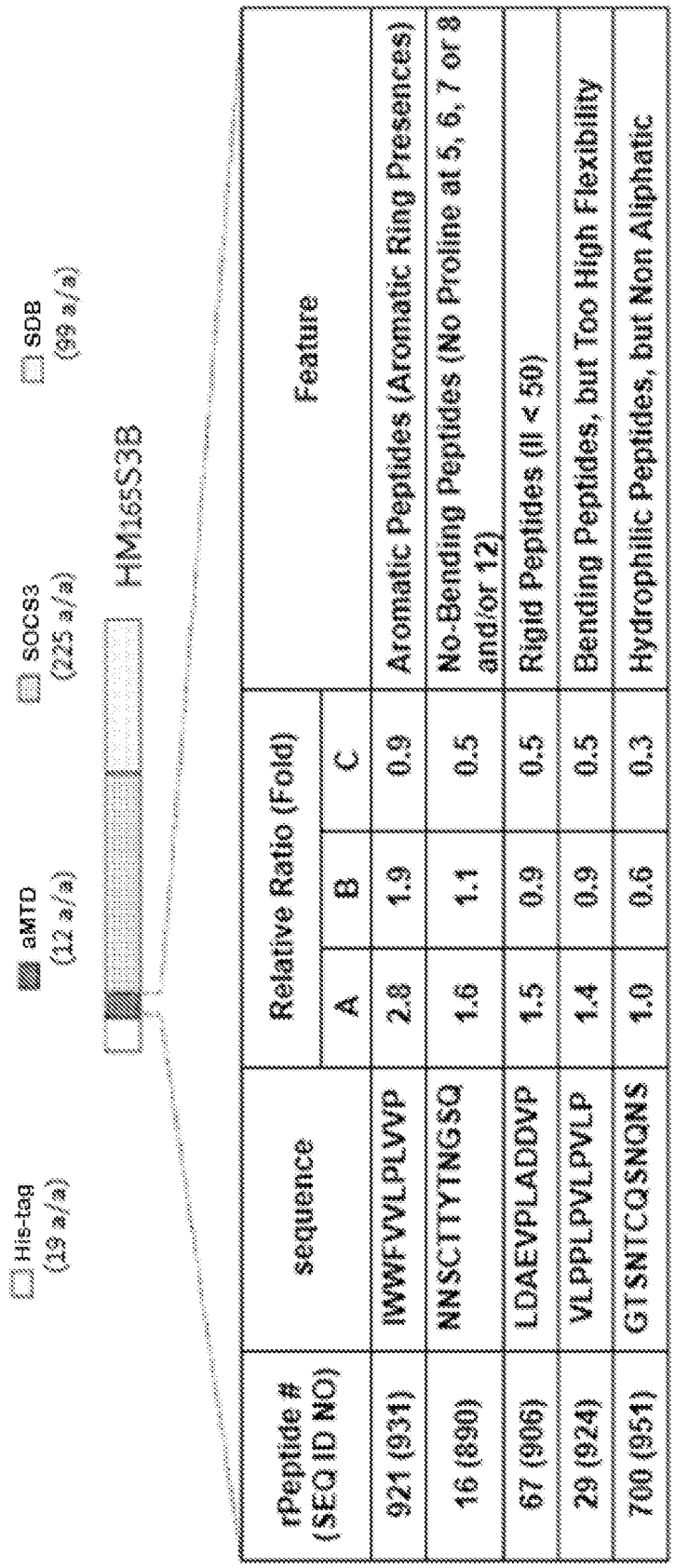

SEQUENCE LISTING

```
<160> NUMBER OF SEQ ID NOS: 1003

<210> SEQ ID NO 1
<211> LENGTH: 12
<212> TYPE: PRT
<213> ORGANISM: Artificial Sequence
<220> FEATURE:
<223> OTHER INFORMATION: Amino acid Sequence of aMTD1

<400> SEQUENCE: 1

Ala Ala Ala Leu Ala Pro Val Val Leu Ala Leu Pro
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Amino acid Sequence of aMTD2

<400> SEQUENCE: 2

Ala Ala Ala Val Pro Leu Leu Ala Val Val Val Pro
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Amino acid Sequence of aMTD3

<400> SEQUENCE: 3

Ala Ala Leu Leu Val Pro Ala Ala Val Leu Ala Pro
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Amino acid Sequence of aMTD4

<400> SEQUENCE: 4

Ala Leu Ala Leu Leu Pro Val Ala Ala Leu Ala Pro
1               5                   10

<210> SEQ ID NO 5
<211> LENGTH: 12
<212> TYPE: PRT
<213> ORGANISM: Artificial Sequence
```

```
<220> FEATURE:
<223> OTHER INFORMATION: Amino acid Sequence of aMTD5

<400> SEQUENCE: 5

Ala Ala Ala Leu Leu Pro Val Ala Leu Val Ala Pro
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Amino acid Sequence of aMTD11

<400> SEQUENCE: 6

Val Val Ala Leu Ala Pro Ala Leu Ala Ala Leu Pro
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Amino acid Sequence of aMTD12

<400> SEQUENCE: 7

Leu Leu Ala Ala Val Pro Ala Val Leu Leu Ala Pro
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Amino acid Sequence of aMTD13

<400> SEQUENCE: 8

Ala Ala Ala Leu Val Pro Val Val Ala Leu Leu Pro
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Amino acid Sequence of aMTD21

<400> SEQUENCE: 9

Ala Val Ala Leu Leu Pro Ala Leu Leu Ala Val Pro
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Amino acid Sequence of aMTD22

<400> SEQUENCE: 10

Ala Val Val Leu Val Pro Val Leu Ala Ala Ala Pro
1               5                   10

<210> SEQ ID NO 11
<211> LENGTH: 12
<212> TYPE: PRT
<213> ORGANISM: Artificial Sequence
<220> FEATURE:
```

```
<223> OTHER INFORMATION: Amino acid Sequence of aMTD23

<400> SEQUENCE: 11

Val Val Leu Val Leu Pro Ala Ala Ala Ala Val Pro
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Amino acid Sequence of aMTD24

<400> SEQUENCE: 12

Ile Ala Leu Ala Ala Pro Ala Leu Ile Val Ala Pro
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Amino acid Sequence of aMTD25

<400> SEQUENCE: 13

Ile Val Ala Val Ala Pro Ala Leu Val Ala Leu Pro
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Amino acid Sequence of aMTD42

<400> SEQUENCE: 14

Val Ala Ala Leu Pro Val Val Ala Val Val Ala Pro
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Amino acid Sequence of aMTD43

<400> SEQUENCE: 15

Leu Leu Ala Ala Pro Leu Val Val Ala Ala Val Pro
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Amino acid Sequence of aMTD44

<400> SEQUENCE: 16

Ala Leu Ala Val Pro Val Ala Leu Leu Val Ala Pro
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Amino acid Sequence of aMTD61
```

```
<400> SEQUENCE: 17

Val Ala Ala Leu Pro Val Leu Ala Ala Leu Pro
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Amino acid Sequence of aMTD62

<400> SEQUENCE: 18

Val Ala Leu Leu Ala Pro Val Ala Leu Ala Val Pro
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Amino acid Sequence of aMTD63

<400> SEQUENCE: 19

Ala Ala Leu Leu Val Pro Ala Leu Val Ala Val Pro
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Amino acid Sequence of aMTD64

<400> SEQUENCE: 20

Ala Ile Val Ala Leu Pro Val Ala Val Leu Ala Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Amino acid Sequence of aMTD65

<400> SEQUENCE: 21

Ile Ala Ile Val Ala Pro Val Val Ala Leu Ala Pro
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Amino acid Sequence of aMTD81

<400> SEQUENCE: 22

Ala Ala Leu Leu Pro Ala Leu Ala Ala Leu Leu Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Amino acid Sequence of aMTD82
```

<400> SEQUENCE: 23

Ala Val Val Leu Ala Pro Val Ala Ala Val Leu Pro
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Amino acid Sequence of aMTD83

<400> SEQUENCE: 24

Leu Ala Val Ala Ala Pro Leu Ala Leu Ala Leu Pro
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Amino acid Sequence of aMTD84

<400> SEQUENCE: 25

Ala Ala Val Ala Ala Pro Leu Leu Leu Ala Leu Pro
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Amino acid Sequence of aMTD85

<400> SEQUENCE: 26

Leu Leu Val Leu Pro Ala Ala Leu Ala Ala Pro
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Amino acid Sequence of aMTD101

<400> SEQUENCE: 27

Leu Val Ala Leu Ala Pro Val Ala Ala Val Leu Pro
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Amino acid Sequence of aMTD102

<400> SEQUENCE: 28

Leu Ala Leu Ala Pro Ala Ala Leu Ala Leu Leu Pro
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Amino acid Sequence of aMTD103

<400> SEQUENCE: 29

```
Ala Leu Ile Ala Ala Pro Ile Leu Ala Leu Ala Pro
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Amino acid Sequence of aMTD104

<400> SEQUENCE: 30

Ala Val Val Ala Ala Pro Leu Val Leu Ala Leu Pro
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Amino acid Sequence of aMTD105

<400> SEQUENCE: 31

Leu Leu Ala Leu Ala Pro Ala Ala Leu Leu Ala Pro
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Amino acid Sequence of aMTD121

<400> SEQUENCE: 32

Ala Ile Val Ala Leu Pro Ala Leu Ala Leu Ala Pro
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Amino acid Sequence of aMTD123

<400> SEQUENCE: 33

Ala Ala Ile Ile Val Pro Ala Ala Leu Leu Ala Pro
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Amino acid Sequence of aMTD124

<400> SEQUENCE: 34

Ile Ala Val Ala Leu Pro Ala Leu Ile Ala Ala Pro
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Amino acid Sequence of aMTD141

<400> SEQUENCE: 35
```

Ala Val Ile Val Leu Pro Ala Leu Ala Val Ala Pro
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Amino acid Sequence of aMTD143

<400> SEQUENCE: 36

Ala Val Leu Ala Val Pro Ala Val Leu Val Ala Pro
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Amino acid Sequence of aMTD144

<400> SEQUENCE: 37

Val Leu Ala Ile Val Pro Ala Val Ala Leu Ala Pro
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Amino acid Sequence of aMTD145

<400> SEQUENCE: 38

Leu Leu Ala Val Val Pro Ala Val Ala Leu Ala Pro
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Amino acid Sequence of aMTD161

<400> SEQUENCE: 39

Ala Val Ile Ala Leu Pro Ala Leu Ile Ala Ala Pro
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Amino acid Sequence of aMTD162

<400> SEQUENCE: 40

Ala Val Val Ala Leu Pro Ala Ala Leu Ile Val Pro
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Amino acid Sequence of aMTD163

<400> SEQUENCE: 41

Leu Ala Leu Val Leu Pro Ala Ala Leu Ala Ala Pro

```
<210> SEQ ID NO 42
<211> LENGTH: 12
<212> TYPE: PRT
<213> ORGANISM: Artificial Sequence
<220> FEATURE:
<223> OTHER INFORMATION: Amino acid Sequence of aMTD164

<400> SEQUENCE: 42

Leu Ala Ala Val Leu Pro Ala Leu Leu Ala Ala Pro
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Amino acid Sequence of aMTD165

<400> SEQUENCE: 43

Ala Leu Ala Val Pro Val Ala Leu Ala Ile Val Pro
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Amino acid Sequence of aMTD182

<400> SEQUENCE: 44

Ala Leu Ile Ala Pro Val Val Ala Leu Val Ala Pro
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Amino acid Sequence of aMTD183

<400> SEQUENCE: 45

Leu Leu Ala Ala Pro Val Val Ile Ala Leu Ala Pro
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Amino acid Sequence of aMTD184

<400> SEQUENCE: 46

Leu Ala Ala Ile Val Pro Ala Ile Ile Ala Val Pro
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Amino acid Sequence of aMTD185

<400> SEQUENCE: 47

Ala Ala Leu Val Leu Pro Leu Ile Ile Ala Ala Pro
1               5                   10
```

```
<210> SEQ ID NO 48
<211> LENGTH: 12
<212> TYPE: PRT
<213> ORGANISM: Artificial Sequence
<220> FEATURE:
<223> OTHER INFORMATION: Amino acid Sequence of aMTD201

<400> SEQUENCE: 48

Leu Ala Leu Ala Val Pro Ala Leu Ala Ala Leu Pro
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Amino acid Sequence of aMTD204

<400> SEQUENCE: 49

Leu Ile Ala Ala Leu Pro Ala Val Ala Ala Leu Pro
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Amino acid Sequence of aMTD205

<400> SEQUENCE: 50

Ala Leu Ala Leu Val Pro Ala Ile Ala Ala Leu Pro
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Amino acid Sequence of aMTD221

<400> SEQUENCE: 51

Ala Ala Ile Leu Ala Pro Ile Val Ala Leu Ala Pro
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Amino acid Sequence of aMTD222

<400> SEQUENCE: 52

Ala Leu Leu Ile Ala Pro Ala Ala Val Ile Ala Pro
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Amino acid Sequence of aMTD223

<400> SEQUENCE: 53

Ala Ile Leu Ala Val Pro Ile Ala Val Val Ala Pro
1               5                   10
```

<210> SEQ ID NO 54
<211> LENGTH: 12
<212> TYPE: PRT
<213> ORGANISM: Artificial Sequence
<220> FEATURE:
<223> OTHER INFORMATION: Amino acid Sequence of aMTD224

<400> SEQUENCE: 54

Ile Leu Ala Ala Val Pro Ile Ala Leu Ala Ala Pro
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Amino acid Sequence of aMTD225

<400> SEQUENCE: 55

Val Ala Ala Leu Leu Pro Ala Ala Ala Val Leu Pro
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Amino acid Sequence of aMTD241

<400> SEQUENCE: 56

Ala Ala Ala Val Val Pro Val Leu Leu Val Ala Pro
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Amino acid Sequence of aMTD242

<400> SEQUENCE: 57

Ala Ala Leu Leu Val Pro Ala Leu Val Ala Ala Pro
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Amino acid Sequence of aMTD243

<400> SEQUENCE: 58

Ala Ala Val Leu Leu Pro Val Ala Leu Ala Ala Pro
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Amino acid Sequence of aMTD245

<400> SEQUENCE: 59

Ala Ala Ala Leu Ala Pro Val Leu Ala Leu Val Pro
1               5                   10

```
<210> SEQ ID NO 60
<211> LENGTH: 12
<212> TYPE: PRT
<213> ORGANISM: Artificial Sequence
<220> FEATURE:
<223> OTHER INFORMATION: Amino acid Sequence of aMTD261

<400> SEQUENCE: 60

Leu Val Leu Val Pro Leu Leu Ala Ala Ala Ala Pro
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Amino acid Sequence of aMTD262

<400> SEQUENCE: 61

Ala Leu Ile Ala Val Pro Ala Ile Ile Val Ala Pro
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Amino acid Sequence of aMTD263

<400> SEQUENCE: 62

Ala Leu Ala Val Ile Pro Ala Ala Ala Ile Leu Pro
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Amino acid Sequence of aMTD264

<400> SEQUENCE: 63

Leu Ala Ala Ala Pro Val Val Ile Val Ile Ala Pro
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Amino acid Sequence of aMTD265

<400> SEQUENCE: 64

Val Leu Ala Ile Ala Pro Leu Leu Ala Ala Val Pro
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Amino acid Sequence of aMTD281

<400> SEQUENCE: 65

Ala Leu Ile Val Leu Pro Ala Ala Val Ala Val Pro
1               5                   10

<210> SEQ ID NO 66
```

```
<211> LENGTH: 12
<212> TYPE: PRT
<213> ORGANISM: Artificial Sequence
<220> FEATURE:
<223> OTHER INFORMATION: Amino acid Sequence of aMTD282

<400> SEQUENCE: 66

Val Leu Ala Val Ala Pro Ala Leu Ile Val Ala Pro
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Amino acid Sequence of aMTD283

<400> SEQUENCE: 67

Ala Ala Leu Leu Ala Pro Ala Leu Ile Val Ala Pro
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Amino acid Sequence of aMTD284

<400> SEQUENCE: 68

Ala Leu Ile Ala Pro Ala Val Ala Leu Ile Val Pro
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Amino acid Sequence of aMTD285

<400> SEQUENCE: 69

Ala Ile Val Leu Leu Pro Ala Ala Val Val Ala Pro
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Amino acid Sequence of aMTD301

<400> SEQUENCE: 70

Val Ile Ala Ala Pro Val Leu Ala Val Leu Ala Pro
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Amino acid Sequence of aMTD302

<400> SEQUENCE: 71

Leu Ala Leu Ala Pro Ala Leu Ala Leu Leu Ala Pro
1               5                   10

<210> SEQ ID NO 72
<211> LENGTH: 12
```

```
<212> TYPE: PRT
<213> ORGANISM: Artificial Sequence
<220> FEATURE:
<223> OTHER INFORMATION: Amino acid Sequence of aMTD304

<400> SEQUENCE: 72

Ala Ile Ile Leu Ala Pro Ile Ala Ala Ile Ala Pro
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Amino acid Sequence of aMTD305

<400> SEQUENCE: 73

Ile Ala Leu Ala Ala Pro Ile Leu Leu Ala Ala Pro
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Amino acid Sequence of aMTD321

<400> SEQUENCE: 74

Ile Val Ala Val Ala Leu Pro Ala Leu Ala Val Pro
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Amino acid Sequence of aMTD322

<400> SEQUENCE: 75

Val Val Ala Ile Val Leu Pro Ala Leu Ala Ala Pro
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Amino acid Sequence of aMTD323

<400> SEQUENCE: 76

Ile Val Ala Val Ala Leu Pro Val Ala Leu Ala Pro
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Amino acid Sequence of aMTD324

<400> SEQUENCE: 77

Ile Val Ala Val Ala Leu Pro Ala Ala Leu Val Pro
1               5                   10

<210> SEQ ID NO 78
<211> LENGTH: 12
<212> TYPE: PRT
```

```
<213> ORGANISM: Artificial Sequence
<220> FEATURE:
<223> OTHER INFORMATION: Amino acid Sequence of aMTD325

<400> SEQUENCE: 78

Ile Val Ala Val Ala Leu Pro Ala Val Ala Leu Pro
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Amino acid Sequence of aMTD341

<400> SEQUENCE: 79

Ile Val Ala Val Ala Leu Pro Ala Val Leu Ala Pro
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Amino acid Sequence of aMTD342

<400> SEQUENCE: 80

Val Ile Val Ala Leu Ala Pro Ala Val Leu Ala Pro
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Amino acid Sequence of aMTD343

<400> SEQUENCE: 81

Ile Val Ala Val Ala Leu Pro Ala Leu Val Ala Pro
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Amino acid Sequence of aMTD345

<400> SEQUENCE: 82

Ala Leu Leu Ile Val Ala Pro Val Ala Val Ala Pro
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Amino acid Sequence of aMTD361

<400> SEQUENCE: 83

Ala Val Val Ile Val Ala Pro Ala Val Ile Ala Pro
1               5                   10

<210> SEQ ID NO 84
<211> LENGTH: 12
<212> TYPE: PRT
<213> ORGANISM: Artificial Sequence
```

```
<220> FEATURE:
<223> OTHER INFORMATION: Amino acid Sequence of aMTD363

<400> SEQUENCE: 84

Ala Val Leu Ala Val Ala Pro Ala Leu Ile Val Pro
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Amino acid Sequence of aMTD364

<400> SEQUENCE: 85

Leu Val Ala Ala Val Ala Pro Ala Leu Ile Val Pro
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Amino acid Sequence of aMTD365

<400> SEQUENCE: 86

Ala Val Ile Val Val Ala Pro Ala Leu Leu Ala Pro
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Amino acid Sequence of aMTD381

<400> SEQUENCE: 87

Val Val Ala Ile Val Leu Pro Ala Val Ala Ala Pro
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Amino acid Sequence of aMTD382

<400> SEQUENCE: 88

Ala Ala Ala Leu Val Ile Pro Ala Ile Leu Ala Pro
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Amino acid Sequence of aMTD383

<400> SEQUENCE: 89

Val Ile Val Ala Leu Ala Pro Ala Leu Leu Ala Pro
1               5                   10

<210> SEQ ID NO 90
<211> LENGTH: 12
<212> TYPE: PRT
<213> ORGANISM: Artificial Sequence
<220> FEATURE:
```

<223> OTHER INFORMATION: Amino acid Sequence of aMTD384

<400> SEQUENCE: 90

Val Ile Val Ala Ile Ala Pro Ala Leu Leu Ala Pro
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Amino acid Sequence of aMTD385

<400> SEQUENCE: 91

Ile Val Ala Ile Ala Val Pro Ala Leu Val Ala Pro
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Amino acid Sequence of aMTD401

<400> SEQUENCE: 92

Ala Ala Leu Ala Val Ile Pro Ala Ala Ile Leu Pro
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Amino acid Sequence of aMTD402

<400> SEQUENCE: 93

Ala Leu Ala Ala Val Ile Pro Ala Ala Ile Leu Pro
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Amino acid Sequence of aMTD403

<400> SEQUENCE: 94

Ala Ala Ala Leu Val Ile Pro Ala Ala Ile Leu Pro
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Amino acid Sequence of aMTD404

<400> SEQUENCE: 95

Leu Ala Ala Ala Val Ile Pro Ala Ala Ile Leu Pro
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Amino acid Sequence of aMTD405

```
<400> SEQUENCE: 96

Leu Ala Ala Ala Val Ile Pro Val Ala Ile Leu Pro
1 5 10

<210> SEQ ID NO 97
<211> LENGTH: 12
<212> TYPE: PRT
<213> ORGANISM: Artificial Sequence
<220> FEATURE:
<223> OTHER INFORMATION: Amino acid Sequence of aMTD421

<400> SEQUENCE: 97

Ala Ala Ile Leu Ala Ala Pro Leu Ile Ala Val Pro
1 5 10

<210> SEQ ID NO 98
<211> LENGTH: 12
<212> TYPE: PRT
<213> ORGANISM: Artificial Sequence
<220> FEATURE:
<223> OTHER INFORMATION: Amino acid Sequence of aMTD422

<400> SEQUENCE: 98

Val Val Ala Ile Leu Ala Pro Leu Leu Ala Ala Pro
1 5 10

<210> SEQ ID NO 99
<211> LENGTH: 12
<212> TYPE: PRT
<213> ORGANISM: Artificial Sequence
<220> FEATURE:
<223> OTHER INFORMATION: Amino acid Sequence of aMTD424

<400> SEQUENCE: 99

Ala Val Val Val Ala Ala Pro Val Leu Ala Leu Pro
1 5 10

<210> SEQ ID NO 100
<211> LENGTH: 12
<212> TYPE: PRT
<213> ORGANISM: Artificial Sequence
<220> FEATURE:
<223> OTHER INFORMATION: Amino acid Sequence of aMTD425

<400> SEQUENCE: 100

Ala Val Val Ala Ile Ala Pro Val Leu Ala Leu Pro
1 5 10

<210> SEQ ID NO 101
<211> LENGTH: 12
<212> TYPE: PRT
<213> ORGANISM: Artificial Sequence
<220> FEATURE:
<223> OTHER INFORMATION: Amino acid Sequence of aMTD442

<400> SEQUENCE: 101

Ala Leu Ala Ala Leu Val Pro Ala Val Leu Val Pro
1 5 10

<210> SEQ ID NO 102
<211> LENGTH: 12
<212> TYPE: PRT
<213> ORGANISM: Artificial Sequence
<220> FEATURE:
<223> OTHER INFORMATION: Amino acid Sequence of aMTD443
```

<400> SEQUENCE: 102

Ala Leu Ala Ala Leu Val Pro Val Ala Leu Val Pro
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Amino acid Sequence of aMTD444

<400> SEQUENCE: 103

Leu Ala Ala Ala Leu Val Pro Val Ala Leu Val Pro
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Amino acid Sequence of aMTD445

<400> SEQUENCE: 104

Ala Leu Ala Ala Leu Val Pro Ala Leu Val Val Pro
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Amino acid Sequence of aMTD461

<400> SEQUENCE: 105

Ile Ala Ala Val Ile Val Pro Ala Val Ala Leu Pro
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Amino acid Sequence of aMTD462

<400> SEQUENCE: 106

Ile Ala Ala Val Leu Val Pro Ala Val Ala Leu Pro
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Amino acid Sequence of aMTD463

<400> SEQUENCE: 107

Ala Val Ala Ile Leu Val Pro Leu Leu Ala Ala Pro
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Amino acid Sequence of aMTD464

<400> SEQUENCE: 108

```
Ala Val Val Ile Leu Val Pro Leu Ala Ala Ala Pro
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Amino acid Sequence of aMTD465

<400> SEQUENCE: 109

Ile Ala Ala Val Ile Val Pro Val Ala Ala Leu Pro
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Amino acid Sequence of aMTD481

<400> SEQUENCE: 110

Ala Ile Ala Ile Ala Ile Val Pro Val Ala Leu Pro
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Amino acid Sequence of aMTD482

<400> SEQUENCE: 111

Ile Leu Ala Val Ala Ala Ile Pro Val Ala Val Pro
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Amino acid Sequence of aMTD483

<400> SEQUENCE: 112

Ile Leu Ala Ala Ala Ile Ile Pro Ala Ala Leu Pro
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Amino acid Sequence of aMTD484

<400> SEQUENCE: 113

Leu Ala Val Val Leu Ala Ala Pro Ala Ile Val Pro
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Amino acid Sequence of aMTD485

<400> SEQUENCE: 114
```

```
Ala Ile Leu Ala Ala Ile Val Pro Leu Ala Val Pro
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Amino acid Sequence of aMTD501

<400> SEQUENCE: 115

Val Ile Val Ala Leu Ala Val Pro Ala Leu Ala Pro
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Amino acid Sequence of aMTD502

<400> SEQUENCE: 116

Ala Ile Val Ala Leu Ala Val Pro Val Leu Ala Pro
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Amino acid Sequence of aMTD503

<400> SEQUENCE: 117

Ala Ala Ile Ile Ile Val Leu Pro Ala Ala Leu Pro
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Amino acid Sequence of aMTD504

<400> SEQUENCE: 118

Leu Ile Val Ala Leu Ala Val Pro Ala Leu Ala Pro
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Amino acid Sequence of aMTD505

<400> SEQUENCE: 119

Ala Ile Ile Ile Val Ile Ala Pro Ala Ala Ala Pro
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Amino acid Sequence of aMTD521

<400> SEQUENCE: 120

Leu Ala Ala Leu Ile Val Val Pro Ala Val Ala Pro
```

<210> SEQ ID NO 121
<211> LENGTH: 12
<212> TYPE: PRT
<213> ORGANISM: Artificial Sequence
<220> FEATURE:
<223> OTHER INFORMATION: Amino acid Sequence of aMTD522

<400> SEQUENCE: 121

Ala Leu Leu Val Ile Ala Val Pro Ala Val Ala Pro
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Amino acid Sequence of aMTD524

<400> SEQUENCE: 122

Ala Val Ala Leu Ile Val Val Pro Ala Leu Ala Pro
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Amino acid Sequence of aMTD525

<400> SEQUENCE: 123

Ala Leu Ala Ile Val Val Ala Pro Val Ala Val Pro
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Amino acid Sequence of aMTD541

<400> SEQUENCE: 124

Leu Leu Ala Leu Ile Ile Ala Pro Ala Ala Ala Pro
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Amino acid Sequence of aMTD542

<400> SEQUENCE: 125

Ala Leu Ala Leu Ile Ile Val Pro Ala Val Ala Pro
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Amino acid Sequence of aMTD543

<400> SEQUENCE: 126

Leu Leu Ala Ala Leu Ile Ala Pro Ala Ala Leu Pro
1               5                   10

```
<210> SEQ ID NO 127
<211> LENGTH: 12
<212> TYPE: PRT
<213> ORGANISM: Artificial Sequence
<220> FEATURE:
<223> OTHER INFORMATION: Amino acid Sequence of aMTD544

<400> SEQUENCE: 127

Ile Val Ala Leu Ile Val Ala Pro Ala Ala Val Pro
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Amino acid Sequence of aMTD545

<400> SEQUENCE: 128

Val Val Leu Val Leu Ala Ala Pro Ala Ala Val Pro
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Amino acid Sequence of aMTD561

<400> SEQUENCE: 129

Ala Ala Val Ala Ile Val Leu Pro Ala Val Val Pro
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Amino acid Sequence of aMTD562

<400> SEQUENCE: 130

Ala Leu Ile Ala Ala Ile Val Pro Ala Leu Val Pro
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Amino acid Sequence of aMTD563

<400> SEQUENCE: 131

Ala Leu Ala Val Ile Val Val Pro Ala Leu Ala Pro
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Amino acid Sequence of aMTD564

<400> SEQUENCE: 132

Val Ala Ile Ala Leu Ile Val Pro Ala Leu Ala Pro
1               5                   10
```

<210> SEQ ID NO 133
<211> LENGTH: 12
<212> TYPE: PRT
<213> ORGANISM: Artificial Sequence
<220> FEATURE:
<223> OTHER INFORMATION: Amino acid Sequence of aMTD565

<400> SEQUENCE: 133

Val Ala Ile Val Leu Val Ala Pro Ala Val Ala Pro
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Amino acid Sequence of aMTD582

<400> SEQUENCE: 134

Val Ala Val Ala Leu Ile Val Pro Ala Leu Ala Pro
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Amino acid Sequence of aMTD583

<400> SEQUENCE: 135

Ala Val Ile Leu Ala Leu Ala Pro Ile Val Ala Pro
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Amino acid Sequence of aMTD585

<400> SEQUENCE: 136

Ala Leu Ile Val Ala Ile Ala Pro Ala Leu Val Pro
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Amino acid Sequence of aMTD601

<400> SEQUENCE: 137

Ala Ala Ile Leu Ile Ala Val Pro Ile Ala Ala Pro
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Amino acid Sequence of aMTD602

<400> SEQUENCE: 138

Val Ile Val Ala Leu Ala Ala Pro Val Leu Ala Pro
1               5                   10

```
<210> SEQ ID NO 139
<211> LENGTH: 12
<212> TYPE: PRT
<213> ORGANISM: Artificial Sequence
<220> FEATURE:
<223> OTHER INFORMATION: Amino acid Sequence of aMTD603

<400> SEQUENCE: 139

Val Leu Val Ala Leu Ala Ala Pro Val Ile Ala Pro
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Amino acid Sequence of aMTD604

<400> SEQUENCE: 140

Val Ala Leu Ile Ala Val Ala Pro Ala Val Val Pro
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Amino acid Sequence of aMTD605

<400> SEQUENCE: 141

Val Ile Ala Ala Val Leu Ala Pro Val Ala Val Pro
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Amino acid Sequence of aMTD622

<400> SEQUENCE: 142

Ala Leu Ile Val Leu Ala Ala Pro Val Ala Val Pro
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Amino acid Sequence of aMTD623

<400> SEQUENCE: 143

Val Ala Ala Ala Ile Ala Leu Pro Ala Ile Val Pro
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Amino acid Sequence of aMTD625

<400> SEQUENCE: 144

Ile Leu Ala Ala Ala Ala Ala Pro Leu Ile Val Pro
1               5                   10

<210> SEQ ID NO 145
```

```
<211> LENGTH: 12
<212> TYPE: PRT
<213> ORGANISM: Artificial Sequence
<220> FEATURE:
<223> OTHER INFORMATION: Amino acid Sequence of aMTD643

<400> SEQUENCE: 145

Leu Ala Leu Val Leu Ala Ala Pro Ala Ile Val Pro
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Amino acid Sequence of aMTD645

<400> SEQUENCE: 146

Ala Leu Ala Val Val Ala Leu Pro Ala Ile Val Pro
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Amino acid Sequence of aMTD661

<400> SEQUENCE: 147

Ala Ala Ile Leu Ala Pro Ile Val Ala Ala Leu Pro
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Amino acid Sequence of aMTD664

<400> SEQUENCE: 148

Ile Leu Ile Ala Ile Ala Ile Pro Ala Ala Ala Pro
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Amino acid Sequence of aMTD665

<400> SEQUENCE: 149

Leu Ala Ile Val Leu Ala Ala Pro Val Ala Val Pro
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Amino acid Sequence of aMTD666

<400> SEQUENCE: 150

Ala Ala Ile Ala Ile Ile Ala Pro Ala Ile Val Pro
1               5                   10

<210> SEQ ID NO 151
<211> LENGTH: 12
```

```
<212> TYPE: PRT
<213> ORGANISM: Artificial Sequence
<220> FEATURE:
<223> OTHER INFORMATION: Amino acid Sequence of aMTD667

<400> SEQUENCE: 151

Leu Ala Val Ala Ile Val Ala Pro Ala Leu Val Pro
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Amino acid Sequence of aMTD683

<400> SEQUENCE: 152

Leu Ala Ile Val Leu Ala Ala Pro Ala Val Leu Pro
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Amino acid Sequence of aMTD684

<400> SEQUENCE: 153

Ala Ala Ile Val Leu Ala Leu Pro Ala Val Leu Pro
1               5                   10

<210> SEQ ID NO 154
<211> LENGTH: 12
<212> TYPE: PRT
<213> ORGANISM: Artificial Sequence
<220> FEATURE:
<223> OTHER INFORMATION: Amino acid Sequence of aMTD685

<400> SEQUENCE: 154

Ala Leu Leu Val Ala Val Leu Pro Ala Ala Leu Pro
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Amino acid Sequence of aMTD686

<400> SEQUENCE: 155

Ala Ala Leu Val Ala Val Leu Pro Val Ala Leu Pro
1               5                   10

<210> SEQ ID NO 156
<211> LENGTH: 12
<212> TYPE: PRT
<213> ORGANISM: Artificial Sequence
<220> FEATURE:
<223> OTHER INFORMATION: Amino acid Sequence of aMTD687

<400> SEQUENCE: 156

Ala Ile Leu Ala Val Ala Leu Pro Leu Leu Ala Pro
1               5                   10

<210> SEQ ID NO 157
<211> LENGTH: 12
<212> TYPE: PRT
```

<213> ORGANISM: Artificial Sequence
<220> FEATURE:
<223> OTHER INFORMATION: Amino acid Sequence of aMTD703

<400> SEQUENCE: 157

Ile Val Ala Val Ala Leu Val Pro Ala Leu Ala Pro
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Amino acid Sequence of aMTD705

<400> SEQUENCE: 158

Ile Val Ala Val Ala Leu Leu Pro Ala Leu Ala Pro
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Amino acid Sequence of aMTD706

<400> SEQUENCE: 159

Ile Val Ala Val Ala Leu Leu Pro Ala Val Ala Pro
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Amino acid Sequence of aMTD707

<400> SEQUENCE: 160

Ile Val Ala Leu Ala Val Leu Pro Ala Val Ala Pro
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Amino acid Sequence of aMTD724

<400> SEQUENCE: 161

Val Ala Val Leu Ala Val Leu Pro Ala Leu Ala Pro
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Amino acid Sequence of aMTD725

<400> SEQUENCE: 162

Ile Ala Val Leu Ala Val Ala Pro Ala Val Leu Pro
1               5                   10

<210> SEQ ID NO 163
<211> LENGTH: 12
<212> TYPE: PRT
<213> ORGANISM: Artificial Sequence

```
<220> FEATURE:
<223> OTHER INFORMATION: Amino acid Sequence of aMTD726

<400> SEQUENCE: 163

Leu Ala Val Ala Ile Ile Ala Pro Ala Val Ala Pro
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Amino acid Sequence of aMTD727

<400> SEQUENCE: 164

Val Ala Leu Ala Ile Ala Leu Pro Ala Val Leu Pro
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Amino acid Sequence of aMTD743

<400> SEQUENCE: 165

Ala Ile Ala Ile Ala Leu Val Pro Val Ala Leu Pro
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Amino acid Sequence of aMTD744

<400> SEQUENCE: 166

Ala Ala Val Val Ile Val Ala Pro Val Ala Leu Pro
1               5                   10

<210> SEQ ID NO 167
<211> LENGTH: 12
<212> TYPE: PRT
<213> ORGANISM: Artificial Sequence
<220> FEATURE:
<223> OTHER INFORMATION: Amino acid Sequence of aMTD746

<400> SEQUENCE: 167

Val Ala Ile Ile Val Val Ala Pro Ala Leu Ala Pro
1               5                   10

<210> SEQ ID NO 168
<211> LENGTH: 12
<212> TYPE: PRT
<213> ORGANISM: Artificial Sequence
<220> FEATURE:
<223> OTHER INFORMATION: Amino acid Sequence of aMTD747

<400> SEQUENCE: 168

Val Ala Leu Leu Ala Ile Ala Pro Ala Leu Ala Pro
1               5                   10

<210> SEQ ID NO 169
<211> LENGTH: 12
<212> TYPE: PRT
<213> ORGANISM: Artificial Sequence
<220> FEATURE:
```

<223> OTHER INFORMATION: Amino acid Sequence of aMTD763

<400> SEQUENCE: 169

Val Ala Val Leu Ile Ala Val Pro Ala Leu Ala Pro
1               5                   10

<210> SEQ ID NO 170
<211> LENGTH: 12
<212> TYPE: PRT
<213> ORGANISM: Artificial Sequence
<220> FEATURE:
<223> OTHER INFORMATION: Amino acid Sequence of aMTD764

<400> SEQUENCE: 170

Ala Val Ala Leu Ala Val Leu Pro Ala Val Val Pro
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Amino acid Sequence of aMTD765

<400> SEQUENCE: 171

Ala Val Ala Leu Ala Val Val Pro Ala Val Leu Pro
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Amino acid Sequence of aMTD766

<400> SEQUENCE: 172

Ile Val Val Ile Ala Val Ala Pro Ala Val Ala Pro
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Amino acid Sequence of aMTD767

<400> SEQUENCE: 173

Ile Val Val Ala Ala Val Val Pro Ala Leu Ala Pro
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Amino acid Sequence of aMTD783

<400> SEQUENCE: 174

Ile Val Ala Leu Val Pro Ala Val Ala Ile Ala Pro
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Amino acid Sequence of aMTD784

<400> SEQUENCE: 175

Val Ala Ala Leu Pro Ala Val Ala Leu Val Val Pro
1               5                   10

<210> SEQ ID NO 176
<211> LENGTH: 12
<212> TYPE: PRT
<213> ORGANISM: Artificial Sequence
<220> FEATURE:
<223> OTHER INFORMATION: Amino acid Sequence of aMTD786

<400> SEQUENCE: 176

Leu Val Ala Ile Ala Pro Leu Ala Val Leu Ala Pro
1               5                   10

<210> SEQ ID NO 177
<211> LENGTH: 12
<212> TYPE: PRT
<213> ORGANISM: Artificial Sequence
<220> FEATURE:
<223> OTHER INFORMATION: Amino acid Sequence of aMTD787

<400> SEQUENCE: 177

Ala Val Ala Leu Val Pro Val Ile Val Ala Ala Pro
1               5                   10

<210> SEQ ID NO 178
<211> LENGTH: 12
<212> TYPE: PRT
<213> ORGANISM: Artificial Sequence
<220> FEATURE:
<223> OTHER INFORMATION: Amino acid Sequence of aMTD788

<400> SEQUENCE: 178

Ala Ile Ala Val Ala Ile Ala Pro Val Ala Leu Pro
1               5                   10

<210> SEQ ID NO 179
<211> LENGTH: 12
<212> TYPE: PRT
<213> ORGANISM: Artificial Sequence
<220> FEATURE:
<223> OTHER INFORMATION: Amino acid Sequence of aMTD803

<400> SEQUENCE: 179

Ala Ile Ala Leu Ala Val Pro Val Leu Ala Leu Pro
1               5                   10

<210> SEQ ID NO 180
<211> LENGTH: 12
<212> TYPE: PRT
<213> ORGANISM: Artificial Sequence
<220> FEATURE:
<223> OTHER INFORMATION: Amino acid Sequence of aMTD805

<400> SEQUENCE: 180

Leu Val Leu Ile Ala Ala Ala Pro Ile Ala Leu Pro
1               5                   10

<210> SEQ ID NO 181
<211> LENGTH: 12
<212> TYPE: PRT
<213> ORGANISM: Artificial Sequence
<220> FEATURE:
<223> OTHER INFORMATION: Amino acid Sequence of aMTD806

<400> SEQUENCE: 181

Leu Val Ala Leu Ala Val Pro Ala Ala Val Leu Pro
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Amino acid Sequence of aMTD807

<400> SEQUENCE: 182

Ala Val Ala Leu Ala Val Pro Ala Leu Val Leu Pro
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Amino acid Sequence of aMTD808

<400> SEQUENCE: 183

Leu Val Val Leu Ala Ala Ala Pro Leu Ala Val Pro
1               5                   10

<210> SEQ ID NO 184
<211> LENGTH: 12
<212> TYPE: PRT
<213> ORGANISM: Artificial Sequence
<220> FEATURE:
<223> OTHER INFORMATION: Amino acid Sequence of aMTD809

<400> SEQUENCE: 184

Leu Ile Val Leu Ala Ala Pro Ala Leu Ala Ala Pro
1               5                   10

<210> SEQ ID NO 185
<211> LENGTH: 12
<212> TYPE: PRT
<213> ORGANISM: Artificial Sequence
<220> FEATURE:
<223> OTHER INFORMATION: Amino acid Sequence of aMTD810

<400> SEQUENCE: 185

Val Ile Val Leu Ala Ala Pro Ala Leu Ala Ala Pro
1               5                   10

<210> SEQ ID NO 186
<211> LENGTH: 12
<212> TYPE: PRT
<213> ORGANISM: Artificial Sequence
<220> FEATURE:
<223> OTHER INFORMATION: Amino acid Sequence of aMTD811

<400> SEQUENCE: 186

Ala Val Val Leu Ala Val Pro Ala Leu Ala Val Pro
1               5                   10

<210> SEQ ID NO 187
<211> LENGTH: 12
<212> TYPE: PRT
<213> ORGANISM: Artificial Sequence
<220> FEATURE:
<223> OTHER INFORMATION: Amino acid Sequence of aMTD824

<400> SEQUENCE: 187

```
Leu Ile Ile Val Ala Ala Ala Pro Ala Val Ala Pro
1               5                   10

<210> SEQ ID NO 188
<211> LENGTH: 12
<212> TYPE: PRT
<213> ORGANISM: Artificial Sequence
<220> FEATURE:
<223> OTHER INFORMATION: Amino acid Sequence of aMTD825

<400> SEQUENCE: 188

Ile Val Ala Val Ile Val Ala Pro Ala Val Ala Pro
1               5                   10

<210> SEQ ID NO 189
<211> LENGTH: 12
<212> TYPE: PRT
<213> ORGANISM: Artificial Sequence
<220> FEATURE:
<223> OTHER INFORMATION: Amino acid Sequence of aMTD826

<400> SEQUENCE: 189

Leu Val Ala Leu Ala Ala Pro Ile Ile Ala Val Pro
1               5                   10

<210> SEQ ID NO 190
<211> LENGTH: 12
<212> TYPE: PRT
<213> ORGANISM: Artificial Sequence
<220> FEATURE:
<223> OTHER INFORMATION: Amino acid Sequence of aMTD827

<400> SEQUENCE: 190

Ile Ala Ala Val Leu Ala Ala Pro Ala Leu Val Pro
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Amino acid Sequence of aMTD828

<400> SEQUENCE: 191

Ile Ala Leu Leu Ala Ala Pro Ile Ile Ala Val Pro
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Amino acid Sequence of aMTD829

<400> SEQUENCE: 192

Ala Ala Leu Ala Leu Val Ala Pro Val Ile Val Pro
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Amino acid Sequence of aMTD830

<400> SEQUENCE: 193
```

```
Ile Ala Leu Val Ala Ala Pro Val Ala Leu Val Pro
1               5                   10

<210> SEQ ID NO 194
<211> LENGTH: 12
<212> TYPE: PRT
<213> ORGANISM: Artificial Sequence
<220> FEATURE:
<223> OTHER INFORMATION: Amino acid Sequence of aMTD831

<400> SEQUENCE: 194

Ile Ile Val Ala Val Ala Pro Ala Ala Ile Val Pro
1               5                   10

<210> SEQ ID NO 195
<211> LENGTH: 12
<212> TYPE: PRT
<213> ORGANISM: Artificial Sequence
<220> FEATURE:
<223> OTHER INFORMATION: Amino acid Sequence of aMTD832

<400> SEQUENCE: 195

Ala Val Ala Ala Ile Val Pro Val Ile Val Ala Pro
1               5                   10

<210> SEQ ID NO 196
<211> LENGTH: 12
<212> TYPE: PRT
<213> ORGANISM: Artificial Sequence
<220> FEATURE:
<223> OTHER INFORMATION: Amino acid Sequence of aMTD843

<400> SEQUENCE: 196

Ala Val Leu Val Leu Val Ala Pro Ala Ala Ala Pro
1               5                   10

<210> SEQ ID NO 197
<211> LENGTH: 12
<212> TYPE: PRT
<213> ORGANISM: Artificial Sequence
<220> FEATURE:
<223> OTHER INFORMATION: Amino acid Sequence of aMTD844

<400> SEQUENCE: 197

Val Val Ala Leu Leu Ala Pro Leu Ile Ala Ala Pro
1               5                   10

<210> SEQ ID NO 198
<211> LENGTH: 12
<212> TYPE: PRT
<213> ORGANISM: Artificial Sequence
<220> FEATURE:
<223> OTHER INFORMATION: Amino acid Sequence of aMTD845

<400> SEQUENCE: 198

Ala Ala Val Val Ile Ala Pro Leu Leu Ala Val Pro
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Amino acid Sequence of aMTD846

<400> SEQUENCE: 199

Ile Ala Val Ala Val Ala Ala Pro Leu Leu Val Pro
```

```
1               5                   10
```

```
<210> SEQ ID NO 200
<211> LENGTH: 12
<212> TYPE: PRT
<213> ORGANISM: Artificial Sequence
<220> FEATURE:
<223> OTHER INFORMATION: Amino acid Sequence of aMTD847

<400> SEQUENCE: 200

Leu Val Ala Ile Val Val Leu Pro Ala Val Ala Pro
1               5                   10

<210> SEQ ID NO 201
<211> LENGTH: 12
<212> TYPE: PRT
<213> ORGANISM: Artificial Sequence
<220> FEATURE:
<223> OTHER INFORMATION: Amino acid Sequence of aMTD848

<400> SEQUENCE: 201

Ala Val Ala Ile Val Val Leu Pro Ala Val Ala Pro
1               5                   10

<210> SEQ ID NO 202
<211> LENGTH: 12
<212> TYPE: PRT
<213> ORGANISM: Artificial Sequence
<220> FEATURE:
<223> OTHER INFORMATION: Amino acid Sequence of aMTD849

<400> SEQUENCE: 202

Ala Val Ile Leu Leu Ala Pro Leu Ile Ala Ala Pro
1               5                   10

<210> SEQ ID NO 203
<211> LENGTH: 12
<212> TYPE: PRT
<213> ORGANISM: Artificial Sequence
<220> FEATURE:
<223> OTHER INFORMATION: Amino acid Sequence of aMTD850

<400> SEQUENCE: 203

Leu Val Ile Ala Leu Ala Ala Pro Val Ala Leu Pro
1               5                   10

<210> SEQ ID NO 204
<211> LENGTH: 12
<212> TYPE: PRT
<213> ORGANISM: Artificial Sequence
<220> FEATURE:
<223> OTHER INFORMATION: Amino acid Sequence of aMTD851

<400> SEQUENCE: 204

Val Leu Ala Val Val Leu Pro Ala Val Ala Leu Pro
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Amino acid Sequence of aMTD852

<400> SEQUENCE: 205

Val Leu Ala Val Ala Ala Pro Ala Val Leu Leu Pro
1               5                   10
```

<210> SEQ ID NO 206
<211> LENGTH: 12
<212> TYPE: PRT
<213> ORGANISM: Artificial Sequence
<220> FEATURE:
<223> OTHER INFORMATION: Amino acid Sequence of aMTD863

<400> SEQUENCE: 206

Ala Ala Val Val Leu Leu Pro Ile Ile Ala Ala Pro
1               5                   10

<210> SEQ ID NO 207
<211> LENGTH: 12
<212> TYPE: PRT
<213> ORGANISM: Artificial Sequence
<220> FEATURE:
<223> OTHER INFORMATION: Amino acid Sequence of aMTD864

<400> SEQUENCE: 207

Ala Leu Leu Val Ile Ala Pro Ala Ile Ala Val Pro
1               5                   10

<210> SEQ ID NO 208
<211> LENGTH: 12
<212> TYPE: PRT
<213> ORGANISM: Artificial Sequence
<220> FEATURE:
<223> OTHER INFORMATION: Amino acid Sequence of aMTD865

<400> SEQUENCE: 208

Ala Val Leu Val Ile Ala Val Pro Ala Ile Ala Pro
1               5                   10

<210> SEQ ID NO 209
<211> LENGTH: 12
<212> TYPE: PRT
<213> ORGANISM: Artificial Sequence
<220> FEATURE:
<223> OTHER INFORMATION: Amino acid Sequence of aMTD867

<400> SEQUENCE: 209

Ala Leu Leu Val Val Ile Ala Pro Leu Ala Ala Pro
1               5                   10

<210> SEQ ID NO 210
<211> LENGTH: 12
<212> TYPE: PRT
<213> ORGANISM: Artificial Sequence
<220> FEATURE:
<223> OTHER INFORMATION: Amino acid Sequence of aMTD868

<400> SEQUENCE: 210

Val Leu Val Ala Ala Ile Leu Pro Ala Ala Ile Pro
1               5                   10

<210> SEQ ID NO 211
<211> LENGTH: 12
<212> TYPE: PRT
<213> ORGANISM: Artificial Sequence
<220> FEATURE:
<223> OTHER INFORMATION: Amino acid Sequence of aMTD870

<400> SEQUENCE: 211

Val Leu Val Ala Ala Val Leu Pro Ile Ala Ala Pro
1               5                   10

```
<210> SEQ ID NO 212
<211> LENGTH: 12
<212> TYPE: PRT
<213> ORGANISM: Artificial Sequence
<220> FEATURE:
<223> OTHER INFORMATION: Amino acid Sequence of aMTD872

<400> SEQUENCE: 212

Val Leu Ala Ala Ala Val Leu Pro Leu Val Val Pro
1               5                   10

<210> SEQ ID NO 213
<211> LENGTH: 12
<212> TYPE: PRT
<213> ORGANISM: Artificial Sequence
<220> FEATURE:
<223> OTHER INFORMATION: Amino acid Sequence of aMTD875

<400> SEQUENCE: 213

Ala Ile Ala Ile Val Val Pro Ala Val Ala Val Pro
1               5                   10

<210> SEQ ID NO 214
<211> LENGTH: 12
<212> TYPE: PRT
<213> ORGANISM: Artificial Sequence
<220> FEATURE:
<223> OTHER INFORMATION: Amino acid Sequence of aMTD877

<400> SEQUENCE: 214

Val Ala Ile Ile Ala Val Pro Ala Val Val Ala Pro
1               5                   10

<210> SEQ ID NO 215
<211> LENGTH: 12
<212> TYPE: PRT
<213> ORGANISM: Artificial Sequence
<220> FEATURE:
<223> OTHER INFORMATION: Amino acid Sequence of aMTD878

<400> SEQUENCE: 215

Ile Val Ala Leu Val Ala Pro Ala Ala Val Val Pro
1               5                   10

<210> SEQ ID NO 216
<211> LENGTH: 12
<212> TYPE: PRT
<213> ORGANISM: Artificial Sequence
<220> FEATURE:
<223> OTHER INFORMATION: Amino acid Sequence of aMTD879

<400> SEQUENCE: 216

Ala Ala Ile Val Leu Leu Pro Ala Val Val Val Pro
1               5                   10

<210> SEQ ID NO 217
<211> LENGTH: 12
<212> TYPE: PRT
<213> ORGANISM: Artificial Sequence
<220> FEATURE:
<223> OTHER INFORMATION: Amino acid Sequence of aMTD881

<400> SEQUENCE: 217

Ala Ala Leu Ile Val Val Pro Ala Val Ala Val Pro
1               5                   10
```

```
<210> SEQ ID NO 218
<211> LENGTH: 12
<212> TYPE: PRT
<213> ORGANISM: Artificial Sequence
<220> FEATURE:
<223> OTHER INFORMATION: Amino acid Sequence of aMTD882

<400> SEQUENCE: 218

Ala Ile Ala Leu Val Val Pro Ala Val Ala Val Pro
1               5                   10

<210> SEQ ID NO 219
<211> LENGTH: 12
<212> TYPE: PRT
<213> ORGANISM: Artificial Sequence
<220> FEATURE:
<223> OTHER INFORMATION: Amino acid Sequence of aMTD883

<400> SEQUENCE: 219

Leu Ala Ile Val Pro Ala Ala Ile Ala Ala Leu Pro
1               5                   10

<210> SEQ ID NO 220
<211> LENGTH: 12
<212> TYPE: PRT
<213> ORGANISM: Artificial Sequence
<220> FEATURE:
<223> OTHER INFORMATION: Amino acid Sequence of aMTD885

<400> SEQUENCE: 220

Leu Val Ala Ile Ala Pro Ala Val Ala Val Leu Pro
1               5                   10

<210> SEQ ID NO 221
<211> LENGTH: 12
<212> TYPE: PRT
<213> ORGANISM: Artificial Sequence
<220> FEATURE:
<223> OTHER INFORMATION: Amino acid Sequence of aMTD887

<400> SEQUENCE: 221

Val Leu Ala Val Ala Pro Ala Val Ala Val Leu Pro
1               5                   10

<210> SEQ ID NO 222
<211> LENGTH: 12
<212> TYPE: PRT
<213> ORGANISM: Artificial Sequence
<220> FEATURE:
<223> OTHER INFORMATION: Amino acid Sequence of aMTD888

<400> SEQUENCE: 222

Ile Leu Ala Val Val Ala Ile Pro Ala Ala Ala Pro
1               5                   10

<210> SEQ ID NO 223
<211> LENGTH: 12
<212> TYPE: PRT
<213> ORGANISM: Artificial Sequence
<220> FEATURE:
<223> OTHER INFORMATION: Amino acid Sequence of aMTD889

<400> SEQUENCE: 223

Ile Leu Val Ala Ala Ala Pro Ile Ala Ala Leu Pro
1               5                   10

<210> SEQ ID NO 224
```

```
<211> LENGTH: 12
<212> TYPE: PRT
<213> ORGANISM: Artificial Sequence
<220> FEATURE:
<223> OTHER INFORMATION: Amino acid Sequence of aMTD891

<400> SEQUENCE: 224

Ile Leu Ala Val Ala Ala Ile Pro Ala Ala Leu Pro
1               5                   10

<210> SEQ ID NO 225
<211> LENGTH: 12
<212> TYPE: PRT
<213> ORGANISM: Artificial Sequence
<220> FEATURE:
<223> OTHER INFORMATION: Amino acid Sequence of aMTD893

<400> SEQUENCE: 225

Val Ile Ala Ile Pro Ala Ile Leu Ala Ala Ala Pro
1               5                   10

<210> SEQ ID NO 226
<211> LENGTH: 12
<212> TYPE: PRT
<213> ORGANISM: Artificial Sequence
<220> FEATURE:
<223> OTHER INFORMATION: Amino acid Sequence of aMTD895

<400> SEQUENCE: 226

Ala Ile Ile Ile Val Val Pro Ala Ile Ala Ala Pro
1               5                   10

<210> SEQ ID NO 227
<211> LENGTH: 12
<212> TYPE: PRT
<213> ORGANISM: Artificial Sequence
<220> FEATURE:
<223> OTHER INFORMATION: Amino acid Sequence of aMTD896

<400> SEQUENCE: 227

Ala Ile Leu Ile Val Val Ala Pro Ile Ala Ala Pro
1               5                   10

<210> SEQ ID NO 228
<211> LENGTH: 12
<212> TYPE: PRT
<213> ORGANISM: Artificial Sequence
<220> FEATURE:
<223> OTHER INFORMATION: Amino acid Sequence of aMTD897

<400> SEQUENCE: 228

Ala Val Ile Val Pro Val Ala Ile Ile Ala Ala Pro
1               5                   10

<210> SEQ ID NO 229
<211> LENGTH: 12
<212> TYPE: PRT
<213> ORGANISM: Artificial Sequence
<220> FEATURE:
<223> OTHER INFORMATION: Amino acid Sequence of aMTD899

<400> SEQUENCE: 229

Ala Val Val Ile Ala Leu Pro Ala Val Val Ala Pro
1               5                   10

<210> SEQ ID NO 230
<211> LENGTH: 12
```

```
<212> TYPE: PRT
<213> ORGANISM: Artificial Sequence
<220> FEATURE:
<223> OTHER INFORMATION: Amino acid Sequence of aMTD900

<400> SEQUENCE: 230

Ala Leu Val Ala Val Ile Ala Pro Val Val Ala Pro
1               5                   10

<210> SEQ ID NO 231
<211> LENGTH: 12
<212> TYPE: PRT
<213> ORGANISM: Artificial Sequence
<220> FEATURE:
<223> OTHER INFORMATION: Amino acid Sequence of aMTD901

<400> SEQUENCE: 231

Ala Leu Val Ala Val Leu Pro Ala Val Ala Val Pro
1               5                   10

<210> SEQ ID NO 232
<211> LENGTH: 12
<212> TYPE: PRT
<213> ORGANISM: Artificial Sequence
<220> FEATURE:
<223> OTHER INFORMATION: Amino acid Sequence of aMTD902

<400> SEQUENCE: 232

Ala Leu Val Ala Pro Leu Leu Ala Val Ala Val Pro
1               5                   10

<210> SEQ ID NO 233
<211> LENGTH: 12
<212> TYPE: PRT
<213> ORGANISM: Artificial Sequence
<220> FEATURE:
<223> OTHER INFORMATION: Amino acid Sequence of aMTD904

<400> SEQUENCE: 233

Ala Val Leu Ala Val Val Ala Pro Val Val Ala Pro
1               5                   10

<210> SEQ ID NO 234
<211> LENGTH: 12
<212> TYPE: PRT
<213> ORGANISM: Artificial Sequence
<220> FEATURE:
<223> OTHER INFORMATION: Amino acid Sequence of aMTD905

<400> SEQUENCE: 234

Ala Val Ile Ala Val Ala Pro Leu Val Val Ala Pro
1               5                   10

<210> SEQ ID NO 235
<211> LENGTH: 12
<212> TYPE: PRT
<213> ORGANISM: Artificial Sequence
<220> FEATURE:
<223> OTHER INFORMATION: Amino acid Sequence of aMTD906

<400> SEQUENCE: 235

Ala Val Ile Ala Leu Ala Pro Val Val Val Ala Pro
1               5                   10

<210> SEQ ID NO 236
<211> LENGTH: 12
<212> TYPE: PRT
```

```
<213> ORGANISM: Artificial Sequence
<220> FEATURE:
<223> OTHER INFORMATION: Amino acid Sequence of aMTD907

<400> SEQUENCE: 236

Val Ala Ile Ala Leu Ala Pro Val Val Val Ala Pro
1               5                   10

<210> SEQ ID NO 237
<211> LENGTH: 12
<212> TYPE: PRT
<213> ORGANISM: Artificial Sequence
<220> FEATURE:
<223> OTHER INFORMATION: Amino acid Sequence of aMTD908

<400> SEQUENCE: 237

Val Ala Leu Ala Leu Ala Pro Val Val Val Ala Pro
1               5                   10

<210> SEQ ID NO 238
<211> LENGTH: 12
<212> TYPE: PRT
<213> ORGANISM: Artificial Sequence
<220> FEATURE:
<223> OTHER INFORMATION: Amino acid Sequence of aMTD910

<400> SEQUENCE: 238

Val Ala Ala Leu Leu Pro Ala Val Val Val Ala Pro
1               5                   10

<210> SEQ ID NO 239
<211> LENGTH: 12
<212> TYPE: PRT
<213> ORGANISM: Artificial Sequence
<220> FEATURE:
<223> OTHER INFORMATION: Amino acid Sequence of aMTD911

<400> SEQUENCE: 239

Val Ala Leu Ala Leu Pro Ala Val Val Val Ala Pro
1               5                   10

<210> SEQ ID NO 240
<211> LENGTH: 12
<212> TYPE: PRT
<213> ORGANISM: Artificial Sequence
<220> FEATURE:
<223> OTHER INFORMATION: Amino acid Sequence of aMTD912

<400> SEQUENCE: 240

Val Ala Leu Leu Ala Pro Ala Val Val Val Ala Pro
1               5                   10

<210> SEQ ID NO 241
<211> LENGTH: 36
<212> TYPE: DNA
<213> ORGANISM: Artificial Sequence
<220> FEATURE:
<223> OTHER INFORMATION: cDNA Sequence of aMTD1

<400> SEQUENCE: 241
gcggcggcgc tggcgccggt ggtgctggcg ctgccg                              36

<210> SEQ ID NO 242
<211> LENGTH: 36
<212> TYPE: DNA
<213> ORGANISM: Artificial Sequence
<220> FEATURE:
```

<223> OTHER INFORMATION: cDNA Sequence of aMTD2

<400> SEQUENCE: 242
gcggcggcgg tgccgctgct ggcggtggtg gtgccg         36

<210> SEQ ID NO 243
<211> LENGTH: 36
<212> TYPE: DNA
<213> ORGANISM: Artificial Sequence
<220> FEATURE:
<223> OTHER INFORMATION: cDNA Sequence of aMTD3

<400> SEQUENCE: 243
gcggcgctgc tggtgccggc ggcggtgctg gcgccg         36

<210> SEQ ID NO 244
<211> LENGTH: 36
<212> TYPE: DNA
<213> ORGANISM: Artificial Sequence
<220> FEATURE:
<223> OTHER INFORMATION: cDNA Sequence of aMTD4

<400> SEQUENCE: 244
gcgctggcgc tgctgccggt ggcggcgctg gcgccg         36

<210> SEQ ID NO 245
<211> LENGTH: 36
<212> TYPE: DNA
<213> ORGANISM: Artificial Sequence
<220> FEATURE:
<223> OTHER INFORMATION: cDNA Sequence of aMTD5

<400> SEQUENCE: 245
gcggcggcgc tgctgccggt ggcgctggtg gcgccg         36

<210> SEQ ID NO 246
<211> LENGTH: 36
<212> TYPE: DNA
<213> ORGANISM: Artificial Sequence
<220> FEATURE:
<223> OTHER INFORMATION: cDNA Sequence of aMTD11

<400> SEQUENCE: 246
gtggtggcgc tggcgccggc gctggcggcg ctgccg         36

<210> SEQ ID NO 247
<211> LENGTH: 36
<212> TYPE: DNA
<213> ORGANISM: Artificial Sequence
<220> FEATURE:
<223> OTHER INFORMATION: cDNA Sequence of aMTD12

<400> SEQUENCE: 247
ctgctggcgg cggtgccggc ggtgctgctg gcgccg         36

<210> SEQ ID NO 248
<211> LENGTH: 36
<212> TYPE: DNA
<213> ORGANISM: Artificial Sequence
<220> FEATURE:
<223> OTHER INFORMATION: cDNA Sequence of aMTD13

<400> SEQUENCE: 248
gcggcggcgc tggtgccggt ggtggcgctg ctgccg         36

```
<210> SEQ ID NO 249
<211> LENGTH: 36
<212> TYPE: DNA
<213> ORGANISM: Artificial Sequence
<220> FEATURE:
<223> OTHER INFORMATION: cDNA Sequence of aMTD21

<400> SEQUENCE: 249
gcggtggcgc tgctgccggc gctgctggcg gtgccg                                36

<210> SEQ ID NO 250
<211> LENGTH: 36
<212> TYPE: DNA
<213> ORGANISM: Artificial Sequence
<220> FEATURE:
<223> OTHER INFORMATION: cDNA Sequence of aMTD22

<400> SEQUENCE: 250
gcggtggtgc tggtgccggt gctggcggcg gcgccg                                36

<210> SEQ ID NO 251
<211> LENGTH: 36
<212> TYPE: DNA
<213> ORGANISM: Artificial Sequence
<220> FEATURE:
<223> OTHER INFORMATION: cDNA Sequence of aMTD23

<400> SEQUENCE: 251
gtggtgctgg tgctgccggc ggcggcggcg gtgccg                                36

<210> SEQ ID NO 252
<211> LENGTH: 36
<212> TYPE: DNA
<213> ORGANISM: Artificial Sequence
<220> FEATURE:
<223> OTHER INFORMATION: cDNA Sequence of aMTD24

<400> SEQUENCE: 252
attgcgctgg cggcgccggc gctgattgtg gcgccg                                36

<210> SEQ ID NO 253
<211> LENGTH: 36
<212> TYPE: DNA
<213> ORGANISM: Artificial Sequence
<220> FEATURE:
<223> OTHER INFORMATION: cDNA Sequence of aMTD25

<400> SEQUENCE: 253
attgtggcgg tggcgccggc gctggtggcg ctgccg                                36

<210> SEQ ID NO 254
<211> LENGTH: 36
<212> TYPE: DNA
<213> ORGANISM: Artificial Sequence
<220> FEATURE:
<223> OTHER INFORMATION: Polynucleotide Sequence of aMTD42

<400> SEQUENCE: 254
gtggcggcgc tgccggtggt ggcggtggtg gcgccg                                36

<210> SEQ ID NO 255
<211> LENGTH: 36
<212> TYPE: DNA
<213> ORGANISM: Artificial Sequence
<220> FEATURE:
<223> OTHER INFORMATION: cDNA Sequence of aMTD43
```

```
<400> SEQUENCE: 255
ctgctggcgg cgccgctggt ggtggcggcg gtgccg                                36

<210> SEQ ID NO 256
<211> LENGTH: 36
<212> TYPE: DNA
<213> ORGANISM: Artificial Sequence
<220> FEATURE:
<223> OTHER INFORMATION: cDNA Sequence of aMTD44

<400> SEQUENCE: 256
gcgctggcgg tgccggtggc gctgctggtg gcgccg                                36

<210> SEQ ID NO 257
<211> LENGTH: 36
<212> TYPE: DNA
<213> ORGANISM: Artificial Sequence
<220> FEATURE:
<223> OTHER INFORMATION: cDNA Sequence of aMTD61

<400> SEQUENCE: 257
gtggcggcgc tgccggtgct gctggcggcg ctgccg                                36

<210> SEQ ID NO 258
<211> LENGTH: 36
<212> TYPE: DNA
<213> ORGANISM: Artificial Sequence
<220> FEATURE:
<223> OTHER INFORMATION: cDNA Sequence of aMTD62

<400> SEQUENCE: 258
gtggcgctgc tggcgccggt ggcgctggcg gtgccg                                36

<210> SEQ ID NO 259
<211> LENGTH: 36
<212> TYPE: DNA
<213> ORGANISM: Artificial Sequence
<220> FEATURE:
<223> OTHER INFORMATION: cDNA Sequence of aMTD63

<400> SEQUENCE: 259
gcggcgctgc tggtgccggc gctggtggcg gtgccg                                36

<210> SEQ ID NO 260
<211> LENGTH: 36
<212> TYPE: DNA
<213> ORGANISM: Artificial Sequence
<220> FEATURE:
<223> OTHER INFORMATION: cDNA Sequence of aMTD64

<400> SEQUENCE: 260
gcgattgtgg cgctgccggt ggcggtgctg gcgccg                                36

<210> SEQ ID NO 261
<211> LENGTH: 36
<212> TYPE: DNA
<213> ORGANISM: Artificial Sequence
<220> FEATURE:
<223> OTHER INFORMATION: cDNA Sequence of aMTD65

<400> SEQUENCE: 261
attgcgattg tggcgccggt ggtggcgctg gcgccg                                36

<210> SEQ ID NO 262
<211> LENGTH: 36
```

```
<212> TYPE: DNA
<213> ORGANISM: Artificial Sequence
<220> FEATURE:
<223> OTHER INFORMATION: cDNA Sequence of aMTD81

<400> SEQUENCE: 262
gcggcgctgc tgccggcgct ggcggcgctg ctgccg                              36

<210> SEQ ID NO 263
<211> LENGTH: 36
<212> TYPE: DNA
<213> ORGANISM: Artificial Sequence
<220> FEATURE:
<223> OTHER INFORMATION: cDNA Sequence of aMTD82

<400> SEQUENCE: 263
gcggtggtgc tggcgccggt ggcggcggtg ctgccg                              36

<210> SEQ ID NO 264
<211> LENGTH: 36
<212> TYPE: DNA
<213> ORGANISM: Artificial Sequence
<220> FEATURE:
<223> OTHER INFORMATION: cDNA Sequence of aMTD83

<400> SEQUENCE: 264
ctggcggtgg cggcgccgct ggcgctggcg ctgccg                              36

<210> SEQ ID NO 265
<211> LENGTH: 36
<212> TYPE: DNA
<213> ORGANISM: Artificial Sequence
<220> FEATURE:
<223> OTHER INFORMATION: cDNA Sequence of aMTD84

<400> SEQUENCE: 265
gcggcggtgg cggcgccgct gctgctggcg ctgccg                              36

<210> SEQ ID NO 266
<211> LENGTH: 36
<212> TYPE: DNA
<213> ORGANISM: Artificial Sequence
<220> FEATURE:
<223> OTHER INFORMATION: cDNA Sequence of aMTD85

<400> SEQUENCE: 266
ctgctggtgc tgccggcggc ggcgctggcg gcgccg                              36

<210> SEQ ID NO 267
<211> LENGTH: 36
<212> TYPE: DNA
<213> ORGANISM: Artificial Sequence
<220> FEATURE:
<223> OTHER INFORMATION: cDNA Sequence of aMTD101

<400> SEQUENCE: 267
ctggtggcgg tggcgccggt ggcggcggtg ctgccg                              36

<210> SEQ ID NO 268
<211> LENGTH: 36
<212> TYPE: DNA
<213> ORGANISM: Artificial Sequence
<220> FEATURE:
<223> OTHER INFORMATION: cDNA Sequence of aMTD102

<400> SEQUENCE: 268
```
ctggcgctgg cgccggcggc gctggcgctg ctgccg         36

<210> SEQ ID NO 269
<211> LENGTH: 36
<212> TYPE: DNA
<213> ORGANISM: Artificial Sequence
<220> FEATURE:
<223> OTHER INFORMATION: cDNA Sequence of aMTD103

<400> SEQUENCE: 269
gcgctgattg cggcgccgat tctggcgctg gcgccg         36

<210> SEQ ID NO 270
<211> LENGTH: 36
<212> TYPE: DNA
<213> ORGANISM: Artificial Sequence
<220> FEATURE:
<223> OTHER INFORMATION: cDNA Sequence of aMTD104

<400> SEQUENCE: 270
gcggtggtgg cggcgccgct ggtgctggcg ctgccg         36

<210> SEQ ID NO 271
<211> LENGTH: 36
<212> TYPE: DNA
<213> ORGANISM: Artificial Sequence
<220> FEATURE:
<223> OTHER INFORMATION: cDNA Sequence of aMTD105

<400> SEQUENCE: 271
ctgctggcgc tggcgccggc ggcgctgctg gcgccg         36

<210> SEQ ID NO 272
<211> LENGTH: 36
<212> TYPE: DNA
<213> ORGANISM: Artificial Sequence
<220> FEATURE:
<223> OTHER INFORMATION: cDNA Sequence of aMTD121

<400> SEQUENCE: 272
gcgattgtgg cgctgccggc gctggcgctg gcgccg         36

<210> SEQ ID NO 273
<211> LENGTH: 36
<212> TYPE: DNA
<213> ORGANISM: Artificial Sequence
<220> FEATURE:
<223> OTHER INFORMATION: cDNA Sequence of aMTD123

<400> SEQUENCE: 273
gcggcgatta ttgtgccggc ggcgctgctg gcgccg         36

<210> SEQ ID NO 274
<211> LENGTH: 36
<212> TYPE: DNA
<213> ORGANISM: Artificial Sequence
<220> FEATURE:
<223> OTHER INFORMATION: cDNA Sequence of aMTD124

<400> SEQUENCE: 274
attgcggtgg cgctgccggc gctgattgcg gcgccg         36

<210> SEQ ID NO 275
<211> LENGTH: 36
<212> TYPE: DNA
<213> ORGANISM: Artificial Sequence

```
<220> FEATURE:
<223> OTHER INFORMATION: Polynucleotide Sequence of aMTD141

<400> SEQUENCE: 275
gcggtgattg tgctgccggc gctggcggtg gcgccg                                36

<210> SEQ ID NO 276
<211> LENGTH: 36
<212> TYPE: DNA
<213> ORGANISM: Artificial Sequence
<220> FEATURE:
<223> OTHER INFORMATION: Polynucleotide Sequence of aMTD143

<400> SEQUENCE: 276
gcggtgctgg cggtgccggc ggtgctggtg gcgccg                                36

<210> SEQ ID NO 277
<211> LENGTH: 36
<212> TYPE: DNA
<213> ORGANISM: Artificial Sequence
<220> FEATURE:
<223> OTHER INFORMATION: Polynucleotide Sequence of aMTD144

<400> SEQUENCE: 277
gtgctggcga ttgtgccggc ggtggcgctg gcgccg                                36

<210> SEQ ID NO 278
<211> LENGTH: 36
<212> TYPE: DNA
<213> ORGANISM: Artificial Sequence
<220> FEATURE:
<223> OTHER INFORMATION: Polynucleotide Sequence of aMTD145

<400> SEQUENCE: 278
ctgctggcgg tggtgccggc ggtggcgctg gcgccg                                36

<210> SEQ ID NO 279
<211> LENGTH: 36
<212> TYPE: DNA
<213> ORGANISM: Artificial Sequence
<220> FEATURE:
<223> OTHER INFORMATION: cDNA Sequence of aMTD161

<400> SEQUENCE: 279
gcggtgattg cgctgccggc gctgattgcg gcgccg                                36

<210> SEQ ID NO 280
<211> LENGTH: 36
<212> TYPE: DNA
<213> ORGANISM: Artificial Sequence
<220> FEATURE:
<223> OTHER INFORMATION: cDNA Sequence of aMTD162

<400> SEQUENCE: 280
gcggtggtgg cgctgccggc ggcgctgatt gtgccg                                36

<210> SEQ ID NO 281
<211> LENGTH: 36
<212> TYPE: DNA
<213> ORGANISM: Artificial Sequence
<220> FEATURE:
<223> OTHER INFORMATION: cDNA Sequence of aMTD163

<400> SEQUENCE: 281
ctggcgctgg tgctgccggc ggcgctggcg gcgccg                                36
```

<210> SEQ ID NO 282
<211> LENGTH: 36
<212> TYPE: DNA
<213> ORGANISM: Artificial Sequence
<220> FEATURE:
<223> OTHER INFORMATION: cDNA Sequence of aMTD164

<400> SEQUENCE: 282
ctggcggcgg tgctgccggc gctgctggcg gcgccg    36

<210> SEQ ID NO 283
<211> LENGTH: 36
<212> TYPE: DNA
<213> ORGANISM: Artificial Sequence
<220> FEATURE:
<223> OTHER INFORMATION: cDNA Sequence of aMTD165

<400> SEQUENCE: 283
gcgctggcgg tgccggtggc gctggcgatt gtgccg    36

<210> SEQ ID NO 284
<211> LENGTH: 36
<212> TYPE: DNA
<213> ORGANISM: Artificial Sequence
<220> FEATURE:
<223> OTHER INFORMATION: cDNA Sequence of aMTD182

<400> SEQUENCE: 284
gcgctgattg cgccggtggt ggcgctggtg gcgccg    36

<210> SEQ ID NO 285
<211> LENGTH: 36
<212> TYPE: DNA
<213> ORGANISM: Artificial Sequence
<220> FEATURE:
<223> OTHER INFORMATION: cDNA Sequence of aMTD183

<400> SEQUENCE: 285
ctgctggcgg cgccggtggt gattgcgctg gcgccg    36

<210> SEQ ID NO 286
<211> LENGTH: 36
<212> TYPE: DNA
<213> ORGANISM: Artificial Sequence
<220> FEATURE:
<223> OTHER INFORMATION: cDNA Sequence of aMTD184

<400> SEQUENCE: 286
ctggcggcga ttgtgccggc gattattgcg gtgccg    36

<210> SEQ ID NO 287
<211> LENGTH: 36
<212> TYPE: DNA
<213> ORGANISM: Artificial Sequence
<220> FEATURE:
<223> OTHER INFORMATION: cDNA Sequence of aMTD185

<400> SEQUENCE: 287
gcggcgctgg tgctgccgct gattattgcg gcgccg    36

<210> SEQ ID NO 288
<211> LENGTH: 36
<212> TYPE: DNA
<213> ORGANISM: Artificial Sequence
<220> FEATURE:
<223> OTHER INFORMATION: cDNA Sequence of aMTD201

<400> SEQUENCE: 288
ctggcgctgg cggtgccggc gctggcggcg ctgccg                36

<210> SEQ ID NO 289
<211> LENGTH: 36
<212> TYPE: DNA
<213> ORGANISM: Artificial Sequence
<220> FEATURE:
<223> OTHER INFORMATION: cDNA Sequence of aMTD204

<400> SEQUENCE: 289
ctgattgcgg cgctgccggc ggtggcggcg ctgccg                36

<210> SEQ ID NO 290
<211> LENGTH: 36
<212> TYPE: DNA
<213> ORGANISM: Artificial Sequence
<220> FEATURE:
<223> OTHER INFORMATION: cDNA Sequence of aMTD205

<400> SEQUENCE: 290
gcgctggcgc tggtgccggc gattgcggcg ctgccg                36

<210> SEQ ID NO 291
<211> LENGTH: 36
<212> TYPE: DNA
<213> ORGANISM: Artificial Sequence
<220> FEATURE:
<223> OTHER INFORMATION: cDNA Sequence of aMTD221

<400> SEQUENCE: 291
gcggcgattc tggcgccgat tgtggcgctg gcgccg                36

<210> SEQ ID NO 292
<211> LENGTH: 36
<212> TYPE: DNA
<213> ORGANISM: Artificial Sequence
<220> FEATURE:
<223> OTHER INFORMATION: cDNA Sequence of aMTD222

<400> SEQUENCE: 292
gcgctgctga ttgcgccggc ggcggtgatt gcgccg                36

<210> SEQ ID NO 293
<211> LENGTH: 36
<212> TYPE: DNA
<213> ORGANISM: Artificial Sequence
<220> FEATURE:
<223> OTHER INFORMATION: cDNA Sequence of aMTD223

<400> SEQUENCE: 293
gcgattctgg cggtgccgat tgcggtggtg gcgccg                36

<210> SEQ ID NO 294
<211> LENGTH: 36
<212> TYPE: DNA
<213> ORGANISM: Artificial Sequence
<220> FEATURE:
<223> OTHER INFORMATION: cDNA Sequence of aMTD224

<400> SEQUENCE: 294
attctggcgg cggtgccgat tgcgctggcg gcgccg                36

<210> SEQ ID NO 295

```
<211> LENGTH: 36
<212> TYPE: DNA
<213> ORGANISM: Artificial Sequence
<220> FEATURE:
<223> OTHER INFORMATION: cDNA Sequence of aMTD225

<400> SEQUENCE: 295
gtggcggcgc tgctgccggc ggcggcggtg ctgccg                                 36

<210> SEQ ID NO 296
<211> LENGTH: 36
<212> TYPE: DNA
<213> ORGANISM: Artificial Sequence
<220> FEATURE:
<223> OTHER INFORMATION: cDNA Sequence of aMTD241

<400> SEQUENCE: 296
gcggcggcgg tggtgccggt gctgctggtg gcgccg                                 36

<210> SEQ ID NO 297
<211> LENGTH: 36
<212> TYPE: DNA
<213> ORGANISM: Artificial Sequence
<220> FEATURE:
<223> OTHER INFORMATION: cDNA Sequence of aMTD242

<400> SEQUENCE: 297
gcggcgctgc tggtgccggc gctggtggcg gcgccg                                 36

<210> SEQ ID NO 298
<211> LENGTH: 36
<212> TYPE: DNA
<213> ORGANISM: Artificial Sequence
<220> FEATURE:
<223> OTHER INFORMATION: cDNA Sequence of aMTD243

<400> SEQUENCE: 298
gcggcggtgc tgctgccggt ggcgctggcg gcgccg                                 36

<210> SEQ ID NO 299
<211> LENGTH: 36
<212> TYPE: DNA
<213> ORGANISM: Artificial Sequence
<220> FEATURE:
<223> OTHER INFORMATION: cDNA Sequence of aMTD245

<400> SEQUENCE: 299
gcggcggcgc tggcgccggt gctggcgctg gtgccg                                 36

<210> SEQ ID NO 300
<211> LENGTH: 36
<212> TYPE: DNA
<213> ORGANISM: Artificial Sequence
<220> FEATURE:
<223> OTHER INFORMATION: cDNA Sequence of aMTD261

<400> SEQUENCE: 300
ctggtgctgg tgccgctgct ggcggcggcg gcgccg                                 36

<210> SEQ ID NO 301
<211> LENGTH: 36
<212> TYPE: DNA
<213> ORGANISM: Artificial Sequence
<220> FEATURE:
<223> OTHER INFORMATION: cDNA Sequence of aMTD262

<400> SEQUENCE: 301
```

```
gcgctgattg cggtgccggc gattattgtg gcgccg                            36

<210> SEQ ID NO 302
<211> LENGTH: 36
<212> TYPE: DNA
<213> ORGANISM: Artificial Sequence
<220> FEATURE:
<223> OTHER INFORMATION: cDNA Sequence of aMTD263

<400> SEQUENCE: 302
gcgctggcgg tgattccggc ggcggcgatt ctgccg                            36

<210> SEQ ID NO 303
<211> LENGTH: 36
<212> TYPE: DNA
<213> ORGANISM: Artificial Sequence
<220> FEATURE:
<223> OTHER INFORMATION: cDNA Sequence of aMTD264

<400> SEQUENCE: 303
ctggcggcgg cgccggtggt gattgtgatt gcgccg                            36

<210> SEQ ID NO 304
<211> LENGTH: 36
<212> TYPE: DNA
<213> ORGANISM: Artificial Sequence
<220> FEATURE:
<223> OTHER INFORMATION: cDNA Sequence of aMTD265

<400> SEQUENCE: 304
gtgctggcga ttgcgccgct gctggcggcg gtgccg                            36

<210> SEQ ID NO 305
<211> LENGTH: 36
<212> TYPE: DNA
<213> ORGANISM: Artificial Sequence
<220> FEATURE:
<223> OTHER INFORMATION: cDNA Sequence of aMTD281

<400> SEQUENCE: 305
gcgctgattg tgctgccggc ggcggtggcg gtgccg                            36

<210> SEQ ID NO 306
<211> LENGTH: 36
<212> TYPE: DNA
<213> ORGANISM: Artificial Sequence
<220> FEATURE:
<223> OTHER INFORMATION: cDNA Sequence of aMTD282

<400> SEQUENCE: 306
gtgctggcgg tggcgccggc gctgattgtg gcgccg                            36

<210> SEQ ID NO 307
<211> LENGTH: 36
<212> TYPE: DNA
<213> ORGANISM: Artificial Sequence
<220> FEATURE:
<223> OTHER INFORMATION: cDNA Sequence of aMTD283

<400> SEQUENCE: 307
gcggcgctgc tggcgccggc gctgattgtg gcgccg                            36

<210> SEQ ID NO 308
<211> LENGTH: 36
<212> TYPE: DNA
```

<213> ORGANISM: Artificial Sequence
<220> FEATURE:
<223> OTHER INFORMATION: cDNA Sequence of aMTD284

<400> SEQUENCE: 308
gcgctgattg cgccggcggt ggcgctgatt gtgccg                              36

<210> SEQ ID NO 309
<211> LENGTH: 36
<212> TYPE: DNA
<213> ORGANISM: Artificial Sequence
<220> FEATURE:
<223> OTHER INFORMATION: cDNA Sequence of aMTD285

<400> SEQUENCE: 309
gcgattgtgc tgctgccggc ggcggtggtg gcgccg                              36

<210> SEQ ID NO 310
<211> LENGTH: 36
<212> TYPE: DNA
<213> ORGANISM: Artificial Sequence
<220> FEATURE:
<223> OTHER INFORMATION: cDNA Sequence of aMTD301

<400> SEQUENCE: 310
gtgattgcgg cgccggtgct ggcggtgctg gcgccg                              36

<210> SEQ ID NO 311
<211> LENGTH: 36
<212> TYPE: DNA
<213> ORGANISM: Artificial Sequence
<220> FEATURE:
<223> OTHER INFORMATION: cDNA Sequence of aMTD302

<400> SEQUENCE: 311
ctggcgctgg cgccggcgct ggcgctgctg gcgccg                              36

<210> SEQ ID NO 312
<211> LENGTH: 36
<212> TYPE: DNA
<213> ORGANISM: Artificial Sequence
<220> FEATURE:
<223> OTHER INFORMATION: cDNA Sequence of aMTD304

<400> SEQUENCE: 312
gcgattattc tggcgccgat tgcggcgatt gcgccg                              36

<210> SEQ ID NO 313
<211> LENGTH: 36
<212> TYPE: DNA
<213> ORGANISM: Artificial Sequence
<220> FEATURE:
<223> OTHER INFORMATION: cDNA Sequence of aMTD305

<400> SEQUENCE: 313
attgcgctgg cggcgccgat tctgctggcg gcgccg                              36

<210> SEQ ID NO 314
<211> LENGTH: 36
<212> TYPE: DNA
<213> ORGANISM: Artificial Sequence
<220> FEATURE:
<223> OTHER INFORMATION: cDNA Sequence of aMTD321

<400> SEQUENCE: 314
attgtggcgg tggcgctgcc ggcgctggcg gtgccg                              36

<210> SEQ ID NO 315
<211> LENGTH: 36
<212> TYPE: DNA
<213> ORGANISM: Artificial Sequence
<220> FEATURE:
<223> OTHER INFORMATION: cDNA Sequence of aMTD322

<400> SEQUENCE: 315
gtggtggcga ttgtgctgcc ggcgctggcg gcgccg       36

<210> SEQ ID NO 316
<211> LENGTH: 36
<212> TYPE: DNA
<213> ORGANISM: Artificial Sequence
<220> FEATURE:
<223> OTHER INFORMATION: cDNA Sequence of aMTD323

<400> SEQUENCE: 316
attgtggcgg tggcgctgcc ggtggcgctg gcgccg       36

<210> SEQ ID NO 317
<211> LENGTH: 36
<212> TYPE: DNA
<213> ORGANISM: Artificial Sequence
<220> FEATURE:
<223> OTHER INFORMATION: cDNA Sequence of aMTD324

<400> SEQUENCE: 317
attgtggcgg tggcgctgcc ggcggcgctg gtgccg       36

<210> SEQ ID NO 318
<211> LENGTH: 36
<212> TYPE: DNA
<213> ORGANISM: Artificial Sequence
<220> FEATURE:
<223> OTHER INFORMATION: cDNA Sequence of aMTD325

<400> SEQUENCE: 318
attgtggcgg tggcgctgcc ggcggtggcg ctgccg       36

<210> SEQ ID NO 319
<211> LENGTH: 36
<212> TYPE: DNA
<213> ORGANISM: Artificial Sequence
<220> FEATURE:
<223> OTHER INFORMATION: cDNA Sequence of aMTD341

<400> SEQUENCE: 319
attgtggcgg tggcgctgcc ggcggtgctg gcgccg       36

<210> SEQ ID NO 320
<211> LENGTH: 36
<212> TYPE: DNA
<213> ORGANISM: Artificial Sequence
<220> FEATURE:
<223> OTHER INFORMATION: cDNA Sequence of aMTD342

<400> SEQUENCE: 320
gtgattgtgg cgctggcgcc ggcggtgctg gcgccg       36

<210> SEQ ID NO 321
<211> LENGTH: 36
<212> TYPE: DNA
<213> ORGANISM: Artificial Sequence
<220> FEATURE:

<223> OTHER INFORMATION: cDNA Sequence of aMTD343

<400> SEQUENCE: 321
attgtggcgg tggcgctgcc ggcgctggtg gcgccg                                    36

<210> SEQ ID NO 322
<211> LENGTH: 36
<212> TYPE: DNA
<213> ORGANISM: Artificial Sequence
<220> FEATURE:
<223> OTHER INFORMATION: cDNA Sequence of aMTD345

<400> SEQUENCE: 322
gcgctgctga ttgtggcgcc ggtggcggtg gcgccg                                    36

<210> SEQ ID NO 323
<211> LENGTH: 36
<212> TYPE: DNA
<213> ORGANISM: Artificial Sequence
<220> FEATURE:
<223> OTHER INFORMATION: cDNA Sequence of aMTD361

<400> SEQUENCE: 323
gcggtggtga ttgtggcgcc ggcggtgatt gcgccg                                    36

<210> SEQ ID NO 324
<211> LENGTH: 36
<212> TYPE: DNA
<213> ORGANISM: Artificial Sequence
<220> FEATURE:
<223> OTHER INFORMATION: cDNA Sequence of aMTD363

<400> SEQUENCE: 324
gcggtgctgg cggtggcgcc ggcgctgatt gtgccg                                    36

<210> SEQ ID NO 325
<211> LENGTH: 36
<212> TYPE: DNA
<213> ORGANISM: Artificial Sequence
<220> FEATURE:
<223> OTHER INFORMATION: cDNA Sequence of aMTD364

<400> SEQUENCE: 325
ctggtggcgg cggtggcgcc ggcgctgatt gtgccg                                    36

<210> SEQ ID NO 326
<211> LENGTH: 36
<212> TYPE: DNA
<213> ORGANISM: Artificial Sequence
<220> FEATURE:
<223> OTHER INFORMATION: cDNA Sequence of aMTD365

<400> SEQUENCE: 326
gcggtgattg tggtggcgcc ggcgctgctg gcgccg                                    36

<210> SEQ ID NO 327
<211> LENGTH: 36
<212> TYPE: DNA
<213> ORGANISM: Artificial Sequence
<220> FEATURE:
<223> OTHER INFORMATION: cDNA Sequence of aMTD381

<400> SEQUENCE: 327
gtggtggcga ttgtgctgcc ggcggtggcg gcgccg                                    36

```
<210> SEQ ID NO 328
<211> LENGTH: 36
<212> TYPE: DNA
<213> ORGANISM: Artificial Sequence
<220> FEATURE:
<223> OTHER INFORMATION: cDNA Sequence of aMTD382

<400> SEQUENCE: 328
gcggcggcgc tggtgattcc ggcgattctg gcgccg                                   36

<210> SEQ ID NO 329
<211> LENGTH: 36
<212> TYPE: DNA
<213> ORGANISM: Artificial Sequence
<220> FEATURE:
<223> OTHER INFORMATION: cDNA Sequence of aMTD383

<400> SEQUENCE: 329
gtgattgtgg cgctggcgcc ggcgctgctg gcgccg                                   36

<210> SEQ ID NO 330
<211> LENGTH: 36
<212> TYPE: DNA
<213> ORGANISM: Artificial Sequence
<220> FEATURE:
<223> OTHER INFORMATION: cDNA Sequence of aMTD384

<400> SEQUENCE: 330
gtgattgtgg cgattgcgcc ggcgctgctg gcgccg                                   36

<210> SEQ ID NO 331
<211> LENGTH: 36
<212> TYPE: DNA
<213> ORGANISM: Artificial Sequence
<220> FEATURE:
<223> OTHER INFORMATION: cDNA Sequence of aMTD385

<400> SEQUENCE: 331
attgtggcga ttgcggtgcc ggcgctggtg gcgccg                                   36

<210> SEQ ID NO 332
<211> LENGTH: 36
<212> TYPE: DNA
<213> ORGANISM: Artificial Sequence
<220> FEATURE:
<223> OTHER INFORMATION: cDNA Sequence of aMTD401

<400> SEQUENCE: 332
gcggcgctgg cggtgattcc ggcggcgatt ctgccg                                   36

<210> SEQ ID NO 333
<211> LENGTH: 36
<212> TYPE: DNA
<213> ORGANISM: Artificial Sequence
<220> FEATURE:
<223> OTHER INFORMATION: Polynucleotide of aMTD402

<400> SEQUENCE: 333
gcgctggcgg cggtgattcc ggcggcgatt ctgccg                                   36

<210> SEQ ID NO 334
<211> LENGTH: 36
<212> TYPE: DNA
<213> ORGANISM: Artificial Sequence
<220> FEATURE:
<223> OTHER INFORMATION: cDNA Sequence of aMTD403
```

<400> SEQUENCE: 334
gcggcggcgc tggtgattcc ggcggcgatt ctgccg        36

<210> SEQ ID NO 335
<211> LENGTH: 36
<212> TYPE: DNA
<213> ORGANISM: Artificial Sequence
<220> FEATURE:
<223> OTHER INFORMATION: cDNA Sequence of aMTD404

<400> SEQUENCE: 335
ctggcggcgg cggtgattcc ggcggcgatt ctgccg        36

<210> SEQ ID NO 336
<211> LENGTH: 36
<212> TYPE: DNA
<213> ORGANISM: Artificial Sequence
<220> FEATURE:
<223> OTHER INFORMATION: cDNA Sequence of aMTD405

<400> SEQUENCE: 336
ctggcggcgg cggtgattcc ggtggcgatt ctgccg        36

<210> SEQ ID NO 337
<211> LENGTH: 36
<212> TYPE: DNA
<213> ORGANISM: Artificial Sequence
<220> FEATURE:
<223> OTHER INFORMATION: cDNA Sequence of aMTD421

<400> SEQUENCE: 337
gcggcgattc tggcggcgcc gctgattgcg gtgccg        36

<210> SEQ ID NO 338
<211> LENGTH: 36
<212> TYPE: DNA
<213> ORGANISM: Artificial Sequence
<220> FEATURE:
<223> OTHER INFORMATION: cDNA Sequence of aMTD422

<400> SEQUENCE: 338
gtggtggcga ttctggcgcc gctgctggcg gcgccg        36

<210> SEQ ID NO 339
<211> LENGTH: 36
<212> TYPE: DNA
<213> ORGANISM: Artificial Sequence
<220> FEATURE:
<223> OTHER INFORMATION: cDNA Sequence of aMTD424

<400> SEQUENCE: 339
gcggtggtgg tggcggcgcc ggtgctggcg ctgccg        36

<210> SEQ ID NO 340
<211> LENGTH: 36
<212> TYPE: DNA
<213> ORGANISM: Artificial Sequence
<220> FEATURE:
<223> OTHER INFORMATION: cDNA Sequence of aMTD425

<400> SEQUENCE: 340
gcggtggtgg cgattgcgcc ggtgctggcg ctgccg        36

<210> SEQ ID NO 341
<211> LENGTH: 36

```
<212> TYPE: DNA
<213> ORGANISM: Artificial Sequence
<220> FEATURE:
<223> OTHER INFORMATION: cDNA Sequence of aMTD442

<400> SEQUENCE: 341
gcgctggcgg cgctggtgcc ggcggtgctg gtgccg                                36

<210> SEQ ID NO 342
<211> LENGTH: 36
<212> TYPE: DNA
<213> ORGANISM: Artificial Sequence
<220> FEATURE:
<223> OTHER INFORMATION: cDNA Sequence of aMTD443

<400> SEQUENCE: 342
gcgctggcgg cgctggtgcc ggtggcgctg gtgccg                                36

<210> SEQ ID NO 343
<211> LENGTH: 36
<212> TYPE: DNA
<213> ORGANISM: Artificial Sequence
<220> FEATURE:
<223> OTHER INFORMATION: cDNA Sequence of aMTD444

<400> SEQUENCE: 343
ctggcggcgg cgctggtgcc ggtggcgctg gtgccg                                36

<210> SEQ ID NO 344
<211> LENGTH: 36
<212> TYPE: DNA
<213> ORGANISM: Artificial Sequence
<220> FEATURE:
<223> OTHER INFORMATION: cDNA Sequence of aMTD445

<400> SEQUENCE: 344
gcgctggcgg cgctggtgcc ggcgctggtg gtgccg                                36

<210> SEQ ID NO 345
<211> LENGTH: 36
<212> TYPE: DNA
<213> ORGANISM: Artificial Sequence
<220> FEATURE:
<223> OTHER INFORMATION: cDNA Sequence of aMTD461

<400> SEQUENCE: 345
attgcggcgg tgattgtgcc ggcggtggcg ctgccg                                36

<210> SEQ ID NO 346
<211> LENGTH: 36
<212> TYPE: DNA
<213> ORGANISM: Artificial Sequence
<220> FEATURE:
<223> OTHER INFORMATION: cDNA Sequence of aMTD462

<400> SEQUENCE: 346
attgcggcgg tgctggtgcc ggcggtggcg ctgccg                                36

<210> SEQ ID NO 347
<211> LENGTH: 36
<212> TYPE: DNA
<213> ORGANISM: Artificial Sequence
<220> FEATURE:
<223> OTHER INFORMATION: cDNA Sequence of aMTD463

<400> SEQUENCE: 347
```
gcggtggcga ttctggtgcc gctgctggcg gcgccg            36

<210> SEQ ID NO 348
<211> LENGTH: 36
<212> TYPE: DNA
<213> ORGANISM: Artificial Sequence
<220> FEATURE:
<223> OTHER INFORMATION: cDNA Sequence of aMTD464

<400> SEQUENCE: 348
gcggtggtga ttctggtgcc gctggcggcg gcgccg            36

<210> SEQ ID NO 349
<211> LENGTH: 36
<212> TYPE: DNA
<213> ORGANISM: Artificial Sequence
<220> FEATURE:
<223> OTHER INFORMATION: cDNA Sequence of aMTD465

<400> SEQUENCE: 349
attgcggcgg tgattgtgcc ggtggcggcg ctgccg            36

<210> SEQ ID NO 350
<211> LENGTH: 36
<212> TYPE: DNA
<213> ORGANISM: Artificial Sequence
<220> FEATURE:
<223> OTHER INFORMATION: cDNA Sequence of aMTD481

<400> SEQUENCE: 350
gcgattgcga ttgcgattgt gccggtggcg ctgccg            36

<210> SEQ ID NO 351
<211> LENGTH: 36
<212> TYPE: DNA
<213> ORGANISM: Artificial Sequence
<220> FEATURE:
<223> OTHER INFORMATION: cDNA Sequence of aMTD482

<400> SEQUENCE: 351
attctggcgg tggcggcgat tccggtggcg gtgccg            36

<210> SEQ ID NO 352
<211> LENGTH: 36
<212> TYPE: DNA
<213> ORGANISM: Artificial Sequence
<220> FEATURE:
<223> OTHER INFORMATION: cDNA Sequence of aMTD483

<400> SEQUENCE: 352
attctggcgg cggcgattat tccggcggcg ctgccg            36

<210> SEQ ID NO 353
<211> LENGTH: 36
<212> TYPE: DNA
<213> ORGANISM: Artificial Sequence
<220> FEATURE:
<223> OTHER INFORMATION: cDNA Sequence of aMTD484

<400> SEQUENCE: 353
ctggcggtgg tgctggcggc gccggcgatt gtgccg            36

<210> SEQ ID NO 354
<211> LENGTH: 36
<212> TYPE: DNA
<213> ORGANISM: Artificial Sequence

```
<220> FEATURE:
<223> OTHER INFORMATION: cDNA Sequence of aMTD485

<400> SEQUENCE: 354
gcgattctgg cggcgattgt gccgctggcg gtgccg                              36

<210> SEQ ID NO 355
<211> LENGTH: 36
<212> TYPE: DNA
<213> ORGANISM: Artificial Sequence
<220> FEATURE:
<223> OTHER INFORMATION: cDNA Sequence of aMTD501

<400> SEQUENCE: 355
gtgattgtgg cgctggcggt gccggcgctg gcgccg                              36

<210> SEQ ID NO 356
<211> LENGTH: 36
<212> TYPE: DNA
<213> ORGANISM: Artificial Sequence
<220> FEATURE:
<223> OTHER INFORMATION: cDNA Sequence of aMTD502

<400> SEQUENCE: 356
gcgattgtgg cgctggcggt gccggtgctg gcgccg                              36

<210> SEQ ID NO 357
<211> LENGTH: 36
<212> TYPE: DNA
<213> ORGANISM: Artificial Sequence
<220> FEATURE:
<223> OTHER INFORMATION: cDNA Sequence of aMTD503

<400> SEQUENCE: 357
gcggcgatta ttattgtgct gccggcggcg ctgccg                              36

<210> SEQ ID NO 358
<211> LENGTH: 36
<212> TYPE: DNA
<213> ORGANISM: Artificial Sequence
<220> FEATURE:
<223> OTHER INFORMATION: cDNA Sequence of aMTD504

<400> SEQUENCE: 358
ctgattgtgg cgctggcggt gccggcgctg gcgccg                              36

<210> SEQ ID NO 359
<211> LENGTH: 36
<212> TYPE: DNA
<213> ORGANISM: Artificial Sequence
<220> FEATURE:
<223> OTHER INFORMATION: cDNA Sequence of aMTD505

<400> SEQUENCE: 359
gcgattatta ttgtgattgc gccggcggcg gcgccg                              36

<210> SEQ ID NO 360
<211> LENGTH: 36
<212> TYPE: DNA
<213> ORGANISM: Artificial Sequence
<220> FEATURE:
<223> OTHER INFORMATION: cDNA Sequence of aMTD521

<400> SEQUENCE: 360
ctggcggcgc tgattgtggt gccggcggtg gcgccg                              36
```

<210> SEQ ID NO 361
<211> LENGTH: 36
<212> TYPE: DNA
<213> ORGANISM: Artificial Sequence
<220> FEATURE:
<223> OTHER INFORMATION: cDNA Sequence of aMTD522

<400> SEQUENCE: 361
gcgctgctgg tgattgcggt gccggcggtg gcgccg                36

<210> SEQ ID NO 362
<211> LENGTH: 36
<212> TYPE: DNA
<213> ORGANISM: Artificial Sequence
<220> FEATURE:
<223> OTHER INFORMATION: cDNA Sequence of aMTD524

<400> SEQUENCE: 362
gcggtggcgc tgattgtggt gccggcgctg gcgccg                36

<210> SEQ ID NO 363
<211> LENGTH: 36
<212> TYPE: DNA
<213> ORGANISM: Artificial Sequence
<220> FEATURE:
<223> OTHER INFORMATION: cDNA Sequence of aMTD525

<400> SEQUENCE: 363
gcgctggcga ttgtggtggc gccggtggcg gtgccg                36

<210> SEQ ID NO 364
<211> LENGTH: 36
<212> TYPE: DNA
<213> ORGANISM: Artificial Sequence
<220> FEATURE:
<223> OTHER INFORMATION: cDNA Sequence of aMTD541

<400> SEQUENCE: 364
ctgctggcgc tgattattgc gccggcggcg gcgccg                36

<210> SEQ ID NO 365
<211> LENGTH: 36
<212> TYPE: DNA
<213> ORGANISM: Artificial Sequence
<220> FEATURE:
<223> OTHER INFORMATION: cDNA Sequence of aMTD542

<400> SEQUENCE: 365
gcgctggcgc tgattattgt gccggcggtg gcgccg                36

<210> SEQ ID NO 366
<211> LENGTH: 36
<212> TYPE: DNA
<213> ORGANISM: Artificial Sequence
<220> FEATURE:
<223> OTHER INFORMATION: cDNA Sequence of aMTD543

<400> SEQUENCE: 366
ctgctggcgg cgctgattgc gccggcggcg ctgccg                36

<210> SEQ ID NO 367
<211> LENGTH: 36
<212> TYPE: DNA
<213> ORGANISM: Artificial Sequence
<220> FEATURE:
<223> OTHER INFORMATION: cDNA Sequence of aMTD544

```
<400> SEQUENCE: 367
attgtggcgc tgattgtggc gccggcggcg gtgccg                              36

<210> SEQ ID NO 368
<211> LENGTH: 36
<212> TYPE: DNA
<213> ORGANISM: Artificial Sequence
<220> FEATURE:
<223> OTHER INFORMATION: cDNA Sequence of aMTD545

<400> SEQUENCE: 368
gtggtgctgg tgctggcggc gccggcggcg gtgccg                              36

<210> SEQ ID NO 369
<211> LENGTH: 36
<212> TYPE: DNA
<213> ORGANISM: Artificial Sequence
<220> FEATURE:
<223> OTHER INFORMATION: cDNA Sequence of aMTD561

<400> SEQUENCE: 369
gcggcggtgg cgattgtgct gccggcggtg gtgccg                              36

<210> SEQ ID NO 370
<211> LENGTH: 36
<212> TYPE: DNA
<213> ORGANISM: Artificial Sequence
<220> FEATURE:
<223> OTHER INFORMATION: cDNA Sequence of aMTD562

<400> SEQUENCE: 370
gcgctgattg cggcgattgt gccggcgctg gtgccg                              36

<210> SEQ ID NO 371
<211> LENGTH: 36
<212> TYPE: DNA
<213> ORGANISM: Artificial Sequence
<220> FEATURE:
<223> OTHER INFORMATION: cDNA Sequence of aMTD563

<400> SEQUENCE: 371
gcgctggcgg tgattgtggt gccggcgctg gcgccg                              36

<210> SEQ ID NO 372
<211> LENGTH: 36
<212> TYPE: DNA
<213> ORGANISM: Artificial Sequence
<220> FEATURE:
<223> OTHER INFORMATION: cDNA Sequence of aMTD564

<400> SEQUENCE: 372
gtggcgattg cgctgattgt gccggcgctg gcgccg                              36

<210> SEQ ID NO 373
<211> LENGTH: 36
<212> TYPE: DNA
<213> ORGANISM: Artificial Sequence
<220> FEATURE:
<223> OTHER INFORMATION: cDNA Sequence of aMTD565

<400> SEQUENCE: 373
gtggcgattg tgctggtggc gccggcggtg gcgccg                              36

<210> SEQ ID NO 374
```

```
<211> LENGTH: 36
<212> TYPE: DNA
<213> ORGANISM: Artificial Sequence
<220> FEATURE:
<223> OTHER INFORMATION: cDNA Sequence of aMTD582

<400> SEQUENCE: 374
gtggcggtgg cgctgattgt gccggcgctg gcgccg                                  36

<210> SEQ ID NO 375
<211> LENGTH: 36
<212> TYPE: DNA
<213> ORGANISM: Artificial Sequence
<220> FEATURE:
<223> OTHER INFORMATION: cDNA Sequence of aMTD583

<400> SEQUENCE: 375
gcggtgattc tggcgctggc gccgattgtg gcgccg                                  36

<210> SEQ ID NO 376
<211> LENGTH: 36
<212> TYPE: DNA
<213> ORGANISM: Artificial Sequence
<220> FEATURE:
<223> OTHER INFORMATION: cDNA Sequence of aMTD585

<400> SEQUENCE: 376
gcgctgattg tggcgattgc gccggcgctg gtgccg                                  36

<210> SEQ ID NO 377
<211> LENGTH: 36
<212> TYPE: DNA
<213> ORGANISM: Artificial Sequence
<220> FEATURE:
<223> OTHER INFORMATION: cDNA Sequence of aMTD601

<400> SEQUENCE: 377
gcggcgattc tgattgcggt gccgattgcg gcgccg                                  36

<210> SEQ ID NO 378
<211> LENGTH: 36
<212> TYPE: DNA
<213> ORGANISM: Artificial Sequence
<220> FEATURE:
<223> OTHER INFORMATION: cDNA Sequence of aMTD602

<400> SEQUENCE: 378
gtgattgtgg cgctggcggc gccggtgctg gcgccg                                  36

<210> SEQ ID NO 379
<211> LENGTH: 36
<212> TYPE: DNA
<213> ORGANISM: Artificial Sequence
<220> FEATURE:
<223> OTHER INFORMATION: cDNA Sequence of aMTD603

<400> SEQUENCE: 379
gtgctggtgg cgctggcggc gccggtgatt gcgccg                                  36

<210> SEQ ID NO 380
<211> LENGTH: 36
<212> TYPE: DNA
<213> ORGANISM: Artificial Sequence
<220> FEATURE:
<223> OTHER INFORMATION: cDNA Sequence of aMTD604

<400> SEQUENCE: 380
```

```
gtggcgctga ttgcggtggc gccggcggtg gtgccg                                    36

<210> SEQ ID NO 381
<211> LENGTH: 36
<212> TYPE: DNA
<213> ORGANISM: Artificial Sequence
<220> FEATURE:
<223> OTHER INFORMATION: cDNA Sequence of aMTD605

<400> SEQUENCE: 381
gtgattgcgg cggtgctggc gccggtggcg gtgccg                                    36

<210> SEQ ID NO 382
<211> LENGTH: 36
<212> TYPE: DNA
<213> ORGANISM: Artificial Sequence
<220> FEATURE:
<223> OTHER INFORMATION: cDNA Sequence of aMTD622

<400> SEQUENCE: 382
gcgctgattg tgctggcggc gccggtggcg gtgccg                                    36

<210> SEQ ID NO 383
<211> LENGTH: 36
<212> TYPE: DNA
<213> ORGANISM: Artificial Sequence
<220> FEATURE:
<223> OTHER INFORMATION: cDNA Sequence of aMTD623

<400> SEQUENCE: 383
gtggcggcgg cgattgcgct gccggcgatt gtgccg                                    36

<210> SEQ ID NO 384
<211> LENGTH: 36
<212> TYPE: DNA
<213> ORGANISM: Artificial Sequence
<220> FEATURE:
<223> OTHER INFORMATION: cDNA Sequence of aMTD625

<400> SEQUENCE: 384
attctggcgg cggcggcggc gccgctgatt gtgccg                                    36

<210> SEQ ID NO 385
<211> LENGTH: 36
<212> TYPE: DNA
<213> ORGANISM: Artificial Sequence
<220> FEATURE:
<223> OTHER INFORMATION: cDNA Sequence of aMTD643

<400> SEQUENCE: 385
ctggcgctgg tgctggcggc gccggcgatt gtgccg                                    36

<210> SEQ ID NO 386
<211> LENGTH: 36
<212> TYPE: DNA
<213> ORGANISM: Artificial Sequence
<220> FEATURE:
<223> OTHER INFORMATION: cDNA Sequence of aMTD645

<400> SEQUENCE: 386
gcgctggcgg tggtggcgct gccggcgatt gtgccg                                    36

<210> SEQ ID NO 387
<211> LENGTH: 36
<212> TYPE: DNA
```

```
<213> ORGANISM: Artificial Sequence
<220> FEATURE:
<223> OTHER INFORMATION: cDNA Sequence of aMTD661

<400> SEQUENCE: 387
gcggcgattc tggcgccgat tgtggcggcg ctgccg                            36

<210> SEQ ID NO 388
<211> LENGTH: 36
<212> TYPE: DNA
<213> ORGANISM: Artificial Sequence
<220> FEATURE:
<223> OTHER INFORMATION: cDNA Sequence of aMTD664

<400> SEQUENCE: 388
attctgattg cgattgcgat tccggcggcg gcgccg                            36

<210> SEQ ID NO 389
<211> LENGTH: 36
<212> TYPE: DNA
<213> ORGANISM: Artificial Sequence
<220> FEATURE:
<223> OTHER INFORMATION: cDNA Sequence of aMTD665

<400> SEQUENCE: 389
ctggcgattg tgctggcggc gccggtggcg gtgccg                            36

<210> SEQ ID NO 390
<211> LENGTH: 36
<212> TYPE: DNA
<213> ORGANISM: Artificial Sequence
<220> FEATURE:
<223> OTHER INFORMATION: cDNA Sequence of aMTD666

<400> SEQUENCE: 390
gcggcgattg cgattattgc gccggcgatt gtgccg                            36

<210> SEQ ID NO 391
<211> LENGTH: 36
<212> TYPE: DNA
<213> ORGANISM: Artificial Sequence
<220> FEATURE:
<223> OTHER INFORMATION: cDNA Sequence of aMTD667

<400> SEQUENCE: 391
ctggcggtgg cgattgtggc gccggcgctg gtgccg                            36

<210> SEQ ID NO 392
<211> LENGTH: 36
<212> TYPE: DNA
<213> ORGANISM: Artificial Sequence
<220> FEATURE:
<223> OTHER INFORMATION: cDNA Sequence of aMTD683

<400> SEQUENCE: 392
ctggcgattg tgctggcggc gccggcggtg ctgccg                            36

<210> SEQ ID NO 393
<211> LENGTH: 36
<212> TYPE: DNA
<213> ORGANISM: Artificial Sequence
<220> FEATURE:
<223> OTHER INFORMATION: cDNA Sequence of aMTD684

<400> SEQUENCE: 393
gcggcgattg tgctggcgct gccggcggtg ctgccg                            36
```

<210> SEQ ID NO 394
<211> LENGTH: 36
<212> TYPE: DNA
<213> ORGANISM: Artificial Sequence
<220> FEATURE:
<223> OTHER INFORMATION: cDNA Sequence of aMTD685

<400> SEQUENCE: 394
gcgctgctgg tggcggtgct gccggcggcg ctgccg                          36

<210> SEQ ID NO 395
<211> LENGTH: 36
<212> TYPE: DNA
<213> ORGANISM: Artificial Sequence
<220> FEATURE:
<223> OTHER INFORMATION: cDNA Sequence of aMTD686

<400> SEQUENCE: 395
gcggcgctgg tggcggtgct gccggtggcg ctgccg                          36

<210> SEQ ID NO 396
<211> LENGTH: 36
<212> TYPE: DNA
<213> ORGANISM: Artificial Sequence
<220> FEATURE:
<223> OTHER INFORMATION: cDNA Sequence of aMTD687

<400> SEQUENCE: 396
attgtggcgg tggcgctggt gccggcgctg gcgccg                          36

<210> SEQ ID NO 397
<211> LENGTH: 36
<212> TYPE: DNA
<213> ORGANISM: Artificial Sequence
<220> FEATURE:
<223> OTHER INFORMATION: cDNA Sequence of aMTD703

<400> SEQUENCE: 397
attgtggcgg tggcgctggt gccggcgctg gcgccg                          36

<210> SEQ ID NO 398
<211> LENGTH: 36
<212> TYPE: DNA
<213> ORGANISM: Artificial Sequence
<220> FEATURE:
<223> OTHER INFORMATION: cDNA Sequence of aMTD705

<400> SEQUENCE: 398
attgtggcgg tggcgctgct gccggcgctg gcgccg                          36

<210> SEQ ID NO 399
<211> LENGTH: 36
<212> TYPE: DNA
<213> ORGANISM: Artificial Sequence
<220> FEATURE:
<223> OTHER INFORMATION: cDNA Sequence of aMTD706

<400> SEQUENCE: 399
attgtggcgg tggcgctgct gccggcggtg gcgccg                          36

<210> SEQ ID NO 400
<211> LENGTH: 36
<212> TYPE: DNA
<213> ORGANISM: Artificial Sequence
<220> FEATURE:

<223> OTHER INFORMATION: cDNA Sequence of aMTD707

<400> SEQUENCE: 400
attgtggcgc tggcggtgct gccggcggtg gcgccg                36

<210> SEQ ID NO 401
<211> LENGTH: 36
<212> TYPE: DNA
<213> ORGANISM: Artificial Sequence
<220> FEATURE:
<223> OTHER INFORMATION: cDNA Sequence of aMTD724

<400> SEQUENCE: 401
gtggcggtgc tggcggtgct gccggcgctg gcgccg                36

<210> SEQ ID NO 402
<211> LENGTH: 36
<212> TYPE: DNA
<213> ORGANISM: Artificial Sequence
<220> FEATURE:
<223> OTHER INFORMATION: cDNA Sequence of aMTD725

<400> SEQUENCE: 402
attgcggtgc tggcggtggc gccggcggtg ctgccg                36

<210> SEQ ID NO 403
<211> LENGTH: 36
<212> TYPE: DNA
<213> ORGANISM: Artificial Sequence
<220> FEATURE:
<223> OTHER INFORMATION: cDNA Sequence of aMTD726

<400> SEQUENCE: 403
ctggcggtgg cgattattgc gccggcggtg gcgccg                36

<210> SEQ ID NO 404
<211> LENGTH: 36
<212> TYPE: DNA
<213> ORGANISM: Artificial Sequence
<220> FEATURE:
<223> OTHER INFORMATION: cDNA Sequence of aMTD727

<400> SEQUENCE: 404
gtggcgctgg cgattgcgct gccggcggtg ctgccg                36

<210> SEQ ID NO 405
<211> LENGTH: 36
<212> TYPE: DNA
<213> ORGANISM: Artificial Sequence
<220> FEATURE:
<223> OTHER INFORMATION: cDNA Sequence of aMTD743

<400> SEQUENCE: 405
gcgattgcga ttgcgctggt gccggtggcg ctgccg                36

<210> SEQ ID NO 406
<211> LENGTH: 36
<212> TYPE: DNA
<213> ORGANISM: Artificial Sequence
<220> FEATURE:
<223> OTHER INFORMATION: cDNA Sequence of aMTD744

<400> SEQUENCE: 406
gcggcggtgg tgattgtggc gccggtggcg ctgccg                36

```
<210> SEQ ID NO 407
<211> LENGTH: 36
<212> TYPE: DNA
<213> ORGANISM: Artificial Sequence
<220> FEATURE:
<223> OTHER INFORMATION: cDNA Sequence of aMTD746

<400> SEQUENCE: 407
gcggcgattc tggcgattgt ggcgccgctg gcgccg                                    36

<210> SEQ ID NO 408
<211> LENGTH: 36
<212> TYPE: DNA
<213> ORGANISM: Artificial Sequence
<220> FEATURE:
<223> OTHER INFORMATION: cDNA Sequence of aMTD747

<400> SEQUENCE: 408
gtggcgctgc tggcgattgc gccggcgctg gcgccg                                    36

<210> SEQ ID NO 409
<211> LENGTH: 36
<212> TYPE: DNA
<213> ORGANISM: Artificial Sequence
<220> FEATURE:
<223> OTHER INFORMATION: cDNA Sequence of aMTD763

<400> SEQUENCE: 409
gtggcggtgc tgattgcggt gccggcgctg gcgccg                                    36

<210> SEQ ID NO 410
<211> LENGTH: 36
<212> TYPE: DNA
<213> ORGANISM: Artificial Sequence
<220> FEATURE:
<223> OTHER INFORMATION: cDNA Sequence of aMTD764

<400> SEQUENCE: 410
gcggtggcgc tggcggtgct gccggcggtg gtgccg                                    36

<210> SEQ ID NO 411
<211> LENGTH: 36
<212> TYPE: DNA
<213> ORGANISM: Artificial Sequence
<220> FEATURE:
<223> OTHER INFORMATION: cDNA Sequence of aMTD765

<400> SEQUENCE: 411
gcggtggcgc tggcggtggt gccggcggtg ctgccg                                    36

<210> SEQ ID NO 412
<211> LENGTH: 36
<212> TYPE: DNA
<213> ORGANISM: Artificial Sequence
<220> FEATURE:
<223> OTHER INFORMATION: cDNA Sequence of aMTD766

<400> SEQUENCE: 412
attgtggtga ttgcggtggc gccggcggtg gcgccg                                    36

<210> SEQ ID NO 413
<211> LENGTH: 36
<212> TYPE: DNA
<213> ORGANISM: Artificial Sequence
<220> FEATURE:
<223> OTHER INFORMATION: cDNA Sequence of aMTD767
```

```
<400> SEQUENCE: 413
attgtggtgg cggcggtggt gccggcgctg gcgccg                                36

<210> SEQ ID NO 414
<211> LENGTH: 36
<212> TYPE: DNA
<213> ORGANISM: Artificial Sequence
<220> FEATURE:
<223> OTHER INFORMATION: cDNA Sequence of aMTD783

<400> SEQUENCE: 414
attgtggcgc tggtgccggc ggtggcgatt gcgccg                                36

<210> SEQ ID NO 415
<211> LENGTH: 36
<212> TYPE: DNA
<213> ORGANISM: Artificial Sequence
<220> FEATURE:
<223> OTHER INFORMATION: cDNA Sequence of aMTD784

<400> SEQUENCE: 415
gtggcggcgc tgccggcggt ggcgctggtg gtgccg                                36

<210> SEQ ID NO 416
<211> LENGTH: 36
<212> TYPE: DNA
<213> ORGANISM: Artificial Sequence
<220> FEATURE:
<223> OTHER INFORMATION: cDNA Sequence of aMTD786

<400> SEQUENCE: 416
ctggtggcga ttgcgccgct ggcggtgctg gcgccg                                36

<210> SEQ ID NO 417
<211> LENGTH: 36
<212> TYPE: DNA
<213> ORGANISM: Artificial Sequence
<220> FEATURE:
<223> OTHER INFORMATION: cDNA Sequence of aMTD787

<400> SEQUENCE: 417
gcggtggcgc tggtgccggt gattgtggcg gcgccg                                36

<210> SEQ ID NO 418
<211> LENGTH: 36
<212> TYPE: DNA
<213> ORGANISM: Artificial Sequence
<220> FEATURE:
<223> OTHER INFORMATION: cDNA Sequence of aMTD788

<400> SEQUENCE: 418
gcgattgcgg tggcgattgc gccggtggcg ctgccg                                36

<210> SEQ ID NO 419
<211> LENGTH: 36
<212> TYPE: DNA
<213> ORGANISM: Artificial Sequence
<220> FEATURE:
<223> OTHER INFORMATION: cDNA Sequence of aMTD803

<400> SEQUENCE: 419
gcgattgcgc tggcggtgcc ggtgctggcg ctgccg                                36

<210> SEQ ID NO 420
<211> LENGTH: 36
```

```
<212> TYPE: DNA
<213> ORGANISM: Artificial Sequence
<220> FEATURE:
<223> OTHER INFORMATION: cDNA Sequence of aMTD805

<400> SEQUENCE: 420
ctggtgctga ttgcggcggc gccgattgcg ctgccg                                36

<210> SEQ ID NO 421
<211> LENGTH: 36
<212> TYPE: DNA
<213> ORGANISM: Artificial Sequence
<220> FEATURE:
<223> OTHER INFORMATION: cDNA Sequence of aMTD806

<400> SEQUENCE: 421
ctggtggcgc tggcggtgcc ggcggcggtg ctgccg                                36

<210> SEQ ID NO 422
<211> LENGTH: 36
<212> TYPE: DNA
<213> ORGANISM: Artificial Sequence
<220> FEATURE:
<223> OTHER INFORMATION: cDNA Sequence of aMTD807

<400> SEQUENCE: 422
gcggtggcgc tggcggtgcc ggcgctggtg ctgccg                                36

<210> SEQ ID NO 423
<211> LENGTH: 36
<212> TYPE: DNA
<213> ORGANISM: Artificial Sequence
<220> FEATURE:
<223> OTHER INFORMATION: cDNA Sequence of aMTD808

<400> SEQUENCE: 423
ctggtggtgc tggcggcggc gccgctggcg gtgccg                                36

<210> SEQ ID NO 424
<211> LENGTH: 36
<212> TYPE: DNA
<213> ORGANISM: Artificial Sequence
<220> FEATURE:
<223> OTHER INFORMATION: cDNA Sequence of aMTD809

<400> SEQUENCE: 424
ctgattgtgc tggcggcgcc ggcgctggcg gcgccg                                36

<210> SEQ ID NO 425
<211> LENGTH: 36
<212> TYPE: DNA
<213> ORGANISM: Artificial Sequence
<220> FEATURE:
<223> OTHER INFORMATION: cDNA Sequence of aMTD810

<400> SEQUENCE: 425
gtgattgtgc tggcggcgcc ggcgctggcg gcgccg                                36

<210> SEQ ID NO 426
<211> LENGTH: 36
<212> TYPE: DNA
<213> ORGANISM: Artificial Sequence
<220> FEATURE:
<223> OTHER INFORMATION: cDNA Sequence of aMTD811

<400> SEQUENCE: 426
```
gcggtggtgc tggcggtgcc ggcgctggcg gtgccg                                    36

<210> SEQ ID NO 427
<211> LENGTH: 36
<212> TYPE: DNA
<213> ORGANISM: Artificial Sequence
<220> FEATURE:
<223> OTHER INFORMATION: cDNA Sequence of aMTD824

<400> SEQUENCE: 427
ctgattattg tggcggcggc gccggcggtg gcgccg                                    36

<210> SEQ ID NO 428
<211> LENGTH: 36
<212> TYPE: DNA
<213> ORGANISM: Artificial Sequence
<220> FEATURE:
<223> OTHER INFORMATION: cDNA Sequence of aMTD825

<400> SEQUENCE: 428
attgtggcgg tgattgtggc gccggcggtg gcgccg                                    36

<210> SEQ ID NO 429
<211> LENGTH: 36
<212> TYPE: DNA
<213> ORGANISM: Artificial Sequence
<220> FEATURE:
<223> OTHER INFORMATION: cDNA Sequence of aMTD826

<400> SEQUENCE: 429
ctggtggcgc tggcggcgcc gattattgcg gtgccg                                    36

<210> SEQ ID NO 430
<211> LENGTH: 36
<212> TYPE: DNA
<213> ORGANISM: Artificial Sequence
<220> FEATURE:
<223> OTHER INFORMATION: cDNA Sequence of aMTD827

<400> SEQUENCE: 430
attgcggcgg tgctggcggc gccggcgctg gtgccg                                    36

<210> SEQ ID NO 431
<211> LENGTH: 36
<212> TYPE: DNA
<213> ORGANISM: Artificial Sequence
<220> FEATURE:
<223> OTHER INFORMATION: cDNA Sequence of aMTD828

<400> SEQUENCE: 431
attgcgctgc tggcggcgcc gattattgcg gtgccg                                    36

<210> SEQ ID NO 432
<211> LENGTH: 36
<212> TYPE: DNA
<213> ORGANISM: Artificial Sequence
<220> FEATURE:
<223> OTHER INFORMATION: cDNA Sequence of aMTD829

<400> SEQUENCE: 432
gcggcgctgg cgctggtggc gccggtgatt gtgccg                                    36

<210> SEQ ID NO 433
<211> LENGTH: 36
<212> TYPE: DNA
<213> ORGANISM: Artificial Sequence

```
<220> FEATURE:
<223> OTHER INFORMATION: cDNA Sequence of aMTD830

<400> SEQUENCE: 433
attgcgctgg tggcggcgcc ggtggcgctg gtgccg                                36

<210> SEQ ID NO 434
<211> LENGTH: 36
<212> TYPE: DNA
<213> ORGANISM: Artificial Sequence
<220> FEATURE:
<223> OTHER INFORMATION: cDNA Sequence of aMTD831

<400> SEQUENCE: 434
attattgtgg cggtggcgcc ggcggcgatt gtgccg                                36

<210> SEQ ID NO 435
<211> LENGTH: 36
<212> TYPE: DNA
<213> ORGANISM: Artificial Sequence
<220> FEATURE:
<223> OTHER INFORMATION: cDNA Sequence of aMTD832

<400> SEQUENCE: 435
gcggtggcgg cgattgtgcc ggtgattgtg gcgccg                                36

<210> SEQ ID NO 436
<211> LENGTH: 36
<212> TYPE: DNA
<213> ORGANISM: Artificial Sequence
<220> FEATURE:
<223> OTHER INFORMATION: cDNA Sequence of aMTD843

<400> SEQUENCE: 436
gcggtgctgg tgctggtggc gccggcggcg gcgccg                                36

<210> SEQ ID NO 437
<211> LENGTH: 36
<212> TYPE: DNA
<213> ORGANISM: Artificial Sequence
<220> FEATURE:
<223> OTHER INFORMATION: cDNA Sequence of aMTD844

<400> SEQUENCE: 437
gtggtggcgc tgctggcgcc gctgattgcg gcgccg                                36

<210> SEQ ID NO 438
<211> LENGTH: 36
<212> TYPE: DNA
<213> ORGANISM: Artificial Sequence
<220> FEATURE:
<223> OTHER INFORMATION: cDNA Sequence of aMTD845

<400> SEQUENCE: 438
gcggcggtgg tgattgcgcc gctgctggcg gtgccg                                36

<210> SEQ ID NO 439
<211> LENGTH: 36
<212> TYPE: DNA
<213> ORGANISM: Artificial Sequence
<220> FEATURE:
<223> OTHER INFORMATION: cDNA Sequence of aMTD846

<400> SEQUENCE: 439
attgcggtgg cggtggcggc gccgctgctg gtgccg                                36
```

<210> SEQ ID NO 440
<211> LENGTH: 36
<212> TYPE: DNA
<213> ORGANISM: Artificial Sequence
<220> FEATURE:
<223> OTHER INFORMATION: cDNA Sequence of aMTD847

<400> SEQUENCE: 440
ctggtggcga ttgtggtgct gccggcggtg gcgccg         36

<210> SEQ ID NO 441
<211> LENGTH: 36
<212> TYPE: DNA
<213> ORGANISM: Artificial Sequence
<220> FEATURE:
<223> OTHER INFORMATION: cDNA Sequence of aMTD848

<400> SEQUENCE: 441
gcggtggcga ttgtggtgct gccggcggtg gcgccg         36

<210> SEQ ID NO 442
<211> LENGTH: 36
<212> TYPE: DNA
<213> ORGANISM: Artificial Sequence
<220> FEATURE:
<223> OTHER INFORMATION: cDNA Sequence of aMTD849

<400> SEQUENCE: 442
gcggtgattc tgctggcgcc gctgattgcg gcgccg         36

<210> SEQ ID NO 443
<211> LENGTH: 36
<212> TYPE: DNA
<213> ORGANISM: Artificial Sequence
<220> FEATURE:
<223> OTHER INFORMATION: cDNA Sequence of aMTD850

<400> SEQUENCE: 443
ctggtgattg cgctggcggc gccggtggcg ctgccg         36

<210> SEQ ID NO 444
<211> LENGTH: 36
<212> TYPE: DNA
<213> ORGANISM: Artificial Sequence
<220> FEATURE:
<223> OTHER INFORMATION: cDNA Sequence of aMTD851

<400> SEQUENCE: 444
gtgctggcgg tggtgctgcc ggcggtggcg ctgccg         36

<210> SEQ ID NO 445
<211> LENGTH: 36
<212> TYPE: DNA
<213> ORGANISM: Artificial Sequence
<220> FEATURE:
<223> OTHER INFORMATION: cDNA Sequence of aMTD852

<400> SEQUENCE: 445
gtgctggcgg tggcggcgcc ggcggtgctg ctgccg         36

<210> SEQ ID NO 446
<211> LENGTH: 36
<212> TYPE: DNA
<213> ORGANISM: Artificial Sequence
<220> FEATURE:
<223> OTHER INFORMATION: cDNA Sequence of aMTD863

```
<400> SEQUENCE: 446
gcggcggtgg tgctgctgcc gattattgcg gcgccg                                36

<210> SEQ ID NO 447
<211> LENGTH: 36
<212> TYPE: DNA
<213> ORGANISM: Artificial Sequence
<220> FEATURE:
<223> OTHER INFORMATION: cDNA Sequence of aMTD864

<400> SEQUENCE: 447
gcgctgctgg tgattgcgcc ggcgattgcg gtgccg                                36

<210> SEQ ID NO 448
<211> LENGTH: 36
<212> TYPE: DNA
<213> ORGANISM: Artificial Sequence
<220> FEATURE:
<223> OTHER INFORMATION: cDNA Sequence of aMTD865

<400> SEQUENCE: 448
gcggtgctgg tgattgcggt gccggcgatt gcgccg                                36

<210> SEQ ID NO 449
<211> LENGTH: 36
<212> TYPE: DNA
<213> ORGANISM: Artificial Sequence
<220> FEATURE:
<223> OTHER INFORMATION: cDNA Sequence of aMTD867

<400> SEQUENCE: 449
gcgctgctgg tggtgattgc gccgctggcg gcgccg                                36

<210> SEQ ID NO 450
<211> LENGTH: 36
<212> TYPE: DNA
<213> ORGANISM: Artificial Sequence
<220> FEATURE:
<223> OTHER INFORMATION: cDNA Sequence of aMTD868

<400> SEQUENCE: 450
gtgctggtgg cggcgattct gccggcggcg attccg                                36

<210> SEQ ID NO 451
<211> LENGTH: 36
<212> TYPE: DNA
<213> ORGANISM: Artificial Sequence
<220> FEATURE:
<223> OTHER INFORMATION: cDNA Sequence of aMTD870

<400> SEQUENCE: 451
gtgctggtgg cggcggtgct gccgattgcg gcgccg                                36

<210> SEQ ID NO 452
<211> LENGTH: 36
<212> TYPE: DNA
<213> ORGANISM: Artificial Sequence
<220> FEATURE:
<223> OTHER INFORMATION: cDNA Sequence of aMTD872

<400> SEQUENCE: 452
gtgctggcgg cggcggtgct gccgctggtg gtgccg                                36

<210> SEQ ID NO 453
```

```
<211> LENGTH: 36
<212> TYPE: DNA
<213> ORGANISM: Artificial Sequence
<220> FEATURE:
<223> OTHER INFORMATION: cDNA Sequence of aMTD875

<400> SEQUENCE: 453
gcgattgcga ttgtggtgcc ggcggtggcg gtgccg                              36

<210> SEQ ID NO 454
<211> LENGTH: 36
<212> TYPE: DNA
<213> ORGANISM: Artificial Sequence
<220> FEATURE:
<223> OTHER INFORMATION: cDNA Sequence of aMTD877

<400> SEQUENCE: 454
gtggcgatta ttgcggtgcc ggcggtggtg gcgccg                              36

<210> SEQ ID NO 455
<211> LENGTH: 36
<212> TYPE: DNA
<213> ORGANISM: Artificial Sequence
<220> FEATURE:
<223> OTHER INFORMATION: cDNA Sequence of aMTD878

<400> SEQUENCE: 455
attgtggcgc tggtggcgcc ggcggcggtg gtgccg                              36

<210> SEQ ID NO 456
<211> LENGTH: 36
<212> TYPE: DNA
<213> ORGANISM: Artificial Sequence
<220> FEATURE:
<223> OTHER INFORMATION: cDNA Sequence of aMTD879

<400> SEQUENCE: 456
gcggcgattg tgctgctgcc ggcggtggtg gtgccg                              36

<210> SEQ ID NO 457
<211> LENGTH: 36
<212> TYPE: DNA
<213> ORGANISM: Artificial Sequence
<220> FEATURE:
<223> OTHER INFORMATION: cDNA Sequence of aMTD881

<400> SEQUENCE: 457
gcggcgctga ttgtggtgcc ggcggtggcg gtgccg                              36

<210> SEQ ID NO 458
<211> LENGTH: 36
<212> TYPE: DNA
<213> ORGANISM: Artificial Sequence
<220> FEATURE:
<223> OTHER INFORMATION: cDNA Sequence of aMTD882

<400> SEQUENCE: 458
gcgattgcgc tggtggtgcc ggcggtggcg gtgccg                              36

<210> SEQ ID NO 459
<211> LENGTH: 36
<212> TYPE: DNA
<213> ORGANISM: Artificial Sequence
<220> FEATURE:
<223> OTHER INFORMATION: cDNA Sequence of aMTD883

<400> SEQUENCE: 459
```
ctggcgattg tgccggcggc gattgcggcg ctgccg        36

<210> SEQ ID NO 460
<211> LENGTH: 36
<212> TYPE: DNA
<213> ORGANISM: Artificial Sequence
<220> FEATURE:
<223> OTHER INFORMATION: cDNA Sequence of aMTD885

<400> SEQUENCE: 460
ctggtggcga ttgcgccggc ggtggcggtg ctgccg        36

<210> SEQ ID NO 461
<211> LENGTH: 36
<212> TYPE: DNA
<213> ORGANISM: Artificial Sequence
<220> FEATURE:
<223> OTHER INFORMATION: cDNA Sequence of aMTD887

<400> SEQUENCE: 461
gtgctggcgg tggcgccggc ggtggcggtg ctgccg        36

<210> SEQ ID NO 462
<211> LENGTH: 36
<212> TYPE: DNA
<213> ORGANISM: Artificial Sequence
<220> FEATURE:
<223> OTHER INFORMATION: cDNA Sequence of aMTD888

<400> SEQUENCE: 462
attctggcgg tggtggcgat tccggcggcg gcgccg        36

<210> SEQ ID NO 463
<211> LENGTH: 36
<212> TYPE: DNA
<213> ORGANISM: Artificial Sequence
<220> FEATURE:
<223> OTHER INFORMATION: cDNA Sequence of aMTD889

<400> SEQUENCE: 463
attctggtgg cggcggcgcc gattgcggcg ctgccg        36

<210> SEQ ID NO 464
<211> LENGTH: 36
<212> TYPE: DNA
<213> ORGANISM: Artificial Sequence
<220> FEATURE:
<223> OTHER INFORMATION: cDNA Sequence of aMTD891

<400> SEQUENCE: 464
attctggcgg tggcggcgat tccggcggcg ctgccg        36

<210> SEQ ID NO 465
<211> LENGTH: 36
<212> TYPE: DNA
<213> ORGANISM: Artificial Sequence
<220> FEATURE:
<223> OTHER INFORMATION: cDNA Sequence of aMTD893

<400> SEQUENCE: 465
gtgattgcga ttccggcgat tctggcggcg gcgccg        36

<210> SEQ ID NO 466
<211> LENGTH: 36
<212> TYPE: DNA

```
<213> ORGANISM: Artificial Sequence
<220> FEATURE:
<223> OTHER INFORMATION: cDNA Sequence of aMTD895

<400> SEQUENCE: 466
gcgattatta ttgtggtgcc ggcgattgcg gcgccg                                36

<210> SEQ ID NO 467
<211> LENGTH: 36
<212> TYPE: DNA
<213> ORGANISM: Artificial Sequence
<220> FEATURE:
<223> OTHER INFORMATION: cDNA Sequence of aMTD896

<400> SEQUENCE: 467
gcgattctga ttgtggtggc gccgattgcg gcgccg                                36

<210> SEQ ID NO 468
<211> LENGTH: 36
<212> TYPE: DNA
<213> ORGANISM: Artificial Sequence
<220> FEATURE:
<223> OTHER INFORMATION: cDNA Sequence of aMTD897

<400> SEQUENCE: 468
gcggtgattg tgccggtggc gattattgcg gcgccg                                36

<210> SEQ ID NO 469
<211> LENGTH: 36
<212> TYPE: DNA
<213> ORGANISM: Artificial Sequence
<220> FEATURE:
<223> OTHER INFORMATION: cDNA Sequence of aMTD899

<400> SEQUENCE: 469
gcggtggtga ttgcgctgcc ggcggtggtg gcgccg                                36

<210> SEQ ID NO 470
<211> LENGTH: 36
<212> TYPE: DNA
<213> ORGANISM: Artificial Sequence
<220> FEATURE:
<223> OTHER INFORMATION: cDNA Sequence of aMTD900

<400> SEQUENCE: 470
gcgctggtgg cggtgattgc gccggtggtg gcgccg                                36

<210> SEQ ID NO 471
<211> LENGTH: 36
<212> TYPE: DNA
<213> ORGANISM: Artificial Sequence
<220> FEATURE:
<223> OTHER INFORMATION: cDNA Sequence of aMTD901

<400> SEQUENCE: 471
gcgctggtgg cggtgctgcc ggcggtggcg gtgccg                                36

<210> SEQ ID NO 472
<211> LENGTH: 36
<212> TYPE: DNA
<213> ORGANISM: Artificial Sequence
<220> FEATURE:
<223> OTHER INFORMATION: cDNA Sequence of aMTD902

<400> SEQUENCE: 472
gcgctggtgg cgccgctgct ggcggtggcg gtgccg                                36
```

<210> SEQ ID NO 473
<211> LENGTH: 36
<212> TYPE: DNA
<213> ORGANISM: Artificial Sequence
<220> FEATURE:
<223> OTHER INFORMATION: cDNA Sequence of aMTD904

<400> SEQUENCE: 473
gcggtgctgg cggtggtggc gccggtggtg gcgccg       36

<210> SEQ ID NO 474
<211> LENGTH: 36
<212> TYPE: DNA
<213> ORGANISM: Artificial Sequence
<220> FEATURE:
<223> OTHER INFORMATION: cDNA Sequence of aMTD905

<400> SEQUENCE: 474
gcggtgattg cggtggcgcc gctggtggtg gcgccg       36

<210> SEQ ID NO 475
<211> LENGTH: 36
<212> TYPE: DNA
<213> ORGANISM: Artificial Sequence
<220> FEATURE:
<223> OTHER INFORMATION: cDNA Sequence of aMTD906

<400> SEQUENCE: 475
gcggtgattg cgctggcgcc ggtggtggtg gcgccg       36

<210> SEQ ID NO 476
<211> LENGTH: 36
<212> TYPE: DNA
<213> ORGANISM: Artificial Sequence
<220> FEATURE:
<223> OTHER INFORMATION: cDNA Sequence of aMTD907

<400> SEQUENCE: 476
gtggcgattg cgctggcgcc ggtggtggtg gcgccg       36

<210> SEQ ID NO 477
<211> LENGTH: 36
<212> TYPE: DNA
<213> ORGANISM: Artificial Sequence
<220> FEATURE:
<223> OTHER INFORMATION: cDNA Sequence of aMTD908

<400> SEQUENCE: 477
gtggcgctgg cgctggcgcc ggtggtggtg gcgccg       36

<210> SEQ ID NO 478
<211> LENGTH: 36
<212> TYPE: DNA
<213> ORGANISM: Artificial Sequence
<220> FEATURE:
<223> OTHER INFORMATION: cDNA Sequence of aMTD910

<400> SEQUENCE: 478
gtggcggcgc tgctgccggc ggtggtggtg gcgccg       36

<210> SEQ ID NO 479
<211> LENGTH: 36
<212> TYPE: DNA
<213> ORGANISM: Artificial Sequence
<220> FEATURE:

```
<223> OTHER INFORMATION: cDNA Sequence of aMTD911

<400> SEQUENCE: 479
gtggcgctgg cgctgccggc ggtggtggtg gcgccg                                36

<210> SEQ ID NO 480
<211> LENGTH: 36
<212> TYPE: DNA
<213> ORGANISM: Artificial Sequence
<220> FEATURE:
<223> OTHER INFORMATION: cDNA Sequence of aMTD912

<400> SEQUENCE: 480
gtggcgctgc tggcgccggc ggtggtggtg gcgccg                                36

<210> SEQ ID NO 481
<211> LENGTH: 69
<212> TYPE: DNA
<213> ORGANISM: Artificial Sequence
<220> FEATURE:
<223> OTHER INFORMATION: cDNA Sequence of aMTD1 5'-primer

<400> SEQUENCE: 481
gggtttcata tggcggcggc gctggcgccg gtggtgctgg cgctgccggc aaatattacc      60
gttttctat                                                             69

<210> SEQ ID NO 482
<211> LENGTH: 69
<212> TYPE: DNA
<213> ORGANISM: Artificial Sequence
<220> FEATURE:
<223> OTHER INFORMATION: cDNA Sequence of aMTD2 5'-primer

<400> SEQUENCE: 482
gggtttcata tggcggcggc ggtgccgctg ctggcggtgg tggtgccggc aaatattacc      60
gttttctat                                                             69

<210> SEQ ID NO 483
<211> LENGTH: 69
<212> TYPE: DNA
<213> ORGANISM: Artificial Sequence
<220> FEATURE:
<223> OTHER INFORMATION: cDNA Sequence of aMTD3 5'-primer

<400> SEQUENCE: 483
gggtttcata tggcggcgct gctggtgccg gcggcggtgc tggcgccggc aaatattacc      60
gttttctat                                                             69

<210> SEQ ID NO 484
<211> LENGTH: 69
<212> TYPE: DNA
<213> ORGANISM: Artificial Sequence
<220> FEATURE:
<223> OTHER INFORMATION: cDNA Sequence of aMTD4 5'-primer

<400> SEQUENCE: 484
gggtttcata tggcgctggc gctgctgccg gtggcggcgc tggcgccggc aaatattacc      60
gttttctat                                                             69

<210> SEQ ID NO 485
<211> LENGTH: 69
<212> TYPE: DNA
<213> ORGANISM: Artificial Sequence
```

```
<220> FEATURE:
<223> OTHER INFORMATION: cDNA Sequence of aMTD5 5'-primer

<400> SEQUENCE: 485
gggtttcata tggcggcggc gctgctgccg gtggcgctgg tggcgccggc aaatattacc      60
gttttctat                                                              69

<210> SEQ ID NO 486
<211> LENGTH: 69
<212> TYPE: DNA
<213> ORGANISM: Artificial Sequence
<220> FEATURE:
<223> OTHER INFORMATION: cDNA Sequence of aMTD6 5'-primer

<400> SEQUENCE: 486
gggtttcata tggtgattgc gatgattccg gcggcgtttt gggtggcggc aaatattacc      60
gttttctat                                                              69

<210> SEQ ID NO 487
<211> LENGTH: 69
<212> TYPE: DNA
<213> ORGANISM: Artificial Sequence
<220> FEATURE:
<223> OTHER INFORMATION: cDNA Sequence of aMTD9 5'-primer

<400> SEQUENCE: 487
gggtttcata tggtggcgct ggtgccggcg gcgctgattc tgccgccggc aaatattacc      60
gttttctat                                                              69

<210> SEQ ID NO 488
<211> LENGTH: 69
<212> TYPE: DNA
<213> ORGANISM: Artificial Sequence
<220> FEATURE:
<223> OTHER INFORMATION: cDNA Sequence of aMTD11 5'-primer

<400> SEQUENCE: 488
gggtttcata tggtggtggc gctggcgccg gcgctggcgg cgctgccggc aaatattacc      60
gttttctat                                                              69

<210> SEQ ID NO 489
<211> LENGTH: 69
<212> TYPE: DNA
<213> ORGANISM: Artificial Sequence
<220> FEATURE:
<223> OTHER INFORMATION: cDNA Sequence of aMTD12 5'-primer

<400> SEQUENCE: 489
gggtttcata tgctgctggc ggcggtgccg gcggtgctgc tggcgccggc aaatattacc      60
gttttctat                                                              69

<210> SEQ ID NO 490
<211> LENGTH: 69
<212> TYPE: DNA
<213> ORGANISM: Artificial Sequence
<220> FEATURE:
<223> OTHER INFORMATION: cDNA Sequence of aMTD13 5'-primer

<400> SEQUENCE: 490
gggtttcata tggcggcggc gctggtgccg gtggtggcgc tgctgccggc aaatattacc      60
gttttctat                                                              69
```

```
<210> SEQ ID NO 491
<211> LENGTH: 69
<212> TYPE: DNA
<213> ORGANISM: Artificial Sequence
<220> FEATURE:
<223> OTHER INFORMATION: cDNA Sequence of aMTD16 5'-primer

<400> SEQUENCE: 491
gggtttcata tgaacaacag ctgcaccacc tataccaacg gcagccaggc aaatattacc    60
gttttctat                                                           69

<210> SEQ ID NO 492
<211> LENGTH: 69
<212> TYPE: DNA
<213> ORGANISM: Artificial Sequence
<220> FEATURE:
<223> OTHER INFORMATION: cDNA Sequence of aMTD17 5'-primer

<400> SEQUENCE: 492
gggtttcata tgggcggctg cagcgcgccg cagaccacct gcagcaacgc aaatattacc    60
gttttctat                                                           69

<210> SEQ ID NO 493
<211> LENGTH: 69
<212> TYPE: DNA
<213> ORGANISM: Artificial Sequence
<220> FEATURE:
<223> OTHER INFORMATION: cDNA Sequence of aMTD18 5'-primer

<400> SEQUENCE: 493
gggtttcata tgaactattg ctgcaccccg accaccaacg gccagagcgc aaatattacc    60
gttttctat                                                           69

<210> SEQ ID NO 494
<211> LENGTH: 69
<212> TYPE: DNA
<213> ORGANISM: Artificial Sequence
<220> FEATURE:
<223> OTHER INFORMATION: cDNA Sequence of aMTD19 5'-primer

<400> SEQUENCE: 494
gggtttcata tgtatgtgag ctgctgcacc tataccaacg gcagccaggc aaatattacc    60
gttttctat                                                           69

<210> SEQ ID NO 495
<211> LENGTH: 69
<212> TYPE: DNA
<213> ORGANISM: Artificial Sequence
<220> FEATURE:
<223> OTHER INFORMATION: cDNA Sequence of aMTD20 5'-primer

<400> SEQUENCE: 495
gggtttcata tgaactattg caacacctgc ccgacctatg gccagagcgc aaatattacc    60
gttttctat                                                           69

<210> SEQ ID NO 496
<211> LENGTH: 69
<212> TYPE: DNA
<213> ORGANISM: Artificial Sequence
<220> FEATURE:
<223> OTHER INFORMATION: cDNA Sequence of aMTD21 5'-primer

<400> SEQUENCE: 496
```
gggtttcata tggcggtggc gctgctgccg gcgctgctgg cggtgccggc aaatattacc     60
gttttctat                                                             69

<210> SEQ ID NO 497
<211> LENGTH: 69
<212> TYPE: DNA
<213> ORGANISM: Artificial Sequence
<220> FEATURE:
<223> OTHER INFORMATION: cDNA Sequence of aMTD22 5'-primer

<400> SEQUENCE: 497
gggtttcata tggcggtggt gctggtgccg gtgctggcgg cggcgccggc aaatattacc     60
gttttctat                                                             69

<210> SEQ ID NO 498
<211> LENGTH: 69
<212> TYPE: DNA
<213> ORGANISM: Artificial Sequence
<220> FEATURE:
<223> OTHER INFORMATION: cDNA Sequence of aMTD23 5'-primer

<400> SEQUENCE: 498
gggtttcata tggtggtgct ggtgctgccg gcggcggcgg cggtgccggc aaatattacc     60
gttttctat                                                             69

<210> SEQ ID NO 499
<211> LENGTH: 69
<212> TYPE: DNA
<213> ORGANISM: Artificial Sequence
<220> FEATURE:
<223> OTHER INFORMATION: cDNA Sequence of aMTD24 5'-primer

<400> SEQUENCE: 499
gggtttcata tgattgcgct ggcggcgccg gcgctgattg tggcgccggc aaatattacc     60
gttttctat                                                             69

<210> SEQ ID NO 500
<211> LENGTH: 69
<212> TYPE: DNA
<213> ORGANISM: Artificial Sequence
<220> FEATURE:
<223> OTHER INFORMATION: cDNA Sequence of aMTD25 5'-primer

<400> SEQUENCE: 500
gggtttcata tgattgtggc ggtggcgccg gcgctggtgg cgctgccggc aaatattacc     60
gttttctat                                                             69

<210> SEQ ID NO 501
<211> LENGTH: 69
<212> TYPE: DNA
<213> ORGANISM: Artificial Sequence
<220> FEATURE:
<223> OTHER INFORMATION: cDNA Sequence of aMTD26 5'-primer

<400> SEQUENCE: 501
gggtttcata tggcggcgat tgcgctggcg gcgccgctgg cgattgtggc aaatattacc     60
gttttctat                                                             69

<210> SEQ ID NO 502
<211> LENGTH: 69
<212> TYPE: DNA

```
<213> ORGANISM: Artificial Sequence
<220> FEATURE:
<223> OTHER INFORMATION: cDNA Sequence of aMTD27 5'-primer

<400> SEQUENCE: 502
gggtttcata tgctggcgat tgtggcggcg gcggcggcgc tggtggcggc aaatattacc    60
gttttctat                                                            69

<210> SEQ ID NO 503
<211> LENGTH: 69
<212> TYPE: DNA
<213> ORGANISM: Artificial Sequence
<220> FEATURE:
<223> OTHER INFORMATION: cDNA Sequence of aMTD28 5'-primer

<400> SEQUENCE: 503
gggtttcata tggcggtgcc gctgctgccg ctggtgccgg cggtgccggc aaatattacc    60
gttttctat                                                            69

<210> SEQ ID NO 504
<211> LENGTH: 69
<212> TYPE: DNA
<213> ORGANISM: Artificial Sequence
<220> FEATURE:
<223> OTHER INFORMATION: cDNA Sequence of aMTD29 5'-primer

<400> SEQUENCE: 504
gggtttcata tggtgctgcc gccgctgccg gtgctgccgg tgctgccggc aaatattacc    60
gttttctat                                                            69

<210> SEQ ID NO 505
<211> LENGTH: 69
<212> TYPE: DNA
<213> ORGANISM: Artificial Sequence
<220> FEATURE:
<223> OTHER INFORMATION: cDNA Sequence of aMTD30 5'-primer

<400> SEQUENCE: 505
gggtttcata tggcgatggc gctgctgccg gcggcggtgg cggtggcggc aaatattacc    60
gttttctat                                                            69

<210> SEQ ID NO 506
<211> LENGTH: 69
<212> TYPE: DNA
<213> ORGANISM: Artificial Sequence
<220> FEATURE:
<223> OTHER INFORMATION: cDNA Sequence of aMTD33 5'-primer

<400> SEQUENCE: 506
gggtttcata tggcggcggc gattctggcg ccggcgtttc tggcggtggc aaatattacc    60
gttttctat                                                            69

<210> SEQ ID NO 507
<211> LENGTH: 69
<212> TYPE: DNA
<213> ORGANISM: Artificial Sequence
<220> FEATURE:
<223> OTHER INFORMATION: cDNA Sequence of aMTD37 5'-primer

<400> SEQUENCE: 507
gggtttcata tgtattataa ccagagcacc tgcggcggcc agtgctatgc aaatattacc    60
gttttctat                                                            69
```

<210> SEQ ID NO 508
<211> LENGTH: 69
<212> TYPE: DNA
<213> ORGANISM: Artificial Sequence
<220> FEATURE:
<223> OTHER INFORMATION: cDNA Sequence of aMTD38 5'-primer

<400> SEQUENCE: 508
gggtttcata tgaccacctg cagccagcag cagtattgca ccaacggcgc aaatattacc    60
gttttctat                                                           69

<210> SEQ ID NO 509
<211> LENGTH: 69
<212> TYPE: DNA
<213> ORGANISM: Artificial Sequence
<220> FEATURE:
<223> OTHER INFORMATION: cDNA Sequence of aMTD39 5'-primer

<400> SEQUENCE: 509
gggtttcata tgtgctataa caccagcccg tgcaccggct gctgctatgc aaatattacc    60
gttttctat                                                           69

<210> SEQ ID NO 510
<211> LENGTH: 69
<212> TYPE: DNA
<213> ORGANISM: Artificial Sequence
<220> FEATURE:
<223> OTHER INFORMATION: cDNA Sequence of aMTD40 5'-primer

<400> SEQUENCE: 510
gggtttcata tgacctataa caccagctgc accccgggca cctgctatgc aaatattacc    60
gttttctat                                                           69

<210> SEQ ID NO 511
<211> LENGTH: 69
<212> TYPE: DNA
<213> ORGANISM: Artificial Sequence
<220> FEATURE:
<223> OTHER INFORMATION: cDNA Sequence of aMTD42 5'-primer

<400> SEQUENCE: 511
gggtttcata tggtggcggc gctgccggtg gtggcggtgg tggcgccggc aaatattacc    60
gttttctat                                                           69

<210> SEQ ID NO 512
<211> LENGTH: 69
<212> TYPE: DNA
<213> ORGANISM: Artificial Sequence
<220> FEATURE:
<223> OTHER INFORMATION: cDNA Sequence of aMTD43 5'-primer

<400> SEQUENCE: 512
gggtttcata tgctgctggc ggcgccgctg gtggtggcgg cggtgccggc aaatattacc    60
gttttctat                                                           69

<210> SEQ ID NO 513
<211> LENGTH: 69
<212> TYPE: DNA
<213> ORGANISM: Artificial Sequence
<220> FEATURE:
<223> OTHER INFORMATION: cDNA Sequence of aMTD44 5'-primer

```
<400> SEQUENCE: 513
gggtttcata tggcgctggc ggtgccggtg gcgctgctgg tggcgccggc aaatattacc    60
gttttctat                                                            69

<210> SEQ ID NO 514
<211> LENGTH: 69
<212> TYPE: DNA
<213> ORGANISM: Artificial Sequence
<220> FEATURE:
<223> OTHER INFORMATION: cDNA Sequence of aMTD49 5'-primer

<400> SEQUENCE: 514
gggtttcata tggtggtgcc ggcggcgccg gcggtgccgg tggtgccggc aaatattacc    60
gttttctat                                                            69

<210> SEQ ID NO 515
<211> LENGTH: 69
<212> TYPE: DNA
<213> ORGANISM: Artificial Sequence
<220> FEATURE:
<223> OTHER INFORMATION: cDNA Sequence of aMTD54 5'-primer

<400> SEQUENCE: 515
gggtttcata tgctggcggt ggcggcgccg ccggtggtgg cgctgctggc aaatattacc    60
gttttctat                                                            69

<210> SEQ ID NO 516
<211> LENGTH: 69
<212> TYPE: DNA
<213> ORGANISM: Artificial Sequence
<220> FEATURE:
<223> OTHER INFORMATION: cDNA Sequence of aMTD57 5'-primer

<400> SEQUENCE: 516
gggtttcata tgcagaacaa ctgcaacacc agcagccagg gcggcggcgc aaatattacc    60
gttttctat                                                            69

<210> SEQ ID NO 517
<211> LENGTH: 69
<212> TYPE: DNA
<213> ORGANISM: Artificial Sequence
<220> FEATURE:
<223> OTHER INFORMATION: cDNA Sequence of aMTD59 5'-primer

<400> SEQUENCE: 517
gggtttcata tggcggtgct ggcggcgccg gtggtggcgg cgctggcggc aaatattacc    60
gttttctat                                                            69

<210> SEQ ID NO 518
<211> LENGTH: 69
<212> TYPE: DNA
<213> ORGANISM: Artificial Sequence
<220> FEATURE:
<223> OTHER INFORMATION: cDNA Sequence of aMTD61 5'-primer

<400> SEQUENCE: 518
gggtttcata tggtggcggc gctgccggtg ctgctggcgg cgctgccggc aaatattacc    60
gttttctat                                                            69

<210> SEQ ID NO 519
<211> LENGTH: 69
```

```
<212> TYPE: DNA
<213> ORGANISM: Artificial Sequence
<220> FEATURE:
<223> OTHER INFORMATION: cDNA Sequence of aMTD62 5'-primer

<400> SEQUENCE: 519
gggtttcata tggtggcgct gctggcgccg gtggcgctgg cggtgccggc aaatattacc      60
gttttctat                                                             69

<210> SEQ ID NO 520
<211> LENGTH: 69
<212> TYPE: DNA
<213> ORGANISM: Artificial Sequence
<220> FEATURE:
<223> OTHER INFORMATION: cDNA Sequence of aMTD63 5'-primer

<400> SEQUENCE: 520
gggtttcata tggcggcgct gctggtgccg gcgctggtgg cggtgccggc aaatattacc      60
gttttctat                                                             69

<210> SEQ ID NO 521
<211> LENGTH: 69
<212> TYPE: DNA
<213> ORGANISM: Artificial Sequence
<220> FEATURE:
<223> OTHER INFORMATION: cDNA Sequence of aMTD64 5'-primer

<400> SEQUENCE: 521
gggtttcata tggcgattgt ggcgctgccg gtggcggtgc tggcgccggc aaatattacc      60
gttttctat                                                             69

<210> SEQ ID NO 522
<211> LENGTH: 69
<212> TYPE: DNA
<213> ORGANISM: Artificial Sequence
<220> FEATURE:
<223> OTHER INFORMATION: cDNA Sequence of aMTD65 5'-primer

<400> SEQUENCE: 522
gggtttcata tgattgcgat tgtggcgccg gtggtggcgc tggcgccggc aaatattacc      60
gttttctat                                                             69

<210> SEQ ID NO 523
<211> LENGTH: 69
<212> TYPE: DNA
<213> ORGANISM: Artificial Sequence
<220> FEATURE:
<223> OTHER INFORMATION: cDNA Sequence of aMTD66 5'-primer

<400> SEQUENCE: 523
gggtttcata tggcgggcgt gctgggcggc ccgattatgg gcgtgccggc aaatattacc      60
gttttctat                                                             69

<210> SEQ ID NO 524
<211> LENGTH: 69
<212> TYPE: DNA
<213> ORGANISM: Artificial Sequence
<220> FEATURE:
<223> OTHER INFORMATION: cDNA Sequence of aMTD67 5'-primer

<400> SEQUENCE: 524
gggtttcata tgctggatgc ggaagtgccg ctggcggatg atgtgccggc aaatattacc      60
``` gttttctat                                                              69

<210> SEQ ID NO 525
<211> LENGTH: 69
<212> TYPE: DNA
<213> ORGANISM: Artificial Sequence
<220> FEATURE:
<223> OTHER INFORMATION: cDNA Sequence of aMTD68 5'-primer

<400> SEQUENCE: 525
gggtttcata tggtggcgcc ggtgctgccg gcggcgccgc tggtgccggc aaatattacc      60
gttttctat                                                              69

<210> SEQ ID NO 526
<211> LENGTH: 69
<212> TYPE: DNA
<213> ORGANISM: Artificial Sequence
<220> FEATURE:
<223> OTHER INFORMATION: cDNA Sequence of aMTD69 5'-primer

<400> SEQUENCE: 526
gggtttcata tgccggtggc ggtgctgccg ccggcggcgc tggtgccggc aaatattacc      60
gttttctat                                                              69

<210> SEQ ID NO 527
<211> LENGTH: 69
<212> TYPE: DNA
<213> ORGANISM: Artificial Sequence
<220> FEATURE:
<223> OTHER INFORMATION: cDNA Sequence of aMTD71 5'-primer

<400> SEQUENCE: 527
gggtttcata tgtttatgtg gatgtggttt ccgtttatgt ggtatccggc aaatattacc      60
gttttctat                                                              69

<210> SEQ ID NO 528
<211> LENGTH: 69
<212> TYPE: DNA
<213> ORGANISM: Artificial Sequence
<220> FEATURE:
<223> OTHER INFORMATION: cDNA Sequence of aMTD77 5'-primer

<400> SEQUENCE: 528
gggtttcata tggcgatgct gctgatgccg attgtgctga ttgcgccggc aaatattacc      60
gttttctat                                                              69

<210> SEQ ID NO 529
<211> LENGTH: 69
<212> TYPE: DNA
<213> ORGANISM: Artificial Sequence
<220> FEATURE:
<223> OTHER INFORMATION: cDNA Sequence of aMTD81 5'-primer

<400> SEQUENCE: 529
gggtttcata tggcggcgct gctgccggcg ctggcggcgc tgctgccggc aaatattacc      60
gttttctat                                                              69

<210> SEQ ID NO 530
<211> LENGTH: 69
<212> TYPE: DNA
<213> ORGANISM: Artificial Sequence
<220> FEATURE:
<223> OTHER INFORMATION: cDNA Sequence of aMTD82 5'-primer

```
<400> SEQUENCE: 530
gggtttcata tggcggtggt gctggcgccg gtggcggcgg tgctgccggc aaatattacc      60
gttttctat                                                              69

<210> SEQ ID NO 531
<211> LENGTH: 69
<212> TYPE: DNA
<213> ORGANISM: Artificial Sequence
<220> FEATURE:
<223> OTHER INFORMATION: cDNA Sequence of aMTD83 5'-primer

<400> SEQUENCE: 531
gggtttcata tgctggcggt ggcggcgccg ctggcgctgg cgctgccggc aaatattacc      60
gttttctat                                                              69

<210> SEQ ID NO 532
<211> LENGTH: 69
<212> TYPE: DNA
<213> ORGANISM: Artificial Sequence
<220> FEATURE:
<223> OTHER INFORMATION: cDNA Sequence of aMTD84 5'-primer

<400> SEQUENCE: 532
gggtttcata tgcggcggt ggcggcgccg ctgctgctgg cgctgccggc aaatattacc       60
gttttctat                                                              69

<210> SEQ ID NO 533
<211> LENGTH: 69
<212> TYPE: DNA
<213> ORGANISM: Artificial Sequence
<220> FEATURE:
<223> OTHER INFORMATION: cDNA Sequence of aMTD85 5'-primer

<400> SEQUENCE: 533
gggtttcata tgctgctggt gctgccggcg gcggcgctgg cggcgccggc aaatattacc      60
gttttctat                                                              69

<210> SEQ ID NO 534
<211> LENGTH: 69
<212> TYPE: DNA
<213> ORGANISM: Artificial Sequence
<220> FEATURE:
<223> OTHER INFORMATION: cDNA Sequence of aMTD97 5'-primer

<400> SEQUENCE: 534
gggtttcata tggcgctgct ggcggcgccg ccggcgctgc tggcgctggc aaatattacc      60
gttttctat                                                              69

<210> SEQ ID NO 535
<211> LENGTH: 69
<212> TYPE: DNA
<213> ORGANISM: Artificial Sequence
<220> FEATURE:
<223> OTHER INFORMATION: cDNA Sequence of aMTD101 5'-primer

<400> SEQUENCE: 535
gggtttcata tgctggtggc ggtggcgccg gtggcggcgg tgctgccggc aaatattacc      60
gttttctat                                                              69

<210> SEQ ID NO 536
```

```
<211> LENGTH: 69
<212> TYPE: DNA
<213> ORGANISM: Artificial Sequence
<220> FEATURE:
<223> OTHER INFORMATION: cDNA Sequence of aMTD102 5'-primer

<400> SEQUENCE: 536
gggtttcata tgctggcgct ggcgccggcg gcgctggcgc tgctgccggc aaatattacc      60
gttttctat                                                             69

<210> SEQ ID NO 537
<211> LENGTH: 69
<212> TYPE: DNA
<213> ORGANISM: Artificial Sequence
<220> FEATURE:
<223> OTHER INFORMATION: cDNA Sequence of aMTD103 5'-primer

<400> SEQUENCE: 537
gggtttcata tggcgctgat tgcggcgccg attctggcgc tggcgccggc aaatattacc      60
gttttctat                                                             69

<210> SEQ ID NO 538
<211> LENGTH: 69
<212> TYPE: DNA
<213> ORGANISM: Artificial Sequence
<220> FEATURE:
<223> OTHER INFORMATION: cDNA Sequence of aMTD104 5'-primer

<400> SEQUENCE: 538
gggtttcata tggcggtggt ggcggcgccg ctggtgctgg cgctgccggc aaatattacc      60
gttttctat                                                             69

<210> SEQ ID NO 539
<211> LENGTH: 69
<212> TYPE: DNA
<213> ORGANISM: Artificial Sequence
<220> FEATURE:
<223> OTHER INFORMATION: cDNA Sequence of aMTD105 5'-primer

<400> SEQUENCE: 539
gggtttcata tgctgctggc gctggcgccg gcggcgctgc tggcgccggc aaatattacc      60
gttttctat                                                             69

<210> SEQ ID NO 540
<211> LENGTH: 69
<212> TYPE: DNA
<213> ORGANISM: Artificial Sequence
<220> FEATURE:
<223> OTHER INFORMATION: cDNA Sequence of aMTD113 5'-primer

<400> SEQUENCE: 540
gggtttcata tgccggtggc ggtggcgctg ctgattgcgg tgccgccggc aaatattacc      60
gttttctat                                                             69

<210> SEQ ID NO 541
<211> LENGTH: 69
<212> TYPE: DNA
<213> ORGANISM: Artificial Sequence
<220> FEATURE:
<223> OTHER INFORMATION: cDNA Sequence of aMTD121 5'-primer

<400> SEQUENCE: 541
gggtttcata tggcgattgt ggcgctgccg gcgctggcgc tggcgccggc aaatattacc      60
```

```
gttttctat                                                             69

<210> SEQ ID NO 542
<211> LENGTH: 69
<212> TYPE: DNA
<213> ORGANISM: Artificial Sequence
<220> FEATURE:
<223> OTHER INFORMATION: cDNA Sequence of aMTD123 5'-primer

<400> SEQUENCE: 542
gggtttcata tggcggcgat tattgtgccg gcggcgctgc tggcgccggc aaatattacc     60
gttttctat                                                             69

<210> SEQ ID NO 543
<211> LENGTH: 69
<212> TYPE: DNA
<213> ORGANISM: Artificial Sequence
<220> FEATURE:
<223> OTHER INFORMATION: cDNA Sequence of aMTD124 5'-primer

<400> SEQUENCE: 543
gggtttcata tgattgcggt ggcgctgccg gcgctgattg cggcgccggc aaatattacc     60
gttttctat                                                             69

<210> SEQ ID NO 544
<211> LENGTH: 69
<212> TYPE: DNA
<213> ORGANISM: Artificial Sequence
<220> FEATURE:
<223> OTHER INFORMATION: cDNA Sequence of aMTD131 5'-primer

<400> SEQUENCE: 544
gggtttcata tgtggattat tgcgccggtg tggctggcgt ggattgcggc aaatattacc     60
gttttctat                                                             69

<210> SEQ ID NO 545
<211> LENGTH: 69
<212> TYPE: DNA
<213> ORGANISM: Artificial Sequence
<220> FEATURE:
<223> OTHER INFORMATION: cDNA Sequence of aMTD138 5'-primer

<400> SEQUENCE: 545
gggtttcata tgccgccggc ggcgctgctg gcgattctgg cggtggcggc aaatattacc     60
gttttctat                                                             69

<210> SEQ ID NO 546
<211> LENGTH: 69
<212> TYPE: DNA
<213> ORGANISM: Artificial Sequence
<220> FEATURE:
<223> OTHER INFORMATION: cDNA Sequence of aMTD139 5'-primer

<400> SEQUENCE: 546
gggtttcata tgaccggcag caccaacagc ccgacctgca ccagcaccgc aaatattacc     60
gttttctat                                                             69

<210> SEQ ID NO 547
<211> LENGTH: 69
<212> TYPE: DNA
<213> ORGANISM: Artificial Sequence
<220> FEATURE:
```

<223> OTHER INFORMATION: cDNA Sequence of aMTD141 5'-primer

<400> SEQUENCE: 547
gggtttcata tggcggtgat tgtgctgccg gcgctggcgg tggcgccggc aaatattacc    60
gttttctat                                                             69

<210> SEQ ID NO 548
<211> LENGTH: 69
<212> TYPE: DNA
<213> ORGANISM: Artificial Sequence
<220> FEATURE:
<223> OTHER INFORMATION: cDNA Sequence of aMTD142 5'-primer

<400> SEQUENCE: 548
gggtttcata tgctgctggc ggcggtgccg gtggcgctgg tggcgccggc aaatattacc    60
gttttctat                                                             69

<210> SEQ ID NO 549
<211> LENGTH: 69
<212> TYPE: DNA
<213> ORGANISM: Artificial Sequence
<220> FEATURE:
<223> OTHER INFORMATION: cDNA Sequence of aMTD143 5'-primer

<400> SEQUENCE: 549
gggtttcata tggcggtgct ggcggtgccg gcggtgctgg tggcgccggc aaatattacc    60
gttttctat                                                             69

<210> SEQ ID NO 550
<211> LENGTH: 69
<212> TYPE: DNA
<213> ORGANISM: Artificial Sequence
<220> FEATURE:
<223> OTHER INFORMATION: cDNA Sequence of aMTD144 5'-primer

<400> SEQUENCE: 550
gggtttcata tggcggtgct ggcggtgccg gcggtgctgg tggcgccggc aaatattacc    60
gttttctat                                                             69

<210> SEQ ID NO 551
<211> LENGTH: 69
<212> TYPE: DNA
<213> ORGANISM: Artificial Sequence
<220> FEATURE:
<223> OTHER INFORMATION: cDNA Sequence of aMTD145 5'-primer

<400> SEQUENCE: 551
gggtttcata tgctgctggc ggtggtgccg gcggtggcgc tggcgccggc aaatattacc    60
gttttctat                                                             69

<210> SEQ ID NO 552
<211> LENGTH: 69
<212> TYPE: DNA
<213> ORGANISM: Artificial Sequence
<220> FEATURE:
<223> OTHER INFORMATION: cDNA Sequence of aMTD152 5'-primer

<400> SEQUENCE: 552
gggtttcata tgctggcggc ggcggtggcg gcggtggcgg cgctgctggc aaatattacc    60
gttttctat                                                             69

<210> SEQ ID NO 553
<211> LENGTH: 69
<212> TYPE: DNA
<213> ORGANISM: Artificial Sequence
<220> FEATURE:
<223> OTHER INFORMATION: cDNA Sequence of aMTD159 5'-primer

<400> SEQUENCE: 553
gggtttcata tgtgctatag cggcagcacc agccagaacc agccgccggc aaatattacc    60
gttttctat                                                           69

<210> SEQ ID NO 554
<211> LENGTH: 69
<212> TYPE: DNA
<213> ORGANISM: Artificial Sequence
<220> FEATURE:
<223> OTHER INFORMATION: cDNA Sequence of aMTD161 5'-primer

<400> SEQUENCE: 554
gggtttcata tggcggtgat tgcgctgccg gcgctgattg cggcgccggc aaatattacc    60
gttttctat                                                           69

<210> SEQ ID NO 555
<211> LENGTH: 69
<212> TYPE: DNA
<213> ORGANISM: Artificial Sequence
<220> FEATURE:
<223> OTHER INFORMATION: cDNA Sequence of aMTD162 5'-primer

<400> SEQUENCE: 555
gggtttcata tggcggtggt ggcgctgccg gcggcgctga ttgtgccggc aaatattacc    60
gttttctat                                                           69

<210> SEQ ID NO 556
<211> LENGTH: 69
<212> TYPE: DNA
<213> ORGANISM: Artificial Sequence
<220> FEATURE:
<223> OTHER INFORMATION: cDNA Sequence of aMTD163 5'-primer

<400> SEQUENCE: 556
gggtttcata tgctggcgct ggtgctgccg gcggcgctgg cggcgccggc aaatattacc    60
gttttctat                                                           69

<210> SEQ ID NO 557
<211> LENGTH: 69
<212> TYPE: DNA
<213> ORGANISM: Artificial Sequence
<220> FEATURE:
<223> OTHER INFORMATION: cDNA Sequence of aMTD164 5'-primer

<400> SEQUENCE: 557
gggtttcata tgctggcggc ggtgctgccg gcgctgctgg cggcgccggc aaatattacc    60
gttttctat                                                           69

<210> SEQ ID NO 558
<211> LENGTH: 69
<212> TYPE: DNA
<213> ORGANISM: Artificial Sequence
<220> FEATURE:
<223> OTHER INFORMATION: cDNA Sequence of aMTD165 5'-primer

<400> SEQUENCE: 558

```
gggtttcata tggcgctggc ggtgccggtg gcgctggcga ttgtgccggc aaatattacc    60
gttttctat                                                            69
```

<210> SEQ ID NO 559
<211> LENGTH: 69
<212> TYPE: DNA
<213> ORGANISM: Artificial Sequence
<220> FEATURE:
<223> OTHER INFORMATION: cDNA Sequence of aMTD167 5'-primer

<400> SEQUENCE: 559

```
gggtttcata tggtggcgat tgcgattccg gcggcgctgg cgattccggc aaatattacc    60
gttttctat                                                            69
```

<210> SEQ ID NO 560
<211> LENGTH: 69
<212> TYPE: DNA
<213> ORGANISM: Artificial Sequence
<220> FEATURE:
<223> OTHER INFORMATION: cDNA Sequence of aMTD169 5'-primer

<400> SEQUENCE: 560

```
gggtttcata tggtggcgct ggtggcgccg gcgctgattc tggcgccggc aaatattacc    60
gttttctat                                                            69
```

<210> SEQ ID NO 561
<211> LENGTH: 69
<212> TYPE: DNA
<213> ORGANISM: Artificial Sequence
<220> FEATURE:
<223> OTHER INFORMATION: cDNA Sequence of aMTD182 5'-primer

<400> SEQUENCE: 561

```
gggtttcata tggcgctgat tgcgccggtg gtggcgctgg tggcgccggc aaatattacc    60
gttttctat                                                            69
```

<210> SEQ ID NO 562
<211> LENGTH: 69
<212> TYPE: DNA
<213> ORGANISM: Artificial Sequence
<220> FEATURE:
<223> OTHER INFORMATION: cDNA Sequence of aMTD183 5'-primer

<400> SEQUENCE: 562

```
gggtttcata tgctgctggc ggcgccggtg gtgattgcgc tggcgccggc aaatattacc    60
gttttctat                                                            69
```

<210> SEQ ID NO 563
<211> LENGTH: 69
<212> TYPE: DNA
<213> ORGANISM: Artificial Sequence
<220> FEATURE:
<223> OTHER INFORMATION: cDNA Sequence of aMTD184 5'-primer

<400> SEQUENCE: 563

```
gggtttcata tgctggcggc gattgtgccg gcgattattg cggtgccggc aaatattacc    60
gttttctat                                                            69
```

<210> SEQ ID NO 564
<211> LENGTH: 69
<212> TYPE: DNA
<213> ORGANISM: Artificial Sequence -continued

```
<220> FEATURE:
<223> OTHER INFORMATION: cDNA Sequence of aMTD185 5'-primer

<400> SEQUENCE: 564
gggtttcata tggcggcgct ggtgctgccg ctgattattg cggcgccggc aaatattacc    60
gttttctat                                                           69

<210> SEQ ID NO 565
<211> LENGTH: 69
<212> TYPE: DNA
<213> ORGANISM: Artificial Sequence
<220> FEATURE:
<223> OTHER INFORMATION: cDNA Sequence of aMTD189 5'-primer

<400> SEQUENCE: 565
gggtttcata tggtgattct ggtggcgccg gcggtgattg cgccgccggc aaatattacc    60
gttttctat                                                           69

<210> SEQ ID NO 566
<211> LENGTH: 69
<212> TYPE: DNA
<213> ORGANISM: Artificial Sequence
<220> FEATURE:
<223> OTHER INFORMATION: cDNA Sequence of aMTD190 5'-primer

<400> SEQUENCE: 566
gggtttcata tggcggcgat tctggcgccg gcggtgattg cgccgccggc aaatattacc    60
gttttctat                                                           69

<210> SEQ ID NO 567
<211> LENGTH: 69
<212> TYPE: DNA
<213> ORGANISM: Artificial Sequence
<220> FEATURE:
<223> OTHER INFORMATION: cDNA Sequence of aMTD201 5'-primer

<400> SEQUENCE: 567
gggtttcata tgctggcgct ggcggtgccg gcgctggcgg cgctgccggc aaatattacc    60
gttttctat                                                           69

<210> SEQ ID NO 568
<211> LENGTH: 69
<212> TYPE: DNA
<213> ORGANISM: Artificial Sequence
<220> FEATURE:
<223> OTHER INFORMATION: cDNA Sequence of aMTD204 5'-primer

<400> SEQUENCE: 568
gggtttcata tgctgattgc ggcgctgccg gcggtggcgg cgctgccggc aaatattacc    60
gttttctat                                                           69

<210> SEQ ID NO 569
<211> LENGTH: 69
<212> TYPE: DNA
<213> ORGANISM: Artificial Sequence
<220> FEATURE:
<223> OTHER INFORMATION: cDNA Sequence of aMTD205 5'-primer

<400> SEQUENCE: 569
gggtttcata tggcgctggc gctggtgccg gcgattgcgg cgctgccggc aaatattacc    60
gttttctat                                                           69
```

<210> SEQ ID NO 570
<211> LENGTH: 69
<212> TYPE: DNA
<213> ORGANISM: Artificial Sequence
<220> FEATURE:
<223> OTHER INFORMATION: cDNA Sequence of aMTD210 5'-primer

<400> SEQUENCE: 570
gggtttcata tggcgctgat tgcgctgccg gcgctgccgg cgctgccggc aaatattacc    60
gttttctat                                                           69

<210> SEQ ID NO 571
<211> LENGTH: 69
<212> TYPE: DNA
<213> ORGANISM: Artificial Sequence
<220> FEATURE:
<223> OTHER INFORMATION: cDNA Sequence of aMTD214 5'-primer

<400> SEQUENCE: 571
gggtttcata tggcgctgat tgtggcgccg gcgctgatgg cgctgccggc aaatattacc    60
gttttctat                                                           69

<210> SEQ ID NO 572
<211> LENGTH: 69
<212> TYPE: DNA
<213> ORGANISM: Artificial Sequence
<220> FEATURE:
<223> OTHER INFORMATION: cDNA Sequence of aMTD221 5'-primer

<400> SEQUENCE: 572
gggtttcata tggcggcgat tctggcgccg attgtggcgc tggcgccggc aaatattacc    60
gttttctat                                                           69

<210> SEQ ID NO 573
<211> LENGTH: 69
<212> TYPE: DNA
<213> ORGANISM: Artificial Sequence
<220> FEATURE:
<223> OTHER INFORMATION: cDNA Sequence of aMTD222 5'-primer

<400> SEQUENCE: 573
gggtttcata tggcgctgct gattgcgccg gcggcggtga ttgcgccggc aaatattacc    60
gttttctat                                                           69

<210> SEQ ID NO 574
<211> LENGTH: 69
<212> TYPE: DNA
<213> ORGANISM: Artificial Sequence
<220> FEATURE:
<223> OTHER INFORMATION: cDNA Sequence of aMTD223 5'-primer

<400> SEQUENCE: 574
gggtttcata tggcgattct ggcggtgccg attgcggtgg tggcgccggc aaatattacc    60
gttttctat                                                           69

<210> SEQ ID NO 575
<211> LENGTH: 69
<212> TYPE: DNA
<213> ORGANISM: Artificial Sequence
<220> FEATURE:
<223> OTHER INFORMATION: cDNA Sequence of aMTD224 5'-primer

<400> SEQUENCE: 575

```
gggtttcata tgattctggc ggcggtgccg attgcgctgg cggcgccggc aaatattacc    60
gttttctat                                                           69
```

<210> SEQ ID NO 576
<211> LENGTH: 69
<212> TYPE: DNA
<213> ORGANISM: Artificial Sequence
<220> FEATURE:
<223> OTHER INFORMATION: cDNA Sequence of aMTD225 5'-primer

<400> SEQUENCE: 576

```
gggtttcata tggtggcggc gctgctgccg gcggcggcgg tgctgccggc aaatattacc    60
gttttctat                                                           69
```

<210> SEQ ID NO 577
<211> LENGTH: 69
<212> TYPE: DNA
<213> ORGANISM: Artificial Sequence
<220> FEATURE:
<223> OTHER INFORMATION: cDNA Sequence of aMTD226 5'-primer

<400> SEQUENCE: 577

```
gggtttcata tggcgctggt ggcggcgatt ccggcgctgg cgattccggc aaatattacc    60
gttttctat                                                           69
```

<210> SEQ ID NO 578
<211> LENGTH: 69
<212> TYPE: DNA
<213> ORGANISM: Artificial Sequence
<220> FEATURE:
<223> OTHER INFORMATION: cDNA Sequence of aMTD227 5'-primer

<400> SEQUENCE: 578

```
gggtttcata tgctggcggc gattgtgccg attgcggcgg cggtgccggc aaatattacc    60
gttttctat                                                           69
```

<210> SEQ ID NO 579
<211> LENGTH: 69
<212> TYPE: DNA
<213> ORGANISM: Artificial Sequence
<220> FEATURE:
<223> OTHER INFORMATION: cDNA Sequence of aMTD241 5'-primer

<400> SEQUENCE: 579

```
gggtttcata tggcggcggc ggtggtgccg gtgctgctgg tggcgccggc aaatattacc    60
gttttctat                                                           69
```

<210> SEQ ID NO 580
<211> LENGTH: 69
<212> TYPE: DNA
<213> ORGANISM: Artificial Sequence
<220> FEATURE:
<223> OTHER INFORMATION: cDNA Sequence of aMTD242 5'-primer

<400> SEQUENCE: 580

```
gggtttcata tggcggcgct gctggtgccg gcgctggtgg cggcgccggc aaatattacc    60
gttttctat                                                           69
```

<210> SEQ ID NO 581
<211> LENGTH: 69
<212> TYPE: DNA

<213> ORGANISM: Artificial Sequence
<220> FEATURE:
<223> OTHER INFORMATION: cDNA Sequence of aMTD243 5'-primer

<400> SEQUENCE: 581
gggtttcata tggcggcggt gctgctgccg gtggcgctgg cggcgccggc aaatattacc    60
gttttctat                                                            69

<210> SEQ ID NO 582
<211> LENGTH: 69
<212> TYPE: DNA
<213> ORGANISM: Artificial Sequence
<220> FEATURE:
<223> OTHER INFORMATION: cDNA Sequence of aMTD245 5'-primer

<400> SEQUENCE: 582
gggtttcata tggcggcggc gctggcgccg gtgctggcgc tggtgccggc aaatattacc    60
gttttctat                                                            69

<210> SEQ ID NO 583
<211> LENGTH: 69
<212> TYPE: DNA
<213> ORGANISM: Artificial Sequence
<220> FEATURE:
<223> OTHER INFORMATION: cDNA Sequence of aMTD246 5'-primer

<400> SEQUENCE: 583
gggtttcata tggtggtggc ggtgccgctg ctggtggcgt tgcggcggc aaatattacc     60 gttttctat                                                            69

<210> SEQ ID NO 584
<211> LENGTH: 69
<212> TYPE: DNA
<213> ORGANISM: Artificial Sequence
<220> FEATURE:
<223> OTHER INFORMATION: cDNA Sequence of aMTD248 5'-primer

<400> SEQUENCE: 584
gggtttcata tggtggcggc gattgtgccg attgcggcgc tggtgccggc aaatattacc    60
gttttctat                                                            69

<210> SEQ ID NO 585
<211> LENGTH: 69
<212> TYPE: DNA
<213> ORGANISM: Artificial Sequence
<220> FEATURE:
<223> OTHER INFORMATION: cDNA Sequence of aMTD261 5'-primer

<400> SEQUENCE: 585
gggtttcata tgctggtgct ggtgccgctg ctggcggcgg cggcgccggc aaatattacc    60
gttttctat                                                            69

<210> SEQ ID NO 586
<211> LENGTH: 69
<212> TYPE: DNA
<213> ORGANISM: Artificial Sequence
<220> FEATURE:
<223> OTHER INFORMATION: cDNA Sequence of aMTD262 5'-primer

<400> SEQUENCE: 586
gggtttcata tggcgctgat tgcggtgccg gcgattattg tggcgccggc aaatattacc    60
gttttctat                                                            69

<210> SEQ ID NO 587
<211> LENGTH: 69
<212> TYPE: DNA
<213> ORGANISM: Artificial Sequence
<220> FEATURE:
<223> OTHER INFORMATION: cDNA Sequence of aMTD263 5'-primer

<400> SEQUENCE: 587
gggtttcata tggcgctggc ggtgattccg gcggcggcga ttctgccggc aaatattacc      60
gttttctat                                                              69

<210> SEQ ID NO 588
<211> LENGTH: 69
<212> TYPE: DNA
<213> ORGANISM: Artificial Sequence
<220> FEATURE:
<223> OTHER INFORMATION: cDNA Sequence of aMTD264 5'-primer

<400> SEQUENCE: 588
gggtttcata tgctggcggc ggcgccggtg gtgattgtga ttgcgccggc aaatattacc      60
gttttctat                                                              69

<210> SEQ ID NO 589
<211> LENGTH: 69
<212> TYPE: DNA
<213> ORGANISM: Artificial Sequence
<220> FEATURE:
<223> OTHER INFORMATION: cDNA Sequence of aMTD265 5'-primer

<400> SEQUENCE: 589
gggtttcata tggtgctggc gattgcgccg ctgctggcgg cggtgccggc aaatattacc      60
gttttctat                                                              69

<210> SEQ ID NO 590
<211> LENGTH: 69
<212> TYPE: DNA
<213> ORGANISM: Artificial Sequence
<220> FEATURE:
<223> OTHER INFORMATION: cDNA Sequence of aMTD281 5'-primer

<400> SEQUENCE: 590
gggtttcata tggcgctgat tgtgctgccg gcggcggtgg cggtgccggc aaatattacc      60
gttttctat                                                              69

<210> SEQ ID NO 591
<211> LENGTH: 69
<212> TYPE: DNA
<213> ORGANISM: Artificial Sequence
<220> FEATURE:
<223> OTHER INFORMATION: cDNA Sequence of aMTD282 5'-primer

<400> SEQUENCE: 591
gggtttcata tggtgctggc ggtggcgccg gcgctgattg tggcgccggc aaatattacc      60
gttttctat                                                              69

<210> SEQ ID NO 592
<211> LENGTH: 69
<212> TYPE: DNA
<213> ORGANISM: Artificial Sequence
<220> FEATURE:
<223> OTHER INFORMATION: cDNA Sequence of aMTD283 5'-primer

```
<400> SEQUENCE: 592
gggtttcata tggcggcgct gctggcgccg gcgctgattg tggcgccggc aaatattacc      60
gttttctat                                                              69

<210> SEQ ID NO 593
<211> LENGTH: 69
<212> TYPE: DNA
<213> ORGANISM: Artificial Sequence
<220> FEATURE:
<223> OTHER INFORMATION: cDNA Sequence of aMTD284 5'-primer

<400> SEQUENCE: 593
gggtttcata tggcgctgat tgcgccggcg gtggcgctga ttgtgccggc aaatattacc      60
gttttctat                                                              69

<210> SEQ ID NO 594
<211> LENGTH: 69
<212> TYPE: DNA
<213> ORGANISM: Artificial Sequence
<220> FEATURE:
<223> OTHER INFORMATION: cDNA Sequence of aMTD285 5'-primer

<400> SEQUENCE: 594
gggtttcata tggcgattgt gctgctgccg gcggcggtgg tggcgccggc aaatattacc      60
gttttctat                                                              69

<210> SEQ ID NO 595
<211> LENGTH: 69
<212> TYPE: DNA
<213> ORGANISM: Artificial Sequence
<220> FEATURE:
<223> OTHER INFORMATION: cDNA Sequence of aMTD301 5'-primer

<400> SEQUENCE: 595
gggtttcata tggtgattgc ggcgccggtg ctggcggtgc tggcgccggc aaatattacc      60
gttttctat                                                              69

<210> SEQ ID NO 596
<211> LENGTH: 69
<212> TYPE: DNA
<213> ORGANISM: Artificial Sequence
<220> FEATURE:
<223> OTHER INFORMATION: cDNA Sequence of aMTD302 5'-primer

<400> SEQUENCE: 596
gggtttcata tgctggcgct ggcgccggcg ctggcgctgc tggcgccggc aaatattacc      60
gttttctat                                                              69

<210> SEQ ID NO 597
<211> LENGTH: 69
<212> TYPE: DNA
<213> ORGANISM: Artificial Sequence
<220> FEATURE:
<223> OTHER INFORMATION: cDNA Sequence of aMTD304 5'-primer

<400> SEQUENCE: 597
gggtttcata tggcgattat tctggcgccg attgcggcga ttgcgccggc aaatattacc      60
gttttctat                                                              69

<210> SEQ ID NO 598
<211> LENGTH: 69
```

```
<212> TYPE: DNA
<213> ORGANISM: Artificial Sequence
<220> FEATURE:
<223> OTHER INFORMATION: cDNA Sequence of aMTD305 5'-primer

<400> SEQUENCE: 598
gggtttcata tgattgcgct ggcggcgccg attctgctgg cggcgccggc aaatattacc      60
gttttctat                                                             69

<210> SEQ ID NO 599
<211> LENGTH: 69
<212> TYPE: DNA
<213> ORGANISM: Artificial Sequence
<220> FEATURE:
<223> OTHER INFORMATION: cDNA Sequence of aMTD321 5'-primer

<400> SEQUENCE: 599
gggtttcata tgattgtggc ggtggcgctg ccggcgctgg cggtgccggc aaatattacc      60
gttttctat                                                             69

<210> SEQ ID NO 600
<211> LENGTH: 69
<212> TYPE: DNA
<213> ORGANISM: Artificial Sequence
<220> FEATURE:
<223> OTHER INFORMATION: cDNA Sequence of aMTD322 5'-primer

<400> SEQUENCE: 600
gggtttcata tggtggtggc gattgtgctg ccggcgctgg cggcgccggc aaatattacc      60
gttttctat                                                             69

<210> SEQ ID NO 601
<211> LENGTH: 69
<212> TYPE: DNA
<213> ORGANISM: Artificial Sequence
<220> FEATURE:
<223> OTHER INFORMATION: cDNA Sequence of aMTD323 5'-primer

<400> SEQUENCE: 601
gggtttcata tgattgtggc ggtggcgctg ccggtggcgc tggcgccggc aaatattacc      60
gttttctat                                                             69

<210> SEQ ID NO 602
<211> LENGTH: 69
<212> TYPE: DNA
<213> ORGANISM: Artificial Sequence
<220> FEATURE:
<223> OTHER INFORMATION: cDNA Sequence of aMTD324 5'-primer

<400> SEQUENCE: 602
gggtttcata tgattgtggc ggtggcgctg ccggcggcgc tggtgccggc aaatattacc      60
gttttctat                                                             69

<210> SEQ ID NO 603
<211> LENGTH: 69
<212> TYPE: DNA
<213> ORGANISM: Artificial Sequence
<220> FEATURE:
<223> OTHER INFORMATION: cDNA Sequence of aMTD325 5'-primer

<400> SEQUENCE: 603
gggtttcata tgattgtggc ggtggcgctg ccggcggtgg cgctgccggc aaatattacc      60
``` gttttctat 69

<210> SEQ ID NO 604
<211> LENGTH: 69
<212> TYPE: DNA
<213> ORGANISM: Artificial Sequence
<220> FEATURE:
<223> OTHER INFORMATION: cDNA Sequence of aMTD329 5'-primer

<400> SEQUENCE: 604
gggtttcata tgctgccggt gctggtgccg gtggtgccgg tggtgccggc aaatattacc    60
gttttctat                                                           69

<210> SEQ ID NO 605
<211> LENGTH: 69
<212> TYPE: DNA
<213> ORGANISM: Artificial Sequence
<220> FEATURE:
<223> OTHER INFORMATION: cDNA Sequence of aMTD331 5'-primer

<400> SEQUENCE: 605
gggtttcata tggtgccggt gctggtgccg ctggtgccgg tggtgccggc aaatattacc    60
gttttctat                                                           69

<210> SEQ ID NO 606
<211> LENGTH: 69
<212> TYPE: DNA
<213> ORGANISM: Artificial Sequence
<220> FEATURE:
<223> OTHER INFORMATION: cDNA Sequence of aMTD341 5'-primer

<400> SEQUENCE: 606
gggtttcata tgattgtggc ggtggcgctg ccggcggtgc tggcgccggc aaatattacc    60
gttttctat                                                           69

<210> SEQ ID NO 607
<211> LENGTH: 69
<212> TYPE: DNA
<213> ORGANISM: Artificial Sequence
<220> FEATURE:
<223> OTHER INFORMATION: cDNA Sequence of aMTD342 5'-primer

<400> SEQUENCE: 607
gggtttcata tggtgattgt ggcgctggcg ccggcggtgc tggcgccggc aaatattacc    60
gttttctat                                                           69

<210> SEQ ID NO 608
<211> LENGTH: 69
<212> TYPE: DNA
<213> ORGANISM: Artificial Sequence
<220> FEATURE:
<223> OTHER INFORMATION: cDNA Sequence of aMTD343 5'-primer

<400> SEQUENCE: 608
gggtttcata tgattgtggc ggtggcgctg ccggcgctgg tggcgccggc aaatattacc    60
gttttctat                                                           69

<210> SEQ ID NO 609
<211> LENGTH: 69
<212> TYPE: DNA
<213> ORGANISM: Artificial Sequence
<220> FEATURE:
<223> OTHER INFORMATION: cDNA Sequence of aMTD345 5'-primer -continued

<400> SEQUENCE: 609
gggtttcata tggcgctgct gattgtggcg ccggtggcgg tggcgccggc aaatattacc    60
gttttctat                                                            69

<210> SEQ ID NO 610
<211> LENGTH: 69
<212> TYPE: DNA
<213> ORGANISM: Artificial Sequence
<220> FEATURE:
<223> OTHER INFORMATION: cDNA Sequence of aMTD349 5'-primer

<400> SEQUENCE: 610
gggtttcata tggtgccggt gctggtgccg gtggtgccgg tggtgccggc aaatattacc    60
gttttctat                                                            69

<210> SEQ ID NO 611
<211> LENGTH: 69
<212> TYPE: DNA
<213> ORGANISM: Artificial Sequence
<220> FEATURE:
<223> OTHER INFORMATION: cDNA Sequence of aMTD350 5'-primer

<400> SEQUENCE: 611
gggtttcata tggtgccgat tctggtgccg gtggtgccgg tggtgccggc aaatattacc    60
gttttctat                                                            69

<210> SEQ ID NO 612
<211> LENGTH: 69
<212> TYPE: DNA
<213> ORGANISM: Artificial Sequence
<220> FEATURE:
<223> OTHER INFORMATION: cDNA Sequence of aMTD361 5'-primer

<400> SEQUENCE: 612
gggtttcata tggcggtggt gattgtggcg ccggcggtga ttgcgccggc aaatattacc    60
gttttctat                                                            69

<210> SEQ ID NO 613
<211> LENGTH: 69
<212> TYPE: DNA
<213> ORGANISM: Artificial Sequence
<220> FEATURE:
<223> OTHER INFORMATION: cDNA Sequence of aMTD363 5'-primer

<400> SEQUENCE: 613
gggtttcata tggcggtgct ggcggtggcg ccggcgctga ttgtgccggc aaatattacc    60
gttttctat                                                            69

<210> SEQ ID NO 614
<211> LENGTH: 69
<212> TYPE: DNA
<213> ORGANISM: Artificial Sequence
<220> FEATURE:
<223> OTHER INFORMATION: cDNA Sequence of aMTD364 5'-primer

<400> SEQUENCE: 614
gggtttcata tgctggtggc ggcggtggcg ccggcgctga ttgtgccggc aaatattacc    60
gttttctat                                                            69

<210> SEQ ID NO 615

```
<211> LENGTH: 69
<212> TYPE: DNA
<213> ORGANISM: Artificial Sequence
<220> FEATURE:
<223> OTHER INFORMATION: cDNA Sequence of aMTD365 5'-primer

<400> SEQUENCE: 615
gggtttcata tggcggtgat tgtggtggcg ccggcgctgc tggcgccggc aaatattacc      60
gttttctat                                                              69

<210> SEQ ID NO 616
<211> LENGTH: 69
<212> TYPE: DNA
<213> ORGANISM: Artificial Sequence
<220> FEATURE:
<223> OTHER INFORMATION: cDNA Sequence of aMTD381 5'-primer

<400> SEQUENCE: 616
gggtttcata tggtggtggc gattgtgctg ccggcggtgg cggcgccggc aaatattacc      60
gttttctat                                                              69

<210> SEQ ID NO 617
<211> LENGTH: 69
<212> TYPE: DNA
<213> ORGANISM: Artificial Sequence
<220> FEATURE:
<223> OTHER INFORMATION: cDNA Sequence of aMTD382 5'-primer

<400> SEQUENCE: 617
gggtttcata tggcggcggc gctggtgatt ccggcgattc tggcgccggc aaatattacc      60
gttttctat                                                              69

<210> SEQ ID NO 618
<211> LENGTH: 69
<212> TYPE: DNA
<213> ORGANISM: Artificial Sequence
<220> FEATURE:
<223> OTHER INFORMATION: cDNA Sequence of aMTD383 5'-primer

<400> SEQUENCE: 618
gggtttcata tggtgattgt ggcgctggcg ccggcgctgc tggcgccggc aaatattacc      60
gttttctat                                                              69

<210> SEQ ID NO 619
<211> LENGTH: 69
<212> TYPE: DNA
<213> ORGANISM: Artificial Sequence
<220> FEATURE:
<223> OTHER INFORMATION: cDNA Sequence of aMTD384 5'-primer

<400> SEQUENCE: 619
gggtttcata tggtgattgt ggcgattgcg ccggcgctgc tggcgccggc aaatattacc      60
gttttctat                                                              69

<210> SEQ ID NO 620
<211> LENGTH: 69
<212> TYPE: DNA
<213> ORGANISM: Artificial Sequence
<220> FEATURE:
<223> OTHER INFORMATION: cDNA Sequence of aMTD385 5'-primer

<400> SEQUENCE: 620
gggtttcata tgattgtggc gattgcggtg ccggcgctgg tggcgccggc aaatattacc      60
``` gttttctat 69

<210> SEQ ID NO 621
<211> LENGTH: 69
<212> TYPE: DNA
<213> ORGANISM: Artificial Sequence
<220> FEATURE:
<223> OTHER INFORMATION: cDNA Sequence of aMTD390 5'-primer

<400> SEQUENCE: 621
gggtttcata tggtgccgct gctggtgccg gtggtgccgg tggtgccggc aaatattacc    60
gttttctat                                                            69

<210> SEQ ID NO 622
<211> LENGTH: 69
<212> TYPE: DNA
<213> ORGANISM: Artificial Sequence
<220> FEATURE:
<223> OTHER INFORMATION: cDNA Sequence of aMTD401 5'-primer

<400> SEQUENCE: 622
gggtttcata tggcggcgct ggcggtgatt ccggcggcga ttctgccggc aaatattacc    60
gttttctat                                                            69

<210> SEQ ID NO 623
<211> LENGTH: 69
<212> TYPE: DNA
<213> ORGANISM: Artificial Sequence
<220> FEATURE:
<223> OTHER INFORMATION: cDNA Sequence of aMTD402 5'-primer

<400> SEQUENCE: 623
gggtttcata tggcgctggc ggcggtgatt ccggcggcga ttctgccggc aaatattacc    60
gttttctat                                                            69

<210> SEQ ID NO 624
<211> LENGTH: 69
<212> TYPE: DNA
<213> ORGANISM: Artificial Sequence
<220> FEATURE:
<223> OTHER INFORMATION: cDNA Sequence of aMTD403 5'-primer

<400> SEQUENCE: 624
gggtttcata tggcggcggc gctggtgatt ccggcggcga ttctgccggc aaatattacc    60
gttttctat                                                            69

<210> SEQ ID NO 625
<211> LENGTH: 69
<212> TYPE: DNA
<213> ORGANISM: Artificial Sequence
<220> FEATURE:
<223> OTHER INFORMATION: cDNA Sequence of aMTD404 5'-primer

<400> SEQUENCE: 625
gggtttcata tgctggcggc ggcggtgatt ccggcggcga ttctgccggc aaatattacc    60
gttttctat                                                            69

<210> SEQ ID NO 626
<211> LENGTH: 69
<212> TYPE: DNA
<213> ORGANISM: Artificial Sequence
<220> FEATURE:

```
<223> OTHER INFORMATION: cDNA Sequence of aMTD405 5'-primer

<400> SEQUENCE: 626
gggtttcata tgctggcggc ggcggtgatt ccggtggcga ttctgccggc aaatattacc    60
gttttctat                                                            69

<210> SEQ ID NO 627
<211> LENGTH: 69
<212> TYPE: DNA
<213> ORGANISM: Artificial Sequence
<220> FEATURE:
<223> OTHER INFORMATION: cDNA Sequence of aMTD421 5'-primer

<400> SEQUENCE: 627
gggtttcata tggcggcgat tctggcggcg ccgctgattg cggtgccggc aaatattacc    60
gttttctat                                                            69

<210> SEQ ID NO 628
<211> LENGTH: 69
<212> TYPE: DNA
<213> ORGANISM: Artificial Sequence
<220> FEATURE:
<223> OTHER INFORMATION: cDNA Sequence of aMTD422 5'-primer

<400> SEQUENCE: 628
gggtttcata tggtggtggc gattctggcg ccgctgctgg cggcgccggc aaatattacc    60
gttttctat                                                            69

<210> SEQ ID NO 629
<211> LENGTH: 69
<212> TYPE: DNA
<213> ORGANISM: Artificial Sequence
<220> FEATURE:
<223> OTHER INFORMATION: cDNA Sequence of aMTD424 5'-primer

<400> SEQUENCE: 629
gggtttcata tggcggtggt ggtggcggcg ccggtgctgg cgctgccggc aaatattacc    60
gttttctat                                                            69

<210> SEQ ID NO 630
<211> LENGTH: 69
<212> TYPE: DNA
<213> ORGANISM: Artificial Sequence
<220> FEATURE:
<223> OTHER INFORMATION: cDNA Sequence of aMTD425 5'-primer

<400> SEQUENCE: 630
gggtttcata tggcggtggt ggcgattgcg ccggtgctgg cgctgccggc aaatattacc    60
gttttctat                                                            69

<210> SEQ ID NO 631
<211> LENGTH: 69
<212> TYPE: DNA
<213> ORGANISM: Artificial Sequence
<220> FEATURE:
<223> OTHER INFORMATION: cDNA Sequence of aMTD426 5'-primer

<400> SEQUENCE: 631
gggtttcata tggcggcggc gctggcgatt ccgctggcga ttattccggc aaatattacc    60
gttttctat                                                            69
```

```
<210> SEQ ID NO 632
<211> LENGTH: 69
<212> TYPE: DNA
<213> ORGANISM: Artificial Sequence
<220> FEATURE:
<223> OTHER INFORMATION: cDNA Sequence of aMTD436 5'-primer

<400> SEQUENCE: 632
gggtttcata tggcggtggt gctggtgatt atgccggcgg cgattccggc aaatattacc    60
gttttctat                                                           69

<210> SEQ ID NO 633
<211> LENGTH: 69
<212> TYPE: DNA
<213> ORGANISM: Artificial Sequence
<220> FEATURE:
<223> OTHER INFORMATION: cDNA Sequence of aMTD442 5'-primer

<400> SEQUENCE: 633
gggtttcata tggcgctggc ggcgctggtg ccggcggtgc tggtgccggc aaatattacc    60
gttttctat                                                           69

<210> SEQ ID NO 634
<211> LENGTH: 69
<212> TYPE: DNA
<213> ORGANISM: Artificial Sequence
<220> FEATURE:
<223> OTHER INFORMATION: cDNA Sequence of aMTD443 5'-primer

<400> SEQUENCE: 634
gggtttcata tggcgctggc ggcgctggtg ccggtggcgc tggtgccggc aaatattacc    60
gttttctat                                                           69

<210> SEQ ID NO 635
<211> LENGTH: 69
<212> TYPE: DNA
<213> ORGANISM: Artificial Sequence
<220> FEATURE:
<223> OTHER INFORMATION: cDNA Sequence of aMTD444 5'-primer

<400> SEQUENCE: 635
gggtttcata tgctggcggc ggcgctggtg ccggtggcgc tggtgccggc aaatattacc    60
gttttctat                                                           69

<210> SEQ ID NO 636
<211> LENGTH: 69
<212> TYPE: DNA
<213> ORGANISM: Artificial Sequence
<220> FEATURE:
<223> OTHER INFORMATION: cDNA Sequence of aMTD445 5'-primer

<400> SEQUENCE: 636
gggtttcata tggcgctggc ggcgctggtg ccggcgctgg tggtgccggc aaatattacc    60
gttttctat                                                           69

<210> SEQ ID NO 637
<211> LENGTH: 69
<212> TYPE: DNA
<213> ORGANISM: Artificial Sequence
<220> FEATURE:
<223> OTHER INFORMATION: cDNA Sequence of aMTD461 5'-primer

<400> SEQUENCE: 637
```

```
gggtttcata tgattgcggc ggtgattgtg ccggcggtgg cgctgccggc aaatattacc    60
gttttctat                                                             69

<210> SEQ ID NO 638
<211> LENGTH: 69
<212> TYPE: DNA
<213> ORGANISM: Artificial Sequence
<220> FEATURE:
<223> OTHER INFORMATION: cDNA Sequence of aMTD462 5'-primer

<400> SEQUENCE: 638
gggtttcata tgattgcggc ggtgctggtg ccggcggtgg cgctgccggc aaatattacc    60
gttttctat                                                             69

<210> SEQ ID NO 639
<211> LENGTH: 69
<212> TYPE: DNA
<213> ORGANISM: Artificial Sequence
<220> FEATURE:
<223> OTHER INFORMATION: cDNA Sequence of aMTD463 5'-primer

<400> SEQUENCE: 639
gggtttcata tggcggtggc gattctggtg ccgctgctgg cggcgccggc aaatattacc    60
gttttctat                                                             69

<210> SEQ ID NO 640
<211> LENGTH: 69
<212> TYPE: DNA
<213> ORGANISM: Artificial Sequence
<220> FEATURE:
<223> OTHER INFORMATION: cDNA Sequence of aMTD464 5'-primer

<400> SEQUENCE: 640
gggtttcata tggcggtggt gattctggtg ccgctggcgg cggcgccggc aaatattacc    60
gttttctat                                                             69

<210> SEQ ID NO 641
<211> LENGTH: 69
<212> TYPE: DNA
<213> ORGANISM: Artificial Sequence
<220> FEATURE:
<223> OTHER INFORMATION: cDNA Sequence of aMTD465 5'-primer

<400> SEQUENCE: 641
gggtttcata tgattgcggc ggtgattgtg ccggtggcgg cgctgccggc aaatattacc    60
gttttctat                                                             69

<210> SEQ ID NO 642
<211> LENGTH: 69
<212> TYPE: DNA
<213> ORGANISM: Artificial Sequence
<220> FEATURE:
<223> OTHER INFORMATION: cDNA Sequence of aMTD466 5'-primer

<400> SEQUENCE: 642
gggtttcata tgattattgc ggcggcggcg ccgctggcga ttattccggc aaatattacc    60
gttttctat                                                             69

<210> SEQ ID NO 643
<211> LENGTH: 69
<212> TYPE: DNA
<213> ORGANISM: Artificial Sequence
```

```
<220> FEATURE:
<223> OTHER INFORMATION: cDNA Sequence of aMTD481 5'-primer

<400> SEQUENCE: 643
gggtttcata tggcgattgc gattgcgatt gtgccggtgg cgctgccggc aaatattacc    60
gttttctat                                                           69

<210> SEQ ID NO 644
<211> LENGTH: 69
<212> TYPE: DNA
<213> ORGANISM: Artificial Sequence
<220> FEATURE:
<223> OTHER INFORMATION: cDNA Sequence of aMTD482 5'-primer

<400> SEQUENCE: 644
gggtttcata tgattctggc ggtggcggcg attccggtgg cggtgccggc aaatattacc    60
gttttctat                                                           69

<210> SEQ ID NO 645
<211> LENGTH: 69
<212> TYPE: DNA
<213> ORGANISM: Artificial Sequence
<220> FEATURE:
<223> OTHER INFORMATION: cDNA Sequence of aMTD483 5'-primer

<400> SEQUENCE: 645
gggtttcata tgattctggc ggcggcgatt attccggcgg cgctgccggc aaatattacc    60
gttttctat                                                           69

<210> SEQ ID NO 646
<211> LENGTH: 69
<212> TYPE: DNA
<213> ORGANISM: Artificial Sequence
<220> FEATURE:
<223> OTHER INFORMATION: cDNA Sequence of aMTD484 5'-primer

<400> SEQUENCE: 646
gggtttcata tgctggcggt ggtgctggcg gcgccggcga ttgtgccggc aaatattacc    60
gttttctat                                                           69

<210> SEQ ID NO 647
<211> LENGTH: 69
<212> TYPE: DNA
<213> ORGANISM: Artificial Sequence
<220> FEATURE:
<223> OTHER INFORMATION: cDNA Sequence of aMTD485 5'-primer

<400> SEQUENCE: 647
gggtttcata tggcgattct ggcggcgatt gtgccgctgg cggtgccggc aaatattacc    60
gttttctat                                                           69

<210> SEQ ID NO 648
<211> LENGTH: 69
<212> TYPE: DNA
<213> ORGANISM: Artificial Sequence
<220> FEATURE:
<223> OTHER INFORMATION: cDNA Sequence of aMTD501 5'-primer

<400> SEQUENCE: 648
gggtttcata tggtgattgt ggcgctggcg gtgccggcgc tggcgccggc aaatattacc    60
gttttctat                                                           69
```

<210> SEQ ID NO 649
<211> LENGTH: 69
<212> TYPE: DNA
<213> ORGANISM: Artificial Sequence
<220> FEATURE:
<223> OTHER INFORMATION: cDNA Sequence of aMTD502 5'-primer

<400> SEQUENCE: 649
gggtttcata tggcgattgt ggcgctggcg gtgccggtgc tggcgccggc aaatattacc    60
gttttctat                                                           69

<210> SEQ ID NO 650
<211> LENGTH: 69
<212> TYPE: DNA
<213> ORGANISM: Artificial Sequence
<220> FEATURE:
<223> OTHER INFORMATION: cDNA Sequence of aMTD503 5'-primer

<400> SEQUENCE: 650
gggtttcata tggcggcgat tattattgtg ctgccggcgg cgctgccggc aaatattacc    60
gttttctat                                                           69

<210> SEQ ID NO 651
<211> LENGTH: 69
<212> TYPE: DNA
<213> ORGANISM: Artificial Sequence
<220> FEATURE:
<223> OTHER INFORMATION: cDNA Sequence of aMTD504 5'-primer

<400> SEQUENCE: 651
gggtttcata tgctgattgt ggcgctggcg gtgccggcgc tggcgccggc aaatattacc    60
gttttctat                                                           69

<210> SEQ ID NO 652
<211> LENGTH: 69
<212> TYPE: DNA
<213> ORGANISM: Artificial Sequence
<220> FEATURE:
<223> OTHER INFORMATION: cDNA Sequence of aMTD505 5'-primer

<400> SEQUENCE: 652
gggtttcata tggcgattat tattgtgatt gcgccggcgg cggcgccggc aaatattacc    60
gttttctat                                                           69

<210> SEQ ID NO 653
<211> LENGTH: 69
<212> TYPE: DNA
<213> ORGANISM: Artificial Sequence
<220> FEATURE:
<223> OTHER INFORMATION: cDNA Sequence of aMTD521 5'-primer

<400> SEQUENCE: 653
gggtttcata tgctggcggc gctgattgtg gtgccggcgg tggcgccggc aaatattacc    60
gttttctat                                                           69

<210> SEQ ID NO 654
<211> LENGTH: 69
<212> TYPE: DNA
<213> ORGANISM: Artificial Sequence
<220> FEATURE:
<223> OTHER INFORMATION: cDNA Sequence of aMTD522 5'-primer

<400> SEQUENCE: 654

-continued

```
gggtttcata tggcgctgct ggtgattgcg gtgccggcgg tggcgccggc aaatattacc    60
gttttctat                                                            69

<210> SEQ ID NO 655
<211> LENGTH: 69
<212> TYPE: DNA
<213> ORGANISM: Artificial Sequence
<220> FEATURE:
<223> OTHER INFORMATION: cDNA Sequence of aMTD524 5'-primer

<400> SEQUENCE: 655
gggtttcata tggcggtggc gctgattgtg gtgccggcgc tggcgccggc aaatattacc    60
gttttctat                                                            69

<210> SEQ ID NO 656
<211> LENGTH: 69
<212> TYPE: DNA
<213> ORGANISM: Artificial Sequence
<220> FEATURE:
<223> OTHER INFORMATION: cDNA Sequence of aMTD525 5'-primer

<400> SEQUENCE: 656
gggtttcata tggcgctggc gattgtggtg gcgccggtgg cggtgccggc aaatattacc    60
gttttctat                                                            69

<210> SEQ ID NO 657
<211> LENGTH: 69
<212> TYPE: DNA
<213> ORGANISM: Artificial Sequence
<220> FEATURE:
<223> OTHER INFORMATION: cDNA Sequence of aMTD527 5'-primer

<400> SEQUENCE: 657
gggtttcata tgctggtgct ggcggcggtg gcgccgattg cgattccggc aaatattacc    60
gttttctat                                                            69

<210> SEQ ID NO 658
<211> LENGTH: 69
<212> TYPE: DNA
<213> ORGANISM: Artificial Sequence
<220> FEATURE:
<223> OTHER INFORMATION: cDNA Sequence of aMTD541 5'-primer

<400> SEQUENCE: 658
gggtttcata tgctgctggc gctgattatt gcgccggcgg cggcgccggc aaatattacc    60
gttttctat                                                            69

<210> SEQ ID NO 659
<211> LENGTH: 69
<212> TYPE: DNA
<213> ORGANISM: Artificial Sequence
<220> FEATURE:
<223> OTHER INFORMATION: cDNA Sequence of aMTD542 5'-primer

<400> SEQUENCE: 659
gggtttcata tggcgctggc gctgattatt gtgccggcgg tggcgccggc aaatattacc    60
gttttctat                                                            69

<210> SEQ ID NO 660
<211> LENGTH: 69
<212> TYPE: DNA
```

```
<213> ORGANISM: Artificial Sequence
<220> FEATURE:
<223> OTHER INFORMATION: cDNA Sequence of aMTD543 5'-primer

<400> SEQUENCE: 660
gggtttcata tgctgctggc ggcgctgatt gcgccggcgg cgctgccggc aaatattacc    60
gttttctat                                                            69

<210> SEQ ID NO 661
<211> LENGTH: 69
<212> TYPE: DNA
<213> ORGANISM: Artificial Sequence
<220> FEATURE:
<223> OTHER INFORMATION: cDNA Sequence of aMTD544 5'-primer

<400> SEQUENCE: 661
gggtttcata tgattgtggc gctgattgtg gcgccggcgg cggtgccggc aaatattacc    60
gttttctat                                                            69

<210> SEQ ID NO 662
<211> LENGTH: 69
<212> TYPE: DNA
<213> ORGANISM: Artificial Sequence
<220> FEATURE:
<223> OTHER INFORMATION: cDNA Sequence of aMTD545 5'-primer

<400> SEQUENCE: 662
gggtttcata tggtggtgct ggtgctggcg gcgccggcgg cggtgccggc aaatattacc    60
gttttctat                                                            69

<210> SEQ ID NO 663
<211> LENGTH: 69
<212> TYPE: DNA
<213> ORGANISM: Artificial Sequence
<220> FEATURE:
<223> OTHER INFORMATION: cDNA Sequence of aMTD561 5'-primer

<400> SEQUENCE: 663
gggtttcata tggcggcggt ggcgattgtg ctgccggcgg tggtgccggc aaatattacc    60
gttttctat                                                            69

<210> SEQ ID NO 664
<211> LENGTH: 69
<212> TYPE: DNA
<213> ORGANISM: Artificial Sequence
<220> FEATURE:
<223> OTHER INFORMATION: cDNA Sequence of aMTD562 5'-primer

<400> SEQUENCE: 664
gggtttcata tggcgctgat tgcggcgatt gtgccggcgc tggtgccggc aaatattacc    60
gttttctat                                                            69

<210> SEQ ID NO 665
<211> LENGTH: 69
<212> TYPE: DNA
<213> ORGANISM: Artificial Sequence
<220> FEATURE:
<223> OTHER INFORMATION: cDNA Sequence of aMTD563 5'-primer

<400> SEQUENCE: 665
gggtttcata tggcgctggc ggtgattgtg gtgccggcgc tggcgccggc aaatattacc    60
gttttctat                                                            69
```

<210> SEQ ID NO 666
<211> LENGTH: 69
<212> TYPE: DNA
<213> ORGANISM: Artificial Sequence
<220> FEATURE:
<223> OTHER INFORMATION: cDNA Sequence of aMTD564 5'-primer

<400> SEQUENCE: 666
gggtttcata tggtggcgat tgcgctgatt gtgccggcgc tggcgccggc aaatattacc    60
gttttctat                                                            69

<210> SEQ ID NO 667
<211> LENGTH: 69
<212> TYPE: DNA
<213> ORGANISM: Artificial Sequence
<220> FEATURE:
<223> OTHER INFORMATION: cDNA Sequence of aMTD565 5'-primer

<400> SEQUENCE: 667
gggtttcata tggtggcgat tgtgctggtg gcgccggcgg tggcgccggc aaatattacc    60
gttttctat                                                            69

<210> SEQ ID NO 668
<211> LENGTH: 69
<212> TYPE: DNA
<213> ORGANISM: Artificial Sequence
<220> FEATURE:
<223> OTHER INFORMATION: cDNA Sequence of aMTD577 5'-primer

<400> SEQUENCE: 668
gggtttcata tggcggcggt gctgattgtg ccgattatgg tgatgccggc aaatattacc    60
gttttctat                                                            69

<210> SEQ ID NO 669
<211> LENGTH: 69
<212> TYPE: DNA
<213> ORGANISM: Artificial Sequence
<220> FEATURE:
<223> OTHER INFORMATION: cDNA Sequence of aMTD582 5'-primer

<400> SEQUENCE: 669
gggtttcata tggtggcggt ggcgctgatt gtgccggcgc tggcgccggc aaatattacc    60
gttttctat                                                            69

<210> SEQ ID NO 670
<211> LENGTH: 69
<212> TYPE: DNA
<213> ORGANISM: Artificial Sequence
<220> FEATURE:
<223> OTHER INFORMATION: cDNA Sequence of aMTD583 5'-primer

<400> SEQUENCE: 670
gggtttcata tggcggtgat tctggcgctg gcgccgattg tggcgccggc aaatattacc    60
gttttctat                                                            69

<210> SEQ ID NO 671
<211> LENGTH: 69
<212> TYPE: DNA
<213> ORGANISM: Artificial Sequence
<220> FEATURE:
<223> OTHER INFORMATION: cDNA Sequence of aMTD585 5'-primer

<400> SEQUENCE: 671
gggtttcata tggcgctgat tgtggcgatt gcgccggcgc tggtgccggc aaatattacc    60
gttttctat                                                           69

<210> SEQ ID NO 672
<211> LENGTH: 69
<212> TYPE: DNA
<213> ORGANISM: Artificial Sequence
<220> FEATURE:
<223> OTHER INFORMATION: cDNA Sequence of aMTD601 5'-primer

<400> SEQUENCE: 672
gggtttcata tggcggcgat tctgattgcg gtgccgattg cggcgccggc aaatattacc    60
gttttctat                                                           69

<210> SEQ ID NO 673
<211> LENGTH: 69
<212> TYPE: DNA
<213> ORGANISM: Artificial Sequence
<220> FEATURE:
<223> OTHER INFORMATION: cDNA Sequence of aMTD602 5'-primer

<400> SEQUENCE: 673
gggtttcata tggtgattgt ggcgctggcg gcgccggtgc tggcgccggc aaatattacc    60
gttttctat                                                           69

<210> SEQ ID NO 674
<211> LENGTH: 69
<212> TYPE: DNA
<213> ORGANISM: Artificial Sequence
<220> FEATURE:
<223> OTHER INFORMATION: cDNA Sequence of aMTD603 5'-primer

<400> SEQUENCE: 674
gggtttcata tggtgctggt ggcgctggcg gcgccggtga ttgcgccggc aaatattacc    60
gttttctat                                                           69

<210> SEQ ID NO 675
<211> LENGTH: 69
<212> TYPE: DNA
<213> ORGANISM: Artificial Sequence
<220> FEATURE:
<223> OTHER INFORMATION: cDNA Sequence of aMTD604 5'-primer

<400> SEQUENCE: 675
gggtttcata tggtggcgct gattgcggtg gcgccggcgg tggtgccggc aaatattacc    60
gttttctat                                                           69

<210> SEQ ID NO 676
<211> LENGTH: 69
<212> TYPE: DNA
<213> ORGANISM: Artificial Sequence
<220> FEATURE:
<223> OTHER INFORMATION: cDNA Sequence of aMTD605 5'-primer

<400> SEQUENCE: 676
gggtttcata tggtgattgc ggcggtgctg gcgccggtgg cggtgccggc aaatattacc    60
gttttctat                                                           69

<210> SEQ ID NO 677
<211> LENGTH: 69

-continued

```
<212> TYPE: DNA
<213> ORGANISM: Artificial Sequence
<220> FEATURE:
<223> OTHER INFORMATION: cDNA Sequence of aMTD606 5'-primer

<400> SEQUENCE: 677
gggtttcata tggcggcggc gattgcggcg attccgatta ttattccggc aaatattacc      60
gttttctat                                                              69

<210> SEQ ID NO 678
<211> LENGTH: 69
<212> TYPE: DNA
<213> ORGANISM: Artificial Sequence
<220> FEATURE:
<223> OTHER INFORMATION: cDNA Sequence of aMTD622 5'-primer

<400> SEQUENCE: 678
gggtttcata tggcggcggc gattgcggcg attccgatta ttattccggc aaatattacc      60
gttttctat                                                              69

<210> SEQ ID NO 679
<211> LENGTH: 69
<212> TYPE: DNA
<213> ORGANISM: Artificial Sequence
<220> FEATURE:
<223> OTHER INFORMATION: cDNA Sequence of aMTD623 5'-primer

<400> SEQUENCE: 679
gggtttcata tggtggcggc ggcgattgcg ctgccggcga ttgtgccggc aaatattacc      60
gttttctat                                                              69

<210> SEQ ID NO 680
<211> LENGTH: 69
<212> TYPE: DNA
<213> ORGANISM: Artificial Sequence
<220> FEATURE:
<223> OTHER INFORMATION: cDNA Sequence of aMTD625 5'-primer

<400> SEQUENCE: 680
gggtttcata tgattctggc ggcggcggcg gcgccgctga ttgtgccggc aaatattacc      60
gttttctat                                                              69

<210> SEQ ID NO 681
<211> LENGTH: 69
<212> TYPE: DNA
<213> ORGANISM: Artificial Sequence
<220> FEATURE:
<223> OTHER INFORMATION: cDNA Sequence of aMTD635 5'-primer

<400> SEQUENCE: 681
gggtttcata tgggcagcac cggcggcagc cagcagaaca accagtatgc aaatattacc      60
gttttctat                                                              69

<210> SEQ ID NO 682
<211> LENGTH: 69
<212> TYPE: DNA
<213> ORGANISM: Artificial Sequence
<220> FEATURE:
<223> OTHER INFORMATION: cDNA Sequence of aMTD643 5'-primer

<400> SEQUENCE: 682
gggtttcata tgctggcgct ggtgctggcg gcgccggcga ttgtgccggc aaatattacc      60
``` gttttctat                                                                    69

<210> SEQ ID NO 683
<211> LENGTH: 69
<212> TYPE: DNA
<213> ORGANISM: Artificial Sequence
<220> FEATURE:
<223> OTHER INFORMATION: cDNA Sequence of aMTD645 5'-primer

<400> SEQUENCE: 683
gggtttcata tggcgctggc ggtggtggcg ctgccggcga ttgtgccggc aaatattacc      60
gttttctat                                                                    69

<210> SEQ ID NO 684
<211> LENGTH: 69
<212> TYPE: DNA
<213> ORGANISM: Artificial Sequence
<220> FEATURE:
<223> OTHER INFORMATION: cDNA Sequence of aMTD661 5'-primer

<400> SEQUENCE: 684
gggtttcata tggcggcgat tctggcgccg attgtggcgg cgctgccggc aaatattacc      60
gttttctat                                                                    69

<210> SEQ ID NO 685
<211> LENGTH: 69
<212> TYPE: DNA
<213> ORGANISM: Artificial Sequence
<220> FEATURE:
<223> OTHER INFORMATION: cDNA Sequence of aMTD664 5'-primer

<400> SEQUENCE: 685
gggtttcata tgattctgat tgcgattgcg attccggcgg cggcgccggc aaatattacc      60
gttttctat                                                                    69

<210> SEQ ID NO 686
<211> LENGTH: 69
<212> TYPE: DNA
<213> ORGANISM: Artificial Sequence
<220> FEATURE:
<223> OTHER INFORMATION: cDNA Sequence of aMTD665 5'-primer

<400> SEQUENCE: 686
gggtttcata tgctggcgat tgtgctggcg gcgccggtgg cggtgccggc aaatattacc      60
gttttctat                                                                    69

<210> SEQ ID NO 687
<211> LENGTH: 69
<212> TYPE: DNA
<213> ORGANISM: Artificial Sequence
<220> FEATURE:
<223> OTHER INFORMATION: cDNA Sequence of aMTD666 5'-primer

<400> SEQUENCE: 687
gggtttcata tggcggcgat tgcgattatt gcgccggcga ttgtgccggc aaatattacc      60
gttttctat                                                                    69

<210> SEQ ID NO 688
<211> LENGTH: 69
<212> TYPE: DNA
<213> ORGANISM: Artificial Sequence
<220> FEATURE:
<223> OTHER INFORMATION: cDNA Sequence of aMTD667 5'-primer -continued

<400> SEQUENCE: 688
gggtttcata tgctggcggt ggcgattgtg gcgccggcgc tggtgccggc aaatattacc    60
gttttctat                                                           69

<210> SEQ ID NO 689
<211> LENGTH: 69
<212> TYPE: DNA
<213> ORGANISM: Artificial Sequence
<220> FEATURE:
<223> OTHER INFORMATION: cDNA Sequence of aMTD676 5'-primer

<400> SEQUENCE: 689
gggtttcata tggtgccgct gctggtgccg gtgccggtgg tggtgccggc aaatattacc    60
gttttctat                                                           69

<210> SEQ ID NO 690
<211> LENGTH: 69
<212> TYPE: DNA
<213> ORGANISM: Artificial Sequence
<220> FEATURE:
<223> OTHER INFORMATION: cDNA Sequence of aMTD683 5'-primer

<400> SEQUENCE: 690
gggtttcata tgctggcgat tgtgctggcg gcgccggcgg tgctgccggc aaatattacc    60
gttttctat                                                           69

<210> SEQ ID NO 691
<211> LENGTH: 69
<212> TYPE: DNA
<213> ORGANISM: Artificial Sequence
<220> FEATURE:
<223> OTHER INFORMATION: cDNA Sequence of aMTD684 5'-primer

<400> SEQUENCE: 691
gggtttcata tggcggcgat tgtgctggcg ctgccggcgg tgctgccggc aaatattacc    60
gttttctat                                                           69

<210> SEQ ID NO 692
<211> LENGTH: 69
<212> TYPE: DNA
<213> ORGANISM: Artificial Sequence
<220> FEATURE:
<223> OTHER INFORMATION: cDNA Sequence of aMTD685 5'-primer

<400> SEQUENCE: 692
gggtttcata tggcgctgct ggtggcggtg ctgccggcgg cgctgccggc aaatattacc    60
gttttctat                                                           69

<210> SEQ ID NO 693
<211> LENGTH: 69
<212> TYPE: DNA
<213> ORGANISM: Artificial Sequence
<220> FEATURE:
<223> OTHER INFORMATION: cDNA Sequence of aMTD686 5'-primer

<400> SEQUENCE: 693
gggtttcata tggcggcgct ggtggcggtg ctgccggtgg cgctgccggc aaatattacc    60
gttttctat                                                           69

<210> SEQ ID NO 694

```
<211> LENGTH: 69
<212> TYPE: DNA
<213> ORGANISM: Artificial Sequence
<220> FEATURE:
<223> OTHER INFORMATION: cDNA Sequence of aMTD687 5'-primer

<400> SEQUENCE: 694
gggtttcata tggcgattct ggcggtggcg ctgccgctgc tggcgccggc aaatattacc    60
gttttctat                                                           69

<210> SEQ ID NO 695
<211> LENGTH: 69
<212> TYPE: DNA
<213> ORGANISM: Artificial Sequence
<220> FEATURE:
<223> OTHER INFORMATION: cDNA Sequence of aMTD692 5'-primer

<400> SEQUENCE: 695
gggtttcata tgccggcgcc gctgccgccg gtggtgattc tggcggtggc aaatattacc    60
gttttctat                                                           69

<210> SEQ ID NO 696
<211> LENGTH: 69
<212> TYPE: DNA
<213> ORGANISM: Artificial Sequence
<220> FEATURE:
<223> OTHER INFORMATION: cDNA Sequence of aMTD693 5'-primer

<400> SEQUENCE: 696
gggtttcata tggcggcgcc ggtgctgccg gtggcggtgc cgattgtggc aaatattacc    60
gttttctat                                                           69

<210> SEQ ID NO 697
<211> LENGTH: 69
<212> TYPE: DNA
<213> ORGANISM: Artificial Sequence
<220> FEATURE:
<223> OTHER INFORMATION: cDNA Sequence of aMTD700 5'-primer

<400> SEQUENCE: 697
gggtttcata tgggcaccag caacacctgc cagagcaacc agaacagcgc aaatattacc    60
gttttctat                                                           69

<210> SEQ ID NO 698
<211> LENGTH: 69
<212> TYPE: DNA
<213> ORGANISM: Artificial Sequence
<220> FEATURE:
<223> OTHER INFORMATION: cDNA Sequence of aMTD703 5'-primer

<400> SEQUENCE: 698
gggtttcata tgattgtggc ggtggcgctg gtgccggcgc tggcgccggc aaatattacc    60
gttttctat                                                           69

<210> SEQ ID NO 699
<211> LENGTH: 68
<212> TYPE: DNA
<213> ORGANISM: Artificial Sequence
<220> FEATURE:
<223> OTHER INFORMATION: cDNA Sequence of aMTD705 5'-primer

<400> SEQUENCE: 699
gggtttcata tattgtggcg gtggcgctgc tgccggcgct ggcgccggca aatattaccg    60
``` ttttctat                                                          68

<210> SEQ ID NO 700
<211> LENGTH: 69
<212> TYPE: DNA
<213> ORGANISM: Artificial Sequence
<220> FEATURE:
<223> OTHER INFORMATION: cDNA Sequence of aMTD706 5'-primer

<400> SEQUENCE: 700
gggtttcata tgattgtggc ggtggcgctg ctgccggcgg tggcgccggc aaatattacc    60
gttttctat                                                          69

<210> SEQ ID NO 701
<211> LENGTH: 69
<212> TYPE: DNA
<213> ORGANISM: Artificial Sequence
<220> FEATURE:
<223> OTHER INFORMATION: cDNA Sequence of aMTD707 5'-primer

<400> SEQUENCE: 701
gggtttcata tgattgtggc gctggcggtg ctgccggcgg tggcgccggc aaatattacc    60
gttttctat                                                          69

<210> SEQ ID NO 702
<211> LENGTH: 69
<212> TYPE: DNA
<213> ORGANISM: Artificial Sequence
<220> FEATURE:
<223> OTHER INFORMATION: cDNA Sequence of aMTD724 5'-primer

<400> SEQUENCE: 702
gggtttcata tggtggcggt gctggcggtg ctgccggcgc tggcgccggc aaatattacc    60
gttttctat                                                          69

<210> SEQ ID NO 703
<211> LENGTH: 69
<212> TYPE: DNA
<213> ORGANISM: Artificial Sequence
<220> FEATURE:
<223> OTHER INFORMATION: cDNA Sequence of aMTD725 5'-primer

<400> SEQUENCE: 703
gggtttcata tgattgcggt gctggcggtg gcgccggcgg tgctgccggc aaatattacc    60
gttttctat                                                          69

<210> SEQ ID NO 704
<211> LENGTH: 69
<212> TYPE: DNA
<213> ORGANISM: Artificial Sequence
<220> FEATURE:
<223> OTHER INFORMATION: cDNA Sequence of aMTD726 5'-primer

<400> SEQUENCE: 704
gggtttcata tgctggcggt ggcgattatt gcgccggcgg tggcgccggc aaatattacc    60
gttttctat                                                          69

<210> SEQ ID NO 705
<211> LENGTH: 69
<212> TYPE: DNA
<213> ORGANISM: Artificial Sequence
<220> FEATURE:

```
<223> OTHER INFORMATION: cDNA Sequence of aMTD727 5'-primer

<400> SEQUENCE: 705
gggtttcata tggtggcgct ggcgattgcg ctgccggcgg tgctgccggc aaatattacc      60
gttttctat                                                             69

<210> SEQ ID NO 706
<211> LENGTH: 69
<212> TYPE: DNA
<213> ORGANISM: Artificial Sequence
<220> FEATURE:
<223> OTHER INFORMATION: cDNA Sequence of aMTD743 5'-primer

<400> SEQUENCE: 706
gggtttcata tggcgattgc gattgcgctg gtgccggtgg cgctgccggc aaatattacc      60
gttttctat                                                             69

<210> SEQ ID NO 707
<211> LENGTH: 69
<212> TYPE: DNA
<213> ORGANISM: Artificial Sequence
<220> FEATURE:
<223> OTHER INFORMATION: cDNA Sequence of aMTD744 5'-primer

<400> SEQUENCE: 707
gggtttcata tggcggcggt ggtgattgtg gcgccggtgg cgctgccggc aaatattacc      60
gttttctat                                                             69

<210> SEQ ID NO 708
<211> LENGTH: 69
<212> TYPE: DNA
<213> ORGANISM: Artificial Sequence
<220> FEATURE:
<223> OTHER INFORMATION: cDNA Sequence of aMTD745 5'-primer

<400> SEQUENCE: 708
gggtttcata tggcggcgat tctggcgatt gtggcgccgc tggcgccggc aaatattacc      60
gttttctat                                                             69

<210> SEQ ID NO 709
<211> LENGTH: 69
<212> TYPE: DNA
<213> ORGANISM: Artificial Sequence
<220> FEATURE:
<223> OTHER INFORMATION: cDNA Sequence of aMTD746 5'-primer

<400> SEQUENCE: 709
gggtttcata tggtggcgat tattgtggtg gcgccggcgc tggcgccggc aaatattacc      60
gttttctat                                                             69

<210> SEQ ID NO 710
<211> LENGTH: 69
<212> TYPE: DNA
<213> ORGANISM: Artificial Sequence
<220> FEATURE:
<223> OTHER INFORMATION: cDNA Sequence of aMTD747 5'-primer

<400> SEQUENCE: 710
gggtttcata tggtggcgct gctggcgatt gcgccggcgc tggcgccggc aaatattacc      60
gttttctat                                                             69
```

```
<210> SEQ ID NO 711
<211> LENGTH: 69
<212> TYPE: DNA
<213> ORGANISM: Artificial Sequence
<220> FEATURE:
<223> OTHER INFORMATION: cDNA Sequence of aMTD750 5'-primer

<400> SEQUENCE: 711
gggtttcata tgctggcgat tgcggcgatt gcgccgctgg cgattccggc aaatattacc    60
gttttctat                                                            69

<210> SEQ ID NO 712
<211> LENGTH: 69
<212> TYPE: DNA
<213> ORGANISM: Artificial Sequence
<220> FEATURE:
<223> OTHER INFORMATION: cDNA Sequence of aMTD763 5'-primer

<400> SEQUENCE: 712
gggtttcata tggtggcggt gctgattgcg gtgccggcgc tggcgccggc aaatattacc    60
gttttctat                                                            69

<210> SEQ ID NO 713
<211> LENGTH: 69
<212> TYPE: DNA
<213> ORGANISM: Artificial Sequence
<220> FEATURE:
<223> OTHER INFORMATION: cDNA Sequence of aMTD764 5'-primer

<400> SEQUENCE: 713
gggtttcata tggcggtggc gctggcggtg ctgccggcgg tggtgccggc aaatattacc    60
gttttctat                                                            69

<210> SEQ ID NO 714
<211> LENGTH: 69
<212> TYPE: DNA
<213> ORGANISM: Artificial Sequence
<220> FEATURE:
<223> OTHER INFORMATION: cDNA Sequence of aMTD765 5'-primer

<400> SEQUENCE: 714
gggtttcata tggcggtggc gctggcggtg gtgccggcgg tgctgccggc aaatattacc    60
gttttctat                                                            69

<210> SEQ ID NO 715
<211> LENGTH: 69
<212> TYPE: DNA
<213> ORGANISM: Artificial Sequence
<220> FEATURE:
<223> OTHER INFORMATION: cDNA Sequence of aMTD766 5'-primer

<400> SEQUENCE: 715
gggtttcata tgattgtggt gattgcggtg gcgccggcgg tggcgccggc aaatattacc    60
gttttctat                                                            69

<210> SEQ ID NO 716
<211> LENGTH: 69
<212> TYPE: DNA
<213> ORGANISM: Artificial Sequence
<220> FEATURE:
<223> OTHER INFORMATION: cDNA Sequence of aMTD767 5'-primer

<400> SEQUENCE: 716
```

```
gggtttcata tgattgtggt ggcggcggtg gtgccggcgc tggcgccggc aaatattacc      60
gttttctat                                                             69

<210> SEQ ID NO 717
<211> LENGTH: 69
<212> TYPE: DNA
<213> ORGANISM: Artificial Sequence
<220> FEATURE:
<223> OTHER INFORMATION: cDNA Sequence of aMTD772 5'-primer

<400> SEQUENCE: 717
gggtttcata tgctgccggt ggcgccggtg attccgatta ttgtgccggc aaatattacc      60
gttttctat                                                             69

<210> SEQ ID NO 718
<211> LENGTH: 69
<212> TYPE: DNA
<213> ORGANISM: Artificial Sequence
<220> FEATURE:
<223> OTHER INFORMATION: cDNA Sequence of aMTD783 5'-primer

<400> SEQUENCE: 718
gggtttcata tgattgtggc gctggtgccg gcggtggcga ttgcgccggc aaatattacc      60
gttttctat                                                             69

<210> SEQ ID NO 719
<211> LENGTH: 69
<212> TYPE: DNA
<213> ORGANISM: Artificial Sequence
<220> FEATURE:
<223> OTHER INFORMATION: cDNA Sequence of aMTD784 5'-primer

<400> SEQUENCE: 719
gggtttcata tggtggcggc gctgccggcg gtggcgctgg tggtgccggc aaatattacc      60
gttttctat                                                             69

<210> SEQ ID NO 720
<211> LENGTH: 69
<212> TYPE: DNA
<213> ORGANISM: Artificial Sequence
<220> FEATURE:
<223> OTHER INFORMATION: cDNA Sequence of aMTD786 5'-primer

<400> SEQUENCE: 720
gggtttcata tgctggtggc gattgcgccg ctggcggtgc tggcgccggc aaatattacc      60
gttttctat                                                             69

<210> SEQ ID NO 721
<211> LENGTH: 69
<212> TYPE: DNA
<213> ORGANISM: Artificial Sequence
<220> FEATURE:
<223> OTHER INFORMATION: cDNA Sequence of aMTD787 5'-primer

<400> SEQUENCE: 721
gggtttcata tggcggtggc gctggtgccg gtgattgtgg cggcgccggc aaatattacc      60
gttttctat                                                             69

<210> SEQ ID NO 722
<211> LENGTH: 69
<212> TYPE: DNA
<213> ORGANISM: Artificial Sequence
```

```
<220> FEATURE:
<223> OTHER INFORMATION: cDNA Sequence of aMTD788 5'-primer

<400> SEQUENCE: 722
gggtttcata tggcgattgc ggtggcgatt gcgccggtgg cgctgccggc aaatattacc    60
gttttctat                                                           69

<210> SEQ ID NO 723
<211> LENGTH: 69
<212> TYPE: DNA
<213> ORGANISM: Artificial Sequence
<220> FEATURE:
<223> OTHER INFORMATION: cDNA Sequence of aMTD803 5'-primer

<400> SEQUENCE: 723
gggtttcata tggcgattgc gctggcggtg ccggtgctgg cgctgccggc aaatattacc    60
gttttctat                                                           69

<210> SEQ ID NO 724
<211> LENGTH: 69
<212> TYPE: DNA
<213> ORGANISM: Artificial Sequence
<220> FEATURE:
<223> OTHER INFORMATION: cDNA Sequence of aMTD805 5'-primer

<400> SEQUENCE: 724
gggtttcata tgctggtgct gattgcggcg gcgccgattg cgctgccggc aaatattacc    60
gttttctat                                                           69

<210> SEQ ID NO 725
<211> LENGTH: 69
<212> TYPE: DNA
<213> ORGANISM: Artificial Sequence
<220> FEATURE:
<223> OTHER INFORMATION: cDNA Sequence of aMTD806 5'-primer

<400> SEQUENCE: 725
gggtttcata tgctggtggc gctggcggtg ccggcggcgg tgctgccggc aaatattacc    60
gttttctat                                                           69

<210> SEQ ID NO 726
<211> LENGTH: 69
<212> TYPE: DNA
<213> ORGANISM: Artificial Sequence
<220> FEATURE:
<223> OTHER INFORMATION: cDNA Sequence of aMTD807 5'-primer

<400> SEQUENCE: 726
gggtttcata tggcggtggc gctggcggtg ccggcgctgg tgctgccggc aaatattacc    60
gttttctat                                                           69

<210> SEQ ID NO 727
<211> LENGTH: 69
<212> TYPE: DNA
<213> ORGANISM: Artificial Sequence
<220> FEATURE:
<223> OTHER INFORMATION: cDNA Sequence of aMTD808 5'-primer

<400> SEQUENCE: 727
gggtttcata tgctggtggt gctggcggcg gcgccgctgg cggtgccggc aaatattacc    60
gttttctat                                                           69
```

<210> SEQ ID NO 728
<211> LENGTH: 69
<212> TYPE: DNA
<213> ORGANISM: Artificial Sequence
<220> FEATURE:
<223> OTHER INFORMATION: cDNA Sequence of aMTD809 5'-primer

<400> SEQUENCE: 728
gggtttcata tgctgattgt gctggcggcg ccggcgctgg cggcgccggc aaatattacc    60
gttttctat                                                           69

<210> SEQ ID NO 729
<211> LENGTH: 69
<212> TYPE: DNA
<213> ORGANISM: Artificial Sequence
<220> FEATURE:
<223> OTHER INFORMATION: cDNA Sequence of aMTD810 5'-primer

<400> SEQUENCE: 729
gggtttcata tggtgattgt gctggcggcg ccggcgctgg cggcgccggc aaatattacc    60
gttttctat                                                           69

<210> SEQ ID NO 730
<211> LENGTH: 69
<212> TYPE: DNA
<213> ORGANISM: Artificial Sequence
<220> FEATURE:
<223> OTHER INFORMATION: cDNA Sequence of aMTD811 5'-primer

<400> SEQUENCE: 730
gggtttcata tggcggtggt gctggcggtg ccggcgctgg cggtgccggc aaatattacc    60
gttttctat                                                           69

<210> SEQ ID NO 731
<211> LENGTH: 69
<212> TYPE: DNA
<213> ORGANISM: Artificial Sequence
<220> FEATURE:
<223> OTHER INFORMATION: cDNA Sequence of aMTD824 5'-primer

<400> SEQUENCE: 731
gggtttcata tgctgattat tgtggcggcg gcgccggcgg tggcgccggc aaatattacc    60
gttttctat                                                           69

<210> SEQ ID NO 732
<211> LENGTH: 69
<212> TYPE: DNA
<213> ORGANISM: Artificial Sequence
<220> FEATURE:
<223> OTHER INFORMATION: cDNA Sequence of aMTD825 5'-primer

<400> SEQUENCE: 732
gggtttcata tgattgtggc ggtgattgtg gcgccggcgg tggcgccggc aaatattacc    60
gttttctat                                                           69

<210> SEQ ID NO 733
<211> LENGTH: 69
<212> TYPE: DNA
<213> ORGANISM: Artificial Sequence
<220> FEATURE:
<223> OTHER INFORMATION: cDNA Sequence of aMTD826 5'-primer

<400> SEQUENCE: 733

```
gggtttcata tgctggtggc gctggcggcg ccgattattg cggtgccggc aaatattacc    60
gttttctat                                                            69

<210> SEQ ID NO 734
<211> LENGTH: 69
<212> TYPE: DNA
<213> ORGANISM: Artificial Sequence
<220> FEATURE:
<223> OTHER INFORMATION: cDNA Sequence of aMTD827 5'-primer

<400> SEQUENCE: 734
gggtttcata tgattgcggc ggtgctggcg gcgccggcgc tggtgccggc aaatattacc    60
gttttctat                                                            69

<210> SEQ ID NO 735
<211> LENGTH: 69
<212> TYPE: DNA
<213> ORGANISM: Artificial Sequence
<220> FEATURE:
<223> OTHER INFORMATION: cDNA Sequence of aMTD828 5'-primer

<400> SEQUENCE: 735
gggtttcata tgattgcgct gctggcggcg ccgattattg cggtgccggc aaatattacc    60
gttttctat                                                            69

<210> SEQ ID NO 736
<211> LENGTH: 69
<212> TYPE: DNA
<213> ORGANISM: Artificial Sequence
<220> FEATURE:
<223> OTHER INFORMATION: cDNA Sequence of aMTD829 5'-primer

<400> SEQUENCE: 736
gggtttcata tggcggcgct ggcgctggtg gcgccggtga ttgtgccggc aaatattacc    60
gttttctat                                                            69

<210> SEQ ID NO 737
<211> LENGTH: 69
<212> TYPE: DNA
<213> ORGANISM: Artificial Sequence
<220> FEATURE:
<223> OTHER INFORMATION: cDNA Sequence of aMTD830 5'-primer

<400> SEQUENCE: 737
gggtttcata tgattgcgct ggtggcggcg ccggtggcgc tggtgccggc aaatattacc    60
gttttctat                                                            69

<210> SEQ ID NO 738
<211> LENGTH: 69
<212> TYPE: DNA
<213> ORGANISM: Artificial Sequence
<220> FEATURE:
<223> OTHER INFORMATION: cDNA Sequence of aMTD831 5'-primer

<400> SEQUENCE: 738
gggtttcata tgattattgt ggcggtggcg ccggcggcga ttgtgccggc aaatattacc    60
gttttctat                                                            69

<210> SEQ ID NO 739
<211> LENGTH: 69
<212> TYPE: DNA
```

```
<213> ORGANISM: Artificial Sequence
<220> FEATURE:
<223> OTHER INFORMATION: cDNA Sequence of aMTD832 5'-primer

<400> SEQUENCE: 739
gggtttcata tggcggtggc ggcgattgtg ccggtgattg tggcgccggc aaatattacc    60
gttttctat                                                           69

<210> SEQ ID NO 740
<211> LENGTH: 69
<212> TYPE: DNA
<213> ORGANISM: Artificial Sequence
<220> FEATURE:
<223> OTHER INFORMATION: cDNA Sequence of aMTD843 5'-primer

<400> SEQUENCE: 740
gggtttcata tggcggtgct ggtgctggtg gcgccggcgg cggcgccggc aaatattacc    60
gttttctat                                                           69

<210> SEQ ID NO 741
<211> LENGTH: 69
<212> TYPE: DNA
<213> ORGANISM: Artificial Sequence
<220> FEATURE:
<223> OTHER INFORMATION: cDNA Sequence of aMTD844 5'-primer

<400> SEQUENCE: 741
gggtttcata tggtggtggc gctgctggcg ccgctgattg cggcgccggc aaatattacc    60
gttttctat                                                           69

<210> SEQ ID NO 742
<211> LENGTH: 69
<212> TYPE: DNA
<213> ORGANISM: Artificial Sequence
<220> FEATURE:
<223> OTHER INFORMATION: cDNA Sequence of aMTD845 5'-primer

<400> SEQUENCE: 742
gggtttcata tggcggcggt ggtgattgcg ccgctgctgg cggtgccggc aaatattacc    60
gttttctat                                                           69

<210> SEQ ID NO 743
<211> LENGTH: 69
<212> TYPE: DNA
<213> ORGANISM: Artificial Sequence
<220> FEATURE:
<223> OTHER INFORMATION: cDNA Sequence of aMTD846 5'-primer

<400> SEQUENCE: 743
gggtttcata tgattgcggt ggcggtggcg gcgccgctgc tggtgccggc aaatattacc    60
gttttctat                                                           69

<210> SEQ ID NO 744
<211> LENGTH: 69
<212> TYPE: DNA
<213> ORGANISM: Artificial Sequence
<220> FEATURE:
<223> OTHER INFORMATION: cDNA Sequence of aMTD847 5'-primer

<400> SEQUENCE: 744
gggtttcata tgctggtggc gattgtggtg ctgccggcgg tggcgccggc aaatattacc    60
gttttctat                                                           69
```

<210> SEQ ID NO 745
<211> LENGTH: 69
<212> TYPE: DNA
<213> ORGANISM: Artificial Sequence
<220> FEATURE:
<223> OTHER INFORMATION: cDNA Sequence of aMTD848 5'-primer

<400> SEQUENCE: 745
gggtttcata tggcggtggc gattgtggtg ctgccggcgg tggcgccggc aaatattacc      60
gttttctat                                                             69

<210> SEQ ID NO 746
<211> LENGTH: 69
<212> TYPE: DNA
<213> ORGANISM: Artificial Sequence
<220> FEATURE:
<223> OTHER INFORMATION: cDNA Sequence of aMTD849 5'-primer

<400> SEQUENCE: 746
gggtttcata tggcggtgat tctgctggcg ccgctgattg cggcgccggc aaatattacc      60
gttttctat                                                             69

<210> SEQ ID NO 747
<211> LENGTH: 69
<212> TYPE: DNA
<213> ORGANISM: Artificial Sequence
<220> FEATURE:
<223> OTHER INFORMATION: cDNA Sequence of aMTD850 5'-primer

<400> SEQUENCE: 747
gggtttcata tgctggtgat tgcgctggcg gcgccggtgg cgctgccggc aaatattacc      60
gttttctat                                                             69

<210> SEQ ID NO 748
<211> LENGTH: 69
<212> TYPE: DNA
<213> ORGANISM: Artificial Sequence
<220> FEATURE:
<223> OTHER INFORMATION: cDNA Sequence of aMTD851 5'-primer

<400> SEQUENCE: 748
gggtttcata tggtgctggc ggtggtgctg ccggcggtgg cgctgccggc aaatattacc      60
gttttctat                                                             69

<210> SEQ ID NO 749
<211> LENGTH: 69
<212> TYPE: DNA
<213> ORGANISM: Artificial Sequence
<220> FEATURE:
<223> OTHER INFORMATION: cDNA Sequence of aMTD852 5'-primer

<400> SEQUENCE: 749
gggtttcata tggtgctggc ggtggcggcg ccggcggtgc tgctgccggc aaatattacc      60
gttttctat                                                             69

<210> SEQ ID NO 750
<211> LENGTH: 69
<212> TYPE: DNA
<213> ORGANISM: Artificial Sequence
<220> FEATURE:
<223> OTHER INFORMATION: cDNA Sequence of aMTD863 5'-primer

<400> SEQUENCE: 750
gggtttcata tggcggcggt ggtgctgctg ccgattattg cggcgccggc aaatattacc    60
gttttctat                                                            69

<210> SEQ ID NO 751
<211> LENGTH: 69
<212> TYPE: DNA
<213> ORGANISM: Artificial Sequence
<220> FEATURE:
<223> OTHER INFORMATION: cDNA Sequence of aMTD864 5'-primer

<400> SEQUENCE: 751
gggtttcata tggcgctgct ggtgattgcg ccggcgattg cggtgccggc aaatattacc    60
gttttctat                                                            69

<210> SEQ ID NO 752
<211> LENGTH: 69
<212> TYPE: DNA
<213> ORGANISM: Artificial Sequence
<220> FEATURE:
<223> OTHER INFORMATION: cDNA Sequence of aMTD865 5'-primer

<400> SEQUENCE: 752
gggtttcata tggcggtgct ggtgattgcg gtgccggcga ttgcgccggc aaatattacc    60
gttttctat                                                            69

<210> SEQ ID NO 753
<211> LENGTH: 69
<212> TYPE: DNA
<213> ORGANISM: Artificial Sequence
<220> FEATURE:
<223> OTHER INFORMATION: cDNA Sequence of aMTD867 5'-primer

<400> SEQUENCE: 753
gggtttcata tggcgctgct ggtggtgatt gcgccgctgg cggcgccggc aaatattacc    60
gttttctat                                                            69

<210> SEQ ID NO 754
<211> LENGTH: 69
<212> TYPE: DNA
<213> ORGANISM: Artificial Sequence
<220> FEATURE:
<223> OTHER INFORMATION: cDNA Sequence of aMTD868 5'-primer

<400> SEQUENCE: 754
gggtttcata tggtgctggt ggcggcgatt ctgccggcgg cgattccggc aaatattacc    60
gttttctat                                                            69

<210> SEQ ID NO 755
<211> LENGTH: 69
<212> TYPE: DNA
<213> ORGANISM: Artificial Sequence
<220> FEATURE:
<223> OTHER INFORMATION: cDNA Sequence of aMTD870 5'-primer

<400> SEQUENCE: 755
gggtttcata tggtgctggt ggcggcggtg ctgccgattg cggcgccggc aaatattacc    60
gttttctat                                                            69

<210> SEQ ID NO 756
<211> LENGTH: 69

```
<212> TYPE: DNA
<213> ORGANISM: Artificial Sequence
<220> FEATURE:
<223> OTHER INFORMATION: cDNA Sequence of aMTD872 5'-primer

<400> SEQUENCE: 756
gggtttcata tggtgctggc ggcggcggtg ctgccgctgg tggtgccggc aaatattacc    60
gttttctat                                                           69

<210> SEQ ID NO 757
<211> LENGTH: 69
<212> TYPE: DNA
<213> ORGANISM: Artificial Sequence
<220> FEATURE:
<223> OTHER INFORMATION: cDNA Sequence of aMTD875 5'-primer

<400> SEQUENCE: 757
gggtttcata tggcgattgc gattgtggtg ccggcggtgg cggtgccggc aaatattacc    60
gttttctat                                                           69

<210> SEQ ID NO 758
<211> LENGTH: 69
<212> TYPE: DNA
<213> ORGANISM: Artificial Sequence
<220> FEATURE:
<223> OTHER INFORMATION: cDNA Sequence of aMTD877 5'-primer

<400> SEQUENCE: 758
gggtttcata tggtggcgat tattgcggtg ccggcggtgg tggcgccggc aaatattacc    60
gttttctat                                                           69

<210> SEQ ID NO 759
<211> LENGTH: 69
<212> TYPE: DNA
<213> ORGANISM: Artificial Sequence
<220> FEATURE:
<223> OTHER INFORMATION: cDNA Sequence of aMTD878 5'-primer

<400> SEQUENCE: 759
gggtttcata tgattgtggc gctggtggcg ccggcggcgg tggtgccggc aaatattacc    60
gttttctat                                                           69

<210> SEQ ID NO 760
<211> LENGTH: 69
<212> TYPE: DNA
<213> ORGANISM: Artificial Sequence
<220> FEATURE:
<223> OTHER INFORMATION: cDNA Sequence of aMTD879 5'-primer

<400> SEQUENCE: 760
gggtttcata tggcggcgat tgtgctgctg ccggcggtgg tggtgccggc aaatattacc    60
gttttctat                                                           69

<210> SEQ ID NO 761
<211> LENGTH: 69
<212> TYPE: DNA
<213> ORGANISM: Artificial Sequence
<220> FEATURE:
<223> OTHER INFORMATION: cDNA Sequence of aMTD881 5'-primer

<400> SEQUENCE: 761
gggtttcata tggcggcgct gattgtggtg ccggcggtgg cggtgccggc aaatattacc    60
``` gttttctat 69

<210> SEQ ID NO 762
<211> LENGTH: 69
<212> TYPE: DNA
<213> ORGANISM: Artificial Sequence
<220> FEATURE:
<223> OTHER INFORMATION: cDNA Sequence of aMTD882 5'-primer

<400> SEQUENCE: 762
gggtttcata tggcgattgc gctggtggtg ccggcggtgg cggtgccggc aaatattacc    60
gttttctat                                                           69

<210> SEQ ID NO 763
<211> LENGTH: 69
<212> TYPE: DNA
<213> ORGANISM: Artificial Sequence
<220> FEATURE:
<223> OTHER INFORMATION: cDNA Sequence of aMTD883 5'-primer

<400> SEQUENCE: 763
gggtttcata tgctggcgat tgtgccggcg gcgattgcgg cgctgccggc aaatattacc    60
gttttctat                                                           69

<210> SEQ ID NO 764
<211> LENGTH: 69
<212> TYPE: DNA
<213> ORGANISM: Artificial Sequence
<220> FEATURE:
<223> OTHER INFORMATION: cDNA Sequence of aMTD884 5'-primer

<400> SEQUENCE: 764
gggtttcata tggtgctgat tgtgccggcg gcgattgcgg cgctgccggc aaatattacc    60
gttttctat                                                           69

<210> SEQ ID NO 765
<211> LENGTH: 69
<212> TYPE: DNA
<213> ORGANISM: Artificial Sequence
<220> FEATURE:
<223> OTHER INFORMATION: cDNA Sequence of aMTD885 5'-primer

<400> SEQUENCE: 765
gggtttcata tgctggtggc gattgcgccg gcggtggcgg tgctgccggc aaatattacc    60
gttttctat                                                           69

<210> SEQ ID NO 766
<211> LENGTH: 69
<212> TYPE: DNA
<213> ORGANISM: Artificial Sequence
<220> FEATURE:
<223> OTHER INFORMATION: cDNA Sequence of aMTD886 5'-primer

<400> SEQUENCE: 766
gggtttcata tggtgctggc ggtgccggcg gcgattgcgg cgctgccggc aaatattacc    60
gttttctat                                                           69

<210> SEQ ID NO 767
<211> LENGTH: 69
<212> TYPE: DNA
<213> ORGANISM: Artificial Sequence
<220> FEATURE:
<223> OTHER INFORMATION: cDNA Sequence of aMTD887 5'-primer -continued

<400> SEQUENCE: 767
gggtttcata tggtgctggc ggtggcgccg gcggtggcgg tgctgccggc aaatattacc    60
gttttctat    69

<210> SEQ ID NO 768
<211> LENGTH: 69
<212> TYPE: DNA
<213> ORGANISM: Artificial Sequence
<220> FEATURE:
<223> OTHER INFORMATION: cDNA Sequence of aMTD888 5'-primer

<400> SEQUENCE: 768
gggtttcata tgattctggc ggtggtggcg attccggcgg cggcgccggc aaatattacc    60
gttttctat    69

<210> SEQ ID NO 769
<211> LENGTH: 69
<212> TYPE: DNA
<213> ORGANISM: Artificial Sequence
<220> FEATURE:
<223> OTHER INFORMATION: cDNA Sequence of aMTD889 5'-primer

<400> SEQUENCE: 769
gggtttcata tgattctggt ggcggcggcg ccgattgcgg cgctgccggc aaatattacc    60
gttttctat    69

<210> SEQ ID NO 770
<211> LENGTH: 69
<212> TYPE: DNA
<213> ORGANISM: Artificial Sequence
<220> FEATURE:
<223> OTHER INFORMATION: cDNA Sequence of aMTD891 5'-primer

<400> SEQUENCE: 770
gggtttcata tgattctggc ggtggcggcg attccggcgg cgctgccggc aaatattacc    60
gttttctat    69

<210> SEQ ID NO 771
<211> LENGTH: 69
<212> TYPE: DNA
<213> ORGANISM: Artificial Sequence
<220> FEATURE:
<223> OTHER INFORMATION: cDNA Sequence of aMTD893 5'-primer

<400> SEQUENCE: 771
gggtttcata tggtgattgc gattccggcg attctggcgg cggcgccggc aaatattacc    60
gttttctat    69

<210> SEQ ID NO 772
<211> LENGTH: 69
<212> TYPE: DNA
<213> ORGANISM: Artificial Sequence
<220> FEATURE:
<223> OTHER INFORMATION: cDNA Sequence of aMTD895 5'-primer

<400> SEQUENCE: 772
gggtttcata tggcgattat tattgtggtg ccggcgattg cggcgccggc aaatattacc    60
gttttctat    69

<210> SEQ ID NO 773

```
<211> LENGTH: 69
<212> TYPE: DNA
<213> ORGANISM: Artificial Sequence
<220> FEATURE:
<223> OTHER INFORMATION: cDNA Sequence of aMTD896 5'-primer

<400> SEQUENCE: 773
gggtttcata tggcgattct gattgtggtg gcgccgattg cggcgccggc aaatattacc      60
gttttctat                                                              69

<210> SEQ ID NO 774
<211> LENGTH: 69
<212> TYPE: DNA
<213> ORGANISM: Artificial Sequence
<220> FEATURE:
<223> OTHER INFORMATION: cDNA Sequence of aMTD897 5'-primer

<400> SEQUENCE: 774
gggtttcata tggcggtgat tgtgccggtg gcgattattg cggcgccggc aaatattacc      60
gttttctat                                                              69

<210> SEQ ID NO 775
<211> LENGTH: 69
<212> TYPE: DNA
<213> ORGANISM: Artificial Sequence
<220> FEATURE:
<223> OTHER INFORMATION: cDNA Sequence of aMTD899 5'-primer

<400> SEQUENCE: 775
gggtttcata tggcggtggt gattgcgctg ccggcggtgg tggcgccggc aaatattacc      60
gttttctat                                                              69

<210> SEQ ID NO 776
<211> LENGTH: 69
<212> TYPE: DNA
<213> ORGANISM: Artificial Sequence
<220> FEATURE:
<223> OTHER INFORMATION: cDNA Sequence of aMTD900 5'-primer

<400> SEQUENCE: 776
gggtttcata tggcgctggt ggcggtgatt gcgccggtgg tggcgccggc aaatattacc      60
gttttctat                                                              69

<210> SEQ ID NO 777
<211> LENGTH: 69
<212> TYPE: DNA
<213> ORGANISM: Artificial Sequence
<220> FEATURE:
<223> OTHER INFORMATION: cDNA Sequence of aMTD901 5'-primer

<400> SEQUENCE: 777
gggtttcata tggcgctggt ggcggtgctg ccggcggtgg cggtgccggc aaatattacc      60
gttttctat                                                              69

<210> SEQ ID NO 778
<211> LENGTH: 69
<212> TYPE: DNA
<213> ORGANISM: Artificial Sequence
<220> FEATURE:
<223> OTHER INFORMATION: cDNA Sequence of aMTD902 5'-primer

<400> SEQUENCE: 778
gggtttcata tggcgctggt ggcgccgctg ctggcggtgg cggtgccggc aaatattacc      60
```

-continued

```
gttttctat                                                             69

<210> SEQ ID NO 779
<211> LENGTH: 69
<212> TYPE: DNA
<213> ORGANISM: Artificial Sequence
<220> FEATURE:
<223> OTHER INFORMATION: cDNA Sequence of aMTD904 5'-primer

<400> SEQUENCE: 779
gggtttcata tggcggtgct ggcggtggtg gcgccggtgg tggcgccggc aaatattacc     60
gttttctat                                                             69

<210> SEQ ID NO 780
<211> LENGTH: 69
<212> TYPE: DNA
<213> ORGANISM: Artificial Sequence
<220> FEATURE:
<223> OTHER INFORMATION: cDNA Sequence of aMTD905 5'-primer

<400> SEQUENCE: 780
gggtttcata tggcggtgat tgcggtggcg ccgctggtgg tggcgccggc aaatattacc     60
gttttctat                                                             69

<210> SEQ ID NO 781
<211> LENGTH: 69
<212> TYPE: DNA
<213> ORGANISM: Artificial Sequence
<220> FEATURE:
<223> OTHER INFORMATION: cDNA Sequence of aMTD906 5'-primer

<400> SEQUENCE: 781
gggtttcata tggcggtgat tgcgctggcg ccggtggtgg tggcgccggc aaatattacc     60
gttttctat                                                             69

<210> SEQ ID NO 782
<211> LENGTH: 69
<212> TYPE: DNA
<213> ORGANISM: Artificial Sequence
<220> FEATURE:
<223> OTHER INFORMATION: cDNA Sequence of aMTD907 5'-primer

<400> SEQUENCE: 782
gggtttcata tggtggcgat tgcgctggcg ccggtggtgg tggcgccggc aaatattacc     60
gttttctat                                                             69

<210> SEQ ID NO 783
<211> LENGTH: 69
<212> TYPE: DNA
<213> ORGANISM: Artificial Sequence
<220> FEATURE:
<223> OTHER INFORMATION: cDNA Sequence of aMTD908 5'-primer

<400> SEQUENCE: 783
gggtttcata tggtggcgct ggcgctggcg ccggtggtgg tggcgccggc aaatattacc     60
gttttctat                                                             69

<210> SEQ ID NO 784
<211> LENGTH: 69
<212> TYPE: DNA
<213> ORGANISM: Artificial Sequence
<220> FEATURE:
```

```
<223> OTHER INFORMATION: cDNA Sequence of aMTD910 5'-primer

<400> SEQUENCE: 784
gggtttcata tggtggcggc gctgctgccg gcggtggtgg tggcgccggc aaatattacc    60
gttttctat                                                            69

<210> SEQ ID NO 785
<211> LENGTH: 69
<212> TYPE: DNA
<213> ORGANISM: Artificial Sequence
<220> FEATURE:
<223> OTHER INFORMATION: cDNA Sequence of aMTD911 5'-primer

<400> SEQUENCE: 785
gggtttcata tggtggcgct ggcgctgccg gcggtggtgg tggcgccggc aaatattacc    60
gttttctat                                                            69

<210> SEQ ID NO 786
<211> LENGTH: 69
<212> TYPE: DNA
<213> ORGANISM: Artificial Sequence
<220> FEATURE:
<223> OTHER INFORMATION: cDNA Sequence of aMTD912 5'-primer

<400> SEQUENCE: 786
gggtttcata tggtggcgct gctggcgccg gcggtggtgg tggcgccggc aaatattacc    60
gttttctat                                                            69

<210> SEQ ID NO 787
<211> LENGTH: 69
<212> TYPE: DNA
<213> ORGANISM: Artificial Sequence
<220> FEATURE:
<223> OTHER INFORMATION: cDNA Sequence of aMTD921 5'-primer

<400> SEQUENCE: 787
gggtttcata tgatttggtg gtttgtggtg ctgccgctgg tggtgccggc aaatattacc    60
gttttctat                                                            69

<210> SEQ ID NO 788
<211> LENGTH: 69
<212> TYPE: DNA
<213> ORGANISM: Artificial Sequence
<220> FEATURE:
<223> OTHER INFORMATION: cDNA Sequence of aMTD922 5'-primer

<400> SEQUENCE: 788
gggtttcata tgtggtatgt gattttttgtg ctgccgctgg tggtgccggc aaatattacc   60
gttttctat                                                            69

<210> SEQ ID NO 789
<211> LENGTH: 69
<212> TYPE: DNA
<213> ORGANISM: Artificial Sequence
<220> FEATURE:
<223> OTHER INFORMATION: cDNA Sequence of aMTD931 5'-primer

<400> SEQUENCE: 789
gggtttcata tggcggtgct gattgcgccg gcgattctgg cggcggcggc aaatattacc    60
gttttctat                                                            69
```

```
<210> SEQ ID NO 790
<211> LENGTH: 69
<212> TYPE: DNA
<213> ORGANISM: Artificial Sequence
<220> FEATURE:
<223> OTHER INFORMATION: cDNA Sequence of aMTD934 5'-primer

<400> SEQUENCE: 790
gggtttcata tgctgattct ggcgccggcg gcggtggtgg cggcggcggc aaatattacc      60
gttttctat                                                             69

<210> SEQ ID NO 791
<211> LENGTH: 69
<212> TYPE: DNA
<213> ORGANISM: Artificial Sequence
<220> FEATURE:
<223> OTHER INFORMATION: cDNA Sequence of aMTD935 5'-primer

<400> SEQUENCE: 791
gggtttcata tggcgctgct gattctgccg gcggcggcgg tggcggcggc aaatattacc      60
gttttctat                                                             69

<210> SEQ ID NO 792
<211> LENGTH: 69
<212> TYPE: DNA
<213> ORGANISM: Artificial Sequence
<220> FEATURE:
<223> OTHER INFORMATION: cDNA Sequence of aMTD936 5'-primer

<400> SEQUENCE: 792
gggtttcata tggcgctgct gattctggcg gcggcggtgg cggcgccggc aaatattacc      60
gttttctat                                                             69

<210> SEQ ID NO 793
<211> LENGTH: 69
<212> TYPE: DNA
<213> ORGANISM: Artificial Sequence
<220> FEATURE:
<223> OTHER INFORMATION: cDNA Sequence of aMTD937 5'-primer

<400> SEQUENCE: 793
gggtttcata tggtgccggt gctggtgccg ctgccggtgc cggtggtggc aaatattacc      60
gttttctat                                                             69

<210> SEQ ID NO 794
<211> LENGTH: 69
<212> TYPE: DNA
<213> ORGANISM: Artificial Sequence
<220> FEATURE:
<223> OTHER INFORMATION: cDNA Sequence of aMTD938 5'-primer

<400> SEQUENCE: 794
gggtttcata tggtgccggt gctgctgccg gtggtggtgc cggtgccggc aaatattacc      60
gttttctat                                                             69

<210> SEQ ID NO 795
<211> LENGTH: 69
<212> TYPE: DNA
<213> ORGANISM: Artificial Sequence
<220> FEATURE:
<223> OTHER INFORMATION: cDNA Sequence of aMTD947 5'-primer

<400> SEQUENCE: 795
```

-continued

```
gggtttcata tgtgctatta taatcagcag tccaataata ataatcaggc aaatattacc    60
gttttctat                                                            69
```

<210> SEQ ID NO 796
<211> LENGTH: 69
<212> TYPE: DNA
<213> ORGANISM: Artificial Sequence
<220> FEATURE:
<223> OTHER INFORMATION: cDNA Sequence of aMTD949 5'-primer

<400> SEQUENCE: 796

```
gggtttcata tgtccggcaa ttcctgccag cagtgcggca attcctccgc aaatattacc    60
gttttctat                                                            69
```

<210> SEQ ID NO 797
<211> LENGTH: 39
<212> TYPE: DNA
<213> ORGANISM: Artificial Sequence
<220> FEATURE:
<223> OTHER INFORMATION: cDNA Sequence of aMTD 3'-primer

<400> SEQUENCE: 797

```
cgcgtcgact tacctcggct gcaccggcac ggagatgac                           39
```

<210> SEQ ID NO 798
<211> LENGTH: 184
<212> TYPE: PRT
<213> ORGANISM: Artificial Sequence
<220> FEATURE:
<223> OTHER INFORMATION: Amino acid Sequence of SDA

<400> SEQUENCE: 798

```
Met Ala Asn Ile Thr Val Phe Tyr Asn Glu Asp Phe Gln Gly Lys Gln
1               5                   10                  15

Val Asp Leu Pro Pro Gly Asn Tyr Thr Arg Ala Gln Leu Ala Ala Leu
            20                  25                  30

Gly Ile Glu Asn Asn Thr Ile Ser Ser Val Lys Val Pro Pro Gly Val
        35                  40                  45

Lys Ala Ile Leu Tyr Gln Asn Asp Gly Phe Ala Gly Asp Gln Ile Glu
    50                  55                  60

Val Val Ala Asn Ala Glu Glu Leu Gly Pro Leu Asn Asn Asn Val Ser
65                  70                  75                  80

Ser Ile Arg Val Ile Ser Val Pro Val Gln Pro Arg Met Ala Asn Ile
                85                  90                  95

Thr Val Phe Tyr Asn Glu Asp Phe Gln Gly Lys Gln Val Asp Leu Pro
            100                 105                 110

Pro Gly Asn Tyr Thr Arg Ala Gln Leu Ala Ala Leu Gly Ile Glu Asn
        115                 120                 125

Asn Thr Ile Ser Ser Val Lys Val Pro Pro Gly Val Lys Ala Ile Leu
    130                 135                 140

Tyr Gln Asn Asp Gly Phe Ala Gly Asp Gln Ile Glu Val Val Ala Asn
145                 150                 155                 160

Ala Glu Glu Leu Gly Pro Leu Asn Asn Asn Val Ser Ser Ile Arg Val
                165                 170                 175

Ile Ser Val Pro Val Gln Pro Arg
            180
```

<210> SEQ ID NO 799
<211> LENGTH: 99

-continued

```
<212> TYPE: PRT
<213> ORGANISM: Artificial Sequence
<220> FEATURE:
<223> OTHER INFORMATION: Amino acid Sequence of SDB

<400> SEQUENCE: 799

Met Ala Glu Gln Ser Asp Lys Asp Val Lys Tyr Tyr Thr Leu Glu Glu
1               5                   10                  15

Ile Gln Lys His Lys Asp Ser Lys Ser Thr Trp Val Ile Leu His His
                20                  25                  30

Lys Val Tyr Asp Leu Thr Lys Phe Leu Glu Glu His Pro Gly Gly Glu
            35                  40                  45

Glu Val Leu Gly Glu Gln Ala Gly Gly Asp Ala Thr Glu Asn Phe Glu
        50                  55                  60

Asp Val Gly His Ser Thr Asp Ala Arg Glu Leu Ser Lys Thr Tyr Ile
65                  70                  75                  80

Ile Gly Glu Leu His Pro Asp Asp Arg Ser Lys Ile Ala Lys Pro Ser
                85                  90                  95

Glu Thr Leu

<210> SEQ ID NO 800
<211> LENGTH: 109
<212> TYPE: PRT
<213> ORGANISM: Artificial Sequence
<220> FEATURE:
<223> OTHER INFORMATION: Amino acid Sequence of SDC

<400> SEQUENCE: 800

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

<210> SEQ ID NO 801
<211> LENGTH: 208
<212> TYPE: PRT
<213> ORGANISM: Artificial Sequence
<220> FEATURE:
<223> OTHER INFORMATION: Amino acid Sequence of SDD

<400> SEQUENCE: 801

Met Lys Lys Ile Trp Leu Ala Leu Ala Gly Leu Val Leu Ala Phe Ser
1               5                   10                  15

Ala Ser Ala Ala Gln Tyr Glu Asp Gly Lys Gln Tyr Thr Thr Leu Glu
                20                  25                  30

Lys Pro Val Ala Gly Ala Pro Gln Val Leu Glu Phe Phe Ser Phe Phe
            35                  40                  45

Cys Pro His Cys Tyr Gln Phe Glu Glu Val Leu His Ile Ser Asp Asn
        50                  55                  60
```

```
Val Lys Lys Lys Leu Pro Glu Gly Val Lys Met Thr Lys Tyr His Val
 65                  70                  75                  80

Asn Phe Met Gly Gly Asp Leu Gly Lys Asp Leu Thr Gln Ala Trp Ala
                 85                  90                  95

Val Ala Met Ala Leu Gly Val Glu Asp Lys Val Thr Val Pro Leu Phe
            100                 105                 110

Glu Gly Val Gln Lys Thr Gln Thr Ile Arg Ser Ala Ser Asp Ile Arg
        115                 120                 125

Asp Val Phe Ile Asn Ala Gly Ile Lys Gly Glu Glu Tyr Asp Ala Ala
130                 135                 140

Trp Asn Ser Phe Val Val Lys Ser Leu Val Ala Gln Gln Glu Lys Ala
145                 150                 155                 160

Ala Ala Asp Val Gln Leu Arg Gly Val Pro Ala Met Phe Val Asn Gly
                165                 170                 175

Lys Tyr Gln Leu Asn Pro Gln Gly Met Asp Thr Ser Asn Met Asp Val
            180                 185                 190

Phe Val Gln Gln Tyr Ala Asp Thr Val Lys Tyr Leu Ser Glu Lys Lys
        195                 200                 205
```

```
<210> SEQ ID NO 802
<211> LENGTH: 100
<212> TYPE: PRT
<213> ORGANISM: Artificial Sequence
<220> FEATURE:
<223> OTHER INFORMATION: Amino acid Sequence of SDE

<400> SEQUENCE: 802

Gly Ser Leu Gln Asp Ser Glu Val Asn Gln Glu Ala Lys Pro Glu Val
1               5                   10                  15

Lys Pro Glu Val Lys Pro Glu Thr His Ile Asn Leu Lys Val Ser Asp
            20                  25                  30

Gly Ser Ser Glu Ile Phe Phe Lys Ile Lys Lys Thr Thr Pro Leu Arg
        35                  40                  45

Arg Leu Met Glu Ala Phe Ala Lys Arg Gln Gly Lys Glu Met Asp Ser
 50                  55                  60

Leu Thr Phe Leu Tyr Asp Gly Ile Glu Ile Gln Ala Asp Gln Thr Pro
 65                  70                  75                  80

Glu Asp Leu Asp Met Glu Asp Asn Asp Ile Ile Glu Ala His Arg Glu
                 85                  90                  95

Gln Ile Gly Gly
            100
```

```
<210> SEQ ID NO 803
<211> LENGTH: 297
<212> TYPE: PRT
<213> ORGANISM: Artificial Sequence
<220> FEATURE:
<223> OTHER INFORMATION: Amino acid Sequence of SDF

<400> SEQUENCE: 803

Gly Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
```

```
                50              55              60
Asp Leu Ile Gly Met Gly Lys Ser Asp Lys Pro Asp Leu Gly Tyr Phe
 65              70              75              80

Phe Asp Asp His Val Arg Phe Met Asp Ala Phe Ile Glu Ala Leu Gly
                 85              90              95

Leu Glu Glu Val Val Leu Val Ile His Asp Trp Gly Ser Ala Leu Gly
                100             105             110

Phe His Trp Ala Lys Arg Asn Pro Glu Arg Val Lys Gly Ile Ala Phe
                115             120             125

Met Glu Phe Ile Arg Pro Ile Pro Thr Trp Asp Glu Trp Pro Glu Phe
        130             135             140

Ala Arg Glu Thr Phe Gln Ala Phe Arg Thr Thr Asp Val Gly Arg Lys
145             150             155             160

Leu Ile Ile Asp Gln Asn Val Phe Ile Glu Gly Thr Leu Pro Met Gly
                165             170             175

Val Val Arg Pro Leu Thr Glu Val Glu Met Asp His Tyr Arg Glu Pro
                180             185             190

Phe Leu Asn Pro Val Asp Arg Glu Pro Leu Trp Arg Phe Pro Asn Glu
                195             200             205

Leu Pro Ile Ala Gly Glu Pro Ala Asn Ile Val Ala Leu Val Glu Glu
        210             215             220

Tyr Met Asp Trp Leu His Gln Ser Pro Val Pro Lys Leu Leu Phe Trp
225             230             235             240

Gly Thr Pro Gly Val Leu Ile Pro Pro Ala Glu Ala Ala Arg Leu Ala
                245             250             255

Lys Ser Leu Pro Asn Cys Lys Ala Val Asp Ile Gly Pro Gly Leu Asn
                260             265             270

Leu Leu Gln Glu Asp Asn Pro Asp Leu Ile Gly Ser Glu Ile Ala Arg
                275             280             285

Trp Leu Ser Thr Leu Glu Ile Ser Gly
        290             295

<210> SEQ ID NO 804
<211> LENGTH: 99
<212> TYPE: PRT
<213> ORGANISM: Artificial Sequence
<220> FEATURE:
<223> OTHER INFORMATION: Amino acid Sequence of SDB' for deimunization

<400> SEQUENCE: 804

Met Ala Glu Gln Ser Asp Lys Asp Val Lys Tyr Tyr Thr Leu Glu Glu
  1               5              10              15

Ile Gln Lys His Lys Asp Ser Lys Ser Thr Trp Leu Ile Leu His His
                 20              25              30

Lys Val Tyr Asp Leu Thr Lys Phe Leu Glu Glu His Pro Gly Gly Glu
         35              40              45

Glu Val Leu Gly Glu Gln Ala Gly Gly Asp Ala Thr Glu Asn Phe Glu
     50              55              60

Asp Val Gly His Ser Thr Asp Ala Arg Glu Leu Ser Lys Thr Tyr Ile
 65              70              75              80

Ile Gly Glu Leu His Pro Asp Asp Arg Ser Lys Ile Ala Lys Pro Ser
                 85              90              95

Glu Thr Leu

<210> SEQ ID NO 805
```

```
<211> LENGTH: 552
<212> TYPE: DNA
<213> ORGANISM: Artificial Sequence
<220> FEATURE:
<223> OTHER INFORMATION: cDNA Sequence of SDA

<400> SEQUENCE: 805
atggcaaata ttaccgtttt ctataacgaa gacttccagg gtaagcaggt cgatctgccg      60
cctggcaact atacccgcgc ccagttggcg gcgctgggca tcgagaataa taccatcagc     120
tcggtgaagg tgccgcctgg cgtgaaggct atcctgtacc agaacgatgg tttcgccggc     180
gaccagatcg aagtggtggc caatgccgag gagttgggcc cgctgaataa taacgtctcc     240
agcatccgcg tcatctccgt gcccgtgcag ccgcgcatgg caaatattac cgttttctat     300
aacgaagact tccagggtaa gcaggtcgat ctgccgcctg caactatac ccgcgcccag      360 ttggcggcgc tgggcatcga gaataatacc atcagctcgg tgaaggtgcc gcctggcgtg     420
aaggctatcc tctaccagaa cgatggtttc gccggcgacc agatcgaagt ggtggccaat     480
gccgaggagc tgggtccgct gaataataac gtctccagca tccgcgtcat ctccgtgccg     540
gtgcagccga gg                                                         552

<210> SEQ ID NO 806
<211> LENGTH: 297
<212> TYPE: DNA
<213> ORGANISM: Artificial Sequence
<220> FEATURE:
<223> OTHER INFORMATION: cDNA Sequence of SDB

<400> SEQUENCE: 806
atggcagaac aaagcgacaa ggatgtgaag tactacactc tggaggagat tcagaagcac      60
aaagacagca gagcacctg gtgatccta catcataagg tgtacgatct gaccaagttt       120
ctcgaagagc atcctggtgg ggaagaagtc ctgggcgagc aagctggggg tgatgctact     180
gagaactttg aggacgtcgg gcactctacg gatgcacgag aactgtccaa acatacatc      240 atcggggagc tccatccaga tgacagatca agatagcca agccttcgga aacccttt       297

<210> SEQ ID NO 807
<211> LENGTH: 327
<212> TYPE: DNA
<213> ORGANISM: Artificial Sequence
<220> FEATURE:
<223> OTHER INFORMATION: cDNA Sequence of SDC

<400> SEQUENCE: 807
atgagcgata aaattattca cctgactgac gacagttttg acacggatgt actcaaagcg      60
gacggggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggcc                                         327

<210> SEQ ID NO 808
<211> LENGTH: 624
<212> TYPE: DNA
<213> ORGANISM: Artificial Sequence
<220> FEATURE:
<223> OTHER INFORMATION: cDNA Sequence of SDD

<400> SEQUENCE: 808
```

```
atgaaaaaga tttggctggc gctggctggt ttagttttag cgtttagcgc atcggcggcg    60
cagtatgaag atggtaaaca gtacactacc ctggaaaaac cggtagctgg cgcgccgcaa   120
gtgctggagt ttttctcttt cttctgcccg cactgctatc agtttgaaga agttctgcat   180
atttctgata atgtgaagaa aaaactgccg gaaggcgtga agatgactaa ataccacgtc   240
aacttcatgg gtggtgacct gggcaaagat ctgactcagg catgggctgt ggcgatggcg   300
ctgggcgtgg aagacaaagt gactgttccg ctgtttgaag cgtacagaa acccagacc    360 attcgttctg cttctgatat ccgcgatgta tttatcaacg caggtattaa aggtgaagag   420
tacgacgcgg cgtggaacag cttcgtggtg aaatctctgg tcgctcagca ggaaaaagct   480
gcagctgacg tgcaattgcg tggcgttccg gcgatgtttg ttaacggtaa atatcagctg   540
aatccgcagg gtatggatac cagcaatatg gatgttttg ttcagcagta tgctgataca   600
gtgaaatatc tgtccgagaa aaaa                                          624
```

<210> SEQ ID NO 809
<211> LENGTH: 300
<212> TYPE: DNA
<213> ORGANISM: Artificial Sequence
<220> FEATURE:
<223> OTHER INFORMATION: cDNA Sequence of SDE

<400> SEQUENCE: 809

```
gggtccctgc aggactcaga agtcaatcaa gaagctaagc cagaggtcaa gccagaagtc    60
aagcctgaga ctcacatcaa tttaaaggtg tccgatggat cttcagagat cttcttcaag   120
atcaaaaaga ccactccttt aagaaggctg atggaagcgt tcgctaaaag acagggtaag   180
gaaatggact ccttaacgtt cttgtacgac ggtattgaaa ttcaagctga tcagacccct   240
gaagatttgg acatggagga taacgatatt attgaggctc accgcgaaca gattggaggt   300
```

<210> SEQ ID NO 810
<211> LENGTH: 891
<212> TYPE: DNA
<213> ORGANISM: Artificial Sequence
<220> FEATURE:
<223> OTHER INFORMATION: cDNA Sequence of SDF

<400> SEQUENCE: 810

```
ggatccgaaa tcggtactgg ctttccattc gacccccatt atgtggaagt cctgggcgag    60
cgcatgcact acgtcgatgt tggtccgcgc gatggcaccc tgtgctgtt cctgcacggt   120 aacccgacct cctcctacgt gtggcgcaac atcatcccgc atgttgcacc gacccatcgc   180
tgcattgctc cagacctgat cggtatgggc aaatccgaca accagacct gggttatttc   240 ttcgacgacc acgtccgctt catggatgcc ttcatcgaag ccctgggtct ggaagaggtc   300
gtcctggtca ttcacgactg gggctccgct ctgggtttcc actgggccaa gcgcaatcca   360
gagcgcgtca aggtattgc atttatgag ttcatccgcc ctatcccgac ctgggacgaa   420
tggccagaat tgcccgcga accttccag gccttccgca ccaccgacgt cggccgcaag   480
ctgatcatcg atcagaacgt ttttatcgag ggtacgctgc cgatgggtgt cgtccgcccg   540
ctgactgaag tcgagatgga ccattaccgc gagccgttcc tgaatcctgt tgaccgcgag   600
ccactgtggc gcttcccaaa cgagctgcca atcgccggtg agccagcgaa catcgtcgcg   660
ctggtcgaag aatacatgga ctggctgcac cagtcccctg tcccgaagct gctgttctgg   720
ggcaccccag gcgttctgat cccaccggcc gaagccgctc gcctggccaa aagcctgcct   780
```

```
aactgcaagg ctgtggacat cggcccgggt ctgaatctgc tgcaagaaga caacccggac      840
ctgatcggca gcgagatcgc gcgctggctg tctactctgg agatttccgg t              891
```

<210> SEQ ID NO 811
<211> LENGTH: 297
<212> TYPE: DNA
<213> ORGANISM: Artificial Sequence
<220> FEATURE:
<223> OTHER INFORMATION: cDNA Sequence of SDB' for deimunization

<400> SEQUENCE: 811

```
atggcagaac aaagcgacaa ggatgtgaag tactacactc tggaggagat tcagaagcac       60
aaagacagca agagcacctg gctgatccta catcataagg tgtacgatct gaccaagttt      120
ctcgaagagc atcctggtgg ggaagaagtc ctgggcgagc aagctggggg tgatgctact      180
gagaactttg aggacgtcgg gcactctacg gatgcacgag aactgtccaa acatacatc      240 atcggggagc tccatccaga tgacagatca aagatagcca agccttcgga aacccttt       297
```

<210> SEQ ID NO 812
<211> LENGTH: 19
<212> TYPE: PRT
<213> ORGANISM: Artificial Sequence
<220> FEATURE:
<223> OTHER INFORMATION: Amino acid Sequence of Histidine Tag

<400> SEQUENCE: 812

```
Met Gly Ser Ser His His His His His His Ser Ser Gly Leu Val Pro
1               5                   10                  15

Arg Gly Ser
```

<210> SEQ ID NO 813
<211> LENGTH: 57
<212> TYPE: DNA
<213> ORGANISM: Artificial Sequence
<220> FEATURE:
<223> OTHER INFORMATION: cDNA Sequence of Histidine Tag

<400> SEQUENCE: 813

```
atgggcagca gccatcatca tcatcatcac agcagcggcc tggtgccgcg cggcagc         57
```

<210> SEQ ID NO 814
<211> LENGTH: 225
<212> TYPE: PRT
<213> ORGANISM: Artificial Sequence
<220> FEATURE:
<223> OTHER INFORMATION: Amino Acid Sequence of Human SOCS3

<400> SEQUENCE: 814

```
Met Val Thr His Ser Lys Phe Pro Ala Ala Gly Met Ser Arg Pro Leu
1               5                   10                  15

Asp Thr Ser Leu Arg Leu Lys Thr Phe Ser Ser Lys Ser Glu Tyr Gln
                20                  25                  30

Leu Val Val Asn Ala Val Arg Lys Leu Gln Glu Ser Gly Phe Tyr Trp
            35                  40                  45

Ser Ala Val Thr Gly Gly Glu Ala Asn Leu Leu Leu Ser Ala Glu Pro
        50                  55                  60

Ala Gly Thr Phe Leu Ile Arg Asp Ser Ser Asp Gln Arg His Phe Phe
65                  70                  75                  80

Thr Leu Ser Val Lys Thr Gln Ser Gly Thr Lys Asn Leu Arg Ile Gln
                85                  90                  95
```

```
              Cys Glu Gly Gly Ser Phe Ser Leu Gln Ser Asp Pro Arg Ser Thr Gln
                          100                 105                 110

Pro Val Pro Arg Phe Asp Cys Val Leu Lys Leu Val His His Tyr Met
                      115                 120                 125

Pro Pro Pro Gly Ala Pro Ser Phe Pro Ser Pro Thr Glu Pro Ser
                  130                 135                 140

Ser Glu Val Pro Glu Gln Pro Ser Ala Gln Pro Leu Pro Gly Ser Pro
              145                 150                 155                 160

Pro Arg Arg Ala Tyr Tyr Ile Tyr Ser Gly Gly Glu Lys Ile Pro Leu
                              165                 170                 175

Val Leu Ser Arg Pro Leu Ser Ser Asn Val Ala Thr Leu Gln His Leu
                          180                 185                 190

Cys Arg Lys Thr Val Asn Gly His Leu Asp Ser Tyr Glu Lys Val Thr
                          195                 200                 205

Gln Leu Pro Gly Pro Ile Arg Glu Phe Leu Asp Gln Tyr Asp Ala Pro
                          210                 215                 220

Leu
              225

<210> SEQ ID NO 815
<211> LENGTH: 675
<212> TYPE: DNA
<213> ORGANISM: Artificial Sequence
<220> FEATURE:
<223> OTHER INFORMATION: cDNA Sequences of Human SOCS3

<400> SEQUENCE: 815
atggtcaccc acagcaagtt tcccgccgcc gggatgagcc gcccctgga caccagcctg          60 cgcctcaaga ccttcagctc caagagcgag taccagctgg tggtgaacgc agtgcgcaag       120
ctgcaggaga gcggcttcta ctggagcgca gtgaccggcg gcgaggcgaa cctgctgctc       180
agtgccgagc cgccggcac ctttctgatc cgcgacagct cggaccagcg ccacttcttc        240
acgctcagcg tcaagaccca gtctgggacc aagaacctgc gcatccagtg tgagggggc        300 agcttctctc tgcagagcga tccccggagc acgcagcccg tgccccgctt cgactgcgtg       360
ctcaagctgg tgcaccacta catgccgccc cctggagccc cctccttccc ctcgccacct       420
actgaaccct cctccgaggt gcccgagcag ccgtctgccc agccactccc tgggagtccc       480
cccagaagag cctattacat ctactccggg ggcgagaaga tcccctggt gttgagccgg        540 cccctctcct ccaacgtggc cactcttcag catctctgtc ggaagaccgt caacggccac       600
ctggactcct atgagaaagt cacccagctg ccggggccca ttcgggagtt cctggaccag       660
tacgatgccc cgctt                                                         675

<210> SEQ ID NO 816
<211> LENGTH: 25
<212> TYPE: DNA
<213> ORGANISM: Artificial Sequence
<220> FEATURE:
<223> OTHER INFORMATION: Unmethyl-F primer

<400> SEQUENCE: 816
tagtgtgtaa gttgtaggag agtgg                                               25

<210> SEQ ID NO 817
<211> LENGTH: 30
<212> TYPE: DNA
<213> ORGANISM: Artificial Sequence
<220> FEATURE:
```

-continued

```
<223> OTHER INFORMATION: Unmethyl-R primer

<400> SEQUENCE: 817
ctaaacataa aaaaataaca ctaatccaaa                                          30

<210> SEQ ID NO 818
<211> LENGTH: 24
<212> TYPE: DNA
<213> ORGANISM: Artificial Sequence
<220> FEATURE:
<223> OTHER INFORMATION: Methyl-F primer

<400> SEQUENCE: 818
gtagtgcgta agttgtagga gagc                                                24

<210> SEQ ID NO 819
<211> LENGTH: 24
<212> TYPE: DNA
<213> ORGANISM: Artificial Sequence
<220> FEATURE:
<223> OTHER INFORMATION: Methyl-R primer

<400> SEQUENCE: 819
gtaaaaaaat aacgctaatc cgaa                                                24

<210> SEQ ID NO 820
<211> LENGTH: 20
<212> TYPE: DNA
<213> ORGANISM: Artificial Sequence
<220> FEATURE:
<223> OTHER INFORMATION: SOCS3 primer F

<400> SEQUENCE: 820
cctactgaac cctcctccga                                                     20

<210> SEQ ID NO 821
<211> LENGTH: 20
<212> TYPE: DNA
<213> ORGANISM: Artificial Sequence
<220> FEATURE:
<223> OTHER INFORMATION: SOCS3 primer R

<400> SEQUENCE: 821
gcagctgggt gactttctca                                                     20

<210> SEQ ID NO 822
<211> LENGTH: 12
<212> TYPE: PRT
<213> ORGANISM: Artificial Sequence
<220> FEATURE:
<223> OTHER INFORMATION: Amino acid Sequence of aMTD662

<400> SEQUENCE: 822

Ala Leu Ala Val Ile Leu Ala Pro Val Ala Val Pro
1               5                   10

<210> SEQ ID NO 823
<211> LENGTH: 36
<212> TYPE: DNA
<213> ORGANISM: Artificial Sequence
<220> FEATURE:
<223> OTHER INFORMATION: cDNA Sequence of aMTD662

<400> SEQUENCE: 823
gcgctggcgg tgattctggc gccggtggcg gtgccg                                   36
```

<210> SEQ ID NO 824
<211> LENGTH: 1005
<212> TYPE: DNA
<213> ORGANISM: Artificial Sequence
<220> FEATURE:
<223> OTHER INFORMATION: cDNA sequence of E.coli codon usage optimized M165S3B'

<400> SEQUENCE: 824

```
gcgctggcgg tgccggttgc gctggcgatc gtgccggtta cccacagcaa gtttccggcg      60
gcgggtatga gccgtccgct ggacaccagc ctgcgtctga agacctttag cagcaaaagc     120
gagtaccagc tggttgtgaa cgcggtgcgt aaactgcaag aaagcggctt ctattggagc     180
gcggttaccg gtggcgaggc gaacctgctg ctgagcgcgg agccggcggg caccttcctg     240
atccgtgaca gcagcgatca gcgtcacttc tttaccctga gcgttaagac ccagagcggc     300
accaaaaacc tgcgtattca atgcgagggt ggcagcttca gcctgcaaag cgacccgcgt     360
agcacccaac cggtgccgcg ttttgattgc gtgctgaagc tggttcacca ctacatgccg     420
ccgccgggtg cgccgagctt cccgagcccg ccgaccgagc cgagcagcga ggttccggaa     480
cagccgagcg cgcaaccgct gccgggtagc ccgccgcgtc gtgcgtacta tatctatagc     540
ggtggcgaaa aaattccgct ggtgctgagc cgtccgctga gcagcaacgt tgcgaccctg     600
caacacctgt gccgtaagac cgtgaacggt cacctggaca gctacgagaa agttacccaa     660
ctgccgggcc cgatccgtga atttctggac cagtatgatg cgccgctgat ggcggaacaa     720
agcgacaagg atgtgaaata ctataccctg gaggaaatcc agaagcacaa agacagcaag     780
agcacctggc tgattctgca ccacaaggtg tacgatctga ccaaattcct ggaggaacat     840
ccgggtggtg aggaagtgct gggcgagcaa gcgggtggcg atgcgaccga gaactttgaa     900
gacgtgggcc acagcaccga tgcgcgtgag ctgagcaaaa cctatatcat tggtgaactg     960
cacccggacg atcgtagcaa gattgcgaaa ccgagcgaaa ccctg              1005
```

<210> SEQ ID NO 825
<211> LENGTH: 335
<212> TYPE: PRT
<213> ORGANISM: Artificial Sequence
<220> FEATURE:
<223> OTHER INFORMATION: Amino acid sequence of E.coli codon usage optimized M165S3B'

<400> SEQUENCE: 825

```
Ala Leu Ala Val Pro Val Ala Leu Ala Ile Val Pro Val Thr His Ser
1               5                   10                  15

Lys Phe Pro Ala Ala Gly Met Ser Arg Pro Leu Asp Thr Ser Leu Arg
                20                  25                  30

Leu Lys Thr Phe Ser Ser Lys Ser Glu Tyr Gln Leu Val Val Asn Ala
            35                  40                  45

Val Arg Lys Leu Gln Glu Ser Gly Phe Tyr Trp Ser Ala Val Thr Gly
        50                  55                  60

Gly Glu Ala Asn Leu Leu Leu Ser Ala Glu Pro Ala Gly Thr Phe Leu
65                  70                  75                  80

Ile Arg Asp Ser Ser Asp Gln Arg His Phe Phe Thr Leu Ser Val Lys
                85                  90                  95

Thr Gln Ser Gly Thr Lys Asn Leu Arg Ile Gln Cys Glu Gly Gly Ser
            100                 105                 110

Phe Ser Leu Gln Ser Asp Pro Arg Ser Thr Gln Pro Val Pro Arg Phe
        115                 120                 125
```

```
Asp Cys Val Leu Lys Leu Val His His Tyr Met Pro Pro Gly Ala
    130                 135                 140

Pro Ser Phe Pro Ser Pro Thr Glu Pro Ser Glu Val Pro Glu
145             150                 155                 160

Gln Pro Ser Ala Gln Pro Leu Pro Gly Ser Pro Pro Arg Arg Ala Tyr
                165                 170                 175

Tyr Ile Tyr Ser Gly Gly Glu Lys Ile Pro Leu Val Leu Ser Arg Pro
            180                 185                 190

Leu Ser Ser Asn Val Ala Thr Leu Gln His Leu Cys Arg Lys Thr Val
            195                 200                 205

Asn Gly His Leu Asp Ser Tyr Glu Lys Val Thr Gln Leu Pro Gly Pro
210                 215                 220

Ile Arg Glu Phe Leu Asp Gln Tyr Asp Ala Pro Leu Met Ala Glu Gln
225                 230                 235                 240

Ser Asp Lys Asp Val Lys Tyr Tyr Thr Leu Glu Glu Ile Gln Lys His
                245                 250                 255

Lys Asp Ser Lys Ser Thr Trp Leu Ile Leu His His Lys Val Tyr Asp
            260                 265                 270

Leu Thr Lys Phe Leu Glu Glu His Pro Gly Gly Glu Glu Val Leu Gly
            275                 280                 285

Glu Gln Ala Gly Gly Asp Ala Thr Glu Asn Phe Glu Asp Val Gly His
290                 295                 300

Ser Thr Asp Ala Arg Glu Leu Ser Lys Thr Tyr Ile Ile Gly Glu Leu
305                 310                 315                 320

His Pro Asp Asp Arg Ser Lys Ile Ala Lys Pro Ser Glu Thr Leu
                325                 330                 335
```

<210> SEQ ID NO 826
<211> LENGTH: 1074
<212> TYPE: DNA
<213> ORGANISM: Artificial Sequence
<220> FEATURE:
<223> OTHER INFORMATION: cDNA sequence of HM165S3B

<400> SEQUENCE: 826

```
atgggcagca gccatcatca tcatcatcac agcagcggcc tggtgccgcg cggcagccat      60
atggcgctgg cggtgccggt ggcgctggcg attgtgccgg tcaccacag caagtttccc     120 gccgccggga tgagccgccc cctggacacc agcctgcgcc tcaagacctt cagctccaag     180
agcgagtacc agctggtggt gaacgcagtg cgcaagctgc aggagagcgg cttctactgg     240
agcgcagtga ccggcggcga ggcgaacctg ctgctcagtg ccgagcccgc cggcaccttt     300
ctgatccgcg acagctcgga ccagcgccac ttcttcacgc tcagcgtcaa gacccagtct     360
gggaccaaga acctgcgcat ccagtgtgag gggggcagct tctctctgca gagcgatccc     420
cggagcacgc agcccgtgcc ccgcttcgac tgcgtgctca agctggtgca ccactacatg     480 ccgcccctg gagccccctc cttcccctcg ccacctactg aaccctcctc cgaggtgccc     540
gagcagccgt ctgcccagcc actccctggg agtccccca agagagccta ttacatctac     600 tccggggcg agaagatccc cctggtgttg agcggccc tcctccaa cgtggccact     660 cttcagcatc tctgtcggaa gaccgtcaac ggccacctgg actcctatga aaagtcacc     720 cagctgccgg ggcccattcg ggagttcctg gaccagtacg atgccccgct tggatccatg     780
gcagaacaaa gcgacaagga tgtgaagtac tacactctgg aggagattca gaagcacaaa     840
gacagcaaga gcacctgggt gatcctacat cataaggtgt acgatctgac caagtttctc     900
```

-continued

```
gaagagcatc ctggtgggga agaagtcctg ggcgagcaag ctgggggtga tgctactgag    960
aactttgagg acgtcgggca ctctacggat gcacgagaac tgtccaaaac atacatcatc   1020
ggggagctcc atccagatga cagatcaaag atagccaagc cttcggaaac cctt         1074
```

<210> SEQ ID NO 827
<211> LENGTH: 362
<212> TYPE: PRT
<213> ORGANISM: Artificial Sequence
<220> FEATURE:
<223> OTHER INFORMATION: Amino acid sequence of HM165S3B

<400> SEQUENCE: 827

```
Met Gly Ser Ser His His His His His Ser Ser Gly Leu Val Pro
1               5                   10                  15

Arg Gly Ser His Met Ala Leu Ala Val Pro Val Ala Leu Ala Ile Val
            20                  25                  30

Pro Val Thr His Ser Lys Phe Pro Ala Ala Gly Met Glu Thr Ser Arg
        35                  40                  45

Pro Leu Asp Thr Ser Leu Arg Leu Lys Thr Phe Ser Ser Lys Ser Glu
    50                  55                  60

Tyr Gln Leu Val Val Asn Ala Val Arg Lys Leu Gln Glu Ser Gly Phe
65                  70                  75                  80

Tyr Trp Ser Ala Val Thr Gly Gly Glu Ala Asn Leu Leu Leu Ser Ala
                85                  90                  95

Glu Pro Ala Gly Thr Phe Leu Ile Arg Asp Ser Ser Asp Gln Arg His
            100                 105                 110

Phe Phe Thr Leu Ser Val Lys Thr Gln Ser Gly Thr Lys Asn Leu Arg
        115                 120                 125

Ile Gln Cys Glu Gly Gly Ser Phe Ser Leu Gln Ser Asp Pro Arg Ser
    130                 135                 140

Thr Gln Pro Val Pro Arg Phe Asp Cys Val Leu Lys Leu Val His His
145                 150                 155                 160

Tyr Met Glu Thr Pro Pro Gly Ala Pro Ser Phe Pro Ser Pro Pro
                165                 170                 175

Thr Glu Pro Ser Ser Glu Val Pro Glu Gln Pro Ser Ala Gln Pro Leu
            180                 185                 190

Pro Gly Ser Pro Pro Arg Arg Ala Tyr Tyr Ile Tyr Ser Gly Gly Glu
        195                 200                 205

Lys Ile Pro Leu Val Leu Ser Arg Pro Leu Ser Ser Asn Val Ala Thr
    210                 215                 220

Leu Gln His Leu Cys Arg Lys Thr Val Asn Gly His Leu Asp Ser Tyr
225                 230                 235                 240

Glu Lys Val Thr Gln Leu Pro Gly Pro Ile Arg Glu Phe Leu Asp Gln
                245                 250                 255

Tyr Asp Ala Pro Leu Gly Ser Met Ala Glu Gln Ser Asp Lys Asp Val
            260                 265                 270

Lys Tyr Tyr Thr Leu Glu Glu Ile Gln Lys His Lys Asp Ser Lys Ser
        275                 280                 285

Thr Trp Val Ile Leu His His Lys Val Tyr Asp Leu Thr Lys Phe Leu
    290                 295                 300

Glu Glu His Pro Gly Gly Glu Glu Val Leu Gly Glu Gln Ala Gly Gly
305                 310                 315                 320

Asp Ala Thr Glu Asn Phe Glu Asp Val Gly His Ser Thr Asp Ala Arg
                325                 330                 335
```

Glu Leu Ser Lys Thr Tyr Ile Ile Gly Glu Leu His Pro Asp Asp Arg
                340                 345                 350

Ser Lys Ile Ala Lys Pro Ser Glu Thr Leu
        355                 360

<210> SEQ ID NO 828
<211> LENGTH: 1014
<212> TYPE: DNA
<213> ORGANISM: Artificial Sequence
<220> FEATURE:
<223> OTHER INFORMATION: cDNA sequence of BS3M165

<400> SEQUENCE: 828
atgatggcag aacaaagcga caaggatgtg aagtactaca ctctggagga gattcagaag      60
cacaaagaca gcaagagcac ctgggtgatc ctacatcata aggtgtacga tctgaccaag     120
tttctcgaag agcatcctgg tggggaagaa gtcctgggcg agcaagctgg gggtgatgct     180
actgagaact tgaggacgt cgggcactct acggatgcac gagaactgtc caaaacatac      240
atcatcgggg agctccatcc agatgacaga tcaaagatag ccaagccttc ggaaacccTT     300
ggatccgtca cccacagcaa gtttcccgcc gccgggatga ccgcccct ggacaccagc       360 ctgcgcctca agaccttcag ctccaagagc gagtaccagc tggtggtgaa cgcagtgcgc     420
aagctgcagg agagcggctt ctactggagc gcagtgaccg cggcgaggc gaacctgctg      480 ctcagtgccg agcccgccgg cacctttctg atccgcgaca gctcggacca gcgccacttc     540
ttcacgctca gcgtcaagac ccagtctggg accaagaacc tgcgcatcca gtgtgagggg     600
ggcagcttct ctctgcagag cgatccccgg agcacgcagc ccgtgccccg cttcgactgc     660
gtgctcaagc tggtgcacca ctacatgccg ccccctggag cccctccctt cccctcgcca     720
cctactgaac cctcctccga ggtgcccgag cagccgtctg cccagccact ccctgggagt     780
ccccccagaa gagcctatta catctactcc gggggcgaga agatccccct ggtgttgagc     840
cggcccctct cctccaacgt ggccactctt cagcatctct gtcggaagac cgtcaacggc     900
cacctggact cctatgagaa agtcaccCag ctgccggggc ccattcggga gttcctggac     960
cagtacgatg ccccgcttcc ggtgattgcg ctggcggtgc cggtggcgct ggcg          1014

<210> SEQ ID NO 829
<211> LENGTH: 342
<212> TYPE: PRT
<213> ORGANISM: Artificial Sequence
<220> FEATURE:
<223> OTHER INFORMATION: Amino acid sequence of BS3M165

<400> SEQUENCE: 829

Met Met Ala Glu Gln Ser Asp Lys Asp Val Lys Tyr Tyr Thr Leu Glu
1               5                   10                  15

Glu Ile Gln Lys His Lys Asp Ser Lys Ser Thr Trp Val Ile Leu His
            20                  25                  30

His Lys Val Tyr Asp Leu Thr Lys Phe Leu Glu Glu His Pro Gly Gly
        35                  40                  45

Glu Glu Val Leu Gly Glu Gln Ala Gly Gly Asp Ala Thr Glu Asn Phe
    50                  55                  60

Glu Asp Val Gly His Ser Thr Asp Ala Arg Glu Leu Ser Lys Thr Tyr
65                  70                  75                  80

Ile Ile Gly Glu Leu His Pro Asp Asp Arg Ser Lys Ile Ala Lys Pro
                85                  90                  95

```
Ser Glu Thr Leu Gly Ser Val Thr His Ser Lys Phe Pro Ala Ala Gly
            100                 105                 110

Met Glu Thr Ser Arg Pro Leu Asp Thr Ser Leu Arg Leu Lys Thr Phe
            115                 120                 125

Ser Ser Lys Ser Glu Tyr Gln Leu Val Val Asn Ala Val Arg Lys Leu
        130                 135                 140

Gln Glu Ser Gly Phe Tyr Trp Ser Ala Val Thr Gly Gly Glu Ala Asn
145                 150                 155                 160

Leu Leu Leu Ser Ala Glu Pro Ala Gly Thr Phe Leu Ile Arg Asp Ser
                165                 170                 175

Ser Asp Gln Arg His Phe Phe Thr Leu Ser Val Lys Thr Gln Ser Gly
            180                 185                 190

Thr Lys Asn Leu Arg Ile Gln Cys Glu Gly Gly Ser Phe Ser Leu Gln
        195                 200                 205

Ser Asp Pro Arg Ser Thr Gln Pro Val Pro Arg Phe Asp Cys Val Leu
    210                 215                 220

Lys Leu Val His His Tyr Met Glu Thr Pro Pro Gly Ala Pro Ser
225                 230                 235                 240

Phe Pro Ser Pro Pro Thr Glu Pro Ser Ser Glu Val Pro Glu Gln Pro
                245                 250                 255

Ser Ala Gln Pro Leu Pro Gly Ser Pro Pro Arg Arg Ala Tyr Tyr Ile
            260                 265                 270

Tyr Ser Gly Gly Glu Lys Ile Pro Leu Val Leu Ser Arg Pro Leu Ser
        275                 280                 285

Ser Asn Val Ala Thr Leu Gln His Leu Cys Arg Lys Thr Val Asn Gly
    290                 295                 300

His Leu Asp Ser Tyr Glu Lys Val Thr Gln Leu Pro Gly Pro Ile Arg
305                 310                 315                 320

Glu Phe Leu Asp Gln Tyr Asp Ala Pro Leu Pro Val Ile Ala Leu Ala
                325                 330                 335

Val Pro Val Ala Leu Ala
            340

<210> SEQ ID NO 830
<211> LENGTH: 1014
<212> TYPE: DNA
<213> ORGANISM: Artificial Sequence
<220> FEATURE:
<223> OTHER INFORMATION: cDNA sequence of B'S3M165

<400> SEQUENCE: 830
atgatggcag aacaaagcga caaggatgtg aagtactaca ctctggagga gattcagaag      60
cacaaagaca gcaagagcac ctggctgatc ctacatcata aggtgtacga tctgaccaag     120
tttctcgaag agcatcctgg tggggaagaa gtcctgggcg agcaagctgg gggtgatgct     180
actgagaact tgaggacgt cgggcactct acggatgcac agaactgtc caaacatac        240 atcatcgggg agctccatcc agatgacaga tcaaagatag ccaagccttc ggaaaccctt     300
ggatccgtca cccacagcaa gtttcccgcc gccgggatga ccgcccccct ggacaccagc     360
ctgcgcctca gaccttcag ctccaagagc gagtaccagc tggtggtgaa cgcagtgcgc      420
aagctgcagg agagcggctt ctactggagc gcagtgaccg gcggcgaggc gaacctgctg     480
ctcagtgccg agcccgccgg cacctttctg atccgcgaca gctcggacca gcgccacttc     540
ttcacgctca gcgtcaagac ccagtctggg accaagaacc tgcgcatcca gtgtgagggg     600
ggcagcttct ctctgcagag cgatccccgg agcacgcagc ccgtgccccg cttcgactgc     660
```

```
gtgctcaagc tggtgcacca ctacatgccg cccctggag ccccctcctt ccctcgcca      720 cctactgaac cctcctccga ggtgcccgag cagccgtctg cccagccact ccctgggagt    780 cccccagaa gagcctatta catctactcc gggggcgaga agatccccct ggtgttgagc    840
cggcccctct cctccaacgt ggccactctt cagcatctct gtcggaagac cgtcaacggc    900
cacctggact cctatgagaa agtcacccag ctgccggggc ccattcggga gttcctggac    960
cagtacgatg ccccgcttcc ggtgattgcg ctggcggtgc cggtggcgct ggcg          1014
```

<210> SEQ ID NO 831
<211> LENGTH: 342
<212> TYPE: PRT
<213> ORGANISM: Artificial Sequence
<220> FEATURE:
<223> OTHER INFORMATION: Amino acid sequence of B'S3M165

<400> SEQUENCE: 831

```
Met Met Ala Glu Gln Ser Asp Lys Asp Val Lys Tyr Tyr Thr Leu Glu
1               5                   10                  15

Glu Ile Gln Lys His Lys Asp Ser Lys Ser Thr Trp Leu Ile Leu His
                20                  25                  30

His Lys Val Tyr Asp Leu Thr Lys Phe Leu Glu Glu His Pro Gly Gly
            35                  40                  45

Glu Glu Val Leu Gly Glu Gln Ala Gly Gly Asp Ala Thr Glu Asn Phe
        50                  55                  60

Glu Asp Val Gly His Ser Thr Asp Ala Arg Glu Leu Ser Lys Thr Tyr
65                  70                  75                  80

Ile Ile Gly Glu Leu His Pro Asp Asp Arg Ser Lys Ile Ala Lys Pro
                85                  90                  95

Ser Glu Thr Leu Gly Ser Val Thr His Ser Lys Phe Pro Ala Ala Gly
            100                 105                 110

Met Glu Thr Ser Arg Pro Leu Asp Thr Ser Leu Arg Leu Lys Thr Phe
        115                 120                 125

Ser Ser Lys Ser Glu Tyr Gln Leu Val Val Asn Ala Val Arg Lys Leu
    130                 135                 140

Gln Glu Ser Gly Phe Tyr Trp Ser Ala Val Thr Gly Gly Glu Ala Asn
145                 150                 155                 160

Leu Leu Leu Ser Ala Glu Pro Ala Gly Thr Phe Leu Ile Arg Asp Ser
                165                 170                 175

Ser Asp Gln Arg His Phe Phe Thr Leu Ser Val Lys Thr Gln Ser Gly
            180                 185                 190

Thr Lys Asn Leu Arg Ile Gln Cys Glu Gly Gly Ser Phe Ser Leu Gln
        195                 200                 205

Ser Asp Pro Arg Ser Thr Gln Pro Val Pro Arg Phe Asp Cys Val Leu
    210                 215                 220

Lys Leu Val His His Tyr Met Glu Thr Pro Pro Gly Ala Pro Ser
225                 230                 235                 240

Phe Pro Ser Pro Pro Thr Glu Pro Ser Ser Glu Val Pro Glu Gln Pro
                245                 250                 255

Ser Ala Gln Pro Leu Pro Gly Ser Pro Pro Arg Arg Ala Tyr Tyr Ile
            260                 265                 270

Tyr Ser Gly Gly Glu Lys Ile Pro Leu Val Leu Ser Arg Pro Leu Ser
        275                 280                 285

Ser Asn Val Ala Thr Leu Gln His Leu Cys Arg Lys Thr Val Asn Gly
    290                 295                 300
```

His Leu Asp Ser Tyr Glu Lys Val Thr Gln Leu Pro Gly Pro Ile Arg
305                 310                 315                 320

Glu Phe Leu Asp Gln Tyr Asp Ala Pro Leu Pro Val Ile Ala Leu Ala
            325                 330                 335

Val Pro Val Ala Leu Ala
            340

<210> SEQ ID NO 832
<211> LENGTH: 11
<212> TYPE: PRT
<213> ORGANISM: Artificial Sequence
<220> FEATURE:
<223> OTHER INFORMATION: Amino acid sequence of TAT

<400> SEQUENCE: 832

Tyr Gly Arg Lys Lys Arg Arg Gln Arg Arg Arg
1               5                   10

<210> SEQ ID NO 833
<211> LENGTH: 33
<212> TYPE: DNA
<213> ORGANISM: Artificial Sequence
<220> FEATURE:
<223> OTHER INFORMATION: Nucleotide sequence of TAT

<400> SEQUENCE: 833
tatggccgca aaaacgccg ccagcgccgc cgc                                    33

<210> SEQ ID NO 834
<211> LENGTH: 9
<212> TYPE: PRT
<213> ORGANISM: Artificial Sequence
<220> FEATURE:
<223> OTHER INFORMATION: Amino acid sequence of PolyR

<400> SEQUENCE: 834

Arg Arg Arg Arg Arg Arg Arg Arg Arg
1               5

<210> SEQ ID NO 835
<211> LENGTH: 27
<212> TYPE: PRT
<213> ORGANISM: Artificial Sequence
<220> FEATURE:
<223> OTHER INFORMATION: Nucleotide sequence of PolyR

<400> SEQUENCE: 835

Cys Gly Thr Cys Gly Thr Cys Gly Thr Cys Gly Thr Cys Gly Thr Cys
1               5                   10                  15

Gly Thr Cys Gly Thr Cys Gly Thr Cys Gly Thr
            20                  25

<210> SEQ ID NO 836
<211> LENGTH: 73
<212> TYPE: DNA
<213> ORGANISM: Artificial Sequence
<220> FEATURE:
<223> OTHER INFORMATION: 5' primer for TAT

<400> SEQUENCE: 836
ggaattccat atgtatggcc gcaaaaaacg ccgccagcgc cgccgcgtca cccacagcaa    60
gtttcccgcc gcc                                                       73

-continued

```
<210> SEQ ID NO 837
<211> LENGTH: 67
<212> TYPE: DNA
<213> ORGANISM: Artificial Sequence
<220> FEATURE:
<223> OTHER INFORMATION: 5' primer for PolyR

<400> SEQUENCE: 837
ggaattccat atgcgtcgtc gtcgtcgtcg tcgtcgtcgt gtcacccaca gcaagtttcc    60
cgccgcc                                                              67

<210> SEQ ID NO 838
<211> LENGTH: 39
<212> TYPE: DNA
<213> ORGANISM: Artificial Sequence
<220> FEATURE:
<223> OTHER INFORMATION: 3' primer for TAT and PolyR

<400> SEQUENCE: 838
cgcgtcgact taaagggttt ccgaaggctt ggctatctt                            39

<210> SEQ ID NO 839
<211> LENGTH: 20
<212> TYPE: DNA
<213> ORGANISM: Artificial Sequence
<220> FEATURE:
<223> OTHER INFORMATION: 5' primer for Cyclin E

<400> SEQUENCE: 839
ccgtttacaa gctaagcagc                                                20

<210> SEQ ID NO 840
<211> LENGTH: 20
<212> TYPE: DNA
<213> ORGANISM: Artificial Sequence
<220> FEATURE:
<223> OTHER INFORMATION: 3' primer for Cyclin E

<400> SEQUENCE: 840
gtggttccaa gtcagaatgc                                                20

<210> SEQ ID NO 841
<211> LENGTH: 21
<212> TYPE: DNA
<213> ORGANISM: Artificial Sequence
<220> FEATURE:
<223> OTHER INFORMATION: 5' primer for Cyclin A1

<400> SEQUENCE: 841
tcagtacttg aggcgacaag g                                              21

<210> SEQ ID NO 842
<211> LENGTH: 21
<212> TYPE: DNA
<213> ORGANISM: Artificial Sequence
<220> FEATURE:
<223> OTHER INFORMATION: 3' primer for Cyclin A1

<400> SEQUENCE: 842
ctccctaatt gcttgctgag g                                              21

<210> SEQ ID NO 843
<211> LENGTH: 20
<212> TYPE: DNA
<213> ORGANISM: Artificial Sequence
<220> FEATURE:
```

<223> OTHER INFORMATION: 5' primer for Bax

<400> SEQUENCE: 843 ccctttgct tcagggtttc                    20

<210> SEQ ID NO 844
<211> LENGTH: 20
<212> TYPE: DNA
<213> ORGANISM: Artificial Sequence
<220> FEATURE:
<223> OTHER INFORMATION: 3' primer for Bax

<400> SEQUENCE: 844
gccactcgga aaaagacctc                    20

<210> SEQ ID NO 845
<211> LENGTH: 20
<212> TYPE: DNA
<213> ORGANISM: Artificial Sequence
<220> FEATURE:
<223> OTHER INFORMATION: 5' primer for FAK

<400> SEQUENCE: 845
tggtgaaagc tgtcatcgag                    20

<210> SEQ ID NO 846
<211> LENGTH: 20
<212> TYPE: DNA
<213> ORGANISM: Artificial Sequence
<220> FEATURE:
<223> OTHER INFORMATION: 3' primer for FAK

<400> SEQUENCE: 846
ctgggccagt ttcatcttgt                    20

<210> SEQ ID NO 847
<211> LENGTH: 20
<212> TYPE: DNA
<213> ORGANISM: Artificial Sequence
<220> FEATURE:
<223> OTHER INFORMATION: 5' primer for p21

<400> SEQUENCE: 847
cagcggaaca aggagtcaga                    20

<210> SEQ ID NO 848
<211> LENGTH: 20
<212> TYPE: DNA
<213> ORGANISM: Artificial Sequence
<220> FEATURE:
<223> OTHER INFORMATION: 3' primer for p21

<400> SEQUENCE: 848
agaaacggga accaggacac                    20

<210> SEQ ID NO 849
<211> LENGTH: 20
<212> TYPE: DNA
<213> ORGANISM: Artificial Sequence
<220> FEATURE:
<223> OTHER INFORMATION: 5' primer for p27

<400> SEQUENCE: 849
gataatcccg ctctgaatgc                    20

```
<210> SEQ ID NO 850
<211> LENGTH: 20
<212> TYPE: DNA
<213> ORGANISM: Artificial Sequence
<220> FEATURE:
<223> OTHER INFORMATION: 3' primer for p27

<400> SEQUENCE: 850
gcttctctta gtgctgtagc                                        20

<210> SEQ ID NO 851
<211> LENGTH: 20
<212> TYPE: DNA
<213> ORGANISM: Artificial Sequence
<220> FEATURE:
<223> OTHER INFORMATION: 5' primer for VEGF

<400> SEQUENCE: 851
cttcaagcca tcctgtgtgc                                        20

<210> SEQ ID NO 852
<211> LENGTH: 20
<212> TYPE: DNA
<213> ORGANISM: Artificial Sequence
<220> FEATURE:
<223> OTHER INFORMATION: 3' primer for VEGF

<400> SEQUENCE: 852
acgcgagtct gtgtttttgc                                        20

<210> SEQ ID NO 853
<211> LENGTH: 21
<212> TYPE: DNA
<213> ORGANISM: Artificial Sequence
<220> FEATURE:
<223> OTHER INFORMATION: 5' primer for HIF-1a

<400> SEQUENCE: 853
atcagacacc tagtccttcc g                                      21

<210> SEQ ID NO 854
<211> LENGTH: 21
<212> TYPE: DNA
<213> ORGANISM: Artificial Sequence
<220> FEATURE:
<223> OTHER INFORMATION: 3' primer for HIF-1a

<400> SEQUENCE: 854
ttgaggactt gcgctttcag g                                      21

<210> SEQ ID NO 855
<211> LENGTH: 20
<212> TYPE: DNA
<213> ORGANISM: Artificial Sequence
<220> FEATURE:
<223> OTHER INFORMATION: 5' primer for GAPDH

<400> SEQUENCE: 855
aagggtcatc atctctgccc                                        20

<210> SEQ ID NO 856
<211> LENGTH: 20
<212> TYPE: DNA
<213> ORGANISM: Artificial Sequence
<220> FEATURE:
<223> OTHER INFORMATION: 3' primer for GAPDH
```

<400> SEQUENCE: 856
gtgatggcat ggactgtggt                                                20

<210> SEQ ID NO 857
<211> LENGTH: 76
<212> TYPE: DNA
<213> ORGANISM: Artificial Sequence
<220> FEATURE:
<223> OTHER INFORMATION: 5' primer of MTM

<400> SEQUENCE: 857
ggaattccat atggcggcgg tgctgctgcc ggtgctgctg gcggcgccgg tcacccacag    60
caagtttccc gccgcc                                                    76

<210> SEQ ID NO 858
<211> LENGTH: 76
<212> TYPE: DNA
<213> ORGANISM: Artificial Sequence
<220> FEATURE:
<223> OTHER INFORMATION: 5' primer of aMTD44

<400> SEQUENCE: 858
ggaattccat atggcgctgg cggtgccggt ggcgctgctg gtggcgccgg tcacccacag    60
caagtttccc gccgcc                                                    76

<210> SEQ ID NO 859
<211> LENGTH: 69
<212> TYPE: DNA
<213> ORGANISM: Artificial Sequence
<220> FEATURE:
<223> OTHER INFORMATION: 5' primer of M165S3B

<400> SEQUENCE: 859
ggaattccat atggcgctgg cggtgccggt ggcgcctggc gattgtgccg gtcacccaca    60
gcaagtttc                                                            69

<210> SEQ ID NO 860
<211> LENGTH: 39
<212> TYPE: DNA
<213> ORGANISM: Artificial Sequence
<220> FEATURE:
<223> OTHER INFORMATION: 3' primer of M165S3B

<400> SEQUENCE: 860
cgcgtcgact taaagggttt ccgaaggctt ggctatctt                            39

<210> SEQ ID NO 861
<211> LENGTH: 76
<212> TYPE: DNA
<213> ORGANISM: Artificial Sequence
<220> FEATURE:
<223> OTHER INFORMATION: 5' primer of aMTD81

<400> SEQUENCE: 861
ggaattccat atggcggcgc tgctgccggc gctggcggcg ctgctgccgg tcacccacag    60
caagtttccc gccgcc                                                    76

<210> SEQ ID NO 862
<211> LENGTH: 76
<212> TYPE: DNA
<213> ORGANISM: Artificial Sequence
<220> FEATURE:
<223> OTHER INFORMATION: 5' primer of aMTD123

-continued

<400> SEQUENCE: 862
ggaattccat atggcggcga ttattgtgcc ggcggcgctg ctggcgccgg tcacccacag    60
caagtttccc gccgcc                                                    76

<210> SEQ ID NO 863
<211> LENGTH: 76
<212> TYPE: DNA
<213> ORGANISM: Artificial Sequence
<220> FEATURE:
<223> OTHER INFORMATION: 5' primer of aMTD162

<400> SEQUENCE: 863
ggaattccat atggcggtgg tggcgctgcc ggcggcgctg attgtgccgg tcacccacag    60
caagtttccc gccgcc                                                    76

<210> SEQ ID NO 864
<211> LENGTH: 76
<212> TYPE: DNA
<213> ORGANISM: Artificial Sequence
<220> FEATURE:
<223> OTHER INFORMATION: 5' primer of aMTD281

<400> SEQUENCE: 864
ggaattccat atggcgctga ttgtgctgcc ggcggcggtg gcggtgccgg tcacccacag    60
caagtttccc gccgcc                                                    76

<210> SEQ ID NO 865
<211> LENGTH: 16
<212> TYPE: PRT
<213> ORGANISM: Artificial Sequence
<220> FEATURE:
<223> OTHER INFORMATION: Amino acid Sequence of MTM

<400> SEQUENCE: 865

Ala Ala Val Ala Leu Leu Pro Ala Val Leu Leu Ala Leu Leu Ala Pro
1               5                   10                  15

<210> SEQ ID NO 866
<211> LENGTH: 12
<212> TYPE: PRT
<213> ORGANISM: Artificial Sequence
<220> FEATURE:
<223> OTHER INFORMATION: Amino acid Sequence of MTS

<400> SEQUENCE: 866

Ala Ala Val Leu Leu Pro Val Leu Leu Ala Ala Pro
1               5                   10

<210> SEQ ID NO 867
<211> LENGTH: 16
<212> TYPE: PRT
<213> ORGANISM: Artificial Sequence
<220> FEATURE:
<223> OTHER INFORMATION: Amino acid Sequence of MTD10

<400> SEQUENCE: 867

Leu Gly Gly Ala Val Val Ala Ala Pro Val Ala Ala Val Ala Pro
1               5                   10                  15

<210> SEQ ID NO 868
<211> LENGTH: 11
<212> TYPE: PRT
<213> ORGANISM: Artificial Sequence -continued

```
<220> FEATURE:
<223> OTHER INFORMATION: Amino acid Sequence of MTD13

<400> SEQUENCE: 868

Leu Ala Ala Ala Ala Leu Ala Val Leu Pro Leu
1               5                   10

<210> SEQ ID NO 869
<211> LENGTH: 10
<212> TYPE: PRT
<213> ORGANISM: Artificial Sequence
<220> FEATURE:
<223> OTHER INFORMATION: Amino acid Sequence of MTD47

<400> SEQUENCE: 869

Ala Ala Ala Val Pro Val Leu Val Ala Ala
1               5                   10

<210> SEQ ID NO 870
<211> LENGTH: 9
<212> TYPE: PRT
<213> ORGANISM: Artificial Sequence
<220> FEATURE:
<223> OTHER INFORMATION: Amino acid Sequence of MTD56

<400> SEQUENCE: 870

Val Leu Leu Ala Ala Ala Leu Ile Ala
1               5

<210> SEQ ID NO 871
<211> LENGTH: 7
<212> TYPE: PRT
<213> ORGANISM: Artificial Sequence
<220> FEATURE:
<223> OTHER INFORMATION: Amino acid Sequence of MTD73

<400> SEQUENCE: 871

Pro Val Leu Leu Leu Leu Ala
1               5

<210> SEQ ID NO 872
<211> LENGTH: 9
<212> TYPE: PRT
<213> ORGANISM: Artificial Sequence
<220> FEATURE:
<223> OTHER INFORMATION: Amino acid Sequence of MTD77

<400> SEQUENCE: 872

Ala Val Ala Leu Leu Ile Leu Ala Val
1               5

<210> SEQ ID NO 873
<211> LENGTH: 11
<212> TYPE: PRT
<213> ORGANISM: Artificial Sequence
<220> FEATURE:
<223> OTHER INFORMATION: Amino acid Sequence of MTD84

<400> SEQUENCE: 873

Ala Val Ala Leu Val Ala Val Val Ala Val Ala
1               5                   10

<210> SEQ ID NO 874
<211> LENGTH: 11
<212> TYPE: PRT
<213> ORGANISM: Artificial Sequence
<220> FEATURE:
```

<223> OTHER INFORMATION: Amino acid Sequence of MTD85

<400> SEQUENCE: 874

Leu Leu Ala Ala Ala Ala Ala Leu Leu Leu Ala
1               5                   10

<210> SEQ ID NO 875
<211> LENGTH: 11
<212> TYPE: PRT
<213> ORGANISM: Artificial Sequence
<220> FEATURE:
<223> OTHER INFORMATION: Amino acid Sequence of MTD86

<400> SEQUENCE: 875

Leu Leu Ala Ala Ala Ala Ala Leu Leu Leu Ala
1               5                   10

<210> SEQ ID NO 876
<211> LENGTH: 9
<212> TYPE: PRT
<213> ORGANISM: Artificial Sequence
<220> FEATURE:
<223> OTHER INFORMATION: Amino acid Sequence of MTD103

<400> SEQUENCE: 876

Leu Ala Leu Pro Val Leu Leu Leu Ala
1               5

<210> SEQ ID NO 877
<211> LENGTH: 12
<212> TYPE: PRT
<213> ORGANISM: Artificial Sequence
<220> FEATURE:
<223> OTHER INFORMATION: Amino acid Sequence of MTD132

<400> SEQUENCE: 877

Ala Val Val Val Pro Ala Ile Val Leu Ala Ala Pro
1               5                   10

<210> SEQ ID NO 878
<211> LENGTH: 9
<212> TYPE: PRT
<213> ORGANISM: Artificial Sequence
<220> FEATURE:
<223> OTHER INFORMATION: Amino acid Sequence of MTD151

<400> SEQUENCE: 878

Ala Ala Ala Pro Val Ala Ala Val Pro
1               5

<210> SEQ ID NO 879
<211> LENGTH: 9
<212> TYPE: PRT
<213> ORGANISM: Artificial Sequence
<220> FEATURE:
<223> OTHER INFORMATION: Amino acid Sequence of MTD173

<400> SEQUENCE: 879

Ala Val Ile Pro Ile Leu Ala Val Pro
1               5

<210> SEQ ID NO 880
<211> LENGTH: 11
<212> TYPE: PRT
<213> ORGANISM: Artificial Sequence
<220> FEATURE:
<223> OTHER INFORMATION: Amino acid Sequence of MTD174

```
<400> SEQUENCE: 880

Leu Ile Leu Leu Leu Pro Ala Val Ala Leu Pro
1               5                   10

<210> SEQ ID NO 881
<211> LENGTH: 9
<212> TYPE: PRT
<213> ORGANISM: Artificial Sequence
<220> FEATURE:
<223> OTHER INFORMATION: Amino acid Sequence of MTD181

<400> SEQUENCE: 881

Ala Val Leu Leu Leu Pro Ala Ala Ala
1               5

<210> SEQ ID NO 882
<211> LENGTH: 12
<212> TYPE: PRT
<213> ORGANISM: Artificial Sequence
<220> FEATURE:
<223> OTHER INFORMATION: Amino acid Sequence of rPeptide ID 931

<400> SEQUENCE: 882

Ala Val Leu Ile Ala Pro Ala Ile Leu Ala Ala Ala
1               5                   10

<210> SEQ ID NO 883
<211> LENGTH: 12
<212> TYPE: PRT
<213> ORGANISM: Artificial Sequence
<220> FEATURE:
<223> OTHER INFORMATION: Amino acid Sequence of rPeptide ID 936

<400> SEQUENCE: 883

Ala Leu Leu Ile Leu Ala Ala Ala Val Ala Ala Pro
1               5                   10

<210> SEQ ID NO 884
<211> LENGTH: 12
<212> TYPE: PRT
<213> ORGANISM: Artificial Sequence
<220> FEATURE:
<223> OTHER INFORMATION: Amino acid Sequence of rPeptide ID 152

<400> SEQUENCE: 884

Leu Ala Ala Ala Val Ala Ala Val Ala Ala Leu Leu
1               5                   10

<210> SEQ ID NO 885
<211> LENGTH: 12
<212> TYPE: PRT
<213> ORGANISM: Artificial Sequence
<220> FEATURE:
<223> OTHER INFORMATION: Amino acid Sequence of rPeptide ID 27

<400> SEQUENCE: 885

Leu Ala Ile Val Ala Ala Ala Ala Ala Leu Val Ala
1               5                   10

<210> SEQ ID NO 886
<211> LENGTH: 12
<212> TYPE: PRT
<213> ORGANISM: Artificial Sequence
<220> FEATURE:
<223> OTHER INFORMATION: Amino acid Sequence of rPeptide ID 935
```

<400> SEQUENCE: 886

Ala Leu Leu Ile Leu Pro Ala Ala Val Ala Ala
1               5                   10

<210> SEQ ID NO 887
<211> LENGTH: 12
<212> TYPE: PRT
<213> ORGANISM: Artificial Sequence
<220> FEATURE:
<223> OTHER INFORMATION: Amino acid Sequence of rPeptide ID 670

<400> SEQUENCE: 887

Ala Leu Leu Ile Leu Ala Ala Ala Val Ala Ala Leu
1               5                   10

<210> SEQ ID NO 888
<211> LENGTH: 12
<212> TYPE: PRT
<213> ORGANISM: Artificial Sequence
<220> FEATURE:
<223> OTHER INFORMATION: Amino acid Sequence of rPeptide ID 934

<400> SEQUENCE: 888

Leu Ile Leu Ala Pro Ala Ala Val Val Ala Ala Ala
1               5                   10

<210> SEQ ID NO 889
<211> LENGTH: 12
<212> TYPE: PRT
<213> ORGANISM: Artificial Sequence
<220> FEATURE:
<223> OTHER INFORMATION: Amino acid Sequence of rPeptide ID 37

<400> SEQUENCE: 889

Thr Thr Cys Ser Gln Gln Gln Tyr Cys Thr Asn Gly
1               5                   10

<210> SEQ ID NO 890
<211> LENGTH: 12
<212> TYPE: PRT
<213> ORGANISM: Artificial Sequence
<220> FEATURE:
<223> OTHER INFORMATION: Amino acid Sequence of rPeptide ID 16

<400> SEQUENCE: 890

Asn Asn Ser Cys Thr Thr Tyr Thr Asn Gly Ser Gln
1               5                   10

<210> SEQ ID NO 891
<211> LENGTH: 12
<212> TYPE: PRT
<213> ORGANISM: Artificial Sequence
<220> FEATURE:
<223> OTHER INFORMATION: Amino acid Sequence of rPeptide ID 113

<400> SEQUENCE: 891

Pro Val Ala Val Ala Leu Leu Ile Ala Val Pro Pro
1               5                   10

<210> SEQ ID NO 892
<211> LENGTH: 12
<212> TYPE: PRT
<213> ORGANISM: Artificial Sequence
<220> FEATURE:
<223> OTHER INFORMATION: Amino acid Sequence of rPeptide ID 226

<400> SEQUENCE: 892

Ala Leu Val Ala Ala Ile Pro Ala Leu Ala Ile Pro
1               5                   10

<210> SEQ ID NO 893
<211> LENGTH: 12
<212> TYPE: PRT
<213> ORGANISM: Artificial Sequence
<220> FEATURE:
<223> OTHER INFORMATION: Amino acid Sequence of rPeptide ID 6

<400> SEQUENCE: 893

Val Ile Ala Met Ile Pro Ala Ala Phe Trp Val Ala
1               5                   10

<210> SEQ ID NO 894
<211> LENGTH: 12
<212> TYPE: PRT
<213> ORGANISM: Artificial Sequence
<220> FEATURE:
<223> OTHER INFORMATION: Amino acid Sequence of rPeptide ID 750

<400> SEQUENCE: 894

Leu Ala Ile Ala Ala Ile Ala Pro Leu Ala Ile Pro
1               5                   10

<210> SEQ ID NO 895
<211> LENGTH: 12
<212> TYPE: PRT
<213> ORGANISM: Artificial Sequence
<220> FEATURE:
<223> OTHER INFORMATION: Amino acid Sequence of rPeptide ID 26

<400> SEQUENCE: 895

Ala Ala Ile Ala Leu Ala Ala Pro Leu Ala Ile Val
1               5                   10

<210> SEQ ID NO 896
<211> LENGTH: 12
<212> TYPE: PRT
<213> ORGANISM: Artificial Sequence
<220> FEATURE:
<223> OTHER INFORMATION: Amino acid Sequence of rPeptide ID 527

<400> SEQUENCE: 896

Leu Val Leu Ala Ala Val Ala Pro Ile Ala Ile Pro
1               5                   10

<210> SEQ ID NO 897
<211> LENGTH: 12
<212> TYPE: PRT
<213> ORGANISM: Artificial Sequence
<220> FEATURE:
<223> OTHER INFORMATION: Amino acid Sequence of rPeptide ID 466

<400> SEQUENCE: 897

Ile Ile Ala Ala Ala Ala Pro Leu Ala Ile Ile Pro
1               5                   10

<210> SEQ ID NO 898
<211> LENGTH: 12
<212> TYPE: PRT
<213> ORGANISM: Artificial Sequence
<220> FEATURE:
<223> OTHER INFORMATION: Amino acid Sequence of rPeptide ID 167

<400> SEQUENCE: 898

Val Ala Ile Ala Ile Pro Ala Ala Leu Ala Ile Pro
1               5                   10

<210> SEQ ID NO 899
<211> LENGTH: 12
<212> TYPE: PRT
<213> ORGANISM: Artificial Sequence
<220> FEATURE:
<223> OTHER INFORMATION: Amino acid Sequence of rPeptide ID 246

<400> SEQUENCE: 899

Val Val Ala Val Pro Leu Leu Val Ala Phe Ala Ala
1               5                   10

<210> SEQ ID NO 900
<211> LENGTH: 12
<212> TYPE: PRT
<213> ORGANISM: Artificial Sequence
<220> FEATURE:
<223> OTHER INFORMATION: Amino acid Sequence of rPeptide ID 426

<400> SEQUENCE: 900

Ala Ala Ala Leu Ala Ile Pro Leu Ala Ile Ile Pro
1               5                   10

<210> SEQ ID NO 901
<211> LENGTH: 12
<212> TYPE: PRT
<213> ORGANISM: Artificial Sequence
<220> FEATURE:
<223> OTHER INFORMATION: Amino acid Sequence of rPeptide ID 606

<400> SEQUENCE: 901

Ala Ala Ala Ile Ala Ala Ile Pro Ile Ile Ile Pro
1               5                   10

<210> SEQ ID NO 902
<211> LENGTH: 12
<212> TYPE: PRT
<213> ORGANISM: Artificial Sequence
<220> FEATURE:
<223> OTHER INFORMATION: Amino acid Sequence of rPeptide ID 66

<400> SEQUENCE: 902

Ala Gly Val Leu Gly Gly Pro Ile Met Gly Val Pro
1               5                   10

<210> SEQ ID NO 903
<211> LENGTH: 12
<212> TYPE: PRT
<213> ORGANISM: Artificial Sequence
<220> FEATURE:
<223> OTHER INFORMATION: Amino acid Sequence of rPeptide ID 248

<400> SEQUENCE: 903

Val Ala Ala Ile Val Pro Ile Ala Ala Leu Val Pro
1               5                   10

<210> SEQ ID NO 904
<211> LENGTH: 12
<212> TYPE: PRT
<213> ORGANISM: Artificial Sequence
<220> FEATURE:
<223> OTHER INFORMATION: Amino acid Sequence of rPeptide ID 227

<400> SEQUENCE: 904

Leu Ala Ala Ile Val Pro Ile Ala Ala Ala Val Pro

<210> SEQ ID NO 905
<211> LENGTH: 12
<212> TYPE: PRT
<213> ORGANISM: Artificial Sequence
<220> FEATURE:
<223> OTHER INFORMATION: Amino acid Sequence of rPeptide ID 17

<400> SEQUENCE: 905

Gly Gly Cys Ser Ala Pro Gln Thr Thr Cys Ser Asn
1               5                   10

<210> SEQ ID NO 906
<211> LENGTH: 12
<212> TYPE: PRT
<213> ORGANISM: Artificial Sequence
<220> FEATURE:
<223> OTHER INFORMATION: Amino acid Sequence of rPeptide ID 67

<400> SEQUENCE: 906

Leu Asp Ala Glu Val Pro Leu Ala Asp Asp Val Pro
1               5                   10

<210> SEQ ID NO 907
<211> LENGTH: 12
<212> TYPE: PRT
<213> ORGANISM: Artificial Sequence
<220> FEATURE:
<223> OTHER INFORMATION: Amino acid Sequence of rPeptide ID 692

<400> SEQUENCE: 907

Pro Ala Pro Leu Pro Pro Val Val Ile Leu Ala Val
1               5                   10

<210> SEQ ID NO 908
<211> LENGTH: 12
<212> TYPE: PRT
<213> ORGANISM: Artificial Sequence
<220> FEATURE:
<223> OTHER INFORMATION: Amino acid Sequence of rPeptide ID 69

<400> SEQUENCE: 908

Pro Val Ala Val Leu Pro Pro Ala Ala Leu Val Pro
1               5                   10

<210> SEQ ID NO 909
<211> LENGTH: 12
<212> TYPE: PRT
<213> ORGANISM: Artificial Sequence
<220> FEATURE:
<223> OTHER INFORMATION: Amino acid Sequence of rPeptide ID 390

<400> SEQUENCE: 909

Val Pro Leu Leu Val Pro Val Val Pro Val Val Pro
1               5                   10

<210> SEQ ID NO 910
<211> LENGTH: 12
<212> TYPE: PRT
<213> ORGANISM: Artificial Sequence
<220> FEATURE:
<223> OTHER INFORMATION: Amino acid Sequence of rPeptide ID 350

<400> SEQUENCE: 910

Val Pro Ile Leu Val Pro Val Val Pro Val Val Pro
1               5                   10

```
<210> SEQ ID NO 911
<211> LENGTH: 12
<212> TYPE: PRT
<213> ORGANISM: Artificial Sequence
<220> FEATURE:
<223> OTHER INFORMATION: Amino acid Sequence of rPeptide ID 331

<400> SEQUENCE: 911

Val Pro Val Leu Val Pro Leu Val Pro Val Val Pro
1               5                   10

<210> SEQ ID NO 912
<211> LENGTH: 12
<212> TYPE: PRT
<213> ORGANISM: Artificial Sequence
<220> FEATURE:
<223> OTHER INFORMATION: Amino acid Sequence of rPeptide ID 9

<400> SEQUENCE: 912

Val Ala Leu Val Pro Ala Ala Leu Ile Leu Pro Pro
1               5                   10

<210> SEQ ID NO 913
<211> LENGTH: 12
<212> TYPE: PRT
<213> ORGANISM: Artificial Sequence
<220> FEATURE:
<223> OTHER INFORMATION: Amino acid Sequence of rPeptide ID 68

<400> SEQUENCE: 913

Val Ala Pro Val Leu Pro Ala Ala Pro Leu Val Pro
1               5                   10

<210> SEQ ID NO 914
<211> LENGTH: 12
<212> TYPE: PRT
<213> ORGANISM: Artificial Sequence
<220> FEATURE:
<223> OTHER INFORMATION: Amino acid Sequence of rPeptide ID 349

<400> SEQUENCE: 914

Val Pro Val Leu Val Pro Val Val Pro Val Val Pro
1               5                   10

<210> SEQ ID NO 915
<211> LENGTH: 12
<212> TYPE: PRT
<213> ORGANISM: Artificial Sequence
<220> FEATURE:
<223> OTHER INFORMATION: Amino acid Sequence of rPeptide ID 937

<400> SEQUENCE: 915

Val Pro Val Leu Val Pro Leu Pro Val Pro Val Val
1               5                   10

<210> SEQ ID NO 916
<211> LENGTH: 12
<212> TYPE: PRT
<213> ORGANISM: Artificial Sequence
<220> FEATURE:
<223> OTHER INFORMATION: Amino acid Sequence of rPeptide ID 938

<400> SEQUENCE: 916

Val Pro Val Leu Leu Pro Val Val Val Pro Val Pro
1               5                   10
```

<210> SEQ ID NO 917
<211> LENGTH: 12
<212> TYPE: PRT
<213> ORGANISM: Artificial Sequence
<220> FEATURE:
<223> OTHER INFORMATION: Amino acid Sequence of rPeptide ID 329

<400> SEQUENCE: 917

Leu Pro Val Leu Val Pro Val Val Pro Val Val Pro
1               5                   10

<210> SEQ ID NO 918
<211> LENGTH: 12
<212> TYPE: PRT
<213> ORGANISM: Artificial Sequence
<220> FEATURE:
<223> OTHER INFORMATION: Amino acid Sequence of rPeptide ID 49

<400> SEQUENCE: 918

Val Val Pro Ala Ala Pro Ala Val Pro Val Val Pro
1               5                   10

<210> SEQ ID NO 919
<211> LENGTH: 12
<212> TYPE: PRT
<213> ORGANISM: Artificial Sequence
<220> FEATURE:
<223> OTHER INFORMATION: Amino acid Sequence of rPeptide ID 772

<400> SEQUENCE: 919

Leu Pro Val Ala Pro Val Ile Pro Ile Ile Val Pro
1               5                   10

<210> SEQ ID NO 920
<211> LENGTH: 12
<212> TYPE: PRT
<213> ORGANISM: Artificial Sequence
<220> FEATURE:
<223> OTHER INFORMATION: Amino acid Sequence of rPeptide ID 210

<400> SEQUENCE: 920

Ala Leu Ile Ala Leu Pro Ala Leu Pro Ala Leu Pro
1               5                   10

<210> SEQ ID NO 921
<211> LENGTH: 12
<212> TYPE: PRT
<213> ORGANISM: Artificial Sequence
<220> FEATURE:
<223> OTHER INFORMATION: Amino acid Sequence of rPeptide ID 28

<400> SEQUENCE: 921

Ala Val Pro Leu Leu Pro Leu Val Pro Ala Val Pro
1               5                   10

<210> SEQ ID NO 922
<211> LENGTH: 12
<212> TYPE: PRT
<213> ORGANISM: Artificial Sequence
<220> FEATURE:
<223> OTHER INFORMATION: Amino acid Sequence of rPeptide ID 693

<400> SEQUENCE: 922

Ala Ala Pro Val Leu Pro Val Ala Val Pro Ile Val
1               5                   10

```
<210> SEQ ID NO 923
<211> LENGTH: 12
<212> TYPE: PRT
<213> ORGANISM: Artificial Sequence
<220> FEATURE:
<223> OTHER INFORMATION: Amino acid Sequence of rPeptide ID 169

<400> SEQUENCE: 923

Val Ala Leu Val Ala Pro Ala Leu Ile Leu Ala Pro
1               5                   10

<210> SEQ ID NO 924
<211> LENGTH: 12
<212> TYPE: PRT
<213> ORGANISM: Artificial Sequence
<220> FEATURE:
<223> OTHER INFORMATION: Amino acid Sequence of rPeptide ID 29

<400> SEQUENCE: 924

Val Leu Pro Pro Leu Pro Val Leu Pro Val Leu Pro
1               5                   10

<210> SEQ ID NO 925
<211> LENGTH: 12
<212> TYPE: PRT
<213> ORGANISM: Artificial Sequence
<220> FEATURE:
<223> OTHER INFORMATION: Amino acid Sequence of rPeptide ID 190

<400> SEQUENCE: 925

Ala Ala Ile Leu Ala Pro Ala Val Ile Ala Pro Pro
1               5                   10

<210> SEQ ID NO 926
<211> LENGTH: 12
<212> TYPE: PRT
<213> ORGANISM: Artificial Sequence
<220> FEATURE:
<223> OTHER INFORMATION: Amino acid Sequence of rPeptide ID 30

<400> SEQUENCE: 926

Trp Phe Phe Ala Gly Pro Ile Met Leu Ile Trp Pro
1               5                   10

<210> SEQ ID NO 927
<211> LENGTH: 12
<212> TYPE: PRT
<213> ORGANISM: Artificial Sequence
<220> FEATURE:
<223> OTHER INFORMATION: Amino acid Sequence of rPeptide ID 33

<400> SEQUENCE: 927

Ala Ala Ala Ile Leu Ala Pro Ala Phe Leu Ala Val
1               5                   10

<210> SEQ ID NO 928
<211> LENGTH: 12
<212> TYPE: PRT
<213> ORGANISM: Artificial Sequence
<220> FEATURE:
<223> OTHER INFORMATION: Amino acid Sequence of rPeptide ID 131

<400> SEQUENCE: 928

Trp Ile Ile Ala Pro Val Trp Leu Ala Trp Ile Ala
1               5                   10

<210> SEQ ID NO 929
```

```
<211> LENGTH: 12
<212> TYPE: PRT
<213> ORGANISM: Artificial Sequence
<220> FEATURE:
<223> OTHER INFORMATION: Amino acid Sequence of rPeptide ID 922

<400> SEQUENCE: 929

Trp Tyr Val Ile Phe Val Leu Pro Leu Val Val Pro
1               5                   10

<210> SEQ ID NO 930
<211> LENGTH: 12
<212> TYPE: PRT
<213> ORGANISM: Artificial Sequence
<220> FEATURE:
<223> OTHER INFORMATION: Amino acid Sequence of rPeptide ID 71

<400> SEQUENCE: 930

Phe Met Trp Met Trp Phe Pro Phe Met Trp Tyr Pro
1               5                   10

<210> SEQ ID NO 931
<211> LENGTH: 12
<212> TYPE: PRT
<213> ORGANISM: Artificial Sequence
<220> FEATURE:
<223> OTHER INFORMATION: Amino acid Sequence of rPeptide ID 921

<400> SEQUENCE: 931

Ile Trp Trp Phe Val Val Leu Pro Leu Val Val Pro
1               5                   10

<210> SEQ ID NO 932
<211> LENGTH: 12
<212> TYPE: PRT
<213> ORGANISM: Artificial Sequence
<220> FEATURE:
<223> OTHER INFORMATION: Amino acid Sequence of rPeptide ID 436

<400> SEQUENCE: 932

Val Val Met Leu Val Val Pro Ala Val Met Leu Pro
1               5                   10

<210> SEQ ID NO 933
<211> LENGTH: 12
<212> TYPE: PRT
<213> ORGANISM: Artificial Sequence
<220> FEATURE:
<223> OTHER INFORMATION: Amino acid Sequence of rPeptide ID 138

<400> SEQUENCE: 933

Pro Pro Ala Ala Leu Leu Ala Ile Leu Ala Val Ala
1               5                   10

<210> SEQ ID NO 934
<211> LENGTH: 12
<212> TYPE: PRT
<213> ORGANISM: Artificial Sequence
<220> FEATURE:
<223> OTHER INFORMATION: Amino acid Sequence of rPeptide ID 77

<400> SEQUENCE: 934

Pro Val Ala Leu Val Leu Val Ala Leu Val Ala Pro
1               5                   10

<210> SEQ ID NO 935
<211> LENGTH: 12
```

```
<212> TYPE: PRT
<213> ORGANISM: Artificial Sequence
<220> FEATURE:
<223> OTHER INFORMATION: Amino acid Sequence of rPeptide ID 577

<400> SEQUENCE: 935

Met Leu Met Ile Ala Leu Val Pro Met Ile Ala Val
1               5                   10

<210> SEQ ID NO 936
<211> LENGTH: 12
<212> TYPE: PRT
<213> ORGANISM: Artificial Sequence
<220> FEATURE:
<223> OTHER INFORMATION: Amino acid Sequence of rPeptide ID 97

<400> SEQUENCE: 936

Ala Leu Leu Ala Ala Pro Pro Ala Leu Leu Ala Leu
1               5                   10

<210> SEQ ID NO 937
<211> LENGTH: 12
<212> TYPE: PRT
<213> ORGANISM: Artificial Sequence
<220> FEATURE:
<223> OTHER INFORMATION: Amino acid Sequence of rPeptide ID 214

<400> SEQUENCE: 937

Ala Leu Ile Val Ala Pro Ala Leu Met Ala Leu Pro
1               5                   10

<210> SEQ ID NO 938
<211> LENGTH: 12
<212> TYPE: PRT
<213> ORGANISM: Artificial Sequence
<220> FEATURE:
<223> OTHER INFORMATION: Amino acid Sequence of rPeptide ID 59

<400> SEQUENCE: 938

Ala Val Leu Ala Ala Pro Val Val Ala Ala Leu Ala
1               5                   10

<210> SEQ ID NO 939
<211> LENGTH: 12
<212> TYPE: PRT
<213> ORGANISM: Artificial Sequence
<220> FEATURE:
<223> OTHER INFORMATION: Amino acid Sequence of rPeptide ID 54

<400> SEQUENCE: 939

Leu Ala Val Ala Ala Pro Pro Val Val Ala Leu Leu
1               5                   10

<210> SEQ ID NO 940
<211> LENGTH: 12
<212> TYPE: PRT
<213> ORGANISM: Artificial Sequence
<220> FEATURE:
<223> OTHER INFORMATION: Amino acid Sequence of rPeptide ID 949

<400> SEQUENCE: 940

Ser Gly Asn Ser Cys Gln Gln Cys Gly Asn Ser Ser
1               5                   10

<210> SEQ ID NO 941
<211> LENGTH: 12
<212> TYPE: PRT
```

```
<213> ORGANISM: Artificial Sequence
<220> FEATURE:
<223> OTHER INFORMATION: Amino acid Sequence of rPeptide ID 39

<400> SEQUENCE: 941

Cys Tyr Asn Thr Ser Pro Cys Thr Gly Cys Cys Tyr
1               5                   10

<210> SEQ ID NO 942
<211> LENGTH: 12
<212> TYPE: PRT
<213> ORGANISM: Artificial Sequence
<220> FEATURE:
<223> OTHER INFORMATION: Amino acid Sequence of rPeptide ID 19

<400> SEQUENCE: 942

Tyr Val Ser Cys Cys Thr Tyr Thr Asn Gly Ser Gln
1               5                   10

<210> SEQ ID NO 943
<211> LENGTH: 12
<212> TYPE: PRT
<213> ORGANISM: Artificial Sequence
<220> FEATURE:
<223> OTHER INFORMATION: Amino acid Sequence of rPeptide ID 947

<400> SEQUENCE: 943

Cys Tyr Tyr Asn Gln Gln Ser Asn Asn Asn Asn Gln
1               5                   10

<210> SEQ ID NO 944
<211> LENGTH: 12
<212> TYPE: PRT
<213> ORGANISM: Artificial Sequence
<220> FEATURE:
<223> OTHER INFORMATION: Amino acid Sequence of rPeptide ID 139

<400> SEQUENCE: 944

Thr Gly Ser Thr Asn Ser Pro Thr Cys Thr Ser Thr
1               5                   10

<210> SEQ ID NO 945
<211> LENGTH: 12
<212> TYPE: PRT
<213> ORGANISM: Artificial Sequence
<220> FEATURE:
<223> OTHER INFORMATION: Amino acid Sequence of rPeptide ID 18

<400> SEQUENCE: 945

Asn Tyr Cys Cys Thr Pro Thr Thr Asn Gly Gln Ser
1               5                   10

<210> SEQ ID NO 946
<211> LENGTH: 12
<212> TYPE: PRT
<213> ORGANISM: Artificial Sequence
<220> FEATURE:
<223> OTHER INFORMATION: Amino acid Sequence of rPeptide ID 20

<400> SEQUENCE: 946

Asn Tyr Cys Asn Thr Cys Pro Thr Tyr Gly Gln Ser
1               5                   10

<210> SEQ ID NO 947
<211> LENGTH: 12
<212> TYPE: PRT
<213> ORGANISM: Artificial Sequence
```

<220> FEATURE:
<223> OTHER INFORMATION: Amino acid Sequence of rPeptide ID 635

<400> SEQUENCE: 947

Gly Ser Thr Gly Gly Ser Gln Gln Asn Asn Gln Tyr
1               5                   10

<210> SEQ ID NO 948
<211> LENGTH: 12
<212> TYPE: PRT
<213> ORGANISM: Artificial Sequence
<220> FEATURE:
<223> OTHER INFORMATION: Amino acid Sequence of rPeptide ID 40

<400> SEQUENCE: 948

Thr Tyr Asn Thr Ser Cys Thr Pro Gly Thr Cys Tyr
1               5                   10

<210> SEQ ID NO 949
<211> LENGTH: 12
<212> TYPE: PRT
<213> ORGANISM: Artificial Sequence
<220> FEATURE:
<223> OTHER INFORMATION: Amino acid Sequence of rPeptide ID 57

<400> SEQUENCE: 949

Gln Asn Asn Cys Asn Thr Ser Ser Gln Gly Gly Gly
1               5                   10

<210> SEQ ID NO 950
<211> LENGTH: 12
<212> TYPE: PRT
<213> ORGANISM: Artificial Sequence
<220> FEATURE:
<223> OTHER INFORMATION: Amino acid Sequence of rPeptide ID 159

<400> SEQUENCE: 950

Cys Tyr Ser Gly Ser Thr Ser Gln Asn Gln Pro Pro
1               5                   10

<210> SEQ ID NO 951
<211> LENGTH: 12
<212> TYPE: PRT
<213> ORGANISM: Artificial Sequence
<220> FEATURE:
<223> OTHER INFORMATION: Amino acid Sequence of rPeptide ID 700

<400> SEQUENCE: 951

Gly Thr Ser Asn Thr Cys Gln Ser Asn Gln Asn Ser
1               5                   10

<210> SEQ ID NO 952
<211> LENGTH: 12
<212> TYPE: PRT
<213> ORGANISM: Artificial Sequence
<220> FEATURE:
<223> OTHER INFORMATION: Amino acid Sequence of rPeptide ID 38

<400> SEQUENCE: 952

Tyr Tyr Asn Gln Ser Thr Cys Gly Gly Gln Cys Tyr
1               5                   10

<210> SEQ ID NO 953
<211> LENGTH: 12
<212> TYPE: PRT
<213> ORGANISM: Artificial Sequence
<220> FEATURE:

<223> OTHER INFORMATION: Amino acid Sequence of MTM12

<400> SEQUENCE: 953

Ala Ala Val Leu Leu Pro Val Leu Leu Ala Ala Pro
1               5                   10

<210> SEQ ID NO 954
<211> LENGTH: 9
<212> TYPE: PRT
<213> ORGANISM: Artificial Sequence
<220> FEATURE:
<223> OTHER INFORMATION: Amino acid Sequence of MTD85

<400> SEQUENCE: 954

Ala Val Ala Leu Leu Ile Leu Ala Val
1               5

<210> SEQ ID NO 955
<211> LENGTH: 40
<212> TYPE: DNA
<213> ORGANISM: Artificial Sequence
<220> FEATURE:
<223> OTHER INFORMATION: 5' primer of HS3

<400> SEQUENCE: 955
ggaattccat atggtcaccc acagcaagtt tcccgccgcc                              40

<210> SEQ ID NO 956
<211> LENGTH: 39
<212> TYPE: DNA
<213> ORGANISM: Artificial Sequence
<220> FEATURE:
<223> OTHER INFORMATION: 3' primer of HS3

<400> SEQUENCE: 956
cccggatcct taaagcgggg catcgtactg gtccaggaa                               39

<210> SEQ ID NO 957
<211> LENGTH: 68
<212> TYPE: DNA
<213> ORGANISM: Artificial Sequence
<220> FEATURE:
<223> OTHER INFORMATION: 5' primer of HM165S3

<400> SEQUENCE: 957
ggaattccat atggcgctgg cggtgccggt ggcgctggcg attgtgccgg tcacccacag        60
caagtttc                                                                68

<210> SEQ ID NO 958
<211> LENGTH: 39
<212> TYPE: DNA
<213> ORGANISM: Artificial Sequence
<220> FEATURE:
<223> OTHER INFORMATION: 3' primer of HM165S3

<400> SEQUENCE: 958
cccggatcct taaagcgggg catcgtactg gtccaggaa                               39

<210> SEQ ID NO 959
<211> LENGTH: 68
<212> TYPE: DNA
<213> ORGANISM: Artificial Sequence
<220> FEATURE:
<223> OTHER INFORMATION: 5' primer of HM165S3A

<400> SEQUENCE: 959

```
ggaattccat atggcgctgg cggtgccggt ggcgctggcg attgtgccgg tcacccacag    60
caagtttc                                                             68
```

<210> SEQ ID NO 960
<211> LENGTH: 38
<212> TYPE: DNA
<213> ORGANISM: Artificial Sequence
<220> FEATURE:
<223> OTHER INFORMATION: 3' primer of HM165S3A

<400> SEQUENCE: 960

```
cgcgtcgact tacctcggct gcaccggcac ggcgatac                            38
```

<210> SEQ ID NO 961
<211> LENGTH: 69
<212> TYPE: DNA
<213> ORGANISM: Artificial Sequence
<220> FEATURE:
<223> OTHER INFORMATION: 5' primer of HM165S3B

<400> SEQUENCE: 961

```
ggaattccat atggcgctgg cggtgccggt ggcgcctggc gattgtgccg gtcacccaca    60
gcaagtttc                                                            69
```

<210> SEQ ID NO 962
<211> LENGTH: 39
<212> TYPE: DNA
<213> ORGANISM: Artificial Sequence
<220> FEATURE:
<223> OTHER INFORMATION: 3' primer of HM165S3B

<400> SEQUENCE: 962

```
cgcgtcgact taaagggttt ccgaaggctt ggctatctt                           39
```

<210> SEQ ID NO 963
<211> LENGTH: 68
<212> TYPE: DNA
<213> ORGANISM: Artificial Sequence
<220> FEATURE:
<223> OTHER INFORMATION: 5' primer of HM165S3C

<400> SEQUENCE: 963

```
ggaattccat atggcgctgg cggtgccggt ggcgctggcg attgtgccgg tcacccacag    60
caagtttc                                                             68
```

<210> SEQ ID NO 964
<211> LENGTH: 28
<212> TYPE: DNA
<213> ORGANISM: Artificial Sequence
<220> FEATURE:
<223> OTHER INFORMATION: 3' primer of HM165S3C

<400> SEQUENCE: 964

```
gcgtcgactt aggcgaggtt agcgtcga                                       28
```

<210> SEQ ID NO 965
<211> LENGTH: 68
<212> TYPE: DNA
<213> ORGANISM: Artificial Sequence
<220> FEATURE:
<223> OTHER INFORMATION: 5' primer of HM165S3D

<400> SEQUENCE: 965

```
ggaattccat atggcgctgg cggtgccggt ggcgctggcc attgtgccgg tcacccacag    60
caagtttc                                                             68
```

<210> SEQ ID NO 966
<211> LENGTH: 30
<212> TYPE: DNA
<213> ORGANISM: Artificial Sequence
<220> FEATURE:
<223> OTHER INFORMATION: 3' primer of HM165S3D

<400> SEQUENCE: 966

```
gcgttcgact tatttttct cggacagata                                      30
```

<210> SEQ ID NO 967
<211> LENGTH: 68
<212> TYPE: DNA
<213> ORGANISM: Artificial Sequence
<220> FEATURE:
<223> OTHER INFORMATION: 5' primer of HM165S3E

<400> SEQUENCE: 967

```
ggaattccat atggcgctgg cggtgccggt ggcgctggcg attgtgccgg tcacccacag    60
caagtttc                                                             68
```

<210> SEQ ID NO 968
<211> LENGTH: 40
<212> TYPE: DNA
<213> ORGANISM: Artificial Sequence
<220> FEATURE:
<223> OTHER INFORMATION: 3' primer of HM165S3E

<400> SEQUENCE: 968

```
acgcgtcgac ttaacctcca atctgttcgc ggtgagcctc                          40
```

<210> SEQ ID NO 969
<211> LENGTH: 40
<212> TYPE: DNA
<213> ORGANISM: Artificial Sequence
<220> FEATURE:
<223> OTHER INFORMATION: 5' primer of HS3B

<400> SEQUENCE: 969

```
ggaattccat atggtcaccc acagcaagtt tcccgccgcc                          40
```

<210> SEQ ID NO 970
<211> LENGTH: 39
<212> TYPE: DNA
<213> ORGANISM: Artificial Sequence
<220> FEATURE:
<223> OTHER INFORMATION: 3' primer of HS3B

<400> SEQUENCE: 970

```
cgcgtcgact taaagggttt ccgaaggctt ggctatctt                           39
```

<210> SEQ ID NO 971
<211> LENGTH: 68
<212> TYPE: DNA
<213> ORGANISM: Artificial Sequence
<220> FEATURE:
<223> OTHER INFORMATION: 5' primer of HM165S3B-humanized

<400> SEQUENCE: 971

```
ggaattccat atggcgctgg cggtgccggt ggcgctggcg attgtgccgg tcacccacag    60
caagtttc                                                             68
```

<210> SEQ ID NO 972
<211> LENGTH: 39
<212> TYPE: DNA
<213> ORGANISM: Artificial Sequence
<220> FEATURE:
<223> OTHER INFORMATION: 3' primer of HM165S3B-humanized

<400> SEQUENCE: 972
cgcgtcgact taaagggttt ccgaaggctt ggctatctt                    39

<210> SEQ ID NO 973
<211> LENGTH: 31
<212> TYPE: DNA
<213> ORGANISM: Artificial Sequence
<220> FEATURE:
<223> OTHER INFORMATION: 5' primer of BS3M165

<400> SEQUENCE: 973
ggaattccat atgatggcag aacaaagcga c                            31

<210> SEQ ID NO 974
<211> LENGTH: 73
<212> TYPE: DNA
<213> ORGANISM: Artificial Sequence
<220> FEATURE:
<223> OTHER INFORMATION: 3' primer of BS3M165

<400> SEQUENCE: 974
acgcgtcgac ttacgccagc gccaccggca ccgccagcgc aatcaccgga agcggggcat    60
cgtactggtc cag                                                73

<210> SEQ ID NO 975
<211> LENGTH: 31
<212> TYPE: DNA
<213> ORGANISM: Artificial Sequence
<220> FEATURE:
<223> OTHER INFORMATION: 5' primer of BS3M165-humanized

<400> SEQUENCE: 975
ggaattccat atgatggcag aacaaagcga c                            31

<210> SEQ ID NO 976
<211> LENGTH: 73
<212> TYPE: DNA
<213> ORGANISM: Artificial Sequence
<220> FEATURE:
<223> OTHER INFORMATION: 3' primer of BS3M165-humanized

<400> SEQUENCE: 976
acgcgtcgac ttacgccagc gccaccggca ccgccagcgc aatcaccgga agcggggcat    60
cgtactggtc cag                                                73

<210> SEQ ID NO 977
<211> LENGTH: 76
<212> TYPE: DNA
<213> ORGANISM: Artificial Sequence
<220> FEATURE:
<223> OTHER INFORMATION: 5' primer of aMTD324

<400> SEQUENCE: 977
ggaattccat atgattgtgg cggtggcgct gccggcggcg ctggtgccgg tcacccacag    60
caagtttccc gccgcc                                             76

<210> SEQ ID NO 978
<211> LENGTH: 76
<212> TYPE: DNA
<213> ORGANISM: Artificial Sequence
<220> FEATURE:
<223> OTHER INFORMATION: 5' primer of aMTD364

<400> SEQUENCE: 978
ggaattccat atgctggtgg cggcggtggc gccggcgctg attgtgccgg tcacccacag    60
caagtttccc gccgcc    76

<210> SEQ ID NO 979
<211> LENGTH: 76
<212> TYPE: DNA
<213> ORGANISM: Artificial Sequence
<220> FEATURE:
<223> OTHER INFORMATION: 5' primer of aMTD365

<400> SEQUENCE: 979
ggaattccat atggcggtga ttgtggtggc gccggcgctg ctggcgccgg tcacccacag    60
caagtttccc gccgcc    76

<210> SEQ ID NO 980
<211> LENGTH: 76
<212> TYPE: DNA
<213> ORGANISM: Artificial Sequence
<220> FEATURE:
<223> OTHER INFORMATION: 5' primer of aMTD622

<400> SEQUENCE: 980
ggaattccat atggcgctga ttgtgctggc ggcgccggtg gcggtgccgg tcacccacag    60
caagtttccc gccgcc    76

<210> SEQ ID NO 981
<211> LENGTH: 76
<212> TYPE: DNA
<213> ORGANISM: Artificial Sequence
<220> FEATURE:
<223> OTHER INFORMATION: 5' primer of aMTD662

<400> SEQUENCE: 981
ggaattccat atggcgctgg cggtgattct ggcgccggtg gcggtgccgg tcacccacag    60
caagtttccc gccgcc    76

<210> SEQ ID NO 982
<211> LENGTH: 76
<212> TYPE: DNA
<213> ORGANISM: Artificial Sequence
<220> FEATURE:
<223> OTHER INFORMATION: 5' primer of aMTD563

<400> SEQUENCE: 982
ggaattccat atggcgctgg cggtgattgt ggtgccggcg ctggcgccgg tcacccacag    60
caagtttccc gccgcc    76

<210> SEQ ID NO 983
<211> LENGTH: 76
<212> TYPE: DNA
<213> ORGANISM: Artificial Sequence
<220> FEATURE:
<223> OTHER INFORMATION: 5' primer of aMTD899

<400> SEQUENCE: 983

```
<210> SEQ ID NO 984
<211> LENGTH: 76
<212> TYPE: DNA
<213> ORGANISM: Artificial Sequence
<220> FEATURE:
<223> OTHER INFORMATION: 5' primer of aMTD897

<400> SEQUENCE: 984
ggaattccat atggcggtga ttgtgccggt ggcgattatt gcggcgccgg tcacccacag    60
caagtttccc gccgcc                                                    76

<210> SEQ ID NO 985
<211> LENGTH: 76
<212> TYPE: DNA
<213> ORGANISM: Artificial Sequence
<220> FEATURE:
<223> OTHER INFORMATION: 5' primer of aMTD623

<400> SEQUENCE: 985
ggaattccat atggtggcgg cggcgattgc gctgccggcg attgtgccgg tcacccacag    60
caagtttccc gccgcc                                                    76

<210> SEQ ID NO 986
<211> LENGTH: 76
<212> TYPE: DNA
<213> ORGANISM: Artificial Sequence
<220> FEATURE:
<223> OTHER INFORMATION: 5' primer of aMTD908

<400> SEQUENCE: 986
ggaattccat atggtggcgc tggcgctggc gccggtggtg gtggcgccgg tcacccacag    60
caagtttccc gccgcc                                                    76

<210> SEQ ID NO 987
<211> LENGTH: 76
<212> TYPE: DNA
<213> ORGANISM: Artificial Sequence
<220> FEATURE:
<223> OTHER INFORMATION: 5' primer of aMTD911

<400> SEQUENCE: 987
ggaattccat atggtggcgc tggcgctgcc ggcggtggtg gtggcgccgg tcacccacag    60
caagtttccc gccgcc                                                    76

<210> SEQ ID NO 988
<211> LENGTH: 76
<212> TYPE: DNA
<213> ORGANISM: Artificial Sequence
<220> FEATURE:
<223> OTHER INFORMATION: 5' primer of aMTD2

<400> SEQUENCE: 988
ggaattccat atggcggcgg cggtgccgct gctggcggtg gtggtgccgg tcacccacag    60
caagtttccc gccgcc                                                    76

<210> SEQ ID NO 989
<211> LENGTH: 76
<212> TYPE: DNA
```

```
<213> ORGANISM: Artificial Sequence
<220> FEATURE:
<223> OTHER INFORMATION: 5' primer of aMTD904

<400> SEQUENCE: 989
ggaattccat atggcggtgc tggcggtggt ggcgccggtg gtggcgccgg tcacccacag    60
caagtttccc gccgcc                                                   76

<210> SEQ ID NO 990
<211> LENGTH: 76
<212> TYPE: DNA
<213> ORGANISM: Artificial Sequence
<220> FEATURE:
<223> OTHER INFORMATION: 5' primer of aMTD481

<400> SEQUENCE: 990
ggaattccat atggcgattg cgattgcgat tgtgccggtg gcgctgccgg tcacccacag    60
caagtttccc gccgcc                                                   76

<210> SEQ ID NO 991
<211> LENGTH: 76
<212> TYPE: DNA
<213> ORGANISM: Artificial Sequence
<220> FEATURE:
<223> OTHER INFORMATION: 5' primer of aMTD787

<400> SEQUENCE: 991
ggaattccat atggcggtgg cgctggtgcc ggtgattgtg gcggcgccgg tcacccacag    60
caagtttccc gccgcc                                                   76

<210> SEQ ID NO 992
<211> LENGTH: 76
<212> TYPE: DNA
<213> ORGANISM: Artificial Sequence
<220> FEATURE:
<223> OTHER INFORMATION: 5' primer of aMTD264

<400> SEQUENCE: 992
ggaattccat atgctggcgg cggcgccggt ggtgattgtg attgcgccgg tcacccacag    60
caagtttccc gccgcc                                                   76

<210> SEQ ID NO 993
<211> LENGTH: 76
<212> TYPE: DNA
<213> ORGANISM: Artificial Sequence
<220> FEATURE:
<223> OTHER INFORMATION: 5' primer of aMTD363

<400> SEQUENCE: 993
ggaattccat atggcggtgc tggcggtggc gccggcgctg attgtgccgg tcacccacag    60
caagtttccc gccgcc                                                   76

<210> SEQ ID NO 994
<211> LENGTH: 76
<212> TYPE: DNA
<213> ORGANISM: Artificial Sequence
<220> FEATURE:
<223> OTHER INFORMATION: 5' primer of aMTD121

<400> SEQUENCE: 994
ggaattccat atggcgattg tggcgctgcc ggcgctggcg ctggcgccgg tcacccacag    60
caagtttccc gccgcc                                                   76
```

<210> SEQ ID NO 995
<211> LENGTH: 39
<212> TYPE: DNA
<213> ORGANISM: Artificial Sequence
<220> FEATURE:
<223> OTHER INFORMATION: 3' primer

<400> SEQUENCE: 995
cgcgtcgact taaagggttt ccgaaggctt ggctatctt                     39

<210> SEQ ID NO 996
<211> LENGTH: 76
<212> TYPE: DNA
<213> ORGANISM: Artificial Sequence
<220> FEATURE:
<223> OTHER INFORMATION: 5' primer of rPeptide ID 921

<400> SEQUENCE: 996
ggaattccat atgatttggt ggtttgtggt gctgccgctg gtggtgccgg tcacccacag     60
caagtttccc gccgcc                                                     76

<210> SEQ ID NO 997
<211> LENGTH: 76
<212> TYPE: DNA
<213> ORGANISM: Artificial Sequence
<220> FEATURE:
<223> OTHER INFORMATION: 5' primer of rPeptide ID 16

<400> SEQUENCE: 997
ggaattccat atgaacaaca gctgcaccac ctataccaac ggcagccagg tcacccacag     60
caagtttccc gccgcc                                                     76

<210> SEQ ID NO 998
<211> LENGTH: 76
<212> TYPE: DNA
<213> ORGANISM: Artificial Sequence
<220> FEATURE:
<223> OTHER INFORMATION: 5' primer of rPeptide ID 67

<400> SEQUENCE: 998
ggaattccat atgctggatg cggaagtgcc gctggcggat gatgtgccgg tcacccacag     60
caagtttccc gccgcc                                                     76

<210> SEQ ID NO 999
<211> LENGTH: 76
<212> TYPE: DNA
<213> ORGANISM: Artificial Sequence
<220> FEATURE:
<223> OTHER INFORMATION: 5' primer of rPeptide ID 29

<400> SEQUENCE: 999
ggaattccat atggtgctgc cgccgctgcc ggtgctgccg gtgctgccgg tcacccacag     60
caagtttccc gccgcc                                                     76

<210> SEQ ID NO 1000
<211> LENGTH: 76
<212> TYPE: DNA
<213> ORGANISM: Artificial Sequence
<220> FEATURE:
<223> OTHER INFORMATION: 5' primer of rPeptide ID 700

<400> SEQUENCE: 1000

```
ggaattccat atgggcacca gcaacacctg ccagagcaac cagaacagcg tcacccacag      60
caagtttccc gccgcc                                                     76

<210> SEQ ID NO 1001
<211> LENGTH: 39
<212> TYPE: DNA
<213> ORGANISM: Artificial Sequence
<220> FEATURE:
<223> OTHER INFORMATION: 3' primer of rPeptides

<400> SEQUENCE: 1001
cgcgtcgact taaagggttt ccgaaggctt ggctatctt                             39

<210> SEQ ID NO 1002
<211> LENGTH: 13
<212> TYPE: PRT
<213> ORGANISM: Artificial Sequence
<220> FEATURE:
<223> OTHER INFORMATION: Amino acid Sequence of Peptide W27

<400> SEQUENCE: 1002

Ser Thr Trp Val Ile Leu His His Lys Val Tyr Asp Leu
1               5                   10

<210> SEQ ID NO 1003
<211> LENGTH: 14
<212> TYPE: PRT
<213> ORGANISM: Artificial Sequence
<220> FEATURE:
<223> OTHER INFORMATION: Amino acid Sequence of Peptide V28

<400> SEQUENCE: 1003

Thr Trp Val Ile Leu His His Lys Val Tyr Asp Leu Thr Lys
1               5                   10
```

CELL-PERMEABLE (ICP)-SOCS3 RECOMBINANT PROTEIN AND USES THEREOF

CROSS REFERENCE TO RELATED APPLICATIONS

This is Divisional Application of U.S. application Ser. No. 15/361,701 filed Nov. 28, 2016, which is a Continuation-in-Part of application Ser. No. 14/838,304 filed Aug. 27, 2015, which claims the benefit of the filing date of U.S. Provisional Application No. 62/042,493, filed on Aug. 27, 2014, in the United States Patent and Trademark Office, the disclosure of which is incorporated herein in its entirety by reference.

TECHNICAL FIELD

The present invention relates to providing improved cell-permeable (iCP)-SOCS3 recombinant protein and uses thereof. Preferably, the iCP-SOCS3 recombinant protein may be used as protein-based anti-solid tumor agent by utilizing the platform technology for macromolecule intracellular transduction.

BACKGROUND ART

The Janus kinase signal transducers and activators of transcription signaling (JAK/STAT) plays important roles in immune responses, including oncogenesis. So many investigations demonstrated that STAT-3, an important member of STAT proteins, was considered as a proto-oncogene in various types of disorder. STAT-3 is phosphorylated and dimerizes by the Janus kinase (JAK), and its overexpression and constitutive activation can significantly induce cell proliferation, tumor angiogenesis, invasion. Meanwhile, inhibition of JAK-STAT signaling led to suppress the cancer cell growth and induce apoptosis. Suppressor of cytokine signaling-3 (SOCS3), a kind of endogenous protein inhibitor of JAK/STAT pathway, was identified to be inversely associated with the STAT3 expression and phosphorylation in vivo and in vitro and aberrant expression of SOCS3 protein was observed in human solid tumors including gastric, colorectal and breast cancer, and glioblastoma.

Gastric cancer remains the second leading cause of cancer-related death in the world. Advances in early detection and decreased chronic *Helicobacter pylori* infection rates have led to a substantial reduction in gastric cancer rates worldwide. However, effective treatment regimens for gastric cancers, especially advanced gastric cancer, are still lacking; therefore, the prognosis of patients with this disease remains poor. SOCS3 mRNA levels are higher in adjacent normal mucosal tissues, however, gastric cancer patients with high simultaneous expression of SOCS3 have a better overall survival than those with low simultaneous expression. Based on this, SOCS3 may represent new therapeutic target to treat gastric cancer.

Colorectal cancer is one of the most fatal neoplastic diseases worldwide and a serious global health problem, with over one million new cases and half million mortalities worldwide each year. It has been reported as being relevant to some inflammatory bowel diseases, such as Crohn's disease and ulcerative colitis. The pathogenesis of colorectal carcinoma is complex, with the involvement of multiple cellular transduction pathways including IL-6/STAT3 signaling. Reduced or silenced SOCS3 has been found in many human types of cancer including colorectal cancer, and restoring SOCS3 expression in the cancer cells inhibits IL-6-mediated STAT3 activation, induces tumor cell apoptosis and decreases cell proliferation. Therefore, suppression of the IL-6/STAT3 pathway via modulation of SOCS3 has been a promising strategy for anti-colon/colorectal cancer therapy.

Glioblastoma, the most common neoplasm among diffuse infiltrating astrocytomas, is notorious for its ability to evade immune-surveillance as well as for its invasive and angiogenic properties. Gliomas are the most common type of primary brain tumors are highly malignant and are associated with a very poor prognosis. Glioblastoma is a very aggressive subtype of glioma with very short life expectancy and limited treatment options. A hallmark of this lethal disorder is the presence of activated STAT3. Because SOCS3 is a negative regulator of STAT-3 activation, it hypothesized that SOCS3 may function as a tumor suppressor in glioblastoma tissues.

Breast cancer is a disease that arises from the accumulation of alterations in the genome of cells that make up the mammary gland. Breast cancer is the most common type of cancer among women, with an estimated 1.38 million new cases of cancer diagnosed in 2008 (23% of all cancers), and the second most common type of cancer overall (10.9% of all cancers). Expression of SOCS3 protein is significantly down-regulated in breast cancer specimens and replacing of SOCS3 protein may directly influence the treatment of breast cancer.

Cytokine signaling is strictly regulated by the SOCS family proteins induced by different classes of agonists, including cytokines, hormones and infectious agents. Among them, SOCS1 and SOCS3 are relatively specific to STAT1 and STAT3, respectively. SOCS1 inhibits JAK activation through its N-terminal kinase inhibitory region (KIR) by the direct binding to the activation loop of JAKs, while SOCS3 binds to janus kinases (JAKs)-proximal sites on the receptor through its SH2 domain and inhibits JAK activity that blocks recruitment of STAT3. Both promote anti-inflammatory effects due to the suppression of inflammation-inducing cytokine signaling. Furthermore, the SOCS box, another domain in SOCS proteins, interacts with E3 ubiquitin ligases and/or couples the SH2 domain-binding proteins to the ubiquitin-proteasome pathway. Therefore, SOCSs inhibit cytokine signaling by suppressing JAK kinase activity and degrading the activated cytokine receptor complex.

In connection with SOCSs and various solid tumors including gastric, colorectal and breast cancer, and glioblastoma, the SOCS1 gene has been implicated as an anti-oncogene in the tumor development. Previous studies have reported that aberrant methylation in the CpG island of SOCS1 induces its transcriptional silencing in cancer cell lines, and SOCS1 heterozygous mice are hypersensitive to various cancers. In addition, abnormalities of SOCS3 are also associated with the solid tumors. Hypermethylation of CpG islands in the SOCS3 promoter is correlated with its transcriptional silencing in tumors cell lines. SOCS3 overexpression down-regulates active STAT3, induces apoptosis, and suppresses growth in cancer cells. The importance of STAT3 to inflammation-associated carcinogenesis is underlined by the previous study that cancer-specific deletion of SOCS3 in a mouse carcinoma model results in larger and more numerous tumors. This means that SOCS3 plays a major role in the negative regulation of the JAK/STAT pathway in carcinogenesis and contributes to the suppression of tumor development by protecting the tissue cells.

REFERENCES

1. Fischer P M., Cellular uptake mechanisms and potential therapeutic utility of peptidic cell delivery vectors: progress 2001-2006, Med Res Rev. 2007; 27:755-95.
2. Heitz F, Morris M C, Divita G., Twenty years of cell-penetrating peptides: from molecular mechanisms to therapeutics, Br J Pharmacol. 2009; 157:195-206.
3. Lapenna S, Giordano A., Cell cycle kinases as therapeutic targets for cancer, Nat Rev Drug Discov. 2009; 8:547-66.
4. Lim J, Kim J, Duong T, Lee G, Kim J, Yoon J. et al., Antitumor activity of cell-permeable p18(INK4c) with enhanced membrane and tissue penetration, Mol Ther. 2012; 20:1540-9.
5. Jo D, Liu D, Yao S, Collins R D, Hawiger J., Intracellular protein therapy with SOCS3 inhibits inflammation and apoptosis, Nat Med. 2005; 11:892-8.
6. Jo D, Nashabi A, Doxsee C, Lin Q, Unutmaz D, Chen J. et al., Epigenetic regulation of gene structure and function with a cell-permeable Cre recombinase, Nat Biotechnol. 2001; 19:929-33.
7. Liu D, Li C, Chen Y, Burnett C, Liu X Y, Downs S. et al., Nuclear import of proinflammatory transcription factors is required for massive liver apoptosis induced by bacterial lipopolysaccharide, J Biol Chem. 2004; 279:48434-42.
8. Liu D, Liu X Y, Robinson D, Burnett C, Jackson C, Seele L. et al., Suppression of Staphylococcal Enterotoxin B-induced Toxicity by a Nuclear Import Inhibitor, J Biol Chem. 2004; 279:19239-46.
9. Liu D, Zienkiewicz J, DiGiandomenico A, Hawiger J., Suppression of acute lung inflammation by intracellular peptide delivery of a nuclear import inhibitor, Mol Ther. 2009; 17:796-802.
10. Moore D J, Zienkiewicz J, Kendall P L, Liu D, Liu X, Veach R A. et al., In vivo islet protection by a nuclear import inhibitor in a mouse model of type 1 diabetes, PLoS One. 2010; 5:e13235.
11. Lim J, Jang G, Kang S, Lee G, Nga do T T, Phuong do TL. et al., Cell-permeable NM23 blocks the maintenance and progression of established pulmonary metastasis, Cancer Res. 2011; 71:7216-25.
12. Duong T, Kim J, Ruley H E, Jo D., Cell-permeable parkin proteins suppress Parkinson disease-associated phenotypes in cultured cells and animals, PLoS One. 2014; 9:e102517.
13. Lim J, Duong T, Do N, Do P, Kim J, Kim H. et al., Antitumor activity of cell-permeable RUNX3 protein in gastric cancer cells. Clin Cancer Res. 2013; 19:680-90.
14. Lim J, Duong T, Lee G, Seong B L, El-Rifai W, Ruley H E et al. The effect of intracellular protein delivery on the anti-tumor activity of recombinant human endostatin, Biomaterials. 2013; 34:6261-71.
15. Lim J, Kim J, Kang J, Jo D., Partial somatic to stem cell transformations induced by cell-permeable reprogramming factors, Scientific Reports. 2014; 4:4361.

DISCLOSURE

Technical Problem

To negatively control JAK/STAT signaling, recombinant SOCS3 proteins that contain a cell-penetrating peptide (CPP)-membrane-translocating motif (MTM) from fibroblast growth factor (FGF)-4 has been reported. These recombinant SOCS3 proteins inhibited STAT phosphorylation, inflammatory cytokines production and MHC-II expression in cultured and primary macrophages. In addition, SOCS3 fused to MTM protected mice challenged with a lethal dose of the SEB super-antigen, by suppressing apoptosis and hemorrhagic necrosis in multiple organs. However, the SOCS3 proteins fused to FGF4-derived MTM displayed extremely low solubility, poor yields and relatively low cell- and tissue-permeability. Therefore, the MTM-fused SOCS3 proteins were not suitable for further clinical development as therapeutic agents.

Technical Solution

For MITT, six critical factors (length, bending potential, instability index, aliphatic index, GRAVY, amino acid composition) have been determined through analysis of baseline hydrophobic CPPs. Advanced macromolecule transduction domain (aMTD), newly designed based on these six critical factors, could optimize cell-/tissue-permeability of SOCS3 proteins that have a therapeutic effects and develop them as protein-based drugs. Further, in order to increase solubility and yield of recombinant protein, solubilization domains (SDs) additionally fused to the aMTD-SOCS3 recombinant protein, thereby notably increased the solubility and manufacturing yield of the recombinant protein.

In this application, aMTD/SD-fused iCP-SOCS3 recombinant proteins (iCP-SOCS3), much improved physicochemical characteristics (solubility and yield) and functional activity (cell-/tissue-permeability) compared with the protein fused only to FGF-4-derived MTM. In addition, the newly developed iCP-SOCS3 proteins have now been demonstrated to have therapeutic application in treating solid tumor, exploiting the ability of SOCS3 to suppress JAK/STAT signaling. The present application represents that macromolecule intracellular transduction technology (MITT) enabled by the new hydrophobic CPPs that are aMTD may provide novel protein therapy through SOCS3-intracellular protein replacement against the solid tumor. These findings suggest that restoration of SOCS3 by replenishing the intracellular SOCS3 with iCP-SOCS3 protein creates a new paradigm for anti-cancer therapy, and the intracellular protein replacement therapy with the SOCS3 recombinant protein fused to the combination of aMTD and SD pair may be useful to treat the solid tumor.

One aspect disclosed in the present application provides an improved Cell-Permeable (iCP)-SOCS3 recombinant protein, which comprises a SOCS3 protein; and an advanced macromolecule transduction domain (aMTD) being composed of 9~13 amino acid sequences and having improved cell and/or tissue permeability, wherein the aMTD is fused to one end or both ends of the SOCS3 protein and has the following features of:

(a) being composed of 3 or more amino acid sequences selected from the group consisting of Ala, Val, Ile, Leu, and Pro;

(b) having proline as amino acid sequences corresponding to any one or more of positions 5 to 8, and 12 of its amino acid sequence; and (c) having an instability index of 40-60; an aliphatic index of 180-220; and a grand average of hydropathy (GRAVY) of 2.1-2.6, as measured by Protparam.

According to one embodiment, one or more solubilization domain (SD)(s) are further fused to the end(s) of one or more of the SOCS3 protein and the aMTD.

According to another embodiment, the aMTD may form α-Helix structure. According to still another embodiment, the aMTD may be composed of 12 amino acid sequences and represented by the formula shown in FIG. 104.

In FIG. 104, X(s) independently refer to Alanine (A), Valine (V), Leucine (L) or Isoleucine (I); and Proline (P) can be positioned in one of U(s) (either 5', 6', 7' or 8'). The remaining U(s) are independently composed of A, V, L or I, P at the 12' is Proline. Another aspect disclosed in the present application provides an iCP-SOCS3 recombinant protein which is represented by any one of the following structural formulae:

A-B-C, A-C-B, B-A-C, B-C-A, C-A-B, C-B-A and A-C-B-C wherein A is an advanced macromolecule transduction domain (aMTD) having improved cell and/or tissue permeability, B is a SOCS3 protein, and C is a solubilization domain (SD); and the aMTD is composed of 9~13 amino acid sequences and has the following features of:

(a) being composed of 3 or more amino acids selected from the group consisting of Ala, Val, Ile, Leu, and Pro;

(b) having proline as amino acid sequences corresponding to any one or more of positions 5 to 8, and 12 of its amino acid sequence;

(c) having an instability index of 40-60; an aliphatic index of 180-220; and a grand average of hydropathy (GRAVY) of 2.1-2.6, as measured by Protparam; and (d) forming α-Helix structure.

According to one embodiment disclosed in the present application, the SOCS3 protein may have an amino acid sequence of SEQ ID NO: 814.

According to another embodiment disclosed in the present application, the SOCS3 protein may be encoded by a polynucleotide sequence of SEQ ID NO: 815.

According to still another embodiment disclosed in the present application, the SOCS3 protein may further include a ligand selectively binding to a receptor of a cell, a tissue, or an organ.

According to still another embodiment disclosed in the present application, the aMTD may have an amino acid sequence selected from the group consisting of SEQ ID NOs: 1-240 and 822.

According to still another embodiment disclosed in the present application, the aMTD may be encoded by a polynucleotide sequence selected from the group consisting of SEQ ID NOs: 241~480 and 823.

According to still another embodiment disclosed in the present application, the SD(s) may have an amino acid sequence independently selected from the group consisting of SEQ ID NOs: 798, 799, 800, 801, 802, 803, and 804.

According to still another embodiment disclosed in the present application, the SD(s) may be encoded by a polynucleotide sequence independently selected from the group consisting of SEQ ID NOs: 805, 806, 807, 808, 809, 810, and 811.

According to still another embodiment disclosed in the present application, the iCP-SOCS3 recombinant protein may have a histidine-tag affinity domain additionally fused to one end thereof.

According to still another embodiment disclosed in the present application, the histidine-tag affinity domain may have an amino acid sequence of SEQ ID NO: 812.

According to still another embodiment disclosed in the present application, the histidine-tag affinity domain may be encoded by a polynucleotide sequence of SEQ ID NO: 813.

According to still another embodiment disclosed in the present application, the fusion may be formed via a peptide bond or a chemical bond.

According to still another embodiment disclosed in the present application, the iCP-SOCS3 recombinant protein may be used for the treating, preventing, or delaying the onset of, solid tumor.

Still another aspect disclosed in the present application provides a polynucleotide sequence encoding the iCP-SOCS3 recombinant protein.

According to one embodiment disclosed in the present application, the polynucleotide sequence may be a polynucleotide sequence represented by SEQ ID NO: 825.

Still another aspect disclosed in the present application provides a recombinant expression vector including the polynucleotide sequence.

Still another aspect disclosed in the present application provides a transformant transformed with the recombinant expression vector.

Still another aspect disclosed in the present application provides a preparing method of the iCP-SOCS3 recombinant protein including preparing the recombinant expression vector; preparing the transformant using the recombinant expression vector; culturing the transformant; and recovering the recombinant protein expressed by the culturing.

Still another aspect disclosed in the present application provides a composition including the iCP-SOCS3 recombinant protein as an active ingredient.

Still another aspect disclosed in the present application provides a pharmaceutical composition for the treating, preventing, or delaying the onset of, solid tumor including the iCP-SOCS3 recombinant protein as an active ingredient; and a pharmaceutically acceptable carrier.

Still another aspect disclosed in the present application provides use of the iCP-SOCS3 recombinant protein as a medicament for the treating, preventing, or delaying the onset of, solid tumor.

Still another aspect disclosed in the present application provides a medicament including the iCP-SOCS3 recombinant protein.

Still another aspect disclosed in the present application provides use of the iCP-SOCS3 recombinant protein in the preparation of a medicament for the treating, preventing, or delaying the onset of, solid tumor.

Still another aspect disclosed in the present application provides a method of treating, preventing, or delaying the onset of, solid tumor in a subject, the method including identifying a subject in need of the treating, preventing, or delaying the onset of, solid tumor; and administering to the subject a therapeutically effective amount of the iCP-SOCS3 recombinant protein.

According to one embodiment disclosed in the present application, the subject may be a mammal.

Unless defined otherwise, all terms used herein have the same meaning as commonly understood by one of ordinary skill in the art to which the present invention belongs. Although a certain method and a material is described herein, it should not be construed as being limited thereto, any similar or equivalent method and material to those may also be used in the practice or testing of the present invention. All publications mentioned herein are incorporated herein by reference in their entirety to disclose and describe the methods and/or materials in connection with which the publications are cited. It must be noted that as used herein and in the appended claims, the singular forms "a," "an," and "the" include plural referents unless the context clearly dictates otherwise.

A "peptide," as used herein, refers to a chain-type polymer formed by amino acid residues which are linked to each other via peptide bonds, and used interchangeably with "polypeptide." Further, a "polypeptide" includes a peptide and a protein.

Further, the term "peptide" includes amino acid sequences that are conservative variations of those peptides specifically exemplified herein. The term "conservative variation," as used herein, denotes the replacement of an amino acid residue by another, biologically similar residue. Examples of conservative variations include substitution of one hydrophobic residue, such as isoleucine, valine, leucine, alanine, cysteine, glycine, phenylalanine, proline, tryptophan, tyrosine, norleucine, or methionine for another, or substitution of one polar residue for another, for example, substitution of arginine for lysine, glutamic acid for aspartic acid, or glutamine for asparagine, and the like. Neutral hydrophilic amino acids which may be substituted for one another include asparagine, glutamine, serine, and threonine.

The term "conservative variation" also includes use of a substituted amino acid in place of an unsubstituted parent amino acid, provided that antibodies raised to the substituted polypeptide also immunoreact with the unsubstituted polypeptide. Such conservative substitutions are within the definition of the classes of the peptides disclosed in the present application.

A person having ordinary skill in the art may make similar substitutions to obtain peptides having higher cell permeability and a broader host range. For example, one aspect disclosed in the present application provides peptides corresponding to amino acid sequences (e.g. SEQ ID NOs: 1 to 240 and 822) provided herein, as well as analogues, homologs, isomers, derivatives, amidated variations, and conservative variations thereof, as long as the cell permeability of the peptide remains.

Minor modifications to primary amino acid sequence disclosed in the present application may result in peptides which have substantially equivalent or enhanced cell permeability, as compared to the specific peptides described herein. Such modifications may be deliberate, as by site-directed mutagenesis, or may be spontaneous.

All peptides may be synthesized using L-amino acids, but D forms of all of the peptides may be synthetically produced. In addition, C-terminal derivatives, such as C-terminal methyl esters and C-terminal amidates, may be produced in order to increase the cell permeability of the peptide according to one embodiment disclosed in the present application.

All of the peptides produced by these modifications are included herein, as long as in the case of amidated versions of the peptide, the cell permeability of the original peptide is altered or enhanced such that the amidated peptide is therapeutically useful. It is envisioned that such modifications are useful for altering or enhancing cell permeability of a particular peptide.

Furthermore, deletion of one or more amino acids may also result in a modification to the structure of the resultant molecule without any significant change in its cell permeability. This may lead to the development of a smaller active molecule which may also have utility. For example, amino- or carboxyl-terminal amino acids which may not be required for the cell permeability of a particular peptide may be removed.

The term "gene" refers to an arbitrary nucleic acid sequence or a part thereof having a functional role in protein coding or transcription, or regulation of other gene expression. The gene may be composed of all nucleic acids encoding a functional protein or a part of the nucleic acid encoding or expressing the protein. The nucleic acid sequence may include a gene mutation in exon, intron, initiation or termination region, promoter sequence, other regulatory sequence, or a unique sequence adjacent to the gene.

The term "primer" refers to an oligonucleotide sequence that hybridizes to a complementary RNA or DNA target polynucleotide and serves as the starting points for the stepwise synthesis of a polynucleotide from mononucleotides by the action of a nucleotidyltransferase as occurs, for example, in a polymerase chain reaction.

The term "coding region" or "coding sequence" refers to a nucleic acid sequence, a complement thereof, or a part thereof which encodes a particular gene product or a fragment thereof for which expression is desired, according to the normal base pairing and codon usage relationships. Coding sequences include exons in genomic DNA or immature primary RNA transcripts, which are joined together by the cellular biochemical machinery to provide a mature mRNA. The anti-sense strand is the complement of the nucleic acid, and the coding sequence may be deduced therefrom.

One aspect disclosed in the present application provides an iCP-SOCS3 recombinant protein, which comprises a SOCS3 protein and an advanced macromolecule transduction domain (aMTD) being composed of 9~13 amino acid sequences, preferably 10~12 amino acid sequences, and having improved cell and/or tissue permeability, wherein the aMTD is fused to one end or both ends of the SOCS3 protein and has the following features of:

(a) being preferably composed of 3 or more amino acid sequences selected from the group consisting of Ala, Val, Ile, Leu, and Pro;

(b) having proline as amino acid sequences corresponding to any one or more of positions 5 to 8, and 12 of its amino acid sequence, and preferably one or more of positions 5 to 8 and position 12 of its amino acid sequence; and (c) having an instability index of preferably 40-60 and more preferably 41-58; an aliphatic index of preferably 180-220 and more preferably 185-225; and a grand average of hydropathy (GRAVY) of preferably 2.1-2.6 and more preferably 2.2-2.6 as measured by Protparam (see http://web.expasy.org/protparam/).

These critical factors that facilitate the cell permeable ability of aMTD sequences were analyzed, identified, and determined according to one embodiment disclosed in the present application. These aMTD sequences are artificially assembled based on the critical factors (CFs) determined from in-depth analysis of previously published hydrophobic CPPs.

The aMTD sequences according to one aspect disclosed in the present application are the first artificially developed cell permeable polypeptides capable of mediating the transduction of biologically active macromolecules—including peptides, polypeptides, protein domains, or full-length proteins—through the plasma membrane of cells.

According to one embodiment, one or more solubilization domain (SD)(s) are further fused to one or more of the SOCS3 protein and the aMTD, preferably one end or both ends of the SOCS3 protein, and more preferably the C-terminus of the SOCS3 protein.

According to another embodiment, the aMTD may form α-Helix structure.

According to still another embodiment, the aMTD may be preferably composed of 12 amino acid sequences and represented by the formula shown in FIG. 104.

In FIG. 104, X(s) independently refer to Alanine (A), Valine (V), Leucine (L) or Isoleucine (I); and Proline (P) can be positioned in one of U(s) (either 5', 6', 7' or 8'). The remaining U(s) are independently composed of A, V, L or I, P at the 12' is Proline. Still another aspect disclosed in the present application provides an iCP-SOCS3 recombinant protein which is represented by any one of structural formulae A-B-C, A-C-B, B-A-C, B-C-A, C-A-B, C-B-A and A-C-B-C, and preferably by A-B-C or C-B-A:

wherein A is an advanced macromolecule transduction domain (aMTD) having improved cell and/or tissue permeability, B is a SOCS3 protein, and C is a solubilization domain (SD); and the aMTD is composed of 9-13, preferably 10~12 amino acid sequences and has the following features of:

(a) being composed of 3 or more amino acid sequences selected from the group consisting of Ala, Val, Ile, Leu, and Pro;

(b) having proline as amino acid sequences corresponding to any one or more of positions 5 to 8, and 12 of its amino acid sequence, and preferably, one or more of positions 5 to 8 and position 12 of its amino acid sequence;

(c) having an instability index of 40-60, preferably 41-58 and more preferably 50-58; an aliphatic index of 180-220. preferably 185-225 and more preferably 195-205; and a grand average of hydropathy (GRAVY) of 2.1-2.6 and preferably 2.2-2.6, as measured by Protparam (see http://web.expasy.org/protparam/); and (d) preferably forming α-Helix structure.

In one embodiment disclosed in the present application, the SOCS3 protein may have an amino acid sequence of SEQ ID NO: 814.

In another embodiment disclosed in the present application, the SOCS3 protein may be encoded by a polynucleotide sequence of SEQ ID NO: 815.

When the iCP-SOCS3 recombinant protein is intended to be delivered to a particular cell, tissue, or organ, the SOCS3 protein may form a fusion product, together with an extracellular domain of a ligand capable of selectively binding to a receptor which is specifically expressed on the particular cell, tissue, or organ, or monoclonal antibody (mAb) capable of specifically binding to the receptor or the ligand and a modified form thereof.

The binding of the peptide and a biologically active substance may be formed either by indirect linkage by a cloning technique using an expression vector at a nucleotide level or by direct linkage via chemical or physical covalent or non-covalent bond of the peptide and the biologically active substance.

In still another embodiment disclosed in the present application, the SOCS3 protein may preferably further include a ligand selectively binding to a receptor of a cell, a tissue, or an organ.

In one embodiment disclosed in the present application, the aMTD may have an amino acid sequence selected from the group consisting of SEQ ID NOs: 1-240 and 822, preferably SEQ ID NOs: 2, 16, 22, 32, 40, 43, 63, 65, 77, 84, 85, 86, 110, 131, 142, 143, 177, 228, 229, 233, 237, 239 and 822, more preferably SEQ ID NO: 43.

In still another embodiment disclosed in the present application, the aMTD may be encoded by a polynucleotide sequence selected from the group consisting of SEQ ID NOs: 241~480 and 823, preferably SEQ ID NOs: 242, 256, 262, 272, 280, 283, 303, 305, 317, 324, 325, 326, 350, 371, 382, 383, 417, 468, 469 473, 477, 479 and 823, more preferably SEQ ID NO: 283.

In still another embodiment disclosed in the present application, the SD(s) may have an amino acid sequence independently selected from the group consisting of SEQ ID NOs: 798, 799, 800, 801, 802, 803, and 804. The SD may be preferably SDA of SEQ ID NO: 798, SDB of SEQ ID NO: 799, or SDB' of SEQ ID NO: 804, and more preferably, SDB of SEQ ID NO: 799 which has superior structural stability, or SDB' of SEQ ID NO: 804 which has a modified amino acid sequence of SDB to avoid immune responses upon in vivo application. The modification of the amino acid sequence in SDB may be replacement of an amino acid residue, Valine, corresponding to position 28 of the amino acid sequence of SDB (SEQ ID NO: 799) by Leucine.

In still another embodiment disclosed in the present application, the SDs may be encoded by a polynucleotide sequence independently selected from the group consisting of SEQ ID NOs: 805, 806, 807, 808, 809, 810, and 811. The SD may be preferably SDA encoded by a polynucleotide sequence of SEQ ID NO: 805, SDB encoded by a polynucleotide sequence of SEQ ID NO: 806, or SDB' for deimmunization (or humanization) encoded by a polynucleotide sequence of SEQ ID NO: 811, and more preferably, SDB having superior structural stability, which is encoded by a polynucleotide sequence of SEQ ID NO: 806, or SDB' having a modified polynucleotide sequence of SDB to avoid immune responses upon in vivo application, which is encoded by a polynucleotide sequence of SEQ ID NO: 811.

In still another embodiment disclosed in the present application, the iCP-SOCS3 recombinant protein may be preferably selected from the group consisting of:

1) a recombinant protein, in which SOCS3 having an amino acid sequence of SEQ ID NO: 814 is fused to the N-terminus or the C-terminus of aMTD having any one amino acid sequence selected from the group consisting of SEQ ID NOs: 1 to 240 and 822, 2, 16, 22, 32, 40, 43, 63, 65, 77, 84, 85, 86, 110, 131, 142, 143, 177, 228, 229, 233, 237, 239 and 822, more preferably SEQ ID NO: 43;

2) a recombinant protein, in which SD having any one amino acid sequence selected from the group consisting of SEQ ID NOs: 798 to 804 is further fused to one or more of the N-terminus or the C-terminus of the SOCS3 and aMTD in the recombinant protein of 1); and 3) a recombinant protein, in which a Histidine tag having an amino acid sequence of 812 is further fused to the N-terminus of the recombinant protein of 1) or 2).

According to one embodiment, the iCP-SOCS3 recombinant protein may be composed of an amino acid sequence selected from the group consisting of SEQ ID NO: 825.

The SOCS3 protein may exhibit a physiological phenomenon-related activity or a therapeutic purpose-related activity by intracellular or in-vivo delivery. The recombinant expression vector may include a tag sequence which makes it easy to purify the recombinant protein, for example, consecutive histidine codon, maltose binding protein codon, Myc codon, etc., and further include a fusion partner to enhance solubility of the recombinant protein, etc. Further, for the overall structural and functional stability of the recombinant protein or flexibility of the proteins encoded by respective genes, the recombinant expression vector may further include one or more glycine, proline, and spacer amino acid or polynucleotide sequences including AAY amino acids. Furthermore, the recombinant expression vector may include a sequence specifically digested by an enzyme in order to remove an unnecessary region of the recombinant protein, an expression regulatory sequence, and a marker or reporter gene sequence to verify intracellular delivery, but is not limited thereto.

In still another embodiment disclosed in the present application, the iCP-SOCS3 recombinant protein may preferably have a histidine-tag affinity domain additionally fused to one end thereof.

In still another embodiment disclosed in the present application, the histidine-tag affinity domain may have an amino acid sequence of SEQ ID NO: 812.

In still another embodiment disclosed in the present application, the histidine-tag affinity domain may be encoded by a polynucleotide sequence of SEQ ID NO: 813.

In still another embodiment disclosed in the present application, the fusion may be formed via a peptide bond or a chemical bond.

The chemical bond may be preferably selected from the group consisting of disulfide bonds, diamine bonds, sulfide-amine bonds, carboxyl-amine bonds, ester bonds, and covalent bonds.

In still another embodiment disclosed in the present application, the iCP-SOCS3 recombinant protein may be used for the treating, preventing, or delaying the onset of, solid tumor.

Still another aspect disclosed in the present application provides a polynucleotide sequence encoding the iCP-SOCS3.

According to still another embodiment disclosed in the present application, the polynucleotide sequence may be fused with a histidine-tag affinity domain.

Still another aspect disclosed in the present application provides a recombinant expression vector including the polynucleotide sequence.

Preferably, the vector may be inserted in a host cell and recombined with the host cell genome, or refers to any nucleic acid including a nucleotide sequence competent to replicate spontaneously as an episome. Such a vector may include a linear nucleic acid, a plasmid, a phagemid, a cosmid, an RNA vector, a viral vector, etc.

Preferably, the vector may be genetically engineered to incorporate the nucleic acid sequence encoding the recombinant protein in an orientation either N-terminal and/or C-terminal to a nucleic acid sequence encoding a peptide, a polypeptide, a protein domain, or a full-length protein of interest, and in the correct reading frame so that the recombinant protein consisting of aMTD, SOCS3 protein, and preferably SD may be expressed. Expression vectors may be selected from those readily available for use in prokaryotic or eukaryotic expression systems.

Standard recombinant nucleic acid methods may be used to express a genetically engineered recombinant protein. The nucleic acid sequence encoding the recombinant protein according to one embodiment disclosed in the present application may be cloned into a nucleic acid expression vector, e.g., with appropriate signal and processing sequences and regulatory sequences for transcription and translation, and the protein may be synthesized using automated organic synthetic methods. Synthetic methods of producing proteins are described in, for example, the literature [Methods in Enzymology, Volume 289: Solid-Phase Peptide Synthesis by Gregg B. Fields (Editor), Sidney P. Colowick, Melvin I. Simon (Editor), Academic Press (1997)].

In order to obtain high level expression of a cloned gene or nucleic acid, for example, a cDNA encoding the recombinant protein according to one embodiment disclosed in the present application, the recombinant protein sequence may be typically subcloned into an expression vector that includes a strong promoter for directing transcription, a transcription/translation terminator, and in the case of a nucleic acid encoding a protein, a ribosome binding site for translational initiation. Suitable bacterial promoters are well known in the art and are described, e.g., in the literatures [Sambrook & Russell, Molecular Cloning: A Laboratory Manual, 3d Edition, Cold Spring Harbor Laboratory, N.Y. (2001); and Ausubel, et al., Current Protocols in Molecular Biology, Greene Publishing Associates and Wiley Interscience, N. Y. (1989)]. Bacterial expression systems for expression of the recombinant protein are available in, e.g., *E. coli, Bacillus* sp., and *Salmonella* (Palva et al., Gene 22: 229-235 (1983); Mosbach et al., Nature 302: 543-545 (1983)). Kits for such expression systems are commercially available. Eukaryotic expression systems for mammalian cells, yeast, and insect cells are well known in the art and are also commercially available. The eukaryotic expression vector may be preferably an adenoviral vector, an adeno-associated vector, or a retroviral vector.

Generally, the expression vector for expressing the cell permeable recombinant protein according to one embodiment disclosed in the present application in which the cargo protein, i.e. ΔSOCS3 protein, is attached to the N-terminus, C-terminus, or both termini of aMTD may include regulatory sequences including, for example, a promoter, operably attached to a sequence encoding the advanced macromolecule transduction domain. Non-limiting examples of inducible promoters that may be used include steroid-hormone responsive promoters (e.g., ecdysone-responsive, estrogen-responsive, and glutacorticoid-responsive promoters), tetracycline "Tet-On" and "Tet-Off" systems, and metal-responsive promoters.

The polynucleotide sequence according to one embodiment disclosed in the present application may be present in a vector in which the polynucleotide sequence is operably linked to regulatory sequences capable of providing for the expression of the polynucleotide sequence by a suitable host cell.

According to one embodiment disclosed in the present application, the polynucleotide sequence may be selected from the following groups:

1) a polynucleotide sequence, in which any one polynucleotide sequence selected from the group consisting of SEQ ID NOs: 241~480 and 823, preferably SEQ ID NOs: 242, 252, 274, 279, 322, 331, 338, 345, 347, 361, 365, 370, 371, 383, 387, 417, 462, 468, 469, 473, 477, 479 and 823, more preferably SEQ ID NO: 283, is operably linked with a polynucleotide sequence of SEQ ID NO: 815; and 2) a polynucleotide sequence, in which any one polynucleotide sequence selected from the group consisting of SEQ ID NOs: 805 to 811 is further operably linked to the polynucleotide sequence of 1), or further operably linked to between: any one polynucleotide sequence selected from the group consisting of SEQ ID NOs: 241~480 and 823, preferably SEQ ID NOs: 242, 256, 262, 272, 280, 283, 303, 305, 317, 324, 325, 326, 350, 371, 382, 383, 417, 468, 469, 473, 477, 479 and 823, more preferably SEQ ID NO: 283; and a polynucleotide sequence of SEQ ID NO: 815.

Within an expression vector, the term "operably linked" is intended to mean that the polynucleotide sequence of interest is linked to the regulatory sequence(s) in a manner which allows for expression of the polynucleotide sequence. The term "regulatory sequence" is intended to include promoters, enhancers, and other expression control elements. Such operable linkage with the expression vector can be achieved by conventional gene recombination techniques known in the art, while site-directed DNA cleavage and linkage are carried out by using conventional enzymes known in the art.

The expression vectors may contain a signal sequence or a leader sequence for membrane targeting or secretion, as well as regulatory sequences such as a promoter, an operator, an initiation codon, a termination codon, a polyadenylation signal, an enhancer and the like. The promoter may be a constitutive or an inducible promoter. Further, the expression vector may include one or more selectable marker genes for selecting the host cell containing the expression vector, and may further include a polynucleotide sequence that enables the vector to replicate in the host cell in question.

The expression vector constructed according to one embodiment disclosed in the present application may be the vector where the polynucleotide encoding the iCP-SOCS3 recombinant protein (where an aMTD is fused to the N-terminus or C-terminus of a SOCS3 protein) is inserted within the multiple cloning sites (MCS), preferably within the Nde1/Sal1 site or BamH1/Sal1 site of a pET-28a(+)(Novagen, Darmstadt, Germany) or pET-26b(+) vector(Novagen, Darmstadt, Germany).

In still another embodiment disclosed in the present application, the polynucleotide encoding the SD being additionally fused to the N-terminus or C-terminus of a SOCS3 protein or an aMTD may be inserted into a cleavage site of restriction enzyme (Nde1, BamH1 and Sal1, etc.) within the multiple cloning sites (MCS) of a pET-28a(+)(Novagen, Darmstadt, Germany) or pET-26b(+) vector(Novagen, Darmstadt, Germany).

In still another embodiment disclosed in the present application, the polynucleotide encoding the iCP-SOCS3 recombinant protein may be cloned into a pET-28a(+) vector bearing a His-tag sequence so as to fuse six histidine residues to the N-terminus of the iCP-SOCS3 recombinant protein to allow easy purification.

According to one embodiment disclosed in the present application, the polynucleotide sequence may be a polynucleotide sequence selected from the group consisting of SEQ ID NOS: 824, 826, 828 and 830.

The recombinant protein may be introduced into an appropriate host cell, e.g., a bacterial cell, a yeast cell, an insect cell, or a tissue culture cell. The recombinant protein may also be introduced into embryonic stem cells in order to generate a transgenic organism. Large numbers of suitable vectors and promoters are known to those skilled in the art and are commercially available for generating the recombinant protein.

Known methods may be used to construct vectors including the polynucleotide sequence according to one embodiment disclosed in the present application and appropriate transcriptional/translational control signals. These methods include in vitro recombinant DNA techniques, synthetic techniques, and in vivo recombination/genetic recombination. For example, these techniques are described in the literatures [Sambrook & Russell, Molecular Cloning: A Laboratory Manual, 3d Edition, Cold Spring Harbor Laboratory, N. Y. (2001); and Ausubel et al., Current Protocols in Molecular Biology Greene Publishing Associates and Wiley Interscience, N.Y. (1989)].

Still another aspect disclosed in the present application provides a transformant transformed with the recombinant expression vector.

The transformation includes transfection, and refers to a process whereby a foreign (extracellular) DNA, with or without an accompanying material, enters into a host cell. The "transfected cell" refers to a cell into which the foreign DNA is introduced into the cell, and thus the cell harbors the foreign DNA. The DNA may be introduced into the cell so that a nucleic acid thereof may be integrated into the chromosome or replicable as an extrachromosomal element. The cell introduced with the foreign DNA, etc. is called a transformant.

As used herein, 'introducing' of a protein, a peptide, an organic compound into a cell may be used interchangeably with the expression of 'carrying,' 'penetrating,' 'transporting,' 'delivering,' 'permeating' or 'passing.'

It is understood that the host cell refers to a eukaryotic or prokaryotic cell into which one or more DNAs or vectors are introduced, and refers not only to the particular subject cell but also to the progeny or potential progeny thereof. Because certain modifications may occur in succeeding generations due to either mutation or environmental influences, such progeny may not, in fact, be identical to the parent cell, but are still included within the scope of the term as used herein.

The host cells may be preferably bacterial cells, and as the bacterial cells, there are, in principle, no limitations. They may be eubacteria (gram-positive or gram-negative) or archaebacteria, as long as they allow genetic manipulation for insertion of a gene of interest, preferably for site-specific integration, and they may be cultured on a manufacturing scale. Preferably, the host cells may have the property to allow cultivation to high cell densities.

Examples of bacterial host cells that may be used in the preparation of the recombinant protein are *E. coli* (Lee, 1996; Hannig and Makrides, 1998), *Bacillus subtilis*, *Pseudomonas fluorescens* (Squires et al., 2004; Retallack et al., 2006) as well as various *Corynebacterium* (US 2006/0003404 A1) and *Lactococcus lactis* (Mierau et al., 2005) strains. Preferably, the host cells are *Escherichia coli* cells.

More preferably, the host cell may include an RNA polymerase capable of binding to a promoter regulating the gene of interest. The RNA polymerase may be endogenous or exogenous to the host cell.

Preferably, host cells with a foreign strong RNA polymerase may be used. For example, *Escherichia coli* strains engineered to carry a foreign RNA polymerase (e.g. like in the case of using a T7 promoter a T7-like RNA polymerase in the so-called "T7 strains") integrated in their genome may be used. Examples of T7 strains, e.g. BL21(DE3), HMS174 (DE3), and their derivatives or relatives (see Novagen, pET System manual, 11$^{th}$ edition), may be widely used and commercially available. Preferably, BL21-CodonPlus (DE3)-RIL or BL21-CodonPlus (DE3)-RIPL (Agilent Technologies) may be used. These strains are DE3 lysogens containing the T7 RNA polymerase gene under control of the lacUV5 promoter. Induction with IPTG allows production of T7 RNA polymerase which then directs the expression of the gene of interest under the control of the T7 promoter.

The host cell strains, *E. coli* BL21(DE3) or HMS174 (DE3), which have received their genome-based T7 RNA polymerase via the phage DE3, are lysogenic. It is preferred that the T7 RNA polymerase contained in the host cell has been integrated by a method which avoids, or preferably excludes, the insertion of residual phage sequences in the host cell genome since lysogenic strains have the disadvantage to potentially exhibit lytic properties, leading to undesirable phage release and cell lysis.

Still another aspect disclosed in the present application provides a preparing method of the iCP-SOCS3 recombinant protein including preparing the recombinant expression vector; preparing the transformant using the recombinant expression vector; culturing the transformant; and recovering the recombinant protein expressed by culturing.

Culturing may be preferably in a mode that employs the addition of a feed medium, this mode being selected from the fed-batch mode, semi-continuous mode, or continuous mode, and the bacterial expression host cells may include a DNA construct, integrated in their genome, carrying the DNA sequence encoding the protein of interest under the control of a promoter that enables expression of said protein.

There are no limitations in the type of the culture medium. The culture medium may be semi-defined, i.e. containing complex media compounds (e.g. yeast extract, soy peptone, casamino acids), or it may be chemically defined, without any complex compounds. Preferably, a defined medium may be used. The defined media (also called minimal or synthetic media) are exclusively composed of chemically defined substances, i.e. carbon sources such as glucose or glycerol, salts, vitamins, and, in view of a possible strain auxotrophy, specific amino acids or other substances such as thiamine. Most preferably, glucose may be used as a carbon source. Usually, the carbon source of the feed medium serves as the growth-limiting component which controls the specific growth rate.

Host cells may be disrupted by any convenient method, including freeze-thaw cycling, sonication, mechanical disruption, or the use of cell lysing agents. The literature [Scopes, Protein Purification: Principles and Practice, New York: Springer-Verlag (1994)] describes a number of general methods for purifying recombinant (and non-recombinant) proteins. The methods may include, e.g., ion-exchange chromatography, size-exclusion chromatography, affinity chromatography, selective precipitation, dialysis, and hydrophobic interaction chromatography. These methods may be adapted to devise a purification strategy for the cell permeable recombinant protein. If the cell permeable recombinant protein includes a purification handle, such as an epitope tag or a metal chelating sequence, affinity chromatography may be used to easily purify the protein.

The amount of the protein produced may be evaluated by detecting the advanced macromolecule transduction domain directly (e.g., using Western analysis) or indirectly (e.g., by assaying materials derived from the cells for specific DNA binding activity, such as by electrophoretic mobility shift assay). Proteins may be detected prior to purification, during any stage of purification, or after purification. In some implementations, purification or complete purification may not be necessary.

The iCP-SOCS3 recombinant proteins according to one embodiment disclosed in the present application are cell permeable proteins, and may be used as protein-based vaccines, particularly in the case where killed or attenuated whole organism vaccines are impractical.

The iCP-SOCS3 recombinant proteins according to one embodiment disclosed in the present application may be preferably used for the treating, preventing, or delaying the onset of, solid tumor. The cell permeable recombinant proteins may be delivered to the interior of the cell, eliminating the need to transfect or transform the cell with a recombinant vector. The cell permeable recombinant proteins may be used in vitro to investigate protein function or may be used to maintain cells in a desired state.

Still another aspect disclosed in the present application provides a composition including the iCP-SOCS3 Recombinant Protein as an active ingredient.

Still another aspect disclosed in the present application provides a pharmaceutical composition for treating, preventing, or delaying the onset of, solid tumor including the iCP-SOCS3 Recombinant Protein as an active ingredient and a pharmaceutically acceptable carrier.

According to one embodiment disclosed in the present application, the iCP-SOCS3 Recombinant Protein may be used in a single agent, or in combination with one or more other anti-cancer agents.

Solid tumor described herein include, but are not limited to, described herein include, but are not limited to, prostate cancer, renal cancer, hepatic cancer, colon cancer, rectal cancer, colorectal cancer, brain cancer, renal cancer, colorectal cancer, pancreatic cancer, gastric cancer, breast cancer, lung cancer, cancers of the head and neck, thyroid cancer, glioblastoma, Kaposi's sarcoma, melanoma, oesophageal cancer, gastro-oesophageal cancer, cervical cancer, hepatocellular carcinoma, endometrial cancer, urothelial cancer, or ovarian cancer.

According to one embodiment disclosed in the present invention, the tumor may be early stage tumor, metastatic tumor, non-metastatic tumor, primary tumor, resected tumor, advanced tumor, locally advanced tumor, unresectable tumor, tumor in remission, or recurrent tumor.

Preferably, the composition may be for injectable (e.g. intraperitoneal, intravenous, and intra-arterial, etc.) and may include the active ingredient in an amount of 0.001 mg/kg to 1000 mg/kg, preferably 0.01 mg/kg to 100 mg/kg, more preferably 0.1 mg/kg to 50 mg/kg for human.

For examples, dosages per day normally fall within the range of about 0.001 to about 1000 mg/kg of body weight. In the treatment of adult humans, the range of about 0.1 to about 50 mg/kg/day, in single or divided dose, is especially preferred. However, it will be understood that the concentration of the iCP-SOCS3 recombinant protein actually administered will be determined by a physician, in the light of the relevant circumstances, including the condition to be treated, the chosen route of administration, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Still another aspect disclosed in the present application provides use of the iCP-SOCS3 recombinant protein as a medicament for treating, preventing, or delaying the onset of, solid tumor.

Still another aspect disclosed in the present application provides a medicament including the iCP-SOCS3 recombinant protein.

Still another aspect disclosed in the present application provides use of the iCP-SOCS3 recombinant protein for the preparation of a medicament for treating, preventing, or delaying the onset of, solid tumor.

Still another aspect disclosed in the present application provides a method of treating, preventing, or delaying the onset of, solid tumor in a subject including identifying a subject in need of treating, preventing, or delaying the onset of, solid tumor; and administering to the subject a therapeutically effective amount of the iCP-SOCS3 recombinant protein.

In one embodiment disclosed in the present application, the subject may be preferably a mammal.

Preferably, the subject in need of treating, preventing, or delaying the onset of, solid tumor may be identified by any conventional diagnostic methods known in the art including ultrasound, CT scan, MRI, alpha-fetoprotein testing, and biopsy, etc.

The pharmaceutical composition according to one embodiment disloced in the present application may be prepared by using pharmaceutically suitable and physiologically acceptable additives, in addition to the active ingredient, and the additives may include excipients, disintegrants, sweeteners, binders, coating agents, blowing agents, lubricants, glidants, flavoring agents, etc.

For administration, the pharmaceutical composition may be preferably formulated by further including one or more pharmaceutically acceptable carriers in addition to the above-described active ingredient.

Dosage forms of the pharmaceutical composition may include granules, powders, tablets, coated tablets, capsules, suppositories, liquid formulations, syrups, juice, suspensions, emulsions, drops, injectable liquid formulations, etc. For formulation of the composition into a tablet or capsule, for example, the active ingredient may be combined with any oral, non-toxic pharmaceutically acceptable inert carrier, such as ethanol, glycerol, water, etc. If desired or necessary, suitable binders, lubricants, disintegrants, and colorants may be additionally included as a mixture.

Examples of the suitable binder may include, but are not limited to, starch, gelatin, natural sugars such as glucose or beta-lactose, corn sweeteners, natural and synthetic gums such as acacia, tragacanth, or sodium oleate, sodium stearate, magnesium stearate, sodium benzoate, sodium acetate, sodium chloride, etc. Examples of the disintegrant may include, but are not limited to, starch, methyl cellulose, agar, bentonite, xanthan gum, etc. For formulation of the composition into a liquid preparation, a pharmaceutically acceptable carrier which is sterile and biocompatible may be used, such as saline, sterile water, a Ringer's solution, buffered saline, an albumin infusion solution, a dextrose solution, a maltodextrin solution, glycerol, and ethanol, and these materials may be used alone or in any combination thereof. If necessary, other common additives, such as antioxidants, buffers, bacteriostatic agents, etc., may be added. Further, diluents, dispersants, surfactants, binders, and lubricants may be additionally added to prepare injectable formulations such as aqueous solutions, suspensions, and emulsions, or pills, capsules, granules, or tablets. Furthermore, the composition may be preferably formulated, depending upon diseases and ingredients, using any appropriate method known in the art, as disclosed in Remington's Pharmaceutical Science, Mack Publishing Company, Easton Pa.

Preferably, the treatment or treating mean improving or stabilizing the subject's condition or disease; or preventing or relieving the development or worsening of symptoms associated with the subject's condition or disease. The prevention, prophylaxis and preventive treatment are used herein as synonyms.

Preferably, the treating, preventing, or delaying the onset of, solid tumor may be any one or more of the following: alleviating one or more symptoms of tumor, delaying progressing of tumor, shrinking tumor size in patient, inhibiting tumor growth, prolonging overall survival, prolonging disease-free survival, prolonging time to disease progression, preventing or delving tumor metastasis, reducing or eradiating preexisting tumor metastasis, reducing incidence or burden of preexisting tumor metastasis, preventing recurrence of tumor.

The subject and patient are used herein interchangeably. They refer to a human or another mammal (e.g., mouse, rat, rabbit, dog, cat, cattle, swine, sheep, horse or primate) that can be afflicted with or is susceptible to a disease or disorder but may or may not have the disease or disorder. In certain embodiments, the subject is a human being.

Preferably, the amount effective or effective amount is the amount of an active ingredient or a pharmaceutical composition disclosed herein that when administered to a subject for treating a disease, is sufficient to effect such treatment of the disease. Any improvement in the patient is considered sufficient to achieve treatment. An effective amount of an active ingredient or a pharmaceutical composition disclosed herein, used for the preventing, or delaying the onset of, solid tumor may vary depending upon the manner of administration, the age, body weight, and general health of the patient. Ultimately, the prescribers or researchers will decide the appropriate amount and dosage regimen.

In the treatment or prevention method according to one embodiment disclosed in the present application, the composition including the iCP-SOCS3 recombinant protein as an active ingredient may be administered in a common manner via oral, buccal, rectal, intravenous, intra-arterial, intraperitoneal, intramuscular, intrasternal, percutaneous, topical, intraocular or subcutaneous route, more preferably via intraperitoneal, intravenous, or intra-arterial injection route.

Advantageous Effects

According to one aspect disclosed in the present application, development and establishment of improved cell-permeable SOCS3 recombinant protein, as therapeutics of solid tumor are provided. Because iCP-SOCS3 was designed based on endogenous proteins, it would be a safety anti-solid tumor drug without side-effect.

However, the effects of the disclosures in the present application are not limited to the above-mentioned effects, and another effects not mentioned will be clearly understood by those skilled in the art from the following description.

DESCRIPTION OF DRAWINGS

FIG. 1 shows Structure of aMTD- or rPeptide-Fused Recombinant Proteins. A schematic diagram of the His-tagged CRA recombinant proteins is illustrated and constructed according to the present invention. The his-tag for affinity purification (white), aMTD or rPeptide (gray) and cargo A (CRA, black) are shown.

FIG. 2a shows Construction of Expression Vectors for aMTDs- or rPeptide-Fused Recombinant Proteins. FIGS. 2b and 2c show the agarose gel electrophoresis analysis showing plasmid DNA fragments at 645 bp insert encoding aMTDs or rPeptide-fused CRA cloned into the pET28a(+) vector according to the present invention.

In FIG. 2b, rP38 has the sequence of SEQ ID NO: 952, MTM12 has the sequence of SEQ ID NO: 953, MTD85 has the sequence of SEQ ID NO: 954, aMTD1 has the sequence of SEQ ID NO: 1, aMTD2 has the sequence of SEQ ID NO: 2, aMTD3 has the sequence of SEQ ID NO: 3, aMTD4 has the sequence of SEQ ID NO:4, aMTD5 has the sequence of SEQ ID NO: 5, aMTD11 has the sequence of SEQ ID NO: 6, aMTD12 has the sequence of SEQ ID NO: 7, aMTD43 has the sequence of SEQ ID NO: 8, aMTD21 has the sequence of SEQ ID NO: 9, aMTD22 has the sequence of SEQ ID NO: 10, aMTD23 has the sequence of SEQ ID NO: 11, aMTD24 has the sequence of SEQ ID NO: 12, aMTD25 has the sequence of SEQ ID NO: 13, aMTD42 has the sequence of SEQ ID NO: 14, aMTD43 has the sequence of SEQ ID NO: 15, aMTD44 has the sequence of SEQ ID NO: 16, aMTD61 has the sequence of SEQ ID NO: 17, aMTD62 has the sequence of SEQ ID NO: 18, aMTD63 has the sequence of SEQ ID NO: 19, aMTD64 has the sequence of SEQ ID NO: 20, aMTD65 has the sequence of SEQ ID NO: 21, aMTD81 has the sequence of SEQ ID NO: 22, aMTD82 has the sequence of SEQ ID NO: 23, aMTD83 has the sequence of SEQ ID NO: 24, aMTD84 has the sequence of SEQ ID NO: 25, aMTD85 has the sequence of SEQ ID NO: 26, aMTD101 has the sequence of SEQ ID NO: 27, aMTD102 has the sequence of SEQ ID NO: 28, aMTD103 has the sequence of SEQ ID NO: 29, aMTD104 has the sequence of SEQ ID NO: 30, aMTD105 has the sequence of SEQ ID NO: 31, aMTD121 has the sequence of SEQ ID NO: 32, aMTD123 has the sequence of SEQ ID NO: 33, aMTD124 has the sequence of SEQ ID NO: 34, aMTD141 has the sequence of SEQ ID NO: 35, aMTD143 has the sequence of SEQ ID NO: 36, aMTD144 has the sequence of SEQ ID NO: 37, aMTD145 has the sequence of SEQ ID NO: 38, aMTD161 has the sequence of SEQ ID NO: 39, aMTD162 has the sequence of SEQ ID NO: 40, aMTD163 has the sequence of SEQ ID NO: 41, aMTD164 has the sequence of SEQ ID NO: 42, aMTD165 has the sequence of SEQ ID NO: 43, aMTD182 has the sequence of SEQ ID NO: 44, aMTD183 has the sequence of SEQ ID NO: 45, aMTD184 has the sequence of SEQ ID NO: 46, aMTD185 has the sequence of SEQ ID NO: 47, aMTD 201 has the sequence of SEQ ID NO: 48, aMTD204 has the sequence of SEQ ID NO: 49, aMTD205 has the sequence of SEQ ID NO: 50, aMTD221 has the sequence of SEQ ID NO: 51, aMTD222 has the sequence of SEQ ID NO: 52, aMTD223 has the sequence of SEQ ID NO: 53, aMTD224 has the sequence of SEQ ID NO: 54, aMTD225 has the sequence of SEQ ID NO: 55, aMTD241 has the sequence of SEQ ID NO: 56, aMTD242 has the sequence of SEQ ID NO: 57, aMTD243 has the sequence of SEQ ID NO: 58, aMTD245 has the sequence of SEQ ID NO: 59, aMTD261 has the sequence of SEQ ID NO: 60, aMTD262 has the sequence of SEQ ID NO: 61, aMTD263 has the sequence of SEQ ID NO: 62, aMTD264 has the sequence of SEQ ID NO: 63, aMTD265 has the sequence of SEQ ID NO: 64, aMTD281 has the sequence of SEQ ID NO: 65, aMTD282 has the sequence of SEQ ID NO: 66, aMTD283 has the sequence of SEQ ID NO: 67, aMTD284 has the sequence of SEQ ID NO: 68, aMTD285 has the sequence of SEQ ID NO: 69, aMTD301 has the sequence of SEQ ID NO: 70, aMTD302 has the sequence of SEQ ID NO: 71, aMTD304 has the sequence of SEQ ID NO: 72, aMTD305 has the sequence of SEQ ID NO: 73, aMTD321 has the sequence of SEQ ID NO: 74, aMTD322 has the sequence of SEQ ID NO: 75, aMTD323 has the sequence of SEQ ID NO: 76, aMTD324 has the sequence of SEQ ID NO: 77, aMTD325 has the sequence of SEQ ID NO: 78, aMTD341 has the sequence of SEQ ID NO: 79, aMTD342 has the sequence of SEQ ID NO: 80, aMTD343 has the sequence of SEQ ID NO: 81, aMTD345 has the sequence of SEQ ID NO: 82, aMTD361 has the sequence of SEQ ID NO: 83, aMTD363 has the sequence of SEQ ID NO: 84, aMTD381 has the sequence of SEQ ID NO: 87, aMTD382 has the sequence of SEQ ID NO: 88, aMTD383 has the sequence of SEQ ID NO: 89, aMTD384 has the sequence of SEQ ID NO: 90, aMTD385 has the sequence of SEQ ID NO: 91, aMTD401 has the sequence of SEQ ID NO: 92, aMTD402 has the sequence of SEQ ID NO: 93, aMTD403 has the sequence of SEQ ID NO: 94, aMTD404 has the sequence of SEQ ID NO: 95, aMTD405 has the sequence of SEQ ID NO: 96, aMTD421 has the sequence of SEQ ID NO: 97, aMTD422 has the sequence of SEQ ID NO: 98, aMTD424 has the sequence of SEQ ID NO: 99, aMTD425 has the sequence of SEQ ID NO: 100, aMTD442 has the sequence of SEQ ID NO: 101, aMTD443 has the sequence of SEQ ID NO: 102, aMTD444 has the sequence of SEQ ID NO: 103, aMTD445 has the sequence of SEQ ID NO: 104, aMTD461 has the sequence of SEQ ID NO: 105, aMTD462 has the sequence of SEQ ID NO: 106, aMTD463 has the sequence of SEQ ID NO: 107, aMTD464 has the sequence of SEQ ID NO: 108, aMTD465 has the sequence of SEQ ID NO: 109, aMTD481 has the sequence of SEQ ID NO: 110, aMTD482 has the sequence of SEQ ID NO: 111, aMTD483 has the sequence of SEQ ID NO: 112, aMTD484 has the sequence of SEQ ID NO: 113, aMTD485 has the sequence of SEQ ID NO: 114, aMTD501 has the sequence of SEQ ID NO: 115, aMTD502 has the sequence of SEQ ID NO: 116, aMTD503 has the sequence of SEQ ID NO: 117, aMTD504 has the sequence of SEQ ID NO: 118, aMTD505 has the sequence of SEQ ID NO: 119, aMTD521 has the sequence of SEQ ID NO: 120, aMTD522 has the sequence of SEQ ID NO: 121, aMTD524 has the sequence of SEQ ID NO: 122, aMTD525 has the sequence of SEQ ID NO: 123, aMTD541 has the sequence of SEQ ID NO: 124, aMTD542 has the sequence of SEQ ID NO: 125, aMTD543 has the sequence of SEQ ID NO: 126, aMTD544 has the sequence of SEQ ID NO: 127, aMTD545 has the sequence of SEQ ID NO: 128, aMTD561 has the sequence of SEQ ID NO: 129, aMTD562 has the sequence of SEQ ID NO: 130, aMTD563 has the sequence of SEQ ID NO: 131, aMTD564 has the sequence of SEQ ID NO: 132, aMTD565 has the sequence of SEQ ID NO: 133, aMTD582 has the sequence of SEQ ID NO: 134, aMTD583 has the sequence of SEQ ID NO: 135, aMTD585 has the sequence of SEQ ID NO: 136, aMTD601 has the sequence of SEQ ID NO: 137, aMTD602 has the sequence of SEQ ID NO: 138, aMTD603 has the sequence of SEQ ID NO: 139, aMTD604 has the sequence of SEQ ID NO: 140, aMTD605 has the sequence of SEQ ID NO: 141, aMTD622 has the sequence of SEQ ID NO: 142, aMTD623 has the sequence of SEQ ID NO: 143, aMTD625 has the sequence of SEQ ID NO: 144, aMTD643 has the sequence of SEQ ID NO: 145, aMTD645 has the sequence of SEQ ID NO: 146, aMTD661 has the sequence of SEQ ID NO: 147, aMTD664 has the sequence of SEQ ID NO: 148, aMTD665 has the sequence of SEQ ID NO: 149, aMTD666 has the sequence of SEQ ID NO: 150, aMTD667 has the sequence of SEQ ID NO: 151, aMTD683 has the sequence of SEQ ID NO: 152, aMTD684 has the sequence of SEQ ID NO:153, aMTD685 has the sequence of SEQ ID NO: 154, aMTD686 has the sequence of SEQ ID NO: 155, aMTD687 has the sequence of SEQ ID NO: 156, aMTD703 has the sequence of SEQ ID NO: 157, aMTD705 has the sequence of SEQ ID NO: 158, aMTD706 has the sequence of SEQ ID NO: 159, aMTD707 has the sequence of SEQ ID NO: 160, aMTD724 has the sequence of SEQ ID NO: 161, aMTD725 has the sequence of SEQ ID NO: 162, aMTD726 has the sequence of SEQ ID NO: 163, aMTD727 has the sequence of SEQ ID NO: 164, aMTD743 has the sequence of SEQ ID NO: 165, aMTD744 has the sequence of SEQ ID NO: 166, aMTD746 has the sequence of SEQ ID NO: 167, aMTD747 has the sequence of SEQ ID NO: 168, aMTD763 has the sequence of SEQ ID NO: 169, aMTD764 has the sequence of SEQ ID NO: 170, aMTD765 has the sequence of SEQ ID NO: 171, aMTD766 has the sequence of SEQ ID NO: 172, aMTD767 has the sequence of SEQ ID NO: 173, aMTD783 has the sequence of SEQ ID NO: 174, aMTD 786 has the sequence of SEQ ID NO: 176, aMTD787 has the sequence of SEQ ID NO: 177, aMTD788 has the sequence of SEQ ID NO: 178, aMTD803 has the sequence of SEQ ID NO: 179, aMTD805 has the sequence of SEQ ID NO: 180, aMTD806 has the sequence of SEQ ID NO: 181, aMTD807 has the sequence of SEQ ID NO: 182, aMTD808 has the sequence of SEQ ID NO: 183, aMTD809 has the sequence of SEQ ID NO: 184, aMTD810 has the sequence of SEQ ID NO: 185, aMTD811 has the sequence of SEQ ID NO: 186.

In FIG. 2c, aMTD824 has the sequence of SEQ ID NO: 187, aMTD825 has the sequence of SEQ ID NO: 188, aMTD826 has the sequence of SEQ ID NO: 189, aMTD827 has the sequence of SEQ ID NO: 190, aMTD828 has the sequence of SEQ ID NO: 191, aMTD829 has the sequence of SEQ ID NO: 192, aMTD830 has the sequence of SEQ ID NO: 193, aMTD831 has the sequence of SEQ ID NO: 194, aMTD832 has the sequence of SEQ ID NO: 195, aMTD843 has the sequence of SEQ ID NO: 196, aMTD844 has the sequence of SEQ ID NO: 197, aMTD845 has the sequence of SEQ ID NO: 198, aMTD846 has the sequence of SEQ ID NO: 199, aMTD847 has the sequence of SEQ ID NO: 200, aMTD848 has the sequence of SEQ ID NO: 201, aMTD849 has the sequence of SEQ ID NO: 202, aMTD850 has the sequence of SEQ ID NO: 203, aMTD851 has the sequence of SEQ ID NO: 204, aMTD852 has the sequence of SEQ ID NO: 205, aMTD863 has the sequence of SEQ ID NO: 206, aMTD864 has the sequence of SEQ ID NO: 207, aMTD865 has the sequence of SEQ ID NO: 208, aMTD867 has the sequence of SEQ ID NO: 209, aMTD868 has the sequence of SEQ ID NO: 210, aMTD870 has the sequence of SEQ ID NO: 211, aMTD872 has the sequence of SEQ ID NO: 212, aMTD875 has the sequence of SEQ ID NO: 213, aMTD877 has the sequence of SEQ ID NO: 214, aMTD878 has the sequence of SEQ ID NO: 215, aMTD879 has the sequence of SEQ ID NO: 216, aMTD881 has the sequence of SEQ ID NO: 217, aMTD882 has the sequence of SEQ ID NO: 218, aMTD883 has the sequence of SEQ ID NO: 219, aMTD885 has the sequence of SEQ ID NO: 220, aMTD887 has the sequence of SEQ ID NO: 221, aMTD888 has the sequence of SEQ ID NO: 222, aMTD889 has the sequence of SEQ ID NO: 223, aMTD891 has the sequence of SEQ ID NO: 224, aMTD893 has the sequence of SEQ ID NO: 225, aMTD895 has the sequence of SEQ ID NO: 226, aMTD896 has the sequence of SEQ ID NO: 227, aMTD897 has the sequence of SEQ ID NO: 228, aMTD899 has the sequence of SEQ ID NO: 229, aMTD900 has the sequence of SEQ ID NO: 230, aMTD901 has the sequence of SEQ ID NO: 231, aMTD902 has the sequence of SEQ ID NO: 232, aMTD904 has the sequence of SEQ ID NO: 233, aMTD905 has the sequence of SEQ ID NO: 234, aMTD906 has the sequence of SEQ ID NO: 235, aMTD907 has the sequence of SEQ ID NO: 236, aMTD908 has the sequence of SEQ ID NO: 237, aMTD910 has the sequence of SEQ ID NO: 238, aMTD911 has the sequence of SEQ ID NO: 239, aMTD912 has the sequence of SEQ ID NO: 240, rP38 has the sequence of SEQ ID NO: 952, MTM12 has the sequence of SEQ ID NO: 953, MTD85 has the sequence of SEQ ID NO: 954, rP6 has the sequence of SEQ ID NO: 893, rP9 has the sequence of SEQ ID NO: 912, rP16 has the sequence of SEQ ID NO: 890, rP17 has the sequence of SEQ ID NO: 905, rP18 has the sequence of SEQ ID NO: 945, rP19 has the sequence of SEQ ID NO: 942, rP20 has the sequence of SEQ ID NO: 946, rP26 has the sequence of SEQ ID NO: 895, rP27 has the sequence of SEQ ID NO: 885, rP28 has the sequence of SEQ ID NO: 921, rP29 has the sequence of SEQ ID NO: 924, rP30 has the sequence of SEQ ID NO: 926, rP33 has the sequence of SEQ ID NO: 927, rP37 has the sequence of SEQ ID NO: 889, rP39 has the sequence of SEQ ID NO: 941, rP40 has the sequence of SEQ ID NO: 948, rP49 has the sequence of SEQ ID NO: 918, rP54 has the sequence of SEQ ID NO: 939, rP57 has the sequence of SEQ ID NO: 949, rP59 has the sequence of SEQ ID NO: 938, rP66 has the sequence of SEQ ID NO: 902, rP67 has the sequence of SEQ ID NO: 906, rP68 has the sequence of SEQ ID NO: 913, rP69 has the sequence of SEQ ID NO: 908, rP71 has the sequence of SEQ. ID NO: 930, rP77 has the sequence of SEQ ID NO: 934, rP97 has the sequence of SEQ ID NO: 936, rP113 has the sequence of SEQ ID NO: 891, rP131 has the sequence of SEQ ID NO: 928, rP138 has the sequence of SEQ ID NO: 933, rP139 has the sequence of SEQ ID NO: 944, rP152 has the sequence of SEQ ID NO: 884, rP159 has the sequence of SEQ ID NO: 950, rP167 has the sequence of SEQ ID NO: 898, rP169 has the sequence of SEQ ID NO: 923, rP190 has the sequence of SEQ ID NO: 925, rP209 has the sequence of SEQ ID NO: rP210 has the sequence of SEQ ID NO: 920, rP214 has the sequence of SEQ ID NO: 937, rP226 has the sequence of SEQ ID NO: 892, rP227 has the sequence of SEQ ID NO: 904, rP246 has the sequence of SEQ ID NO: 899, rP248 has the sequence of SEQ ID NO: 903, rP329 has the sequence of SEQ ID NO: 917, rP331 has the sequence of SEQ ID NO: 911, rP349 has the sequence of SEQ ID NO: 914, rP350 has the sequence of SEQ ID NO: 910, rP390 has the sequence of SEQ ID NO: 909, rP426 has the sequence of SEQ ID NO: 900, rP436 has the sequence of SEQ ID NO: 932, rP466 has the sequence of SEQ ID NO: 897, rP527 has the sequence of SEQ ID NO: 896, rP577 has the sequence of SEQ ID NO: 935, rP606 has the sequence of SEQ ID NO: 901, rP635 has the sequence of SEQ ID NO: 947, rP692 has the sequence of SEQ ID NO: 907, rP693 has the sequence of SEQ ID NO: 922, rP700 has the sequence of SEQ ID NO: 951, rP750 has the sequence of SEQ ID NO: 894, rP772 has the sequence of SEQ ID NO: 919, rP921 has the sequence of SEQ ID NO: 931, rP922 has the sequence of SEQ ID NO: 929, rP934 has the sequence of SEQ ID NO: 888, rP935 has the sequence of SEQ ID NO: 886, rP936 has the sequence of SEQ ID NO: 883, rP937 has the sequence of SEQ ID NO: 915, rP938 has the sequence of SEQ ID NO: 916, rP947 has the sequence of SEQ ID NO: 943, rP949 has the sequence of SEQ ID NO: 940.

FIGS. 3a to 3d show Inducible Expression of aMTD- or rPeptide-Fused Recombinant Proteins. Expressed recombinant aMTD- or random peptide-fused CRA recombinant proteins were transformed in *E. coli* BL21 (DE3) strain. Expression of recombinant proteins in *E.coli* before (−) and after (+) induction with IPTG was monitored by SDS-PAGE, and stained with Coomassie blue.

In FIG. 3a, MTM12 has the sequence of SEQ ID NO: 953, MTM16 has the sequence of SEQ ID NO: 865, MTD85 has the sequence of SEQ ID NO: 954, rP38 has the sequence of SEQ ID NO: 952, SDA has the sequence of SEQ ID NO: 798, MTD73 has the sequence of SEQ ID NO: 871, MTD103 has the sequence of SEQ ID NO: 876, aMTD562 has the sequence of SEQ ID NO: 130, aMTD563 has the sequence of SEQ ID NO: 131, aMTD564 has the sequence of SEQ ID NO: 132, aMTD542 has the sequence of SEQ ID NO: 125, aMTD543 has the sequence of SEQ ID NO: 126, aMTD322 has the sequence of SEQ ID NO: 75, aMTD323 has the sequence of SEQ ID NO: 76, aMTD403 has the sequence of SEQ ID NO: 94, aMTD405 has the sequence of SEQ ID NO: 96, aMTD421 has the sequence of SEQ ID NO: 337, aMTD422 has the sequence of SEQ ID NO: 98, aMTD443 has the sequence of SEQ ID NO: 102, aMTD445 has the sequence of SEQ ID NO: 104, aMTD461 has the sequence of SEQ ID NO: 105, aMTD462 has the sequence of SEQ ID NO: 106, aMTD363 has the sequence of SEQ ID NO: 84, aMTD364 has the sequence of SEQ ID NO: 986, aMTD365 has the sequence of SEQ ID NO: 86, aMTD424 has the sequence of SEQ ID NO: 99, aMTD442 has the sequence of SEQ ID NO: 101, aMTD603 has the sequence of SEQ ID NO: 139, aMTD625 has the sequence of SEQ ID NO: 144, aMTD381 has the sequence of SEQ ID NO: 87, aMTD383 has the sequence of SEQ ID NO: 89, aMTD384 has the sequence of SEQ ID NO: 90, aMTD385 has the sequence of SEQ ID NO: 91, aMTD402 has the sequence of SEQ ID NO: 93, aMTD582 has the sequence of SEQ ID NO: 134, aMTD601 has the sequence of SEQ ID NO: 137, aMTD902 has the sequence of SEQ ID NO: 232, aMTD875 has the sequence of SEQ ID NO: 213, aMTD877 has the sequence of SEQ ID NO: 214, aMTD345 has the sequence of SEQ ID NO: 82, aMTD163 has the sequence of SEQ ID NO: 41, aMTD61 has the sequence of SEQ ID NO: 17, aMTD62 has the sequence of SEQ ID NO: 18, aMTD63 has the sequence of SEQ ID NO: 19, aMTD64 has the sequence of SEQ ID NO: 20, aMTD65 has the sequence of SEQ ID NO: 21, aMTD504 has the sequence of SEQ ID NO: 118, aMTD42 has the sequence of SEQ ID NO: 14, aMTD81 has the sequence of SEQ ID NO: 22, aMTD82 has the sequence of SEQ ID NO: 23, aMTD83 has the sequence of SEQ ID NO: 24, aMTD84 has the sequence of SEQ ID NO: 25, aMTD124 has the sequence of SEQ ID NO: 34, aMTD145 has the sequence of SEQ ID NO: 38, aMTD161 has the sequence of SEQ ID NO: 39, aMTD182 has the sequence of SEQ ID NO: 44, aMTD204 has the sequence of SEQ ID NO: 49, aMTD205 has the sequence of SEQ ID NO: 50, aMTD324 has the sequence of SEQ ID NO: 77, aMTD225 has the sequence of SEQ ID NO: 55, aMTD263 has the sequence of SEQ ID NO: 62, aMTD643 has the sequence of SEQ ID NO: 145, aMTD1 has the sequence of SEQ ID NO: 1, aMTD2 has the sequence of SEQ ID NO: 2, aMTD3 has the sequence of SEQ ID NO: 3, aMTD4 has the sequence of SEQ ID NO: 4, aMTD5 has the sequence of SEQ ID NO: 5, aMTD325 has the sequence of SEQ ID NO: 78, aMTD382 has the sequence of SEQ ID NO: 88, aMTD425 has the sequence of SEQ ID NO: 100, aMTD482 has the sequence of SEQ ID NO: 111, aMTD401 has the sequence of SEQ ID NO: 92, aMTD444 has the sequence of SEQ ID NO: 103, aMTD464 has the sequence of SEQ ID NO: 108, aMTD485 has the sequence of SEQ ID NO: 114, aMTD501 has the sequence of SEQ ID NO: 115, aMTD505 has the sequence of SEQ ID NO: 119, aMTD524 has the sequence of SEQ ID NO: 122, aMTD525 has the sequence of SEQ ID NO: 123, aMTD683 has the sequence of SEQ ID NO: 152, aMTD684 has the sequence of SEQ ID NO: 153, aMTD685 has the sequence of SEQ ID NO: 154, aMTD864 has the sequence of SEQ ID NO: 207, aMTD85 has the sequence of SEQ ID NO: 26, aMTD102 has the sequence of SEQ ID NO: 28, aMTD103 has the sequence of SEQ ID NO: 29, aMTD104 has the sequence of SEQ ID NO: 30, aMTD105 has the sequence of SEQ ID NO: 31, aMTD121 has the sequence of SEQ ID NO: 32, aMTD165 has the sequence of SEQ ID NO: 43, aMTD12 has the sequence of SEQ ID NO: 7, aMTD21 has the sequence of SEQ ID NO: 9, aMTD22 has the sequence of SEQ ID NO: 10, aMTD23 has the sequence of SEQ ID NO: 11, aMTD25 has the sequence of SEQ ID NO: 13, aMTD43 has the sequence of SEQ ID NO: 15, aMTD44 has the sequence of SEQ ID NO: 16, aMTD321 has the sequence of SEQ ID NO: 74, aMTD661 has the sequence of SEQ ID NO: 147, aMTD243 has the sequence of SEQ ID NO: 58, aMTD245 has the sequence of SEQ ID NO: 59, aMTD264 has the sequence of SEQ ID NO: 63, aMTD282 has the sequence of SEQ ID NO: 66, aMTD602 has the sequence of SEQ ID NO: 138, aMTD604 has the sequence of SEQ ID NO: 140.

In FIG. 3b, aMTD284 has the sequence of SEQ ID NO: 68, aMTD285 has the sequence of SEQ ID NO: 69, aMTD141 has the sequence of SEQ ID NO: 35, aMTD201 has the sequence of SEQ ID NO: 48, aMTD265 has the sequence of SEQ ID NO: 64, aMTD281 has the sequence of SEQ ID NO: 65, aMTD304 has the sequence of SEQ ID NO: 72, aMTD305 has the sequence of SEQ ID NO: 73, aMTD343 has the sequence of SEQ ID NO: 81, aMTD341 has the sequence of SEQ ID NO: 79, aMTD301 has the sequence of SEQ ID NO: 70, aMTD522 has the sequence of SEQ ID NO: 121, aMTD645 has the sequence of SEQ ID NO: 146, aMTD746 has the sequence of SEQ ID NO: 167, aMTD747 has the sequence of SEQ ID NO: 168, aMTD763 has the sequence of SEQ ID NO: 169, aMTD846 has the sequence of SEQ ID NO: 199, aMTD849 has the sequence of SEQ ID NO: 202, aMTD101 has the sequence of SEQ ID NO: 27, aMTD185 has the sequence of SEQ ID NO: 47, aMTD667 has the sequence of SEQ ID NO: 151, aMTD766 has the sequence of SEQ ID NO: 172 aMTD783 has the sequence of SEQ ID NO: 174, aMTD850 has the sequence of SEQ ID NO: 203, aMTD865 has the sequence of SEQ ID NO: 208, aMTD162 has the sequence of SEQ ID NO: 40, aMTD184 has the sequence of SEQ ID NO: 46, aMTD483 has the sequence of SEQ ID NO: 112, aMTD484 has the sequence of SEQ ID NO: 113, aMTD481 has the sequence of SEQ ID NO: 110, aMTD544 has the sequence of SEQ ID NO: 127, aMTD561 has the sequence of SEQ ID NO: 129, aMTD565 has the sequence of SEQ ID NO: 133, aMTD583 has the sequence of SEQ ID NO: 135, aMTD585 has the sequence of SEQ ID NO: 136, aMTD803 has the sequence of SEQ ID NO: 179, aMTD805 has the sequence of SEQ ID NO: 180, aMTD811 has the sequence of SEQ ID NO: 186, aMTD824 has the sequence of SEQ ID NO: 187, aMTD825 has the sequence of SEQ ID NO: 188, aMTD826 has the sequence of SEQ ID NO: 189, aMTD828 has the sequence of SEQ ID NO: 191, aMTD829 has the sequence of SEQ ID NO: 192, aMTD851 has the sequence of SEQ ID NO: 204, aMTD164 has the sequence of SEQ ID NO: 42, aMTD623 has the sequence of SEQ ID NO: 143, aMTD764 has the sequence of SEQ ID NO: 170, aMTD784 has the sequence of SEQ ID NO: 175, aMTD788 has the sequence of SEQ ID NO: 178, aMTD808 has the sequence of SEQ ID NO: 183, aMTD847 has the sequence of SEQ ID NO: 200, aMTD664 has the sequence of SEQ ID NO: 148, aMTD666 has the sequence of SEQ ID NO: 150, aMTD725 has the sequence of SEQ ID NO: 162, aMTD743 has the sequence of SEQ ID NO: 165, aMTD744 has the sequence of SEQ ID NO: 166, aMTD747 has the sequence of SEQ ID NO: 168, aMTD809 has the sequence of SEQ ID NO: 184, aMTD830 has the sequence of SEQ ID NO: 193, aMTD703 has the sequence of SEQ ID NO: 157, aMTD705 has the sequence of SEQ ID NO: 158, aMTD707 has the sequence of SEQ ID NO: 160, aMTD727 has the sequence of SEQ ID NO: 164, aMTD787 has the sequence of SEQ ID NO: 177, aMTD810 has the sequence of SEQ ID NO: 185, aMTD827 has the sequence of SEQ ID NO: 190, aMTD844 has the sequence of SEQ ID NO: 197, aMTD852 has the sequence of SEQ ID NO: 205, aMTD882 has the sequence of SEQ ID NO: 218, aMTD885 has the sequence of SEQ ID NO: 220, aMTD888 has the sequence of SEQ ID NO: 222, aMTD889 has the sequence of SEQ ID NO: 223, aMTD891 has the sequence of SEQ ID NO: 224, aMTD845 has the sequence of SEQ ID NO: 198, aMTD896 has the sequence of SEQ ID NO: 227, aMTD904 has the sequence of SEQ ID NO: 233, aMTD905 has the sequence of SEQ ID NO: 234, aMTD906 has the sequence of SEQ ID NO: 235, aMTD907 has the sequence of SEQ ID NO: 236, aMTD908 has the sequence of SEQ ID NO: 237, aMTD910 has the sequence of SEQ ID NO: 238, aMTD911 has the sequence of SEQ ID NO: 239, aMTD832 has the sequence of SEQ ID NO: 195, aMTD843 has the sequence of SEQ ID NO: 196, aMTD863 has the sequence of SEQ ID NO: 206, aMTD867 has the sequence of SEQ ID NO: 209, aMTD868 has the sequence of SEQ ID NO: 210, aMTD883 has the sequence of SEQ ID NO: 219, aMTD901 has the sequence of SEQ ID NO: 231, aMTD831 has the sequence of SEQ ID NO: 194, aMTD870 has the sequence of SEQ ID NO: 211, aMTD223 has the sequence of SEQ ID NO: 53, aMTD224 has the sequence of SEQ ID NO: 54, aMTD765 has the sequence of SEQ ID NO: 171, aMTD897 has the sequence of SEQ ID NO: 228.

In FIG. 3c aMTD302 has the sequence of SEQ ID NO: 71, aMTD361 has the sequence of SEQ ID NO: 84, aMTD502 has the sequence of SEQ ID NO: 116, aMTD545 has the sequence of SEQ ID NO: 128, aMTD605 has the sequence of SEQ ID NO: 141, aMTD622 has the sequence of SEQ ID NO: 142, aMTD686 has the sequence of SEQ ID NO: 155, aMTD665 has the sequence of SEQ ID NO: 149, aMTD806 has the sequence of SEQ ID NO: 181, aMTD912 has the sequence of SEQ ID NO: 240, aMTD724 has the sequence of SEQ ID NO: 161, aMTD726 has the sequence of SEQ ID NO: 163, aMTD807 has the sequence of SEQ ID NO: 182, aMTD872 has the sequence of SEQ ID NO: 212, aMTD881 has the sequence, of SEQ ID NO: 217, aMTD878 has the sequence of SEQ ID NO: 215, aMTD879 has the sequence of SEQ ID NO: 216, aMTD241 has the sequence of SEQ ID NO: 56, aMTD221 has the sequence of SEQ ID NO: 51, aMTD222 has the sequence of SEQ ID NO: 52, aMTD242 has the sequence of SEQ ID NO: 57, aMTD261 has the sequence of SEQ ID NO: 60, aMTD521 has the sequence of SEQ ID NO: 120, aMTD11 has the sequence of SEQ ID NO: 6, aMTD13 has the sequence of SEQ ID NO: 8, aMTD887 has the sequence of SEQ ID NO: 221, aMTD893 has the sequence of SEQ ID NO: 225, aMTD899 has the sequence of SEQ ID NO: 229, aMTD900 has the sequence of SEQ ID NO: 230, aMTD143 has the sequence of SEQ ID NO: 36, aMTD24 has the sequence of SEQ ID NO: 12, aMTD123 has the sequence of SEQ ID NO: 33, aMTD183 has the sequence of SEQ ID NO: 45, aMTD262 has the sequence of SEQ ID NO: 61, aMTD283 has the sequence of SEQ ID NO: 67, aMTD503 has the sequence of SEQ ID NO: 117, aMTD465 has the sequence of SEQ ID NO: 109, aMTD687 has the sequence of SEQ ID NO: 156, aMTD342 has the sequence of SEQ ID NO: 80, aMTD404 has the sequence of SEQ ID NO: 95, aMTD463 has the sequence of SEQ ID NO: 107, aMTD706 has the sequence of SEQ ID NO: 159, aMTD144 has the sequence of SEQ ID NO: 37, aMTD786 has the sequence of SEQ ID NO: 176, aMTD895 has the sequence of SEQ ID NO: 226, aMTD541 has the sequence of SEQ ID NO: 124, rP6 has the sequence of SEQ ID NO: 893, rP9 has the sequence of SEQ ID NO: 912, rP19 has the sequence of SEQ ID NO: 942, rP20 has the sequence of SEQ ID NO: 946, rP37 has the sequence of SEQ ID NO: 889, rP40 has the sequence of SEQ ID NO: 948, rP54 has the sequence of SEQ ID NO: 939, rP27 has the sequence of SEQ ID NO: 885, rP49 has the sequence of SEQ ID NO: 918, rP59 has the sequence of SEQ ID NO: 938, rP152 has the sequence of SEQ ID NO: 884, rP30 has the sequence of SEQ ID NO: 926, rP33 has the sequence of SEQ ID NO: 927, rP68 has the sequence of SEQ ID NO: 913, rP69 has the sequence of SEQ ID NO: 908, rP131 has the sequence of SEQ ID NO: 928, rP227 has the sequence of SEQ ID NO: 904, rP138 has the sequence of SEQ ID NO: 933, rP935 has the sequence of SEQ ID NO: 886, rP947 has the sequence of SEQ ID NO: 943, rP949 has the sequence of SEQ ID NO: 940, rP169 has the sequence of SEQ ID NO: 923, rP16 has the sequence of SEQ ID NO: 890, rP17 has the sequence of SEQ ID NO: 905, rP18 has the sequence of SEQ ID NO: 945, rP28 has the sequence of SEQ ID NO: 921, rP29 has the sequence of SEQ ID NO: 924, rP246 has the sequence of SEQ ID NO: 899, rP248 has the sequence of SEQ ID NO: 903, rP66 has the sequence of SEQ ID NO: 902, rP67 has the sequence of SEQ ID NO: 906, rP113 has the sequence of SEQ ID NO: 891, rP159 has the sequence of SEQ ID NO: 950, rP190 has the sequence of SEQ ID NO: 925, rP349 has the sequence of SEQ ID NO: rP350 has the sequence of SEQ ID NO: rP390 has the sequence of SEQ ID NO: 914, rP426 has the sequence of SEQ ID NO: 900, rP436 has the sequence of SEQ ID NO: 932, rP635 has the sequence of SEQ ID NO: 947, rP921 has the sequence of SEQ ID NO: 931, rP922 has the sequence of SEQ ID NO: 929.

In FIG. 3d, rP527 has the sequence of SEQ ID NO: 896, rP606 has the sequence of SEQ ID NO: 901, rP750 has the sequence of SEQ ID NO: 894, rP329 has the sequence of SEQ ID NO: 917, rP466 has the sequence of SEQ ID NO: 897, rP934 has the sequence of SEQ ID NO: 888, rP936 has the sequence of SEQ ID NO: 883, rP937 has the sequence of SEQ ID NO: 915, rP938 has the sequence of SEQ ID NO: 916, rP26 has the sequence of SEQ ID NO: 895, rP39 has the sequence of SEQ ID NO: rP97 has the sequence of SEQ ID NO: rP139 has the sequence of SEQ ID NO: 941, rP226 has the sequence of SEQ ID NO: 892, rP210 has the sequence of SEQ ID NO: 92, rP214 has the sequence of SEQ ID NO: 937, rP692 has the sequence of SEQ ID NO: 907, rP693 has the sequence of SEQ ID NO: 922, rP700 has the sequence of SEQ ID NO: 951, rP57 has the sequence of SEQ ID NO: 949, rP71 has the sequence of SEQ ID NO: 930, rP77 has the sequence of SEQ ID NO: 934, rP167 has the sequence of SEQ ID NO: 898, rP331 has the sequence of SEQ ID NO: 911, rP577 has the sequence of SEQ ID NO: 935, rP772 has the sequence of SEQ ID NO: 919.

FIGS. 4a and 4b show Purification of aMTD- or rPeptide-Fused Recombinant Proteins. Expressed recombinant proteins were purified by $Ni^{2+}$ affinity chromatography under the natural condition. Purification of recombinant proteins displayed through SDS-PAGE analysis.

In FIG. 4a, aMTD1 has the sequence of SEQ ID NO: 1, aMTD 2 has the sequence of SEQ ID NO: 2, aMTD3 has the sequence of SEQ ID NO: 3, aMTD4 has the sequence of SEQ ID NO: 4, aMTD5 has the sequence of SEQ ID NO: 5, aMTD21 has the sequence of SEQ ID NO: 9, aMTD124 has the sequence of SEQ ID NO: 34, aMTD161 has the sequence of SEQ ID NO: 39, aMTD165 has the sequence of SEQ ID NO: 43, aMTD182 has the sequence of SEQ ID NO: 44, aMTD204 has the sequence of SEQ ID NO: 49, aMTD12 has the sequence of SEQ ID NO: 7, aMTD24 has the sequence of SEQ ID NO: 12, aMTD25 has the sequence of SEQ ID NO: 13, aMTD43 has the sequence of SEQ ID NO: 15, aMTD44 has the sequence of SEQ ID NO: 16, aMTD62 has the sequence of SEQ ID NO: 18, aMTD63 has the sequence of SEQ ID NO: 19, aMTD23 has the sequence of SEQ ID NO: 11, aMTD61 has the sequence of SEQ ID NO: 17, aMTD82 has the sequence of SEQ ID NO: 23, aMTD284 has the sequence of SEQ ID NO: 68, aMTD64 has the sequence of SEQ ID NO: 20, aMTD65 has the sequence of SEQ ID NO: 21, aMTD83 has the sequence of SEQ ID NO: 24, aMTD85 has the sequence of SEQ ID NO:26, aMTD102 has the sequence of SEQ ID NO: 28, aMTD264 has the sequence of SEQ ID NO: 63, aMTD285 has the sequence of SEQ ID NO:69, aMTD103 has the sequence of SEQ ID NO: 29, aMTD104 has the sequence of SEQ ID NO: 30, aMTD105 has the sequence of SEQ ID NO: 31, aMTD121 has the sequence of SEQ ID NO: 32, aMTD123 has the sequence of SEQ ID NO: 33, aMTD141 has the sequence of SEQ ID NO: 35, aMTD143 has the sequence of SEQ ID NO: 36, aMTD145 has the sequence of SEQ ID NO: 38, aMTD42 has the sequence of SEQ ID NO:

14, aMTD163 has the sequence of SEQ ID NO: 41, aMTD809 has the sequence of SEQ ID NO: 184, aMTD667 has the sequence of SEQ ID NO: 151, aMTD13 has the sequence of SEQ ID NO: 8, aMTD205 has the sequence of SEQ ID NO: 50, aMTD243 has the sequence of SEQ ID NO: 58, aMTD245 has the sequence of SEQ ID NO: 59, aMTD282 has the sequence of SEQ ID NO: 66, aMTD301 has the sequence of SEQ ID NO: 70, aMTD304 has the sequence of SEQ ID NO: 72, aMTD305 has the sequence of SEQ ID NO: 73, aMTD281 has the sequence of SEQ ID NO: 65, aMTD321 has the sequence of SEQ ID NO: 74, aMTD343 has the sequence of SEQ ID NO: 81, aMTD385 has the sequence of SEQ ID NO: 91, aMTD341 has the sequence of SEQ ID NO: 79, aMTD522 has the sequence of SEQ ID NO: 121, aMTD201 has the sequence of SEQ ID NO: 48, aMTD361 has the sequence of SEQ ID NO: 83, aMTD183 has the sequence of SEQ ID NO: 45, aMTD222 has the sequence of SEQ ID NO: 52, aMTD262 has the sequence of SEQ ID NO: 61, aMTD265 has the sequence of SEQ ID NO: 64, aMTD283 has the sequence of SEQ ID NO: 67, aMTD363 has the sequence of SEQ ID NO: 84, aMTD365 has the sequence of SEQ ID NO: 86, aMTD364 has the sequence of SEQ ID NO: 85, aMTD381 has the sequence of SEQ ID NO: 87, aMTD383 has the sequence of SEQ ID NO: 89, aMTD384 has the sequence of SEQ ID NO: 90, aMTD402 has the sequence of SEQ ID NO: 93, aMTD703 has the sequence of SEQ ID NO: 157, aMTD724 has the sequence of SEQ ID NO: 161, aMTD726 has the sequence of SEQ ID NO:163, aMTD845 has the sequence of SEQ ID NO: 198, aMTD897 has the sequence of SEQ ID NO: 228, aMTD831 has the sequence of SEQ ID NO: 194, aMTD881 has the sequence of SEQ ID NO: 217, aMTD544 has the sequence of SEQ ID NO: 127, aMTD561 has the sequence of SEQ ID NO: 129, aMTD583 has the sequence of SEQ ID NO: 135, aMTD585 has the sequence of SEQ ID NO: 136, aMTD763 has the sequence of SEQ ID NO: 169, aMTD846 has the sequence of SEQ ID NO: 199, aMTD849 has the sequence of SEQ ID NO: 202, aMTD864 has the sequence of SEQ ID NO: 207, aMTD11 has the sequence of SEQ ID NO: 6, aMTD261 has the sequence of SEQ ID NO: 60, aMTD521 has the sequence of SEQ ID NO: 120, aMTD524 has the sequence of SEQ ID NO: 122, aMTD542 has the sequence of SEQ ID NO: 125, aMTD545 has the sequence of SEQ ID NO: 128, aMTD564 has the sequence of SEQ ID NO: 132, aMTD582 has the sequence of SEQ ID NO: 134, aMTD601 has the sequence of SEQ ID NO: 137, aMTD603 has the sequence of SEQ ID NO: 139, aMTD625 has the sequence of SEQ ID NO: 144, aMTD322 has the sequence of SEQ ID NO: 75, aMTD323 has the sequence of SEQ ID NO: 76, aMTD403 has the sequence of SEQ ID NO: 94, aMTD404 has the sequence of SEQ ID NO: 95, aMTD405 has the sequence of SEQ ID NO: 96, aMTD421 has the sequence of SEQ ID NO: 97, aMTD422 has the sequence of SEQ ID NO: 98, aMTD424 has the sequence of SEQ ID NO: 99, aMTD425 has the sequence of SEQ ID NO: 100, aMTD442 has the sequence of SEQ ID NO: 101, aMTD443 has the sequence of SEQ ID NO: 102, aMTD445 has the sequence of SEQ ID NO: 104, aMTD461 has the sequence of SEQ ID NO: 105, aMTD525 has the sequence of SEQ ID NO: 123, aMTD543 has the sequence of SEQ ID NO: 126, aMTD645 has the sequence of SEQ ID NO: 146, aMTD462 has the sequence of SEQ ID NO: 106, aMTD463 has the sequence of SEQ ID NO: 107, aMTD81 has the sequence of SEQ ID NO: 22, aMTD221 has the sequence of SEQ ID NO: 51, aMTD302 has the sequence of SEQ ID NO: 71, aMTD562 has the sequence of SEQ ID NO: 130, aMTD563 has the sequence of SEQ ID NO: 131, aMTD241 has the sequence of SEQ ID NO: 56, aMTD830 has the sequence of SEQ ID NO: 193, aMTD832 has the sequence of SEQ ID NO: 195, aMTD883 has the sequence of SEQ ID NO: 219, aMTD843 has the sequence of SEQ ID NO: 196, aMTD863 has the sequence of SEQ ID NO: 206, aMTD868 has the sequence of SEQ ID NO: 210, aMTD867 has the sequence of SEQ ID NO: 209, aMTD901 has the sequence of SEQ ID NO: 231, aMTD482 has the sequence of SEQ ID NO: 111, aMTD505 has the sequence of SEQ ID NO: 119, aMTD664 has the sequence of SEQ ID NO: 148, aMTD686 has the sequence of SEQ ID NO: 155, aMTD382 has the sequence of SEQ ID NO: 88, aMTD325 has the sequence of SEQ ID NO: 78, aMTD324 has the sequence of SEQ ID NO: 77, aMTD263 has the sequence of SEQ ID NO: 62, aMTD225 has the sequence of SEQ ID NO: 55, aMTD661 has the sequence of SEQ ID NO: 147, aMTD686 has the sequence of SEQ ID NO: 155, aMTD602 has the sequence of SEQ ID NO: 138, aMTD485 has the sequence of SEQ ID NO: 114, aMTD483 has the sequence of SEQ ID NO: 112, aMTD22 has the sequence of SEQ ID NO: 10, aMTD42 has the sequence of SEQ ID NO: 14, aMTD84 has the sequence of SEQ ID NO: 25, aMTD401 has the sequence of SEQ ID NO: 92, aMTD444 has the sequence of SEQ ID NO: 103, aMTD464 has the sequence of SEQ ID NO: 108, aMTD501 has the sequence of SEQ ID NO: 115, aMTD503 has the sequence of SEQ ID NO: 117, aMTD605 has the sequence of SEQ ID NO: 141, aMTD622 has the sequence of SEQ ID NO: 142, aMTD144 has the sequence of SEQ ID NO: 37, aMTD484 has the sequence of SEQ ID NO: 113, aMTD665 has the sequence of SEQ ID NO: 149, aMTD806 has the sequence of SEQ ID NO: 181, aMTD875 has the sequence of SEQ ID NO: 213, aMTD877 has the sequence of SEQ ID NO: 214, aMTD887 has the sequence of SEQ ID NO: 221, aMTD893 has the sequence of SEQ ID NO: 225, aMTD912 has the sequence of SEQ ID NO: 240, aMTD185 has the sequence of SEQ ID NO: 47, aMTD164 has the sequence of SEQ ID NO: 42, aMTD184 has the sequence of SEQ ID NO: 46, aMTD899 has the sequence of SEQ ID NO: 229, aMTD904 has the sequence of SEQ ID NO: 233, aMTD101 has the sequence of SEQ ID NO: 27, aMTD223 has the sequence of SEQ ID NO: 53, aMTD224 has the sequence of SEQ ID NO: 54, aMTD345 has the sequence of SEQ ID NO: 82, aMTD481 has the sequence of SEQ ID NO: 110, aMTD900 has the sequence of SEQ ID NO: 230, aMTD905 has the sequence of SEQ ID NO: 234, aMTD906 has the sequence of SEQ ID NO: 235, aMTD908 has the sequence of SEQ ID NO: 237, aMTD910 has the sequence of SEQ ID NO: 238, aMTD911 has the sequence of SEQ ID NO: 239, aMTD828 has the sequence of SEQ ID NO: 191, aMTD829 has the sequence of SEQ ID NO: 192, aMTD852 has the sequence of SEQ ID NO: 205, aMTD882 has the sequence of SEQ ID NO: 218, aMTD885 has the sequence of SEQ ID NO: 220, aMTD888 has the sequence of SEQ ID NO: 222, aMTD889 has the sequence of SEQ ID NO: 223, aMTD891 has the sequence of SEQ ID NO: 224, aMTD727 has the sequence of SEQ ID NO: 164, aMTD786 has the sequence of SEQ ID NO: 176, aMTD787 has the sequence of SEQ ID NO:177, aMTD803 has the sequence of SEQ ID NO: 179, aMTD805 has the sequence of SEQ ID NO: 180, aMTD810 has the sequence of SEQ ID NO: 185, aMTD811 has the sequence of SEQ ID NO:186, aMTD824 has the sequence of SEQ ID NO: 187, aMTD604 has the sequence of SEQ ID NO: 140, aMTD684 has the sequence of SEQ ID NO: 153, aMTD685 has the sequence of SEQ ID NO: 154, aMTD683 has the sequence of SEQ ID NO: 152, aMTD687 has the sequence of SEQ ID NO: 156, aMTD765 has the sequence of SEQ ID NO: 171, aMTD767 has the sequence of SEQ ID NO: 173, aMTD706 has the sequence of SEQ ID NO: 159, aMTD865 has the sequence of SEQ ID NO: 208, aMTD465 has the sequence of SEQ ID NO: 109, aMTD162 has the sequence of SEQ ID NO: 40, aMTD705 has the sequence of SEQ ID NO: 158, aMTD707 has the sequence of SEQ ID NO: 160, aMTD725 has the sequence of SEQ ID NO: 162, aMTD743 has the sequence of SEQ ID NO: 165, aMTD744 has the sequence of SEQ ID NO: 166.

In FIG. 4b, aMTD623 has the sequence of SEQ ID NO: 143, aMTD764 has the sequence of SEQ ID NO: 170, aMTD783 has the sequence of SEQ ID NO: 174, aMTD784 has the sequence of SEQ ID NO: 175, aMTD788 has the sequence of SEQ ID NO:178, aMTD808 has the sequence of SEQ ID NO: 183, aMTD848 has the sequence of SEQ ID NO: 201, aMTD850 has the sequence of SEQ ID NO: 203, aMTD826 has the sequence of SEQ ID NO: 189, aMTD827 has the sequence of SEQ ID NO: 190, aMTD502 has the sequence of SEQ ID NO: 116, aMTD643 has the sequence of SEQ ID NO: 145, aMTD807 has the sequence of SEQ ID NO: 182, aMTD844 has the sequence of SEQ ID NO: 197, aMTD851 has the sequence of SEQ ID NO: 204, aMTD870 has the sequence of SEQ ID NO: 211, aMTD872 has the sequence of SEQ ID NO: 212, aMTD878 has the sequence of SEQ ID NO: 215, aMTD879 has the sequence of SEQ ID NO: 216, aMTD902 has the sequence of SEQ ID NO: 232, aMTD907 has the sequence of SEQ ID NO: 236, aMTD504 has the sequence of SEQ ID NO: 118, aMTD565 has the sequence of SEQ ID NO: 133, aMTD746 has the sequence of SEQ ID NO: 167, aMTD766 has the sequence of SEQ ID NO: 172, aMTD825 has the sequence of SEQ ID NO: 188, aMTD847 has the sequence of SEQ ID NO: 200, aMTD895 has the sequence of SEQ ID NO: 226, aMTD896 has the sequence of SEQ ID NO: 227, aMTD541 has the sequence of SEQ ID NO: 124, aMTD342 has the sequence of SEQ ID NO: 80, aMTD747 has the sequence of SEQ ID NO: 168, rP19 has the sequence of SEQ ID NO: 942, rP20 has the sequence of SEQ ID NO: 946, rP27 has the sequence of SEQ ID NO: 885, rP29 has the sequence of SEQ ID NO: 924, rP37 has the sequence of SEQ ID NO: 889, rP152 has the sequence of SEQ ID NO: 884, rP169 has the sequence of SEQ ID NO: 923, rP69 has the sequence of SEQ ID NO: 908, rP68 has the sequence of SEQ ID NO: 913, rP40 has the sequence of SEQ ID NO: 948, rP49 has the sequence of SEQ ID NO: 918, rP54 has the sequence of SEQ ID NO: 939, rP226 has the sequence of SEQ ID NO: 892, rP6 has the sequence of SEQ ID NO: 893, rP131 has the sequence of SEQ ID NO: 928, rP30 has the sequence of SEQ ID NO: 926, rP167 has the sequence of SEQ ID NO: 898, rP329 has the sequence of SEQ ID NO: 917, rP466 has the sequence of SEQ ID NO: 897, rP527 has the sequence of SEQ ID NO: 896, rP606 has the sequence of SEQ ID NO: 901, rP750 has the sequence of SEQ ID NO: 894, rP246 has the sequence of SEQ ID NO: 899, rP248 has the sequence of SEQ ID NO: 903, rP59 has the sequence of SEQ ID NO: 938, rP390 has the sequence of SEQ ID NO: 909, rP426 has the sequence of SEQ ID NO: 900, rP66 has the sequence of SEQ ID NO: 902, rP227 has the sequence of SEQ ID NO: 904, rP349 has the sequence of SEQ ID NO: 914, rP33 has the sequence of SEQ ID NO: 927, rP436 has the sequence of SEQ ID NO: 932, rP77 has the sequence of SEQ ID NO: 934, rP935 has the sequence of SEQ ID NO: 886, rP57 has the sequence of SEQ ID NO: 949, rP577 has the sequence of SEQ ID NO: 935, rP921 has the sequence of SEQ ID NO: 931, rP922 has the sequence of SEQ ID NO: 929, rP26 has the sequence of SEQ ID NO: 895, rP39 has the sequence of SEQ ID NO: 941, rP97 has the sequence of SEQ ID NO: 936, rP139 has the sequence of SEQ ID NO: 944, rP67 has the sequence of SEQ ID NO: 906, rP113 has the sequence of SEQ ID NO: 891, rP190 has the sequence of SEQ ID NO: 925, rP210 has the sequence of SEQ ID NO: 920, rP214 has the sequence of SEQ ID NO: 937, rP635 has the sequence of SEQ ID NO: 947, rP692 has the sequence of SEQ ID NO: 907, rP693 has the sequence of SEQ ID NO: 922, rP772 has the sequence of SEQ ID NO: 919, rP934 has the sequence of SEQ ID NO: 888, rP936 has the sequence of SEQ ID NO: 883, rP937 has the sequence of SEQ ID NO: 915, rP938 has the sequence of SEQ ID NO: 916, rP350 has the sequence of SEQ ID NO: 910, rP331 has the sequence of SEQ ID NO: 911, rP947 has the sequence of SEQ ID NO: 943, rP16 has the sequence of SEQ ID NO: 890, rP17 has the sequence of SEQ ID NO: 905, rP18 has the sequence of SEQ ID NO: 945, rP28 has the sequence of SEQ ID NO: 921, rP159 has the sequence of SEQ ID NO: 950, rP700 has the sequence of SEQ ID NO: 951, rP71 has the sequence of SEQ ID NO: 930.

FIGS. 5a to 5u show Determination of aMTD-Mediated Cell-Permeability. Cell-permeability of a negative control (A: rP38 (SEQ ID NO: 952)) and reference hydrophobic CPPs (MTM12 (SEQ ID NO: 953) and MTD85 (SEQ ID NO: 954)) are shown. The cell-permeability of each aMTD and/or rPeptide is visually compared to that of the cargo protein lacking peptide sequence (HCA). Gray shaded area represents untreated RAW 264.7 cells (vehicle); thin light gray line represents the cells treated with equal molar concentration of FITC (FITC only); dark thick line indicates the cells treated with FITC-his-tagged CRA protein (HCA); and the cells treated with the FITC-proteins (HMCA) fused to negative control (rP38 (SEQ ID NO: 952)), reference CPP (MTM12 (SEQ ID NO: 953) or MTD85 (SEQ ID NO: 954)) or new hydrophobic CPP (aMTD) are shown with light thick line and indicated by arrows.

In FIG. 5a, rP38 has the sequence of SEQ ID NO: 952; MTM12 has the sequence of SEQ ID NO: 953, MTD85 has the sequence of SEQ ID NO: 954, aMTD285 has the sequence of SEQ ID NO: 69, aMTD361 has the sequence of SEQ ID NO: 83, aMTD301 has the sequence of SEQ ID NO: 70, aMTD305 has the sequence of SEQ ID NO: 73, aMTD343 has the sequence of SEQ ID NO: 81, and aMTD243 has the sequence of SEQ ID NO: 58. In FIG. 5b, aMTD282 has the sequence of SEQ ID NO: 66, aMTD245 has the sequence of SEQ ID NO: 59, aMTD302 has the sequence of SEQ ID NO: 71, aMTD264 has the sequence of SEQ ID NO: 63, aMTD341 has the sequence of SEQ ID NO: 79, aMTD645 has the sequence of SEQ ID NO: 146, aMTD201 has the sequence of SEQ ID NO: 48, aMTD13 has the sequence of SEQ ID NO: 8, aMTD522 has the sequence of SEQ ID NO: 121, aMTD24 has the sequence of SEQ ID NO: 59, aMTD283 has the sequence of SEQ ID NO: 67, and aMTD262 has the sequence of SEQ ID NO: 301, In FIG. 5c, aMTD304 has the sequence of SEQ ID NO: 72, aMTD265 has the sequence of SEQ ID NO: 64, aMTD123 has the sequence of SEQ ID NO: 33, aMTD183 has the sequence of SEQ ID NO: 45, aMTD143 has the sequence of SEQ ID NO: 36, aMTD900 has the sequence of SEQ ID NO: 230, aMTD807 has the sequence of SEQ ID NO: 182, aMTD381 has the sequence of SEQ ID NO: 87, aMTD601 has the sequence of SEQ ID NO: 137, aMTD603 has the sequence of SEQ ID NO: 139, aMTD383 has the sequence of SEQ ID NO: 89, and aMTD261 has the sequence of SEQ ID NO: 60, In FIG. 5d, aMTD807 has the sequence of SEQ ID NO: 182, aMTD381 has the sequence of SEQ ID NO: 87, aMTD601 has the sequence of SEQ ID NO: 137, aMTD603 has the sequence of SEQ ID NO: 139, aMTD383 has the sequence of SEQ ID NO: 89, aMTD261 has the sequence of SEQ ID NO: 60, aMTD364 has the sequence of SEQ ID NO:

85, aMTD564 has the sequence of SEQ ID NO: 132, aMTD384 has the sequence of SEQ ID NO: 90, aMTD625 has the sequence of SEQ ID NO: 144, aMTD543 has the sequence of SEQ ID NO: 126, and aMTD545 has the sequence of SEQ ID NO: 128. In FIG. 5e, aMTD363 has the sequence of SEQ ID NO: 84, aMTD342 has the sequence of SEQ ID NO: 80, aMTD382 has the sequence of SEQ ID NO: 88, aMTD443 has the sequence of SEQ ID NO: 102, aMTD829 has the sequence of SEQ ID NO: 192, aMTD421 has the sequence of SEQ ID NO: 97, aMTD241 has the sequence of SEQ ID NO: 56, aMTD284 has the sequence of SEQ ID NO: 68, aMTD525 has the sequence of SEQ ID NO: 123, aMTD442 has the sequence of SEQ ID NO: 101, aMTD422 has the sequence of SEQ ID NO: 98, aMTD424 has the sequence of SEQ ID NO: 99. In FIG. 5f, aMTD405 has the sequence of SEQ ID NO: 96, aMTD323 has the sequence of SEQ ID NO: 76, aMTD84 has the sequence of SEQ ID NO: 25, aMTD62 has the sequence of SEQ ID NO: 18, aMTD63 has the sequence of SEQ ID NO: 19, aMTD25 has the sequence of SEQ ID NO: 13, aMTD889 has the sequence of SEQ ID NO: 223, aMTD504 has the sequence of SEQ ID NO: 118, aMTD103 has the sequence of SEQ ID NO: 29, aMTD23 has the sequence of SEQ ID NO: 11, aMTD82 has the sequence of SEQ ID NO: 23, aMTD105 has the sequence of SEQ ID NO: 31. In FIG. 5g, aMTD462 has the sequence of SEQ ID NO: 106, aMTD461 has the sequence of SEQ ID NO: 105, aMTD1 has the sequence of SEQ ID NO: 1, aMTD2 has the sequence of SEQ ID NO: 2, aMTD61 has the sequence of SEQ ID NO: 17, aMTD124 has the sequence of SEQ ID NO: 34, aMTD165 has the sequence of SEQ ID NO: 43, aMTD404 has the sequence of SEQ ID NO: 95, aMTD182 has the sequence of SEQ ID NO: 44, aMTD3 has the sequence of SEQ ID NO: 3, aMTD204 has the sequence of SEQ ID NO: 49, aMTD141 has the sequence of SEQ ID NO: 35. In FIG. 5h, aMTD524 has the sequence of SEQ ID NO: 122, aMTD22 has the sequence of SEQ ID NO: 10, aMTD65 has the sequence of SEQ ID NO: 21, aMTD83 has the sequence of SEQ ID NO: 24, aMTD4 has the sequence of SEQ ID NO:4, aMTD5 has the sequence of SEQ ID NO: 5, aMTD81 has the sequence of SEQ ID NO: 22, aMTD44 has the sequence of SEQ ID NO: 16, aMTD145 has the sequence of SEQ ID NO: 38, aMTD43 has the sequence of SEQ ID NO: 15, aMTD104 has the sequence of SEQ ID NO: 30, aMTD221 has the sequence of SEQ ID NO: 51. In FIG. 5i, aMTD222 has the sequence of SEQ ID NO: 52, aMTD242 has the sequence of SEQ ID NO: 57, aMTD827 has the sequence of SEQ ID NO: 190, aMTD501 has the sequence of SEQ ID NO: 115, aMTD726 has the sequence of SEQ ID NO: 163, aMTD706 has the sequence of SEQ ID NO: 159, aMTD602 has the sequence of SEQ ID NO: 138, aMTD281 has the sequence of SEQ ID NO: 65, aMTD683 has the sequence of SEQ ID NO: 152, aMTD893 has the sequence of SEQ ID NO: 225, aMTD879 has the sequence of SEQ ID NO: 216, aMTD746 has the sequence of SEQ ID NO: 167. In FIG. 5j, aMTD864 has the sequence of SEQ ID NO: 207, aMTD865 has the sequence of SEQ ID NO: 208, aMTD604 has the sequence of SEQ ID NO: 140, aMTD765 has the sequence of SEQ ID NO: 171, aMTD163 has the sequence of SEQ ID NO: 41, aMTD684 has the sequence of SEQ ID NO: 153, aMTD783 has the sequence of SEQ ID NO: 174, aMTD846 has the sequence of SEQ ID NO: 199, aMTD483 has the sequence of SEQ ID NO: 112, aMTD685 has the sequence of SEQ ID NO: 154, aMTD585 has the sequence of SEQ ID NO: 136, aMTD687 has the sequence of SEQ ID NO: 156. In FIG. 5k, aMTD541 has the sequence of SEQ ID NO: 124, aMTD485 has the sequence of SEQ ID NO: 114, aMTD784 has the sequence of SEQ ID NO: 175, aMTD184 has the sequence of SEQ ID NO: 46, aMTD764 has the sequence of SEQ ID NO: 170, aMTD808 has the sequence of SEQ ID NO: 183, aMTD544 has the sequence of SEQ ID NO: 127, aMTD224 has the sequence of SEQ ID NO: 54, aMTD848 has the sequence of SEQ ID NO: 201, aMTD766 has the sequence of SEQ ID NO: 172, aMTD164 has the sequence of SEQ ID NO: 42, aMTD565 has the sequence of SEQ ID NO: 133. In FIG. 5l, aMTD847 has the sequence of SEQ ID NO: 200, aMTD850 has the sequence of SEQ ID NO: 203, aMTD225 has the sequence of SEQ ID NO: 55, aMTD686 has the sequence of SEQ ID NO: 155, aMTD64 has the sequence of SEQ ID NO: 20, aMTD325 has the sequence of SEQ ID NO: 78, aMTD263 has the sequence of SEQ ID NO: 62, aMTD667 has the sequence of SEQ ID NO: 151, aMTD324 has the sequence of SEQ ID NO: 77, aMTD464 has the sequence of SEQ ID NO: 108, aMTD482 has the sequence of SEQ ID NO: 111, aMTD425 has the sequence of SEQ ID NO: 100. In FIG. 5m, aMTD503 has the sequence of SEQ ID NO: 117, aMTD505 has the sequence of SEQ ID NO: 119, aMTD883 has the sequence of SEQ ID NO: 219, aMTD830 has the sequence of SEQ ID NO: 193, aMTD867 has the sequence of SEQ ID NO: 209, aMTD809 has the sequence of SEQ ID NO: 184, aMTD843 has the sequence of SEQ ID NO: 196, aMTD622 has the sequence of SEQ ID NO: 142, aMTD162 has the sequence of SEQ ID NO: 40, aMTD747 has the sequence of SEQ ID NO: 168, aMTD743 has the sequence of SEQ ID NO: 165, aMTD705 has the sequence of SEQ ID NO: 158. In FIG. 5n, aMTD725 has the sequence of SEQ ID NO: 162, aMTD832 has the sequence of SEQ ID NO: 195, aMTD852 has the sequence of SEQ ID NO: 205, aMTD810 has the sequence of SEQ ID NO: 185, aMTD888 has the sequence of SEQ ID NO: 222, aMTD908 has the sequence of SEQ ID NO: 237, aMTD885 has the sequence of SEQ ID NO: 220, aMTD868 has the sequence of SEQ ID NO: 210, aMTD786 has the sequence of SEQ ID NO: 176, aMTD803 has the sequence of SEQ ID NO: 179, aMTD787 has the sequence of SEQ ID NO: 177, aMTD904 has the sequence of SEQ ID NO: 233. In FIG. 5o, aMTD882 has the sequence of SEQ ID NO: 218, aMTD910 has the sequence of SEQ ID NO: 238, aMTD899 has the sequence of SEQ ID NO: 229, aMTD891 has the sequence of SEQ ID NO: 224, aMTD727 has the sequence of SEQ ID NO: 164, aMTD805 has the sequence of SEQ ID NO: 180, aMTD896 has the sequence of SEQ ID NO: 227, aMTD828 has the sequence of SEQ ID NO: 191, aMTD811 has the sequence of SEQ ID NO: 186, aMTD805 has the sequence of SEQ ID NO: 180, aMTD806 has the sequence of SEQ ID NO: 181, aMTD905 has the sequence of SEQ ID NO: 234. In FIG. 5p, aMTD851 has the sequence of SEQ ID NO: 204, aMTD881 has the sequence of SEQ ID NO: 217, aMTD875 has the sequence of SEQ ID NO: 213, aMTD703 has the sequence of SEQ ID NO: 157, aMTD887 has the sequence of SEQ ID NO: 221, aMTD831 has the sequence of SEQ ID NO: 194, aMTD11 has the sequence of SEQ ID NO: 6, aMTD912 has the sequence of SEQ ID NO: 240, aMTD897 has the sequence of SEQ ID NO: 228, aMTD877 has the sequence of SEQ ID NO: 214, aMTD724 has the sequence of SEQ ID NO: 161, aMTD845 has the sequence of SEQ ID NO: 198. In FIG. 5q, aMTD666 has the sequence of SEQ ID NO: 150, aMTD605 has the sequence of SEQ ID NO: 141, aMTD401 has the sequence of SEQ ID NO: 92, aMTD444 has the sequence of SEQ ID NO: 103, aMTD826 has the sequence of SEQ ID NO: 189, aMTD907 has the sequence of SEQ ID NO: 236, aMTD902 has the sequence of SEQ ID NO: 232, aMTD664 has the sequence of SEQ ID NO: 148, aMTD870 has the sequence of SEQ ID NO: 211, aMTD345 has the sequence of SEQ ID NO: 82, aMTD502 has the sequence of SEQ ID NO: 116, aMTD878 has the sequence of SEQ ID NO: 215. In FIG. 5r, aMTD643 has the sequence of SEQ ID NO: 145, aMTD365 has the sequence of SEQ ID NO: 86, aMTD521 has the sequence of SEQ ID NO: 120, aMTD385 has the sequence of SEQ ID NO: 91, aMTD542 has the sequence of SEQ ID NO: 125, aMTD562 has the sequence of SEQ ID NO: 130, aMTD563 has the sequence of SEQ ID NO: 131, aMTD465 has the sequence of SEQ ID NO: 109, aMTD402 has the sequence of SEQ ID NO: 93, aMTD445 has the sequence of SEQ ID NO: 104, aMTD582 has the sequence of SEQ ID NO: 134, aMTD463 has the sequence of SEQ ID NO: 107. In FIG. 5s, aMTD322 has the sequence of SEQ ID NO: 75, aMTD102 has the sequence of SEQ ID NO: 28, aMTD21 has the sequence of SEQ ID NO: 9, aMTD12 has the sequence of SEQ ID NO: 7, aMTD101 has the sequence of SEQ ID NO: 27, aMTD665 has the sequence of SEQ ID NO: 149, aMTD403 has the sequence of SEQ ID NO: 94, aMTD121 has the sequence of SEQ ID NO: 32, aMTD42 has the sequence of SEQ ID NO: 14, aMTD85 has the sequence of SEQ ID NO: 26, aMTD205 has the sequence of SEQ ID NO: 50, aMTD844 has the sequence of SEQ ID NO: 197. In FIG. 5t, aMTD321 has the sequence of SEQ ID NO: 74, aMTD849 has the sequence of SEQ ID NO: 202, aMTD661 has the sequence of SEQ ID NO: 147, aMTD872 has the sequence of SEQ ID NO: 212, aMTD767 has the sequence of SEQ ID NO: 173, aMTD763 has the sequence of SEQ ID NO: 169, aMTD583 has the sequence of SEQ ID NO: 135, aMTD623 has the sequence of SEQ ID NO: 143, aMTD144 has the sequence of SEQ ID NO: 37, aMTD101 has the sequence of SEQ ID NO: 27, aMTD788 has the sequence of SEQ ID NO: 178, aMTD561 has the sequence of SEQ ID NO: 129. In FIG. 5u, aMTD185 has the sequence of SEQ ID NO: 47, aMTD901 has the sequence of SEQ ID NO: 231, aMTD223 has the sequence of SEQ ID NO: 53, aMTD707 has the sequence of SEQ ID NO: 160, aMTD484 has the sequence of SEQ ID NO: 113, aMTD863 has the sequence of SEQ ID NO: 206, aMTD911 has the sequence of SEQ ID NO: 239, aMTD824 has the sequence of SEQ ID NO: 187, aMTD481 has the sequence of SEQ ID NO: 110, aMTD825 has the sequence of SEQ ID NO: 188, aMTD744 has the sequence of SEQ ID NO: 166, aMTD906 has the sequence of SEQ ID NO: 235.

FIGS. 6a to 6c show Determination of rPeptide-Mediated Cell-Permeability. The cell-permeability of each aMTD and/or rPeptide was visually compared to that of the cargo protein lacking peptide sequence (HCA). Gray shaded area represents untreated RAW 264.7 cells (vehicle); thin light gray line represents the cells treated with equal molar concentration of FITC (FITC only); dark thick line indicates the cells treated with FITC-his-tagged CRA protein (HCA); and the cells treated with the FITC-proteins fused to rPeptides are shown with light thick line and indicated by arrows.

In FIG. 6a, rP26 has the sequence of SEQ ID NO: 895, rP39 has the sequence of SEQ ID NO: 941, rP426 has the sequence of SEQ ID NO: 900, rP139 has the sequence of SEQ ID NO: 944, rP606 has the sequence of SEQ ID NO: 901, rP635 has the sequence of SEQ ID NO: 947. In FIG. 6b, rP97 has the sequence of SEQ ID NO: 936, rP66 has the sequence of SEQ ID NO: 902, rP921 has the sequence of SEQ ID NO: 931, rP772 has the sequence of SEQ ID NO: 919, rP693 has the sequence of SEQ ID NO: 922, rP113 has the sequence of SEQ ID NO: 891, rP167 has the sequence of SEQ ID NO: 898, rP700 has the sequence of SEQ ID NO: 951, rP49 has the sequence of SEQ ID NO: 918, rP390 has the sequence of SEQ-ID NO: 909, rP934 has the sequence of SEQ ID NO: 888, rP692 has the sequence of SEQ ID NO: 907. In FIG. 6c, rP57 has the sequence of SEQ ID NO: 949, rP67 has the sequence of SEQ ID NO: 906, rP329 has the sequence of SEQ ID NO: 917, rP17 has the sequence of SEQ ID NO: 905, rP68 has the sequence of SEQ ID NO: 913, rP938 has the sequence of SEQ ID NO: 916, rP16 has the sequence of SEQ ID NO: 890, rP18 has the sequence of SEQ ID NO: 945, rP29 has the sequence of SEQ ID NO: 924, rP466 has the sequence of SEQ ID NO: 897, rP227 has the sequence of SEQ ID NO: 904, rP214 has the sequence of SEQ ID NO: 937.

FIGS. 7a to 7k shows Visualized Cell-Permeability of aMTD-Fused Recombinant Proteins. NIH3T3 cells were treated with FITC-labeled protein (10 μM) fused to aMTD for 1 hour at 37. Cell-permeability of the proteins was visualized by laser scanning confocal microscopy (LSM700 version).

In FIG. 7a, rP38 has the sequence of SEQ ID NO: 952, MTM12 has the sequence of SEQ ID NO: 953, MTD85 has the sequence of SEQ ID NO: 954, aMTD1 has the sequence of SEQ ID NO: 1, aMTD2 has the sequence of SEQ ID NO: 2, aMTD3 has the sequence of SEQ ID NO: 3, aMTD4 has the sequence of SEQ ID NO:4, aMTD5 has the sequence of SEQ ID NO: 5, aMTD11 has the sequence of SEQ ID NO: 6, aMTD13 has the sequence of SEQ ID NO: 8, aMTD21 has the sequence of SEQ ID NO: 9, aMTD22 has the sequence of SEQ ID NO: 10, aMTD23 has the sequence of SEQ ID NO: 11, aMTD24 has the sequence of SEQ ID NO: 12, aMTD25 has the sequence of SEQ ID NO: 13, aMTD43 has the sequence of SEQ ID NO: 15, aMTD44 has the sequence of SEQ ID NO: 16, aMTD61 has the sequence of SEQ ID NO: 17, aMTD63 has the sequence of SEQ ID NO: 19, aMTD64 has the sequence of SEQ ID NO: 20, aMTD65 has the sequence of SEQ ID NO: 21. In FIG. 7b, aMTD82 has the sequence of SEQ ID NO: 23, aMTD83 has the sequence of SEQ ID NO: 24, aMTD84 has the sequence of SEQ ID NO: 25, aMTD85 has the sequence of SEQ ID NO: 26, aMTD101 has the sequence of SEQ ID NO: 27, aMTD102 has the sequence of SEQ ID NO: 28, aMTD105 has the sequence of SEQ ID NO: 31, aMTD872 has the sequence of SEQ ID NO: 212, aMTD121 has the sequence of SEQ ID NO: 32, aMTD123 has the sequence of SEQ ID NO: 33, aMTD124 has the sequence of SEQ ID NO: 34, aMTD141 has the sequence of SEQ ID NO: 35, aMTD143 has the sequence of SEQ ID NO: 36, aMTD144 has the sequence of SEQ ID NO: 37, aMTD145 has the sequence of SEQ ID NO: 38, aMTD906 has the sequence of SEQ ID NO: 235, aMTD161 has the sequence of SEQ ID NO: 39, aMTD164 has the sequence of SEQ ID NO: 42, aMTD182 has the sequence of SEQ ID NO: 44, aMTD183 has the sequence of SEQ ID NO: 45, aMTD184 has the sequence of SEQ ID NO: 46, aMTD185 has the sequence of SEQ ID NO: 47, aMTD 201 has the sequence of SEQ ID NO: 48, aMTD204 has the sequence of SEQ ID NO: 49. In FIG. 7c, aMTD221 has the sequence of SEQ ID NO: 51, aMTD222 has the sequence of SEQ ID NO: 52, aMTD223 has the sequence of SEQ ID NO: 53, aMTD224 has the sequence of SEQ ID NO: 54, aMTD882 has the sequence of SEQ ID NO: 218, aMTD908 has the sequence of SEQ ID NO: 237, aMTD242 has the sequence of SEQ ID NO: 57, aMTD243 has the sequence of SEQ ID NO: 58, aMTD245 has the sequence of SEQ ID NO: 59, aMTD261 has the sequence of SEQ ID NO: 60, aMTD262 has the sequence of SEQ ID NO: 61, aMTD263 has the sequence of SEQ ID NO: 62, aMTD265 has the sequence of SEQ JD NO: 64, aMTD281 has the sequence of SEQ ID NO: 65, aMTD282 has the sequence of SEQ ID NO: 66, aMTD302 has the sequence of SEQ ID NO: 71, aMTD284 has the sequence of SEQ ID NO:

68, aMTD285 has the sequence of SEQ ID NO: 69, aMTD881 has the sequence of SEQ ID NO: 217, aMTD325 has the sequence of SEQ ID NO: 78, aMTD304 has the sequence of SEQ ID NO: 72, aMTD305 has the sequence of SEQ ID NO: 73, aMTD321 has the sequence of SEQ ID NO: 74, aMTD322 has the sequence of SEQ ID NO: 75. In FIG. 7d, aMTD879 has the sequence of SEQ ID NO: 216, aMTD893 has the sequence of SEQ ID NO: 225, aMTD341 has the sequence of SEQ ID NO: 79, aMTD342 has the sequence of SEQ ID NO: 80, aMTD343 has the sequence of SEQ ID NO: 81, aMTD345 has the sequence of SEQ ID NO: 82, aMTD363 has the sequence of SEQ ID NO: 84, aMTD364 has the sequence of SEQ ID NO: 85, aMTD365 has the sequence of SEQ ID NO: 86, aMTD381 has the sequence of SEQ ID NO: 87, aMTD382 has the sequence of SEQ ID NO: 88, aMTD383 has the sequence of SEQ ID NO: 89, aMTD385 has the sequence of SEQ ID NO: 91, aMTD401 has the sequence of SEQ ID NO: 92, aMTD402 has the sequence of SEQ ID NO: 93, aMTD403 has the sequence of SEQ ID NO: 94, aMTD404 has the sequence of SEQ ID NO: 95, aMTD405 has the sequence of SEQ ID NO: 96, aMTD422 has the sequence of SEQ ID NO: 98, aMTD424 has the sequence of SEQ ID NO: 99, aMTD425 has the sequence of SEQ ID NO: 100, aMTD910 has the sequence of SEQ ID NO: 238, aMTD442 has the sequence of SEQ ID NO: 101, aMTD443 has the sequence of SEQ ID NO: 102. In FIG. 7e, aMTD461 has the sequence of SEQ ID NO: 105, aMTD462 has the sequence of SEQ ID NO: 106, aMTD463 has the sequence of SEQ ID NO: 107, aMTD464 has the sequence of SEQ ID NO: 108, aMTD465 has the sequence of SEQ ID NO: 109, aMTD481 has the sequence of SEQ ID NO: 110, aMTD483 has the sequence of SEQ ID NO: 112, aMTD501 has the sequence of SEQ ID NO: 115, aMTD503 has the sequence of SEQ ID NO: 117, aMTD504 has the sequence of SEQ ID NO: 118, aMTD505 has the sequence of SEQ ID NO: 119, aMTD521 has the sequence of SEQ ID NO: 120, aMTD524 has the sequence of SEQ ID NO: 122, aMTD525 has the sequence of SEQ ID NO: 123, aMTD541 has the sequence of SEQ ID NO: 124, aMTD542 has the sequence of SEQ ID NO: 125, aMTD543 has the sequence of SEQ ID NO: 126, aMTD544 has the sequence of SEQ ID NO: 127, aMTD561 has the sequence of SEQ ID NO: 129, aMTD562 has the sequence of SEQ ID NO: 130, aMTD563 has the sequence of SEQ ID NO: 131, aMTD564 has the sequence of SEQ ID NO: 132, aMTD565 has the sequence of SEQ ID NO: 133, aMTD582 has the sequence of SEQ ID NO: 134. In FIG. 7f, aMTD585 has the sequence of SEQ ID NO: 136, aMTD601 has the sequence of SEQ ID NO: 137, aMTD603 has the sequence of SEQ ID NO: 139, aMTD605 has the sequence of SEQ ID NO: 141, aMTD622 has the sequence of SEQ ID NO: 142, aMTD623 has the sequence of SEQ ID NO: 143, aMTD645 has the sequence of SEQ ID NO: 146, aMTD661 has the sequence of SEQ ID NO: 147, aMTD664 has the sequence of SEQ ID NO: 148, aMTD666 has the sequence of SEQ ID NO: 150, aMTD667 has the sequence of SEQ ID NO: 151, aMTD684 has the sequence of SEQ ID NO: 153, aMTD746 has the sequence of SEQ ID NO: 167, aMTD763 has the sequence of SEQ ID NO: 169, aMTD764 has the sequence of SEQ ID NO: 170, aMTD766 has the sequence of SEQ ID NO: 172, aMTD783 has the sequence of SEQ ID NO: 174, aMTD784 has the sequence of SEQ ID NO: 175, aMTD808 has the sequence of SEQ ID NO: 183, aMTD846 has the sequence of SEQ ID NO: 199, aMTD847 has the sequence of SEQ ID NO: 200, aMTD848 has the sequence of SEQ ID NO: 201, aMTD849 has the sequence of SEQ ID NO: 202, aMTD850 has the sequence of SEQ ID NO: 203. In FIG. 7g, aMTD865 has the sequence. of SEQ ID NO: 208, aMTD727 has the sequence of SEQ ID NO: 164, aMTD887 has the sequence of SEQ ID NO: 221, aMTD787 has the sequence of SEQ ID NO: 177, aMTD803 has the sequence of SEQ ID NO: 179, aMTD805 has the sequence of SEQ ID NO: 180, aMTD824 has the sequence of SEQ ID NO: 187, aMTD825 has the sequence of SEQ ID NO: 188, aMTD826 has the sequence of SEQ ID NO: 189, aMTD827 has the sequence of SEQ ID NO: 190, aMTD829 has the sequence of SEQ ID NO: 192, aMTD885 has the sequence of SEQ ID NO: 220, aMTD901 has the sequence of SEQ ID NO: 231, aMTD912 has the sequence of SEQ ID NO: 240, aMTD891 has the sequence of SEQ ID NO: 224, aMTD895 has the sequence of SEQ ID NO: 226, aMTD896 has the sequence of SEQ ID NO: 227, aMTD900 has the sequence of SEQ ID NO: 230, aMTD899 has the sequence of SEQ ID NO: 229, aMTD162 has the sequence of SEQ ID NO: 40, aMTD686 has the sequence of SEQ ID NO: 155, aMTD225 has the sequence of SEQ ID NO: 55, aMTD899 has the sequence of SEQ ID NO: 229, aMTD897 has the sequence of SEQ ID NO: 228. In FIG. 7h, aMTD705 has the sequence of SEQ ID NO: 158, aMTD707 has the sequence of SEQ ID NO: 160, aMTD725 has the sequence of SEQ ID NO: 162, aMTD743 has the sequence of SEQ ID NO: 165, aMTD744 has the sequence of SEQ ID NO: 166, aMTD747 has the sequence of SEQ ID NO: 168, aMTD830 has the sequence of SEQ ID NO: 193, aMTD832 has the sequence of SEQ ID NO: 195, aMTD843 has the sequence of SEQ ID NO: 196, aMTD863 has the sequence of SEQ ID NO: 206, aMTD867 has the sequence of SEQ ID NO: 209, aMTD868 has the sequence of SEQ ID NO: 210, aMTD703 has the sequence of SEQ ID NO: 157, aMTD724 has the sequence of SEQ ID NO: 161, aMTD726 has the sequence of SEQ ID NO: 163, aMTD786 has the sequence of SEQ ID NO: 176, aMTD806 has the sequence of SEQ ID NO: 181, aMTD810 has the sequence of SEQ ID NO: 185, aMTD845 has the sequence of SEQ ID NO: 198, aMTD852 has the sequence of SEQ ID NO: 205, aMTD875 has the sequence of SEQ ID NO: 213, aMTD877 has the sequence of SEQ ID NO: 214, aMTD902 has the sequence of SEQ ID NO: 232, aMTD907 has the sequence of SEQ ID NO: 236. In FIG. 7i, aMTD62 has the sequence of SEQ ID NO: 18, aMTD103 has the sequence of SEQ ID NO: 29, aMTD163 has the sequence of SEQ ID NO: 41, aMTD283 has the sequence of SEQ ID NO: 67, aMTD444 has the sequence of SEQ ID NO: 103, aMTD484 has the sequence of SEQ ID NO: 113, aMTD502 has the sequence of SEQ ID NO: 116, aMTD602 has the sequence of SEQ ID NO: 138, aMTD604 has the sequence of SEQ ID NO: 140, aMTD643 has the sequence of SEQ ID NO: 145, aMTD665 has the sequence of SEQ ID NO: 149, aMTD683 has the sequence of SEQ ID NO: 152, aMTD687 has the sequence of SEQ ID NO: 156, aMTD706 has the sequence of SEQ ID NO: 159, aMTD765 has the sequence of SEQ ID NO: 171, aMTD767 has the sequence of SEQ ID NO: 173, aMTD807 has the sequence of SEQ ID NO: 182, aMTD828 has the sequence of SEQ ID NO: 191, aMTD844 has the sequence of SEQ ID NO: 197, aMTD851 has the sequence of SEQ ID NO: 204, aMTD12 has the sequence of SEQ ID NO: 7, aMTD81 has the sequence of SEQ ID NO: 22, aMTD104 has the sequence of SEQ ID NO: 30, aMTD904 has the sequence of SEQ ID NO: 233. In FIG. 7j, aMTD165 has the sequence of SEQ ID NO: 43, aMTD205 has the sequence of SEQ ID NO: 50, aMTD241 has the sequence of SEQ ID NO: 56, aMTD264 has the sequence of SEQ ID NO: 63, aMTD301 has the sequence of SEQ ID NO: 70, aMTD323 has the sequence of SEQ ID NO: 76, aMTD361 has the sequence of SEQ ID NO: 83, aMTD384 has the sequence of SEQ ID NO: 90, aMTD421 has the sequence of SEQ ID NO: 97, aMTD445 has the sequence of SEQ ID NO: 104, aMTD482 has the sequence of SEQ ID NO: 111, aMTD522 has the sequence of SEQ ID NO: 121, aMTD545 has the sequence of SEQ ID NO: 128, aMTD583 has the sequence of SEQ ID NO: 135, aMTD625 has the sequence of SEQ ID NO: 144, aMTD870 has the sequence of SEQ ID NO: 211, aMTD788 has the sequence of SEQ ID NO: 178, aMTD864 has the sequence of SEQ ID NO: 207, aMTD811 has the sequence of SEQ ID NO: 186, aMTD888 has the sequence of SEQ ID NO: 222, aMTD905 has the sequence of SEQ ID NO: 234, aMTD324 has the sequence of SEQ ID NO: 77, aMTD809 has the sequence of SEQ ID NO: 184, aMTD883 has the sequence of SEQ ID NO: 219. In FIG. 7k, aMTD831 has the sequence of SEQ ID NO: 194, aMTD911 has the sequence of SEQ ID NO: 239, aMTD485 has the sequence of SEQ ID NO: 114, aMTD685 has the sequence of SEQ ID NO: 154, aMTD878 has the sequence of SEQ ID NO: 215, aMTD42 has the sequence of SEQ ID NO: 14.

FIG. 8 shows Visualized Cell-Permeability of rPeptide-Fused Recombinant Proteins. Cell-permeability of rPeptide-fused recombinant proteins was visualized by laser scanning confocal microscopy (LSM700 version).

In FIG. 8, rP692 has the sequence of SEQ ID NO: 907, rP26 has the sequence of SEQ ID NO: 895, rP113 has the sequence of SEQ ID NO: 891, rP466 has the sequence of SEQ ID NO: 897, rP167 has the sequence of SEQ ID NO: 898, rP97 has the sequence of SEQ ID NO: 936, rP390 has the sequence of SEQ ID NO: 909, rP426 has the sequence of SEQ ID NO: 900, rP214 has the sequence of SEQ ID NO: 937, rP68 has the sequence of SEQ ID NO: 913, rP39 has the sequence of SEQ ID NO: 941, rP934 has the sequence of SEQ ID NO: 888, rP938 has the sequence of SEQ ID NO: 916, rP329 has the sequence of SEQ ID NO: 917, rP606 has the sequence of SEQ ID NO: 901, rP49 has the sequence of SEQ ID NO: 918, rP139 has the sequence of SEQ ID NO: 944, rP772 has the sequence of SEQ ID NO: 919, rP921 has the sequence of SEQ ID NO: 931, rP66 has the sequence of SEQ ID NO: 902, rP693 has the sequence of SEQ ID NO: 922, rP18 has the sequence of SEQ ID NO: 945, rP16 has the sequence of SEQ ID NO: 890, rP227 has the sequence of SEQ ID NO: 904, rP17 has the sequence of SEQ ID NO: 905, rP67 has the sequence of SEQ ID NO: 906, rP635 has the sequence of SEQ ID NO: 947, rP29 has the sequence of SEQ ID NO: 924, rP57 has the sequence of SEQ ID NO: 949, rP700 has the sequence of SEQ ID NO: 951.

FIGS. 9a to 9c show Relative Cell-Permeability of aMTD-Fused Recombinant Proteins Compared to Negative Control (rP38 (SEQ ID NO: 952)). The FIG shows graphs comparing the cell-permeability of the recombinant proteins fused to aMTDs and a negative control (A: rP38 (SEQ ID NO: 952)).

In FIG. 9a, rP38 has the sequence of SEQ ID NO: 952, aMTD899 has the sequence of SEQ ID NO: 229, aMTD908 has the sequence of SEQ ID NO: 237, aMTD910 has the sequence of SEQ ID NO: 238, aMTD810 has the sequence of SEQ ID NO: 185, aMTD904 has the sequence of SEQ ID NO: 233, aMTD321 has the sequence of SEQ ID NO: 74, aMTD851 has the sequence of SEQ ID NO: 204, aMTD911 has the sequence of SEQ ID NO: 239, aMTD852 has the sequence of SEQ ID NO: 205, aMTD803 has the sequence of SEQ ID NO: 179, aMTD888 has the sequence of SEQ ID NO: 222, aMTD825 has the sequence of SEQ ID NO: 188, aMTD895 has the sequence of SEQ ID NO: 226, aMTD896 has the sequence of SEQ ID NO: 227, aMTD727 has the sequence of SEQ ID NO: 164, aMTD603 has the sequence of SEQ ID NO: 139, aMTD847 has the sequence of SEQ ID NO: 200, aMTD826 has the sequence of SEQ ID NO: 189, aMTD724 has the sequence of SEQ ID NO: 161, aMTD564 has the sequence of SEQ ID NO: 132, aMTD811 has the sequence of SEQ ID NO: 186, aMTD831 has the sequence of SEQ ID NO: 194, aMTD829 has the sequence of SEQ ID NO: 192, aMTD891 has the sequence of SEQ ID NO: 224, aMTD905 has the sequence of SEQ ID NO: 234, aMTD564 has the sequence of SEQ ID NO: 132, aMTD124 has the sequence of SEQ ID NO: 34, aMTD827 has the sequence of SEQ ID NO: 190, aMTD2 has the sequence of SEQ ID NO: 2, aMTD385 has the sequence of SEQ ID NO: 91, aMTD828 has the sequence of SEQ ID NO: 191, aMTD806 has the sequence of SEQ ID NO: 181, aMTD845 has the sequence of SEQ ID NO: 198, aMTD882 has the sequence of SEQ ID NO: 218, aMTD545 has the sequence of SEQ ID NO: 128, aMTD161 has the sequence of SEQ ID NO: 39, aMTD481 has the sequence of SEQ ID NO: 110, aMTD900 has the sequence of SEQ ID NO: 230, aMTD223 has the sequence of SEQ ID NO: 53, aMTD824 has the sequence of SEQ ID NO: 187, aMTD562 has the sequence of SEQ ID NO: 130, aMTD222 has the sequence of SEQ ID NO: 52, aMTD61 has the sequence of SEQ ID NO: 17, aMTD582 has the sequence of SEQ ID NO: 134, aMTD889 has the sequence of SEQ ID NO: 223, aMTD787 has the sequence of SEQ ID NO: 177, aMTD703 has the sequence of SEQ ID NO: 157, aMTD705 has the sequence of SEQ ID NO: 158, aMTD885 has the sequence of SEQ ID NO: 220, aMTD3 has the sequence of SEQ ID NO: 3, aMTD601 has the sequence of SEQ ID NO: 137, aMTD843 has the sequence of SEQ ID NO: 196, aMTD403 has the sequence of SEQ ID NO: 94, aMTD544 has the sequence of SEQ ID NO: 127, aMTD522 has the sequence of SEQ ID NO: 121, aMTD805 has the sequence of SEQ ID NO: 180, aMTD464 has the sequence of SEQ ID NO: 108, aMTD405 has the sequence of SEQ ID NO: 96, aMTD747 has the sequence of SEQ ID NO: 168, aMTD501 has the sequence of SEQ ID NO: 115, aMTD661 has the sequence of SEQ ID NO: 147, aMTD786 has the sequence of SEQ ID NO: 176, aMTD625 has the sequence of SEQ ID NO: 144, aMTD442 has the sequence of SEQ ID NO: 101, aMTD686 has the sequence of SEQ ID NO: 155, aMTD343 has the sequence of SEQ ID NO: 81, aMTD323 has the sequence of SEQ ID NO: 76, aMTD461 has the sequence of SEQ ID NO: 105, aMTD21 has the sequence of SEQ ID NO: 9, aMTD404 has the sequence of SEQ ID NO: 95, aMTD261 has the sequence of SEQ ID NO: 60, aMTD524 has the sequence of SEQ ID NO: 122, aMTD225 has the sequence of SEQ ID NO: 55, aMTD264 has the sequence of SEQ ID NO: 63, aMTD524 has the sequence of SEQ ID NO: 122, aMTD225 has the sequence of SEQ ID NO: 55, aMTD264 has the sequence of SEQ ID NO: 63, aMTD1 has the sequence of SEQ ID NO: 1, aMTD382 has the sequence of SEQ ID NO: 88, aMTD463 has the sequence of SEQ ID NO: 107, aMTD322 has the sequence of SEQ ID NO: 75, aMTD503 has the sequence of SEQ ID NO: 117, aMTD870 has the sequence of SEQ ID NO: 211, aMTD241 has the sequence of SEQ ID NO: 56, aMTD726 has the sequence of SEQ ID NO: 163, aMTD341 has the sequence of SEQ ID NO: 79, aMTD542 has the sequence of SEQ ID NO: 125, aMTD361 has the sequence of SEQ ID NO: 83, aMTD224 has the sequence of SEQ ID NO: 54, aMTD482 has the sequence of SEQ ID NO: 111.

In FIG. 9b, aMTD64 has the sequence of SEQ ID NO: 20, aMTD484 has the sequence of SEQ ID NO: 113, aMTD868 has the sequence of SEQ ID NO: 210, aMTD541 has the sequence of SEQ ID NO: 124, aMTD666 has the sequence of SEQ ID NO: 150, aMTD665 has the sequence of SEQ ID NO: 149, aMTD363 has the sequence of SEQ ID NO: 84, aMTD242 has the sequence of SEQ ID NO: 57, aMTD384 has the sequence of SEQ ID NO: 90, aMTD877 has the sequence of SEQ ID NO: 214, aMTD863 has the sequence of SEQ ID NO: 206, aMTD525 has the sequence of SEQ ID NO: 123, aMTD875 has the sequence of SEQ ID NO: 213, aMTD285 has the sequence of SEQ ID NO: 69, aMTD281 has the sequence of SEQ ID NO: 65, aMTD867 has the sequence of SEQ ID NO: 209, aMTD766 has the sequence of SEQ ID NO: 172, aMTD342 has the sequence of SEQ ID NO: 80, aMTD881 has the sequence of SEQ ID NO: 217, aMTD505 has the sequence of SEQ ID NO: 119, aMTD763 has the sequence of SEQ ID NO: 169, aMTD706 has the sequence of SEQ ID NO: 159, aMTD687 has the sequence of SEQ ID NO: 156, aMTD643 has the sequence of SEQ ID NO: 145, aMTD282 has the sequence of SEQ ID NO: 66, aMTD543 has the sequence of SEQ ID NO: 126, aMTD325 has the sequence of SEQ ID NO: 78, aMTD846 has the sequence of SEQ ID NO: 199, aMTD383 has the sequence of SEQ ID NO: 89, aMTD381 has the sequence of SEQ ID NO: 87, aMTD808 has the sequence of SEQ ID NO: 183, aMTD865 has the sequence of SEQ ID NO: 208, aMTD725 has the sequence of SEQ ID NO: 162, aMTD844 has the sequence of SEQ ID NO: 197, aMTD897 has the sequence of SEQ ID NO: 228, aMTD605 has the sequence of SEQ ID NO: 141, aMTD744 has the sequence of SEQ ID NO: 166, aMTD221 has the sequence of SEQ ID NO: 51, aMTD622 has the sequence of SEQ ID NO: 142, aMTD401 has the sequence of SEQ ID NO: 92, aMTD324 has the sequence of SEQ ID NO: 77, aMTD878 has the sequence of SEQ ID NO: 215, aMTD302 has the sequence of SEQ ID NO: 71, aMTD685 has the sequence of SEQ ID NO: 154, aMTD848 has the sequence of SEQ ID NO: 201, aMTD602 has the sequence of SEQ ID NO: 138, aMTD788 has the sequence of SEQ ID NO: 178, aMTD145 has the sequence of SEQ ID NO: 38, aMTD11,has the sequence of SEQ ID NO: 6, aMTD141 has the sequence of SEQ ID NO: 35, aMTD521 has the sequence of SEQ ID NO: 120, aMTD425 has the sequence of SEQ ID NO: 100, aMTD365 has the sequence of SEQ ID NO: 86, aMTD263 has the sequence of SEQ ID NO: 62, aMTD345 has the sequence of SEQ ID NO: 82, aMTD850 has the sequence of SEQ ID NO: 203, aMTD144 has the sequence of SEQ ID NO: 37, aMTD767 has the sequence of SEQ ID NO: 173, aMTD185 has the sequence of SEQ ID NO: 47, aMTD849 has the sequence of SEQ ID NO: 202, aMTD864 has the sequence of SEQ ID NO: 207, aMTD162 has the sequence of SEQ ID NO: 40, aMTD164 has the sequence of SEQ ID NO: 42, aMTD907 has the sequence of SEQ ID NO: 236, aMTD444 has the sequence of SEQ ID NO: 103, aMTD443 has the sequence of SEQ ID NO: 102, aMTD901 has the sequence of SEQ ID NO: 231, aMTD887 has the sequence of SEQ ID NO: 221, aMTD746 has the sequence of SEQ ID NO: 167, aMTD902 has the sequence of SEQ ID NO: 232, aMTD565 has the sequence of SEQ ID NO: 133, aMTD245 has the sequence of SEQ ID NO: 59, aMTD743 has the sequence of SEQ ID NO: 165, aMTD464 has the sequence of SEQ ID NO: 108, aMTD104 has the sequence of SEQ ID NO: 30, aMTD707 has the sequence of SEQ ID NO: 160, aMTD872 has the sequence of SEQ ID NO: 212, aMTD583 has the sequence of SEQ ID NO: 135, aMTD879 has the sequence of SEQ ID NO: 216, aMTD784 has the sequence of SEQ ID NO: 175, aMTD893 has the sequence of SEQ ID NO: 225, aMTD13 has the sequence of SEQ ID NO: 8, aMTD809 has the sequence of SEQ ID NO: 184, aMTD445 has the sequence of SEQ ID NO: 104, aMTD81 has the sequence of SEQ ID NO: 22, aMTD667 has the sequence of SEQ ID NO: 151, aMTD906 has the sequence of SEQ ID NO: 235, aMTD483 has the sequence of SEQ ID NO: 112, aMTD485 has the sequence of SEQ ID NO: 114, aMTD421 has the sequence of SEQ ID NO: 97.

In FIG. 9c, aMTD585 has the sequence of SEQ ID NO: 136, aMTD424 has the sequence of SEQ ID NO: 99, aMTD364 has the sequence of SEQ ID NO: 85, aMTD402 has the sequence of SEQ ID NO: 93, aMTD462 has the sequence of SEQ ID NO: 106, aMTD265 has the sequence of SEQ ID NO: 64, aMTD301 has the sequence of SEQ ID NO: 70, aMTD183 has the sequence of SEQ ID NO: 45, aMTD243 has the sequence of SEQ ID NO: 58, aMTD664 has the sequence of SEQ ID NO: 148, aMTD783 has the sequence of SEQ ID NO: 174, aMTD502 has the sequence of SEQ ID NO: 116, aMTD262 has the sequence of SEQ ID NO: 61, aMTD683 has the sequence of SEQ ID NO: 152, aMTD830 has the sequence of SEQ ID NO: 193, aMTD764 has the sequence of SEQ ID NO: 170, aMTD807 has the sequence of SEQ ID NO: 182, aMTD184 has the sequence of SEQ ID NO: 46, aMTD305 has the sequence of SEQ ID NO: 73, aMTD101 has the sequence of SEQ ID NO: 27, aMTD304 has the sequence of SEQ ID NO: 72, aMTD604 has the sequence of SEQ ID NO: 140, aMTD645 has the sequence of SEQ ID NO: 146, aMTD201 has the sequence of SEQ ID NO: 48, aMTD163 has the sequence of SEQ ID NO: 41, aMTD832 has the sequence of SEQ ID NO: 195, aMTD182 has the sequence of SEQ ID NO: 44, aMTD23 has the sequence of SEQ ID NO: 11, aMTD105 has the sequence of SEQ ID NO: 31, aMTD561 has the sequence of SEQ ID NO: 129, aMTD765 has the sequence of SEQ ID NO: 171, aMTD684 has the sequence of SEQ ID NO: 153, aMTD143 has the sequence of SEQ ID NO: 36, aMTD504 has the sequence of SEQ ID NO: 118, aMTD22 has the sequence of SEQ ID NO: 10, aMTD5 has the sequence of SEQ ID NO: 5, aMTD283 has the sequence of SEQ ID NO: 67, aMTD65 has the sequence of SEQ ID NO: 21, aMTD883 has the sequence of SEQ ID NO: 219, aMTD123 has the sequence of SEQ ID NO: 33, aMTD284 has the sequence of SEQ ID NO: 68, aMTD205 has the sequence of SEQ ID NO: 50, aMTD42 has the sequence of SEQ ID NO: 14, aMTD121 has the sequence of SEQ ID NO: 32, aMTD25 has the sequence of SEQ ID NO: 13, aMTD24 has the sequence of SEQ ID NO: 12, aMTD204 has the sequence of SEQ ID NO: 49, aMTD12 has the sequence of SEQ ID NO: 7, aMTD43 has the sequence of SEQ ID NO: 15, aMTD103 has the sequence of SEQ ID NO: 29, aMTD82 has the sequence of SEQ ID NO: 23, aMTD4 has the sequence of SEQ ID NO:4, aMTD85 has the sequence of SEQ ID NO: 26, aMTD63 has the sequence of SEQ ID NO: 19, aMTD44 has the sequence of SEQ ID NO: 16, aMTD84 has the sequence of SEQ ID NO: 25, aMTD62 has the sequence of SEQ ID NO: 18, aMTD83 has the sequence of SEQ ID NO: 24, aMTD102 has the sequence of SEQ ID NO: 28, aMTD623 has the sequence of SEQ ID NO: 143.

FIGS. 10a to 10c show Relative Cell-Permeability of aMTD-Fused Recombinant Proteins Compared to Reference CPP (MTM12 (SEQ ID NO: 953)). The FIG shows graphs comparing the cell-permeability of the recombinant proteins fused to aMTDs and a reference CPP (MTM12 (SEQ ID NO: 953)).

In FIG. 10a, MTM12 has the sequence of SEQ ID NO: 953, aMTD899 has the sequence of SEQ ID NO: 229, aMTD908 has the sequence of SEQ ID NO: 237, aMTD910 has the sequence of SEQ ID NO: 238, aMTD810 has the sequence of SEQ ID NO: 185, aMTD904 has the sequence of SEQ ID NO: 233, aMTD321 has the sequence of SEQ ID NO: 74, aMTD851 has the sequence of SEQ ID NO: 204, aMTD911 has the sequence of SEQ ID NO: 239, aMTD852 has the sequence of SEQ ID NO: 205, aMTD803 has the sequence of SEQ ID NO: 179, aMTD888 has the sequence of SEQ ID NO: 222, aMTD825 has the sequence of SEQ ID NO: 188, aMTD895 has the sequence of SEQ ID NO: 226, aMTD896 has the sequence of SEQ ID NO: 227, aMTD727 has the sequence of SEQ ID NO: 164, aMTD603 has the sequence of SEQ ID NO: 139, aMTD847 has the sequence of SEQ ID NO: 200, aMTD826 has the sequence of SEQ ID NO: 189, aMTD724 has the sequence of SEQ ID NO: 161, aMTD564 has the sequence of SEQ ID NO: 132, aMTD811 has the sequence of SEQ ID NO: 186, aMTD831 has the sequence of SEQ ID NO: 194, aMTD829 has the sequence of SEQ ID NO: 192, aMTD891 has the sequence of SEQ ID NO: 224, aMTD905 has the sequence of SEQ ID NO: 234, aMTD564 has the sequence of SEQ ID NO: 132, aMTD124 has the sequence of SEQ ID NO: 34, aMTD827 has the sequence of SEQ ID NO: 190, aMTD2 has the sequence of SEQ ID NO: 2, aMTD385 has the sequence of SEQ ID NO: 91, aMTD828 has the sequence of SEQ ID NO: 191, aMTD806 has the sequence of SEQ ID NO: 181, aMTD845 has the sequence of SEQ ID NO: 198, aMTD882 has the sequence of SEQ ID NO: 218, aMTD545 has the sequence of SEQ ID NO: 128, aMTD161 has the sequence of SEQ ID NO: 39, aMTD481 has the sequence of SEQ ID NO: 110, aMTD900 has the sequence of SEQ ID NO: 230, aMTD223 has the sequence of SEQ ID NO: 53, aMTD824 has the sequence of SEQ ID NO: 187, aMTD562 has the sequence of SEQ ID NO: 130, aMTD222 has the sequence of SEQ ID NO: 52, aMTD61 has the sequence of SEQ ID NO: 17, aMTD582 has the sequence of SEQ ID NO: 134, aMTD889 has the sequence of SEQ ID NO: 223, aMTD787 has the sequence of SEQ ID NO: 177, aMTD703 has the sequence of SEQ ID NO: 157, aMTD705 has the sequence of SEQ ID NO: 158, aMTD885 has the sequence of SEQ ID NO: 220, aMTD3 has the sequence of SEQ ID NO: 3, aMTD601 has the sequence of SEQ ID NO: 137, aMTD843 has the sequence of SEQ ID NO: 196, aMTD403 has the sequence of SEQ ID NO: 94, aMTD544 has the sequence of SEQ ID NO: 127, aMTD522 has the sequence of SEQ ID NO: 121, aMTD805 has the sequence of SEQ ID NO: 180, aMTD464 has the sequence of SEQ ID NO: 108, aMTD405 has the sequence of SEQ ID NO: 96, aMTD747 has the sequence of SEQ ID NO: 168, aMTD501 has the sequence of SEQ ID NO: 115, aMTD661 has the sequence of SEQ ID NO: 147, aMTD786 has the sequence of SEQ ID NO: 176, aMTD625 has the sequence of SEQ ID NO: 144, aMTD442 has the sequence of SEQ ID NO: 101, aMTD686 has the sequence of SEQ ID NO: 155, aMTD343 has the sequence of SEQ ID NO: 81, aMTD323 has the sequence of SEQ ID NO: 76, aMTD461 has the sequence of SEQ ID NO: 105, aMTD21 has the sequence of SEQ ID NO: 9, aMTD404 has the sequence of SEQ ID NO: 95, aMTD261 has the sequence of SEQ ID NO: 60, aMTD524 has the sequence of SEQ ID NO: 122, aMTD225 has the sequence of SEQ ID NO: 55, aMTD264 has the sequence of SEQ ID NO: 63, aMTD524 has the sequence of SEQ ID NO: 122, aMTD225 has the sequence of SEQ ID NO: 55, aMTD264 has the sequence of SEQ ID NO: 63, aMTD1 has the sequence of SEQ ID NO: 1, aMTD382 has the sequence of SEQ ID NO: 88, aMTD463 has the sequence of SEQ ID NO: 107, aMTD322 has the sequence of SEQ ID NO: 75, aMTD503 has the sequence of SEQ ID NO: 117, aMTD870 has the sequence of SEQ ID NO: 211, aMTD241 has the sequence of SEQ ID NO: 56, aMTD726 has the sequence of SEQ ID NO: 163, aMTD341 has the sequence of SEQ ID NO: 79, aMTD542 has the sequence of SEQ ID NO: 125, aMTD361 has the sequence of SEQ ID NO: 83, aMTD224 has the sequence of SEQ ID NO: 54, aMTD482 has the sequence of SEQ ID NO: 111.

In FIG. 10b, aMTD64 has the sequence of SEQ ID NO: 20, aMTD484 has the sequence of SEQ ID NO: 113, aMTD868 has the sequence of SEQ ID NO: 210, aMTD666 has the sequence of SEQ ID NO: 150, aMTD541 has the sequence of SEQ ID NO: 124, aMTD665 has the sequence of SEQ ID NO: 149, aMTD363 has the sequence of SEQ ID NO: 84, aMTD242 has the sequence of SEQ ID NO: 57, aMTD384 has the sequence of SEQ ID NO: 90, aMTD877 has the sequence of SEQ ID NO: 214, aMTD863 has the sequence of SEQ ID NO: 206, aMTD525 has the sequence of SEQ ID NO: 123, aMTD875 has the sequence of SEQ ID NO: 213, aMTD285 has the sequence of SEQ ID NO: 69, aMTD281 has the sequence of SEQ ID NO: 65, aMTD867 has the sequence of SEQ ID NO: 209, aMTD766 has the sequence of SEQ ID NO: 172, aMTD881 has the sequence of SEQ ID NO: 217, aMTD342 has the sequence of SEQ ID NO: 80, aMTD505 has the sequence of SEQ ID NO: 119, aMTD643 has the sequence of SEQ ID NO: 145, aMTD282 has the sequence of SEQ ID NO: 66, aMTD325 has the sequence of SEQ ID NO: 78, aMTD543 has the sequence of SEQ ID NO: 126, aMTD383 has the sequence of SEQ ID NO: 89, aMTD381 has the sequence of SEQ ID NO: 87, aMTD763 has the sequence of SEQ ID NO: 169, aMTD687 has the sequence of SEQ ID NO: 156, aMTD706 has the sequence of SEQ ID NO: 159, aMTD846 has the sequence of SEQ ID NO: 199, aMTD808 has the sequence of SEQ ID NO: 183, aMTD865 has the sequence of SEQ ID NO: 208, aMTD725 has the sequence of SEQ ID NO: 162, aMTD844 has the sequence of SEQ ID NO: 197, aMTD897 has the sequence of SEQ ID NO: 228, aMTD605 has the sequence of SEQ ID NO: 141, aMTD744 has the sequence of SEQ ID NO: 166, aMTD221 has the sequence of SEQ ID NO: 51, aMTD622 has the sequence of SEQ ID NO: 142, aMTD401 has the sequence of SEQ ID NO: 92, aMTD324 has the sequence of SEQ ID NO: 77, aMTD878 has the sequence of SEQ ID NO: 215, aMTD302 has the sequence of SEQ ID NO: 71, aMTD848 has the sequence of SEQ ID NO: 201, aMTD788 has the sequence of SEQ ID NO: 178, aMTD145 has the sequence of SEQ ID NO: 38, aMTD11 has the sequence of SEQ ID NO: 6, aMTD425 has the sequence of SEQ ID NO: 100, aMTD141 has the sequence of SEQ ID NO: 35, aMTD521 has the sequence of SEQ ID NO: 120, aMTD365 has the sequence of SEQ ID NO: 86, aMTD263 has the sequence of SEQ ID NO: 62, aMTD345 has the sequence of SEQ ID NO: 82, aMTD685 has the sequence of SEQ ID NO: 154, aMTD850 has the sequence of SEQ ID NO: 203, aMTD144 has the sequence of SEQ ID NO: 37, aMTD185 has the sequence of SEQ ID NO: 47, aMTD767 has the sequence of SEQ ID NO: 173, aMTD849 has the sequence of SEQ ID NO: 202, aMTD162 has the sequence of SEQ ID NO: 40, aMTD164 has the sequence of SEQ ID NO: 42, aMTD907 has the sequence of SEQ ID NO: 236, aMTD444 has the sequence of SEQ ID NO: 103, aMTD443 has the sequence of SEQ ID NO: 102, aMTD901 has the sequence of SEQ ID NO: 231, aMTD887 has the sequence of SEQ ID NO: 221, aMTD902 has the sequence of SEQ ID NO: 232, aMTD565 has the sequence of SEQ ID NO: 133, aMTD245 has the sequence of SEQ ID NO: 59, aMTD743 has the sequence of SEQ ID NO: 165, aMTD465 has the sequence of SEQ ID NO: 109, aMTD707 has the sequence of SEQ ID NO: 160, aMTD104 has the sequence of SEQ ID NO: 30, aMTD872 has the sequence of SEQ ID NO: 212, aMTD864 has the sequence of SEQ ID NO: 207, aMTD583 has the sequence of SEQ ID NO: 135, aMTD879 has the sequence of SEQ ID NO: 216, aMTD784 has the sequence of SEQ ID NO: 175, aMTD893 has the sequence of SEQ ID NO: 225, aMTD809 has the sequence of SEQ ID NO: 184, aMTD13 has the sequence of SEQ ID NO: 8, aMTD445 has the sequence of SEQ ID NO: 104, aMTD667 has the sequence of SEQ ID NO: 151, aMTD81 has the sequence of SEQ ID NO: 22, aMTD906 has the sequence of SEQ ID NO: 235, aMTD483 has the sequence of SEQ ID NO: 112, aMTD421 has the sequence of SEQ ID NO: 97, aMTD746 has the sequence of SEQ ID NO: 167.

In FIG. 10c, aMTD585 has the sequence of SEQ ID NO: 136, aMTD424 has the sequence of SEQ ID NO: 99, aMTD364 has the sequence of SEQ ID NO: 85, aMTD402 has the sequence of SEQ ID NO: 93, aMTD462 has the sequence of SEQ ID NO: 106, aMTD265 has the sequence of SEQ ID NO: 64, aMTD402 has the sequence of SEQ ID NO: 93, aMTD462 has the sequence of SEQ ID NO: 106, aMTD265 has the sequence of SEQ ID NO: 64, aMTD301 has the sequence of SEQ ID NO: 70, aMTD183 has the sequence of SEQ ID NO: 45, aMTD243 has the sequence of SEQ ID NO: 58, aMTD664 has the sequence of SEQ ID NO: 148, aMTD783 has the sequence of SEQ ID NO: 174, aMTD502 has the sequence of SEQ ID NO: 116, aMTD262 has the sequence of SEQ ID NO: 61, aMTD807 has the sequence of SEQ ID NO: 182, aMTD683 has the sequence of SEQ ID NO: 152, aMTD184 has the sequence of SEQ ID NO: 46, aMTD305 has the sequence of SEQ ID NO: 73, aMTD101 has the sequence of SEQ ID NO: 27, aMTD304 has the sequence of SEQ ID NO: 72, aMTD645 has the sequence of SEQ ID NO: 146, aMTD201 has the sequence of SEQ ID NO: 48, aMTD832 has the sequence of SEQ ID NO: 195, aMTD182 has the sequence of SEQ ID NO: 44, aMTD23 has the sequence of SEQ ID NO: 11, aMTD105 has the sequence of SEQ ID NO: 31, aMTD561 has the sequence of SEQ ID NO: 129, aMTD604 has the sequence of SEQ ID NO: 140, aMTD163 has the sequence of SEQ ID NO: 41, aMTD765 has the sequence of SEQ ID NO: 171, aMTD684 has the sequence of SEQ ID NO: 153, aMTD143 has the sequence of SEQ ID NO: 36, aMTD504 has the sequence of SEQ ID NO: 118, aMTD22 has the sequence of SEQ ID NO: 10, aMTD5 has the sequence of SEQ ID NO: 5, aMTD283 has the sequence of SEQ ID NO: 67, aMTD65 has the sequence of SEQ ID NO: 21, aMTD883 has the sequence of SEQ ID NO: 219, aMTD123 has the sequence of SEQ ID NO: 33, aMTD284 has the sequence of SEQ ID NO: 68, aMTD205 has the sequence of SEQ ID NO: 50, aMTD42 has the sequence of SEQ ID NO: 14, aMTD121 has the sequence of SEQ ID NO: 32, aMTD25 has the sequence of SEQ ID NO: 13, aMTD24 has the sequence of SEQ ID NO: 12, aMTD204 has the sequence of SEQ ID NO: 49, aMTD12 has the sequence of SEQ ID NO: 7, aMTD43 has the sequence of SEQ ID NO: 15, aMTD103 has the sequence of SEQ ID NO: 29, aMTD82 has the sequence of SEQ ID NO: 23, aMTD4 has the sequence of SEQ ID NO:4, aMTD85 has the sequence of SEQ ID NO: 26, aMTD63 has the sequence of SEQ ID NO: 19, aMTD44 has the sequence of SEQ ID NO: 16, aMTD84 has the sequence of SEQ ID NO: 25, aMTD62 has the sequence of SEQ ID NO: 18, aMTD83 has the sequence of SEQ ID NO: 24, aMTD102 has the sequence of SEQ ID NO: 28, aMTD623 has the sequence of SEQ ID NO: 143.

FIGS. 11a to 11c show Relative Cell-Permeability of aMTD-Fused Recombinant Proteins Compared to Reference CPP (MTD85 (SEQ ID NO: 954)). The FIG shows graphs comparing the cell-permeability of the recombinant proteins fused to aMTDs and a reference CPP (MTD85 (SEQ ID NO: 954)).

In FIG. 11a, MTD85 has the sequence of SEQ ID NO: 954, aMTD899 has the sequence of SEQ ID NO: 229, aMTD908 has the sequence of SEQ ID NO: 237, aMTD910 has the sequence of SEQ ID NO: 238, aMTD810 has the sequence of SEQ ID NO: 185, aMTD904 has the sequence of SEQ ID NO: 233, aMTD321 has the sequence of SEQ ID NO: 74, aMTD851 has the sequence of SEQ ID NO: 204, aMTD911 has the sequence of SEQ ID NO: 239, aMTD852 has the sequence of SEQ ID NO: 205, aMTD803 has the sequence of SEQ ID NO: 179, aMTD888 has the sequence of SEQ ID NO: 222, aMTD825 has the sequence of SEQ ID NO: 188, aMTD895 has the sequence of SEQ ID NO: 226, aMTD896 has the sequence of SEQ ID NO: 227, aMTD727 has the sequence of SEQ ID NO: 164, aMTD603 has the sequence of SEQ ID NO: 139, aMTD847 has the sequence of SEQ ID NO: 200, aMTD826 has the sequence of SEQ ID NO: 189, aMTD724 has the sequence of SEQ ID NO: 161, aMTD564 has the sequence of SEQ ID NO: 132, aMTD811 has the sequence of SEQ ID NO: 186, aMTD831 has the sequence of SEQ ID NO: 194, aMTD829 has the sequence of SEQ ID NO: 192, aMTD891 has the sequence of SEQ ID NO: 224, aMTD905 has the sequence of SEQ ID NO: 234, aMTD564 has the sequence of SEQ ID NO: 132, aMTD124 has the sequence of SEQ ID NO: 34, aMTD827 has the sequence of SEQ ID NO: 190, aMTD2 has the sequence of SEQ ID NO: 2, aMTD385 has the sequence of SEQ ID NO: 91, aMTD828 has the sequence of SEQ ID NO: 191, aMTD806 has the sequence of SEQ ID NO: 181, aMTD845 has the sequence of SEQ ID NO: 198, aMTD882 has the sequence of SEQ ID NO: 218, aMTD545 has the sequence of SEQ ID NO: 128, aMTD161 has the sequence of SEQ ID NO: 39, aMTD481 has the sequence of SEQ ID NO: 110, aMTD900 has the sequence of SEQ ID NO: 230, aMTD223 has the sequence of SEQ ID NO: 53, aMTD824 has the sequence of SEQ ID NO: 187, aMTD562 has the sequence of SEQ ID NO: 130, aMTD222 has the sequence of SEQ ID NO: 52, aMTD61 has the sequence of SEQ ID NO: 17, aMTD582 has the sequence of SEQ ID NO: 134, aMTD889 has the sequence of SEQ ID NO: 223, aMTD787 has the sequence of SEQ ID NO: 177, aMTD703 has the sequence of SEQ ID NO: 157, aMTD705 has the sequence of SEQ ID NO: 158, aMTD885 has the sequence of SEQ ID NO: 220, aMTD3 has the sequence of SEQ ID NO: 3, aMTD601 has the sequence of SEQ ID NO: 137, aMTD843 has the sequence of SEQ ID NO: 196, aMTD403 has the sequence of SEQ ID NO: 94, aMTD544 has the sequence of SEQ ID NO: 127, aMTD522 has the sequence of SEQ ID NO: 121, aMTD805 has the sequence of SEQ ID NO: 180, aMTD464 has the sequence of SEQ ID NO: 108, aMTD405 has the sequence of SEQ ID NO: 96, aMTD747 has the sequence of SEQ ID NO: 168, aMTD501 has the sequence of SEQ ID NO: 115, aMTD661 has the sequence of SEQ ID NO: 147, aMTD786 has the sequence of SEQ ID NO: 176, aMTD625 has the sequence of SEQ ID NO: 144, aMTD442 has the sequence of SEQ ID NO: 101, aMTD686 has the sequence of SEQ ID NO: 155, aMTD343 has the sequence of SEQ ID NO: 81, aMTD323 has the sequence of SEQ ID NO: 76, aMTD461 has the sequence of SEQ ID NO: 105, aMTD21 has the sequence of SEQ ID NO: 9, aMTD404 has the sequence of SEQ ID NO: 95, aMTD261 has the sequence of SEQ ID NO: 60, aMTD524 has the sequence of SEQ ID NO: 122, aMTD225 has the sequence of SEQ ID NO: 55, aMTD264 has the sequence of SEQ ID NO: 63, aMTD524 has the sequence of SEQ ID NO: 122, aMTD225 has the sequence of SEQ ID NO: 55, aMTD264 has the sequence of SEQ ID NO: 63, aMTD1 has the sequence of SEQ ID NO: 1, aMTD382 has the sequence of SEQ ID NO: 88, aMTD463 has the sequence of SEQ ID NO: 107, aMTD322 has the sequence of SEQ ID NO: 75, aMTD503 has the sequence of SEQ ID NO: 117, aMTD870 has the sequence of SEQ ID NO: 211, aMTD241 has the sequence of SEQ ID NO: 56, aMTD726 has the sequence of SEQ ID NO: 163, aMTD341 has the sequence of SEQ ID NO: 79, aMTD542 has the sequence of SEQ ID NO: 125, aMTD361 has the sequence of SEQ ID NO: 83, aMTD224 has the sequence of SEQ ID NO: 54, aMTD482 has the sequence of SEQ ID NO: 111.

In FIG. 11b, aMTD64 has the sequence of SEQ ID NO: 20, aMTD484 has the sequence of SEQ ID NO: 113, aMTD868 has the sequence of SEQ ID NO: 210, aMTD541 has the sequence of SEQ ID NO: 124, aMTD666 has the sequence of SEQ ID NO: 150, aMTD665 has the sequence of SEQ ID NO: 149, aMTD363 has the sequence of SEQ ID NO: 84, aMTD242 has the sequence of SEQ ID NO: 57, aMTD384 has the sequence of SEQ ID NO: 90, aMTD877 has the sequence of SEQ ID NO: 214, aMTD863 has the sequence of SEQ ID NO: 206, aMTD525 has the sequence of SEQ ID NO: 123, aMTD875 has the sequence of SEQ ID NO: 213, aMTD285 has the sequence of SEQ ID NO: 69, aMTD281 has the sequence of SEQ ID NO: 65, aMTD867 has the sequence of SEQ ID NO: 209, aMTD766 has the sequence of SEQ ID NO: 172, aMTD342 has the sequence of SEQ ID NO: 80, aMTD881 has the sequence of SEQ ID NO: 217, aMTD505 has the sequence of SEQ ID NO: 119, aMTD763 has the sequence of SEQ ID NO: 169, aMTD706 has the sequence of SEQ ID NO: 159, aMTD687 has the sequence of SEQ ID NO: 156, aMTD643 has the sequence of SEQ ID NO: 145, aMTD282 has the sequence of SEQ ID NO: 66, aMTD543 has the sequence of SEQ ID NO: 126, aMTD325 has the sequence of SEQ ID NO: 78, aMTD846 has the sequence of SEQ ID NO: 199, aMTD383 has the sequence of SEQ ID NO: 89, aMTD381 has the sequence of SEQ ID NO: 87, aMTD808 has the sequence of SEQ ID NO: 183, aMTD865 has the sequence of SEQ ID NO: 208, aMTD725 has the sequence of SEQ ID NO: 162, aMTD844 has the sequence of SEQ ID NO: 197, aMTD897 has the sequence of SEQ ID NO: 228, aMTD605 has the sequence of SEQ ID NO: 141, aMTD744 has the sequence of SEQ ID NO: 166, aMTD221 has the sequence of SEQ ID NO: 51, aMTD622 has the sequence of SEQ ID NO: 142, aMTD401 has the sequence of SEQ ID NO: 92, aMTD324 has the sequence of SEQ ID NO: 77, aMTD878 has the sequence of SEQ ID NO: 215, aMTD302 has the sequence of SEQ ID NO: 71, aMTD685 has the sequence of SEQ ID NO: 154, aMTD848 has the sequence of SEQ ID NO: 201, aMTD602 has the sequence of SEQ ID NO: 138, aMTD788 has the sequence of SEQ ID NO: 178, aMTD145 has the sequence of SEQ ID NO: 38, aMTD11 has the sequence of SEQ ID NO: 6, aMTD141 has the sequence of SEQ ID NO: 35, aMTD521 has the sequence of SEQ ID NO: 120, aMTD425 has the sequence of SEQ ID NO: 100, aMTD365 has the sequence of SEQ ID NO: 86, aMTD263 has the sequence of SEQ ID NO: 62, aMTD345 has the sequence of SEQ ID NO: 82, aMTD850 has the sequence of SEQ ID NO: 203, aMTD144 has the sequence of SEQ ID NO: 37, aMTD767 has the sequence of SEQ ID NO: 173, aMTD185 has the sequence of SEQ ID NO: 47, aMTD849 has the sequence of SEQ ID NO: 202, aMTD864 has the sequence of SEQ ID NO: 207, aMTD162 has the sequence of SEQ ID NO: 40, aMTD164 has the sequence of SEQ ID NO: 42, aMTD907 has the sequence of SEQ ID NO: 236, aMTD444 has the sequence of SEQ ID NO: 103, aMTD443 has the sequence of SEQ ID NO: 102, aMTD901 has the sequence of SEQ ID NO: 231, aMTD887 has the sequence of SEQ ID NO: 221, aMTD746 has the sequence of SEQ ID NO: 167, aMTD902 has the sequence of SEQ ID NO: 232, aMTD565 has the sequence of SEQ ID NO: 133, aMTD245 has the sequence of SEQ ID NO: 59, aMTD743 has the sequence of SEQ ID NO: 165, aMTD464 has the sequence of SEQ ID NO: 108, aMTD104 has the sequence of SEQ ID NO: 30, aMTD707 has the sequence of SEQ ID NO: 160, aMTD872 has the sequence of SEQ ID NO: 212, aMTD583 has the sequence of SEQ ID NO: 135, aMTD879 has the sequence of SEQ ID NO: 216, aMTD784 has the sequence of SEQ ID NO: 175, aMTD893 has the sequence of SEQ ID NO: 225, aMTD13 has the sequence of SEQ ID NO: 8, aMTD809 has the sequence of SEQ ID NO: 184, aMTD445 has the sequence of SEQ ID NO: 104, aMTD81 has the sequence of SEQ ID NO: 22, aMTD667 has the sequence of SEQ ID NO: 151, aMTD906 has the sequence of SEQ ID NO: 235, aMTD483 has the sequence of SEQ ID NO: 112, aMTD485 has the sequence of SEQ ID NO: 114, aMTD421 has the sequence of SEQ ID NO: 97.

In FIG. 11c, aMTD585 has the sequence of SEQ ID NO: 136, aMTD424 has the sequence of SEQ ID NO: 99, aMTD364 has the sequence of SEQ ID NO: 85, aMTD402 has the sequence of SEQ ID NO: 93, aMTD462 has the sequence of SEQ ID NO: 106, aMTD265 has the sequence of SEQ ID NO: 64, aMTD301 has the sequence of SEQ ID NO: 70, aMTD183 has the sequence of SEQ ID NO: 45, aMTD243 has the sequence of SEQ ID NO: 58, aMTD664 has the sequence of SEQ ID NO: 148, aMTD783 has the sequence of SEQ ID NO: 174, aMTD502 has the sequence of SEQ ID NO: 116, aMTD262 has the sequence of SEQ ID NO: 61, aMTD683 has the sequence of SEQ ID NO: 152, aMTD830 has the sequence of SEQ-ID NO: 193, aMTD764 has the sequence of SEQ ID NO: 170, aMTD807 has the sequence of SEQ ID NO: 182, aMTD184 has the sequence of SEQ ID NO: 46, aMTD305 has the sequence of SEQ ID NO: 73, aMTD101 has the sequence of SEQ ID NO: 27, aMTD304 has the sequence of SEQ ID NO: 72, aMTD604 has the sequence of SEQ ID NO: 140, aMTD645 has the sequence of SEQ ID NO: 146, aMTD201 has the sequence of SEQ ID NO: 48, aMTD163 has the sequence of SEQ ID NO: 41, aMTD832 has the sequence of SEQ ID NO: 195, aMTD182 has the sequence of SEQ ID NO: 44, aMTD23 has the sequence of SEQ ID NO: 11, aMTD105 has the sequence of SEQ ID NO: 31, aMTD561 has the sequence of SEQ ID NO: 129, aMTD765 has the sequence of SEQ ID NO: 171, aMTD684 has the sequence of SEQ ID NO: 153, aMTD143 has the sequence of SEQ ID NO: 36, aMTD504 has the sequence of SEQ ID NO: 118, aMTD22 has the sequence of SEQ ID NO: 10, aMTD5 has the sequence of SEQ ID NO: 5, aMTD283 has the sequence of SEQ ID NO: 67, aMTD65 has the sequence of SEQ ID NO: 21, aMTD883 has the sequence of SEQ ID NO: 219, aMTD123 has the sequence of SEQ ID NO: 33, aMTD284 has the sequence of SEQ ID NO: 68, aMTD205 has the sequence of SEQ ID NO: 50, aMTD42 has the sequence of SEQ ID NO: 14, aMTD121 has the sequence of SEQ ID NO: 32, aMTD25 has the sequence of SEQ ID NO: 13, aMTD24 has the sequence of SEQ ID NO: 12, aMTD204 has the sequence of SEQ ID NO: 49, aMTD12 has the sequence of SEQ ID NO: 7, aMTD43 has the sequence of SEQ ID NO: 15, aMTD103 has the sequence of SEQ ID NO: 29, aMTD82 has the sequence of SEQ ID NO: 23, aMTD4 has the sequence of SEQ ID NO:4, aMTD85 has the sequence of SEQ ID NO: 26, aMTD63 has the sequence of SEQ ID NO: 19, aMTD44 has the sequence of SEQ ID NO: 16, aMTD84 has the sequence of SEQ ID NO: 25, aMTD62 has the sequence of SEQ ID NO: 18, aMTD83 has the sequence of SEQ ID NO: 24, aMTD102 has the sequence of SEQ ID NO: 28, aMTD623 has the sequence of SEQ ID NO: 143.

FIG. 12 shows Relative Cell-Permeability of rPeptide-Mediated Recombinant Proteins Compared to Average that of aMTDs. The FIG shows graphs comparing the cell-permeability of the recombinant proteins fused to rPeptides and that (average value: aMTD AVE) of aMTDs.

In FIG. 12, rP692 has the sequence of SEQ ID NO: 907, rP26 has the sequence of SEQ ID NO: 895, rP113 has the sequence of SEQ ID NO: 891, rP466 has the sequence of SEQ ID NO: 897, rP167 has the sequence of SEQ ID NO: 898, rP97 has the sequence of SEQ ID NO: 936, rP390 has the sequence of SEQ ID NO: 909, rP426 has the sequence of SEQ ID NO: 900, rP214 has the sequence of SEQ ID NO: 937, rP68 has the sequence of SEQ ID NO: 913, rP39 has the sequence of SEQ ID NO: 941, rP934 has the sequence of SEQ ID NO: 888, rP938 has the sequence of SEQ ID NO: 916, rP329 has the sequence of SEQ ID NO: 917, rP606 has the sequence of SEQ ID NO: 901, rP49 has the sequence of SEQ ID NO: 918, rP139 has the sequence of SEQ ID NO: 944, rP772 has the sequence of SEQ ID NO: 919, rP921 has the sequence of SEQ ID NO: 931, rP66 has the sequence of SEQ ID NO: 902, rP693 has the sequence of SEQ ID NO: 922, rP18 has the sequence of SEQ ID NO: 945, rP16 has the sequence of SEQ ID NO: 890, rP227 has the sequence of SEQ ID NO: 904, rP17 has the sequence of SEQ ID NO: 905, rP67 has the sequence of SEQ ID NO: 906, rP227 has the sequence of SEQ ID NO: 904, rP17 has the sequence of SEQ ID NO: 905, rP67 has the sequence of SEQ ID NO: 906, rP635 has the sequence of SEQ ID NO: 947, rP29 has the sequence of SEQ ID NO: 924, rP57 has the sequence of SEQ ID NO: 949, rP700 has the sequence of SEQ ID NO: 951, rP38 has the sequence of SEQ ID NO: 952.

FIGS. 13a and 13b show Association of Cell-Permeability with Amino Acid Composition in aMTD Sequences. These graphs display delivery potential (Geometric Mean) of aMTDs influenced with amino acid composition (A, I, V and L).

FIGS. 14a and 14b show Association of Cell-Permeability with Critical Factors in aMTDs. These graphs show the association of cell-permeability with critical factors [bending potential: proline position (PP), rigidity/flexibility: instability index (II), structural feature: aliphatic index (AI) and hydropathy: grand average of hydropathy (GRAVY)].

FIGS. 15a and 15b show Relative Relevance of aMTD-Mediated Cell-Permeability with Critical Factors. Cell-permeability of 10 high and 10 low ranked aMTDs in their delivery potential were examined for their association with the critical factors [bending potential: proline position (PP), rigidity/flexibility: instability index (II), structural feature: aliphatic index (AI) and hydropathy: grand average of hydropathy (GRAVY)].

In FIGS. 15a and 15b, aMTD888 has the sequence of SEQ ID NO: 222, aMTD825 has the sequence of SEQ ID NO: 188, aMTD895 has the sequence of SEQ ID NO: 226, aMTD896 has the sequence of SEQ ID NO: 227, aMTD727 has the sequence of SEQ ID NO: 164, aMTD603 has the sequence of SEQ ID NO: 139, aMTD847 has the sequence of SEQ ID NO: 200, aMTD826 has the sequence of SEQ ID NO: 189, aMTD724 has the sequence of SEQ ID NO: 161, aMTD563 has the sequence of SEQ ID NO: 131, aMTD43 has the sequence of SEQ ID NO: 15, aMTD103 has the sequence of SEQ ID NO: 29, aMTD4 has the sequence of SEQ ID NO:4, aMTD85 has the sequence of SEQ ID NO: 26, aMTD63 has the sequence of SEQ ID NO: 19, aMTD44 has the sequence of SEQ ID NO: 16, aMTD84 has the sequence of SEQ ID NO: 25, aMTD62 has the sequence of SEQ ID NO: 18, aMTD83 has the sequence of SEQ ID NO: 24, aMTD102 has the sequence of SEQ ID NO: 28.

FIG. 16 shows Relative Relevance of rPeptide-Mediated Cell-Permeability with Hydropathy Range (GRAVY). This graph and a chart illustrate relative relevance of rPeptide-mediated cell-permeability with its hydropathy range (GRAVY).

In FIG. 16, rP33 has the sequence of SEQ ID NO: 927, rP931 has the sequence of SEQ ID NO: 882, rP436 has the sequence of SEQ ID NO: 932, rP138 has the sequence of SEQ ID NO: 933, rP77 has the sequence of SEQ ID NO: 934, rP936 has the sequence of SEQ ID NO: 883, rP226 has the sequence of SEQ ID NO: 892, rP30 has the sequence of SEQ ID NO: 926, rP6 has the sequence of SEQ ID NO: 893, rP750 has the sequence of SEQ ID NO: 894, rP67 has the sequence of SEQ ID NO: 906, rP20 has the sequence of SEQ ID NO: 946, rP635 has the sequence of SEQ ID NO: 947, rP29 has the sequence of SEQ ID NO: 924, rP40 has the sequence of SEQ ID NO: 948, rP190 has the sequence of SEQ ID NO: 925, rP57 has the sequence of SEQ ID NO: 949, rP159 has the sequence of SEQ ID NO: 950, rP700 has the sequence of SEQ ID NO: 951.

FIG. 17 shows a structure of iCP-SOCS3 recombinant protein designed according to example 6-1.

In FIG. 17, aMTD165 has the sequence of SEQ ID NO: 43, SOCS3 has the sequence of SEQ ID NO: 814, SDA has the sequence of SEQ ID NO: 798, SDB has the sequence of SEQ ID NO: 799, SDC has the sequence of SEQ ID NO: 800, SDD has the sequence of SEQ ID NO: 801, SDF has the sequence of SEQ ID NO: 803, HS3 has SOCS3. SOCS3 has the sequence of SEQ ID NO: 814, $HM_{165}S3$ has aMTD165 and SOCS3. aMTD165 has the sequence of SEQ ID NO: 43, SOCS3 has the sequence of SEQ ID NO: 814. $HM_{165}S3A$ has aMTD165, SOCS3 and SDA. aMTD165 has the sequence of SEQ ID NO: 43, SOCS3 has the sequence of SEQ ID NO: 814, SDA has the sequence of SEQ ID NO: 798. $HM_{165}S3B$ has the sequence of SEQ ID NO:827. $HM_{165}S3C$ has aMTD165, SOCS3 and SDC. aMTD165 has the sequence of SEQ ID NO: 43, SOCS3 has the sequence of SEQ ID NO: 814, SDC has the sequence of SEQ ID NO: 800. $HM_{165}S3D$ has aMTD165, SOCS3 and SDD. aMTD165 has the sequence of SEQ ID NO: 43, SOCS3 has the sequence of SEQ ID NO: 814, SDD has the sequence of SEQ ID NO: 801. $HM_{165}S3E$ has aMTD165, SOCS3 and SDF. aMTD165 has the sequence of SEQ ID NO: 43, SOCS3 has the sequence of SEQ ID NO: 814, SDE has the sequence of SEQ ID NO: 802.

FIG. 18 shows the agarose gel electrophoresis analysis showing plasmid DNA fragments insert encoding His-SOCS3-SDB (HS3B), His-aMTD$_{165}$-SOCS3-SDB (HM$_{165}$S3B), His-aMTD$_{165}$-SOCS3-SDC (HM$_{165}$S3C), His-aMTD$_{165}$-SOCS3-SDD (HM$_{165}$S3D), His-aMTD$_{165}$-SOCS3-SDE (HM$_{165}$S3E) cloned into the pET28a (+) vector according to example 6-1.

In FIG. 18 upper left panel, HS3B has SOCS3 and SDB. SOCS3 has the sequence of SEQ ID NO: 814, SDB has the sequence of SEQ ID NO: 799. HM$_{165}$S3 has aMTD165 and SOCS3. aMTD165 has the sequence of SEQ ID NO: 43, SOCS3 has the sequence of SEQ ID NO: 814. HM$_{165}$S3B has the sequence of SEQ ID NO:827.

In FIG. 18 upper middle panel, HM$_{165}$53A has aMTD165, SOCS3 and SDA. aMTD165 has the sequence of SEQ ID NO: 43, SOCS3 has the sequence of SEQ ID NO: 814, SDA has the sequence of SEQ ID NO: 798. HM$_{165}$S3B has the sequence of SEQ ID NO:827. In FIG. 18 upper right panel, HM$_{165}$S3B has the sequence of SEQ ID NO:827.

In FIG. 18 lower panel, HM$_{165}$S3C has aMTD165, SOCS3 and SDC. aMTD165 has the sequence of SEQ ID NO: 43, SOCS3 has the sequence of SEQ ID NO: 814, SDC has the sequence of SEQ ID NO: 800. HM$_{165}$S3D has aMTD165, SOCS3 and SDD. aMTD165 has the sequence of SEQ ID NO: 43, SOCS3 has the sequence of SEQ ID NO: 814. SDD has the sequence of SEQ ID NO: 801. HM$_{165}$S3E has aMTD165, SOCS3 and SDF. aMTD165 has the sequence of SEQ ID NO: 43, SOCS3 has the sequence of SEQ ID NO: 814, SDE has the sequence of SEQ ID NO: 802.

FIG. 19 shows inducible expression and purification of iCP-SOCS3 recombinant protein in *E.coli* according to example 6-2 and improvement of solubility/yield of iCP-SOCS3 recombinant protein by fusing aMTD/SD according to example 6-3.

In FIG. 19, HS3 has SOCS3. SOCS3 has the sequence of SEQ ID NO: 814. HM$_{165}$S3 has aMTD165 and SOCS3. aMTD165 has the sequence of SEQ ID NO: 43, SOCS3 has the sequence of SEQ ID NO: 814. HM$_{165}$S3A has aMTD165, SOCS3 and SDA. aMTD165 has the sequence of SEQ ID NO: 43, SOCS3 has the sequence of SEQ ID NO: 814, SDA has the sequence of SEQ ID NO: 798. HM$_{165}$53B has the sequence of SEQ ID NO:827. HM$_{165}$S3C has aMTD165, SOCS3 and SDC. aMTD165 has the sequence of SEQ ID NO: 43, SOCS3 has the sequence, of SEQ ID NO: 814, SDC has the sequence of SEQ ID NO: 800. HM$_{165}$S3D has aMTD165, SOCS3 and SDD. aMTD165 has the sequence of SEQ ID NO: 43, SOCS3 has the sequence of SEQ ID NO: 814, SDD has the sequence of SEQ ID NO: 801. HM$_{165}$S3E has aMTD165, SOCS3 and SDF. aMTD165 has the sequence of SEQ ID NO: 43, SOCS3 has the sequence of SEQ ID NO: 814, SDE has the sequence of SEQ ID NO: 802.

FIG. 20 shows aMTD-Mediated cell-permeability of SOCS3 recombinant proteins in RAW 264.7 cells according to example 7-1.

In FIG. 20, HS3 has SOCS3. SOCS3 has the sequence of SEQ ID NO:814. HM$_{165}$S3 has aMTD165 and SOCS3. aMTD165 has the sequence of SEQ ID NO:43, and SOCS3 has the sequence of SEQ ID NO:814. HM$_{165}$S3A has aMTD165, SOCS3 and SDA. aMTD165 has the sequence of SEQ ID NO:43, SOCS3 has the sequence of SEQ ID NO:814 and SDA has the sequence of SEQ ID NO:798. HM$_{165}$S3B has the sequence of SEQ ID NO:827.

FIG. 21 shows aMTD-Mediated intracellular delivery and localization of SOCS3 Recombinant Proteins in NIH3T3 cells cells according to example 7-1.

In FIG. 21, HS3 has SOCS3. SOCS3 has the sequence of SEQ ID NO:814. HM$_{165}$S3 has aMTD165 and SOCS3. aMTD165 has the sequence of SEQ ID NO:43, and SOCS3 has the sequence of SEQ ID NO:814. HM$_{165}$S3A has aMTD165, SOCS3 and SDA. aMTD165 has the sequence of SEQ ID NO:43, SOCS3 has the sequence of SEQ ID NO:814 and SDA has the sequence of SEQ ID NO:798. HM$_{165}$S3B has the sequence of SEQ ID NO:827.

FIG. 22 shows systemic delivery of aMTD/SD-fused SOCS3 recombinant proteins in vivo according to example 7-2.

In FIG. 22, HS3 has SOCS3. SOCS3 has the sequence of SEQ ID NO:814. HM$_{165}$S3 has aMTD165 and SOCS3. aMTD165 has the sequence of SEQ ID NO:43, and SOCS3 has the sequence of SEQ ID NO:814. HM$_{165}$S3A has aMTD165, SOCS3 and SDA. aMTD165 has the sequence of SEQ ID NO:43, SOCS3 has the sequence of SEQ ID NO:814 and SDA has the sequence of SEQ ID NO:798. HM$_{165}$S3B has the sequence of SEQ ID NO:827.

FIG. 23 shows inhibition of IFN-γ-induced STAT phosphorylation by iCP-SOCS3 recombinant protein according to example 8-1.

In FIG. 23, HS3 has SOCS3. SOCS3 has the sequence of SEQ ID NO:814. HM$_{165}$S3 has aMTD165 and SOCS3. aMTD165 has the sequence of SEQ ID NO:43, and SOCS3 has the sequence of SEQ ID NO:814. HM$_{165}$S3A has aMTD165, SOCS3 and SDA. aMTD165 has the sequence of SEQ ID NO:43, SOCS3 has the sequence of SEQ ID NO:814 and SDA has the sequence of SEQ ID NO:798. HM$_{165}$S3B has the sequence of SEQ ID NO:827.

FIG. 24 shows inhibition of LPS-induced cytokines secretion by iCP-SOCS3 recombinant protein according to example 8-2.

In FIG. 24, HS3 has SOCS3. SOCS3 has the sequence of SEQ ID NO:814. HM$_{165}$S3 has aMTD165 and SOCS3. aMTD165 has the sequence of SEQ ID NO:43, and SOCS3 has the sequence of SEQ ID NO:814. HM$_{165}$S3A has aMTD165, SOCS3 and SDA. aMTD165 has the sequence of SEQ ID NO:43, SOCS3 has the sequence of SEQ ID NO:814 and SDA has the sequence of SEQ ID NO:798. HM$_{165}$S3B has the sequence of SEQ ID NO:827.

FIG. 25 shows the structures of SOCS3 recombinant protein lacking aMTD prepared as a negative control according to example 9.

In FIG. 25, SOSCS3 has the sequence of SEQ ID NO:814, and SDB has the sequence of SEQ ID NO:799. HS3B has SOCS3 and SDB. SOCS3 has the sequence of SEQ ID NO:814 and SDB has the sequence of SEQ ID NO: 799.

FIG. 26 shows expression, purification, and solubility/yield of HS3 (lacking aMTD and SD) and HS3B (lacking aMTD) determined according to example 6-3.

In FIG. 26, HS3B has SOCS3 and SDB. SOCS3 has the sequence of SEQ ID NO:814 and SDB has the sequence of SEQ ID NO: 799. HS3 has SOCS3. SOCS3 has the sequence of SEQ ID NO:814.

FIG. 27 shows the agarose gel electrophoresis analysis showing plasmid DNA fragments insert encoding His-aMTD#-SOCS3-SDB (HM$_#$S3B) and His-rP#-SOCS3-SDB cloned into the pET28a (+) vector according to example 10.

In FIG. 27, aMTD44 has the sequence of SEQ ID NO:16, aMTD81 has the sequence of SEQ ID NO:22, aMTD123 has the sequence of SEQ ID NO:33, aMTD162 has the sequence of SEQ ID NO:40, aMTD281 has the sequence of SEQ ID NO:65, aMTD324 has the sequence of SEQ ID NO:77, aMTD364 has the sequence of SEQ ID NO:85, aMTD365 has the sequence of SEQ ID NO:86, aMTD622 has the sequence of SEQ ID NO:142, aMTD662 has the sequence of SEQ ID NO:822, aMTD563 has the sequence of SEQ ID NO:131, aMTD899 has the sequence of SEQ ID NO:223, aMTD897 has the sequence of SEQ ID NO:228, aMTD623 has the sequence of SEQ ID NO:143, aMTD908 has the sequence of SEQ ID NO:237, aMTD911 has the sequence of SEQ ID NO:239, aMTD904 has the sequence of SEQ ID NO:233, aMTD481 has the sequence of SEQ ID NO:110, aMTD787 has the sequence of SEQ ID NO:177, aMTD363 has the sequence of SEQ ID NO:84, aMTD121 has the sequence of SEQ ID NO:32, rP921 has the sequence of SEQ ID NO:931, rP16 has the sequence of SEQ ID NO:890, rP67 has the sequence of SEQ ID NO:906, rP29 has the sequence of SEQ ID NO:924, and rP700 has the sequence of SEQ ID NO:951.

FIGS. 28*a* and 28*b* show expression, purification, and solubility/yield of His-aMTD#-SOCS3-SDB (HM$_#$S3B) determined according to example 10.

In FIG. 28*a*, aMTD44 has the sequence of SEQ ID NO:16, aMTD81 has the sequence of SEQ ID NO:22, aMTD281 has the sequence of SEQ ID NO:65, aMTD324 has the sequence of SEQ ID NO:77, aMTD364 has the sequence of SEQ ID NO:85, and aMTD365 has the sequence of SEQ ID NO:86.

In FIG. 28b, aMTD563 has the sequence of SEQ ID NO:131, aMTD662 has the sequence of SEQ ID NO:822, aMTD622 has the sequence of SEQ ID NO:142, aMTD904 has the sequence of SEQ ID NO:233, aMTD908 has the sequence of SEQ ID NO:237, aMTD911 has the sequence of SEQ ID NO:239, aMTD897 has the sequence of SEQ ID NO:228, aMTD899 has the sequence of SEQ ID NO:223, and aMTD623 has the sequence of SEQ ID NO:143.

FIG. 29 shows expression, purification, and solubility/yield of His-rP#-SOCS3-SDB (HrP$_#$S3B) determined according to example 10.

In FIG. 29, rP700 has the sequence of SEQ ID NO:951, and rP921 has the sequence of SEQ ID NO:93.1.

FIG. 30 shows solubility/yield of His-aMTD#-SOCS3-SDB (HM$_#$S3B) determined according to example 10.

In FIG. 30, aMTD121 has the sequence of SEQ ID NO:32, aMTD623 has the sequence of SEQ ID NO:143, aMTD165 has the sequence of SEQ ID NO:43, aMTD81 has the sequence of SEQ ID NO:22, aMTD162 has the sequence of SEQ ID NO:40, aMTD365 has the sequence of SEQ ID NO:86, aMTD481 has the sequence of SEQ ID NO:110, aMTD2 has the sequence of SEQ ID NO:2, aMTD281 has the sequence of SEQ ID NO:65, aMTD324 has the sequence of SEQ ID NO:77, aMTD908 has the sequence of SEQ ID NO:237, aMTD363 has the sequence of SEQ ID NO:84, aMTD911 has the sequence of SEQ ID NO:239, aMTD264 has the sequence of SEQ ID NO:63, aMTD662 has the sequence of SEQ ID NO:142, aMTD563 has the sequence of SEQ ID NO:131, aMTD662 has the sequence of SEQ ID NO:822, aMTD897 has the sequence of SEQ ID NO:228, aMTD44 has the sequence of SEQ ID NO:16, aMTD899 has the sequence of SEQ ID NO:223, aMTD364 has the sequence of SEQ ID NO:85, and aMTD904 has the sequence of SEQ ID NO:233.

FIG. 31 show aMTD-mediated cell-permeability. The cell-permeability of each SOCS3 recombinant protein fused with SD and various aMTD is visually compared to that of the cargo protein lacking CPP (HS3B) or lacking CPP and SD (HS3). Gray shaded area represents untreated E. coli cells (diluent); green line represents the cells treated with equal molar concentration of FITC (FITC only); black line indicates the cells treated with FITC-his-SOCS protein (FITC-HS3); blue line indicates the cells treated with FITC-his-SOCS-SDB protein (FITC-HS3B) purple line indicates the cells treated with FITC-his-aMTD$_#$-SOCS-SDB protein (FITC-HM$_#$S3B).

In FIG. 31, HS3 has SOCS3. SOCS3 has the sequence of SEQ ID NO:814. HS3B has SOCS3 and SDB. SOCS3 has the sequence of SEQ ID NO:814 and SDB has the sequence of SEQ ID NO: 799. HM$_{165}$S3B has the sequence of SEQ ID NO:827.

aMTD2 has the sequence of SEQ ID NO:2, aMTD44 has the sequence of SEQ ID NO:16, aMTD81 has the sequence of SEQ ID NO:22, aMTD121 has the sequence of SEQ ID NO:32, aMTD162 has the sequence of SEQ ID NO:40, aMTD284 has the sequence of SEQ ID NO:68, aMTD281 has the sequence of SEQ ID NO:65, aMTD324 has the sequence of SEQ ID NO:77, aMTD363 has the sequence of SEQ ID NO:84, aMTD364 has the sequence of SEQ ID NO:85, aMTD365 has the sequence of SEQ ID NO:86, aMTD481 has the sequence of SEQ ID NO:110, aMTD563 has the sequence of SEQ ID NO:131, aMTD622 has the sequence of SEQ ID NO:142, aMTD623 has the sequence of SEQ ID NO:143, aMTD662 has the sequence of SEQ ID NO:822, aMTD897 has the sequence of SEQ ID NO:228, aMTD889 has the sequence of SEQ ID NO:223, aMTD904 has the sequence of SEQ ID NO:233, aMTD908 has the sequence of SEQ ID NO:237, and aMTD911 has the sequence of SEQ ID NO:239.

FIG. 32 shows relative cell-permeability of His-aMTD#-SOCS3-SDB-Fused recombinant proteins Compared to control (Vehicle, FITC only, HS3 and HS3B).

In FIG. 32, HS3 has SOCS3. SOCS3 has the sequence of SEQ ID NO:814. HS3B has SOCS3 and SDB. SOCS3 has the sequence of SEQ ID NO:814 and SDB has the sequence of SEQ ID NO: 799. aMTD121 has the sequence of SEQ ID NO:32, aMTD623 has the sequence of SEQ ID NO:143, aMTD165 has the sequence of SEQ ID NO:43, aMTD81 has the sequence of SEQ ID NO:22, aMTD162 has the sequence of SEQ ID NO:40, aMTD365 has the sequence of SEQ ID NO:86, aMTD481 has the sequence of SEQ ID NO:110, aMTD2 has the sequence of SEQ ID NO:2, aMTD281 has the sequence of SEQ ID NO:65, aMTD324 has the sequence of SEQ ID NO:77, aMTD908 has the sequence of SEQ ID NO:237, aMTD363 has the sequence of SEQ ID NO:84, aMTD911 has the sequence of SEQ ID NO:239, aMTD264 has the sequence of SEQ ID NO:63, aMTD662 has the sequence of SEQ ID NO:822, aMTD563 has the sequence of SEQ ID NO:131, aMTD622 has the sequence of SEQ ID NO:142, aMTD897 has the sequence of SEQ ID NO:228, aMTD44 has the sequence of SEQ ID NO:16, aMTD899 has the sequence of SEQ ID NO:223, aMTD364 has the sequence of SEQ ID NO:85, and aMTD904 has the sequence of SEQ ID NO:233.

FIG. 33 shows random Peptide-Mediated cell-permeability. The cell-permeability of each SOCS3 recombinant protein fused with SDB and aMTD165 or various rP is visually compared to that of the cargo protein lacking CPP (HS3B) or lacking CPP and SD (HS3). Gray shaded area represents untreated E. coli cells (diluent); green line represents the cells treated with equal molar concentration of FITC (FITC only); black line indicates the cells treated with FITC-his-SOCS protein (FITC-HS3); blue line indicates the cells treated with FITC-his-SOCS-SDB protein (FITC-HS3B) and purple line indicates the cells treated with FITC-his-rPeptide$_#$-SOCS-SDB protein (FITC-HrP$_#$S3B).

In FIG. 33, HS3 has SOCS3. SOCS3 has the sequence of SEQ ID NO:814. HS3B has SOCS3 and SDB. SOCS3 has the sequence of SEQ ID NO:814 and SDB has the sequence of SEQ ID NO: 799. HM$_{165}$S3B has the sequence of SEQ ID NO:827.

rP16 has the sequence of SEQ ID NO:890, rP29 has the sequence of SEQ ID NO:924, rP67 has the sequence of SEQ ID NO:906, rP700 has the sequence of SEQ ID NO:951, and rP921 has the sequence of SEQ ID NO:931.

FIG. 34 shows relative cell-permeability of His-rP#-SOCS3-SDB-Fused recombinant proteins Compared to control (Vehicle, FITC only, HS3 and HS3B).

In FIG. 34, HS3 has SOCS3. SOCS3 has the sequence of SEQ ID NO:814. HS3B has SOCS3 and SDB. SOCS3 has the sequence of SEQ ID NO:814 and SDB has the sequence of SEQ ID NO: 799. rP921 has the sequence of SEQ ID NO:931, rP700 has the sequence of SEQ ID NO:951, rP16 has the sequence of SEQ ID NO:890, rP67 has the sequence of SEQ ID NO:906, and rP29 has the sequence of SEQ ID NO:924.

FIG. 35 shows apoptotic cells analysis according to example 11-1.

In FIG. 35, HS3B has SOCS3 and SDB. SOCS3 has the sequence of SEQ ID NO:814 and SDB has the sequence of SEQ ID NO: 799. HM$_{165}$S3B has aMTD165, SOCS3 and SDB. aMTD165 has the sequence of SEQ ID NO:43, SOCS3 has the sequence of SEQ ID NO:814 and SDB has the sequence of SEQ ID NO: 799. HM$_{281}$S3B has aMTD281, SOCS3 and SDB. aMTD281 has the sequence of SEQ ID NO:65, SOCS3 has the sequence of SEQ ID NO:814 and SDB has the sequence of SEQ ID NO: 799. HM$_{324}$S3B has aMTD324, SOCS3 and SDB. aMTD324 has the sequence of SEQ ID NO:77, SOCS3 has the sequence of SEQ ID NO:814 and SDB has the sequence of SEQ ID NO: 799. HM$_{563}$S3B has aMTD563, SOCS3 and SDB. aMTD563 has the sequence of SEQ ID NO:131, SOCS3 has the sequence of SEQ ID NO:814 and SDB has the sequence of SEQ ID NO: 799. HM$_{904}$S3B has aMTD904, SOCS3 and SDB. aMTD904 has the sequence of SEQ ID NO:233, SOCS3 has the sequence of SEQ ID NO:814 and SDB has the sequence of SEQ ID NO: 799.

FIG. 36 shows induction of apoptosis by iCP-SOCS3 recombinant proteins according to example 11-2.

In FIG. 36, HS3B has SOCS3 and SDB. SOCS3 has the sequence of SEQ ID NO:814 and SDB has the sequence of SEQ ID NO: 799. HM$_{165}$S3B has aMTD165, SOCS3 and SDB. aMTD165 has the sequence of SEQ ID NO:43, SOCS3 has the sequence of SEQ ID NO:814 and SDB has the sequence of SEQ ID NO: 799. HM$_{281}$S3B has aMTD281, SOCS3 and SDB. aMTD281 has the sequence of SEQ ID NO:65, SOCS3 has the sequence of SEQ ID NO:814 and SDB has the sequence of SEQ ID NO: 799. HM$_{324}$S3B has aMTD324, SOCS3 and SDB, aMTD324 has the sequence of SEQ ID NO:77, SOCS3 has the sequence of SEQ ID NO:814 and SDB has the sequence of SEQ ID NO: 799. HM$_{563}$S3B has aMTD563, SOCS3 and SDB. aMTD563 has the sequence of SEQ ID NO:131, SOCS3 has the sequence of SEQ ID NO:814 and SDB has the sequence of SEQ ID NO: 799. HM$_{904}$S3B has aMTD904, SOCS3 and SDB. aMTD904 has the sequence of SEQ ID NO:233, SOCS3 has the sequence of SEQ ID NO:814 and SDB has the sequence of SEQ ID NO: 799.

FIG. 37 shows cell migration inhibition by iCP-SOCS3 recombinant protein according to example 11-3.

In FIG. 37, HS3B has SOCS3 and SDB. SOCS3 has the sequence of SEQ ID NO:814 and SDB has the sequence of SEQ ID NO: 799. HM$_{165}$S3B has the sequence of SEQ ID NO:827. HM$_{281}$S3B has aMTD281, SOCS3 and SDB. aMTD281 has the sequence of SEQ ID NO:65, SOCS3 has the sequence of SEQ ID NO:814 and SDB has the sequence of SEQ ID NO: 799. HM$_{324}$S3B has aMTD324 and SDB. aMTD324 has the sequence of SEQ ID NO:77, SOCS3 has the sequence of SEQ ID NO:814 and SDB has the sequence of SEQ ID NO: 799. HM$_{563}$S3B has aMTD563, SOCS3 and SDB. aMTD563 has the sequence of SEQ ID NO:131, SOCS3 has the sequence of SEQ ID NO:814 and SDB has the sequence of SEQ ID NO: 799. HM$_{904}$S3B has aMTD904, SOCS3 and SDB. aMTD904 has the sequence of SEQ ID NO:233, SOCS3 has the sequence of SEQ ID NO:814 and SDB has the sequence of SEQ ID NO: 799.

FIG. 38 shows solubility/yield, permeability and biological activity of His-aMTD#-SOCS3-SDB (HM$_{#}$S3B) determined according to example 10 to 11-3.

In FIG. 38, aMTD481 has the sequence of SEQ ID NO:110, aMTD364 has the sequence of SEQ ID NO:85, aMTD363 has the sequence of SEQ ID NO:84, aMTD324 has the sequence of SEQ ID NO:77, aMTD281 has the sequence of SEQ ID NO:65, aMTD2 has the sequence of SEQ ID NO:2, aMTD563 has the sequence of SEQ ID NO:131, aMTD165 has the sequence of SEQ ID NO:43, aMTD897 has the sequence of SEQ ID NO:228, aMTD622 has the sequence of SEQ ID NO:822, aMTD44 has the sequence of SEQ ID NO:16, aMTD121 has the sequence of SEQ ID NO:32, aMTD623 has the sequence of SEQ ID NO:143, aMTD81 has the sequence of SEQ ID NO:22, aMTD162 has the sequence of SEQ ID NO:40, and aMTD365 has the sequence of SEQ ID NO:86.

FIG. 39 shows expression, purification, and solubility/yield of M$_{165}$S3SB (lacking his-tag) determined according to example 12-1.

In FIG. 39, aMTD165 has the sequence of SEQ ID NO:43, SOCS3 has the sequence of SEQ ID NO:814, SDB has the sequence of SEQ ID NO:799, and M$_{165}$S3B has aMTD165, SOCS3 and SDB. aMTD165 has the sequence of SEQ ID NO:43, SOCS3 has the sequence of SEQ ID NO:814, and SDB has the sequence of SEQ ID NO: 799.

FIG. 40 shows cell-permeability of SOCS3 recombinant proteins (lacking his-tag) in RAW 264.7 cells according to example 12-2.

In FIG. 40, HM$_{165}$S3B has the sequence of SEQ ID NO: 827, and M165S3B has aMTD165, SOCS3 and SDB. aMTD165 has the sequence of SEQ ID NO:43, SOCS3 has the sequence of SEQ ID NO:814, and SDB has the sequence of SEQ ID NO: 799.

FIG. 41 shows Annexin V analysis according to example 12-3.

In FIG. 41, HM$_{165}$S3B has the sequence of SEQ ID NO: 827, and M$_{165}$S3B has aMTD165, SOCS3 and SDB. aMTD165 has the sequence of SEQ ID NO:43, SOCS3 has the sequence of SEQ ID NO:814, and SDB has the sequence of SEQ ID NO: 799.

FIG. 42 shows cell migration inhibition (bottom) by iCP-SOCS3 recombinant protein according to example 12-3.

In FIG. 42, HM$_{165}$S3B has the sequence of SEQ ID NO: 827, and M165S3B has aMTD165, SOCS3 and SDB. aMTD165 has the sequence of SEQ ID NO:43, SOCS3 has the sequence of SEQ ID NO:814, and SDB has the sequence of SEQ ID NO: 799.

FIG. 43 shows a structure of iCP-SOCS3 recombinant protein (His-aMTD$_{165}$-SOCS3-SDB) constructed according to example 12-4.

In FIG. 43, HM$_{165}$S3B has the sequence of SEQ ID NO:827. HM$_{165}$S3B (V28L) has aMTD165, SOCS3 and SDB'. aMTD165 has the sequence of SEQ ID NO:43, SOCS3 has the sequence of SEQ ID NO:814, and SDB' has the sequence of SEQ ID NO:804.

FIG. 44 shows expression, purification, and solubility/yield of HM$_{165}$S3SB (SEQ ID NO: 827) and HM$_{165}$S3SB' determined according to example 12-4.

In FIG. 44, In FIG. 43, HM$_{165}$S3B has the sequence of SEQ ID NO:827. HM$_{165}$S3B (V28L) has aMTD165, SOCS3 and SDB'. aMTD165 has the sequence of SEQ ID NO:43, SOCS3 has the sequence of SEQ ID NO:814, and SDB' has the sequence of SEQ ID NO:804.

FIG. 45 shows aMTD-Mediated cell-permeability of iCP-SOCS3 recombinant proteins (HM$_{165}$S3B (SEQ ID NO:827) and HM$_{165}$S3B'(V28L)) in RAW 264.7 cells according to example 12-5.

In FIG. 45, In FIG. 43, HM$_{165}$S3B has the sequence of SEQ ID NO:827. HM$_{165}$S3B (V28L) has aMTD165, SOCS3 and SDB'. aMTD165 has the sequence of SEQ ID NO:43, SOCS3 has the sequence of SEQ ID NO:814, and SDB' has the sequence of SEQ ID NO:804.

FIG. 46 shows antiproliferative activity of iCP-SOCS3 recombinant proteins (HM$_{165}$S3B (SEQ ID NO:827) and HM$_{165}$S3B' (V28L)) according to example 12-6.

In FIG. 46, HM$_{165}$S3B has the sequence of SEQ ID NO:827. HM$_{165}$S3B (V28L) has aMTD165, SOCS3 and SDB'. aMTD165 has the sequence of SEQ ID NO:43, SOCS3 has the sequence of SEQ ID NO:814, and SDB' has the sequence of SEQ ID NO:804.

FIG. 47 shows induction of apoptosis by iCP-SOCS3 recombinant proteins (HM$_{165}$S3B (SEQ ID NO:827) and HM$_{165}$S3B' (V28L)) according to example 12-6.

In FIG. 47, HM$_{165}$S3B has the sequence of SEQ ID NO:827. HM$_{165}$S3B (V28L) has aMTD165, SOCS3 and SDB'. aMTD165 has the sequence of SEQ ID NO:43, SOCS3 has the sequence of SEQ ID NO:814, and SDB' has the sequence of SEQ ID NO:804.

FIG. 48 shows cell migration inhibition by SOCS3 recombinant proteins (HM$_{165}$S3B (SEQ ID NO:827) and HM$_{165}$S3B'(V28L)) according to example 12-6.

In FIG. 48, HM$_{165}$S3B has the sequence of SEQ ID NO:827. HM$_{165}$S3B (V28L) has aMTD165, SOCS3 and SDB'. aMTD165 has the sequence of SEQ ID NO:43, SOCS3 has the sequence of SEQ ID NO:814, and SDB' has the sequence of SEQ ID NO:804.

FIG. 49 a shows a structure of iCP-SOCS3 recombinant proteins (top) and agarose gel electrophoresis analysis (bottom) according to example 12-7 and FIG. 49 b shows inducible expressions and purifications of iCP-SOCS3 recombinant protein in E. coli (bottom) according to example 12-7.

In FIG. 49a, aMTD165 has the sequence of SEQ ID NO:43, SOCS3 has the sequence of SEQ ID NO:814, SDB has the sequence of SEQ ID NO:799. BS3M$_{165}$ has SDB, SOCS3 and aMTD165. SDB has the sequence of SEQ ID NO: 799, SOCS3 has the sequence of SEQ ID NO:814 and aMTD165 has the sequence of SEQ ID NO:43. (V28L) BS3M165 has SDB', SOCS3 and aTMD165. SDB' has the sequence of SEQ ID NO:804, SOCS3 has the sequence of SEQ ID NO:814, aMTD165 has the sequence of SEQ ID NO:43. In FIG. 49b, BS3M165 has SDB, SOCS3 and aMTD165. SDB has the sequence of SEQ ID NO: 799, SOCS3 has the sequence of SEQ ID NO:814 and aMTD165 has the sequence of SEQ ID NO:43. (V28L) BS3M165 has SDB', SOCS3 and aMTD165. SDB' has the sequence of SEQ ID NO:804, SOCS3 has the sequence of SEQ ID NO:814, aMTD165 has the sequence of SEQ ID NO:43.

FIG. 50 shows inhibition of IFN-γ-induced STAT phosphorylation by iCP-SOCS3 recombinant protein according to example 13.

In FIG. 50, HS3B has SOCS3 and SDB. SOCS3 has the sequence of SEQ ID NO:814 and SDB has the sequence of SEQ ID NO: 799. HM$_{165}$S3B has the sequence of SEQ ID NO:827.

FIG. 51 shows effect of treating EDTA (FIG. 51A) and proteinase K (FIG. 51B) on aMTD-mediated SOCS3 protein uptake into cells according to example 14.

In FIG. 51, HS3B has SOCS3 and SDB. SOCS3 has the sequence of SEQ ID NO:814 and SDB has the sequence of SEQ ID NO: 799. HM$_{165}$S3B has the sequence of SEQ ID NO:827.

FIG. 52 shows effect of treating taxol (FIG. 52 A) and antimycin (FIG. 52 B) on aMTD-mediated SOCS3 protein uptake into cells according to example 14.

In FIG. 52, HS3 has SOCS3. SOCS3 has the sequence of SEQ ID NO:814. HS3B has SOCS3 and SDB. SOCS3 has the sequence of SEQ ID NO:814 and SDB has the sequence of SEQ 1D NO: 799. HM$_{165}$S3B has the sequence of SEQ ID NO:827.

FIG. 53 shows effect of temperature on aMTD-mediated SOCS3 protein uptake into cells according to example 14.

In FIG. 53, HS3 has SOCS3. SOCS3 has the sequence of SEQ ID NO:814. HS3B has SOCS3 and SDB. SOCS3 has the sequence of SEQ ID NO:814 and SDB has the sequence of SEQ ID NO: 799. HM$_{165}$S3B has the sequence of SEQ ID NO:827.

FIG. 54 shows aMTD-mediated cell-to-cell delivery assessed according to example 14.

In FIG. 54, HS3 has SOCS3. SOCS3 has the sequence of SEQ ID NO:814. HS3B has SOCS3 and SDB. SOCS3 has the sequence of SEQ ID NO:814 and SDB has the sequence of SEQ JD NO: 799. HM$_{165}$S3B has the sequence of SEQ ID NO:827.

FIG. 55 shows bioavailability of iCP-SOCS3 recombinant protein in PBMC, splenocytes and hepatocytes analyzed by fluorescence microscopy according to example 15.

FIG. 56 shows biodistribution of iCP-SOCS3 recombinant protein in pancreas tissues analyzed by confocal microscope according to example 15.

FIG. 57 shows aMTD-Mediated cell-permeability of SOCS3 recombinant proteins in various cancer cells according to example 16.

In FIG. 57, HS3 has SOCS3. SOCS3 has the sequence of SEQ ID NO:814. HS3B has SOCS3 and SDB. SOCS3 has the sequence of SEQ ID NO:814 and SDB has the sequence of SEQ ID NO: 799. HM$_{165}$S3B has the sequence of SEQ ID NO:827.

FIG. 58 shows systemic delivery of aMTD/SD-fused SOCS3 recombinant proteins into Various Tissues according to example 16.

In FIG. 58, HS3B has SOCS3 and SDB. SOCS3 has the sequence of SEQ ID NO:814 and SDB has the sequence of SEQ ID NO: 799. HM$_{165}$S3 has aMTD165 and SOCS3. aMTD165 has the sequence of SEQ ID NO:43, SOCS3 has the sequence of SEQ ID NO:814. HM$_{165}$S3B has the sequence of SEQ ID NO:827.

FIG. 59 shows expression level of endogenous SOCS3 mRNA in gastric cell line analyzed by the agarose gel electrophoresis according to example 17-1-2. In FIG. 59, SOCS3 has the sequence of SEQ ID NO:814.

FIG. 60 shows expression level of SOCS3 gene, and phosphorylation of JAK1 and JAK2 in gastric cancer cell line analyzed by western blot analysis according to example 17-1-3. In FIG. 60, SOCS3 has the sequence of SEQ ID NO:814.

FIG. 61 shows expression level of endogenous SOCS3 mRNA in colon cancer cell line analyzed by the agarose gel electrophoresis according to example 17-2-2. In FIG. 61, SOCS3 has the sequence of SEQ ID NO:814.

FIG. 62 shows expression level of SOCS3 gene, and phosphorylation of JAK1 and JAK2 in colon cancer cell line analyzed by western blot analysis according to example 17-2-3. In FIG. 62, SOCS3 has the sequence of SEQ ID NO:814.

FIG. 63 shows methylation and unmethylation level of endogenous SOCS3 in glioblastoma cell line analyzed by the agarose gel electrophoresis according to example 17-3-1. In FIG. 63, SOCS3 has the sequence of SEQ ID NO:814.

FIG. 64 shows expression level of SOCS3 gene, and phosphorylation of JAK1 and JAK2 in glioblastoma cancer cell line analyzed by western blot analysis according to example 17-3-2. In FIG. 64, SOCS3 has the sequence of SEQ ID NO:814.

FIG. 65 shows expression level of endogenous SOCS3 mRNA in breast cancer cell line analyzed by the agarose gel electrophoresis according to example 17-4-1. In FIG. 65, SOCS3 has the sequence of SEQ ID NO:814.

FIG. 66 shows methylation and unmethylation level of endogenous SOCS3 in breast cancer cell line analyzed by the agarose gel electrophoresis according to example 17-4-2. In FIG. 66, SOCS3 has the sequence of SEQ ID NO:814.

FIG. 67 shows expression level of SOCS3 gene, and phosphorylation of JAK1 and JAK2 in breast cancer cell line analyzed by western blot analysis according to example 17-4-3. In FIG. 67, SOCS3 has the sequence of SEQ ID NO:814.

FIG. 68 shows antiproliferative activity of iCP-SOCS3 recombinant protein in gastric cancer cell line according to example 18-1.

In FIG. 68, HS3 has SOCS3. SOC3 has the sequence of SEQ ID NO:814. $HM_{165}S3$ has aMTD165 and SOCS3. aMTD165 has the sequence of SEQ ID NO:43, SOC3 has the sequence of SEQ ID NO:814. $HM_{165}S3A$ has aMTD165, SOCS3 and SDA. aMTD165 has the sequence of SEQ ID NO:43, SOC3 has the sequence of SEQ ID NO:814 and SDA has the sequence of SEQ ID NO:798. $HM_{165}S3B$ has the sequence of SEQ ID NO:827.

FIG. 69 shows antiproliferative activity of iCP-SOCS3 recombinant protein in colorectal cancer cell line according to example 18-1.

In FIG. 69, HS3 has SOCS3. SOC3 has the sequence of SEQ ID NO:814. $HM_{165}S3$ has aMTD165 and SOCS3. aMTD165 has the sequence of SEQ ID NO:43, SOC3 has the sequence of SEQ ID NO:814. $HM_{165}S3A$ has aMTD165, SOCS3 and SDA. aMTD165 has the sequence of SEQ ID NO:43, SOC3 has the sequence of SEQ ID NO:814 and SDA has the sequence of SEQ ID NO:798. $HM_{165}S3B$ has the sequence of SEQ ID NO:827.

FIG. 70 shows antiproliferative activity of iCP-SOCS3 recombinant protein in glioblastoma cell line according to example 18-1.

In FIG. 70, HS3 has SOCS3. SOC3 has the sequence of SEQ ID NO:814. $HM_{165}S3$ has aMTD165 and SOCS3. aMTD165 has the sequence of SEQ ID NO:43, SOC3 has the sequence of SEQ ID NO:814. $HM_{165}S3A$ has aMTD165, SOCS3 and SDA. aMTD165 has the sequence of SEQ ID NO:43, SOC3 has the sequence of SEQ ID NO:814 and SDA has the sequence of SEQ ID NO:798. $HM_{165}S3B$ has the sequence of SEQ ID NO:827.

FIG. 71 shows antiproliferative activity of iCP-SOCS3 recombinant protein in breast cancer cell line according to example 18-1.

In FIG. 71, HS3 has SOCS3. SOC3 has the sequence of SEQ ID NO:814. $HM_{165}S3$ has aMTD165 and SOCS3. aMTD165 has the sequence of SEQ ID NO:43, SOC3 has the sequence of SEQ ID NO:814. $HM_{165}S3A$ has aMTD165, SOCS3 and SDA. aMTD165 has the sequence of SEQ ID NO:43, SOC3 has the sequence of SEQ ID NO:814 and SDA has the sequence of SEQ ID NO:798. $HM_{165}S3B$ has the sequence of SEQ ID NO:827.

FIG. 72 shows cell migration inhibition activity by iCP-SOCS3 recombinant protein in gastric cancer cell line (AGS) according to example 18-2.

In FIG. 72, HS3B has SOCS3 and SDB. SOCS3 has the sequence of SEQ ID NO:814 and SDB has the sequence of SEQ ID NO: 799. $HM_{165}S3B$ has the sequence of SEQ ID NO:827.

FIG. 73 shows cell migration inhibition activity by iCP-SOCS3 recombinant protein in colorectal cancer cell line (HCT116) according to example 18-2.

In FIG. 73, HS3B has SOCS3 and SDB. SOCS3 has the sequence of SEQ ID NO:814 and SDB has the sequence of SEQ ID NO: 799. $HM_{165}S3B$ has the sequence of SEQ ID NO:827.

FIG. 74 shows cell migration inhibition activity by iCP-SOCS3 recombinant protein in glioblastoma cell line (U-87 MG) according to example 18-2.

In FIG. 74, HS3B has SOCS3 and SDB. SOCS3 has the sequence of SEQ ID NO:814 and SDB has the sequence of SEQ ID NO: 799. $HM_{165}S3B$ has the sequence of SEQ ID NO:827.

FIG. 75 shows cell migration inhibition activity by iCP-SOCS3 recombinant protein in breast cancer cell line (MDA-MB-231) according to example 18-2.

In FIG. 75, HS3B has SOCS3 and SDB. SOCS3 has the sequence of SEQ ID NO:814 and SDB has the sequence of SEQ ID NO: 799. $HM_{165}S3B$ has the sequence of SEQ ID NO:827.

FIG. 76 show transwell migration inhibition activity by iCP-SOCS3 recombinant protein in gastric cancer cell line (AGS) (FIG. 76, left), and decrease in invasion by iCP-SOCS3 recombinant protein in gastric cancer cell line (AGS) (FIG. 76, right) analyzed according to example 18-2.

In FIG. 76, HS3B has SOCS3 and SDB. SOCS3 has the sequence of SEQ ID NO:814 and SDB has the sequence of SEQ ID NO: 799. $HM_{165}S3B$ has the sequence of SEQ ID NO:827.

FIG. 77 show transwell migration inhibition activity by iCP-SOCS3 recombinant protein in glioblastoma cell line (U-87 MG) analyzed according to example 18-2. In FIG. 77, SOCS3 has the sequence of SEQ ID NO:814.

FIGS. 78 to 82 show induction of apoptosis in normal cells (FIG. 78), in gastric cancer cells (FIG. 79), in colorectal cancer cells (HCT116, FIG. 80), in glioblastoma cells (U-87 MG, FIG. 81), and in breast cancer cells (MDA-MB-231, FIG. 82) by iCP-SOCS3 recombinant proteins assessed by Annexin V staining according to example 18-3.

In FIGS. 78 and 79, SOCS3 has the sequence of SEQ ID NO:814. In FIGS. 80 to 82, HS3B has SOCS3 and SDB. SOCS3 has the sequence of SEQ ID NO:814 and SDB has the sequence of SEQ ID NO: 799. $HM_{165}S3B$ has the sequence of SEQ ID NO:827.

FIG. 83 show induction of apoptosis in colon cancer cells (HCT116) by iCP-SOCS3 recombinant proteins analyzed by TUNEL assay according to example 18-4.

In FIG. 83, HS3B has SOCS3 and SDB. SOCS3 has the sequence of SEQ ID NO:814 and SDB has the sequence of SEQ ID NO: 799. $HM_{165}S3B$ has the sequence of SEQ ID NO:827.

FIGS. 84 to 88 show inhibition of cell cycle progression in normal cells (FIG. 84), in gastric cancer cells (AGS, FIG. 85), in colon cancer cells (HCT116, FIG. 86), in glioblastoma cells (U-87 MG, FIG. 87), and in breast cancer cells (MDA-MB-231, FIG. 88) by iCP-SOCS3 recombinant proteins assessed by flow cytometric analysis according to example 18-5. In FIGS. 84 to 88, SOCS3 has the sequence of SEQ ID NO:814.

FIG. 89 shows down regulation of expression of apoptosis by iCP-SOCS3 recombinant proteins in breast cancer cells (MDA-MB-231) determined by immunoblotting according to example 18-6.

In FIG. 89, HS3B has SOCS3 and SDB. SOCS3 has the sequence of SEQ ID NO:814 and SDB has the sequence of SEQ ID NO: 799. $HM_{165}S3B$ has the sequence of SEQ ID NO:827.

FIG. 90 shows suppression of the tumor growth by iCP-SOCS3 recombinant proteins in gastric cancer cells (NCI-N87) assessed according to example 19-1. In FIG. 90, SOCS3 has the sequence of SEQ ID NO:814.

FIG. 91 shows suppression of the tumor growth by iCP-SOCS3 recombinant proteins in colorectal cancer cells (HCT116) assessed according to example 19-2. In FIG. 91, SOCS3 has the sequence of SEQ ID NO:814.

FIG. 92 shows suppression of the tumor growth by iCP-SOCS3 recombinant proteins in glioblastoma cells (U-87 MG) assessed according to example 19-3. In FIG. 92, SOCS3 has the sequence of SEQ ID NO:814.

FIG. 93 shows suppression of the tumor growth by iCP-SOCS3 recombinant proteins in breast cancer cells (MDA-MB-231) assessed according to example 19-4. In FIG. 93, SOCS3 has the sequence of SEQ ID NO:814.

FIG. 94 shows humanized SDB domain according to example 12-4.

In FIG. 94, Peptide W27 has the sequence of SEQ ID NO:1002, and Peptide V28 has the sequence of SEQ ID NO:1003.

FIG. 95 shows methylation and unmethylation level of endogenous SOCS3 in gastric cancer cell line analyzed by the agarose gel electrophoresis according to example 17-1-1. In FIG. 95, SOCS3 has the sequence of SEQ ID NO:814.

FIG. 96 shows methylation and unmethylation level of endogenous SOCS3 in colon cancer cell line analyzed by the agarose gel electrophoresis according to example 17-2-1. In FIG. 96, SOCS3 has the sequence of SEQ ID NO:814.

FIG. 97 shows sequences of amino acid and nucleotide of basic CPP, and primers used in example 6-4. In FIG. 97, SOCS3 has the sequence of SEQ ID NO:814.

FIG. 98 shows structure, expression, purification and solubility/yield of aMTD/SD-fused SOCS3 recombinant protein and basic CPP/SD-fused SOCS3 recombinant protein according to example 6-4.

In FIG. 98, HS3B has SOCS3 and SDB. SOC3 has the sequence of SEQ ID NO:814 and SDB has the sequence of SEQ ID NO: 799. $HM_{165}S3B$ has the sequence of SEQ ID NO:827, HTS3B has TAT, SOCS3 and SDB. TAT has the sequence of SEQ ID NO:832, SOC3 has the sequence of SEQ ID NO:814 and SDB has the sequence of SEQ ID NO: 799. HRS3B has Poly R, SOCS3 and SDB. Poly R has the sequence of SEQ ID NO:834, SOC3 has the sequence of SEQ ID NO:814 and SDB has the sequence of SEQ ID NO: 799.

FIG. 99 shows comparison of cell-permeability between aMTD/SD fused SOCS3 recombinant proteins and basic/SD-fused in RAW 264.7 cells according to example 7-1-2.

In FIG. 99, HS3B has SOCS3 and SDB. SOC3 has the sequence of SEQ ID NO:814 and SDB has the sequence of SEQ ID NO: 799. $HM_{165}S3B$ has the sequence of SEQ ID NO:827. HTS3B has TAT, SOCS3 and SDB. TAT has the sequence of SEQ ID NO:832, SOC3 has the sequence of SEQ ID NO:814 and SDB has the sequence of SEQ ID NO: 799. HRS3B has Poly R, SOCS3 and SDB. Poly R has the sequence of SEQ ID NO:834, SOC3 has the sequence of SEQ ID NO:814 and SDB has the sequence of SEQ ID NO: 799.

FIG. 100 shows comparison of tissue-permeability between aMTD/SD fused SOCS3 recombinant proteins and basic/SD-fused in various tissues of ICR mice according to example 7-2-2.

In FIG. 100, HS3B has SOCS3 and SDB. SOC3 has the sequence of SEQ ID NO:814 and SDB has the sequence of SEQ ID NO: 799, $HM_{165}S3B$ has the sequence of SEQ ID NO:827. HTS3B has TAT, SOCS3 and SDB. TAT has the sequence of SEQ ID NO:832, SOC3 has the sequence of SEQ ID NO:814 and SDB has the sequence of SEQ ID NO: 799. HRS3B has Poly R, SOCS3 and SDB. Poly R has the sequence of SEQ ID NO:834, SOC3 has the sequence of SEQ ID NO:814 and SDB has the sequence of SEQ ID NO: 799.

FIG. 101 shows effect of treating protein K (FIG. 101 A) and Taxol (FIG. 101 B) on aMTD (or basic CPP)-mediated SOCS3 protein uptake into cells according to example 14-2.

In FIG. 101, HS3B has SOCS3 and SDB. SOC3 has the sequence of SEQ ID NO:814 and SDB has the sequence of SEQ ID NO: 799. $HM_{165}S3B$ has the sequence of SEQ ID NO:827. HTS3B has TAT, SOCS3 and SDB. TAT has the sequence of SEQ ID NO:832, SOC3 has the sequence of SEQ ID NO:814 and SDB has the sequence of SEQ ID NO: 799. HRS3B has Poly R, SOCS3 and SDB. Poly R has the sequence of SEQ ID NO:834, SOC3 has the sequence of SEQ ID NO:814 and SDB has the sequence of SEQ ID NO: 799.

FIGS. 102 and 103 show aMTD (or basic CPP)-mediated cell-to-cell delivery (FIG. 102) and cell-to-cell function assessed according to example 14-2.

In FIGS. 102 and 103, HS3B has SOCS3 and SDB. SOC3 has the sequence of SEQ ID NO:814 and SDB has the sequence of SEQ ID NO: 799. $HM_{165}S3B$ has the sequence of SEQ ID NO:827. HTS3B has TAT, SOCS3 and SDB. TAT has the sequence of SEQ ID NO:832, SOC3 has the sequence of SEQ ID NO:814 and SDB has the sequence of SEQ ID NO: 799. HRS3B has Poly R, SOCS3 and SDB. Poly R has the sequence of SEQ ID NO:834, SOC3 has the sequence of SEQ ID NO:814 and SDB has the sequence of SEQ ID NO: 799.

FIG. 104 shows the formula for the aMTD composed of 12 amino acid sequences. In FIG. 104, X(s) independently refer to Alanine (A), Valine (V), Leucine (L) or Isoleucine (I); Proline (P) can be positioned in one of U(s) (either 5', 6', 7' or 8'); the remaining U(s) are independently composed of A, V, L or I; and P at the 12' is Proline.

FIG. 105 shows aMTDs selected for development of iCP-SOCS3 recombinant protein based on the critical Factors.

FIG. 106 shows aMTDs selected for development of iCP-SOCS3 recombinant protein, based on the critical Factors.

FIG. 107 shows five kinds of random peptides that do not satisfy one or more critical factors.

MODE FOR INVENTION

1. Analysis of Reference Hydrophobic CPPs to Identify 'Critical Factors' for Development of Advanced MTDs Previously reported MTDs were selected from a screen of more than 1,500 signal peptide sequences. Although the MTDs that have been developed did not have a common sequence or sequence motif, they were all derived from the hydrophobic (H) regions of signal sequences (HRSSs) that also lack common sequences or motifs except their hydrophobicity and the tendency to adopt alpha-helical conformations. The wide variation in H-region sequences may reflect prior evolution for proteins with membrane translocating activity and subsequent adaptation to the SRP/Sec61 machinery, which utilizes a methionine-rich signal peptide binding pocket in SRP to accommodate a wide-variety of signal peptide sequences.

Previously described hydrophobic CPPs (e.g. MTS/MTM and MTD) were derived from the hydrophobic regions present in the signal peptides of secreted and cell surface proteins. The prior art consists first, of ad hoc use of H-region sequences (MTS/MTM), and second, of H-region sequences (with and without modification) with highest CPP activity selected from a screen of 1,500 signal sequences (MTM). Second prior art, the modified H-region derived hydrophobic CPP sequences had advanced in diversity with multiple number of available sequences apart from MTS/MTM derived from fibroblast growth factor (FGF) 4. However, the number of MTDs that could be modified from naturally occurring secreted proteins are somewhat limited. Because there is no set of rules in determining their cell-permeability, no prediction for the cell-permeability of modified MTD sequences can be made before testing them.

The hydrophobic CPPs, like the signal peptides from which they originated, did not conform to a consensus sequence, and they had adverse effects on protein solubility when incorporated into protein cargo. We therefore set out to identify optimal sequence and structural determinants, namely critical factors (CFs), to design new hydrophobic CPPs with enhanced ability to deliver macromolecule cargoes including proteins into the cells and tissues while maintaining protein solubility. These newly developed CPPs, advanced macromolecule transduction domains (aMTDs) allowed almost infinite number of possible designs that could be designed and developed based on the critical factors. Also, their cell-permeability could be predicted by their character analysis before conducting any in vitro and/or in vivo experiments. These critical factors below have been developed by analyzing all published reference hydrophobic CPPs.

1-1. Analysis of hydrophobic CPPs

Seventeen different hydrophobic CPPs (Table 1) published from 1995 to 2014 (Table 2) were selected. After physiological and chemical properties of selected hydrophobic CPPs were analyzed, 11 different characteristics that may be associated with cell-permeability have been chosen for further analysis. These 11 characteristics are as follows: sequence, amino acid length, molecular weight, pI value, bending potential, rigidity/flexibility, structural feature, hydropathy, residue structure, amino acid composition and secondary structure of the sequences (Table 3).

Table 1 shows the summary of published hydrophobic Cell-Penetrating Peptides which were chosen.

TABLE 1

| # | SEQ ID NO: | Peptide | Origin | Protein | Ref. |
|---|---|---|---|---|---|
| 1 | 865 | MTM | *Homo sapiens* | NP_001998 Kaposi fibroblast growth factor (K-FGF) | 1 |
| 2 | 865 | MTS | *Homo sapiens* | NP_001998 Kaposi fibroblast growth factor (K-FGF) | 2 |
| 3 | 867 | MTD10 | *Streptomyces coelicolor* | NP_625021 Glycosyl hydrolase | 8 |
| 4 | 888 | MTD13 | *Streptomyces coelicolor* | NP_639877 Putative secreted protein | 5 |
| 5 | 869 | MTD47 | *Streptomyces coelicolor* | NP_627512 Secreted protein | 7 |
| 6 | 870 | MTD56 | *Homo sapiens* | P23274 Peptidyl-prolyl cis-trans isomerase B precursor | 6 |
| 7 | 871 | MTD73 | *Drosophila melanogaster* | AAA17887 Spatzle (spz) protein | 6 |
| 8 | 872 | MTD77 | *Homo sapiens* | NP_003231 Kaposi fibroblast growth factor (K-FGF) | 3 |
| 9 | 873 | MTD84 | Phytophthora cactorum | AAK63068 Phytotoxic protein PcF precursor | 7 |
| 10 | 874 | MTD85 | *Streptomyces coelicolor* | NP_629842 Peptide transport system peptide binding protein | 5 |
| 11 | 875 | MTD86 | *Streptomyces coelicolor* | NP_629842 Peptide transport system secreted peptide binding protein | 7 |
| 12 | 876 | MTD103 | *Homo sapiens* | TMBV19 domain family member B | 4 |
| 13 | 877 | MTD132 | *Streptomyces coelicolor* | NP_62377 P60-family secreted protein | 7 |
| 14 | 878 | MTD151 | *Streptomyces coelicolor* | NP_630126 Secreted chitinase | 8 |
| 15 | 879 | MTD173 | *Streptomyces coelicolor* | NP_624384 Secreted protein | 7 |
| 16 | 880 | MTD174 | *Streptomyces coelicolor* | NP_733505 Large, multifunctional secreted protein | 8 |
| 17 | 881 | MTD181 | *Neisseria meningitidis* Z2491 | CAB84257.1 Putative secreted protein | 7 |

Table 2 summarizes reference information

TABLE 2

| # | Title | Journal | Year | Vol | Issue | Page |
|---|---|---|---|---|---|---|
| 1 | Inhibition of Nuclear Translocation of Transcription Factor NF-kB by a Synthetic peptide Containing a Cell Membrane-permeable Motif and Nuclear Localization Sequence | JOURNAL OF BIOLOGICAL CHEMISTRY | 1995 | 270 | 24 | 14255 |
| 2 | Epigenetic Regulation of Gene Structure and Function with a Cell-Permeable Cre Recombinase | NATURE BIOTECHNOLOGY | 2001 | 19 | 10 | 929 |
| 3 | Cell-Permeable NM23 Blocks the Maintenance and Progression of Established Pulmonary Metastasis | CANCER RESEARCH | 2011 | 71 | 23 | 7216 |
| 4 | Antitumor Activity Of Cell-Permeable p18INK4c With Enhanced Membrane and Tissue Penetration | MOLECULAR THERAPY | 2012 | 20 | 8 | 1540 |
| 5 | Antitumor Activity of Cell-Permeable RUNX3 Protein in Gastric Cancer Cells | CLINICAL CANCER RESEARCH | 2012 | 19 | 3 | 680 |
| 6 | The Effect of Intracellular Protein Delivery on the Anti-Tumor Activity of Recombinant Human Endostatin | BIOMATERIALS | 2013 | 34 | 26 | 6261 |
| 7 | Partial Somatic to Stem Cell Transformations Induced By Cell-Permeable Reprogramming Factors | SCIENTIFIC REPORTS | 2014 | 4 | 10 | 4361 |
| 8 | Cell-Permeable Parkin Proteins Suppress Parkinson Disease-Associated Phenotypes in Cultured Cells and Animals | PLOS ONE | 2014 | 9 | 7 | 17 |

Table 3 shows characteristics of published hydrophobic Cell-Penetrating Peptides (A) which were analyzed.

TABLE 3

| SEQ ID NOS | Peptide | Sequence | Length | Molecular Weight | pI | Bending Potential | Rigidity/Flexibility (Instability Index: II) | Structural Feature (Aliphatic Index: AI) | Hydropathy (GRAVY) | Residue Structure | A/a Composition | | | | | | Secondary Structure | Cargo | Ref. |
|---|---|---|---|---|---|---|---|---|---|---|---|---|---|---|---|---|---|---|---|
| | | | | | | | | | | | A | V | L | I | P | G | | | |
| 865 | MTM | AAVALLPAVLLALLAP | 16 | 1,515.9 | 5.6 | Bending | 45.5 | 220.0 | 2.4 | Aliphatic Ring | 6 | 2 | 6 | 0 | 2 | 0 | Helix | p50 | 1 |
| 866 | MTS | AAVLLPVLLAAP | 12 | 1,147.4 | 5.6 | Bending | 57.3 | 211.7 | 2.3 | Aliphatic Ring | 4 | 2 | 4 | 0 | 2 | 0 | No-Helix | CRE | 2 |
| 867 | MTD10 | LGGAVVAAPVAAAVAP | 16 | 1,333.5 | 5.5 | Bending | 47.9 | 140.6 | 1.8 | Aliphatic Ring | 7 | 4 | 1 | 0 | 2 | 2 | Helix | Parkin | 8 |
| 868 | MTD13 | LAAAALAVLPL | 11 | 1,022.3 | 5.5 | Bending | 26.6 | 213.6 | 2.4 | Aliphatic Ring | 5 | 1 | 4 | 0 | 1 | 0 | No-Helix | RUNX3 | 5 |
| 869 | MTD47 | AAAVPVLVAA | 10 | 881.0 | 5.5 | Bending | 47.5 | 176.0 | 2.4 | Aliphatic Ring | 5 | 3 | 1 | 0 | 1 | 0 | No-Helix | CMYC | 7 |
| 870 | MTD56 | VLLAAAALIA | 9 | 854.1 | 5.5 | No-Bending | 8.9 | 250.0 | 3.0 | Aliphatic Ring | 4 | 1 | 3 | 1 | 0 | 0 | Helix | ES | 6 |
| 871 | MTD73 | PVLLLLA | 7 | 737.9 | 6.0 | No-Bending | 36.1 | 278.6 | 2.8 | Aliphatic Ring | 1 | 1 | 4 | 0 | 1 | 0 | Helix | ES | 6 |
| 872 | MTD77 | AVALLILAV | 9 | 882.0 | 5.6 | No-Bending | 30.3 | 271.1 | 3.3 | Aliphatic Ring | 3 | 2 | 3 | 1 | 0 | 0 | Helix | NM23 | 3 |
| 873 | MTD84 | AVALVAVVAVA | 11 | 982.2 | 5.6 | No-Bending | 9.1 | 212.7 | 3.1 | Aliphatic Ring | 5 | 5 | 1 | 0 | 0 | 0 | Helix | OCT4 | 7 |
| 874 | MTD85 | LLAAAAALLLA | 11 | 1,010.2 | 5.5 | No-Bending | 9.1 | 231.8 | 2.7 | Aliphatic Ring | 6 | 0 | 5 | 0 | 0 | 0 | No-Helix | RUNX3 | 5 |
| 875 | MTD86 | LLAAAAALLLA | 11 | 1,010.2 | 5.5 | No-Bending | 9.1 | 231.8 | 2.7 | Aliphatic Ring | 6 | 0 | 5 | 0 | 0 | 0 | No-Helix | SOX2 | 7 |
| 876 | MTD103 | LALPVLLLA | 9 | 922.2 | 5.5 | Bending | 51.7 | 271.1 | 2.8 | Aliphatic Ring | 2 | 1 | 5 | 0 | 1 | 0 | Helix | p18 | 4 |
| 877 | MTD132 | AVVVPAIVLAAP | 12 | 1,119.4 | 5.6 | Bending | 50.3 | 195.0 | 2.4 | Aliphatic Ring | 4 | 4 | 1 | 1 | 2 | 0 | No-Helix | LIN28 | 7 |
| 878 | MTD151 | AAAPVAAVP | 9 | 1,031.4 | 5.5 | Bending | 73.1 | 120.0 | 1.6 | Aliphatic Ring | 5 | 2 | 0 | 0 | 2 | 0 | No-Helix | Parkin | 8 |
| 879 | MTD173 | AVIPILAVP | 9 | 892.1 | 5.6 | Bending | 48.5 | 216.7 | 2.4 | Aliphatic Ring | 2 | 2 | 1 | 2 | 2 | 0 | Helix | KLF4 | 7 |
| 880 | MTD174 | LILLPAVALP | 11 | 1,011.8 | 5.5 | Bending | 79.1 | 257.3 | 2.6 | Aliphatic Ring | 2 | 1 | 5 | 1 | 2 | 0 | Helix | Parkin | 8 |
| 881 | MTD181 | AVLLLPAAA | 9 | 838.0 | 5.6 | Bending | 51.7 | 206.7 | 2.4 | Aliphatic Ring | 4 | 1 | 3 | 0 | 1 | 0 | No-Helix | SOX2 | 7 |
| | AVE | | 10.8 ± 2.4 | 1,011 ± 189.6 | 5.6 ± 0.1 | Proline Presence | 40.1 ± 21.9 | 217.9 ± 43.6 | 2.5 ± 0.4 | | | | | | | | | | |

Two peptide/protein analysis programs were used (ExPasy: SoSui: bio.ac.ip/sosui/sosui_submit.html) to determine various indexes and structural features of the peptide sequences and to design new sequence. Followings are important factors analyzed.

1-2. Characteristics of Analyzed Peptides: Length, Molecular Weight and PI Value Average length, molecular weight and pI value of the peptides analyzed were 10.8±2.4, 1,011±189.6 and 5.6±0.1, respectively (Table 4)

Table 4 summarizes Critical Factors (CFs) of published hydrophobic Cell-Penetrating Peptides (A) which were analyzed.

TABLE 4

Length: 10.8 ± 2.4
Molecular Weight: 1,011 ± 189.6
pI: 5.6 ± 0.1
Bending Potential (BP): Proline presences in the middle and/or the end of peptides, or No Proline.
Instability Index (II): 40.1 ± 21.9
Residue Structure & Aliphatic Index (AI): 217.9 ± 43.6
Hydropathy (GRAVY): 2.5 ± 0.4
Aliphatic Ring: Non polar hydrophobic & aliphatic amino acid (A, V, L, I).
Secondary Structure: α-Helix is favored but not required.

1-3. Characteristics of Analyzed Peptides: Bending Potential—Proline Position (PP)

Bending potential (bending or no-bending) was determined based on the fact whether proline (P) exists and/or where the amino acid(s) providing bending potential to the peptide in recombinant protein is/are located. Proline differs from the other common amino acids in that its side chain is bonded to the backbone nitrogen atom as well as the alpha-carbon atom. The resulting cyclic structure markedly influences protein architecture which is often found in the bends of folded peptide/protein chain.

Eleven out of 17 were determined as 'Bending' peptide which means that proline is present in the middle of sequence for peptide bending and/or located at the end of the peptide for protein bending. As indicated above, peptide sequences could penetrate the plasma membrane in a "bent" configuration. Therefore, bending or no-bending potential is considered as one of the critical factors for the improvement of current hydrophobic CPPs.

1-4. Characteristics of Analyzed Peptides: Rigidity/Flexibility—Instability Index Since one of the crucial structural features of any peptide is based on the fact whether the motif is rigid or flexible, which is an intact physicochemical characteristic of the peptide sequence, instability index (II) of the sequence was determined. The index value representing rigidity/flexibility of the peptide was extremely varied (8.9-79.1), but average value was 40.1±21.9 which suggested that the peptide should be somehow flexible, but not too much rigid or flexible (Table 3).

1-5. Characteristics of Analyzed Peptides: Structural Features—Structural Feature (Aliphatic Index: AI) and Hydropathy (Grand Average of Hydropathy: GRAVY)

Alanine (V), valine (V), leucine (L) and isoleucine (I) contain aliphatic side chain and are hydrophobic—that is, they have an aversion to water and like to cluster. These amino acids having hydrophobicity and aliphatic residue enable them to pack together to form compact structure with few holes. Analyzed peptide sequence showed that all composing amino acids were hydrophobic (A, V, L and I) except glycine (G) in only one out of 17 (MTD10-Table 3) and aliphatic (A, V, L, 1, and P). Their hydropathic index (Grand Average of Hydropathy: GRAVY) and aliphatic index (AI) were 2.5±0.4 and 217.9±43.6, respectively. Their amino acid composition is also indicated in the Table 3.

1-6. Characteristics of Analyzed Peptides: Secondary Structure (Helicity)

As explained above, the CPP sequences may be supposed to penetrate the plasma membrane directly after inserting into the membranes in a "bent" configuration with hydrophobic sequences having a-helical conformation. In addition, our analysis strongly indicated that betiding potential was crucial for membrane penetration. Therefore, structural analysis of the peptides was conducted to determine whether the sequences were to form helix or not. Nine peptides were helix and eight were not (Table 3). It seems to suggest that helix structure may not be required.

1-7. Determination of Critical Factors (CFs)

In the 11 characteristics analyzed, the following 6 are selected namely "Critical Factors" for the development of new hydrophobic CPPs—advanced MTDs: amino acid length, bending potential (proline presence and location), rigidity/flexibility (instability index: II), structural feature (aliphatic index: AI), hydropathy (GRAVY) and amino acid composition/residue structure (hydrophobic and aliphatic A/a) (Table 3 and Table 4).

2. Analysis of Selected Hydrophobic CPPs to Optimize 'Critical Factors'

Since the analyzed data of the 17 different hydrophobic CPPs (analysis A, Table 3 and 4) previously developed during the past 2 decades showed high variation and were hard to make common- or consensus-features, analysis B (Table 5 and 6) and C (Table 7 and 8) were also conducted to optimize the critical factors for better design of improved CPPs-aMTDs. Therefore, 17 hydrophobic CPPs have been grouped into two groups and analyzed the groups for their characteristics in relation to the cell permeable property. The critical factors have been optimized by comparing and contrasting the analytical data of the groups and determining the common homologous features that may be critical for the cell permeable property.

2-1. Selective Analysis (B) of Peptides Used to Biologically Active Cargo Protein for In Vivo In analysis B, eight CPPs were used with each biologically active cargo in vivo. Length was 11±3.2, but 3 out of 8 CPPs possessed little bending potential. Rigidity/Flexibility (instability index: II) was 41±15, but removing one [MTD85 (SEQ ID NO: 954): rigid, with minimal II (9.1)] of the peptides increased the overall instability index to 45.6±9.3. This suggested that higher flexibility (40 or higher II) is potentially be better. All other characteristics of the 8 CPPs were similar to the analysis A, including structural feature and hydropathy (Table 5 and 6)

Table 5 shows characteristics of published hydrophobic Cell-Penetrating Peptides (B): selected CPPs that were used to each cargo in vivo.

TABLE 5

| SEQ | | Rigidity/ Flexibility | Structural Feature |
|---|---|---|---|

TABLE 5-continued

| ID NOS | Peptide | Sequence | Length | Molecular Weight | pI | Bending Potential | (Instablility Index: II) | (Aliphatic Index: AI) |
|---|---|---|---|---|---|---|---|---|
| 865 | MTM | AAVALLPAVLLALLAP | 16 | 1,515.9 | 5.6 | Bending | 45.5 | 220.0 |
| 866 | MTS | AAVLLPVLLAAP | 12 | 1,147.4 | 5.6 | Bending | 57.3 | 211.7 |
| 867 | MTD10 | LGGAVVAAPVAAAVAP | 16 | 1,333.5 | 5.5 | Bending | 47.9 | 140.6 |
| 871 | MTD73 | PVLLLLA | 7 | 737.9 | 6.0 | No-Bending | 36.1 | 278.6 |
| 872 | MTD77 | AVALLILAV | 9 | 882.1 | 5.6 | No-Bending | 30.3 | 271.1 |
| 874 | MTD85 | LLAAAAALLLA | 11 | 1,010.2 | 5.5 | No-Bending | 9.1* | 231.8 |
| 876 | MTD103 | LALPVLLLA | 9 | 922.2 | 5.5 | Bending | 51.7 | 271.1 |
| 877 | MTD132 | AVVVPAIVLAAP | 12 | 1,119.4 | 5.6 | Bending | 50.3 | 195.0 |
| | AVE | | 11 ± 3.2 | 1,083 ± 252 | 5.6 ± 0.1 | Proline Presence | 41 ± 15 | 227 ± 47 |

| SEQ ID NOS | Hydropathy (GRAVY) | Residue Structure | A/a Composition A | V | L | I | P | G | Secondary Structure | Cargo | Ref. |
|---|---|---|---|---|---|---|---|---|---|---|---|
| 865 | 2.4 | Aliphatic Ring | 6 | 2 | 6 | 0 | 2 | 0 | Helix | p50 | 1 |
| 866 | 2.3 | — | 4 | 2 | 4 | 0 | 2 | 0 | No-Helix | CRE | 2 |
| 867 | 1.8 | — | 7 | 4 | 1 | 0 | 2 | 2 | Helix | Parkin | 8 |
| 871 | 2.8 | — | 1 | 1 | 4 | 0 | 1 | 0 | Helix | ES | 6 |
| 872 | 3.3 | — | 3 | 2 | 3 | 1 | 0 | 0 | Helix | NM23 | 3 |
| 874 | 2.7 | — | 6 | 0 | 5 | 0 | 0 | 0 | No-Helix | RUNX3 | 5 |
| 876 | 2.8 | — | 2 | 1 | 5 | 0 | 1 | 0 | Helix | p18 | 4 |
| 877 | 2.4 | — | 4 | 4 | 1 | 1 | 2 | 0 | No-Helix | LIN28 | 7 |
| | 2.5 ± 0.4 | | | | | | | | | | |

*Removing the MTD85 increases II to 45.6 ± 9.3.

Table 6 shows summarized Critical Factors of published hydrophobic Cell-Penetrating Peptides (B).

TABLE 6

Length: 11 ± 3.2
Molecular Weight 1,083 ± 252
pI: 5.6 ± 0.1
Bending Potential (BP): Proline presences in the middle and/or the end of peptides, or No Proline.
Instability Index (II): 41.0 ± 15 ('Removing the MTD85 increases II to 45.6 ± 9.3)
Residue Structure & Aliphatic Index (AI): 227 ± 47
Hydropathy (GRAVY): 2.5 ± 0.4
Aliphatic Ring: Nonpolar hydrophobic & aliphatic amino acid (A, V, L, I).
Secondary Structure: α-Helix is favored but not required.

2-2. Selective Analysis (C) of Peptides that Provided Bending Potential and Higher Flexibility To optimize the 'Common Range and/or Consensus Feature of Critical Factor' for the practical design of aMTDs and the random peptides (rPs or rPeptides), which were to prove that the 'Critical Factors' determined in the analysis A, B and C were correct to improve the current problems of hydrophobic CPPs—protein aggregation, low solubility/yield, and poor cell-/tissue-permeability of the recombinant proteins fused to the MTS/MTM or MTD, and non-common sequence and non-homologous structure of the peptides, empirically selected peptides were analyzed for their structural features and physicochemical factor indexes.

Hydrophobic CPPs which did not have a bending potential, rigid or too much flexible sequences (too much low or too much high Instability Index), or too low or too high hydrophobic CPPs were unselected, but secondary structure was not considered because helix structure of sequence was not required.

In analysis C, eight selected CPP sequences that could provide a bending potential and higher flexibility were finally analyzed (Table 7 and 8). Common amino acid length is 12 (11.6±3.0). Proline is presence in the middle of and/or the end of sequence. Rigidity/Flexibility (II) is 45.5-57.3 (Avg: 50.1±3.6). AI and GRAVY representing structural feature and hydrophobicity of the peptide are 204.7±37.5 and 2.4±0.3, respectively. All peptides are consisted with hydrophobic and aliphatic amino acids (A, V, L, I, and P). Therefore, analysis C was chosen as a standard for the new design of new hydrophobic CPPs-aMTDs.

Table 7 shows characteristics of published hydrophobic Cell-Penetrating Peptides (C): selected CPPs that provided bending potential and higher flexibility.

TABLE 7

| SEQ ID NOS | Peptide | Sequence | Length | Molecular Weight | pI | Bending Potential | Rigidity/ Flexibility (Instablility Index: II) | Structural Feature (Aliphatic Index: AI) |
|---|---|---|---|---|---|---|---|---|
| 865 | MTM | AAVALLPAVLLALLAP | 16 | 1,515.9 | 5.6 | Bending | 45.5 | 220.0 |
| 866 | MTS | AAVLLPVLLAAP | 12 | 1,147.4 | 5.6 | Bending | 57.3 | 211.7 |
| 867 | MTD10 | LGGAVVAAPVAAAVAP | 16 | 1,333.5 | 5.5 | Bending | 47.9 | 140.6 |
| 869 | MTD47 | AAAVPVLVAA | 10 | 881.0 | 5.6 | Bending | 47.5 | 176.0 |
| 876 | MTD103 | LALPVLLLA | 9 | 922.2 | 5.5 | Bending | 51.7 | 271.1 |

TABLE 7-continued

| | | | | | | | | | |
|---|---|---|---|---|---|---|---|---|---|
| 877 | MTD132 | AVVVPAIVLAAP | 12 | 1,119.4 | 5.6 | Bending | | 50.3 | 195.0 |
| 879 | MTD173 | AVIPILAVP | 9 | 892.1 | 5.6 | Bending | | 48.5 | 216.7 |
| 881 | MTD181 | AVLLLPAAA | 9 | 838.0 | 5.6 | Bending | | 51.7 | 206.7 |
| | | AVE | 11.6 ± 3.0 | 1,081 ± 244.6 | 5.6 ± 0.1 | Proline Presence | | 50.1 ± 3.6 | 204.7 ± 37.5 |

| SEQ ID NOS | Hydropathy (GRAVY) | Residue Structure | A/a Composition | | | | | Secondary Structure | Cargo | Ref. |
|---|---|---|---|---|---|---|---|---|---|---|
| | | | A | V | L | I | P | G | | | |
| 865 | 2.4 | Aliphatic Ring | 6 | 2 | 6 | 0 | 2 | 0 | Helix | p50 | 1 |
| 866 | 2.3 | Aliphatic Ring | 4 | 2 | 4 | 0 | 2 | 0 | No-Helix | CRE | 2 |
| 867 | 1.8 | Aliphatic Ring | 7 | 4 | 1 | 0 | 2 | 2 | Helix | PARKIN | 8 |
| 869 | 2.4 | Aliphatic Ring | 5 | 3 | 1 | 0 | 1 | 0 | No-Helix | CMYC | 7 |
| 876 | 2.8 | Aliphatic Ring | 2 | 1 | 5 | 0 | 1 | 0 | Helix | p18 INK4C | 4 |
| 877 | 2.4 | Aliphatic Ring | 4 | 4 | 1 | 1 | 2 | 0 | No-Helix | LIN28 | 7 |
| 879 | 2.4 | Aliphatic Ring | 2 | 2 | 1 | 2 | 2 | 0 | Helix | KLF4 | 7 |
| 881 | 2.4 | Aliphatic Ring | 4 | 1 | 3 | 0 | 1 | 0 | No-Helix | SOX2 | 7 |
| | 2.4 ± 0.3 | | | | | | | | | | |

Table 8 shows summarized Critical Factors of published hydrophobic Cell-Penetrating Peptides (C)

TABLE 8

Length: 11.6 ± 3.0
Molecular Weight: 1,081.2 ± 224.6
pI: 5.6 ± 0.1
Bending Potential (BP): Proline presences in the middle and/or the end of peptides.
Instability Index (II): 50.1 ± 3.6
Residue Structure & Aliphatic Index (AI): 204.7 ± 37.5
Hydropathy (GRAVY): 2.4 ± 0.3
Aliphatic Ring: Non-polar hydrophobic & aliphatic amino acid (A, V, L, I).
Secondary Structure: α-Helix is favored but not required.

3. New Design of Improved Hydrophobic CPPs—aMTDs Based on the Optimized Critical Factors 3-1. Determination of Common Sequence and/or Common Homologous Structure As mentioned above, H-regions of signal sequence (HRSS)-derived CPPs (MTS/MTM and MTD) do not have a common sequence, sequence motif, and/or common-structural homologous feature. In this invention, the aim is to develop improved hydrophobic CPPs formatted in the common sequence- and structural-motif which satisfy newly determined 'Critical Factors' to have 'Common Function,' namely, to facilitate protein translocation across the membrane with similar mechanism to the analyzed reference CPPs. Based on the analysis A, B and C, the common homologous features have been analyzed to determine the critical factors that influence the cell-permeability. The range value of each critical factor has been determined to include the analyzed index of each critical factor from analysis A, B and C to design novel aMTDs (Table 9). These features have been confirmed experimentally with newly designed aMTDs in their cell-permeability.

Table 9 shows comparison the range/feature of each Critical Factor between the value of analyzed CPPs and the value determined for new design of novel aMTDs sequences

TABLE 9

Summarized Critical Factors of aMTD

| Critical Factor | Selected CPPs Range | Newly Designed CPPs Range |
|---|---|---|
| Bending Potential (Proline Position: PP) | Proline presences in the middle and/or at the end of peptides | Proline presences in the middle (5', 6', 7' or 8') and at the end of peptides |
| Rigidity/Flexibility (Instability Index: II) | 45.5-57.3 (50.1 ± 3.6) | 40-60 |
| Structural Feature (Aliphatic Index: AI) | 140.6-220.0 (204.7 ± 37.5) | 180-220 |
| Hydropathy (Grand Average of Hydropathy GRAVY) | 1.8-2.8 (2.4 ± 0.3) | 2.1-2.6 |
| Length (Number of Amino Acid) | 11.6 ± 3.0 | 9-13 |
| Amino acid Composition | A, V, I, L, P | A, V, I, L, P |

In Table 9, universal common features and sequence/structural motif are provided. Length is 9-13 amino acids, and bending potential is provided with the presence of proline in the middle of sequence (at 5', 6', 7' or 8' amino acid) for peptide bending and at the end of peptide for recombinant protein bending and Rigidity/Flexibility of aMTDs is II>40 are described in Table 9.

3-2. Critical Factors for Development of Advanced MTDs

Recombinant cell-permeable proteins fused to the hydrophobic CPPs to deliver therapeutically active cargo molecules including proteins into live cells had previously been reported, but the fusion proteins expressed in bacteria system were hard to be purified as a soluble form due to their low solubility and yield. To address the crucial weakness for further clinical development of the cell-permeable proteins as protein-based biotherapeutics, greatly improved form of the hydrophobic CPP, named as advanced MTD (aMTD) has newly been developed through critical factors-based peptide analysis. The critical factors used for the current invention of the aMTDs are herein (Table 9).

1. Amino Acid Length: 9-13

2. Bending Potential (Proline Position: PP)
: Proline, presences in the middle (from 5' to 8' amino acid) and at the end of sequence
  3. Rigidity/Flexibility (Instability Index: II): 40-60
  4. Structural Feature (Aliphatic Index: AI): 180-220
  5. Hydropathy (GRAVY): 2.1-2.6
  6. Amino Acid Composition: Hydrophobic and Aliphatic amino acids—A, V, L, I and P 3-3. Design of Potentially Best aMTDs that all Critical Factors are Considered and Satisfied After careful consideration of six critical factors derived from analysis of unique features of hydrophobic CPPs, advanced macromolecule transduction domains (aMTDs) have been designed and developed based on the common 12 amino acid platform (FIG. 104) which satisfies the critical factors including amino acid length (9-13) determined from the analysis.

Unlike previously published hydrophobic CPPs that require numerous experiments to determine their cell-permeability, newly developed aMTD sequences could be designed by performing just few steps as follows using above mentioned platform to follow the determined range value/feature of each critical factor.

First, prepare the 12 amino acid sequence platform for aMTD. Second, place proline (P) in the end (12') of sequence and determine where to place proline in one of four U(s) in 5', 6', 7', and 8. Third, alanine (A), valine (V), leucine (L) or isoleucine (I) is placed in either X(s) and/or U(s), where proline is not placed. Lastly, determine whether the amino acid sequences designed based on the platform, satisfy the value or feature of six critical factors to assure the cell permeable property of aMTD sequences. Through these processes, numerous novel aMTD sequences have been constructed. The expression vectors for preparing non-functional cargo recombinant proteins fused to each aMTD, expression vectors have been constructed and forcedly expressed in bacterial cells. These aMTD-fused recombinant proteins have been purified in soluble form and determined their cell-permeability quantitatively. aMTD sequences have been newly designed, numbered from 1 to 240, as shown in Table 10-15. In Table 10-15, sequence ID Number is a sequence listings for reference, and aMTD numbers refer to amino acid listing numbers that actually have been used at the experiments. For further experiments, aMTD numbers have been used. In addition, polynucleotide sequences shown in the sequence lists have been numbered from SEQ ID NO: 241 to SEQ ID NO: 480.

Tables 10 to 15 shows 240 new hydrophobic aMTD sequences that were developed to satisfy all critical factors.

TABLE 10

| Sequence ID Number | aMTD | Sequences | Length | Rigidity/ Flexibility (II) | Structural Feature (AI) | Hydro- pathy (GRAVY) | Residue Structure |
|---|---|---|---|---|---|---|---|
| 1 | 1 | AAALAPVVLALP | 12 | 57.3 | 187.5 | 2.1 | Aliphatic |
| 2 | 2 | AAAVPLLAVVVP | 12 | 41.3 | 195.0 | 2.4 | Aliphatic |
| 3 | 3 | AALLVPAAVLAP | 12 | 57.3 | 187.5 | 2.1 | Aliphatic |
| 4 | 4 | ALALLPVAALAP | 12 | 57.3 | 195.8 | 2.1 | Aliphatic |
| 5 | 5 | AAALLPVALVAP | 12 | 57.3 | 187.5 | 2.1 | Aliphatic |
| 6 | 11 | VVALAPALAALP | 12 | 57.3 | 187.5 | 2.1 | Aliphatic |
| 7 | 12 | LLAAVPAVLLAP | 12 | 57.3 | 211.7 | 2.3 | Aliphatic |
| 8 | 13 | AAALVPVVALLP | 12 | 57.3 | 203.3 | 2.3 | Aliphatic |
| 9 | 21 | AVALLPALLAVP | 12 | 57.3 | 211.7 | 2.3 | Aliphatic |
| 10 | 22 | AVVLVPVLAAAP | 12 | 57.3 | 195.0 | 2.4 | Aliphatic |
| 11 | 23 | VVLVLPAAAAVP | 12 | 57.3 | 195.0 | 2.4 | Aliphatic |
| 12 | 24 | IALAAPALIVAP | 12 | 50.2 | 195.8 | 2.2 | Aliphatic |
| 13 | 25 | IVAVAPALVALP | 12 | 50.2 | 203.3 | 2.4 | Aliphatic |
| 14 | 42 | VAALPVVAVVAP | 12 | 57.3 | 186.7 | 2.4 | Aliphatic |
| 15 | 43 | LLAAPLVVAAVP | 12 | 41.3 | 187.5 | 2.1 | Aliphatic |
| 16 | 44 | ALAVPVALLVAP | 12 | 57.3 | 203.3 | 2.3 | Aliphatic |
| 17 | 61 | VAALPVLLAALP | 12 | 57.3 | 211.7 | 2.3 | Aliphatic |
| 18 | 62 | VALLAPVALAVP | 12 | 57.3 | 203.3 | 2.3 | Aliphatic |
| 19 | 63 | AALLVPALVAVP | 12 | 57.3 | 203.3 | 2.3 | Aliphatic |

TABLE 11

| Sequence ID Number | aMTD | Sequences | Length | Rigidity/ Flexibility (II) | Structural Feature (AI) | Hydro-pathy (GRAVY) | Residue Structure |
|---|---|---|---|---|---|---|---|
| 20 | 64 | AIVALPVAVLAP | 12 | 50.2 | 203.3 | 2.4 | Aliphatic |
| 21 | 65 | IAIVAPVVALAP | 12 | 50.2 | 203.3 | 2.4 | Aliphatic |
| 22 | 81 | AALLPALAALLP | 12 | 57.3 | 204.2 | 2.1 | Aliphatic |
| 23 | 82 | AVVLAPVAAVLP | 12 | 57.3 | 195.0 | 2.4 | Aliphatic |
| 24 | 83 | LAVAAPLALALP | 12 | 41.3 | 195.8 | 2.1 | Aliphatic |
| 25 | 84 | AAVAAPLLLALP | 12 | 41.3 | 195.8 | 2.1 | Aliphatic |
| 26 | 85 | LLVLPAAALAAP | 12 | 57.3 | 195.8 | 2.1 | Aliphatic |
| 27 | 101 | LVALAPVAAVLP | 12 | 57.3 | 203.3 | 2.3 | Aliphatic |
| 28 | 102 | LALAPAALALLP | 12 | 57.3 | 204.2 | 2.1 | Aliphatic |
| 29 | 103 | ALIAAPILALAP | 12 | 57.3 | 204.2 | 2.2 | Aliphatic |
| 30 | 104 | AVVAAPLVLALP | 12 | 41.3 | 203.3 | 2.3 | Aliphatic |
| 31 | 105 | LLALAPAALLAP | 12 | 57.3 | 204.1 | 2.1 | Aliphatic |
| 32 | 121 | AIVALPALALAP | 12 | 50.2 | 195.8 | 2.2 | Aliphatic |
| 33 | 123 | AAIIVPAALLAP | 12 | 50.2 | 195.8 | 2.2 | Aliphatic |
| 34 | 124 | IAVALPALIAAP | 12 | 50.3 | 195.8 | 2.2 | Aliphatic |
| 35 | 141 | AVIVLPALAVAP | 12 | 50.2 | 203.3 | 2.4 | Aliphatic |
| 36 | 143 | AVLAVPAVLVAP | 12 | 57.3 | 195.0 | 2.4 | Aliphatic |
| 37 | 144 | VLAIVPAVALAP | 12 | 50.2 | 203.3 | 2.4 | Aliphatic |
| 38 | 145 | LLAVVPAVALAP | 12 | 57.3 | 203.3 | 2.3 | Aliphatic |
| 39 | 161 | AVIALPALIAAP | 12 | 57.3 | 195.8 | 2.2 | Aliphatic |
| 40 | 162 | AVVALPAALIVP | 12 | 50.2 | 203.3 | 2.4 | Aliphatic |
| 41 | 163 | LALVLPAALAAP | 12 | 57.3 | 195.8 | 2.1 | Aliphatic |
| 42 | 164 | LAAVLPALLAAP | 12 | 57.3 | 195.8 | 2.1 | Aliphatic |
| 43 | 165 | ALAVPVALAIVP | 12 | 50.2 | 203.3 | 2.4 | Aliphatic |
| 44 | 182 | ALIAPVVALVAP | 12 | 57.3 | 203.3 | 2.4 | Aliphatic |
| 45 | 183 | LLAAPVVIALAP | 12 | 57.3 | 211.6 | 2.4 | Aliphatic |
| 46 | 184 | LAAIVPAIIAVP | 12 | 50.2 | 211.6 | 2.4 | Aliphatic |
| 47 | 185 | AALVLPLIIAAP | 12 | 41.3 | 220.0 | 2.4 | Aliphatic |
| 48 | 201 | LALAVPALAALP | 12 | 57.3 | 195.8 | 2.1 | Aliphatic |
| 49 | 204 | LIAALPAVAALP | 12 | 57.3 | 195.8 | 2.2 | Aliphatic |
| 50 | 205 | ALALVPAIAALP | 12 | 57.3 | 195.8 | 2.2 | Aliphatic |
| 51 | 221 | AAILAPIVALAP | 12 | 50.2 | 195.8 | 2.2 | Aliphatic |
| 52 | 222 | ALLIAPAAVIAP | 12 | 57.3 | 195.8 | 2.2 | Aliphatic |
| 53 | 223 | AILAVPIAVVAP | 12 | 57.3 | 203.3 | 2.4 | Aliphatic |
| 54 | 224 | ILAAVPIALAAP | 12 | 57.3 | 195.8 | 2.2 | Aliphatic |
| 55 | 225 | VAALLPAAAVLP | 12 | 57.3 | 187.5 | 2.1 | Aliphatic |
| 56 | 241 | AAAVVPVLLVAP | 12 | 57.3 | 195.0 | 2.4 | Aliphatic |
| 57 | 242 | AALLVPALVAAP | 12 | 57.3 | 187.5 | 2.1 | Aliphatic |

TABLE 11-continued

| Sequence ID Number | aMTD | Sequences | Length | Rigidity/ Flexibility (II) | Structural Feature (AI) | Hydropathy (GRAVY) | Residue Structure |
|---|---|---|---|---|---|---|---|
| 58 | 243 | AAVLLPVALAAP | 12 | 57.3 | 187.5 | 2.1 | Aliphatic |
| 59 | 245 | AAALAPVLALVP | 12 | 57.3 | 187.5 | 2.1 | Aliphatic |
| 60 | 261 | LVLVPLLAAAAP | 12 | 41.3 | 211.6 | 2.3 | Aliphatic |
| 61 | 262 | ALIAVPAIIVAP | 12 | 50.2 | 211.6 | 2.4 | Aliphatic |
| 62 | 263 | ALAVIPAAAILP | 12 | 54.9 | 195.8 | 2.2 | Aliphatic |
| 63 | 264 | LAAAPVVIVIAP | 12 | 50.2 | 203.3 | 2.4 | Aliphatic |
| 64 | 265 | VLAIAPLLAAVP | 12 | 41.3 | 211.6 | 2.3 | Aliphatic |
| 65 | 281 | ALIVLPAAVAVP | 12 | 50.2 | 203.3 | 2.4 | Aliphatic |
| 66 | 282 | VLAVAPALIVAP | 12 | 50.2 | 203.3 | 2.4 | Aliphatic |
| 67 | 283 | AALLAPALIVAP | 12 | 50.2 | 195.8 | 2.2 | Aliphatic |
| 68 | 284 | ALIAPAVALIVP | 12 | 50.2 | 211.7 | 2.4 | Aliphatic |
| 69 | 285 | AIVLLPAAVVAP | 12 | 50.2 | 203.3 | 2.4 | Aliphatic |

TABLE 12

| Sequence ID Number | aMTD | Sequences | Length | Rigidity/ Flexibility (II) | Structural Feature (AI) | Hydropathy (GRAVY) | Residue Structure |
|---|---|---|---|---|---|---|---|
| 70 | 301 | VIAAPVLAVLAP | 12 | 57.3 | 203.3 | 2.4 | Aliphatic |
| 71 | 302 | LALAPALALLAP | 12 | 57.3 | 204.2 | 2.1 | Aliphatic |
| 72 | 304 | AIILAPIAAIAP | 12 | 57.3 | 204.2 | 2.3 | Aliphatic |
| 73 | 305 | IALAAPILLAAP | 12 | 57.3 | 204.2 | 2.2 | Aliphatic |
| 74 | 321 | IVAVALPALAVP | 12 | 50.2 | 203.3 | 2.3 | Aliphatic |
| 75 | 322 | VVAIVLPALAAP | 12 | 50.2 | 203.3 | 2.3 | Aliphatic |
| 76 | 323 | IVAVALPVALAP | 12 | 50.2 | 203.3 | 2.3 | Aliphatic |
| 77 | 324 | IVAVALPAALVP | 12 | 50.2 | 203.3 | 2.3 | Aliphatic |
| 78 | 325 | IVAVALPAVALP | 12 | 50.2 | 203.3 | 2.3 | Aliphatic |
| 79 | 341 | IVAVALPAVLAP | 12 | 50.2 | 203.3 | 2.3 | Aliphatic |
| 80 | 342 | VIVALAPAVLAP | 12 | 50.2 | 203.3 | 2.3 | Aliphatic |
| 81 | 343 | IVAVALPALVAP | 12 | 50.2 | 203.3 | 2.3 | Aliphatic |
| 82 | 345 | ALLIVAPVAVAP | 12 | 50.2 | 203.3 | 2.3 | Aliphatic |
| 83 | 361 | AVVIVAPAVIAP | 12 | 50.2 | 195.0 | 2.4 | Aliphatic |
| 84 | 363 | AVLAVAPALIVP | 12 | 50.2 | 203.3 | 2.3 | Aliphatic |
| 85 | 364 | LVAAVAPALIVP | 12 | 50.2 | 203.3 | 2.3 | Aliphatic |
| 86 | 365 | AVIVVAPALLAP | 12 | 50.2 | 203.3 | 2.3 | Aliphatic |
| 87 | 381 | VVAIVLPAVAAP | 12 | 50.2 | 195.0 | 2.4 | Aliphatic |
| 88 | 382 | AAALVIPAILAP | 12 | 54.9 | 195.8 | 2.2 | Aliphatic |
| 89 | 383 | VIVALAPALLAP | 12 | 50.2 | 211.6 | 2.3 | Aliphatic |
| 90 | 384 | VIVAIAPALLAP | 12 | 50.2 | 211.6 | 2.4 | Aliphatic |
| 91 | 385 | IVAIAVPALVAP | 12 | 50.2 | 203.3 | 2.4 | Aliphatic |

TABLE 12-continued

| Sequence ID Number | aMTD | Sequences | Length | Rigidity/ Flexibility (II) | Structural Feature (AI) | Hydro- pathy (GRAVY) | Residue Structure |
|---|---|---|---|---|---|---|---|
| 92 | 401 | AALAVIPAAILP | 12 | 54.9 | 195.8 | 2.2 | Aliphatic |
| 93 | 402 | ALAAVIPAAILP | 12 | 54.9 | 195.8 | 2.2 | Aliphatic |
| 94 | 403 | AAALVIPAAILP | 12 | 54.9 | 195.8 | 2.2 | Aliphatic |
| 95 | 404 | LAAAVIPAAILP | 12 | 54.9 | 195.8 | 2.2 | Aliphatic |
| 96 | 405 | LAAAVIPVAILP | 12 | 54.9 | 211.7 | 2.4 | Aliphatic |
| 97 | 421 | AAILAAPLIAVP | 12 | 57.3 | 195.8 | 2.2 | Aliphatic |
| 98 | 422 | VVAILAPLLAAP | 12 | 57.3 | 211.7 | 2.4 | Aliphatic |
| 99 | 424 | AVVVAAPVLALP | 12 | 57.3 | 195.0 | 2.4 | Aliphatic |
| 100 | 425 | AVVAIAPVLALP | 12 | 57.3 | 203.3 | 2.4 | Aliphatic |
| 101 | 442 | ALAALVPAVLVP | 12 | 57.3 | 203.3 | 2.3 | Aliphatic |
| 102 | 443 | ALAALVPVALVP | 12 | 57.3 | 203.3 | 2.3 | Aliphatic |
| 103 | 444 | LAAALVPVALVP | 12 | 57.3 | 203.3 | 2.3 | Aliphatic |
| 104 | 445 | ALAALVPALVVP | 12 | 57.3 | 203.3 | 2.3 | Aliphatic |
| 105 | 461 | IAAVIVPAVALP | 12 | 50.2 | 203.3 | 2.4 | Aliphatic |
| 106 | 462 | IAAVLVPAVALP | 12 | 57.3 | 203.3 | 2.4 | Aliphatic |
| 107 | 463 | AVAILVPLLAAP | 12 | 57.3 | 211.7 | 2.4 | Aliphatic |
| 108 | 464 | AVVILVPLAAAP | 12 | 57.3 | 203.3 | 2.4 | Aliphatic |
| 109 | 465 | IAAVIVPVAALP | 12 | 50.2 | 203.3 | 2.4 | Aliphatic |
| 110 | 481 | AIAIAIVPVALP | 12 | 50.2 | 211.6 | 2.4 | Aliphatic |
| 111 | 482 | ILAVAAIPVAVP | 12 | 54.9 | 203.3 | 2.4 | Aliphatic |
| 112 | 483 | ILAAAIIPAALP | 12 | 54.9 | 204.1 | 2.2 | Aliphatic |
| 113 | 484 | LAVVLAAPAIVP | 12 | 50.2 | 203.3 | 2.4 | Aliphatic |
| 114 | 485 | AILAAIVPLAVP | 12 | 50.2 | 211.6 | 2.4 | Aliphatic |
| 115 | 501 | VIVALAVPALAP | 12 | 50.2 | 203.3 | 2.4 | Aliphatic |
| 116 | 502 | AIVALAVPVLAP | 12 | 50.2 | 203.3 | 2.4 | Aliphatic |
| 117 | 503 | AAIIIVLPAALP | 12 | 50.2 | 220.0 | 2.4 | Aliphatic |
| 118 | 504 | LIVALAVPALAP | 12 | 50.2 | 211.7 | 2.4 | Aliphatic |
| 119 | 505 | AIIIVIAPAAAP | 12 | 50.2 | 195.8 | 2.3 | Aliphatic |

TABLE 13

| Sequence ID Number | aMTD | Sequences | Length | Rigidity/ Flexibility (II) | Structural Feature (AI) | Hydro- pathy (GRAVY) | Residue Structure |
|---|---|---|---|---|---|---|---|
| 120 | 521 | LAALIVVPAVAP | 12 | 50.2 | 203.3 | 2.4 | Aliphatic |
| 121 | 522 | ALLVIAVPAVAP | 12 | 57.3 | 203.3 | 2.4 | Aliphatic |
| 122 | 524 | AVALIVVPALAP | 12 | 50.2 | 203.3 | 2.4 | Aliphatic |
| 123 | 525 | ALAIVVAPVAVP | 12 | 50.2 | 195.0 | 2.4 | Aliphatic |
| 124 | 541 | LLALIIAPAAAP | 12 | 57.3 | 204.1 | 2.1 | Aliphatic |

TABLE 13-continued

| Sequence ID Number | aMTD | Sequences | Length | Rigidity/ Flexibility (II) | Structural Feature (AI) | Hydro-pathy (GRAVY) | Residue Structure |
|---|---|---|---|---|---|---|---|
| 125 | 542 | ALALIIVPAVAP | 12 | 50.2 | 211.6 | 2.4 | Aliphatic |
| 126 | 543 | LLAAL1APAALP | 12 | 57.3 | 204.1 | 2.1 | Aliphatic |
| 127 | 544 | IVALIVAPAAVP | 12 | 43.1 | 203.3 | 2.4 | Aliphatic |
| 128 | 545 | VVLVLAAPAAVP | 12 | 57.3 | 195.0 | 2.3 | Aliphatic |
| 129 | 561 | AAVAIVLPAVVP | 12 | 50.2 | 195.0 | 2.4 | Aliphatic |
| 130 | 562 | ALIAAIVPALVP | 12 | 50.2 | 211.7 | 2.4 | Aliphatic |
| 131 | 563 | ALAVIVVPALAP | 12 | 50.2 | 203.3 | 2.4 | Aliphatic |
| 132 | 564 | VAIALIVPALAP | 12 | 50.2 | 211.7 | 2.4 | Aliphatic |
| 133 | 565 | VAIVLVAPAVAP | 12 | 50.2 | 195.0 | 2.4 | Aliphatic |
| 134 | 582 | VAVALIVPALAP | 12 | 50.2 | 203.3 | 2.4 | Aliphatic |
| 135 | 583 | AVILALAPIVAP | 12 | 50.2 | 211.6 | 2.4 | Aliphatic |
| 136 | 585 | ALIVAIAPALVP | 12 | 50.2 | 211.6 | 2.4 | Aliphatic |
| 137 | 601 | AAILIAVPIAAP | 12 | 57.3 | 195.8 | 2.3 | Aliphatic |
| 138 | 602 | VIVALAAPVLAP | 12 | 50.2 | 203.3 | 2.4 | Aliphatic |
| 139 | 603 | VLVALAAPVIAP | 12 | 57.3 | 203.3 | 2.4 | Aliphatic |
| 140 | 604 | VALIAVAPAVVP | 12 | 57.3 | 195.0 | 2.4 | AllPhatie |
| 141 | 605 | VIAAVLAPVAVP | 12 | 57.3 | 195.0 | 2.4 | Aliphatic |
| 142 | 622 | ALIVLAAPVAVP | 12 | 50.2 | 203.3 | 2.4 | Aliphatic |
| 143 | 623 | VAAAIALPAIVP | 12 | 50.2 | 187.5 | 2.3 | Aliphatic |
| 144 | 625 | ILAAAAAPLIVP | 12 | 50.2 | 195.8 | 2.2 | Aliphatic |
| 145 | 643 | LALVLAAPAIVP | 12 | 50.2 | 211.6 | 2.4 | Aliphatic |
| 146 | 645 | ALAVVALPAIVP | 12 | 50.2 | 203.3 | 2.4 | Aliphatic |
| 147 | 661 | AAILAPIVAALP | 12 | 50.2 | 195.8 | 2.2 | Aliphatic |
| 148 | 664 | ILIAIAIPAAAP | 12 | 54.9 | 204.1 | 2.3 | Aliphatic |
| 149 | 665 | LAIVLAAPVAVP | 12 | 50.2 | 203.3 | 2.3 | Aliphatic |
| 150 | 666 | AAIAIIAPAIVP | 12 | 50.2 | 195.8 | 2.3 | Aliphatic |
| 151 | 667 | LAVAIVAPALVP | 12 | 50.2 | 203.3 | 2.3 | Aliphatic |
| 152 | 683 | LAIVLAAPAVLP | 12 | 50.2 | 211.7 | 2.4 | Aliphatic |
| 153 | 684 | AAIVLALPAVLP | 12 | 50.2 | 211.7 | 2.4 | Aliphatic |
| 154 | 685 | ALLYAVLPAALP | 12 | 57.3 | 211.7 | 2.3 | Aliphatic |
| 155 | 686 | AALVAVLPVALP | 12 | 57.3 | 203.3 | 2.3 | Aliphatic |
| 156 | 687 | AILAVALPLLAP | 12 | 57.3 | 220.0 | 2.3 | Aliphatic |
| 157 | 703 | IVAVALVPALAP | 12 | 50.2 | 203.3 | 2.4 | Aliphatic |
| 158 | 705 | IVAVALLPALAP | 12 | 50.2 | 211.7 | 2.4 | Aliphatic |
| 159 | 706 | IVAVALLPAVAP | 12 | 50.2 | 203.3 | 2.4 | Aliphatic |
| 160 | 707 | IVALAVLPAVAP | 12 | 50.2 | 203.3 | 2.4 | Aliphatic |
| 161 | 724 | VAVLAVLPALAP | 12 | 57.3 | 203.3 | 2.3 | Aliphatic |
| 162 | 725 | IAVLAVAPAVLP | 12 | 57.3 | 203.3 | 2.3 | Aliphatic |

TABLE 13-continued

| Sequence ID Number | aMTD | Sequences | Length | Rigidity/ Flexibility (II) | Structural Feature (AI) | Hydro- pathy (GRAVY) | Residue Structure |
|---|---|---|---|---|---|---|---|
| 163 | 726 | LAVAIIAPAVAP | 12 | 57.3 | 187.5 | 2.2 | Aliphatic |
| 164 | 727 | VALAIALPAVLP | 12 | 57.3 | 211.6 | 2.3 | Aliphatic |
| 165 | 743 | AIAIALVPVALP | 12 | 57.3 | 211.6 | 2.4 | Aliphatic |
| 166 | 744 | AAVVIVAPVALP | 12 | 50.2 | 195.0 | 2.4 | Aliphatic |
| 167 | 746 | VAIIVVAPALAP | 12 | 50.2 | 203.3 | 2.4 | Aliphatic |
| 168 | 747 | VALLAIAPALAP | 12 | 57.3 | 195.8 | 2.2 | Aliphatic |
| 169 | 763 | VAVLIAVPALAP | 12 | 57.3 | 203.3 | 2.3 | Aliphatic |

TABLE 14

| Sequence ID Number | aMTD | Sequences | Length | Rigidity/ Flexibility (II) | Structural Feature (AI) | Hydro- pathy (GRAVY) | Residue Structure |
|---|---|---|---|---|---|---|---|
| 170 | 764 | AVALAVLPAVVP | 12 | 57.3 | 195.0 | 2.3 | Aliphatic |
| 171 | 765 | AVALAVVPAVLP | 12 | 57.3 | 195.0 | 2.3 | Aliphatic |
| 172 | 766 | IVVIAVAPAVAP | 12 | 50.2 | 195.0 | 2.4 | Aliphatic |
| 173 | 767 | IVVAAVVPALAP | 12 | 50.2 | 195.0 | 2.4 | Aliphatic |
| 174 | 783 | IVALVPAVAIAP | 12 | 50.2 | 203.3 | 2.5 | Aliphatic |
| 175 | 784 | VAALPAVALVVP | 12 | 57.3 | 195.0 | 2.4 | Aliphatic |
| 176 | 786 | LVAIAPLAVLAP | 12 | 41.3 | 211.7 | 2.4 | Aliphatic |
| 177 | 787 | AVALVPVIVAAP | 12 | 50.2 | 195.0 | 2.4 | Aliphatic |
| 178 | 788 | AIAVAIAPVALP | 12 | 57.3 | 187.5 | 2.3 | Aliphatic |
| 179 | 803 | AIALAVPVLALP | 12 | 57.3 | 211.7 | 2.4 | Aliphatic |
| 180 | 805 | LVLIAAAPIALP | 12 | 41.3 | 220.0 | 2.4 | Aliphatic |
| 181 | 806 | LVALAVPAAVLP | 12 | 57.3 | 203.3 | 2.3 | Aliphatic |
| 182 | 807 | AVALAVPALVLP | 12 | 57.3 | 203.3 | 2.3 | Aliphatic |
| 183 | 808 | LVVLAAAPLAVP | 12 | 41.3 | 203.3 | 2.3 | Aliphatic |
| 184 | 809 | LIVLAAPALAAP | 12 | 50.2 | 195.8 | 2.2 | Aliphatic |
| 185 | 810 | VIVLAAPALAAP | 12 | 50.2 | 187.5 | 2.2 | Aliphatic |
| 186 | 811 | AVVLAVPALAVP | 12 | 57.3 | 195.0 | 2.3 | Aliphatic |
| 187 | 824 | LIIVAAAPAVAP | 12 | 50.2 | 187.5 | 2.3 | Aliphatic |
| 188 | 825 | IVAVIVAPAVAP | 12 | 43.2 | 195.0 | 2.5 | Aliphatic |
| 189 | 826 | LVALAAPIIAVP | 12 | 41.3 | 211,7 | 2.4 | Aliphatic |
| 190 | 827 | IAAVLAAPALVP | 12 | 57.3 | 187.5 | 2.2 | Aliphatic |
| 191 | 828 | IALLAAPIIAVP | 12 | 41.3 | 220.0 | 2.4 | Aliphatic |
| 192 | 829 | AALALVAPVIVP | 12 | 50.2 | 203.3 | 2.4 | Aliphatic |
| 193 | 830 | IALVAAPVALVP | 12 | 57.3 | 203.3 | 2.4 | Aliphatic |
| 194 | 831 | IIVAVAPAAIVP | 12 | 43.2 | 203.3 | 2.5 | Aliphatic |
| 195 | 832 | AVAAIVPVIVAP | 12 | 43.2 | 195.0 | 2.5 | Aliphatic |
| 196 | 843 | AVLVLVAPAAAP | 12 | 41.3 | 219.2 | 2.5 | Aliphatic |

TABLE 14-continued

| Sequence ID Number | aMTD | Sequences | Length | Rigidity/ Flexibility (II) | Structural Feature (AI) | Hydro-pathy (GRAVY) | Residue Structure |
|---|---|---|---|---|---|---|---|
| 197 | 844 | VVALLAPLIAAP | 12 | 41.3 | 211.8 | 2.4 | Aliphatic |
| 198 | 845 | AAVVIAPLLAVP | 12 | 41.3 | 203.3 | 2.4 | Aliphatic |
| 199 | 846 | IAVAVAAPLLVP | 12 | 41.3 | 200.3 | 2.4 | Aliphatic |
| 200 | 847 | LVAIVVLPAVAP | 12 | 50.2 | 219.2 | 2.6 | Aliphatic |
| 201 | 848 | AVAIVVLPAVAP | 12 | 50.2 | 195.0 | 2.4 | Aliphatic |
| 202 | 849 | AVILLAPLIAAP | 12 | 57.3 | 220.0 | 2.4 | Aliphatic |
| 203 | 850 | LVIALAAPVALP | 12 | 57.3 | 211.7 | 2.4 | Aliphatic |
| 204 | 851 | VLAVVLPAVALP | 12 | 57.3 | 219.2 | 2.5 | Aliphatic |
| 205 | 852 | VLAVAAPAVLLP | 12 | 57.3 | 203.3 | 2.3 | Aliphatic |
| 206 | 863 | AAVVLLPIIAAP | 12 | 41.3 | 211.7 | 2.4 | Aliphatic |
| 207 | 864 | ALLVIAPAIAVP | 12 | 57.3 | 211.7 | 2.4 | Aliphatic |
| 208 | 865 | AVLVIAVPAIAP | 12 | 57.3 | 203.3 | 2.5 | Aliphatic |
| 209 | 867 | ALLVVIAPLAAP | 12 | 41.3 | 211.7 | 2.4 | Aliphatic |
| 210 | 868 | VLVAAILPAAIP | 12 | 54.9 | 211.7 | 2.4 | Aliphatic |
| 211 | 870 | VLVAAVLPIAAP | 12 | 41.3 | 203.3 | 2.4 | Aliphatic |
| 212 | 872 | VLAAAVLPLVVP | 12 | 41.3 | 219.2 | 2.5 | Aliphatic |
| 213 | 875 | AIAIVVPAVAVP | 12 | 50.2 | 195.0 | 2.4 | Aliphatic |
| 214 | 877 | VAIIAVPAVVAP | 12 | 57.3 | 195.0 | 2.4 | Aliphatic |
| 215 | 878 | IVALVAPAAVVP | 12 | 50.2 | 195.0 | 2.4 | Aliphatic |
| 216 | 879 | AAIVLLPAVVVP | 12 | 50.2 | 219.1 | 2.5 | Aliphatic |
| 217 | 881 | AALIVVPAVAVP | 12 | 50.2 | 195.0 | 2.4 | Aliphatic |
| 218 | 882 | AIALVVPAVAVP | 12 | 57.3 | 195.0 | 2.4 | Aliphatic |
| 219 | 883 | LAIVPAAIAALP | 12 | 50.2 | 195.8 | 2.2 | Aliphatic |

TABLE 15

| Sequence ID Number | aMTD | Sequences | Length | Rigidity/ Flexibility (II) | Structural Feature (AI) | Hydro-pathy (GRAVY) | Residue Structure |
|---|---|---|---|---|---|---|---|
| 220 | 885 | LVAIAPAVAVLP | 12 | 57.3 | 203.3 | 2.4 | Aliphatic |
| 221 | 887 | VLAVAPAVAVLP | 12 | 57.3 | 195.0 | 2.4 | Aliphatic |
| 222 | 888 | ILAVVAIPAAAP | 12 | 54.9 | 187.5 | 2.3 | Aliphatic |
| 223 | 889 | ILVAAAPIAALP | 12 | 57.3 | 195.8 | 2.2 | Aliphatic |
| 224 | 891 | ILAVAAIPAALP | 12 | 54.9 | 195.8 | 2.2 | Aliphatic |
| 225 | 893 | VIAIPAILAAAP | 12 | 54.9 | 195.8 | 2.3 | Aliphatic |
| 226 | 895 | AIIVVPAIAAP | 12 | 50.2 | 211.7 | 2.5 | Aliphatic |
| 227 | 896 | AILIVVAPIAAP | 12 | 50.2 | 211.7 | 2.5 | Aliphatic |

TABLE 15-continued

| Sequence ID Number | aMTD | Sequences | Length | Rigidity/ Flexibility (II) | Structural Feature (AI) | Hydropathy (GRAVY) | Residue Structure |
|---|---|---|---|---|---|---|---|
| 228 | 897 | AVIVPVAIIAAP | 12 | 50.2 | 203.3 | 2.5 | Aliphatic |
| 229 | 899 | AVVIALPAVVAP | 12 | 57.3 | 195.0 | 2.4 | Aliphatic |
| 230 | 900 | ALVAVIAPVVAP | 12 | 57.3 | 195.0 | 2.4 | Aliphatic |
| 231 | 901 | ALVAVLPAVAVP | 12 | 57.3 | 195.0 | 2.4 | Aliphatic |
| 232 | 902 | ALVAPLLAVAVP | 12 | 41.3 | 203.3 | 2.3 | Aliphatic |
| 233 | 904 | AVLAVVAPVVAP | 12 | 57.3 | 186.7 | 2.4 | Aliphatic |
| 234 | 905 | AVIAVAPLVVAP | 12 | 41.3 | 195.0 | 2.4 | Aliphatic |
| 235 | 906 | AVIALAPVVVAP | 12 | 57.3 | 195.0 | 2.4 | Aliphatic |
| 236 | 907 | VAIALAPVVVAP | 12 | 57.3 | 195.0 | 2.4 | Aliphatic |
| 237 | 908 | VALALAPVVVAP | 12 | 57.3 | 195.0 | 2.3 | Aliphatic |
| 238 | 910 | VAALLPAVVVAP | 12 | 57.3 | 195,0 | 2.3 | Aliphatic |
| 239 | 911 | VALALPVVVAP | 12 | 57.3 | 195.0 | 2.3 | Aliphatic |
| 240 | 912 | VALLAPAVVVAP | 12 | 57.3 | 195.0 | 2.3 | Aliphatic |
| | | | | 52.6 ± 05.1 | 201.7 ± 7.8 | 2.3 ± 0.1 | |

3-4. Design of the Peptides that Did not Satisfy at Least One Critical Factor To demonstrate that this invention of new hydrophobic CPPs—aMTDs, which satisfy all critical factors described above, are correct and rationally designed, the peptides which do not satisfy at least one critical factor have also been designed. Total of 31 rPeptides (rPs) are designed, developed and categorized as follows: no bending peptides, either no proline in the middle as well at the end and/or no central proline; rigid peptides (II<40); too much flexible peptides; aromatic peptides (aromatic ring presences); hydrophobic, with non-aromatic peptides but have amino acids other than A, V, L, I, P or additional proline residues; hydrophilic, but non-aliphatic peptides.

3-4-1. Peptides that do not Satisfy the Bending Potential

Table 16 shows the peptides that do not have any proline in the middle (at 5', 6', 7' or 8') and at the end of the sequences. In addition, Table 16 describes the peptides that do not have proline in the middle of the sequences. All these peptides are supposed to have no-bending potential.

To prove that rigidity/flexibility of the sequence is a crucial critical factor, rigid (Avg. II: 21.8±6.6) and too high flexible sequences (Avg. II: 82.3±21.0) were also designed. Rigid peptides that instability index is much lower than that of new aMTDs (II: 41.3-57.3, Avg. II: 53.3±5.7) are shown in Table 17. Bending, but too high flexible peptides that II is much higher than that of new aMTDs are also provided in Table 18.

TABLE 16

| Group | rPeptide ID (SEQ ID NO) | Sequences | Length | Proline Position (PP) | Rigidity/ Flexibility (II) | Structural Feature (AI) | Hydropathy (GRAVY) |
|---|---|---|---|---|---|---|---|
| No-Bending Peptides [No Proline at 5, 6, 7 or 8 and/or 12] | 931 (882) | AVLIAPAILAAA | 12 | 6 | 57.3 | 204.2 | 2.5 |
| | 936 (883) | ALLILAAAVAAP | 12 | 12 | 41.3 | 204.2 | 2.4 |
| | 152 (884) | LAAAVAAVAALL | 12 | None | 9.2 | 204.2 | 2.7 |
| | 27 (885) | LAIVAAAAALVA | 12 | None | 2.1 | 204.2 | 2.8 |
| | 935 (886) | ALLILPAAAVAA | 12 | 6 | 57.3 | 204.2 | 2.4 |
| | 670 (887) | ALLILAAAVAAL | 12 | None | 25.2 | 236.6 | 2.8 |
| | 934 (888) | LILAPAAVVAAA | 12 | 5 | 57.3 | 195.8 | 2.5 |
| | 37 (889) | TTCSQQQYCTNG | 12 | None | 53.1 | 0.0 | −1.1 |
| | 16 (890) | NNSCTTYTNGSQ | 12 | None | 47.4 | 0.0 | −1.4 |
| | 113 (891) | PVAVALLIAVPP | 12 | 1, 11, 12 | 57.3 | 195.0 | 2.1 |

3-4-2. Peptides that do not Satisfy the Rigidity/Flexibility

TABLE 17

| Group | rPeptide ID (SEQ ID NO) | Sequences | Length | Proline Position (PP) | Rigidity/ Flexibility (II) | Structural Feature (AI) | Hydro- pathy (GRAVY) |
|---|---|---|---|---|---|---|---|
| Rigid Peptides [II < 50] | 226 (892) | ALVAAIPALAIP | 12 | 6 | 20.4 | 195.8 | 2.2 |
| | 6 (893) | VIAMIPAAFWVA | 12 | 6 | 15.7 | 146.7 | 2.2 |
| | 750 (894) | LAIAAIAPLAIP | 12 | 8, 12 | 22.8 | 204.2 | 2.2 |
| | 26 (895) | AAIALAAPLAIV | 12 | 8 | 18.1 | 204.2 | 2.5 |
| | 527 (896) | LVLAAVAPIAIP | 12 | 8, 12 | 22.8 | 211.7 | 2.4 |
| | 466 (897) | IIAAAAPLAIIP | 12 | 7, 12 | 22.8 | 204.2 | 2.3 |
| | 167 (898) | VAIAIPAALAIP | 12 | 6, 12 | 20.4 | 195.8 | 2.3 |
| | 246 (899) | VVAVPLLVAFAA | 12 | 5 | 25.2 | 195.0 | 2.7 |
| | 426 (900) | AAALAIPLAIIP | 12 | 7, 12 | 4.37 | 204.2 | 2.2 |
| | 606 (901) | AAAIAAIPIIIP | 12 | 8, 12 | 4.4 | 204.2 | 2.4 |
| | 66 (902) | AGVLGGPIMGVP | 12 | 7, 12 | 35.5 | 121.7 | 1.3 |
| | 248 (903) | VAAIVPIAALVP | 12 | 6, 12 | 34.2 | 203.3 | 2.5 |
| | 227 (904) | LAAIVPIAAAVP | 12 | 6, 12 | 34.2 | 187.5 | 2.2 |
| | 17 (905) | GGCSAPQTTCSN | 12 | 6 | 51.6 | 8.3 | -0.5 |
| | 67 (906) | LDAEVPLADDVP | 12 | 6, 12 | 34.2 | 130.0 | 0.3 |

TABLE 18

| Group | rPeptide ID (SEQ ID NO) | Sequences | Length | Proline Position (PP) | Rigidity/ Flexibility (II) | Structural Feature (AI) | Hydro- pathy (GRAVY) |
|---|---|---|---|---|---|---|---|
| Bending Peptides, but Too High Flexibility | 692 (907) | PAPLPPVVILAV | 12 | 1, 3, 5, 6 | 105.5 | 186.7 | 1.8 |
| | 69 (908) | PVAVLPPAALVP | 12 | 1, 6, 7, 12 | 89.4 | 162.5 | 1.6 |
| | 390 (909) | VPLLVPVVPVVP | 12 | 2, 6, 9, 12 | 105.4 | 210.0 | 2.2 |
| | 350 (910) | VPILVPVVPVVP | 12 | 2, 6, 9, 12 | 121.5 | 210.0 | 2.2 |
| | 331 (911) | VPVLVPLVPVVP | 12 | 2, 6, 9, 12 | 105.4 | 210.0 | 2.2 |
| | 9 (912) | VALVPAALILPP | 12 | 5, 11, 12 | 89.4 | 203.3 | 2.1 |
| | 68 (913) | VAPVLPAAPLVP | 12 | 3, 6, 9, 12 | 105.5 | 162.5 | 1.6 |
| | 349 (914) | VPVLVPVVPVVP | 12 | 2, 6, 9, 12 | 121.5 | 201.6 | 2.2 |
| | 937 (915) | VPVLVPLVPVVV | 12 | 2, 6, 8, 10 | 121.5 | 210.0 | 2.2 |
| | 938 (916) | VPVLLPVVVPVP | 12 | 2, 6, 10, 12 | 121.5 | 210.0 | 2.2 |
| | 329 (917) | LPVLVPVVPVVP | 12 | 2, 6, 9, 12 | 121.5 | 210.0 | 2.2 |
| | 49 (918) | VVPAAPAVPVVP | 12 | 3, 6, 9, 12 | 121.5 | 145.8 | 1.7 |
| | 772 (919) | LPVAPVIPIIVP | 12 | 2, 5, 8, 12 | 79.9 | 210.8 | 2.1 |
| | 210 (920) | ALIALPALPALP | 12 | 6, 9, 12 | 89.4 | 195.8 | 1.8 |
| | 28 (921) | AVPLLPLVPAVP | 12 | 3, 6, 9, 12 | 89.4 | 185.8 | 1.8 |
| | 693 (922) | AAPVLPVAVPIV | 12 | 3, 6, 10 | 82.3 | 185.7 | 2.1 |
| | 169 (923) | VALVAPALILAP | 12 | 6, 12 | 73.4 | 211.7 | 2.4 |
| | 29 (924) | VLPPLPVLPVLP | 12 | 3, 4, 6, 9, 12 | 121.5 | 202.5 | 1.7 |
| | 190 (925) | AAILAPAVIAPP | 12 | 6, 11, 12 | 89.4 | 163.3 | 1.8 |

3-4-3. Peptides that do not Satisfy the Structural Features

New hydrophobic CPPs—aMTDs are consisted with only hydrophobic and aliphatic amino acids (A, V, L, I and P) with average ranges of the indexes—AI: 180-220 and GRAVY: 2.1-2.6 (Table 9). Based on the structural indexes, the peptides which contain an aromatic residue (W, F or Y) are shown in Table 19 and the peptides which are hydrophobic with non-aromatic sequences but have amino acids residue other than A, V, L, I, P or additional proline residues are designed (Table 20). Finally, hydrophilic and/or bending peptides which are consisted with non-aliphatic amino acids are shown in Table 21.

TABLE 19

| Group | rPeptide ID (SEQ ID NO) | Sequences | Length | Proline Position (PP) | Rigidity/ Flexibility (II) | Structural Feature (AI) | Hydro- pathy (GRAVY) |
|---|---|---|---|---|---|---|---|
| Aromatic Peptides [Aromatic Ring Presence] | 30 (926) | AMALLPAAVAVA | 12 | 6 | 51.6 | 163.3 | 2.3 |
| | 33 (927) | AAAILAPAFLAV | 12 | 7 | 57.3 | 171.7 | 2.4 |
| | 131 (928) | WIIAPVWLAWIA | 12 | 5 | 51.6 | 179.2 | 1.9 |
| | 922 (929) | WYVIFVLPLVVP | 12 | 8, 12 | 41.3 | 194.2 | 2.2 |
| | 71 (930) | FMWMWFPFMWYP | 12 | 7, 12 | 71.3 | 0.0 | 0.6 |
| | 921 (931) | IWWFVVLPLVVP | 12 | 8, 12 | 41.3 | 194.2 | 2.2 |

TABLE 20

| Group | rPeptide ID (SEQ ID NO) | Sequences | Length | Proline Position (PP) | Rigidity/ Flexibility (II) | Structural Feature (AI) | Hydro- pathy (GRAVY) |
|---|---|---|---|---|---|---|---|
| Hydrophobic Peptides, but Non Aromatic Peptides | 436 (932) | VVMLVVPAVMLP | 12 | 7, 12 | 57.3 | 194.2 | 2.6 |
| | 138 (933) | PPAALLAILAVA | 12 | 1, 2 | 57.3 | 195.8 | 2.2 |
| | 77 (934) | PVALVLVALVAP | 12 | 1, 12 | 41.3 | 219.2 | 2.5 |
| | 577 (935) | MLMIALVPMIAV | 12 | 8 | 18.9 | 195.0 | 2.7 |
| | 97 (936) | ALLAAPPALLAL | 12 | 6, 7 | 57.3 | 204.2 | 2.1 |
| | 214 (937) | ALIVAPALMALP | 12 | 6, 12 | 60.5 | 187.5 | 2.2 |
| | 59 (938) | AVLAAPVVAALA | 12 | 6 | 41.3 | 187.5 | 2.5 |
| | 54 (939) | LAVAAPPVVALL | 12 | 6, 7 | 57.3 | 203.3 | 2.3 |

TABLE 21

| Group | rPeptide ID (SEQ ID NO) | Sequences | Length | Proline Position (PP) | Rigidity/ Flexibility (II) | Structural Feature (AI) | Hydro- pathy (GRAVY) |
|---|---|---|---|---|---|---|---|
| Hydrophilic Peptides, but Non Aliphatic | 949 (940) | SGNSCQQCGNSS | 12 | None | 41.7 | 0.0 | -1.1 |
| | 39 (941) | CYNTSPCTGCCY | 12 | 6 | 52.5 | 0.0 | 0.0 |
| | 19 (942) | YVSCCTYTNGSQ | 12 | None | 47.7 | 0.0 | -1.0 |
| | 947 (943) | CYYNQQSNNNNQ | 12 | None | 59.6 | 0.0 | -2.4 |
| | 139 (944) | TGSTNSPTCTST | 12 | 7 | 53.4 | 0.0 | -0.7 |
| | 18 (945) | NYCCTPTTNGQS | 12 | 6 | 47.9 | 0.0 | -0.9 |
| | 20 (946) | NYCNTCPTYGQS | 12 | 7 | 47.4 | 0.0 | -0.9 |
| | 635 (947) | GSTGGSQQNNQY | 12 | None | 31.9 | 0.0 | -1.9 |
| | 40 (948) | TYNTSCTPGTCY | 12 | 8 | 49.4 | 0,0 | -0.6 |
| | 57 (949) | QNNCNTSSQGGG | 12 | None | 52.4 | 0.0 | -1.6 |
| | 159 (950) | CYSGSTSQNQPP | 12 | 11, 12 | 51.0 | 0.0 | -1.3 |
| | 700 (951) | GTSNTCQSNQNS | 12 | None | 19.1 | 0.0 | -1.6 |
| | 38 (952) | YYNQSTCGGQCY | 12 | None | 53.8 | 0.0 | -1.0 |

3-5. Summary of Newly Designed Peptides

Total of 457 sequences have been designed based on the critical factors. Designed potentially best aMTDs (hydrophobic, flexible, bending, aliphatic and 12-A/a length peptides) that do satisfy all range/feature of critical factors are 316. Designed rPeptides that do not satisfy at least one of the critical factors are 141 that no bending peptide sequences are 26; rigid peptide (II<40) sequences are 23; too much flexible peptides are 24; aromatic peptides (aromatic ring presences) are 27; hydrophobic, but non-aromatic peptides are 23; and hydrophilic, but non-aliphatic peptides are 18.

4. Preparation of Recombinant Report Proteins Fused to aMTDs and rPeptides

Recombinant proteins fused to aMTDs and others [rPeptides, reference hydrophobic CPP sequences (MTM and MTD)] were expressed in a bacterial system, purified with single-step affinity chromatography and prepared as soluble proteins in physiological condition. These recombinant proteins have been tested for the ability of their cell-permeability by utilizing flow cytometry and laser scanning confocal microscopy.

4-1. Selection of Cargo Protein for Recombinant Proteins Fused to Peptide sequences For clinical/non-clinical application, aMTD-fused cargo materials would be biologically active molecules that could be one of the following: enzymes, transcription factors, toxic, antigenic peptides, antibodies and antibody fragments. Furthermore, biologically active molecules could be one of these following macromolecules: enzymes, hormones, carriers, immunoglobulin, membrane-bound proteins, transmembrane proteins, internal proteins, external proteins, secreted proteins, virus proteins, native proteins, glycoproteins, fragmented proteins, disulfide bonded proteins, recombinant proteins, chemically modified proteins and prions. In addition, these biologically active molecules could be one of the following: nucleic acid, coding nucleic acid sequence, mRNAs, antisense RNA molecule, carbohydrate, lipid and glycolipid.

According to these pre-required conditions, a non-functional cargo to evaluate aMTD-mediated protein uptake has been selected and called as Cargo A (CRA) that should be soluble and non-functional. The domain (Ala 289-840; 184 Ala length) is derived from protein S (Genbank ID: CP000113.1).

4-2. Construction of Expression Vector and Preparation of Recombinant Proteins

Coding sequences for recombinant proteins fused to each aMTD are cloned NdeI (5') and SalI (3') in pET-28a(+) (Novagen, Darmstadt, Germany) from PCR-amplified DNA segments. PCR primers for the recombinant proteins fused to aMTD and rPeptides are SEQ ID NOs: 481~797. Structure of the recombinant proteins is displayed in FIG. 1.

The recombinant proteins were forcedly expressed in $E.$ $coli$ BL21 (DE3) cells grown to an $OD_{600}$ of 0.6 and induced for 2 hours with 0.7 mM isopropyl-β-D-thiogalactopyranoside (IPTG). The proteins were purified by $Ni^{2+}$ affinity chromatography as directed by the supplier (Qiagen, Hilden, Germany) in natural condition. After the purification, purified proteins were dissolved in a physiological buffer such as DMEM medium.

TABLE 22

| | |
|---|---|
| Potentially Best aMTDs (Hydrophobic, Flexible, Bending, Aliphatic & Helical) | 240 |
| Random Peptides | 31 |
| No Bending Peptides (No Praline at 5 or 6 and/or 12) | 02 |
| No Bending Peptides (No Central Proline) | 01 |
| Rigid Peptides (II < 50) | 09 |
| Too Much Flexible Peptides | 09 |
| Aromatic Peptides (Aromatic Ring Presences) | 01 |
| Hydrophobic, But Non-Aromatic Peptides | 02 |
| Hydrophilic, But Non-Aliphatic Peptides | 07 |

4-3. Expression of aMTD- or Random Peptide (rP)-Fused Recombinant Proteins

Using the standardized six critical factors, 316 aMTD sequences have been designed. In addition, 141 rPeptides are also developed that lack one of these critical factors: no bending peptides: i) absence of proline both in the middle and at the end of sequence or ii) absence of proline either in the middle or at the end of sequence, rigid peptides, too much flexible peptides, aromatic peptides (aromatic ring presence), hydrophobic but non-aromatic peptides, and hydrophilic but non-aliphatic peptides (Table 22).

These rPeptides are devised to be compared and contrasted with aMTDs in order to analyze structure/sequence activity relationship (SAR) of each critical factor with regard to the peptides' intracellular delivery potential. All peptide (aMTD or rPeptide)-containing recombinant proteins have been fused to the CRA to enhance the solubility of the recombinant proteins to be expressed, purified, prepared and analyzed.

These designed 316 aMTDs and 141 rPeptides fused to CRA were all cloned (FIG. 2) and tested for inducible expression in $E.$ $coli$ (FIG. 3). Out of these peptides, 240 aMTDs were inducibly expressed, purified and prepared in soluble form (FIG. 4). In addition, 31 rPeptides were also prepared as soluble form (FIG. 4).

To prepare the proteins fused to rPeptides, 60 proteins were expressed that were 10 out of 26 rPeptides in the category of no bending peptides (Table 16); 15 out of 23 in the category of rigid peptides [instability index (II)<40] (Table 17); 19 out of 24 in the category of too much flexible peptides (Table 18); 6 out of 27 in the category of aromatic peptides (Table 19); 8 out of 23 in the category of hydrophobic but non-aromatic peptides (Table 20); and 12 out of 18 in the category of hydrophilic but non-aliphatic peptides (Table 21).

4-4. Quantitative Cell-Permeability of aMTD-Fused Recombinant Proteins

The aMTDs and rPeptides were fluorescently labeled and compared based on the critical factors for cell-permeability by using flow cytometry and confocal laser scanning microscopy (FIGS. 5 to 8). The cellular uptake of the peptide-fused non-functional cargo recombinant proteins could quantitatively be evaluated in flow cytometry, while confocal laser scanning microscopy allows intracellular uptake to be assessed visually. The analysis included recombinant proteins fused to a negative control [rP38] that has opposite characteristics (hydrophilic and aromatic sequence: YYNQSTCGGQCY)(SEQ ID NO: 952) to the aMTDs (hydrophobic and aliphatic sequences). Relative cell-permeability (relative fold) of aMTDs to the negative control was also analyzed (Table 23 and FIG. 9).

Table 23 shows Comparison Analysis of Cell-Permeability of aMTDs with a Negative Control (A: rP38).

TABLE 23

| | Negative Control rP38 |
|---|---|
| aMTD | 19.6 ± 1.6* |
| The Average of 240 aMTDs | (Best: 164.2) |

*Relative Fold (aMTD in Geo Mean in its comparison to rP38)

Relative cell-permeability (relative fold) of aMTDs to the reference CPPs [B: MTM12 (AAVLLPVLLAAP) (SEQ ID NO: 953), C: MTD85 (AVALLILAV) (SEQ ID NO: 954)] was also analyzed (Tables 40 and 41)

Table 24 shows Comparison Analysis of Cell-Permeability of aMTDs with a Reference CPP (B: MTM12).

TABLE 24

| | MTM12 |
|---|---|
| aMTD | 13.1 ± 1.1* |
| The Average of 240 aMTDs | (Best: 109.9) |

*Relative Fold (aMTD in Geo Mean in its comparison to MTM12)

Table 25 shows Comparison Analysis of Cell-Permeability of aMTDs with a Reference CPP (C: MTD85 (SEQ ID NO: 954)).

TABLE 25

| | MTD85 |
|---|---|
| aMTD | 6.6 ± 0.5* |
| The Average of 240 aMTDs | (Best: 55.5) |

*Relative Fold (aMTD in Geo Mean in its comparison to MTD85)

Geometric means of negative control (histidine-tagged rP38-fused CRA recombinant protein) subtracted by that of naked protein (histidine-tagged CRA protein) lacking any peptide (rP38(SEQ ID NO: 952) or aMTD) was standardized as relative fold of 1. Relative cell-permeability of 240 aMTDs to the negative control (A type) was significantly increased by up to 164 fold, with average increase of 19.6±1.6 (Table 26-31).

TABLE 26

| Sequence ID Number | aMTD | Sequences | Length | Proline Position (PP) | Rigidity/ Flexibility (II) | Sturctural Feature (AI) | Hydro- pathy (GRAVY) | Relative Ratio (Fold) | | |
|---|---|---|---|---|---|---|---|---|---|---|
| | | | | | | | | A | B | C |
| 229 | 899 | AVVIALPAVVAP | 12 | 7 | 57.3 | 195.0 | 2.4 | 164.2 | 109.9 | 55.5 |
| 237 | 908 | VALALAPVVVAP | 12 | 7 | 57.3 | 195.0 | 2.3 | 150.6 | 100.8 | 50.9 |
| 238 | 910 | VAALLPAVVVAP | 12 | 6 | 57.3 | 195.0 | 2.3 | 148.5 | 99.4 | 50.2 |
| 185 | 810 | VIVLAAPALAAP | 12 | 7 | 50.2 | 187.5 | 2.2 | 120.0 | 80.3 | 40.6 |
| 233 | 904 | AVLAVVAPVVAP | 12 | 8 | 57.3 | 186.7 | 2.4 | 105.7 | 70.8 | 35.8 |
| 74 | 321 | IVAVALPALAVP | 12 | 7 | 50.2 | 203.3 | 2.3 | 97.8 | 65.2 | 32.9 |
| 204 | 851 | VLAVVLPAVALP | 12 | 7 | 57.3 | 219.2 | 2.5 | 96.6 | 64.7 | 32.7 |
| 239 | 911 | VALALPAVVVAP | 12 | 6 | 57.3 | 195.0 | 2.3 | 84.8 | 56.8 | 28.7 |
| 205 | 852 | VLAVAAPAVLLP | 12 | 7 | 57.3 | 203.3 | 2.3 | 84.6 | 56.6 | 28.6 |
| 179 | 803 | AIALAVPVLALP | 12 | 7 | 57.3 | 211.7 | 2.4 | 74.7 | 50.0 | 25.3 |
| 222 | 888 | ILAVVAIPAAAP | 12 | 8 | 54.9 | 187.5 | 2.3 | 71.0 | 47.5 | 24.0 |
| 188 | 825 | IVAVIVAPAVAP | 12 | 8 | 43.2 | 195.0 | 2.5 | 69.7 | 46.6 | 23.6 |
| 226 | 895 | AIIIVVPAIAAP | 12 | 7 | 50.2 | 211.7 | 2.5 | 60.8 | 40.7 | 20.6 |
| 227 | 896 | AILIVVAPIAAP | 12 | 8 | 50.2 | 211.7 | 2.5 | 57.5 | 38.5 | 19.4 |
| 164 | 727 | VALAIALPAVLP | 12 | 8 | 57.3 | 211.6 | 2.3 | 54.7 | 36.7 | 18.5 |
| 139 | 603 | VLVALAAPVIAP | 12 | 8 | 57.3 | 203.3 | 2.4 | 54.1 | 36.1 | 18.2 |
| 200 | 847 | LVAIVVLPAVAP | 12 | 8 | 50.2 | 219.2 | 2.6 | 50.2 | 33.4 | 16.9 |
| 189 | 826 | LVALAAPIIAVP | 12 | 7 | 41.3 | 211.7 | 2.4 | 49.2 | 32.9 | 16.6 |
| 161 | 724 | VAVLAVLPALAP | 12 | 8 | 57.3 | 203.3 | 2.3 | 47.5 | 31.8 | 16.1 |
| 131 | 563 | ALAVIVVPALAP | 12 | 8 | 50.2 | 203.3 | 2.4 | 47.1 | 31.4 | 15.9 |
| 186 | 811 | AVVLAVPALAVP | 12 | 7 | 57.3 | 195.0 | 2.3 | 46.5 | 31.1 | 15.7 |
| 194 | 831 | IIVAVAPAAIVP | 12 | 7 | 43.2 | 203.3 | 2.5 | 46.3 | 31.0 | 15.7 |
| 192 | 829 | AALALVAPVIVP | 12 | 8 | 50.2 | 203.3 | 2.4 | 44.8 | 30.0 | 15.2 |
| 224 | 891 | ILAVAAIPAALP | 12 | 8 | 54.9 | 195.8 | 2.2 | 44.7 | 29.9 | 15.1 |
| 234 | 905 | AVIAVAPLVVAP | 12 | 7 | 41.3 | 195.0 | 2.4 | 44.0 | 29.5 | 14.9 |
| 132 | 564 | VAIALIVPALAP | 12 | 8 | 50.2 | 211.7 | 2.4 | 43.6 | 29.1 | 14.7 |
| 34 | 124 | IAVALPALIAAP | 12 | 6 | 50.3 | 195.8 | 2.2 | 43.6 | 29.0 | 14.7 |
| 190 | 827 | IAAVLAAPALVP | 12 | 8 | 57.3 | 187.5 | 2.2 | 43.0 | 28.8 | 14.6 |
| 2 | 2 | AAAVPLLAVVVP | 12 | 5 | 41.3 | 195.0 | 2.4 | 40.9 | 27.2 | 13.8 |
| 91 | 385 | IVAIAVPALVAP | 12 | 7 | 50.2 | 203.3 | 2.4 | 38.8 | 25.9 | 13.1 |
| 191 | 828 | IALLAAPIIAVP | 12 | 7 | 41.3 | 220.0 | 2.4 | 36.8 | 24.6 | 12.4 |
| 181 | 806 | LVALAVPAAVLP | 12 | 7 | 57.3 | 203.3 | 2.3 | 36.7 | 24.6 | 12.4 |
| 198 | 845 | AAVVIAPLLAVP | 12 | 7 | 41.3 | 203.3 | 2.4 | 35.8 | 24.0 | 12.1 |
| 218 | 882 | AIALVVPAVAVP | 12 | 7 | 57.3 | 195.0 | 2.4 | 35.0 | 23.4 | 11.8 |
| 128 | 545 | VVLVLAAPAAVP | 12 | 8 | 57.3 | 195.0 | 2.3 | 34.6 | 23.1 | 11.7 |
| 39 | 161 | AVIALPALIAAP | 12 | 6 | 57.3 | 195.8 | 2.2 | 34.5 | 23.0 | 11.6 |
| 110 | 481 | AIAIAIVPVALP | 12 | 8 | 50.2 | 211.6 | 2.4 | 34.3 | 23.0 | 11.6 |
| 230 | 900 | ALVAVIAPVVAP | 12 | 8 | 57.3 | 195.0 | 2.4 | 34.3 | 22.9 | 11.6 |

TABLE 26-continued

| Sequence ID Number | aMTD | Sequences | Length | Proline Position (PP) | Rigidity/ Flexibility (II) | Structural Feature (AI) | Hydro- pathy (GRAVY) | Relative Ratio (Fold) | | |
|---|---|---|---|---|---|---|---|---|---|---|
| | | | | | | | | A | B | C |
| 53 | 223 | AILAVPIAVVAP | 12 | 6 | 57.3 | 203.3 | 2.4 | 33.0 | 22.1 | 11.2 |
| 187 | 824 | LIIVAAAPAVAP | 12 | 8 | 50.2 | 187.5 | 2.3 | 32.8 | 21.9 | 11.1 |
| 130 | 562 | ALIAAIVPALVP | 12 | 8 | 50.2 | 211.7 | 2.4 | 32.7 | 21.8 | 11.0 |
| 52 | 222 | ALLIAPAAVIAP | 12 | 6 | 57.3 | 195.8 | 2.2 | 32.6 | 21.7 | 11.0 |
| 17 | 61 | VAALPVLLAALP | 12 | 5 | 57.3 | 211.7 | 2.3 | 31.2 | 20.8 | 10.5 |
| 134 | 582 | VAVALIVPALAP | 12 | 8 | 50.2 | 203.3 | 2.4 | 30.6 | 20.4 | 10.3 |
| 223 | 889 | ILVAAAPIAALP | 12 | 7 | 57.3 | 195.8 | 2.2 | 30.3 | 20.3 | 10.3 |
| 177 | 787 | AVALVPVIVAAP | 12 | 6 | 50.2 | 195.0 | 2.4 | 29.3 | 19.6 | 9.9 |
| 157 | 703 | IVAVLVPALAP | 12 | 8 | 50.2 | 203.3 | 2.4 | 29.2 | 19.5 | 9.9 |
| 158 | 705 | IVAVALLPALAP | 12 | 8 | 50.2 | 211.7 | 2.4 | 28.6 | 19.1 | 9.7 |
| 220 | 885 | LVAIAPAVAVLP | 12 | 6 | 57.3 | 203.3 | 2.4 | 28.3 | 19.0 | 9.6 |
| 3 | 3 | AALLVPAAVLAP | 12 | 6 | 57.3 | 187.5 | 2.1 | 27.0 | 18.0 | 9.1 |
| 137 | 601 | AAILIAVPIAAP | 12 | 8 | 57.3 | 195.8 | 2.3 | 26.8 | 17.9 | 9.0 |
| 196 | 843 | AVLVLVAPAAAP | 12 | 8 | 41.3 | 219.2 | 2.5 | 26.4 | 17.7 | 8.9 |
| 94 | 403 | AAALVIPAAILP | 12 | 7 | 54.9 | 195.8 | 2.2 | 25.2 | 16.8 | 8.5 |
| 127 | 544 | IVALIVAPAAVP | 12 | 8 | 43.1 | 203.3 | 2.4 | 23.4 | 15.6 | 7.9 |
| 121 | 522 | ALLVIAVPAVAP | 12 | 8 | 57.3 | 203.3 | 2.4 | 22.7 | 15.2 | 7.7 |

TABLE 27

| Sequence ID Number | aMTD | Sequences | Length | Proline Position (PP) | Rigidity/ Flexibility (II) | Sturctural Feature (AI) | Hydro- pathy (GRAVY) | Relative Ratio (Fold) | | |
|---|---|---|---|---|---|---|---|---|---|---|
| | | | | | | | | A | B | C |
| 180 | 805 | LVLIAAAPIALP | 12 | 8 | 41.3 | 220.0 | 2.4 | 22.3 | 14.9 | 7.6 |
| 108 | 464 | AVVILVPLAAAP | 12 | 7 | 57.3 | 203.3 | 2.4 | 22.3 | 14.9 | 7.5 |
| 96 | 405 | LAAAVIPVAILP | 12 | 7 | 54.9 | 211.7 | 2.4 | 22.2 | 14.8 | 7.5 |
| 168 | 747 | VALLAIAPALAP | 12 | 8 | 57.3 | 195.8 | 2.2 | 22.0 | 14.8 | 7.5 |
| 115 | 501 | VIVALAVPALAP | 12 | 8 | 50.2 | 203.3 | 2.4 | 21.5 | 14.4 | 7.3 |
| 147 | 661 | AAILAPIVAALP | 12 | 6 | 50.2 | 195.8 | 2.2 | 21.4 | 14.3 | 7.2 |
| 176 | 786 | LVAIAPLAVLAP | 12 | 6 | 41.3 | 211.7 | 2.4 | 21.2 | 14.2 | 7.2 |
| 144 | 625 | ILAAAAPLIVP | 12 | 8 | 50.2 | 195.8 | 2.2 | 20.9 | 13.9 | 7.0 |
| 101 | 442 | ALAALVPAVLVP | 12 | 7 | 57.3 | 203.3 | 2.3 | 20.4 | 13.6 | 6.9 |
| 240 | 912 | VALLAPAVVVAP | 12 | 6 | 57.3 | 195.0 | 2.3 | 19.9 | 13.3 | 6.7 |
| 43 | 165 | ALAVPVALAIVP | 12 | 5 | 50.2 | 203.3 | 2.4 | 19.8 | 13.2 | 6.7 |
| 98 | 422 | VVAILAPLLAAP | 12 | 7 | 57.3 | 211.7 | 2.4 | 19.6 | 13.1 | 6.6 |
| 155 | 686 | AALVAVLPVALP | 12 | 8 | 57.3 | 203.3 | 2.3 | 19.5 | 13.1 | 6.6 |
| 81 | 343 | IVAVALPALVAP | 12 | 7 | 50.2 | 203.3 | 2.3 | 19.4 | 12.9 | 6.5 |
| 76 | 323 | IVAVALPVALAP | 12 | 7 | 50.2 | 203.3 | 2.3 | 19.1 | 12.8 | 6.4 |

TABLE 27-continued

| Sequence ID Number | aMTD | Sequences | Length | Proline Position (PP) | Rigidity/ Flexibility (II) | Sturctural Feature (AI) | Hydro- pathy (GRAVY) | Relative Ratio (Fold) | | |
|---|---|---|---|---|---|---|---|---|---|---|
| | | | | | | | | A | B | C |
| 105 | 461 | IAAVIVPAVALP | 12 | 7 | 50.2 | 203.3 | 2.4 | 19.0 | 12.7 | 6.4 |
| 9 | 21 | AVALLPALLAVP | 12 | 6 | 57.3 | 211.7 | 2.3 | 18.9 | 12.6 | 6.4 |
| 95 | 404 | LAAAVIPAAILP | 12 | 7 | 54.9 | 195.8 | 2.2 | 18.9 | 12.6 | 6.4 |
| 60 | 261 | LVLVPLLAAAAP | 12 | 5 | 41.3 | 211.6 | 2.3 | 18.5 | 12.3 | 6.2 |
| 122 | 524 | AVALIVVPALAP | 12 | 8 | 50.2 | 203.3 | 2.4 | 18.3 | 12.2 | 6.2 |
| 55 | 225 | VAALLPAAAVLP | 12 | 6 | 57.3 | 187.5 | 2.1 | 18.3 | 12.2 | 6.2 |
| 63 | 264 | LAAAPVVIVIAP | 12 | 5 | 50.2 | 203.3 | 2.4 | 18.2 | 12.1 | 6.1 |
| 1 | 1 | AAALAPVVLALP | 12 | 6 | 57.3 | 187.5 | 2.1 | 17.7 | 11.8 | 6.0 |
| 88 | 382 | AAALVIPAILAP | 12 | 7 | 54.9 | 195.8 | 2.2 | 17.7 | 11.8 | 6.0 |
| 107 | 463 | AVAILVPLLAAP | 12 | 7 | 57.3 | 211.7 | 2.4 | 17.6 | 11.7 | 5.9 |
| 75 | 322 | VVAIVLPALAAP | 12 | 7 | 50.2 | 203.3 | 2.3 | 17.6 | 11.7 | 5.9 |
| 117 | 503 | AAIIVLPAALP | 12 | 8 | 50.2 | 220.0 | 2.4 | 17.6 | 11.8 | 5.9 |
| 211 | 870 | VLVAAVLPIAAP | 12 | 8 | 41.3 | 203.3 | 2.4 | 16.6 | 11.1 | 5.6 |
| 56 | 241 | AAAVVPVLLVAP | 12 | 6 | 57.3 | 195.0 | 2.4 | 16.6 | 11.0 | 5.6 |
| 163 | 726 | LAVAIIAPAVAP | 12 | 8 | 57.3 | 187.5 | 2.2 | 16.5 | 11.0 | 5.6 |
| 79 | 341 | IVAVALPAVLAP | 12 | 7 | 50.2 | 203.3 | 2.3 | 16.4 | 10.9 | 5.5 |
| 125 | 542 | ALALIIVPAVAP | 12 | 8 | 50.2 | 211.6 | 2.4 | 16.2 | 10.8 | 5.5 |
| 83 | 361 | AVVIVAPAVIAP | 12 | 7 | 50.2 | 195.0 | 2.4 | 16.0 | 10.7 | 5.4 |
| 54 | 224 | ILAAVPIALAAP | 12 | 6 | 57.3 | 195.8 | 2.2 | 15.8 | 10.6 | 5.3 |
| 20 | 64 | AIVALPVAVLAP | 12 | 6 | 50.2 | 203.3 | 2.4 | 15.8 | 10.6 | 5.3 |
| 111 | 482 | ILAVAAIPVAVP | 12 | 8 | 54.9 | 203.3 | 2.4 | 15.8 | 10.6 | 5.3 |
| 113 | 484 | LAVVLAAPAIVP | 12 | 8 | 50.2 | 203.3 | 2.4 | 15.6 | 10.4 | 5.3 |
| 210 | 868 | VLVAAILPAAIP | 12 | 8 | 54.9 | 211.7 | 2.4 | 14.9 | 10.0 | 5.0 |
| 124 | 541 | LLALIIAPAAAP | 12 | 8 | 57.3 | 204.1 | 2.1 | 14.8 | 9.9 | 5.0 |
| 150 | 666 | AAIAIIAPAIVP | 12 | 8 | 50.2 | 195.8 | 2.3 | 14.7 | 9.9 | 5.0 |
| 149 | 665 | LAIVLAAPVAVP | 12 | 8 | 50.2 | 203.3 | 2.3 | 14.7 | 9.9 | 5.0 |
| 84 | 363 | AVLAVAPALIVP | 12 | 7 | 50.2 | 203.3 | 2.3 | 14.7 | 9.8 | 4.9 |
| 57 | 242 | AALLVPALVAAP | 12 | 6 | 57.3 | 187.5 | 2.1 | 14.6 | 9.7 | 4.9 |
| 90 | 384 | VIVAIAPALLAP | 12 | 7 | 50.2 | 211.6 | 2.4 | 14.0 | 9.4 | 4.7 |
| 214 | 877 | VAIIAVPVVAP | 12 | 7 | 57.3 | 195.0 | 2.4 | 14.0 | 9.4 | 4.7 |
| 206 | 863 | AAVVLLPIIAAP | 12 | 7 | 41.3 | 211.7 | 2.4 | 13.8 | 9.3 | 4.7 |
| 123 | 525 | ALAIVVAPVAVP | 12 | 8 | 50.2 | 195.0 | 2.4 | 13.8 | 9.2 | 4.7 |
| 213 | 875 | AIAIVVPAVAVP | 12 | 7 | 50.2 | 195.0 | 2.4 | 13.8 | 9.2 | 4.7 |
| 69 | 285 | AIVLLPAAVVAP | 12 | 6 | 50.2 | 203.3 | 2.4 | 13.3 | 8.9 | 4.5 |
| 65 | 281 | ALIVLPAAVAVP | 12 | 6 | 50.2 | 203.3 | 2.4 | 13.3 | 8.9 | 4.5 |
| 209 | 867 | ALLVVIAPLAAP | 12 | 8 | 41.3 | 211.7 | 2.4 | 13.2 | 8.8 | 4.4 |
| 172 | 766 | IVVIAVAPAVAP | 12 | 8 | 50.2 | 195.0 | 2.4 | 12.9 | 8.6 | 4.4 |
| 80 | 342 | VIVALAPAVLAP | 12 | 7 | 50.2 | 203.3 | 2.3 | 12.7 | 8.5 | 4.3 |

TABLE 27-continued

| Sequence ID Number | aMTD | Sequences | Length | Proline Position (PP) | Rigidity/ Flexibility (II) | Sturctural Feature (AI) | Hydro- pathy (GRAVY) | Relative Ratio (Fold) A | B | C |
|---|---|---|---|---|---|---|---|---|---|---|
| 217 | 881 | AALIVVPAVAVP | 12 | 7 | 50.2 | 195.0 | 2.4 | 12.7 | 8.5 | 4.3 |
| 119 | 505 | AIIIVIAPAAAP | 12 | 8 | 50.2 | 195.8 | 2.3 | 12.4 | 8.3 | 4.2 |

TABLE 28

| Sequence ID Number | aMTD | Sequences | Length | Proline Position (PP) | Rigidity/ Flexibility (II) | Sturctural Feature (AI) | Hydro- pathy (GRAVY) | Relative Ratio (Fold) A | B | C |
|---|---|---|---|---|---|---|---|---|---|---|
| 169 | 763 | VAVLIAVPALAP | 12 | 8 | 57.3 | 203.3 | 2.3 | 12.3 | 7.2 | 4.2 |
| 159 | 706 | IVAVALLPAVAP | 12 | 8 | 50.2 | 203.3 | 2.4 | 12.0 | 7.0 | 4.1 |
| 156 | 687 | AILAVALPLLAP | 12 | 8 | 57.3 | 220.0 | 2.3 | 12.0 | 7.0 | 4.1 |
| 145 | 643 | LALVLAAPAIVP | 12 | 8 | 50.2 | 211.6 | 2.4 | 11.8 | 7.9 | 4.0 |
| 66 | 282 | VLAVAPALIVAP | 12 | 6 | 50.2 | 203.3 | 2.4 | 11.8 | 7.9 | 4.0 |
| 126 | 543 | LLAALIAPAALP | 12 | 8 | 57.3 | 204.1 | 2.1 | 11.7 | 7.8 | 4.0 |
| 78 | 325 | IVAVALPAVALP | 12 | 7 | 50.2 | 203.3 | 2.3 | 11.7 | 7.8 | 4.0 |
| 199 | 846 | IAVAVAAPLLVP | 12 | 8 | 41.3 | 203.3 | 2.4 | 11.7 | 6.8 | 4.0 |
| 89 | 383 | VIVALAPALLAP | 12 | 7 | 50.2 | 211.6 | 2.3 | 11.6 | 7.7 | 3.9 |
| 87 | 381 | VVAIVLPAVAAP | 12 | 7 | 50.2 | 195.0 | 2.4 | 11.5 | 7.7 | 3.9 |
| 183 | 808 | LVVLAAAPLAVP | 12 | 8 | 41.3 | 203.3 | 2.3 | 11.5 | 7.6 | 3.9 |
| 208 | 865 | AVLVIAVPAIAP | 12 | 8 | 57.3 | 203.3 | 2.5 | 11.3 | 7.5 | 3.8 |
| 162 | 725 | IAVLAVAPAVLP | 12 | 8 | 57.3 | 203.3 | 2.3 | 11.2 | 7.5 | 3.8 |
| 197 | 844 | VVALLAPLIAAP | 12 | 7 | 41.3 | 211.8 | 2.4 | 11.2 | 7.5 | 3.8 |
| 228 | 897 | AVIVPVAIIAAP | 12 | 5 | 50.2 | 203.3 | 2.5 | 11.2 | 7.5 | 3.8 |
| 141 | 605 | VIAAVLAPVAVP | 12 | 8 | 57.3 | 195.0 | 2.4 | 11.0 | 7.4 | 3.7 |
| 166 | 744 | AAVVIVAPVALP | 12 | 8 | 50.2 | 195.0 | 2.4 | 11.0 | 7.3 | 3.7 |
| 51 | 221 | AAILAPIVALAP | 12 | 6 | 50.2 | 195.8 | 2.2 | 10.9 | 7.3 | 3.7 |
| 142 | 622 | ALIVLAAPVAVP | 12 | 8 | 50.2 | 203.3 | 2.4 | 10.6 | 7.1 | 3.6 |
| 92 | 401 | AALAVIPAAILP | 12 | 7 | 54.9 | 195.8 | 2.2 | 10.6 | 7.1 | 3.6 |
| 77 | 324 | IVAVALPAALVP | 12 | 7 | 50.2 | 203.3 | 2.3 | 10.3 | 6.9 | 3.5 |
| 215 | 878 | IVALVAPAAVVP | 12 | 7 | 50.2 | 195.0 | 2.4 | 10.3 | 6.9 | 3.5 |
| 71 | 302 | LALAPALALLAP | 12 | 5 | 57.3 | 204.2 | 2.1 | 10.2 | 6.8 | 3.4 |
| 154 | 685 | ALLVAVLPAALP | 12 | 8 | 57.3 | 211.7 | 2.3 | 10.2 | 5.9 | 3.4 |
| 201 | 848 | AVAIVVLPAVAP | 12 | 8 | 50.2 | 195.0 | 2.4 | 10.0 | 6.7 | 3.4 |
| 138 | 602 | VIVALAAPVLAP | 12 | 8 | 50.2 | 203.3 | 2.4 | 9.9 | 5.8 | 3.4 |
| 178 | 788 | AIAVAIAPVALP | 12 | 8 | 57.3 | 187.5 | 2.3 | 9.8 | 6.6 | 3.3 |
| 38 | 145 | LLAVVPAVALAP | 12 | 6 | 57.3 | 203.3 | 2.3 | 9.5 | 6.3 | 3.2 |
| 6 | 11 | VVALAPALAALP | 12 | 6 | 57.3 | 187.5 | 2.1 | 9.5 | 6.3 | 3.2 |
| 35 | 141 | AVIVLPALAVAP | 12 | 6 | 50.2 | 203.3 | 2.4 | 9.4 | 6.3 | 3.2 |

TABLE 28-continued

| Sequence ID Number | aMTD | Sequences | Length | Proline Position (PP) | Rigidity/ Flexibility (II) | Structural Feature (AI) | Hydropathy (GRAVY) | Relative Ratio (Fold) A | B | C |
|---|---|---|---|---|---|---|---|---|---|---|
| 120 | 521 | LAALIVVPAVAP | 12 | 8 | 50.2 | 203.3 | 2.4 | 9.4 | 6.3 | 3.2 |
| 100 | 425 | AVVAIAPVLALP | 12 | 7 | 57.3 | 203.3 | 2.4 | 9.4 | 6.3 | 3.2 |
| 86 | 365 | AVIVVAPALLAP | 12 | 7 | 50.2 | 203.3 | 2.3 | 9.3 | 6.2 | 3.1 |
| 62 | 263 | ALAVIPAAAILP | 12 | 6 | 54.9 | 195.8 | 2.2 | 9.0 | 6.0 | 3.0 |
| 82 | 345 | ALLIVAPVAVAP | 12 | 7 | 50.2 | 203.3 | 2.3 | 8.9 | 5.9 | 3.0 |
| 203 | 850 | LVIALAAPVALP | 12 | 8 | 57.3 | 211.7 | 2.4 | 8.8 | 5.9 | 3.0 |
| 37 | 144 | VLAIVPAVALAP | 12 | 6 | 50.2 | 203.3 | 2.4 | 8.8 | 5.9 | 3.0 |
| 173 | 767 | IVVAAVVPALAP | 12 | 8 | 50.2 | 195.0 | 2.4 | 8.5 | 5.0 | 2.9 |
| 47 | 185 | AALVLPLIIAAP | 12 | 6 | 41.3 | 220.0 | 2.4 | 8.5 | 5.7 | 2.9 |
| 202 | 849 | AVILLAPLIAAP | 12 | 7 | 57.3 | 220.0 | 2.4 | 8.3 | 4.8 | 2.8 |
| 207 | 864 | ALLVIAPAIAVP | 12 | 7 | 57.3 | 211.7 | 4.8 | 8.2 | 2.4 | 2.8 |
| 40 | 162 | AVVALPAALIVP | 12 | 6 | 50.2 | 203.3 | 2.4 | 8.2 | 5.5 | 2.8 |
| 42 | 164 | LAAVLPALLAAP | 12 | 6 | 57.3 | 195.8 | 2.1 | 8.2 | 5.5 | 2.8 |
| 236 | 907 | VAIALAPVVVAP | 12 | 7 | 57.3 | 195.0 | 2.4 | 8.1 | 5.4 | 2.8 |
| 103 | 444 | LAAALVPVALVP | 12 | 7 | 57.3 | 203.3 | 2.3 | 8.1 | 5.4 | 2.7 |
| 102 | 443 | ALAALVPVALVP | 12 | 7 | 57.3 | 203.3 | 2.3 | 8.0 | 5.3 | 2.7 |
| 231 | 901 | ALVAVLPAVAVP | 12 | 7 | 57.3 | 195.0 | 2.4 | 7.7 | 5.1 | 2.6 |
| 221 | 887 | VLAVAPAVAVLP | 12 | 6 | 57.3 | 195.0 | 2.4 | 7.7 | 5.1 | 2.6 |
| 167 | 746 | VAIIVVAPALAP | 12 | 8 | 50.2 | 203.3 | 2.4 | 7.6 | 4.4 | 2.6 |
| 232 | 902 | ALVAPLLAVAVP | 12 | 5 | 41.3 | 203.3 | 2.3 | 7.6 | 5.1 | 2.6 |
| 133 | 565 | VAIVLVAPAVAP | 12 | 8 | 50.2 | 195.0 | 2.4 | 7.5 | 5.0 | 2.5 |
| 59 | 245 | AAALAPVLALVP | 12 | 6 | 57.3 | 187.5 | 2.1 | 7.5 | 5.0 | 5.2 |
| 165 | 743 | AIAIALVPVALP | 12 | 8 | 57.3 | 211.6 | 2.4 | 7.4 | 4.9 | 2.5 |
| 109 | 465 | AVVILVPLAAAP | 12 | 7 | 57.3 | 203.3 | 2.4 | 7.4 | 4.9 | 2.5 |
| 30 | 104 | AVVAAPLVLALP | 12 | 6 | 41.3 | 203.3 | 2.3 | 7.3 | 4.9 | 2.5 |

TABLE 29

| Sequence ID Number | aMTD | Sequences | Length | Proline Position (PP) | Rigidity/ Flexibility (II) | Structural Feature (AI) | Hydropathy (GRAVY) | Relative Ratio (Fold) A | B | C |
|---|---|---|---|---|---|---|---|---|---|---|
| 160 | 707 | IVALAVLPAVAP | 12 | 8 | 50.2 | 203.3 | 2.4 | 7.3 | 4.9 | 2.5 |
| 212 | 872 | VLAAVLPLVVP | 12 | 8 | 41.3 | 219.2 | 2.5 | 7.3 | 4.9 | 2.5 |
| 135 | 583 | AVILALAPIVAP | 12 | 8 | 50.2 | 211.6 | 2.4 | 7.3 | 4.8 | 2.4 |
| 216 | 879 | AAIVLLPAVVP | 12 | 7 | 50.2 | 219.1 | 2.5 | 7.2 | 4.8 | 2.4 |
| 175 | 784 | VAALPAVALVVP | 12 | 5 | 57.3 | 195.0 | 2.4 | 7.1 | 4.7 | 2.4 |
| 225 | 893 | VIAIPAILAAAP | 12 | 5 | 54.9 | 195.8 | 2.3 | 7.0 | 4.7 | 2.4 |
| 8 | 13 | AAALVPVVALLP | 12 | 6 | 57.3 | 203.3 | 2.3 | 7.0 | 4.7 | 2.4 |
| 184 | 809 | LIVLAAPALAAP | 12 | 7 | 50.2 | 195.8 | 2.2 | 7.0 | 4.7 | 2.4 |

TABLE 29-continued

| Sequence ID Number | aMTD | Sequences | Length | Proline Position (PP) | Rigidity/ Flexibility (II) | Stuctural Feature (AI) | Hydropathy (GRAVY) | Relative Ratio (Fold) A | B | C |
|---|---|---|---|---|---|---|---|---|---|---|
| 104 | 445 | ALAALVPALVVP | 12 | 7 | 57.3 | 203.3 | 2.3 | 6.9 | 4.6 | 2.3 |
| 22 | 81 | AALLPALAALLP | 12 | 5 | 57.3 | 204.2 | 2.1 | 6.9 | 4.6 | 2.3 |
| 151 | 667 | LAVAIVAPALVP | 12 | 8 | 50.2 | 203.3 | 2.3 | 6.9 | 4.6 | 2.3 |
| 235 | 906 | AVIALAPVVVAP | 12 | 7 | 57.3 | 195.0 | 2.4 | 6.8 | 4.6 | 2.3 |
| 112 | 483 | ILAAAIIPAALP | 12 | 8 | 54.9 | 204.1 | 2.2 | 6.8 | 4.5 | 2.3 |
| 114 | 485 | AILAAIVPLAVP | 12 | 8 | 50.2 | 211.6 | 2.4 | 6.8 | 4.5 | 2.3 |
| 97 | 421 | AAILAAPLIAVP | 12 | 7 | 57.3 | 195.8 | 2.2 | 6.7 | 4.5 | 2.3 |
| 136 | 585 | ALIVAIAPALVP | 12 | 8 | 50.2 | 211.6 | 2.4 | 6.6 | 4.4 | 2.2 |
| 99 | 424 | AVVVAAPVLALP | 12 | 7 | 57.3 | 195.0 | 2.4 | 6.6 | 4.4 | 2.2 |
| 85 | 364 | LVAAVAPALIVP | 12 | 7 | 50.2 | 203.3 | 2.3 | 6.5 | 4.3 | 2.2 |
| 93 | 402 | ALAAVIPAAILP | 12 | 7 | 54.9 | 195.8 | 2.2 | 6.4 | 4.3 | 2.2 |
| 106 | 462 | IAAVLVPAVALP | 12 | 7 | 57.3 | 203.3 | 2.4 | 6.3 | 4.2 | 2.1 |
| 64 | 265 | VLAIAPLLAAVP | 12 | 6 | 41.3 | 211.6 | 2.3 | 6.0 | 4.0 | 2.0 |
| 70 | 301 | VIAAPVLAVLAP | 12 | 6 | 57.3 | 203.3 | 2.4 | 6.0 | 4.0 | 2.0 |
| 45 | 183 | LLAAPVVIALAP | 12 | 6 | 57.3 | 211.6 | 2.4 | 6.0 | 4.0 | 2.0 |
| 58 | 243 | AAVLLPVALAAP | 12 | 6 | 57.3 | 187.5 | 2.1 | 5.9 | 3.9 | 2.0 |
| 148 | 664 | ILIAIAIPAAAP | 12 | 8 | 54.9 | 204.1 | 2.3 | 5.7 | 3.8 | 1.9 |
| 174 | 783 | IVALVPAVAIAP | 12 | 6 | 50.2 | 203.3 | 2.5 | 5.7 | 3.8 | 1.9 |
| 116 | 502 | AIVALAVPVLAP | 12 | 8 | 50.2 | 203.3 | 2.4 | 5.6 | 3.7 | 1.9 |
| 61 | 262 | ALIAVPAIIVAP | 12 | 6 | 50.2 | 211.6 | 2.4 | 5.5 | 3.7 | 1.9 |
| 152 | 683 | LAIVLAAPAVLP | 12 | 8 | 50.2 | 211.7 | 2.4 | 5.5 | 3.2 | 1.9 |
| 193 | 830 | IALVAAPVALVP | 12 | 7 | 57.3 | 203.3 | 2.4 | 5.3 | 3.5 | 1.8 |
| 170 | 764 | AVALAVLPAVVP | 12 | 8 | 57.3 | 195.0 | 2.3 | 5.0 | 3.4 | 1.7 |
| 182 | 807 | AVALAVPALVLP | 12 | 7 | 57.3 | 203.3 | 2.3 | 5.0 | 3.3 | 1.7 |
| 46 | 184 | LAAIVPAIIAVP | 12 | 6 | 50.2 | 211.6 | 2.4 | 4.8 | 3.2 | 1.6 |
| 73 | 305 | IALAAPILLAAP | 12 | 6 | 57.3 | 204.2 | 2.2 | 4.8 | 3.2 | 1.6 |
| 27 | 101 | LVALAPVAAVLP | 12 | 6 | 57.3 | 203.3 | 2.3 | 4.5 | 3.0 | 1.5 |
| 72 | 304 | AIILAPIAAIAP | 12 | 6 | 57.3 | 204.2 | 2.3 | 4.4 | 3.0 | 1.5 |
| 140 | 604 | VALIAVAPVVP | 12 | 8 | 57.3 | 195.0 | 2.4 | 4.3 | 2.5 | 1.5 |
| 146 | 645 | ALAVVALPAIVP | 12 | 8 | 50.2 | 203.3 | 2.4 | 4.3 | 2.9 | 1.5 |
| 48 | 201 | LALAVPALAALP | 12 | 6 | 57.3 | 195.8 | 2.1 | 4.2 | 2.8 | 1.4 |
| 41 | 163 | LALVLPAALAAP | 12 | 6 | 57.3 | 195.8 | 2.1 | 4.1 | 2.4 | 1.4 |
| 195 | 832 | AVAAIVPVIVAP | 12 | 7 | 43.2 | 195.0 | 2.5 | 4.1 | 2.7 | 1.4 |
| 44 | 182 | ALIAPVVALVAP | 12 | 6 | 57.3 | 203.3 | 2.4 | 4.0 | 2.7 | 1.4 |
| 11 | 23 | VVLVLPAAAAVP | 12 | 6 | 57.3 | 195.0 | 2.4 | 4.0 | 2.6 | 1.3 |
| 31 | 105 | LLALAPAALLAP | 12 | 6 | 57.3 | 204.1 | 2.1 | 4.0 | 2.6 | 1.3 |
| 129 | 561 | AAVAIVLPAVVP | 12 | 8 | 50.2 | 195.0 | 2.4 | 3.9 | 2.6 | 1.3 |

TABLE 29-continued

| Sequence ID Number | aMTD | Sequences | Length | Proline Position (PP) | Rigidity/ Flexibility (II) | Sturctural Feature (AI) | Hydro- pathy (GRAVY) | Relative Ratio (Fold) A | B | C |
|---|---|---|---|---|---|---|---|---|---|---|
| 171 | 765 | AVALAVVPAVLP | 12 | 8 | 57.3 | 195.0 | 2.3 | 3.8 | 2.2 | 1.3 |
| 153 | 684 | AAIVLALPAVLP | 12 | 8 | 50.2 | 211.7 | 2.4 | 3.5 | 2.1 | 1.2 |
| 36 | 143 | AVLAVPAVLVAP | 12 | 6 | 57.3 | 195.0 | 2.4 | 3.3 | 2.2 | 1.1 |
| 118 | 504 | LIVALAVPALAP | 12 | 8 | 50.2 | 211.7 | 2.4 | 3.3 | 2.2 | 1.1 |
| 10 | 22 | AVVLVPVLAAAP | 12 | 6 | 57.3 | 195.0 | 2.4 | 3.1 | 2.1 | 1.1 |
| 5 | 5 | AAALLPVALVAP | 12 | 6 | 57.3 | 187.5 | 2.1 | 3.1 | 2.1 | 1.0 |
| 67 | 283 | AALLAPALIVAP | 12 | 6 | 50.2 | 195.8 | 2.2 | 3.1 | 2.0 | 1.0 |
| 21 | 65 | IAIVAPVVALAP | 12 | 6 | 50.2 | 203.3 | 2.4 | 3.0 | 2.0 | 1.0 |
| 219 | 883 | LAIVPAAIAALP | 12 | 6 | 50.2 | 195.8 | 2.2 | 3.0 | 2.0 | 1.0 |
| 33 | 123 | AAIIVPAALLAP | 12 | 6 | 50.2 | 195.8 | 2.2 | 2.9 | 2.0 | 1.0 |

TABLE 30

| Sequence ID Number | aMTD | Sequences | Length | Proline Position (PP) | Rigidity/ Flexibility (II) | Sturctural Feature (AI) | Hydro- pathy (GRAVY) | Relative Ratio (Fold) A | B | C |
|---|---|---|---|---|---|---|---|---|---|---|
| 68 | 284 | ALIAPAVALIVP | 12 | 5 | 50.2 | 211.7 | 2.4 | 2.8 | 1.8 | 0.9 |
| 50 | 205 | ALALVPAIAALP | 12 | 6 | 57.3 | 195.8 | 2.2 | 2.6 | 1.7 | 0.9 |
| 14 | 42 | VAALPVVAVVAP | 12 | 5 | 57.3 | 186.7 | 2.4 | 2.5 | 1.7 | 0.8 |
| 32 | 121 | AIVALPAIALAP | 12 | 6 | 50.2 | 195.8 | 2.2 | 2.5 | 1.7 | 0.8 |
| 13 | 25 | IVAVAPALVALP | 12 | 6 | 50.2 | 203.3 | 2.4 | 2.4 | 1.6 | 0.8 |
| 12 | 24 | IALAAPALIVAP | 12 | 6 | 50.2 | 195.8 | 2.2 | 2.3 | 1.6 | 0.8 |
| 49 | 204 | LIAALPAVAALP | 12 | 6 | 57.3 | 195.8 | 2.2 | 2.2 | 1.5 | 0.8 |
| 7 | 12 | LLAAVPAVLLAP | 12 | 6 | 57.3 | 211.7 | 2.3 | 2.2 | 1.5 | 0.7 |
| 15 | 43 | LLAAPLVVAAVP | 12 | 5 | 41.3 | 187.5 | 2.1 | 2.1 | 1.4 | 0.7 |
| 29 | 103 | ALIAAPILALAP | 12 | 6 | 57.3 | 204.2 | 2.2 | 2.1 | 1.4 | 0.7 |
| 23 | 82 | AVVLAPVAAVLP | 12 | 6 | 57.3 | 195.0 | 2.4 | 2.1 | 1.4 | 0.7 |
| 4 | 4 | ALALLPVAALAP | 12 | 6 | 57.3 | 195.8 | 2.1 | 2.0 | 1.3 | 0.7 |
| 26 | 85 | LLVLPAAALAAP | 12 | 5 | 57.3 | 195.8 | 2.1 | 1.9 | 1.3 | 0.7 |
| 19 | 63 | AALLVPALVAVP | 12 | 6 | 57.3 | 203.3 | 2.3 | 1.9 | 1.3 | 0.7 |
| 16 | 44 | ALAVPVALLVAP | 12 | 5 | 57.3 | 203.3 | 2.3 | 1.6 | 1.1 | 0.5 |
| 25 | 84 | AAVAAPLLLALP | 12 | 6 | 41.3 | 195.8 | 2.1 | 1.5 | 1.0 | 0.5 |
| 18 | 62 | VALLAPVALAVP | 12 | 6 | 57.3 | 203.3 | 2.3 | 1.4 | 0.9 | 0.5 |
| 24 | 83 | LAVAAPLALALP | 12 | 6 | 41.3 | 195.8 | 2.1 | 1.4 | 0.9 | 0.5 |
| 28 | 102 | LALAPAALALLP | 12 | 5 | 57.3 | 204.2 | 2.1 | 1.4 | 0.9 | 0.5 |
| 143 | 623 | VAAAIALPAIVP | 12 | 8 | 50.2 | 187.5 | 2.3 | 0.8 | 0.6 | 0.3 |
|  |  |  |  |  |  |  |  | 19.6 ± 1.6 | 13.1 ± 1.1 | 6.6 ± 0.5 |

Moreover, compared to reference CPPs (B type: MTM12 (SEQ ID NO: 953) and C type: MTD85 (SEQ ID NO: 954)), novel 240 aMTDs averaged of 13±1.1 (maximum 109.9) and 6.6±0.5 (maximum 55.5) fold higher cell-permeability, respectively (Tables 26-31).

TABLE 31

|  | Negative Control rP38 | MTM12 | MTD85 |
|---|---|---|---|
| aMTD | 19.6 ± 1.6* | 13.1 ± 1.1* | 6.6 ± 0.5* |

TABLE 31-continued

|  | Negative Control rP38 | MTM12 | MTD85 |
|---|---|---|---|
| The Average of 240 aMTDs | (Best: 164.2) | (Best: 109.9) | (Best: 55.5) |

*Relative Fold (aMTD in Geo Mean in its comparison to rP38, MTM12 or MTD85)

In addition, cell-permeability of 31 rPeptides has been compared with that of 240 aMTDs (0.3±0.04; Tables 32 and 33).

TABLE 32

| Number SEQ ID NOS) | ID | Sequence | Length | Proline Position (PP) | Rigidity/ Flexibility (II) | Structural Feature (AI) | Hydro- pathy (GRAVY) | Relative Ratio To aMTD AVE |
|---|---|---|---|---|---|---|---|---|
| 907 | 692 | PAPLPPVVILAV | 12 | 1, 3, 5, 6 | 105.5 | 186.7 | 1.8 | 0.74 |
| 895 | 26 | AAIAKLAAPLAIV | 12 | 8 | 18.1 | 204.2 | 2.5 | 0.65 |
| 891 | 113 | PVAVALLIAVPP | 12 | 1, 11, 12 | 57.3 | 195.0 | 2.1 | 0.61 |
| 897 | 466 | IIAAAAPLAIIP | 12 | 7, 12 | 22.8 | 204.2 | 2.3 | 0.52 |
| 898 | 167 | VAIAIPAALAIP | 12 | 6, 12 | 20.4 | 195.8 | 2.3 | 0.50 |
| 936 | 97 | ALLAAPPALLAL | 12 | 6, 7 | 57.3 | 204.2 | 2.1 | 0.41 |
| 909 | 390 | VPLLVPVVPVVP | 12 | 2, 6, 9, 12 | 105.4 | 210.0 | 2.2 | 0.41 |
| 900 | 426 | AAALAIPLAIIP | 12 | 7, 12 | 4.37 | 204.2 | 2.2 | 0.40 |
| 937 | 241 | ALIVAPALMALP | 12 | 6, 12 | 60.5 | 187.5 | 2.2 | 0.33 |
| 913 | 68 | VAPVLPAAPLVP | 12 | 3, 6, 9, 12 | 105.5 | 162.5 | 1.6 | 0.32 |
| 941 | 39 | CYNTSPCTGCCY | 12 | 6 | 52.5 | 0.0 | 0.0 | 0.29 |
| 888 | 934 | LILAPAAVVAAA | 12 | 5 | 57.5 | 195.8 | 2.5 | 0.28 |
| 916 | 938 | VPVLLPVVVPVP | 12 | 2, 6, 10, 12 | 121.5 | 210.0 | 2.2 | 0.28 |
| 917 | 329 | LPVLVPVVVPVP | 12 | 2, 6, 9, 12 | 121.5 | 210.0 | 2.2 | 0.23 |
| 901 | 606 | AAAIAAIPIIIP | 12 | 8, 12 | 4.4 | 204.2 | 2.4 | 0.20 |
| 918 | 49 | VVPAAPAVPVVP | 12 | 3, 6, 9, 12 | 121.5 | 145.8 | 1.7 | 0.18 |
| 944 | 139 | TGSTNSPTCTST | 12 | 7 | 53.4 | 0.0 | -0.7 | 0.17 |
| 919 | 772 | LPVAPVIPIIVP | 12 | 2, 5, 8, 12 | 79.9 | 210.8 | 2.1 | 0.16 |
| 931 | 921 | IWWFVVLPLVVP | 12 | 8, 12 | 41.3 | 194.2 | 2.2 | 0.14 |
| 902 | 66 | AGVLGGPIMGVP | 12 | 7, 12 | 35.5 | 121.7 | 1.3 | 0.13 |
| 922 | 693 | AAPVLPVAVPIV | 12 | 3, 6, 10 | 82.3 | 186.7 | 2.1 | 0.13 |
| 945 | 18 | NYCCTPTTNGQS | 12 | 6 | 47.9 | 0.0 | -0.9 | 0.10 |
| 890 | 16 | NNSCITYINGSQ | 12 | None | 47.4 | 0.0 | -1.4 | 0.08 |
| 904 | 227 | LAAIVPIAAAVP | 12 | 6, 12 | 34.2 | 187.5 | 2.2 | 0.08 |
| 905 | 17 | GGCSAPQTTCSN | 12 | 6 | 51.6 | 8.3 | -0.5 | 0.08 |
| 906 | 67 | LDAEVPLADDVP | 12 | 6, 12 | 34.2 | 130.0 | 0.3 | 0.08 |
| 947 | 635 | GSTGGSQQNNQY | 12 | None | 31.9 | 0.0 | -1.9 | 0.07 |
| 924 | 29 | VLPPLPVLPVLP | 12 | 3, 4, 6, 9, 12 | 121.5 | 202.5 | 1.7 | 0.07 |
| 949 | 57 | QNNCNTSSQGGG | 12 | None | 52.4 | 0.0 | -1.6 | 0.06 |
| 951 | 700 | GTSNTCQSNQNS | 12 | None | 19.1 | 0.0 | -1.6 | 0.05 |

TABLE 32-continued

| Number SEQ ID NOS) | ID | Sequence | Length | Proline Position (PP) | Rigidity/ Flexibility (II) | Sturctural Feature (AI) | Hydro- pathy (GRAVY) | Relative Ratio To aMTD AVE |
|---|---|---|---|---|---|---|---|---|
| 952 | 38 | YYNQSTCGGQCY | 12 | ND | 53.8 | 0.0 | -1.0 | 0.05 |
|  |  |  |  |  |  |  | AVE | 0.3 ± 0.04 |

TABLE 33

|  | Relative Ratio to aMTD AVE* |
|---|---|
| rPeptide The Average of 31 aMTDs | 0.3 ± 0.04 |

*Out of 240 aMTDs, average relative fold of aMTD had been 19.6 fold compared to type A (rP38).

In summary, relative cell-permeability of aMTDs has shown maximum of 164.0, 109.9 and 55.5 fold higher to rP38, MTM12 and MTD85, respectively. In average of total 240 aMTD sequences, 19.6±1.6, 13.1±1.1 and 6.6±0.5 fold higher cell-permeability are shown to the rP38, MTM12 (SEQ ID NO: 953) and MTD85 (SEQ ID NO: 954), respectively (Tables 26-31). Relative cell-permeability of negative control (rP38 (SEQ ID NO: 952)) to the 240 aMTDs is only 0.3±0.04 fold.

4-5. Intracellular Delivery and Localization of aMTD-Fused Recombinant Proteins

Recombinant proteins fused to the aMTDs were tested to determine their intracellular delivery and localization by laser scanning confocal microscopy with a negative control (rP38 (SEQ ID NO: 952)) and previous published CPPs (MTM12 (SEQ ID NO: 953) and MTD85 (SEQ ID NO: 954)) as the positive control references. NIH3T3 cells were exposed to 10 µM of FITC-labeled protein for 1 hour at 37, and nuclei were counterstained with DAPI. Then, cells were examined by confocal laser scanning microscopy (FIG. 7). Recombinant proteins fused to aMTDs clearly display intracellular delivery and cytoplasmic localization (FIG. 7) that are typically higher than the reference CPPs (MTM12 (SEQ ID NO: 953) and MTD85 (SEQ ID NO: 954)). The rP38 (SEQ ID NO: 952)-fused recombinant protein did not show internalized fluorescence signal (FIG. 7a). In addition, as seen in FIG. 8, rPeptides (his-tagged CRA recombinant proteins fused to each rPeptide) display lower- or non-cell-permeability.

4-6. Summary of Quantitative and Visual Cell-Permeability of Newly Developed aMTDs Histidine-tagged aMTD-fused cargo recombinant proteins have been greatly enhanced in their solubility and yield. Thus, FITC-conjugated recombinant proteins have also been tested to quantitate and visualize intracellular localization of the proteins and demonstrated higher cell-permeability compared to the reference CPPs.

In the previous studies using the hydrophobic signal-sequence-derived CPPs-MTS/MTM or MTDs, 17 published sequences have been identified and analyzed in various characteristics such as length, molecular weight, pI value, bending potential, rigidity, flexibility, structural feature, hydropathy, amino acid residue and composition, and secondary structure of the peptides. Based on these analytical data of the sequences, novel artificial and non-natural peptide sequences designated as advanced MTDs (aMTDs) have been invented and determined their functional activity in intracellular delivery potential with aMTD-fused recombinant proteins.

aMTD-fused recombinant proteins have promoted the ability of protein transduction into the cells compared to the recombinant proteins containing rPeptides and/or reference hydrophobic CPPs (MTM12 (SEQ ID NO: 953) and MTD85 (SEQ ID NO: 954)). According to the results, it has been demonstrated that critical factors of cell-penetrating peptide sequences play a major role to determine peptide-mediated intracellular delivery by penetrating plasma membrane. In addition, cell-permeability can considerably be improved by following the rational that all satisfy the critical factors.

5. Structure/Sequence Activity Relationship (SAR) of aMTDs on Delivery Potential After determining the cell-permeability of novel aMTDs, structure/sequence activity relationship (SAR) has been analyzed for each critical factor in selected some of and all of novel aMTDs (FIGS. 13 to 16 and Table 34).

TABLE 34

| Rank of Delivery Potential | Rigidity/ Flexibility (II) | Sturctural Feature (AI) | Hydropathy (GRAVY) | Relative Ratio (Fold) | | | Amino Acid Composition | | | | |
|---|---|---|---|---|---|---|---|---|---|---|---|
|  |  |  |  | A | B | C | A | V | I | L |
| 1~10 | 55.9 | 199.2 | 2.3 | 112.7 | 75.5 | 38.1 | 4.0 | 3.5 | 0.4 | 2.1 |
| 11~20 | 51.2 | 205.8 | 2.4 | 56.2 | 37.6 | 19.0 | 4.0 | 2.7 | 1.7 | 1.6 |
| 21~30 | 49.1 | 199.2 | 2.3 | 43.6 | 28.9 | 14.6 | 4.3 | 2.7 | 1.4 | 1.6 |
| 31~40 | 52.7 | 201.0 | 2.4 | 34.8 | 23.3 | 11.8 | 4.2 | 2.7 | 1.5 | 1.6 |
| 41~50 | 53.8 | 201.9 | 2.3 | 30.0 | 20.0 | 10.1 | 4.3 | 2.3 | 1.1 | 2.3 |
| 51~60 | 51.5 | 205.2 | 2.4 | 23.5 | 15.7 | 7.9 | 4.4 | 2.1 | 1.5 | 2.0 |
| 222~231 | 52.2 | 197.2 | 2.3 | 2.2 | 1.5 | 0.8 | 4.5 | 2.1 | 1.0 | 2.4 |
| 232~241 | 54.1 | 199.7 | 2.2 | 1.7 | 1.2 | 0.6 | 4.6 | 1.7 | 0.2 | 3.5 |

5-1. Proline Position: In regards to the bending potential (proline position: PP), aMTDs with its proline at 7' or 8' amino acid in their sequences have much higher cell-permeability compared to the sequences in which their proline position is at 5' or 6' (FIGS. 14a and 15a).

5-2. Hydropathy: In addition, when the aMTDs have GRAVY (Grand Average of Hydropathy) ranging in 2.1-2.2, these sequences display relatively lower cell-permeability, while the aMTDs with 2.3-2.6 GRAVY are shown significantly higher one (FIGS. 14b and 15b).

5-3. rPeptide SAR: To the SAR of aMTDs, rPeptides have shown similar SAR correlations in the cell-permeability, pertaining to their proline position (PP) and hydropathy (GRAVY). These results confirms that rPeptides with high GRAVY (2.4~2.6) have better cell-permeability (FIG. 16).

5-4. Analysis of amino acid composition: In addition to proline position and hydropathy, the difference of amino acid composition is also analyzed. Since aMTDs are designed based on critical factors, each aMTD-fused recombinant protein has equally two proline sequences in the composition. Other hydrophobic and aliphatic amino acids—alanine, isoleucine, leucine and valine—are combined to form the rest of aMTD peptide sequences.

Alanine: In the composition of amino acids, the result does not show a significant difference by the number of alanine in terms of the aMTD's delivery potential because all of the aMTDs have three to five alanines. In the sequences, however, four alanine compositions show the most effective delivery potential (geometric mean) (FIG. 13a).

Leucine and Isoleucine: Also, the compositions of isoleucine and leucine in the aMTD sequences show inverse relationship between the number of amino acid (I and L) and delivery potential of aMTDs. Lower number of isoleucine and leucine in the sequences tends to have higher delivery potential (geometric mean) (FIGS. 13a and 13b).

Valine: Conversely, the composition of valine of aMTD sequences shows positive correlation with their cell-permeability. When the number of valine in the sequence is low, the delivery potential of aMTD is also relatively low (FIG. 13b).

Ten aMTDs having the highest cell-permeability are selected (average geometric mean: 2584±126). Their average number of valine in the sequences is 3.5; 10 aMTDs having relatively low cell-permeability (average geometric mean: 80±4) had average of 1.9 valine amino acids. The average number of valine in the sequences is lowered as their cell-permeability is also lowered as shown in FIG. 13b. Compared to higher cell-permeable aMTDs group, lower sequences had average of 1.9 in their valine composition. Therefore, to obtain high cell-permeable sequence, an average of 2-4 valines should be composed in the sequence.

5-5. Conclusion of SAR analysis: As seen in FIG. 15, all 240 aMTDs have been examined for these association of the cell-permeability and the critical factors: bending potential (PP), rigidity/flexibility (II), structure feature (AI), and hydropathy (GRAVY), amino acid length and composition. Through this analysis, cell-permeability of aMTDs tends to be lower when their central proline position is at 5' or 6' and GRAVY is 2.1 or lower (FIG. 15). Moreover, after investigating 10 higher and 10 lower cell-permeable aMTDs, these trends are clearly shown to confirm the association of cell-permeability with the central proline position and hydropathy.

6. Experimental Confirmation of Index Range/Feature of Critical Factors

The range and feature of five out of six critical factors have been empirically and experimentally determined that are also included in the index range and feature of the critical factors initially proposed before conducting the experiments and SAR analysis. In terms of index range and feature of critical factors of newly developed 240 aMTDs, the bending potential (proline position: PP), rigidity/flexibility (Instability Index: II), structural feature (Aliphatic Index: AI), hydropathy (GRAVY), amino acid length and composition are all within the characteristics of the critical factors derived from analysis of reference hydrophobic CPPs.

Therefore, our hypothesis to design and develop new hydrophobic CPP sequences as advanced MTDs is empirically and experimentally proved and demonstrated that critical factor-based new aMTD rational design is correct.

TABLE 35

Summarized Critical Factors of aMTD

| Critical Factor | Newly Designed CPPs Range | Analysis of Experimental Results Range |
|---|---|---|
| Bending Potential (Proline Position: PP) | Proline presences in the middle (5', 6', 7' or 8') and at the end of peptides | Proline presences in the middle (5', 6', 7' or 8') and at the end of peptides |
| Rigidity/Flexibility (Instability Index: II) | 40-60 | 41.3-57.3 |
| Structural Feature (Aliphatic Index: AI) | 180-220 | 187.5-220.0 |
| Hydropathy (Grand Average of Hydropathy GRAVY) | 2.1-2.6 | 2.2-2.6 |
| Length (Number of Amino Acid) | 9-13 | 12 |
| Amino acid Composition | A, V, I, L, P | A, V, I, L, P |

7. Discovery and Development of Protein-Based New Biotherapeutics with MITT Enabled by aMTDs for Protein Therapy Total of 240 aMTD sequences have been designed and developed based on the critical factors. Quantitative and visual cell-permeability of 240 aMTDs (hydrophobic, flexible, bending, aliphatic and 12 a/a-length peptides) are all practically determined.

To measure the cell-permeability of aMTDs, rPeptides have also been designed and tested. As seen in FIGS. 13 to 15, there are vivid association of cell-permeability and the critical factors of the peptides. Out of these critical factors, we are able to configure that the most effective cell-permeable aMTDs have the amino acid length of 12; composition of A, V, L, I and P; multiple proline located at either 7' or 8' and at the end (12'); instability index ranged of 41.3-57.3; aliphatic index ranged of 187.5-220.0; and hydropathy (GRAVY) ranged of 2.2-2.6.

These examined critical factors are within the range that we have set for our critical factors; therefore, we are able to confirm that the aMTDs that satisfy these critical factors have relatively high cell-permeability and much higher intracellular delivery potential compared to reference hydrophobic CPPs reported during the past two decades.

It has been widely evident that many human diseases are caused by proteins with deficiency or over-expression that causes mutations such as gain-of-function or loss-of-function. If biologically active proteins could be delivered for replacing abnormal proteins within a short time frame, possibly within an hour or two, in a quantitative manner, the dosage may be regulated depending on when and how proteins may be needed. By significantly improving the solubility and yield of novel aMTD in this invention (Table 31), one could expect its practical potential as an agent to effectively deliver therapeutic macromolecules such as proteins, peptides, nucleic acids, and other chemical compounds into live cells as well as live mammals including human. Therefore, newly developed MITT utilizing the pool (240) of novel aMTDs can be used as a platform technology for discovery and development of protein-based biotherapeutics to apprehend intracellular protein therapy after determining the optimal cargo-aMTD relationship.

The following examples are presented to aid practitioners of the invention, to provide experimental support for the invention, and to provide model protocols. In no way are these examples to be understood to limit the invention.

Example 1. Development of Novel Advanced Macromolecule Transduction Domain (aMTD)

H-regions of signal sequences (HRSP)-derived CPPs (MTS/MTM and MTD) do not have a common sequence, a sequence motif, and/or a common structural homologous feature. In this invention, the aim is to develop improved hydrophobic CPPs formatted in the common sequence and structural motif that satisfy newly determined 'critical factors' to have a 'common function,' to facilitate protein translocation across the plasma membrane with similar mechanism to the analyzed CPPs.

The structural motif is shown in FIG. 104. In FIG. 104, X(s) independently refer to Alanine (A), Valine (V), Leucine (L) or Isoleucine (I); and Proline (P) can be positioned in one of U(s) (either 5', 6', 7' or 8'). The remaining U(s) are independently composed of A, V, L or I, P at the 12' is Proline.

In Table 9, universal common sequence/structural motif is provided as follows. The amino acid length of the peptides in this invention ranges from 9 to 13 amino acids, mostly 12 amino acids, and their bending potentials are dependent with the presence and location of proline in the middle of sequence (at 5', 6', 7' or 8' amino acid) and at the end of peptide (at 12') for recombinant protein bending. Instability index (II) for rigidity/flexibility of aMTDs is II<40, grand average of hydropathy (GRAVY) for hydropathy is around 2.2, and aliphatic index (AI) for structural features is around 200 (Table 9). Based on these standardized critical factors, new hydrophobic peptide sequences, namely advanced macromolecule transduction domain peptides (aMTDs), in this invention have been developed and summarized in Tables 10 to 15.

Example 2. Construction of Expression Vectors for Recombinant Proteins Fused to aMTDs Our newly developed technology has enabled us to expand the method for making cell-permeable recombinant proteins. The expression vectors were designed for histidine-tagged CRA proteins fused with aMTDs or rPeptides. To construct expression vectors for recombinant proteins, polymerase chain reaction (PCR) had been devised to amplify each designed aMTD or rPeptide fused to CRA.

The PCR reactions (100 ng genomic DNA, 10 pmol each primer, each 0.2 mM dNTP mixture, 1× reaction buffer and 2.5 U Pfu(+) DNA polymerase (Doctor protein, Korea) was digested on the restriction enzyme site between Nde I (5') and Sal I (3') involving 35 cycles of denaturation (95° C.), annealing (62° C.), and extension (72° C.) for 30 seconds each. For the last extension cycle, the PCR reactions remained for 5 minutes at 72° C. Then, they were cloned into the site of pET-28a(+) vectors (Novagen, Darmstadt, Germany). DNA ligation was performed using T4 DNA ligase at 4° C. overnight. These plasmids were mixed with competent cells of *E. coli* DH5-alpha strain on the ice for 10 minutes. This mixture was placed on the ice for 2 minutes after it was heat shocked in the water bath at 42° C. for 90 seconds. Then, the mixture added with LB broth media was recovered in 37° C. shaking incubator for 1 hour. Transformant was plated on LB broth agar plate with kanamycin (50 µg/mL) (Biopure, Johnson City, Tenn., USA) before incubating at 37° C. overnight. From a single colony, plasmid DNA was extracted, and after the digestion of Nde I and Sal I restriction enzymes, digested DNA was confirmed at 645 bp by using 1.2% agarose gels electrophoresis (FIG. 2). PCR primers for the CRA recombinant proteins fused to aMTD and random peptides (rPeptide) are summarized in Tables 23 to 30. Amino acid sequences of aMTD and rPeptide primers are shown in Tables 31 to 38.

Example 3. Inducible Expression, Purification and Preparation of Recombinant Proteins Fused to aMTDs and rPeptides To express recombinant proteins, pET-28a(+) vectors for the expression of CRA proteins fused to a negative control [rPeptide 38 (rP38) (SEQ ID NO: 952)], reference hydrophobic CPPs (MTM$_{12}$ (SEQ ID NO: 953) and MTD$_{85}$ (SEQ ID NO: 954)) and aMTDs were transformed in *E. coli* BL21 (DE3) strains. Cells were grown at 37° C. in LB medium containing kanamycin (50 µg/ml) with a vigorous shaking and induced at OD$_{600}$=0.6 by adding 0.7 mM IPTG (Biopure) for 2 hours at 37° C. Induced recombinant proteins were loaded on 15% SDS-PAGE gel and stained with Coomassie Brilliant Blue (InstantBlue, Expedeon, Novexin, UK) (FIG. 3).

The *E. coli* cultures were harvested by centrifugation at 5,000×rpm for 10 minutes, and the supernatant was discarded. The pellet was re-suspended in the lysis buffer (50 mM NaH$_2$PO$_4$, 10 mM Imidazol, 300 mM NaCl, pH 8.0). The cell lysates were sonicated on ice using a sonicator (Sonics and Materials, Inc., Newtown, Conn., USA) equipped with a probe. After centrifuging the cell lysates at 5,000×rpm for 10 minutes to pellet the cellular debris, the supernatant was incubated with lysis buffer-equilibrated Ni-NTA resin (Qiagen, Hilden, Germany) gently by open-column system (Bio-rad, Hercules, Calif., USA). After washing protein-bound resin with 200 ml wash buffer (50 mM NaH$_2$PO$_4$, 20 mM Imidazol, 300 mM NaCl, pH 8.0), the bounded proteins were eluted with elution buffer (50 mM NaH$_2$PO$_4$, 250 mM Imidazol, 300 mM NaCl, pH 8.0).

Recombinant proteins purified under natural condition were analyzed on 15% SDS-PAGE gel and stained with Coomassie Brilliant Blue (FIG. 4). All of the recombinant proteins were dialyzed for 8 hours and overnight against physiological buffer, a 1:1 mixture of cell culture medium (Dulbecco's Modified Eagle's Medium: DMEM, Hyclone, Logan, Utah, USA) and Dulbecco's phosphate buffered saline (DPBS, Gibco, Grand Island, N.Y., USA). From 316 aMTDs and 141 rPeptides cloned, 240 aMTD- and 31 rPeptide-fused recombinant proteins were induced, purified, prepared and analyzed for their cell-permeability.

Example 4. Determination of Quantitative Cell-Permeability of Recombinant Proteins For quantitative cell-permeability, the aMTD- or rPeptide-fused recombinant proteins were conjugated to fluorescein isothiocyanate (FITC) according to the manufacturer's instructions (Sigma-Aldrich, St. Louis, Mo., USA). RAW 264.7 cells were treated with 10 µM FITC-labeled recombinant proteins for 1 hour at 37° C., washed three times with cold PBS, treated with 0.25% tripsin/EDTA (Sigma-Aldrich, St. Louis, Mo.) for 20 minutes at 37° C. to remove cell-surface bound proteins. Cell-permeability of these recombinant proteins were analyzed by flow cytometry (Guava, Millipore, Darmstadt, Germany) using the FlowJo cytometric analysis software (FIGS. 5 to 6). The relative cell-permeability of aMTDs were measured and compared with the negative control (rP38 (SEQ ID NO: 952)) and reference hydrophobic CPPs (MTM12 (SEQ ID NO: 953) and MTD85 (SEQ ID NO: 954)) (Table 31).

Example 5. Determination of Cell-Permeability and Intracellular Localization of Recombinant Proteins For a visual reference of cell-permeability, NIH3T3 cells were cultured for 24 hours on coverslip in 24-wells chamber slides, treated with 10 μM FITC-conjugated recombinant proteins for 1 hour at 37° C., and washed three times with cold PBS. Treated cells were fixed in 4% paraformaldehyde (PFA, Junsei, Tokyo, Japan) for 10 minutes at room temperature, washed three times with PBS, and mounted with VECTASHIELD Mounting Medium (Vector laboratories, Burlingame, Calif., USA), and counter stained with DAPI (4',6-diamidino-2-phenylindole). The intracellular localization of the fluorescent signal was determined by confocal laser scanning microscopy (LSM700, Zeiss, Germany; FIGS. 7 and 8).

Example 6-1. Cloning of aMTD/SD-Fused SOCS3 Recombinant Protein

Full-length cDNA for human SOCS3 (SEQ ID NO: 815) was purchased from Origene (USA). Histidine-tagged human SOCS3 proteins were constructed by amplifying the SOCS3 cDNA (225 amino acids) using primers for aMTD fused to SOCS3 cargo. The PCR reactions (100 ng genomic DNA, 10 pmol each primer, each 0.2 mM dNTP mixture, 1× reaction buffer and 2.5 U Pfu(+) DNA polymerase (Doctor protein, Korea)) were digested on the restriction enzyme site between Nde I (5') and Sal I (3') involving 35 cycles of denaturing (95° C.), annealing (62° C.), and extending (72° C.) for 45 sec each. For the last extension cycle, the PCR reactions remained for 10 min at 72° C. The PCR products were subcloned into 6× His expression vector, pET-28a(+) (Novagen, Darmstadt, Germany). Coding sequence for SDA or SDB fused to C terminus of his-tagged aMTD-SOCS3 was cloned at BamHI (5') and SalI (3') in pET-28a(+) from PCR-amplified DNA segments and confirmed by DNA sequence analysis of the resulting plasmids.

TABLE 36

| Cargo | SD | Recombinant Protein | 5' Primers | 3' Primers |
|---|---|---|---|---|
| SOCS3 | — | HS3 | 5'-GGAATTCCATATGGTCA CCCACAGCAAGTTTCCCGC CGCC-3' (SEQ ID NO: 955) | 5'-CCCGGATCCTTAAAGC GGGGCATCGTACTGGTCC AGGAA-3' (SEQ ID NO: 956) |
| | — | HM$_{165}$S3 | 5'-GGAATTCCATATGGCGCT GGCGGTGCCGGTGGCGCT GGCGATTGTGCCGGTCACC CACAGCAAGTTTC-3' (SEQ ID NO: 957) | 5'-CCCGGATCCTTAAAG CGGGGCATCGTACTGGT CCAGGAA-3' (SEQ ID NO: 958) |
| | A | HM$_{165}$S3A | 5'-GGAATTCCATATGGCGC TGGCGGTGCCGGTGGCGC TGGCGATTGTGCCGGTCAC CCACAGCAAGTTTC-3' (SEQ ID NO: 959) | 5'-CGCGTCGACTTACCTCG GCTGCACCGG CACGGAG ATGAC-3' (SEQ ID NO: 960) |
| | B | HM$_{165}$S3B | 5'-GGAATTCCATATGGCGCT GGCGGTGCCGGTGGCGCT GGCGATTGTGCCGGTCACC CACAGCAAGTTTC-3' (SEQ ID NO: 961) | 5'-CGCGTCGACTTAAAGG GTTTCCGAAGGCTTGGCT ATCTT-3' (SEQ ID NO: 962) |
| | C | HM$_{165}$S3C | 5'-GGAATTCCATATGGCGC TGGCGGTGCCGGTGGCGCT GGCGATTGTGCCGGTCACC CACAGCAAGTTTC-3' (SEQ ID NO: 963) | 5'-GCGTCGACTTAGGC CAGGTTAGCGTCGAG-3' (SEQ ID NO: 964) |
| | D | HM$_{165}$S3D | 5'-GGAATTCCATATGGCGC TGGCGGTGCCGGTGGCGC TGGCGATTGTGCCGGTCAC CCACAGCAAGTTTC-3' (SEQ ID NO: 965) | 5'-GCGTCGACTTATTTT TTCTCGGACAGATA-3' (SEQ ID NO: 966) |
| | E | HM$_{165}$S3E | 5'-GGAATTCCATATGGCGC TGGCGGTGCCGGTGGCGC TGGCGATTGTGCCGGTCA CCCACAGCAAGTTTC-3' (SEQ ID NO: 967) | 5'-ACGCGTCGACTTAA CCTCCAATCTGTTCGCG GTGAGCCTC-3' (SEQ ID NO: 968) |

Example 6-2. Preparation of aMTD/SD-Fused SOCS3 Recombinant Protein

To determine a stable structure of the cell-permeable aMTD/SD-fused SOCS3 recombinant protein, a pET-28a(+) vector and an E. coli BL21-CodonPlus (DE3)-RIL were subjected to the following experiment.

Each of the recombinant expression vectors, HS3, HMS3, HMS3A, HMS3B, HMS3C, HMS3D, and HMS3E prepared in example 6-1 was transformed into E. coli BL21 Codon-Plus(DE3)-RIL by a heat shock method, and then 600 ul of each was incubated in an LB medium (Biopure, Johnson City, Tenn., USA) containing 50 μg/ml of kanamycin at 37° C. for 1 hour. Thereafter, the recombinant protein gene-introduced E. coli was inoculated in 7 ml of LB medium, and then incubated at 37° C. overnight. The E. coli was inoculated in 700 ml of LB medium and incubated at 37° C. until OD$_{600}$ reached 0.6. To this culture medium, 0.6 mM of isopropyl-β-D-thiogalactoside (IPTG, Gen Depot, USA)

was added as a protein expression inducer, followed by further incubation at 37° C. for 3 hours. This culture medium was centrifuged at 4° C. and 8,000 rpm for 10 minutes and a supernatant was discarded to recover a cell pellet. The cell pellet thus recovered was suspended in a lysis buffer (100 mM $NaH_2PO_4$, 10 mM Tris-HCl, 8 M Urea, pH 8.0), and cells were disrupted by sonication (on/off time: 30 sec/30 sec, on time 2 hours, amplify 40%), and centrifuged at 15,000 rpm for 30 min to obtain a soluble fraction and an insoluble fraction.

This insoluble fraction was suspended in a denature lysis buffer (8 M Urea, 10 mM Tris, 100 mM Sodium phosphate) and purified by $Ni^{e+}$ affinity chromatography as directed by the supplier(Qiagen, Hilden, Germany) and refolded by dialyzing with a refolding buffer (0.55 M guanidine HCl, 0.44 M L-arginine, 50 mM Tris-HCl, 150 mM NaCl, 1 mM EDTA, 100 mM NDSB, 2 mM reduced glutathione, and 0.2 mM oxidized glutathione). After purification, the proteins were put in a SnakeSkin Dialysis Tubing bag (pore size: 10000 mw, Thermo scientific, USA) and then they were dialyzed by physiological buffer (DMEM). The strain lysate where protein expression was not induced, the strain lysate where protein expression was induced by addition of IPTG, and purified proteins were loaded on SDS-PAGE to analyze protein expression characteristics and expression levels (FIGS. 19 and 20).

As shown in FIG. 19, it was confirmed that SOCS3 recombinant proteins showed high expression levels in the BL21CodonPlus(DE3)-RIL strain. SOCS3 recombinant proteins containing aMTD165 and solubilization domain ($HM_{165}$S3A and $HM_{165}$S3B) had little tendency to precipitate whereas recombinant SOCS3 proteins lacking a solubilization domain ($HM_{165}$S3) or lacking an aMTD and a SD (HS3) were largely insoluble. Solubility of aMTD/SD-fused SOCS3 proteins was scored on a 5 point scale compared with that of SOCS3 proteins lacking the solubilization domain.

Example 6-3. Determination of Solubility/Yield of aMTD/SD-Fused SOCS3 Recombinant Proteins According to SD Type To determine aMTD/SD-fused SOCS3 recombinant proteins having optimal cell-permeability, solubilization domains were replaced in the same manner as in Example 6-2 to prepare 5 kinds of aMTD/SD-fused SOCS3 recombinant proteins, and their solubility/yield were measured (FIG. 19).

As shown in FIG. 19, it was confirmed that the aMTD/SD-fused SOCS3 recombinant protein prepared by fusing with SDB among the different SDs showed the highest solubility/yield. Therefore, the SDB-fused iCP-SOCS3 recombinant protein was used in the subsequent experiment.

Example 6-4. Comparison Between aMTD/SD-Fused SOCS3 Recombinant Protein and Basic CPP/SD-Fused SOCS3 Recombinant Protein To compare the solubility/yield, cell/tissue-permeability, mechanism of cytopermeability of aMTD/SD-fused SOCS3 recombinant proteins to those of conventional basic CPP/SD-fused SOCS3 recombinant proteins, cloning, preparation, and measurement of solubility/yield of the basic CPP/SD-fused SOCS3 recombinant proteins were performed in the same manner as in Examples 6-1 to 6-3 except for a known basic CPP (TAT or PolyR) being used instead of aMTD. Sequences of amino acids and nucleotides of basic CPP, and the primers used in this example are shown in FIG. 97.

The solubility/yield of aMTD165/SD-fused SOCS3 recombinant proteins was much higher than that of TAT/SD-fused SOCS3 or PolyR/SD-fused SOCS3 recombinant proteins (FIG. 98).

Example 7-1. Cell-Permeability Test

To examine cell-permeability of SOCS3 recombinant protein, SOCS3 recombinant proteins were conjugated to 5/6-fluorescein isothiocyanate (FITC). RAW 264.7 (KCLB, Seoul, South Korea) (FIG. 20) or NIH3T3 cells (KCLB, Seoul, South Korea) (FIG. 21) were treated with 10 μM FITC-labeled SOCS3 recombinant proteins and cultivated for 1 hr at 37° C.

In this regard, RAW 264.7 cells were cultured in a DMEM medium containing 10% fetal bovine serum (FBS, Hyclone, USA) and 500 mg/ml of 1% penicillin/streptomycin (Hyclone, USA).

After cultivation, the cells were washed three times with ice-cold PBS (Phosphate-buffered saline, Hyclone, USA) and treated with proteinase K (10 μg/mL, SIGMA, USA) to remove surface-bound proteins, and internalized proteins were measured by flow cytometry (FlowJo cytometric analysis software, Guava, Millipore, Darmstadt, Germany). Untreated cells (gray) and equimolar concentration of unconjugated FITC (FITC only, green)-treated cells were served as control (FIG. 20). Each of NIH3T3 cells was incubated for 1 hour at 37° C. with 10 μM FITC-labeled SOCS3 protein. For nuclear staining, a mixture of VECTASHIELD Mounting Medium (Vector Laboratories, Burlingame, Calif.) and DAPI (4',6-diamidino-2-phenylindole) was added to NIH3T3 cells, and visualized using a confocal laser microscope (LSM700, Zeiss, Germany) (FIG. 21).

As shown in FIGS. 20 and 21, SOCS3 recombinant proteins containing $aMTD_{165}$ ($HM_{165}$S3, $HM_{165}$S3A and $HM_{165}$S3B) efficiently entered the cells (FIGS. 20 and 21) and were localized to various extents in cytoplasm (FIG. 21). In contrast, SOCS3 protein containing non-aMTD (HS3) did not appear to enter cells. While all SOCS3 proteins containing aMTD165 transduced into the cells, $HM_{165}$S3B displayed more uniform cellular distribution, and protein uptake of $HM_{165}$S3B was also very efficient.

Example 7-1-2. Comparison Between aMTD/SD-Fused SOCS3 Recombinant Protein and Basic CPP/SD-Fused SOCS3 Recombinant Protein The cell-permeability of basic CPP/SD-fused SOCS3 recombinant proteins was assessed by the same method as used in Example 7-1 except for a known basic CPP (TAT or PolyR) being used instead of aMTD. The results of the assessment were shown in FIG. 99.

According to the results, all recombinant proteins exhibited cell-permeability. Among the proteins, aMTD/SD-fused SOCS3 recombinant protein ($HM_{165}$S3B) showed the highest cell-permeability.

Example 7-2. Tissue-Permeability Test

To further investigate in vivo delivery of SOCS3 recombinant proteins, ICR mice (Doo-Yeol Biotech Co. Ltd., Seoul, Korea) were intraperitoneal (IP) injected with 600 μg/head of 10 μM FITC (Fluorescein isothiocyanate, SIGMA, USA)-labeled SOCS3 proteins and sacrificed after 2 hrs. From the mice, the liver, kidney, spleen, lung, heart, and brain were removed and washed with PBS, and then placed on a dry ice, and embedded with an O.C.T. compound (Sakura). After cryosectioning at 20 μm, tissue distributions of fluorescence-labeled-SOCS3 proteins in different organs was analyzed by fluorescence microscopy (Carl Zeiss, Gottingen, Germany)(FIG. 22).

As shown in FIG. 22, SOCS3 recombinant proteins fused to aMTD165 ($HM_{165}S3$, $HM_{165}S3A$ and $HM_{165}S3B$) were distributed to a variety of tissues (liver, kidney, spleen, lung, heart and, to a lesser extent, brain). Liver showed highest levels of fluorescent cell-permeable SOCS3 since intraperitoneal administration favors the delivery of proteins to this organ via the portal circulation. SOCS3 containing aMTD165 was detectable to a lesser degree in lung, spleen and heart. aMTD/SDB-fused SOCS3 recombinant protein ($HM_{165}S3B$) showed the highest systemic delivery of SOCS3 protein to the tissues compared to the SOCS3 containing only aMTD ($HM_{165}S3$) or aMTD/SDA ($HM_{165}S3A$) proteins. These data suggest that SOCS3 protein containing both of aMTD 165 and SDB leads to higher cell-/tissue-permeability due to the increase in solubility and stability of the protein, and it displayed a dramatic synergic effect on cell-/tissue-permeability.

Example 7-2-2. Comparison Between aMTD/SD-Fused SOCS3 Recombinant Protein and Basic CPP/SD-Fused SOCS3 Recombinant Protein The tissue-permeability of basic CPP/SD-fused SOCS3 recombinant proteins was assessed by the same method as used in Example 7-2 except for a known basic CPP (TAT or PolyR) being used instead of aMTD. The results of the assessment were shown in FIG. 100.

According to the results, only aMTD/SD-fused SOCS3 recombinant protein ($HM_{165}S3B$) exhibited superior cell-permeability.

Example 8-1 Biological Activity Test of iCP-SOCS3—Inhibition Activity of IFN-γ-Induced STAT Phosphorylation It was examined whether the iCP-SOCS3 recombinant proteins prepared by fusion with combinations of aMTD and SD inhibits activation of the JAK/STAT-signaling pathway.

PANC-1 Cells (KCLB, Seoul, South Korea) were treated with 10 ng/ml IFN-γ (R&D systems, Abingdon, UK) for 15 min and treated with either DMEM (vehicle) or 10 μM aMTD/SD-fused SOCS3 recombinant proteins for 2 hrs. The cells were lysed in RIPA lysis buffer (Biosesang, Seongnam, Korea) containing proteinase inhibitor cocktail (Roche, Indianapolis, Ind., USA), incubated for 15 min at 4° C., and centrifuged at 13,000 rpm for 10 min at 4° C. Equal amounts of lysates were separated on 10% SDS-PAGE gels and transferred to a nitrocellulose membrane. The membranes were blocked using 5% skim milk in TBST and for western blot analysis incubated with the following antibodies: anti-phospho-STAT1 (Cell Signaling Technology, USA) and anti-phospho-STAT3 (Cell Signaling Technology, USA), then HRP conjugated anti-rabbit secondary antibody (Santacruz).

The well-known cytokine signaling inhibitory actions of SOCS3 are inflammation inhibition through i) inhibition of IFN-γ-mediated JAK/STAT and ii) inhibition of LPS-mediated cytokine secretion. The ultimate test of cell-penetrating efficiency is a determination of intracellular activity of SOCS3 proteins transported by aMTD. Since endogenous SOCS3 are known to block phosphorylation of STAT1 and STAT3 by IFN-γ-mediated Janus kinases (JAK) 1 and 2 activation, we demonstrated whether cell-permeable SOCS3 inhibits the phosphorylation of STATs. As shown in FIG. 23, All SOCS3 recombinant proteins containing aMTD ($HM_{165}S3$, $HM_{165}S3A$ and $HM_{165}S3B$), suppressed IFN-γ-induced phosphorylation of STAT1 and STAT3. In contrast, STAT phosphorylation was readily detected in cells exposed to HS3, which lacks the aMTD motif required for membrane penetration, indicating that HS3, which lacks an MTD sequence did not enter the cells, has no biological activity.

Example 8-2. Biological Activity Test of iCP-SOCS3

Peritoneal macrophages were obtained from C3H/HeJ mice (Doo-Yeol Biotech Co. Ltd. Korea) Peritoneal macrophages were incubated with 10 μM SOCS3 recombinant proteins (1:HS3, 2:$HM_{165}S3$, 3:$HM_{165}S3A$ and 4:$HM_{165}S3B$, respectively) for 1 hr at 37° C. and then stimulated them with LPS (Lipopolysaccharide)(500 ng/ml) and/or IFN-γ (100 U/ml) without removing iCP-SOCS3 proteins for 3, 6, or 9 hrs. The culture media were collected, and the extracellular levels of cytokine (TNF-α, IL-6) were measured by a cytometric bead array (BD Pharmingen, San Diego, Calif., USA) according to the manufacturer's instructions.

The effect of cell-permeable SOCS3 proteins on cytokines secretion was investigated. Treatment of C3H/HeJ primary peritoneal macrophages with SOCS3 proteins containing $aMTD_{165}$ suppressed TNF-α and IL-6 secretion induced by the combination of IFN-γ and LPS by 50-90% during subsequent 9 hrs of incubation (FIG. 24). In particular, $aMTD_{165}$/SDB-fused SOCS3 recombinant protein showed the greatest inhibitory effect on cytokine secretion. In contrast, cytokine secretion in macrophages treated with non-permeable SOCS3 protein (HS3) was unchanged, indicating that recombinant SOCS3 lacking the aMTD doesn't affect intracellular signaling. Therefore, we conclude that differences in the biological activities of $HM_{165}S3B$ as compared to HS3B are due to the differences in protein uptake mediated by the aMTD sequence. In light of solubility/yield, cell-/tissue-permeability, and biological effect, SOCS3 recombinant protein containing aMTD and SDB ($HM_{165}S3B$) is a prototype of a new generation of improved cell-permeable SOCS3 (iCP-SOCS3), and will be selected for further evaluation as a potential anti-tumor agent.

Example 9. Preparation of Control Protein (Non-CP-SOCS3: HS3B Recombinant Protein)

As an experimental negative control, a SOCS3 recombinant protein having no cell permeability was prepared.

According to Example 6-2, SOCS3 recombinant proteins lacking SD ($HM_{165}S3$) or both aMTD and SD (HS3) were found to be less soluble, produced lower yields, and showed tendency to precipitate when they were expressed and purified in E. coli. Therefore, we additionally designed and constructed SOCS3 recombinant protein containing only SDB (without $aMTD_{165}$: HS3B) as a negative control (FIG. 25). Preparation, expression and purification, and measurement of solubility/yield of the recombinant proteins were performed in the same manner as in Examples 6-2 and 6-3.

TABLE 37

| Cargo | SD | Recombinant Protein | 5' Primers | 3' Primers |
|---|---|---|---|---|
| SOCS3 | B | HS3B | 5'-GGAATTCCATATGGTC ACCCACAGCAAGTTTCC CGCCGCC-3' (SEQ ID NO: 969) | 5'-CGCGTCGACTTAAA GGGTTTCCGAAGGCTT GGCTATCTT-3' (SEQ ID NO: 970) |

As expected, its solubility and yield increased compared to that of SOCS3 proteins lacking SDB (HS3; FIG. 26). Therefore, HS3B proteins were used as a control protein.

Example 10. Selection of aMTD for Cell-Permeability

After a basic structure of the stable recombinant proteins fused with combinations of aMTD and SD was determined, 22 aMTDs were selected for development of iCP-SOCS3 recombinant protein (FIGS. 105 and 106), based on the critical Factors, in order to examine which aMTD provides the highest cell-/tissue-permeability.

For comparison, 5 kinds of random peptides that do not satisfying one or more critical factors were selected (FIG. 107).

Solubility/yield and cell-permeability of 22 kinds of aMTD/SDB-fused SOCS3 recombinant proteins, prepared by using primers of Table 38 in the same manner as in Example 6-2, were analyzed according to Examples 6-3 and 7-1, respectively.

TABLE 38

| aMTD CargoID | Amino Acid Sequence | 5' Primers | 3' Primers |
|---|---|---|---|
| SOCS3MTM | AAVLLPVLLAAP (SEQ ID NO: 865) | GGAATTCCATATGGCGGCGGTGCTGCTGCCGGTG CTGCTGGCGGCGCCGGTCACCCACAGCAAGTTTC CCGCCGCC (SEQ ID NO: 857) | CGCGTCGACTTAAAGGG TTTCCGAAGGCTTGGCT ATCCTT (SEQ ID NO: 995) |
| 44 | ALAVPVALLVAP (SEQ ID NO: 16) | GGAATTCCATATGGCGCTGGCGGTGCCGGTGGCGC TGCTGGTGGCGCCGGTCACCCACAGCAAGTTTCCC GCCGCC (SEQ ID NO: 858) | |
| 81 | AALLPALAALLP (SEQ ID NO: 22) | GGAATTCCATATGGCGGCGCTGCTGCCGGCGCTGG CGGCGCTGCTGCCGGTCACCCACAGCAAGTTTCCC GCCGCC (SEQ ID NO: 861) | |
| 123 | AAIIVPAALLAP (SEQ ID NO: 33) | GGAATTCCATATGGCGGCGATTATTGTGCCGGCGG CGCTGCTGGCGCCGGTCACCCACAGCAAGTTTCCC GCCGCC (SEQ ID NO: 862) | |
| 162 | AVVALPAALIVP (SEQ ID NO: 40) | GGAATTCCATATGGCGGTGGTGGCGCTGCCGGCGG CGCTGATTGTGCCGGTCACCCACAGCAAGTTTCCCG CCGCC (SEQ ID NO: 863) | |
| 281 | ALIVLPAAVAVP (SEQ ID NO: 65) | GGAATTCCATATGGCGCTGATTGTGCTGCCGGCGG CGGTGGCGGTGCCGGTCACCCACAGCAAGTTTCCC GCCGCC (SEQ ID NO: 864) | |
| 324 | IVAVALPAALVP (SEQ ID NO: 77) | GGAATTCCATATGATTGTGGCGGTGGCGCTGCCGG CGGCGCTGGTGCCGGTCACCCACAGCAAGTTTCCC GCCGCC (SEQ ID NO: 977) | |
| 364 | LVAAVAPALIVP (SEQ ID NO: 85) | GGAATTCCATATGCTGGTGGCGGCGGTGGCGCCGG CGCTGATTGTGCCGGTCACCCACAGCAAGTTTCCCG CCGCC (SEQ ID NO: 978) | |
| 365 | AVIVVAPALLAP (SEQ ID NO: 86) | GGAATTCCATATGGCGGTGATTGTGGTGGCGCCGG CGCTGCTGGCGCCGGTCACCCACAGCAAGTTTCCC GCCGCC (SEQ ID NO: 979) | |
| 622 | ALIVLAAPVAVP (SEQ ID NO: 142) | GGAATTCCATATGGCGCTGATTGTGCTGGCGGCGC CGGTGGCGGTGCCGGTCACCCACAGCAAGTTTCCC GCCGCC (SEQ ID NO: 980) | |
| 662 | ALAVILAPVAVP (SEQ ID NO: 822) | GGAATTCCATATGGCGCTGGCGGTGATTCTGGCGC CGGTGGCGGTGCCGGTCACCCACAGCAAGTTTCCC GCCGCC (SEQ ID NO: 981) | |
| 563 | ALAVIVVPALAP (SEQ ID NO: 131) | GGAATTCCATATGGCGCTGGCGGTGATTGTGGTGC CGGCGCTGGCGCCGGTCACCCACAGCAAGTTTCCC GCCGCC (SEQ ID NO: 982) | |
| 899 | AVVIALPAVVAP (SEQ ID NO: 229) | GGAATTCCATATGGCGGTGGTGATTGCGCTGCCGG CGGTGGTGGCGCCGGTCACCCACAGCAAGTTTCCC GCCGCC (SEQ ID NO: 983) | |
| 897 | AVIVPVAIIAAP (SEQ ID NO: 228) | GGAATTCCATATGGCGGTGATTGTGCCGGTGGCGAT TATTGCGGCGCCGGTCACCCACAGCAAGTTTCCCG CCGCC (SEQ ID NO: 984) | |
| 623 | VAAAIALPAIVP (SEQ ID NO: 143) | GGAATTCCATATGGTGGCGGCGGCGATTGCGCTGC CGGCGATTGTGCCGGTCACCCACAGCAAGTTTCCC GCCGCC (SEQ ID NO: 985) | |
| 908 | VALALAPVVVAP (SEQ ID NO: 237) | GGAATTCCATATGGTGGCGCTGGCGCTGGCGCCGG TGGTGGTGGCGCCGGTCACCCACAGCAAGTTTCCC GCCGCC (SEQ ID NO: 986) | |
| 911 | VALALPAVVVAP (SEQ ID NO: 239) | GGAATTCCATATGGTGGCGCTGGCGCTGCCGGCGG TGGTGGTGGCGCCGGTCACCCACAGCAAGTTTCCC GCCGCC (SEQ ID NO: 987) | |
| 2 | AAAVPLLAVVVP (SEQ ID NO: 2) | GGAATTCCATATGGCGGCGGCGGTGCCGCTGCTGG CGGTGGTGGTGCCGGTCACCCACAGCAAGTTTCCC GCCGCC (SEQ ID NO: 988) | |
| 904 | AVLAVVAPVVAP (SEQ ID NO: 233) | GGAATTCCATATGGCGGTGCTGGCGGTGGTGGCGC CGGTGGTGGCGCCGGTCACCCACAGCAAGTTTCCC GCCGCC (SEQ ID NO: 989) | |

TABLE 38-continued

| | | | |
|---|---|---|---|
| 481 | AIAIAIVPVALP (SEQ ID NO: 110) | GGAATTCCATATGGCGATTGCGATTGCGATTGTGCC GGTGGCGCTGCCGGTCACCCACAGCAAGTTTCCCG CCGCC (SEQ ID NO: 990) | |
| 787 | AVALVPVIVAAP (SEQ ID NO: 177) | GGAATTCCATATGGCGGTGGCGCTGGTGCCGGTGA TTGTGGCGGCGCCGGTCACCCACAGCAAGTTTCCC GCCGCC (SEQ ID NO: 991) | |
| 264 | LAAAPVVIVIAP (SEQ ID NO: 63) | GGAATTCCATATGCTGGCGGCGGCGCCGGTGGTGA TTGTGATTGCGCCGGTCACCCACAGCAAGTTTCCCG CCGCC (SEQ ID NO: 992) | |
| 363 | AVLAVAPALIVP (SEQ ID NO: 84) | GGAATTCCATATGGCGGTGCTGGCGGTGGCGCCGG CGCTGATTGTGCCGGTCACCCACAGCAAGTTTCCCG CCGCC (SEQ ID NO: 993) | |
| 121 | AIVALPALALAP (SEQ ID NO: 32) | GGAATTCCATATGGCGATTGTGGCGCTGCCGGCGC TGGCGCTGGCGCCGGTCACCCACAGCAAGTTTCCC GCCGCC (SEQ ID NO: 994) | |

| rPEPTIDE CargoID | Amino Acid Sequence | 5' Primers | 3' Primers |
|---|---|---|---|
| SOCS3921 | IEWFVVLPLVVP (SEQ ID NO: 931) | GGAATTCCATATGATTTGGTGGTTTGTGGTGCT GCCGCTGGTGGTGCCGGTCACCCACAGCAAG TTTCCCGCCGCC (SEQ ID NO: 996) | CGCGTCGACTTAAAGG GTTTCCGAAGGCTTGG CTATCTT (SEQ ID NO: 1001) |
| 16 | NNSCTTYTNGSQ (SEQ ID NO: 890) | GGAATTCCATATGAACAACAGCTGCACCACCTA TACCAACGGCAGCCAGGTCACCCACAGCAAGT TTCCCGCCGCC (SEQ ID NO: 997) | |
| 67 | LDAEVPLADDVP (SEQ ID NO: 906) | GGAATTCCATATGCTGGATGCGGAAGTGCCGC TGGCGGATGATGTGCCGGTCACCCACAGCAAG TTTCCCGCCGCC (SEQ ID NO: 998) | |
| 29 | VLPPLPVLPVLP (SEQ ID NO: 924) | GGAATTCCATATGGTGCTGCCGCCGCTGCCGG TGCTGCCGGTGCTGCCGGTCACCCACAGCAA GTTTCCCGCCGCC (SEQ ID NO: 999) | |
| 700 | GTSNTCQSNQNS (SEQ ID NO: 951) | GGAATTCCATATGGGCACCAGCAACACCTGCC AGAGCAACCAGAACAGCGTCACCCACAGCAAG TTTCCCGCCGCC (SEQ ID NO: 1000) | |

As shown in FIGS. 27 to 34, it was confirmed that most of the aMTD/SDB-fused SOCS3 recombinant proteins showed high solubility and yield and high cell permeability by aMTD. However, Random peptide-SOCS3-SDB recombinant protein showed remarkably low cell permeability.

Example 11-1. Investigation of Biological Activity for Determination of Optimal aMTD-Fused SOCS3 Recombinant Protein-1

Four kinds of aMTD/SD-fused SOCS3 recombinant proteins having high cell permeability and one kind of aMTD/SD-fused SOCS3 recombinant protein having the lowest cell permeability were selected, and their biological activity was analyzed.

PANC-1 cells (pancreatic carcinoma cell line) were seeded in a 16-well chamber slide at a density of 5×10³ cells/well, and then treated with 10 uM of aMTD/SD-fused SOCS3 for 24 hours. Apoptotic cells were analyzed using terminal dUTP nick-end labeling (TUNEL) assay with In Situ Cell Death Detection kit TMR red (Roche, 4056 Basel, Switzerland). Cells were treated with either 10 μM SOCS3 recombinant protein or buffer alone for 16 hrs with 2% fetal bovine serum (Hyclone, Logan, Utah, USA). Treated cells were washed with cold PBS two times, fixed in 4% paraformaldehyde (PFA, Junsei, Tokyo, Japan) for 1 hr at room temperature, and incubated in 0.1% Triton X-100 for 2 min on the ice. Cells were washed with cold PBS twice, and treated TUNEL reaction mixture for 1 hr at 37° C. in dark, washed cold PBS three times and observed by fluorescence microscopy (Nikon, Tokyo, Japan).

As shown in FIG. 35, most of the aMTD/SDB-fused SOCS3 recombinant proteins induced cell death of pancreatic carcinoma cells, and of them, aMTD$_{165}$ or aMTD$_{32}$4-fused SOCS3 recombinant protein induced death of the largest number of cancer cells.

Example 11-2. Investigation of Biological Activity for Determination of Optimal aMTD-Fused SOCS3 Recombinant Protein-2

AGS cells (gastric carcinoma cell line) (American Type Culture Collection; ATCC) were seeded in a 12-well plate at a density of 1×10⁵ cells/well, and then treated with 10 uM of aMTD/SD-fused SOCS3 for 14 hours. Cancer cell death was analyzed by Annexin V analysis. Annexin V/7-Aminoactinomycin D (7-AAD) staining was performed using flow cytometry according to the manufacturer's guidelines (BD Pharmingen, San Diego, Calif., USA). Briefly, cells were washed three times with ice-cold PBS. The cells were then resuspended in 100 μl of binding buffer and incubated with 1 μl of 7-AAD and 1 μl of annexin V-PE for 30 min in the dark at 37° C. Flow cytometric analysis was immediately performed using a guava easyCyte™ 8 Instrument (Merck Millipore, Darmstadt, Germany).

As shown in FIG. 36, most of the aMTD/SDB-fused SOCS3 recombinant proteins induced cell death of gastric carcinoma cells, and of them, aMTD$_{165}$ or aMTD$_{281}$-fused SOCS3 recombinant protein induced death of the largest number of cancer cells.

Example 11-3. Investigation of Biological Activity for Determination of Optimal aMTD-Fused SOCS3 Recombinant Protein-3

AGS cells (gastric cancer cell line) were seeded in a 12 well plate at a density of 2.5×10$^5$ per well, grown to 90% confluence. Confluent AGS cells were incubated with 10 µM HM#S3B in serum-free medium for 2 hrs prior to changing the growth medium (DMEM/F12, Hyclone, Logan, Utah, USA) and washed twice with PBS, and the monolayer at the center of the well was "wounded" by scraping with a sterilized white pipette tip. Cells were cultured for an additional 24 hrs and cell migration was observed by phase contrast microscopy (Nikon, ECLIPSE Ts2). The migration was quantified by counting the number of cells that migrated from the wound edge into the clear area.

As shown in FIG. 37, most of the aMTD/SDB-fused SOCS3 recombinant proteins inhibited cell migration of gastric carcinoma cells, and of them, aMTD$_{165}$ or aMTD$_{904}$-fused SOCS3 recombinant protein showed the most effective inhibition of cancer cell migration.

Solubility/yield, permeability, and biological activity of 22 kinds of the aMTD-fused recombinant proteins were examined in Examples 10 to 11-3, and as a result, the aMTD$_{165}$/SDB-fused SOCS3 recombinant protein was found to show the most excellent effect (FIG. 38). Therefore, the aMTD$_{165}$-fused recombinant protein was used in the subsequent experiment.

Example 12-1. Preparation of iCP-SOCS3 Recombinant Protein and Investigation of Equivalence Thereof-1

To develop a new drug as an anticancer agent, His-tag-removed iCP-SOCS3 recombinant protein was prepared and equivalence of His-Tag+, −iCP-SOCS3 was investigated.

Histidine-tag free human SOCS3 proteins were constructed by amplifying the SOCS3 cDNA (225 amino acids) for aMTD fused to SOCS3 cargo. The PCR reactions (100 ng genomic DNA, 10 pmol each primer, each 0.2 mM dNTP mixture, 1× reaction buffer and 2.5 U Pfu(+) DNA polymerase (Doctor protein, Korea)) were digested on the restriction enzyme site between Nde I (5') and Sal I (3') involving 35 cycles of denaturing (95° C.), annealing (62° C.), and extending (72° C.) for 45 sec each. For the last extension cycle, the PCR reactions remained for 10 min at 72° C. The PCR products were subcloned into pET-26b(+) (Novagen, Darmstadt, Germany). Coding sequence for SDB fused to C terminus of aMTD-SOCS3 was cloned at BamHI (5') and SalI (3') in pET-26b(+) from PCR-amplified DNA segments and confirmed by DNA sequence analysis of the resulting plasmids.

TABLE 39

| Cargo | SD | Recombinant Protein | 5' Primers | 3' Primers |
|---|---|---|---|---|
| SOCS3 | — | HS3 | 5'-GGAATTCCATATGGTCA CCCACAGCAAGTTTCCCGC CGCC-3' (SEQ ID NO: 955) | 5'-CCCGGATCCTTAAAGC GGGGCATCGTACTGGTCC AGGAA-3' (SEQ ID NO: 956) |
|  |  | HM$_{165}$S3 | 5'-GGAATTCCATATGGCGCT GGCGGTGCCGGTGGCGCT GGCGATTGTGCCGGTCACC CACAGCAAGTTTC-3' (SEQ ID NO: 957) | 5'-CCCGGATCCTTAAAG CGGGGCATCGTACTGGT CCAGGAA-3' (SEQ ID NO: 958) |
|  | A | HM$_{165}$S3A | 5'-GGAATTCCATATGGCGC TGGCGGTGCCGGTGGCGC TGGCGATTGTGCCGGTCAC CCACAGCAAGTTTC-3' (SEQ ID NO: 959) | 5'-CGCGTCGACTTACCTCG GCTGCACCGG CACGGAG ATGAC-3' (SEQ ID NO: 960) |
|  | B | HM$_{165}$S3B | 5'-GGAATTCCATATGGCGCT GGCGGTGCCGGTGGCGCT GGCGATTGTGCCGGTCACC CACAGCAAGTTTC-3' (SEQ ID NO: 961) | 5'-CGCGTCGACTTAAAGG GTTTCCGAAGGCTTGGCT ATCTT-3' (SEQ ID NO: 962) |
|  | C | HM$_{165}$S3C | 5'-GGAATTCCATATGGCGC TGGCGGTGCCGGTGGCGCT GGCGATTGTGCCGGTCACC CACAGCAAGTTTC-3' (SEQ ID NO: 963) | 5'-GCGTCGACTTAGGC CAGGTTAGCGTCGAG-3' (SEQ ID NO: 964) |

TABLE 39-continued

| Cargo | SD | Recombinant Protein | 5' Primers | 3' Primers |
|---|---|---|---|---|
| | D | HM$_{165}$S3D | 5'-GGAATTCCATATGGCGC TGGCGGTGCCGGTGGCGC TGGCGATTGTGCCGGTCAC CCACAGCAAGTTTC-3' (SEQ ID NO: 965) | 5'-GCGTCGACTTATTTT TTCTCGGACAGATA-3' (SEQ ID NO: 966) |
| | E | HM$_{165}$S3E | 5'-GGAATTCCATATGGCGC TGGCGGTGCCGGTGGCGC TGGCGATTGTGCCGGTCA CCCACAGCAAGTTTC (SEQ ID NO: 967) | 5'-ACGCGTCGACTTAA CCTCCAATCTGTTCGCG GTGAGCCTC-3' (SEQ ID NO: 968) |
| | B | HM$_{165}$S3B | 5'-GGAATTCCATATGGCGCTGGC GGTGCCGGTGGCGCTGGCGATT GTGCCGGTCACCCACAGCAAGT TTC-3' (SEQ ID NO: 859) | 5'-CGCGTCGACTTAAAGGGTTT CCGAAGGCTTGGCTATCTT-3' (SEQ ID NO: 860) |

Expression, purification and solubility/yield were measured in the same manner as in Example 6-2 to 6-3, and as a result, his-tag-removed M$_{165}$S3B was found to have high solubility/yield (FIG. 39).

Example 12-2. Preparation of iCP-SOCS3 Recombinant Protein and Investigation of Equivalence Thereof-2

In the same manner as in Example 7-1, RAW264.7 cells were treated with FITC-labeled HS3B, HM$_{165}$S3B, and M$_{165}$S3B proteins, and cell permeability was evaluated.

As shown in FIG. 40, both HM$_{165}$S3B and M$_{165}$S3B were found to have high cell permeability.

Example 12-3. Preparation of iCP-SOCS3 Recombinant Protein and Investigation of Equivalence Thereof-3

To investigate biological activity equivalence of the HM$_{165}$S3B and M$_{165}$S3B recombinant proteins, induction of apoptosis of gastric carcinoma cell line (AGS) was analyzed by Annexin V staining in the same manner as in Example 11-2, and inhibition of migration was analyzed in the same manner as in Example 11-3.

As shown in FIG. 41, it was confirmed that both HM$_{165}$S3B and M165S3B showed high anticancer efficacy and M165S3B exhibited efficacy equivalent to or higher than HM$_{165}$S3B.

Example 12-4. Preparation of iCP-SOCS3 Recombinant Protein and Investigation of Equivalence Thereof-4

In silico MHC class II binding analysis using iTope™ (ANTITOPE.LTD) revealed changing the V28 pl anchor residue in SDB sequence to L makes this region human germline and as such both MHC class II binding peptides within this region would be expected to be low risk due to T cell tolerance.

To prepare humanized SDB domain, iCP-SOCS3 was prepared in the same manner as in Example 6-1, except that SDB having a substitution of valine with leucine at an amino acid position 28 was used (FIG. 94). Further, protein purification was performed in the same manner as in Example 6-2 using the primer as below (Table 40).

TABLE 40

| Cargo | SD | Recombinant Protein | 5' Primers | 3' Primers |
|---|---|---|---|---|
| SOCS3 | — | HS3 | 5'-GGAATTCCATATGGTCA CCCACAGCAAGTTTCCCGC CGCC-3' (SEQ ID NO: 955) | 5'-CCCGGATCCTTAAAGC GGGGCATCGTACTGGTCC AGGAA-3' (SEQ ID NO: 956) |
| | | $HM_{165}S3$ | 5'-GGAATTCCATATGGCGCT GGCGGTGCCGGTGGCGCT GGCGATTGTGCCGGTCACC CACAGCAAGTTTC-3' (SEQ ID NO: 957) | 5'-CCCGGATCCTTAAAG CGGGGCATCGTACTGGT CCAGGAA-3' (SEQ ID NO: 958) |
| | A | $HM_{165}S3A$ | 5'-GGAATTCCATATGGCGC TGGCGGTGCCGGTGGCGC TGGCGATTGTGCCGGTCAC CCACAGCAAGTTTC-3' (SEQ ID NO: 959) | 5'-CGCGTCGACTTACCTCG GCTGCACCGG CACGGAG ATGAC-3' (SEQ ID NO: 960) |
| | B | $HM_{165}S3B$ | 5'-GGAATTCCATATGGCGCT GGCGGTGCCGGTGGCGCT GGCGATTGTGCCGGTCACC | 5'-CGCGTCGACTTAAAGG GTTTCCGAAGGCTTGGCT ATCTT-3' |

TABLE 40-continued

| Cargo | SD | Recombinant Protein | 5' Primers | 3' Primers |
|---|---|---|---|---|
| | | | CACAGCAAGTTTC-3'<br>(SEQ ID NO: 961) | (SEQ ID NO: 962) |
| | C | HM$_{165}$S3C | 5'-GGAATTCCATATGGCGC<br>TGGCGGTGCCGGTGGCGCT<br>GGCGATTGTGCCGGTCACC<br>CACAGCAAGTTTC-3'<br>(SEQ ID NO: 963) | 5'-GCGTCGACTTAGGC<br>CAGGTTAGCGTCGAG-3'<br>(SEQ ID NO: 964) |
| | D | HM$_{165}$S3D | 5'-GGAATTCCATATGGCGC<br>TGGCGGTGCCGGTGGCGC<br>TGGCGATTGTGCCGGTCAC<br>CCACAGCAAGTTTC-3'<br>(SEQ ID NO: 965) | 5'-GCGTCGACTTATTTT<br>TTCTCGGACAGATA-3'<br>(SEQ ID NO: 966) |
| | E | HM$_{165}$S3E | 5'-GGAATTCCATATGGCGC<br>TGGCGGTGCCGGTGGCGC<br>TGGCGATTGTGCCGGTCA<br>CCCACAGCAAGTTTC<br>(SEQ ID NO: 967) | 5'-ACGCGTCGACTTAA<br>CCTCCAATCTGTTCGCG<br>GTGAGCCTC-3'<br>(SEQ ID NO: 968) |
| | B* | HM$_{165}$S3B* | 5'-GGAATTCCATATGGCGCTGG<br>CGGTGCCGGTGGCGCTGGCGA<br>TTGTGCCGGTCACCCACAGCA<br>AGTTTC-3'<br>(SEQ ID NO: 971) | 5'-CGCGTCGACTTAAAGG<br>GTTTCCGAAGGCTTGGCT<br>ATCTT-3'<br>(SEQ ID NO: 972) |

As shown in FIG. 44, both HM$_{165}$S3B and HM$_{165}$S3B' (V28L) were found to have high solubility/yield.

Example 12-5. Preparation of iCP-SOCS3 Recombinant Protein and Investigation of Equivalence Thereof-5

In the same manner as in Example 7-1, RAW264.7 cells were treated with FITC-labeled HM$_{165}$S3B and HM$_{165}$S3B' (V28L) proteins, and cell permeability was evaluated.

As shown in FIG. 45, both HM$_{165}$S3B and HM$_{165}$S3B' (V28L) were found to have high cell permeability.

Example 12-6. Preparation of iCP-SOCS3 Recombinant Protein and Investigation of Equivalence Thereof-6

To investigate biological activity equivalence of the HM$_{165}$S3B and HM$_{165}$S3B'(V28L) recombinant proteins, anti-proliferative activity was examined and induction of apoptosis of gastric carcinoma cell line (AGS) was analyzed by Annexin V staining in the same manner as in Example 11-2, and inhibition of migration was analyzed in the same manner as in Example 11-3.

Antiproliferative activity were evaluated with the CellTiter-Glo Cell Viability Assay. AGS cells (3×10³/well) were seeded in 96 well plates. The next day, cells were treated with DMEM (vehicle) or 10 μM HM$_{165}$S3B, HM$_{165}$S3B' (V28L) for 96 hrs in the presence of serum (2%). Proteins were replaced daily. Cell growth and survival were evaluated with the CellTiter-Glo Cell Viability Assay (Promega, Madison, Wis.). Measurements using a Luminometer (Turner Designs, Sunnyvale, Calif.) were conducted following the manufacturer's protocol.

It was confirmed that both HM$_{165}$S3B and HM$_{165}$S3B' (V28L) showed high anti-proliferative effects on gastric carcinoma cells (FIG. 46), and also effects of inducing apoptosis (FIG. 47) and of inhibiting migration of gastric carcinoma cells (FIG. 48), and in particular, HM$_{165}$S3B' (V28L) exhibited efficacy equivalent to or higher than HM$_{165}$S3B.

Example 12-7. Preparation of iCP-SOCS3 Recombinant Protein and Investigation of Equivalence Thereof-7 iCP-SOCS3 of BS3M165 structure was prepared in the same manner as in Example 6-1, and B'S3M165 iCP-SOCS3 was also prepared by humanized SDB domain (FIG. 49a).

TABLE 41

| Cargo | SD | Recombinant Protein | 5' Primers | 3' Primers |
|---|---|---|---|---|
| SOCS3 | B | BS3M$_{165}$ | 5'-GGAATTCCATATG<br>ATGGCAGAACAAAGCGAC-3'<br>(SEQ ID NO: 973) | 5'-ACGCGTCGACTTAC<br>GCCAGCGCCACCG<br>GCACCGCCAGCGC<br>AATCACCGGAAGCG<br>GGGCATCGTACTGG<br>TCCAG-3'<br>(SEQ ID NO: 974) |
| | B* | B*S3M$_{165}$ | 5'-GGAATTCCATATG<br>ATGGCAGAACAAAGCGAC-3' | 5'-ACGCGTCGACTTAC<br>GCCAGCGCCACCG |

TABLE 41-continued

| Cargo | Recombinant SD Protein | 5' Primers | 3' Primers |
|---|---|---|---|
| | | (SEQ ID NO: 975) | GCACCGCCAGCGC AATCACCGGAAGCG GGGCATCGTACTGG TCCAG-3' (SEQ ID NO: 976) |

Expressions and purifications of iCP-SOCS3 recombinant protein (BS3M165, B'S3M$_{165}$) in *E. coli* (bottom) were analyzed in the same manner as in Examples 6-2 and 6-3, respectively, and shown in FIG. 49b. Further, *E. coli* codon-optimized iCP-SOCS3 was prepared.

Example 13. Test of Biological Activity of iCP-SOCS3—Inhibition Activity of IFN-γ-Induced STAT Phosphorylation Whether iCP-SOCS3 (HM$_{165}$S3B) recombinant protein inhibits activation of the JAK/STAT-signaling pathway was examined by the method of Example 8-1.

PANC-1 Cells (KCLB, Seoul, South Korea) were treated with 10 ng/ml IFN-γ (R&D systems, Abingdon, UK) for 15 min and treated with either DMEM (vehicle) or 1, 5, 10 μM aMTD/SD-fused SOCS3 recombinant proteins for 2 hrs. The cells were lysed in RIPA lysis buffer (Biosesang, Seongnam, Korea) containing proteinase inhibitor cocktail (Roche, Indianapolis, Ind., USA), incubated for 15 min at 4° C., and centrifuged at 13,000 rpm for 10 min at 4° C. Equal amounts of lysates were separated on 10% SDS-PAGE gels and transferred to a nitrocellulose membrane. The membranes were blocked using 5% skim milk in TBST and for western blot analysis incubated with the following antibodies: anti-phospho-STAT3 (Cell Signaling Technology, USA), then HRP conjugated anti-rabbit secondary antibody (Santacruz).

The well-known cytokine signaling inhibitory actions of SOCS3 are inflammation inhibition through i) inhibition of IFN-γ-mediated JAK/STAT and ii) inhibition of LPS-mediated cytokine secretion. The ultimate test of cell-penetrating efficiency is a determination of intracellular activity of SOCS3 proteins transported by aMTD. Since endogenous SOCS3 are known to block phosphorylation of STAT3 by IFN-γ-mediated Janus kinases (JAK) 1 and 2 activation, we demonstrated whether cell-permeable SOCS3 inhibits the phosphorylation of STATs. As shown in FIG. 50, iCP-SOCS3 (HM$_{165}$S3B) suppressed IFN-γ-induced phosphorylation of STAT3 in dose dependent manner. In contrast, STAT phosphorylation was readily detected in cells exposed to HS3B, which lacks the aMTD motif required for membrane penetration, indicating that HS3B, which lacks an MTD sequence did not enter the cells, has no biological activity.

Example 14. Investigation of aMTD-Mediated Intracellular Delivery Mechanism

The mechanism of aMTD165-mediated intracellular delivery was investigated.

(1) RAW, 264.7 cells were pretreated with 100 mM EDTA for 3 hours, and then treated with 10 μM of iCP-SOCS3 (HM$_{165}$S3B) recombinant protein for 1 hour, followed by flow cytometry in the same manner as in Example 7-1 (FIG. 51A).

(2) RAW 264.7 cells were pretreated with 5 μg/ml of proteinase K for 10 minutes, and then treated with 10 μM of iCP-SOCS3 (HM$_{165}$S3B) recombinant protein for 1 hour, followed by flow cytometry (FIG. 51B).

(3) RAW 264.7 cells were pretreated with 20 μM taxol for 30 minutes, and then treated with 10 μM of iCP-SOCS3 (HM$_{165}$S3B) recombinant protein for 1 hour, followed by flow cytometry (FIG. 52A).

(4) RAW'264.7 cells were pretreated with 1 mM ATP and 10 μM antimycin singly or in combination for 2 hours, and then treated with 10 μM of iCP-SOCS3 (HM$_{165}$S3B) recombinant protein for 1 hour, followed by flow cytometry (FIG. 52B).

(5) RAW 264.7 cells were left at 4° C. and 37° C. for 1 hour, respectively, and then treated with 10 μM of iCP-SOCS3 (HM$_{165}$S3B) recombinant protein for 1 hour, followed by flow cytometry (FIG. 53).

The aMTD-mediated intracellular delivery of SOCS3 protein did not require protease-sensitive protein domains displayed on the cell surface (FIG. 51B), microtubule function (FIG. 52A), or ATP utilization (FIG. 52B), since aMTD165-dependent uptake, compare to HS3 and HS3B, was essentially unaffected by treating cells with proteinase K, taxol, or the ATP depleting agent, antimycin. Conversely, iCP-SOCS3 (HM$_{165}$S3B) proteins uptake was blocked by treatment with EDTA and low temperature (FIGS. 51A and 53), indicating the importance of membrane integrity and fluidity for aMTD-mediated protein transduction.

Moreover, whether cells treated with iCP-SOCS3 (HM$_{165}$S3B) protein could transfer the protein to neighboring cells were also tested.

For this, RAW 264.7 cells were treated with 10 μM of FITC-labeled iCP-SOCS3 (HM$_{165}$S3B) recombinant protein for 1 hour. Thereafter, these cells were co-cultured with PerCP-Cy5.5-CD14-stained RAW 264.7 cells for 2 hours. Cell-to-cell protein transfer was assessed by flow cytometry, scoring for CD14/FITC double-positive cells. Efficient cell-to-cell transfer of HM$_{165}$S3B, but not HS3 or HS3B (FIG. 54), suggests that SOCS3 recombinant proteins containing aMTD$_{165}$ are capable of bidirectional passage across the plasma membrane.

Example 14-2. Investigation of Basic CPP-Mediated Intracellular Delivery Mechanism The mechanism of basic CPP (TAT and PolyR)-mediated intracellular delivery was also investigated in the same manner as in Example 7-1 and Example 14.

As shown in FIG. 101, it was confirmed that aMTD165/SD-fused SOCS3 recombinant proteins are independent to cell surface receptor (FIG. 101A) and the cell-permeability of aMTD165/SD-fused SOCS3 recombinant proteins is not due to endocytosis (FIG. 101B).

Whether cells treated with aMTD165/SD-fused SOCS3, TAT/SD-fused SOCS3, and PolyR/SD-fused SOCS3 could transfer the protein to neighboring cells were also tested on a molecular level in the same manner as in Example 13.

For this, RAW 264.7 cells were treated with 5 µM of FITC-labeled $HM_{165}S3B$, HTS3B for 2 hour and washed with PBS two times. Thereafter, they were seeded on PANC-1 cell, incubated for 2 hours and treated with 20 ng/ml of IFN-γ for 15 minutes, followed by Western blotting in the same manner as in Example 8-1. And Cell-to-cell protein transfer was assessed by flow cytometry.

As shown in FIG. 102, efficient cell-to-cell transfer of $HM_{165}S3B$, but not HTS3B or HRS3B, suggests that only SOCS3 recombinant proteins containing aMTD165 are capable of bidirectional passage across the plasma membrane.

Moreover, as shown in FIG. 103, phospho-STAT3 was only reduced in cells treated with $HM_{165}S3B$.

Example 15. Investigation of Bioavailability of iCP-SOCS3

To investigate BA of the iCP-SOCS3 ($HM_{165}S3B$) recombinant proteins, ICR mice (Doo-Yeol Biotech Co. Ltd., Seoul, Korea) were intravenous (IV) injected with 600 µg/head of 10 µM FITC (Fluorescein isothiocyanate, SIGMA, USA)-labeled SOCS3 recombinant proteins (HS3B, $HM_{165}S3B$) and after 15 min. 30 min. 1H, 2H, 4H, 8H, 12H, 16H, 24H, 36H, 48H, mice of each group were sacrificed. From the mice, peripheral blood mononuclear cells (PBMCs), splenocytes, and hepatocytes were separated.

Further, the spleen was removed and washed with PBS, and then placed on a dry ice and embedded in an O.C.T. compound (Sakura). After cryosectioning at 20 µm, tissue distributions of fluorescence-labeled-SOCS3 proteins in different organs was analyzed by fluorescence microscopy (Carl Zeiss, Gottingen, Germany).

Isolation of PBMC

After anesthesia with ether, ophthalmectomy was performed and the blood was collected therefrom using a 1 ml syringe. The collected blood was immediately put in an EDTA tube and mixed well. The blood was centrifuged at 4,000 rpm and 4° C. for 5 minutes, and plasma was discarded and only buffy coat was collected in a new microtube. 0.5 ml of RBC lysis buffer (Sigma) was added thereto, followed by vortexing. The microtube was left at room temperature for 5 minutes, and then centrifuged at 4,000 rpm and 4° C. for 5 minutes. 0.3 ml of PBS was added to a pellet, followed by pipetting and flow cytometry (FlowJo cytometric analysis software, Guava, Millipore, Darmstadt, Germany).

Isolation of Splenocytes and Hepatocytes Mice were laparotomized and the spleen or liver were removed. The spleen or liver thus removed was separated into single cells using a Cell Strainer (SPL, Korea). These cells were collected in a microtube, followed by centrifugation at 4,000 rpm and 4° C. for 5 minutes. 0.5 ml of RBC lysis buffer was added thereto, followed by vortexing. The microtube was left at room temperature for 5 minutes, and then centrifuged at 4,000 rpm and 4° C. for 5 minutes. 0.5 ml of PBS was added to a pellet, followed by pipetting and flow cytometry (FlowJo cytometric analysis software, Guava, Millipore, Darmstadt, Germany).

As shown in FIG. 55, in PBMCs, the maximum permeability of iCP-SOCS3 was observed at 30 minutes, and in splenocytes, the maximum permeability of iCP-SOCS3 was observed at 2 hours and maintained up to 16 hours. In hepatocytes, the maximum permeability of iCP-SOCS3 was observed at 15 minutes and maintained up to 16 hours. As shown in FIG. 56, in the pancreas tissue, very high distribution of iCP-SOCS3 was observed at 2 hours, and maintained up to 8 hours. Therefore, it can be seen that iCP-SOCS3 is rapidly delivered from blood to various tissues within 2 hours, and maintained up to 8-16 hours depending on the tissues.

Example 16. Investigation of Anticancer Efficacy of iCP-SOCS3 Recombinant Protein To develop the iCP-SOCS3 recombinant protein as a therapeutic agent for solid tumors, its permeability to solid tumors (gastric cancer, colorectal cancer, breast cancer, glioblastoma cell line) and various tissues was investigated.

AGS (gastric cancer cell line), HCT116 (colorectal cancer cell line), MDA-MB-231 (breast cancer cell line), and U-87 MG (glioblastoma cell line) cells (Korean cell line bank, Korea) were seeded in a 12 well plate, grown to 90% confluence. Cells were treated with 10 µM FITC-labeled iCP-SOCS3 recombinant proteins and cultivated for 1 hr at 37° C.

After cultivation, the cells were treated with proteinase K (10 µg/mL, SIGMA, USA) and washed three times with ice-cold PBS (Phosphate-buffered saline, Hyclone, USA) to remove surface-bound proteins, and internalized proteins were measured by flow cytometry (FlowJo cytometric analysis software, Guava, Millipore, Darmstadt, Germany). Untreated cells (gray) and equimolar concentration of unconjugated FITC (FITC only, green)-treated cells were served as control (FIG. 57).

The permeability to various tissues was analyzed at 2 hours after protein injection by the method described in Example 7-3.

As shown in FIG. 57, iCP-SOCS3 recombinant proteins (FITC-$HM_{165}$S3SB) promoted the transduction into cultured various cancer cells. In contrast, SOCS3 proteins containing non-aMTD (FITC-HS3 and FITC-HS3B) did not appear to enter cells.

In addition, iCP-SOCS3 recombinant proteins (FITC-$HM_{165}$S3SB) enhanced the systemic delivery to various tissues after intraperitoneal injection (FIG. 58). Therefore, these data indicate that iCP-SOCS3 protein could be intracellularly delivered and distributed to the various cancer cells and various tissues, contributing for beneficial biotherapeutic effects.

Example 17. Investigation of Anticancer Efficacy of iCP-SOCS3 Recombinant Protein

Example 17-1. Investigation of Anti-Cancer Efficacy of iCP-SOCS3 Recombinant Protein in Gastric Cancer Cells To develop the iCP-SOCS3 recombinant protein as a mechanism-specific therapeutic agent for solid tumors, SOCS3 levels endogenously expressed and activation of JAKISTAT-signaling pathway were investigated in different gastric cancer cell lines and normal cells, and normal hepatic cells.

Example 17-1-1. Analysis of Hypermethylation Level in Gastric Cancer Cells

SOCS3 expression is suppressed due to methylation in cancer cells, and therefore, inflammation or cancer development is increased. Further, to investigate the effect of cell permeable SOCS3, a cancer cell line where endogenous SOCS3 expression is suppressed should be selected or applied to a model, and therefore, the present experiments were performed.

Genomic DNA was extracted from cancer cell line using an Exgene™ Tissue SV mini kit (Geneall®, Korea). DNA was quantified, and experiments were performed using 500 ng of gDNA and an EZ DNA Methylation-Gold™ kit (ZYMO Research, Orange, Calif., USA) according to the manufacturer's instructions. DNA was used to perform PCR, and methylation and unmethylation of endogenous SOCS3 were qualitatively analyzed by electrophoresis. In this regard, the primers used are as follows.

Unmethyl-F was 5'-tag tgt gta agt tgt agg aga gtg g-3' (SEQ ID NO: 816), Unmethyl-R was 5'-cta aac ata aaa aaa taa cac taa tcc aaa-3' (SEQ ID NO: 817), Methyl-F was 5'-gta gtg cgt aag ttg tag gag agc-3' (SEQ ID NO: 818), Methyl-R was 5'-gta aaa aaa taa cgc taa tcc gaa-3' (SEQ ID NO: 819), PCR was performed for 30 cycles consisting of pre-denaturation at 95° C. for 5 minutes, denaturation at 95° C. for 30 seconds, annealing at 60° C. for 45 seconds, extension at 72° C. for 1 minute, and final extension at 72° C. for 8 minutes.

As shown in FIG. 95, unmethylation of SOCS3 was observed in HEK293 and HaCaT cells which are normal cells, whereas hypermethylation of the promoter region of SOCS3 gene was observed in MNK75, MKN74, MKN28, AGS, STKM2, NCI-N87 which are gastric cancer cell lines (U: unmethylated SOCS3, M: methylated SOCS3). These results indicate that SOCS3 is silenced by hypermethylation in gastric cancer cell lines.

Example 17-1-2. Analysis of Expression Level of Endogenous SOCS3 mRNA in Gastric Cell Line SOCS3 mRNA expression levels in cancer cells were analyzed by RT-PCR. mRNAs were isolated from normal cell lines and cancer cell lines according to a method provided in a manufacturer's sheet of Hybrid-R (Geneall, Korea), and PCR was performed using SOCS3 primer F 5'-cct act gaa ccc tcc tcc ga-3' (SEQ ID NO: 820) and SOCS3 primer R 5'-gca gct ggg tga ctt tct ca-3' (SEQ ID NO: 821) for 30 cycles consisting of denaturing (95° C.), annealing (60° C.), and extending (72° C.) for 45 seconds each.

It was confirmed that high expression levels of SOCS3 were observed in the normal HEK293 whereas low expression levels of SOCS3 were observed in the gastric cancer cell lines, except MKN74 (FIG. 59).

Example 17-1-3. Analysis of Endogenous SOCS3 and JAKISTAT Signaling Activation Status in Gastric Cell Line JAK/STAT3 activation in cancer cells was analyzed by Western blot analysis. The normal HEK293 cells, and gastric cancer cell lines, MKN75, MKN74, MKN45, MKN28, AGS, STKM2, and NCI-N87 were washed with PBS, and then the cells were lysed in RIPA lysis buffer (Biosesang, Seongnam, Korea) containing protease inhibitor cocktail (Roche, Indianapolis, Ind., USA), incubated for 15 min at 4° C., and centrifuged at 13,000 rpm for 10 min at 4° C. to isolate proteins, followed by Western blotting in the same manner as in Example 8-1.

As shown in FIG. 60, high expression levels of SOCS3 and low levels of phosphorylations of p-JAK1, p-JAK2, p-STAT1, and p-STAT3 were observed in normal HEK293 cells. Low expression levels of SOCS3 gene were observed in the gastric cancer cell lines, compared to the normal cell line, and high levels of p-JAK1 and p-JAK2 in MKN75, high levels of p-STAT1 in MKN75, MKN74, MKN28, and NCI-N87, and high levels of p-STAT3 in MKN75, MKN45, AGS, STKN2, and NCI-N87. These results suggest a possibility of developing a mechanism-specific anticancer agent, because SOCS3-deficient cancer cells can be replenished with cell permeable proteins, and activated JAK/STAT-signaling can be negatively regulated.

Example 17-2. Investigation of Anti-Cancer Efficacy of iCP-SOCS3 Recombinant Protein To develop the iCP-SOCS3 recombinant protein as a mechanism-specific therapeutic agent for solid tumors, SOCS3 levels endogenously expressed and activation of JAK/STAT-signaling pathway were investigated in different colorectal cell lines, normal cells, and normal hepatic cells.

Example 17-2-1. Analysis of Hypermethylation Level in Colorectal Cancer Cells

SOCS3 expression is suppressed due to methylation in cancer cells, and therefore, inflammation or cancer development is increased. Further, to investigate the effect of cell permeable SOCS3, a cancer cell line where endogenous SOCS3 expression is suppressed should be selected or applied to a model, and therefore, the present experiments were performed.

Genomic DNA was extracted from cancer cell line using an Exgene™ Tissue SV mini kit (Geneall®, Korea). DNA was quantified, and experiments were performed using 500 ng of gDNA and an EZ DNA Methylation-Gold™ kit (ZYMO Research, Orange, Calif., USA) according to the manufacturer's instructions. DNA was used to perform PCR, and methylation and unmethylation of endogenous SOCS3 were qualitatively analyzed by electrophoresis. In this regard, the primers used are as follows.

Unmethyl-F was 5'-tag tgt gta agt tgt agg aga gtg g-3' (SEQ ID NO: 816), Unmethyl-R was 5'-cta aac ata aaa aaa taa cac taa tcc aaa-3' (SEQ ID NO: 817), Methyl-F was 5'-gta gtg cgt aag ttg tag gag agc-3' (SEQ ID NO: 818), Methyl-R was 5'-gta aaa aaa taa cgc taa tcc gaa-3' (SEQ ID NO: 819), PCR was performed for 30 cycles consisting of pre-denaturation at 95° C. for 5 minutes, denaturation at 95° C. for 30 seconds, annealing at 60° C. for 45 seconds, extension at 72° C. for 1 minute, and final extension at 72° C. for 8 minutes.

As shown in FIG. 96, unmethylation of SOCS3 was observed in HEK293 and HaCaT cells which are normal cells, whereas hypermethylation of the promoter region of SOCS3 gene was observed in HCT116, SW480, RKO, HT29 which are colorectal cell lines (U: unmethylated SOCS3, M: methylated SOCS3). These results indicate that SOCS3 is silenced by hypermethylation in colorectal cancer cell lines.

Example 17-2-2. Analysis of Expression Level of Endogenous SOCS3 mRNA in Colorectal Cancer Cell Line SOCS3 mRNA expression levels in cancer cells were analyzed by RT-PCR. mRNAs were isolated from normal cell lines and cancer cell lines according to a method provided in a manufacturer's sheet of Hybrid-R (Geneall, Korea), and PCR was performed using SOCS3 primer F 5'-cct act gaa ccc tcc tcc ga-3' (SEQ ID NO: 820) and SOCS3 primer R 5'-gca get ggg tga ctt tct ca-3' (SEQ ID NO: 821) for 30 cycles consisting of denaturing (95° C.), annealing (60° C.), and extending (72° C.) for 45 seconds each.

The results of electrophoresis showed that high expression levels of SOCS3 were observed in the normal HEK293 cells whereas low expression levels of SOCS3 gene were observed in the colorectal cancer cell lines, SW480 and HT29 (FIG. 61).

Example 17-2-3. Analysis of Expression of Endogenous SOCS3 and JAK/STAT Signaling Activation Status in Colorectal Cancer Cell Line JAK/STAT3 activation in cancer cells was analyzed by Western blot analysis. The normal HEK293 cells, and colorectal cancer cell lines, HCT116, SW480, RKO, and HT29 were washed with PBS, and then the cells were lysed in RIPA lysis buffer (Biosesang, Seongnam, Korea) containing proteinase inhibitor cocktail (Roche, Indianapolis, Ind., USA), incubated for 15 min at 4° C., and centrifuged at 13,000 rpm for 10 min at 4° C. to isolate proteins, followed by western blotting in the same manner as in Example 8-1.

As shown in FIG. 62, high expression level of SOCS3 and low phosphorylation levels of p-JAK1, p-JAK2, p-STAT1, and p-STAT3 were observed in normal HEK293 cells. Low expression level of SOCS3 gene was observed in the colorectal cancer cell lines, compared to the normal cell line, and similar levels of p-JAK1, p-JAK2, and p-STAT3 were observed in HCT116 and HT29. These results suggest a possibility of developing a mechanism-specific anticancer agent, because SOCS3-deficient cancer cells can be replenished with cell permeable proteins, and activated JAK/STAT-signaling can be negatively regulated.

Example 17-3. Investigation of Anticancer Efficacy of iCP-SOCS3 Recombinant Protein (Glioblastoma Cells)

To develop the iCP-SOCS3 recombinant protein as a mechanism-specific therapeutic agent for solid tumors, SOCS3 levels endogenously expressed and activation of JAK/STAT-signaling pathway were investigated in different glioblastoma cells, normal cells, and normal hepatic cells.

Example 17-3-1. Analysis of Hypermethylation Level in Glioblastoma Cell Line

SOCS3 expression is suppressed due to methylation in cancer cells, and therefore, inflammation or cancer development is increased. Further, to investigate the effect of cell permeable SOCS3, a cancer cell line where endogenous SOCS3 expression is suppressed should be selected or applied to a model, and therefore, the present experiments were performed.

Genomic DNA was extracted from cancer cell line using an Exgene™ Tissue SV mini kit (Geneall®, Korea). DNA was quantified, and experiments were performed using 500 ng of gDNA and an EZ DNA Methylation-Gold™ kit (ZYMO Research, Orange, Calif., USA) according to the manufacturer's instructions. DNA was used to perform PCR, and methylation and unmethylation of endogenous SOCS3 were qualitatively analyzed by electrophoresis. In this regard, the primers used are as follows.

Unmethyl-F was 5'-tag tgt gta agt tgt agg aga gtg g-3' (SEQ ID NO: 816), Unmethyl-R was 5'-cta aac ata aaa aaa taa cac taa tcc aaa-3' (SEQ ID NO: 817), Methyl-F was 5'-gta gtg cgt aag ttg tag gag agc-3' (SEQ ID NO: 818), and Methyl-R was 5'-gta aaa aaa taa cgc taa tcc gaa-3' (SEQ ID NO: 819). PCR was performed for 30 cycles consisting of pre-denaturation at 95° C. for 5 minutes, denaturation at 95° C. for 30 seconds, annealing at 60° C. for 45 seconds, and extension at 72° C. for 1 minute, and then final extension at 72° C. for 8 minutes.

As shown in FIG. 63, unmethylation of SOCS3 was observed in HEK293 and HaCaT cells which are normal cells, whereas hypermethylation of the promoter region of SOCS3 gene was observed in U-87 MG, U-118 MG, T98G, LN229 which are glioblastoma cell lines (U: unmethylated SOCS3, M: methylated SOCS3). These results indicate that SOCS3 is silenced by hypermethylation in glioblastoma cell lines.

Example 17-3-2. Analysis of Expression of Endogenous SOCS3 and JAK/STAT Signaling Activation Status in Glioblastoma Cells JAK/STAT3 activation in cancer cells was analyzed by Western blot analysis. The normal HaCaT and HEK293 cells, and glioblastoma cells, U-87 MG, U-118 MG, T98G, and LN229 were washed with PBS, and then the cells were lysed in RIPA lysis buffer (Biosesang, Seongnam, Korea) containing protease inhibitor cocktail (Roche, Indianapolis, Ind., USA), incubated for 15 min at 4° C., and centrifuged at 13,000 rpm for 10 min at 4° C. to isolate proteins, followed by western blotting in the same manner as in Example 8-1.

As shown in FIG. 64, high expression levels of SOCS3 and low phosphorylation levels of p-STAT1, p-STAT3, and p-p65 were observed in normal HaCaT and HEK293 cells. Low expression level of SOCS3 gene was observed in the glioblastoma cell lines, compared to the normal cell line, and high levels of p-STAT1 and p-STAT3 were observed in LN229 and T98G. High levels of P-p65 were observed in all 4 types of glioblastoma cell lines. These results suggest a possibility of developing a mechanism-specific anticancer agent, because SOCS3-deficient cancer cells can be replenished with cell permeable proteins, and activated JAK/STAT-signaling can be negatively regulated.

Example 17-4. Investigation of Anticancer Efficacy of iCP-SOCS3 Recombinant Protein To develop the iCP-SOCS3 recombinant protein as a mechanism-specific therapeutic agent for solid tumors, SOCS3 levels endogenously expressed and activation of JAK/STAT-signaling pathway were investigated in different breast cancer cell lines, normal cells, and normal hepatic cells.

Example 17-4-1. Analysis of Expression Level of Endogenous SOCS3 mRNA in Breast Cancer Cell Line SOCS3 mRNA expression levels in cancer cells were analyzed by RT-PCR. mRNAs were isolated from normal cell lines and cancer cell lines according to a method provided in a manufacturer's sheet of Hybrid-R (Geneall, Korea), and PCR was performed using SOCS3 primer F 5'-cct act gaa ccc tcc tcc ga-3' (SEQ ID NO: 820) and SOCS3 primer R 5'-gca get ggg tga ctt tct ca-3' (SEQ ID NO: 821) for 30 cycles consisting of denaturing (95° C.), annealing (60° C.), and extending (72° C.) for 45 seconds each.

The results of electrophoresis showed that high expression levels of SOCS3 were observed in the normal HEK293 cells whereas low expression levels of SOCS3 were observed in the breast cancer cell lines, except MDA-MB-231 (FIG. 65).

Example 17-4-2. Analysis of Hypermethylation Level in Breast Cancer Cell Line

SOCS3 expression is suppressed due to methylation in cancer cells, and therefore, inflammation or cancer development is increased. Further, to investigate the effect of cell permeable SOCS, a cancer cell line where endogenous SOCS3 expression is suppressed should be selected or applied to a model, and therefore, the present experiments were performed.

Genomic DNA was extracted from cancer cell line using an Exgene™ Tissue SV mini kit (Geneall®, Korea). DNA was quantified, and experiments were performed using 500 ng of gDNA and an EZ DNA Methylation-Gold™ kit (ZYMO Research, Orange, Calif., USA) according to the manufacturer's instructions. DNA was used to perform PCR, and methylation and unmethylation of endogenous SOCS3 were qualitatively analyzed by electrophoresis. In this regard, the primers used are as follows.

Unmethyl-F was 5'-tag tgt gta agt tgt agg aga gtg g-3' (SEQ ID NO: 816), Unmethyl-R was 5'-cta aac ata aaa aaa taa cac taa tcc aaa-3' (SEQ ID NO: 817), Methyl-F was 5'-gta gtg cgt aag ttg tag gag agc-3' (SEQ ID NO: 818), and Methyl-R was 5'-gta aaa aaa taa cgc taa tcc gaa-3' (SEQ ID NO: 819). PCR was performed for 30 cycles consisting of pre-denaturation at 95° C. for 5 minutes, denaturation at 95° C. for 30 seconds, annealing at 60° C. for 45 seconds, and extension at 72° C. for 1 minute, and then final extension at 72° C. for 8 minutes.

As shown in FIG. 66, unmethylation of SOCS3 was observed in HEK293 cells which are normal cells, whereas hypermethylation of the promoter region of SOCS3 gene was observed in breast cancer cell lines, MDA-MB-231, MCF7, SK-BR3, and T47D (U: unmethylated SOCS3, M: methylated SOCS3). These results indicate that SOCS3 is silenced by hypermethylation in breast cancer cell lines.

Example 17-4-3. Analysis of Expression of Endogenous SOCS3 and JAK/STAT Signaling Activation Status in Breast Cancer Cell Line JAK/STAT3 activation in cancer cells was analyzed by Western blot analysis. The normal HEK293 cells, and breast cancer cell lines, MDA-MB-231, MCF7, SK-BR3, and T47D were washed with PBS, and then the cells were lysed in RIPA lysis buffer (Biosesang, Seongnam, Korea) containing protease inhibitor cocktail (Roche, Indianapolis, Ind., USA), incubated for 15 min at 4° C., and centrifuged at 13,000 rpm for 10 min at 4° C. to isolate proteins, followed by western blotting in the same manner as in Example 8-1.

As shown in FIG. 67, high expression levels of SOCS3 and low phosphorylation levels of p-STAT1 and p-STAT3 were observed in normal HEK293 cells. Low expression level of SOCS3 gene was observed in the breast cancer cell lines, compared to the normal cell line. Further, high levels of p-STAT1 were observed in SK-BR3 and T47D, and high levels of p-STAT3 were observed in MDA-MB-231 and T47D. These results suggest a possibility of developing a mechanism-specific anticancer agent, because SOCS3-deficient cancer cells can be replenished with cell permeable proteins, and activated JAK/STAT-signaling can be negatively regulated.

Example 18. Investigation of Anti-Cancer Efficacy of iCP-SOCS3

Example 18-1. Investigation of Anti-Cancer Efficacy (Anti-Proliferative Activity) of iCP-SOCS3

In order to develop the iCP-SOCS3 recombinant protein as a therapeutic agent for solid tumors, efficacy of iCP-SOCS3 on proliferation of solid tumors (gastric cancer, colorectal cancer, breast cancer, and glioblastoma cell lines) was investigated.

Cells originated from human gastric cancer cells (AGS, MKN45, MKN75, NCI-N87), colorectal cancer cells (HCT116), glioblastoma (U-87 MG), breast cancer cells (MDA-MB-231), and mouse fibroblast (NIH3T3) were purchased from ATCC (Manassas, Va., USA) and KCLB (Seoul, Korea). All the cells were maintained as recommended by the supplier. These cells ($3 \times 10^3$/well) were seeded in 96 well plates. The next day, cells were treated with DMEM (vehicle) or 10 μM recombinant SOCS3 proteins for 96 hrs in the presence of serum (2%). Proteins were replaced daily. Cell growth and survival were evaluated with the CellTiter-Glo Cell Viability Assay (Promega, Madison, Wis.). Measurements using a Luminometer (Turner Designs, Sunnyvale, Calif.) were conducted following the manufacturer's protocol.

Since the endogenous level of SOCS3 protein is reduced in solid tumor patient, and SOCS3 negatively regulates cell growth and motility in cultured solid tumor cells, we investigated whether iCP-SOCS3 inhibits cell viability through SOCS3 intracellular replacement in solid tumor cells. As shown in FIG. 68, SOCS3 recombinant proteins containing aMTD$_{165}$ significantly suppressed cancer cell proliferation. HM$_{165}$S3B (iCP-SOCS3) protein was the most cytotoxic to gastric cancer cells—over 40% in 10 μM treatment ($p<0.01$)—especially compared to vehicle alone (i.e. exposure of cells to culture media without recombinant proteins; left).

As shown in FIG. 69, SOCS3 recombinant proteins containing aMTD$_{165}$ significantly suppressed cancer cell proliferation. HM$_{165}$S3B (iCP-SOCS3) protein was the most cytotoxic to colorectal cancer cells—over 60% in 10 μM treatment ($p<0.01$)—especially compared to vehicle alone (i.e. exposure of cells to culture media without recombinant proteins; left).

As shown in FIG. 70, SOCS3 recombinant proteins containing aMTD$_{165}$ significantly suppressed cancer cell proliferation. HM$_{165}$S3B (iCP-SOCS3) protein was the most cytotoxic to glioblastoma cells—over 80% in 10 μM treatment ($p<0.01$)—especially compared to vehicle alone (i.e. exposure of cells to culture media without recombinant proteins; left).

As shown in FIG. 71, SOCS3 recombinant proteins containing aMTD$_{165}$ significantly suppressed cancer cell proliferation. HM$_{165}$S3B (iCP-SOCS3) protein was the most cytotoxic to breast cancer cells—over 40% in 10 μM treatment ($p<0.01$)—especially compared to vehicle alone (i.e. exposure of cells to culture media without recombinant proteins; left).

However, neither cell-permeable SOCS3 protein adversely affected the cell viability of non-cancer cells (NIH3T3) even after exposing these cells to equal concentrations (10 μM) of protein over 4 days. These results suggest that the iCP-SOCS3 protein is not overly toxic to normal cells and selectively kills tumor cells, and would have a great ability to inhibit cell survival-associated phenotypes in various cancer without any severe aberrant effects as a protein-based biotherapeutics.

Example 18-2. Investigation of Anti-Cancer Efficacy (Cell Migration Inhibition) of iCP-SOCS3

In order to develop the iCP-SOCS3 recombinant protein as a therapeutic agent for solid tumors, efficacy of iCP-SOCS3 on migration and metastasis of solid tumors (gastric cancer, colorectal cancer, breast cancer, and glioblastoma cell lines) was investigated.

Cells were seeded into 12-well plates, grown to 90% confluence, and incubated with 10 µM Non-CP-SOCS3 (HS3B), iCP-SOCS3 ($HM_{165}S3B$) in serum-free medium for 2 hrs prior to changing the growth medium (recommended medium by the supplier). The cells were washed twice with PBS, and the monolayer at the center of the well was "wounded" by scraping with a pipette tip. Cells were cultured for an additional 24-48 hrs and cell migration was observed by phase contrast microscopy (Nikon, ECLIPSE Ts2). The migration was quantified by counting the number of cells that migrated from the wound edge into the clear area.

As shown in FIGS. 72-75, iCP-SOCS3 ($HM_{165}S3B$) suppressed the repopulation of wounded monolayer although SOCS3 protein lacking aMTD 165 (HS3B) had no effect on the cell migration, in AGS (FIG. 72), HCT116 (FIG. 73), U-87 MG (FIG. 74), and MDA-MB-231 (FIG. 75), respectly. In normal cells (NIH3T3), iCP-SOCS3 ($HM_{165}S3B$) had no effect on the cell migration.

Transwell Migration Assay

The lower surface of Transwell inserts (Costar) was coated with 0.1% gelatin, and the membranes were allowed to dry for 1 hr at room temperature. The Transwell inserts were assembled into a 24-well plate, and the lower chamber was filled with growth media containing 10% FBS and FGF2 (40 ng/ml). Cells were added to each upper chamber at a density of $5\times10^5$, and the plate was incubated at 37° C. in a 5% $CO_2$ incubator for 24 hrs. Migrated cells were stained with 0.6% hematoxylin and 0.5% eosin and counted.

As shown in FIG. 76 (left) and 77, AGS (FIG. 76) and U-87 MG (FIG. 77) cells treated with iCP-SOCS3 ($HM_{165}S3B$) protein also showed significant inhibitory effect on their Transwell migration compared with untreated cells (Vehicle) and non-permeable SOCS3 protein-treated cells.

Invasion Assay

The lower surface of Transwell inserts (Costar) was coated with 0.1% gelatin, the upper surface of Transwell inserts was coated with matrigel (40 µg per well; BD Pharmingen, San Diego, Calif., USA), and the membranes were allowed to dry for 1 hr at room temperature. The Transwell inserts were assembled into a 24-well plate, and the lower chamber was filled with growth media containing 10% FBS and FGF2 (40 ng/ml). Cells ($5\times10^5$) were added to each upper chamber, and the plate was incubated at 37° C. in a 5% $CO_2$ incubator for 24 hrs. Migrated cells were stained with 0.6% hematoxylin and 0.5% eosin and counted.

As shown in FIG. 76 (right), AGS treated with iCP-SOCS3 ($HM_{165}S3B$) protein caused remarkable decrease in invasion compared with the control proteins. Taken together, these data indicate that iCP-SOCS3 contributes to inhibit tumorigenic activities of solid tumors.

Example 18-3. Investigation of Anti-Cancer Efficacy (Induction of Apoptosis) of iCP-SOCS3

To further determine the effect of iCP-SOCS3 on the tumorigenicity of solid tumors, we subsequently investigated whether iCP-SOCS3 regulates apoptosis in various cancer cells, such as gastric cancer cells (AGS and MKN45), colorectal cancer cells (HCT116), glioblastoma cells (U-87 MG), and breast cancer cells (MDA-MB-231).

Annexin V/7-Aminoactinomycin D (7-AAD) staining was performed using flow cytometry according to the manufacturer's guidelines (BD Pharmingen, San Diego, Calif., USA). Briefly, $1\times10^6$ cells were washed three times with ice-cold PBS. The cells were then resuspended in 100 µl of binding buffer and incubated with 1 µl of 7-AAD and 1 µl of Annexin V-7-AAD for 30 min in the dark at 4° C. Flow cytometric analysis was immediately performed using a guava easyCyte™ 8 Instrument (Merck Millipore, Darmstadt, Germany). In this regard, gemcitabine (0.1~10 µM) was used as a reference drug.

As shown in FIG. 78, 10 uM of iCP-SOCS3 ($HM_{165}S3B$) protein did not induce apoptosis in normal cell lines (NIH3T3 and HEK293). Whereas, as shown in FIGS. 79-82, 10 uM iCP-SOCS3 ($HM_{165}S3B$) was efficient inducer of apoptosis in cancer cells, as assessed by Annexin V staining. Consistently, no changes in Annexin V staining were observed in cancer cells treated with HS3B compared to untreated cell (Vehicle).

Example 18-4. Investigation of Anti-Cancer Efficacy (Induction of Apoptosis) of iCP-SOCS3

To further determine the effect of iCP-SOCS3 on the tumorigenicity of solid tumors, we subsequently investigated whether iCP-SOCS3 regulates apoptosis in colorectal cancer cells.

Apoptotic cells were analyzed using terminal dUTP nick-end labeling (TUNEL) assay with In Situ Cell Death Detection kit TMR red (Roche, 4056 Basel, Switzerland). Cells were treated for 24 hr with 10 µM HS3B or $HM_{165}S3B$ proteins with 2% fetal bovine serum and apoptotic cells were visualized by TUNEL staining. Treated cells were washed with cold PBS two times, fixed in 4% paraformaldehyde (PFA, Junsei, Tokyo, Japan) for 1 hr at room temperature, and incubated in 0.1% Triton X-100 for 2 min on the ice. Cells were washed with cold PBS twice, and treated TUNEL reaction mixture for 1 hr at 37° C. in dark, washed cold PBS three times and observed by fluorescence microscopy (Nikon, Tokyo, Japan).

iCP-SOCS3 ($HM_{165}S3B$) protein was considerably efficient inducer of apoptosis in HCT116 cells (FIG. 83), as assessed by a fluorescent terminal dUTP nick-end labeling (TUNEL) assay. Consistently, no changes in TUNEL was observed in HCT116 cells treated with HS3B compared to untreated cell (Vehicle).

Example 18-5. Investigation of Anti-Cancer Efficacy (Inhibition of Cell Cycle Progression) of iCP-SOCS3

To further determine the effect of iCP-SOCS3 on the tumorigenicity of solid tumors, we subsequently investigated whether iCP-SOCS3 regulates cell cycle progression in various cancer cells, such as gastric cancer cells (AGS), colorectal cancer cells (HCT116), glioblastoma cells (U-87 MG, and breast cancer cells (MDA-MB-231).

Cancer cells and normal cells (NIH3T3, HaCaT, and HEK293) were treated with 10 uM protein (Non-CP-SOCS3 (HS3B) and iCP-SOSC3 ($HM_{165}S3B$)) for 8 hrs. After the treatment, cells were washed twice with cold PBS and re-suspended in 1 nil cold PBS, fixed in cold 70% ethanol, washed with cold PBS twice and re-suspended in PI master mix (PI 10 ug/ml (sigma), 50 ug/ml RNase A (invitrogen) in staining buffer) at a final cell density of 2×10$^5$ cell/ml. The cell mixtures were incubated 30 min in the dark at 4° C. Flow cytometric analysis was immediately performed using a guava easyCyte™ 8 Instrument (Merck Millipore, Darmstadt, Germany).

iCP-SOCS3 (HM$_{165}$S3B) protein efficiently inhibited cell cycle progression in various cancer cells, such as AGS, HCT116, U-87 MG, and MDA-MB-231 (FIGS. 85 to 88), while iCP-SOCS3 (HM$_{165}$S3B) protein did not inhibit cell cycle progression in normal cells (FIG. 84).

Example 18-6. Investigation of Anti-Cancer Efficacy (Effect on Molecular Mechanism-Mode of Action) of iCP-SOCS3

To further determine the effect of iCP-SOCS3 on the tumorigenicity of solid tumors, we subsequently investigated whether iCP-SOCS3 regulates apoptosis in breast cancer cells (MDA-MB-231).

Cells were treated for 24 hr with 10 μM HS3B or HM$_{165}$S3B proteins, lysed in RIPA lysis buffer containing proteinase inhibitor cocktail, incubated for 15 min at 4° C., and centrifuged at 13,000 rpm for 10 min at 4° C. Equal amounts of lysates were separated on 15% SDS-PAGE gels and transferred to a nitrocellulose membrane. The membranes were blocked using 5% skim milk or 5% Albumin in TBST and incubated with the following antibodies: anti-Bcl-2 (Santa Cruz biotechnology), anti-Cleaved Caspase 3 (Cell Signaling Technology), then HRP conjugated anti-mouse or anti-rabbit secondary antibody. The expression of each protein was determined by immunoblotting with indicated antibodies. An antibody against β-actin was used as a loading control.

MDA-MB-231 cells treated with iCP-SOCS3 (HM$_{165}$S3B) protein dramatically reduced the expression of anti-apoptotic protein such as B-cell lymphoma 2 (Bcl-2) and increased the level of cleaved cysteine-aspartic acid protease (caspase-3) at 24 hr (FIG. 89). These results indicate that iCP-SOCS3 induces apoptosis of breast cancer cells and may suppress the cancer progression by this pathway.

Example 19. Investigation of Anti-Cancer Efficacy of iCP-SOCS3 in Xenograft Model (Cell-Derived Xenograft (CDX)-Model)

Example 19-1. Investigation of Anti-Cancer Efficacy of iCP-SOCS3 in Gastric Cancer Cell (NCI-N87)-Derived Xenograft (CDX) Model In the following experiments, Western blotting was performed in the same manner as in Example 8-1, and RT-PCR and IHC were performed by the following method.

RT-PCR

Tumor tissues were finely minced using a homogenizer according to the manufacturer's protocol of Hybrid-R (gene-all, Korea), and then mRNA was isolated therefrom. 1 ug of mRNA thus separated was used to synthesize cDNA using an Accupower RT Premix (Bioneer, Korea). PCR was performed using 2 ul of cDNA and the primers of Table 42. PCR was performed using an Accupower PCR Premix (Bioneer, Korea) for 30 cycles consisting of denaturing (95° C.), annealing (60° C.), and extending (72° C.) for 45 seconds each.

TABLE 42

| Genes | Forward Sequence | Reverse Sequence |
|---|---|---|
| Cyclin E | CCGTTTACAAGCTAAGCAGC (SEQ ID NO: 839) | GTGGTTCCAAGTCAGAATGC (SEQ ID NO: 840) |
| Cyclin A1 | TCAGTACTTGAGGCGACAAGG (SEQ ID NO: 841) | CTCCCTAATTGCTTGCTGAGG (SEQ ID NO: 842) |
| Bax | CCCTTTTGCTTCAGGGTTTC (SEQ ID NO: 843) | GCCACTCGGAAAAAGACCTC (SEQ ID NO: 844) |
| FAK | TGGTGAAAGCTGTCATCGAG (SEQ ID NO: 845) | CTGGGCCAGTTTCATCTTGT (SEQ ID NO: 846) |
| p21 | CAGCGGAACAAGGAGTCAGA (SEQ ID NO: 847) | AGAAACGGGAACCAGGACAC (SEQ ID NO: 848) |
| p27 | GATAATCCCGCTCTGAATGC (SEQ ID NO: 849) | GCTTCTCTTAGTGCTGTAGC (SEQ ID NO: 850) |
| VEGF | CTTCAAGCCATCCTGTGTGC (SEQ ID NO: 851) | ACGCGAGTCTGTGTTTTTGC (SEQ ID NO: 852) |
| HIF-1α | ATCAGACACCTAGTCCTTCCG (SEQ ID NO: 853) | TTGAGGACTTGCGCTTTCAGG (SEQ ID NO: 854) |
| GAPDH | AAGGGTCATCATCTCTGCCC (SEQ ID NO: 855) | GTGATGGCATGGACTGTGGT (SEQ ID NO: 856) |

Immunohistochemistry (IHC)

Tissue samples were fixed in 4% Paraformaldehyde (Duksan, South Korea) for 3 days, dehydrated, cleared with xylene and embedded in Paraplast. Sections (6 an thick) of tumor were placed onto poly-L-lysine coated slides. To block endogenous peroxidase activity, sections were incubated for 15 min with 3% H$_2$O$_2$ in methanol. After washing three times with PBS, slides were incubated for 30 min with blocking solution (5% fetal bovine serum in PBS). Mouse anti-Bax antibody (sc-7480, Santa Cruz Biotechnology; SantaCruz, Calif., USA) and rabbit anti-VEGF (ab46154, Abcam, Cambridge, UK) were diluted 1:1000 (to protein concentration 0.1 μg/ml) in blocking solution, applied to sections, and incubated at 4° C. for 24 hrs. After washing three times with PBS, sections were incubated with biotinylated mouse and rabbit IgG (Vector Laboratories, Burlingame, Calif., USA) at a 1:1000 dilution for 1 hr at room temperature, then incubated with avidin-biotinylated peroxidase complex using a Vectorstain ABC Kit (Vector Laboratories, Burlingame, Calif., USA) for 30 min at room temperature. After the slides are reacted with oxidized 3, 3-diaminobenzidine as a chromogen, they were counter-stained with Harris hematoxylin (Sigma-Aldrich, USA). Permanently mounted slides were observed and photographed using a microscope equipped with a digital imaging system (ECLIPSE Ti, Nikon, Japan).

Anti-tumor activity of iCP-SOCS3 against human cancer xenografts was assessed. Female Balb/c$^{nu/nu}$ mice (5-week-old, Doo-Yeol Biotech Co. Ltd. Korea) were subcutaneously implanted with Hep3B2.1-7 tumor block (1 mm$^3$) into the left back side of the mouse. Tumor-bearing mice were intravenously administered with 600 μg/head of iCP-SOCS3 (HM$_{165}$S3B) or the control proteins (HS3B) for 21 days and observed for 2 weeks following the termination of the treatment. After protein treatment, mice were killed, and six organs (brain, heart, lung, liver, kidney, and spleen) from each were collected and kept in a suitable fixation solution until the next step. Tumor size was monitored by measuring the longest (length) and shortest dimensions (width) once a day with a dial caliper, and tumor volume was calculated as width2×length×0.5.

As shown in FIG. 90, HM$_{165}$S3B protein significantly suppressed the tumor growth (p<0.05) during the treatment and the effect persisted for at least 2 weeks after the treatment was terminated (65% inhibition at day 35, respectively). Whereas, the growth of HS3B-treated tumors increased, matching the rates observed in control mice (Vehicle). These results suggest that iCP-SOCS3 inhibits the growth of established tumors as well as the tumor growth of gastric cancer cells.

mRNA levels were analyzed using the tumor tissues removed at 2 weeks (Day 35) after termination of drug administration to analyze changes in expressions of major biomarker genes by iCP-SOCS3.

Expressions of cell cycle (cyclinA1) and angiogenesis (VEGF)-related genes were significantly regulated by treatment of iCP-SOCS3.

Accordingly, it was confirmed that iCP-SOCS3 is able to inhibit development of gastric cancer through expressions of various factors regulating cancer activity such as cell cycle, angiogenesis, etc.

Further, tumor tissues removed at 2 weeks (Day 35) after termination of drug administration were used to perform Western blotting and IHC, and increase or decrease in the expressions of cancer activity regulating factors by iCP-SOCS3 was observed.

In iCP-SOCS3-treated tumor tissues, expressions of a cell cycle regulator, p21 and apoptosis inducers, Bax and cleaved caspase-3 were increased. Further, expression of an angiogenesis inducer VEGF was also remarkably decreased (FIG. 90). Accordingly, it was demonstrated that cell cycle, apoptosis, and angiogenesis are also regulated by iCP-SOCS3 in-vivo.

Example 19-2. Investigation of Anti-Cancer Efficacy of iCP-SOCS3 in Colorectal Cancer Cell (HCT116)-Derived Xenograft (CDX) Model The following experiments were performed in the same manner as in Example 19-1. As shown in FIG. 91, HM$_{165}$S3B protein significantly suppressed the tumor growth (p<0.05) during the treatment and the effect persisted for at least 2 weeks after the treatment was terminated (79% at day 35, respectively). Whereas, the growth of HS3B-treated tumors increased, matching the rates observed in control mice (Vehicle). These results suggest that iCP-SOCS3 inhibits the growth of established tumors as well as the tumor growth of colorectal cancer cells.

mRNA levels were analyzed using the tumor tissues removed at 2 weeks (Day 35) after termination, of drug administration to analyze changes in expressions of major biomarker genes by iCP-SOCS3.

Expressions of apoptosis (Bax) and angiogenesis (VEGF)-related genes were significantly regulated by treatment of iCP-SOCS3.

Accordingly, it was confirmed that iCP-SOCS3 is able to inhibit development of colorectal cancer through expressions of various factors regulating cancer activity such as apoptosis, angiogenesis, etc.

Further, tumor tissues removed at 2 weeks (Day 35) after termination of drug administration were used to perform Western blotting and IHC, and increase or decrease in the expressions of cancer activity regulating factors by iCP-SOCS3 was observed.

In iCP-SOCS3-treated tumor tissues, expressions of a cell cycle regulator, p21 and an apoptosis inducer, Bax were increased. Further, expression of an angiogenesis inducer VEGF was also remarkably decreased (FIG. 91). Accordingly, it was demonstrated that cell cycle, apoptosis, and angiogenesis are also regulated by iCP-SOCS3 in-vivo.

Example 19-3. Investigation of Anti-Cancer Efficacy of iCP-SOCS3 in Glioblastoma Cell (U-87 MG)-Derived Xenograft (CDX) Model The following experiments were performed in the same manner as in Example 19-1.

As shown in FIG. 92, HM$_{165}$S3B protein significantly suppressed the tumor growth (p<0.05) during the treatment and the effect persisted for at least 2 weeks after the treatment was terminated (76% at day 42, respectively). Whereas, the growth of HS3B-treated tumors increased, matching the rates observed in control mice (Vehicle). These results suggest that iCP-SOCS3 inhibits the growth of established tumors as well as the tumor growth of glioblastoma cells.

mRNA levels were analyzed using the tumor tissues removed at 3 weeks (Day 42) after termination of drug administration to analyze changes in expressions of major biomarker genes by iCP-SOCS3.

Expressions of apoptosis (Bax), cell cycle (CDK4, CDK2, cyclinE, cyclinA1), angiogenesis (HIF1a, VEGF), and migration (FAK)-related genes were significantly regulated by treatment of iCP-SOCS3.

Expressions of NSE, FSTL-1, and GFAT which are biomarker genes of glioblastoma were remarkably decreased by iCP-SOCS3.

Expressions of VEGF and angiopoietin I which are biomarker genes of angiogenesis were significantly decreased by treatment of iCP-SOCS3.

Accordingly, it was confirmed that iCP-SOCS3 is able to inhibit development of glioblastoma through expressions of various factors regulating cancer activity such as apoptosis, cell cycle, migration, angiogenesis, etc.

Example 19-4. Investigation of Anti-Cancer Efficacy of iCP-SOCS3 in Breast Cancer Cell (MDA-MB-231)-Derived Xenograft (CDX) Model The following experiments were performed in the same manner as in Example 19-1. As shown in FIG. 93, HM$_{165}$S3B protein significantly suppressed the tumor growth (p<0.05) during the treatment and the effect persisted for at least 2 weeks after the treatment was terminated (63% at day 35, respectively). Whereas, the growth of HS3B-treated tumors increased, matching the rates observed in control mice (Vehicle). These results suggest that iCP-SOCS3 inhibits the growth of established tumors as well as the tumor growth of breast cancer cells.

mRNA levels were analyzed using the tumor tissues removed at 2 weeks (Day 35) after termination of drug administration to analyze changes in expressions of major biomarker genes by iCP-SOCS3.

Expressions of cell cycle (p21, p27, cyclinE), proliferation (PCNA), and angiogenesis (HIF1a, VEGF)-related genes were significantly regulated by treatment of iCP-SOCS3.

Accordingly, it was confirmed that iCP-SOCS3 is able to inhibit development of breast cancer through expressions of various factors regulating cancer activity such as cell cycle, angiogenesis, etc., indicating characteristics of iCP-SOCS3 as a mechanism-specific therapeutic agent targeting solid tumors.

Further, tumor tissues removed at 2 weeks (Day 35) after termination of drug administration were used to perform Western blotting and IHC, and increase or decrease in the expressions of cancer activity regulating factors by iCP-SOCS3 was observed.

In iCP-SOCS3-treated tumor tissues, expression of a cell cycle regulator, p21 was increased and expressions of angiogenesis inducers, VEGF and CD31 were remarkably decreased (FIG. 93). Accordingly, it was demonstrated that cell cycle and angiogenesis are also regulated by iCP-SOCS3 in-vivo.

Statistical Analysis

Statistical analysis and graphic presentation have been performed using GraphPad Prism 5.01 software (GraphPad, La Jolla, Calif., USA). All experimental data are presented as means±SEM. Statistical significance was analyzed by the Student's t-test or ANOVA method. Experimental differences between groups were assessed using paired Student's t-tests. For animal experiments, ANOVA was used for comparing between and within groups to determine the significance. Differences with $p<0.05$ are considered to be statistically significant.

Those skilled in the art to which the present invention pertains will appreciate that the present invention may be implemented in different forms without departing from the essential characteristics thereof. Therefore, it should be understood that the disclosed embodiments are not limitative, but illustrative in all aspects. The scope of the present invention is made to the appended claims rather than to the foregoing description, and all variations which come within the range of equivalency of the claims are therefore intended to be embraced therein.

---

The invention claimed is:

1. A method of treating solid tumor in a subject in need thereof comprising:
 administering to the subject a therapeutically effective amount of an iCP-SOCS3 recombinant protein,
 wherein the iCP-SOCS3 recombinant protein comprises a SOCS3 protein, an advanced macromolecule transduction domain (aMTD) and a solubilization domain (SD), and the iCP-SOCS3 recombinant protein is represented by following structural formula:
  A-B-C,
 wherein A is the aMTD,
 B is the SOCS3 protein, and
 C is the SD,
 wherein the aMTD has the amino acid sequence of SEQ ID NO: 122, and the SD has an amino acid sequence independently selected from the group consisting of SEQ ID NOs: 798, 799, 800, 801, 802, 803, and 804.

2. The method of claim 1, wherein the SOCS3 protein has the amino sequence of SEQ ID NO: 814.

3. The method of claim 2, wherein the SOCS3 protein is encoded by the polynucleotide sequence of SEQ ID NO: 815.

4. The method claim 1, wherein the aMTD is encoded by the polynucleotide sequence of SEQ ID NO: 362.

5. The method of claim 1, wherein the SD is encoded by a polynucleotide sequence independently selected from the group consisting of SEQ ID NOs: 805, 806, 807, 808, 809, 810, and 811.

6. The method of claim 1, wherein the iCP-SOCS3 recombinant protein has a histidine-tag affinity domain additionally fused to one end thereof.

7. The method of claim 6, wherein the histidine-tag affinity domain has the amino acid sequence of SEQ ID NO: 812.

8. The method of claim 7, wherein the histidine-tag affinity domain is encoded by the polynucleotide sequence of SEQ ID NO: 813.

* * * * *